(12) United States Patent
Blaney et al.

(10) Patent No.: US 12,098,148 B2
(45) Date of Patent: Sep. 24, 2024

(54) THERAPEUTIC COMPOUNDS

(71) Applicant: C4X Discovery Limited, Manchester (GB)

(72) Inventors: Emma L. Blaney, Manchester (GB); Duncan J. Crick, Manchester (GB); Simon R. Crumpler, Essex (GB); George Hynd, Harlow (GB); Cathy L Lucas, Manchester (GB); Barrie P. Martin, Manchester (GB); Nick C. Ray, London (GB); Eileen M. Seward, Essex (GB); David G. Evans, Essex (GB); Lucille Le Bozec, Walden (GB); Thorsten Nowak, Manchester (GB); Michael G. Russell, Essex (GB); Siew K. Yeap, Essex (GB); Fabien J. Roussel, Essex (GB); Sanjeet S. Sehmi, Essex (GB)

(73) Assignee: C4X Discovery Limited, Manchester (GB)

( * ) Notice: Subject to any disclaimer, the term of this patent is extended or adjusted under 35 U.S.C. 154(b) by 716 days.

(21) Appl. No.: 17/287,942

(22) PCT Filed: Oct. 22, 2019

(86) PCT No.: PCT/GB2019/053012
§ 371 (c)(1),
(2) Date: Apr. 22, 2021

(87) PCT Pub. No.: WO2020/084300
PCT Pub. Date: Apr. 30, 2020

(65) Prior Publication Data
US 2022/0002286 A1 Jan. 6, 2022

(30) Foreign Application Priority Data

Oct. 22, 2018 (GB) ..................... 1817193
May 30, 2019 (GB) ..................... 1907674

(51) Int. Cl.
*C07D 417/14* (2006.01)
*C07D 401/14* (2006.01)
*C07D 405/14* (2006.01)
*C07D 413/14* (2006.01)
*C07D 471/04* (2006.01)
*C07D 487/04* (2006.01)
*C07D 498/04* (2006.01)

(52) U.S. Cl.
CPC ......... *C07D 417/14* (2013.01); *C07D 401/14* (2013.01); *C07D 405/14* (2013.01); *C07D 413/14* (2013.01); *C07D 471/04* (2013.01); *C07D 487/04* (2013.01); *C07D 498/04* (2013.01)

(58) Field of Classification Search
None
See application file for complete search history.

(56) References Cited

U.S. PATENT DOCUMENTS

| 4,954,509 A * | 9/1990 | Vecchietti | ............ C07D 409/06 544/5 |
|---|---|---|---|
| 5,389,638 A | 2/1995 | DeBernardis et al. | |
| 8,642,660 B2 | 2/2014 | Goldfarb | |
| 2010/0152234 A1 | 6/2010 | Kuhnert et al. | |
| 2023/0159511 A1* | 5/2023 | Lucas | ................... C07D 471/04 514/210.18 |
| 2023/0167084 A1* | 6/2023 | Lucas | ....................... A61P 3/10 514/230.8 |

FOREIGN PATENT DOCUMENTS

| CN | 103450079 A * | 12/2013 |
|---|---|---|
| CN | 112409331 A | 2/2021 |
| EP | 0330469 A2 | 8/1989 |
| EP | 1113007 A1 | 7/2001 |
| WO | WO-98/40385 A1 | 9/1998 |
| WO | WO-98/45263 A1 | 10/1998 |
| WO | WO-2004/039365 A1 | 5/2004 |
| WO | WO-2007/047991 A1 | 4/2007 |
| WO | WO-2009/73545 A2 | 6/2009 |
| WO | WO-2009/105746 A2 | 8/2009 |
| WO | WO-2010/048207 A2 | 4/2010 |
| WO | WO-2010/75973 A1 | 7/2010 |
| WO | WO-2012/83866 A1 | 6/2012 |
| WO | WO-2013/055984 A1 | 4/2013 |
| WO | WO-2013/067036 A1 | 5/2013 |
| WO | WO-2016/149248 A1 | 9/2016 |
| WO | WO-2016/203400 A1 | 12/2016 |
| WO | WO-2018/181345 A1 | 10/2018 |

(Continued)

OTHER PUBLICATIONS

Xu et al., Org. Biomol. Chem., 2015, 13, 5656-5673 (Year: 2015).*
Dai et al., "Development of Novel Nrf2/ARE Inducers Bearing Pyrazino [2, 1-a] isoquinolin Scaffold with Potent In Vitro Efficacy and Enhanced Physiochemical Properties," Mol Online, 22(9): 1541 (15 pages) (2017).
International Preliminary Report on Patentability for International Application No. PCT/GB2019/053012 mailed May 6, 2021.
Richardson et al., "Replacement of a Napthalene Scaffold in Kelch-like ECH-Associated Protein 1 (KEAP1)/Nuclear Factor (Erythoid-derived 2)-like 2 (NRF2) Inhibitors," J Med Chem, 61(17): 8029-8047 (2018).

(Continued)

*Primary Examiner* — Jeffrey S Lundgren
*Assistant Examiner* — Anthony Joseph Seitz
(74) *Attorney, Agent, or Firm* — Foley Hoag LLP; David P. Halstead; Alexander J. Chatterley

(57) ABSTRACT

The present invention relates to compounds that are Nrf2 activators. The compounds have the structural formula I defined herein. The present invention also relates to processes for the preparation of these compounds, to pharmaceutical compositions comprising them, and to their use in the treatment of diseases or disorders associated with Nrf2 activation.

32 Claims, No Drawings

(56) References Cited

FOREIGN PATENT DOCUMENTS

| WO | WO-2019/006005 A2 | 1/2019 |
|---|---|---|
| WO | WO-2019/204781 A1 | 10/2019 |
| WO | WO-2019/217757 A1 | 11/2019 |
| WO | WO-2020/084300 A1 | 4/2020 |
| WO | WO-2020/210229 A1 | 10/2020 |
| WO | WO-2021/214470 A1 | 10/2021 |
| WO | WO-2021/214472 A1 | 10/2021 |

OTHER PUBLICATIONS

Hu et al, "Discovery of a small-molecule inhibitor and cellular probe of Keap1-Nrf2 protein-protein interaction", *Bioorg. Med. Chem Letters* 23: 3039-3043 (2013).

Jnoff et al, "Binding Mode and Structure-Activity Relationships around Direct Inhibitors of the Nrf2-Keap1 Complex", *ChemMedChem*, 9: 699-705 (2014).

UK Search Report for Application No. GB 1817193.4 dated May 24, 2019.

Abed et al., "Discovery of disubstituted xylylene derivatives as small molecule direct inhibitors of Keap1-Nrf2 protein-protein interaction", Bioorganic & Medicinal Chemistry, 28(6), 115343 (2020).

Almazari et al., "Evaluation of antioxidant activation by potential nuclear factor (erythroid-derived 2)-like 2 (Nrf2)/Keap1 complex inhibitors", Tropical Journal of Pharmaceutical Research, 20(9), 1861-1873 (2021).

Ando et al., "Synthesis of coumarin derivatives and their cytoprotective effects on t-BHP-induced oxidative damage in HepG2 cells", Bioorganic & Medicinal Chemistry Letters, 28(14), 2422-2425 (2018).

Jiang et al., "Structure-Activity and Structure-Property Relationship and Exploratory in Vivo Evaluation of the Nanomolar Keap1-Nrf2 Protein-Protein Interaction Inhibitor" Journal of Medicinal Chemistry, 58(16), 6410-6421 (2015).

Li et al,"COPD lung studies of Nrf2 expression and the effects of Nrf2 activators", Inflammopharmacology vol. 30, pp. 1431-1443 (2022).

Lucas et al. "Ligand Conformational Analysis Enabling Improved Nrf2 Activators", Poster presentation (2016).

Nowak et al., "Ligand Conformational Analysis Enabling Improved Nrf-2 Activators", 5thInternational Congress on Medicinal Chemistry & CADD, Dec. 2016 Phoenix, Arizona, USA, Slide presentation.

Nowak, "Conformetrics and its application in drug discovery", 1st Anglo-Nordic-MedChem Conference, Slide presentation Jun. 2017.

Ontoria et al., "Combined Peptide and Small-Molecule Approach toward Nonacidic THIQ Inhibitors of the KEAP1/NRF2 Interaction" ACS Medicinal Chemistry Letters, 11(5), 740-746 (2020).

Pallesen et al., "Non-covalent Small-Molecule Kelch-like ECH-Associated Protein 1-Nuclear Factor Erythroid 2-Related Factor 2 (Keap1-Nrf2) Inhibitors and Their Potential for Targeting Central Nervous System Diseases", J. Med. Chem. , 61, 8088-8103 (2018).

Richardson et al., "Non-electrophilic modulators of the canonical Keap1/Nrf2 pathway", Bioorganic & Medicinal Chemistry Letters, 25(11), 2261-2268 (2015).

Shen et al. "Enantiomeric characterization and structure elucidation of LH601A using vibrational circular dichroism spectroscopy" Spectrochimica Acta, Part A: Molecular and Biomolecular Spectroscopy, 192, 312-317 (2018).

Tran et al. "A Comparative Assessment Study of Known Small-Molecule Keap1-Nrf2 Protein- Protein Interaction Inhibitors: Chemical Synthesis, Binding Properties, and Cellular Activity", Journal of Medicinal Chemistry, 62(17), 8028-8052 (2019).

Zhuang et al. "Rapid Identification of Keap1-Nrf2 Small-Molecule Inhibitors through Structure-Based Virtual Screening and Hit-Based Substructure Search" Journal of Medicinal Chemistry, 57(3), 1121-1126 (2014).

\* cited by examiner

THERAPEUTIC COMPOUNDS

RELATED APPLICATIONS

This application is the U.S. national phase of International Patent Application No. PCT/GB2019/053012, filed Oct. 22, 2019, which claims the benefit of priority to United Kingdom Patent Application Nos. GB 1817193.4 filed Oct. 22, 2018; and GB 1907674.4 filed May 30, 2019. The contents of the International Patent Application are incorporated herein by reference in their entirety.

INTRODUCTION

The present invention relates to tetrahydroisoquinoline compounds. More specifically, the present invention relates to tetrahydroisoquinoline compounds that are Nrf2 activators. The present invention also relates to processes for the preparation of these compounds, to pharmaceutical compositions comprising them, and to their use in the treatment of diseases or disorders associated with Nrf2 activation and/or inhibition of Keap1-Nrf2 protein-protein interactions.

BACKGROUND OF THE INVENTION

Nuclear factor erythroid 2-related factor 2 (Nrf2) is a basic leucine zipper (bZIP) transcription factor and a member of the Cap 'n' Collar (CNC) family of transcription factors. It is a key master of the inducible cell defence system, mediating the expression of more than 100 oxidative stress-related genes that include phase I and II detoxification enzymes and antioxidant proteins. These genes all contain the antioxidant response element (ARE) in their promoter regulatory regions, which is the binding target of Nrf2. Under basal conditions the levels of Nrf2 are tightly regulated by the adaptor protein Keap1, a cytosolic actin-bound repressor protein, which binds to Nrf2 and leads to proteasomal degradation via the Cul3-based E3 ubiquitin ligase complex. Under conditions of oxidative stress, Keap1 is inactivated leading to an increase in the level of de novo synthesised Nrf2 which translocates to the nucleus, binds to AREs with a resulting up-regulation in cytoprotective gene expression.

It has been shown that Nrf2 mRNA expression in COPD subjects was significantly lower than that in control subjects and Nrf2 mRNA were negatively correlated with pack year. Nrf2 protein in COPD subjects was significantly lower than that in control subjects. CSE-induced A549 cell apoptosis was increased in a time-dependent and concentration-dependent manner, and was significantly increased by Nrf2 knockdown (Yamada, *BMC Pulmonary Medicine*, doi: 10.1186/s12890-016-0189-1). Therefore, elevation of Nrf2 levels in the lungs of COPD patients should lead to a reduction in the inflammatory processes that lead to deleterious structural modifications of the lung and slow disease progression. Nrf2 may also be expected to show positive benefits in other respiratory diseases that exhibit oxidative stress components (Cho, *Toxicol Appl Pharmacol*, doi: 10.1016/j.taap.2009.07.024) such as acute, chronic and severe asthma (Sussan, *Am J Physiol Lung Cell Mol Physiol*, doi: 10.1152/ajplung.00398.2014), acute lung injury/acute respiratory distress syndrome, with or without accompanying multi organ dysfunction syndrome (Yan, *Free Radical Biol Med*, doi: 10.1016/j.freeradbiomed.2018.04.557; de la Vega *Curr Pharmacol Rep*, doi: 10.1007/s40495-016-0053-2), pulmonary fibrosis, including idiopathic pulmonary fibrosis (Kikuchi, *Respir Res*, doi: 10.1186/1465-9921-11-31) and cystic fibrosis (Chen, *PLoS One*, doi:10.1371/journal.pone.0003367).

The cardiac protective nature of Nrf2 in models of atherosclerosis, ischaemia, reperfusion, cardiac hypertrophy and heart failure has been demonstrated (Chen, *Physiol Genomics*, doi: 10.1152/physiolgenomics.00041.2017). The Nrf2 activator Bardoxolone methyl has recently completed a Phase II study in patients with pulmonary arterial hypertension (PAH), with a Phase III study underway based on a significant improvements in 6 minute walking distance. Bardoxolone reacts covalently with Keap1 but compounds activating Nrf2 via alternative mechanisms of Keap1 binding should also be expected to be therapeutically useful in PAH, particularly in patients that also have an underlying connective tissue disorder (CTD), such as scleroderma or lupus erythematosus. Oxidative stress is elevated in the diseased myocardium, leading to raised levels of reactive oxygen species which impact negatively on cardiac function (Bolli, *Circ*, doi: 10.1161/circ.76.2.3111744). Nrf2 activation has been shown to suppress myocardial oxidative stress, cardiac apoptosis, hypertrophy, fibrosis and dysfunction in mouse models of pressure overload (Wang, *J Card Failure*, doi: 10.1016/j.cardfail.2012.06.003) and to protect against cardiac ischemic/reperfusion injury in rodent models (Zhang, *J Mol Cell Cardiol*, doi: 10.1016/j.yjmcc.2010.05.01). Furthermore, excessive production of oxidizing agents in detriment of antioxidant defences in the cardiovascular system has also been described in metabolic diseases such as obesity, metabolic syndrome and diabetes mellitus where activation of Nrf2 has also been suggested as a promising therapeutic strategy (da Costa et al, *Front Pharmacol.* 2019 Apr. 12; 10:382). In addition, the Nrf2 activator sulforaphane reduces hepatic glucose production and improves glucose control in patients with type 2 diabetes (Axelsson et al, *Sci Trans! Med.* 2017 Jun. 14; 9(394). Thus, it is expected that drugs leading to activation of Nrf2 should be useful in a number of cardiovascular and metabolic diseases including, but not limited to, atherosclerosis, hypertension, heart failure, myocardial infarction and repair, cardiac remodelling, cardiac arrhythmias, heart failure with reduced ejection fraction, diabetic cardiomyopathy, diabetic nephropathy, metabolic syndrome, obesity, diabetes mellitus (type 1 or type 2) and insulin resistance.

Subarachnoid haemorrhage (SAH) is a devastating condition with high morbidity and mortality rates due to the lack of effective therapy. Early brain injury (EBI) and cerebral vasospasm (CVS) are the two most important pathophysiological mechanisms for brain injury and poor outcomes for patients with SAH (clinicaltrials.gov/ct2/show/NCT0261474, SFX01 After Subarachnoid Haemorrhage (SAS)). Evidence from experimental SAH research indicates a protective role of the Nrf2/ARE pathway in EBI and CVS after SAH. Administration of sulforaphane (SFN) to rats following SAH enhances the activity of the Nrf2-ARE pathway, attenuates vasospasm in basilar arteries and suppresses the release of proinflammatory cytokines (Zhao, *Brain Res.*, doi: 10.1016/j.brainres.2016.09.035). Intracerebral haemorrhage (ICH) is the primary event in 10-15% of the 15 million strokes occurring annually worldwide. In vitro studies demonstrated that Nrf2 activators rapidly increased HO-1 expression in astrocytes and reduced their vulnerability to haemoglobin or hemin. Systemic treatment with small molecule Nrf2 activators increased HO-1 expression in perivascular cells, particularly astrocytes. When tested in mouse or rat ICH models, Nrf2 activators were consistently protective, improving barrier function and attenuating edema, inflammation, neuronal loss and neurological deficits (Chen-Roetling, *Curr Pharm Des*, doi: 10.2174/1381612822666161027150616). Ischemic stroke induces reactive oxygen species, causing oxidative and inflammatory responses in ischemic brain. To date, recombinant tissue plasminogen activator is the only available therapy for the treatment of ischemic stroke. However, the treatment does not prevent oxidative stress and inflammation in the ischemic brain. D3T, a sulfur-containing dithiolethione compound, is found in cruciferous vegetables and has been reported to induce anti-oxidant genes through activation of Nrf2. D3T has been shown (Yen, *J Immunol* 2017, 198 (1 supplement) 206.20) to attenuate brain infarct and ameliorate neurological deficits in stroke animals. In addition, D3T reduced CNS infiltrating inflammatory immune cells including neutrophils and monocytes in the ischemic brain. Moreover, D3T-induced suppression of inflammatory cytokine production was observed in wild-type but not in Nrf2-deficient microglia. Furthermore, the protective effect of D3T on the attenuation of ischemic brain infarct was abolished in Nrf2-deficient stroke animals and in the stroke animals administered with HO-1 inhibitor. These results suggest that D3T-mediated suppression of inflammation in the ischemic brain is mediated through Nrf2/HO-1 pathway, and thus that targeting the Nrf2/HO-1 pathway may be a promising therapeutic strategy for the amelioration of neuroinflammation in ischemic stroke.

Nrf2 is believed to play a key role in some hemoglobinopathies, such as beta-thalassemia and sickle cell disease (SCD). SCD is a recessive inherited disorder caused by a single missense mutation which leads to the mutated beta-globin protein haemoglobin S (HbS). At low oxygen concentrations HbS polymerises, leading to misshapen red blood cells which are prone to rupture, releasing free heme into plasma. The resulting oxidative stress and inflammation leads to damage in multiple organs of the body. Ablation of Keap1 and the resulting constitutive activation of Nrf2 has been shown to lead to improved outcomes in SCD model mice (Zhu, *Blood*, doi:10.1182/blood-2017-10-810531; Keleku-Lukwete *PNAS*, doi:10.1073/pnas.1509158112). Nrf2 activation has been shown to slow down the progression of haemolytic anemia and organ disfunction (Ghosh, *JCI Insight*, doi: 10.1172/jci.insight.81090) and loss of Nrf2 function worsens the pathophysiology of SCD in transgenic SCD mice (Zhu, *Blood*, doi.org/10.1182/blood-2017-10-810531). Global activation of Nrf2 with the known compound D3T reduces lethality in a haem-induced acute chest syndrome model in transgenic SCD mice (Ghosh, *Brit. J. Heamtology* doi: 10.1111/bjh.15401). In addition, Nrf2 activators have also been shown to modulate foetal haemoglobin (HbF) expression through direct binding in the gamma-globin promoter and modification of chromatin structure in the beta-globin locus. In sickle erythroid cells, Nrf2 provides unique benefits through HbF induction to inhibit haemoglobin S polymerization and protection against oxidative stress due to chronic haemolysis (Zhu et al, *Exp Biol Med* (Maywood). 2019 February; 244(2):171-182). Thus, the development of small molecule activators of Nrf2 has the potential to ameliorate the clinical severity of sickle cell disease and other diseases where increasing HbF is beneficial such as beta-thalassemia.

The function of Nrf2 is altered in many neurodegenerative disorders, such as Huntington's disease, Parkinson's Disease, Alzheimer's disease, amyotrophic lateral sclerosis, frontotemporal dementia, multiple sclerosis and Friedreich's ataxia (Dinkova-Kostova, *FEBS*, doi:10.1111/febs.14379). Nrf2 activation mitigates multiple pathogenic processes involved in these neurodegenerative disorders through upregulation of antioxidant defences, inhibition of inflammation, improvement of mitochondrial function, and maintenance of protein homeostasis. Small molecule pharmacological activators of Nrf2 have shown protective effects in numerous animal models of neurodegenerative diseases (Joshi, *Neurobiol Aging*, doi:10.1016/j.neurobiolaging.2014.09.004; Alarcon-Aguilar, *Neurobiol Aging*, doi: 10.1016/j.neurobiolaging.2014.01.143 and in cultures of human cells expressing mutant proteins. Tecfidera (dimethyl fumarate) activates Nrf2 (in addition to other mechanisms) and is approved in the US to treat relapsing-remitting multiple sclerosis. The Nrf2 activator Omaveloxolone (RTA-408) currently in Phase II trials for the treatment of the inherited neurodegenerative disorder Friedrich's ataxia, has met its primary endpoint of change in the modified Friedrich's Ataxia Rating Scale (mFARS) relative to placebo after 48 weeks of treatment. Targeting Nrf2 signalling may therefore provide a therapeutic option to delay onset, slow progression, and ameliorate symptoms of neurodegenerative disorders.

Rheumatoid arthritis (RA) is an autoimmune disease that causes chronic inflammation of the joints and is characterized by periods of disease flares and remissions. Multiple joints can be affected sometimes resulting in permanent joint destruction and deformity. Nrf2 has been found to be activated in the joints of arthritic mice and of RA patients. Nrf2-knockout mice have more severe cartilage injuries and more oxidative damage, with the expression of Nrf2 target genes being enhanced in Nrf2-wild-type but not in knockout mice during antibody-induced arthritis (Wruck, *BMJ Annals of Rheumatic Diseases*, doi:10.1136/ard.2010.132720). Additionally, in an animal model of rheumatoid arthritis, using the transfer of serum from K/BxN transgenic mice to Nrf2(-/-) mice, Nrf2 deficiency accelerated the incidence of arthritis, and animals showed a widespread disease affecting both front and hind paws (Maicas, *Antioxidants & Redox Signaling*, doi:10.1089/ars.2010.3835).

Ulcerative colitis (UC) and Crohn's disease (CD) are chronic relapsing-remitting forms of inflammatory bowel disease (IBD) that are caused by dysfunction of the intestinal epithelium. Damage to the intestinal epithelial cells can disrupt the barrier function of the intestinal epithelium, facilitating an aberrant immune response and inflammatory conditions. Thus, the intact intestinal epithelium is critical for the healthy gut, and cytoprotective agents that could target the intestinal epithelial cells would be beneficial for the treatment of UC and CD. CPUY192018, a small-molecule inhibitor of the Keap1-Nrf2 protein-protein interaction (and hence Nrf2 activator) has demonstrated a cytoprotective effect in an experimental model of UC induced by dextran sodium sulphate in both NCM460 cells and mouse colon (Lu, *Scientific Reports*, doi:10.1038/srep26585). It has also been shown that Nrf2 knockout mice show an increased susceptibility to colitis-associated colorectal cancer (Khor, *Cancer Prev Res* (Phila), doi:10.1158/1940-6207).

Fumaderm, a mixture of dimethyl fumarate (DMF) and three salts of monoethyl fumarate, was licensed in Germany in 1994 for the treatment of psoriasis. The likely bioactive form of DMF, monomethyl fumarate (MMF) has been shown to increase total and nuclear Nrf2 levels in primary mouse keratinocytes and lead to enhanced mRNA expression of several Nrf2-downstream effectors such as heme oxygenase-1 and peroxiredoxin-6. (Helwa, *J Pharmacol. Exp. Ther.*, doi:10.1124/jpet.116.239715). Other skin disorders may benefit from treatment with Nrf2 activators such as radiation-induced dermatitis/skin damage, atopic dermatitis and wound healing (Wu et al, *Mol Med Rep.* 2019 August; 20(2):1761-1771).

Activation of Nrf2 has been shown to have beneficial effects in diseases of both the liver and kidney. NAFLD (Non-alcoholic fatty liver disease) is recognized as the leading cause of chronic liver disease worldwide. NAFLD represents a spectrum of diseases, some of which can progress to cirrhosis and hepatocellular carcinoma (HCC). Although all subtypes of NAFLD increase the risk for cardiovascular events and mortality, NASH (non-alcoholic steatohepatitis) is the main diagnostic subtype of NAFLD which predisposes patients to cirrhosis and liver-related complications. There are currently approved drug treatments for NAFLD and NASH. However, knockout of Nrf2 in mice profoundly predisposes to NASH stimulated by either a methionine- and choline-deficient (MCD) diet (Chowdry, *Free Radic Biol Med*, doi:10.1016/j.freeradbiomed.2009.11.007) or a high fat (HF) diet (Okada, *J Gastroenterol*, doi:10.1007/s00535-012-0659-z), and pharmacologic activation of Nrf2 has been shown to reverse NASH in mouse models (Sharma, *Cell Mol Gastroenterol Hepatol*, doi:10.1016/j.jcmgh.2017.11.016). Other liver diseases may benefit from treatment with Nrf2 activators such as toxin-induced liver disease, viral hepatitis and cirrhosis. Oxidative-stress molecules, such as reactive oxygen species, accumulate in the kidneys of animal models for acute kidney injury (AKI), in which Nrf2 is transiently and slightly activated. Genetic or pharmacological enhancement of Nrf2 activity in the renal tubules significantly ameliorates damage related to AKI and prevents AKI progression to chronic kidney disease (CKD) by reducing oxidative stress. However, a Phase III clinical trial of a KEAP1 inhibitor, CDDO-Me or bardoxolone-methyl, for patients with stage 4 CKD and type-2 diabetes mellitus (T2DM) was terminated due to the occurrence of cardiovascular events. Because recent basic studies have accumulated positive effects of KEAP1 inhibitors in moderate stages of CKD, Phase II trials have been restarted. The data from the ongoing projects demonstrate that a Nrf2 activator/KEAP1 inhibitor improves the glomerular filtration rate in patients with stage 3 CKD and T2DM without safety concerns (Nezu, *Am J Nephrol*, doi: 10.1159/000475890). Inflammatory reactions and oxidative stress are implicated in the pathogenesis of focal segmental glomerulosclerosis (FSGS), a common chronic kidney disease with relatively poor prognosis and unsatisfactory treatment regimens. CXA-10 which upregulates Nrf2 pathways is currently in clinical trials for Focal Segmental Glomerulosclerosis (FIRSTx—A Study of Oral CXA-10 in Primary Focal Segmental Glomerulosclerosis (FSGS); clinicaltrials.gov/ct2/show/NCT03422510). Bardoxolone methyl has been shown in a PhII trial to lead to significant improvement in kidney function in patients with either autosomal dominant polycystic kidney disease (ADPKD), CKD associated with type 1 diabetes (T1D), IgA nephropathy (IgAN) or FSGS after 12 weeks of treatment (https://www.reatapharma.com/press-releases/reata-announces-positive-phase-2-data-for-bardoxolone-methyl-in-patients-with-focal-segmental-glomerulosclerosis-and-in-patients-from-all-four-cohorts-of-phoenix/). Alport Syndrome is the second most common inherited cause of kidney failure caused by a genetic defect in type IV collagen, a component in building the glomerular basement membrane. As bardoxolone methyl is thought to affect the underlying pathologic processes associated with mitochondrial dysfunction, inflammation and oxidative stress, it is currently being studied in these patients suggesting Nrf2 activators will be potentially useful in this disease.

Oxidative stress plays a critical role in the initiation and progression of cancer (Gorrini, *Nat Rev Drug Discov.*, doi:10.1038/nrd4002). Due to its importance in the maintenance of redox cellular homeostasis, Nrf2 is considered a cytoprotective transcription factor and tumour suppressor. At lower homeostatic levels Nrf2 is able to eliminate ROS, carcinogens and other DNA-damaging agents, leading to the inhibition of tumour initiation and metastasis (Milkovic et al. *Redox Biol.* doi:10.1016/j.redox.2017.04.013). Evgen is currently evaluating SFX-01 (sulforaphane-cyclodextrin complex) in the Treatment and Evaluation of Metastatic Breast Cancer (STEM) (clinicaltrials.gov/ct2/show/NCT02970682) which includes ER+/HER− metastatic breast cancer. Bardoxolone derivatives have been shown to prevent lung cancer induced by vinyl carbamate in A/J mice (Liby, *Cancer Res.* doi:10.1158/0008-5472). Thus, activators of Nrf2 may have a role in the prevention of cancer.

Age related macular degeneration (AMD) is the principal cause of blindness in western countries and oxidative stress plays a major role in AMD pathogenesis and progression. It has been shown that Nrf2 activators are able to protect cells cultured to mimic the external layer of the retina from oxidative stress suggesting the potential for vision preservation in early AMD patients (Bellezza, *Front Pharmacol.* 2018; 9: 1280). In addition, Nrf2 activators may also be useful in other eye conditions such as Fuchs Endothelial Corneal Dystrophy and uveitis.

Therefore, there is an ongoing need for agents capable of Nrf2 activation, given the role of Nrf2 in multiple indications.

SUMMARY OF THE INVENTION

In one aspect, the present invention provides a compound, or a pharmaceutically acceptable salt thereof as defined herein.

In another aspect, the present invention provides a pharmaceutical composition comprising a compound of the invention as defined herein, or a pharmaceutically acceptable salt thereof, and one or more pharmaceutically acceptable excipients.

In another aspect, the present invention relates to a compound of the invention as defined herein, or a pharmaceutically acceptable salt thereof, or a pharmaceutical composition as defined herein, for use in therapy.

In another aspect, the present invention relates to a compound of the invention as defined herein, or a pharmaceutically acceptable salt thereof, or a pharmaceutical composition as defined herein, for use in the treatment of diseases or disorders mediated by Nrf2 activation.

In another aspect, the present invention relates to the use of a compound of the invention as defined herein, or a pharmaceutically acceptable salt thereof, in the manufacture of a medicament for use in the treatment of diseases or disorders mediated by Nrf2 activation.

In another aspect, the present invention relates to a method of treating a disease or disorder mediated by Nrf2 activation, said method comprising administering to a subject in need of such treatment a therapeutically effective amount of a compound of the invention as defined herein, or a pharmaceutically acceptable salt thereof, or a pharmaceutical composition as defined herein.

Examples of diseases or disorders mediated by Nrf2 activation include chronic obstructive pulmonary disease, asthma, pulmonary arterial hypertension, diabetes mellitus, chronic kidney disease, Friedreich's ataxia, sickle cell disease and non-alcoholic steatohepatitis.

In another aspect, the present invention provides a compound, or a pharmaceutically acceptable salt thereof, or a pharmaceutical composition as defined herein, for use in the treatment of chronic obstructive pulmonary disease, asthma, pulmonary arterial hypertension, diabetes mellitus, chronic kidney disease, Friedreich's ataxia, sickle cell disease or non-alcoholic steatohepatitis.

In another aspect, the present invention provides the use of a compound, or a pharmaceutically acceptable salt, in the manufacture of a medicament for use in the treatment of chronic obstructive pulmonary disease, asthma, pulmonary arterial hypertension, diabetes mellitus, chronic kidney disease, Friedreich's ataxia, sickle cell disease or non-alcoholic steatohepatitis.

In another aspect, the present invention provides a method of treating chronic obstructive pulmonary disease, asthma, pulmonary arterial hypertension, diabetes mellitus, chronic kidney disease, Friedreich's ataxia, sickle cell disease or non-alcoholic steatohepatitis, said method comprising administering to a subject in need of such treatment a therapeutically effective amount of a compound, or a pharmaceutically acceptable salt thereof, or a pharmaceutical composition as defined herein.

The present invention further provides a method of synthesising a compound, or a pharmaceutically acceptable salt thereof, as defined herein.

In another aspect, the present invention provides a compound, or a pharmaceutically acceptable salt thereof, obtainable by, or obtained by, or directly obtained by a method of synthesis as defined herein.

In another aspect, the present invention provides novel intermediates as defined herein which are suitable for use in any one of the synthetic methods set out herein.

Preferred, suitable, and optional features of any one particular aspect of the present invention are also preferred, suitable, and optional features of any other aspect.

DETAILED DESCRIPTION OF THE INVENTION

Definitions

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

In this specification the term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "(1-6C)alkyl" includes (1-4C)alkyl, (1-3C)alkyl, propyl, isopropyl and t-butyl. A similar convention applies to other radicals, for example "phenyl(1-6C)alkyl" includes phenyl(1-4C)alkyl, benzyl, 1-phenylethyl and 2-phenylethyl.

In this specification the term "alkylene" includes both straight and branched chain divalent alkyl groups. For example, "$C_{1-4}$alkylene" includes methylene ($—CH_2—$), ethylene ($—CH_2CH_2—$), propylene and butylene.

In this specification the term "alkoxy" includes both straight and branched chain alkyl groups singularly bonded to oxygen. For example, "$C_{1-4}$alkoxy" includes methoxy, ethoxy, isopropoxy and t-butoxy.

The term "(m-nC)" or "(m-nC) group" used alone or as a prefix, refers to any group having m to n carbon atoms.

"Cycloalkyl" means a hydrocarbon monocyclic or bicyclic ring containing carbon atoms. Examples of monocyclic cycloalkyl groups include cyclopropyl, cyclobutyl, cyclopentyl, cyclohexyl, cycloheptyl. Bicyclic rings may be fused or spiro attached; examples of bicyclic cycloalkyl groups include bicyclo[2.2.2]octane, bicyclo[2.1.1]hexane, bicyclo[1.1.1]pentane, spiro[2.4]heptane, bicyclo[4.1.0]heptane and bicyclo[2.2.1]heptane.

The term "halo" refers to fluoro, chloro, bromo and iodo.

The term "haloalkyl" is used herein to refer to an alkyl group respectively in which one or more hydrogen atoms have been replaced by halogen (e.g. fluorine) atoms. Examples of haloalkyl groups include fluoroalkyl groups such as $—CHF_2$, $—CH_2CF_3$, or perfluoroalkyl/alkoxy groups such as $—CF_3$, or $—CF_2CF_3$.

The term "heterocyclyl", "heterocyclic" or "heterocycle" means a non-aromatic saturated or partially saturated monocyclic, fused, bridged, or spiro bicyclic heterocyclic ring system(s). Monocyclic heterocyclic rings contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles containing nitrogen include, for example, azetidinyl, pyrrolidinyl, piperidinyl, piperazinyl, tetrahydrotriazinyl, tetrahydropyrazolyl, and the like. Typical sulfur containing heterocycles include tetrahydrothienyl, dihydro-1,3-dithiol, tetrahydro-2H-thiopyran, and hexahydrothiepine. Other heterocycles include dihydro-oxathiolyl, dihydroisoxazolyl (such as 4,5-dihydroisoxazolyl), dihydropyridinyl (such as 1,2-dihydropyridinyl or 1,6-dihydropyridinyl), tetrahydro-oxazolyl, tetrahydro-oxadiazolyl, tetrahydro-dioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (=O) or thioxo (=S) substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. Suitably, the term "heterocyclyl", "heterocyclic" or "heterocycle" will refer to 4, 5, 6 or 7 membered monocyclic rings as defined above.

The term "heteroaryl" or "heteroaromatic" means an aromatic mono-, bi-, or polycyclic ring incorporating one or more (for example 1-4, particularly 1, 2 or 3) heteroatoms selected from nitrogen, oxygen or sulfur. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically, the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general, the number of basic nitrogen atoms present in the heteroaryl group, including any amino group substituents of the ring, will be less than five. Suitably, the term "heteroaryl" or "heteroaromatic" will refer to 5 or 6 membered monocyclic heteroaryl rings as defined above.

Non-limiting examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-4-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzofuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl, 3,4-dihydro-2H-pyrido[3,2-b][1,4]oxazinyl, 4,5,6,7-tetrahydrobenzo[d]isoxazolyl, 4,5,6,7-tetrahydro-[1,2,3]triazolo[1,5-a]pyridinyl, 5,6-dihydro-8H-[1,2,4]triazolo[3,4-c][1,4]oxazinyl, 5,6-dihydro-4H-pyrrolo[1,2-c][1,2,3]triazolyl, 6,7-dihydro-5H-pyrrolo[2,1-c][1,2,4]triazolyl, 5,6,7,8-tetrahydro-[1,2,4]triazolo[4,3-a]pyridinyl, 6,7-dihydro-4H-[1,2,3]triazolo[5,1-c][1,4]oxazinyl and 1,4,5,6-tetrahydrocyclopenta[d][1,2,3]triazol-5-yl.

Non-limiting examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Non-limiting examples of six membered heteroaryl groups include but are not limited to pyridyl, pyrazinyl, pyridazinyl, pyrimidinyl and triazinyl.

Particular non-limiting examples of bicyclic heteroaryl groups containing a six membered ring fused to a five membered ring include but are not limited to benzofuranyl, benzothiophenyl, benzimidazolyl, benzoxazolyl, benzisoxazolyl, benzothiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl, pyrrolopyridine, and pyrazolopyridinyl groups.

Particular non-limiting examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

Particular non-limiting examples of bicyclic heteroaryl groups containing a five membered ring fused to a five membered ring include but are not limited to 6,7-dihydro-5H-pyrrolo[2,1-c][1,2,4]triazolyl, 5,6-dihydro-4H-pyrrolo[1,2-c][1,2,3]triazolyl and 1,4,5,6-tetrahydrocyclopenta[d][1,2,3]triazol-5-yl.

The term "aryl" means a cyclic or polycyclic aromatic ring having from 5 to 12 carbon atoms. The term aryl includes both monovalent species and divalent species. Examples of aryl groups include, but are not limited to, phenyl, biphenyl, naphthyl and the like. In this particular embodiment, an aryl is phenyl or naphthyl, especially phenyl.

The term "carboxylic acid mimetic group" refers to surrogate structures or isosteres of the carboxylic acid group, which typically maintain the features of the carboxylic acid group needed for biological activity, but modify the physicochemical properties of the resultant compound, such as acidity or lipophilicity. Such carboxylic acid mimetic groups are known to those skilled in the art of medicinal chemistry. Examples of carboxylic acid mimetic groups include, but are not limited to, tetrazole, 3-trifluoromethyl-1,2,4-triazole, hydroxamic acids, hydroxamic esters, phosphonic acids, phosphinic acids, sulfonic acids, sulfinic acids, sulphonamides, sulfonyl ureas, acyl ureas, thiazolidine dione, oxazolidine dione, oxadiazol-5(4H)-one, thiadiazol-5(4H)-one, oxathiadiazole-2-oxide, oxadiazol-5(4H)-thione, isoxazole, tetramic acid, cyclopentane-1,3-diones and cyclopentane-1,2-diones.

The term "optionally substituted" refers to either groups, structures, or molecules that are substituted and those that are not substituted.

Where optional substituents are chosen from "one or more" groups it is to be understood that this definition includes all substituents being chosen from one of the specified groups or the substituents being chosen from two or more of the specified groups.

The phrase "compound of the invention" means those compounds which are disclosed herein, both generically and specifically.

Compounds of the Invention

In a first aspect, the present invention provides a compound of Formula I

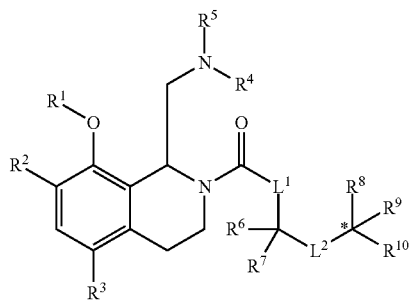

(I)

wherein:
- $R^1$ is selected from $C_{1-4}$alkylene-$R^{11}$, heterocyclyl and 8-10 membered bicyclic heteroaryl, wherein said heterocyclyl is optionally substituted with one or more substituents independently selected from $C_{1-4}$alkyl, —C(O)—$R^{12}$, $SO_2$—$R^{13}$, $C_{1-3}$alkylene-$OR^{14}$ and heteroaryl which is optionally substituted with one or more substituents independently selected from $C_{1-4}$alkyl, $C_{3-7}$cycloalkyl, halo, OH, $C_{1-3}$alkoxy and cyano; and wherein said 8-10 membered bicyclic heteroaryl is optionally substituted with one or more substituents independently selected from $C_{1-4}$alkyl, $C_{3-7}$cycloalkyl, halo, OH and $C_{1-3}$alkoxy;
- $R^2$ is selected from hydrogen, fluoro, chloro and $C_{1-3}$alkyl;
- $R^3$ is selected from hydrogen, fluoro, chloro, bromo, $C_{1-3}$alkoxy, $C_{1-3}$alkyl, $C_{1-3}$haloalkyl and cyano;
- $R^4$ is hydrogen or $C_{1-4}$alkyl;
- $R^5$ is —C(O)—$C_{1-4}$alkyl, —C(O)-heteroaryl or —C(O)-aryl, wherein said heteroaryl and aryl are optionally substituted with one or more substituents selected from $C_{1-4}$alkyl, halo, hydroxy, $C_{1-3}$alkoxy, $CO_2R^{15}$ and cyano; or
- $R^4$ and $R^5$, taken together with the nitrogen atom to which they are attached, form a 4-, 5-, or 6-membered heteroaryl or heterocyclyl ring, wherein:
  - said heterocyclyl ring comprises one or more —C(O)— moieties attached to the nitrogen atom and is optionally fused to an aryl or heteroaryl ring, or optionally spiro-attached to a $C_{3-7}$cycloalkyl group; and
  - said heteroaryl and heterocyclyl rings are optionally substituted with one or more substituents independently selected from $C_{1-4}$alkyl, halo, OH, $C_{1-3}$alkoxy, $C_{1-3}$haloalkyl, cyano, $NR^{16}R^{17}$, $C(O)R^{18}$, $S(O)R^{19}$ and $SO_2R^{26}$;
- $L^1$ and $L^2$ are independently selected from a bond and —$CR^{21}R^{22}$—;
- $R^6$ and $R^7$ are independently selected from hydrogen, $C_{1-4}$alkyl, and $C_{3-7}$cycloalkyl; or
- $R^6$ and $R^7$, taken together with the carbon atom to which they are attached, form a 3-, 4-, 5-, or 6-membered cycloalkyl ring;
- $R^8$ is selected from $CO_2R^{23}$, $C(O)NHSO_2C_{1-3}$alkyl, tetrazolyl, 3-trifluoromethyl-1,2,4-triazol-5-yl and a carboxylic acid mimetic group selected from hydroxamic acids, hydroxamic esters, phosphonic acids, phosphinic acids, sulfonic acids, sulfinic acids, sulphonamides, sulfonyl ureas, acyl ureas, thiazolidine dione, oxazolidine dione, oxadiazol-5(4H)-one, thiadiazol-5(4H)-one, oxathiadiazole-2-oxide, oxadiazol-5(4H)-thione, isoxazole, tetramic acid, cyclopentane-1,3-diones and cyclopentane-1,2-diones;
- $R^9$ is selected from hydrogen, $C_{1-4}$alkyl, hydroxy, $C_{1-3}$alkoxy and halo;
- $R^{10}$ is selected from hydrogen and $C_{1-4}$alkyl; or
- $R^9$ and $R^{10}$, taken together with the carbon atom to which they are attached, form a 3-, 4-, 5-, or 6-membered cycloalkyl ring; or
- $L^2$ is a bond and $R^7$ and $R^{10}$, taken together with the atoms to which they are attached, form a 4-, 5-, 6- or 7-membered cycloalkyl or heterocyclyl ring, wherein:
  - said heterocyclyl ring contains 1 or 2 heteroatoms independently selected from nitrogen, oxygen and sulfur;
  - said cycloalkyl ring optionally comprises 1 or 2 carbon-carbon double bonds and is optionally bridged by a $C_{1-3}$alkylene group connecting two carbon atoms of the ring, or $R^9$ is optionally a $C_{1-3}$alkylene group connecting C* to a carbon atom of the ring; and
  - said cycloalkyl and heterocyclyl rings are optionally substituted with one or more substituents independently selected from $C_{1-4}$alkyl, halo, OH, $C_{1-3}$alkoxy, $C_{1-3}$haloalkyl and deuterium;
- $R^{11}$ is selected from —C(O)—$R^{24}$, —$SO_2$—$R^{26}$, —$NR^{26}C(O)$—$R^{27}$, —$NR^{28}SO_2$—$R^{29}$, heterocyclyl, aryl and heteroaryl, wherein said aryl and heteroaryl groups are optionally substituted with one or more substituents independently selected from $C_{1-4}$alkyl, $C_{1-3}$haloalkyl, $C_{3-7}$cycloalkyl, $C_{1-4}$alkylene-$R^{39}$, halo, OH, $C_{1-3}$alkoxy, heterocyclyl and cyano; and said heterocyclyl group is optionally substituted with one or more substituents independently selected from $C_{1-4}$alkyl, $C_{1-3}$haloalkyl, $C_{3-7}$cycloalkyl, $C_{1-4}$alkylene-$R^{30}$, halo, OH, $C_{1-3}$alkoxy, oxo and cyano;
- $R^{12}$ is selected from $C_{1-4}$alkyl, $C_{3-7}$cycloalkyl, $OR^{31}$, $NR^{32}R^{33}$, aryl and heteroaryl, wherein said aryl and heteroaryl are optionally substituted with one or more substituents independently selected from $C_{1-4}$alkyl, halo, OH, $C_{1-3}$alkoxy and cyano;
- $R^{13}$ is selected from $C_{1-4}$alkyl, $C_{3-7}$cycloalkyl, heteroaryl, heterocyclyl and $NR^{34}R^{35}$, wherein said heteroaryl and heterocyclyl are optionally substituted with one or more substituents independently selected from $C_{1-4}$alkyl, halo, OH, $C_{1-3}$alkoxy and cyano;
- $R^{17}$ is selected from hydrogen, $C_{1-4}$alkyl, $C(O)C_{1-3}$alkyl and $C(O)NR^{36}R^{37}$;
- $R^{18}$, $R^{19}$ and $R^{20}$ are independently selected from $C_{1-4}$alkyl, OH, $C_{1-3}$alkoxy and $NR^{38}R^{39}$;
- $R^{24}$ is selected from $C_{1-4}$alkyl, $NR^{40}R^{41}$ and $OR^{42}$;
- $R^{25}$ is selected from $C_{1-4}$alkyl and $NR^{43}R^{44}$;
- $R^{27}$ is selected from $C_{1-4}$alkyl, $C_{3-7}$cycloalkyl, $C_{1-3}$haloalkyl, heterocyclyl, aryl and heteroaryl, wherein said aryl and heteroaryl are optionally substituted with one or more substituents independently selected from $C_{1-4}$alkyl, $C_{1-3}$haloalkyl, $C_{3-7}$cycloalkyl, $C_{1-4}$alkylene-$R^{45}$, halo, OH, $C_{1-3}$alkoxy and cyano;
- $R^{29}$ is selected from $C_{1-4}$alkyl, $C_{3-7}$cycloalkyl, $C_{1-3}$haloalkyl, aryl and heteroaryl, wherein said aryl and heteroaryl are optionally substituted with one or more substituents independently selected from $C_{1-4}$alkyl, $C_{1-3}$haloalkyl, $C_{3-7}$cycloalkyl, $C_{1-4}$alkylene-$R^{46}$ halo, OH, $C_{1-3}$alkoxy and cyano;

$R^{30}$ is selected from hydroxy, $C_{1-3}$alkoxy, $C_{3-7}$cycloalkyl, cyano and $NR^{47}R^{48}$;

$R^{40}$ is selected from hydrogen and $C_{1-4}$alkyl;

$R^{41}$ is selected from hydrogen, $C_{1-4}$alkyl, $C_{3-7}$cycloalkyl, $C_{1-3}$alkoxy, aryl and heteroaryl; or $R^{40}$ and $R^{41}$, taken together with the nitrogen atom to which they are attached, form a 4-, 5-, or 6-membered heteroaryl or heterocyclyl ring, wherein said heteroaryl and heterocyclyl rings are optionally substituted with one or more substituents independently selected from $C_{1-4}$alkyl, halo, OH, $C_{1-3}$alkoxy, $C_{3-7}$cycloalkyl and cyano;

$R^{45}$ and $R^{46}$ are independently selected from hydroxy, $C_{1-3}$alkoxy and $C_{3-7}$cycloalkyl; and $R^{14}, R^{15}, R^{16}, R^{21}, R^{22}, R^{23}, R^{26}, R^{28}, R^{31}, R^{32}, R^{33}, R^{34}, R^{35}, R^{36}, R^{37}, R^{38}, R^{39}, R^{42}, R^{43}, R^{44}, R^{47}$ and $R^{48}$ are independently selected from hydrogen, $C_{1-4}$alkyl and $C_{3-7}$cycloalkyl;

or a pharmaceutically acceptable salt thereof.

Particular compounds of the invention include, for example, compounds of the formula I, or pharmaceutically acceptable salts thereof, wherein, unless otherwise stated, each of $R^1, R^2, R^3, R^4, R^5, L^1, L^2, R^6, R^7, R^8, R^9, R^{10}, R^{11}, R^{12}, R^{13}, R^{17}, R^{18}, R^{19}, R^{20}, R^{24}, R^{25}, R^{27}, R^{29}, R^{30}, R^{40}$ and $R^{41}$ has any of the meanings defined hereinbefore or in any of paragraphs (1) to (86) hereinafter:

(1) $R^1$ is $C_{1-4}$alkylene-$R^{11}$;
(2) $R^1$ is $CH_2$—$R^{11}$;
(3) $R^1$ is $CH_2CH_2$—$R^{11}$;
(4) $R^1$ is $CH(Me)$-$R^{11}$;
(5) $R^1$ is heterocyclyl, optionally substituted with one or more substituents independently selected from $C_{1-4}$alkyl, —(CO)—$R^{12}$, $SO_2$—$R^{13}$, heteroaryl and $C_{1-3}$alkylene-$OR^{14}$, wherein said heteroaryl is optionally substituted with one or more substituents independently selected from $C_{1-4}$alkyl, $C_{3-7}$cycloalkyl, halo, OH, $C_{1-3}$alkoxy and cyano;
(6) $R^1$ is heterocyclyl, optionally substituted with one or more substituents independently selected from $C_{1-4}$alkyl, —(CO)—$R^{12}$, $SO_2$—$R^{13}$, heteroaryl and $C_{1-3}$alkylene-$OR^{14}$, wherein said heteroaryl is optionally substituted with one or more substituents independently selected from $C_{1-4}$alkyl and $C_{3-7}$cycloalkyl;
(7) $R^1$ is piperidinyl or pyrrolidinyl, each optionally substituted with one or more substituents independently selected from —(CO)—$R^{12}$, $SO_2$—$R^{13}$, heteroaryl and $C_{1-3}$alkylene-$OR^{14}$, wherein said heteroaryl is optionally substituted with one or more substituents independently selected from $C_{1-4}$alkyl, $C_{3-7}$cycloalkyl, halo, OH, $C_{1-3}$alkoxy and cyano;
(8) $R^1$ is pyrrolidinyl, optionally substituted with one or more substituents independently selected from —(CO)—$R^{12}$, $SO_2$—$R^{13}$, heteroaryl and $C_{1-3}$alkylene-$OR^{14}$, wherein said heteroaryl is optionally substituted with $C_{1-4}$alkyl or $C_{3-7}$cycloalkyl;
(9) $R^1$ is selected from one of the following groups:

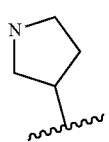 and 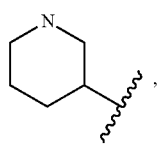

wherein ⌇ represents the point of attachment of the group to the oxygen atom of the rest of the compound and wherein each group is optionally substituted with one or more substituents independently selected from —(CO)—$R^{12}$, $SO_2$—$R^{13}$, heteroaryl and $C_{1-3}$alkylene-$OR^{14}$, wherein said heteroaryl is optionally substituted with $C_{1-4}$alkyl or $C_{3-7}$cycloalkyl;

(10) $R^1$ is an 8-10 membered bicyclic heteroaryl optionally substituted with one or more substituents independently selected from $C_{1-4}$alkyl, $C_{3-7}$cycloalkyl, halo, OH and $C_{1-3}$alkoxy;

(11) $R^1$ is an 8 membered bicyclic heteroaryl optionally substituted with one or more substituents independently selected from $C_{1-4}$alkyl, OH and $C_{1-3}$alkoxy;

(12) $R^1$ is 6,7-dihydro-5H-pyrrolo[2,1-c][1,2,4]triazolyl, 5,6-dihydro-4H-pyrrolo[1,2-c][1,2,3]triazolyl or 1,4,5,6-tetrahydrocyclo-penta[d][1,2,3]triazol-5-yl each optionally substituted with one or more substituents independently selected from $C_{1-4}$alkyl, $C_{3-7}$cycloalkyl, halo, OH and $C_{1-3}$alkoxy;

(13) $R^1$ is selected from one of the following groups:

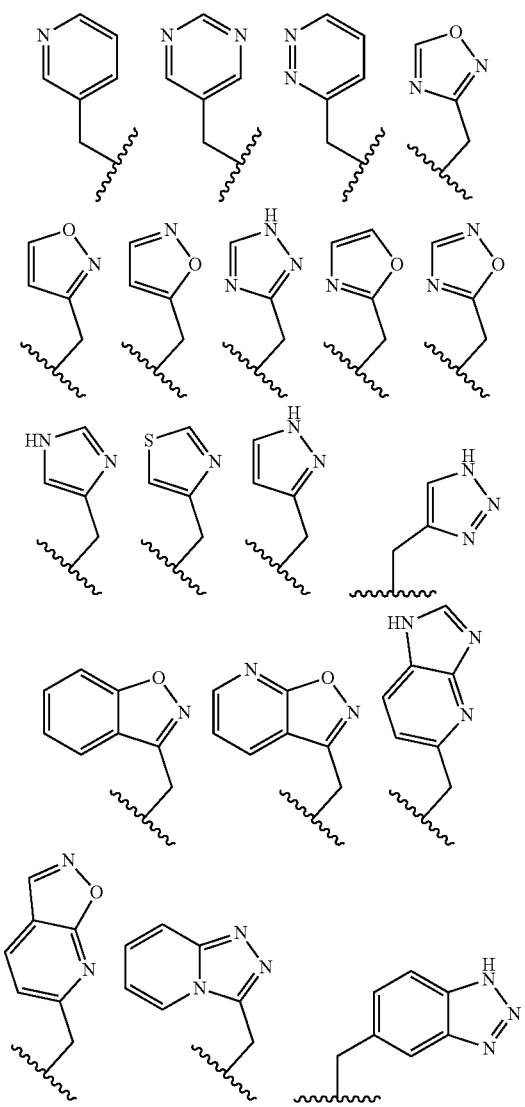

-continued

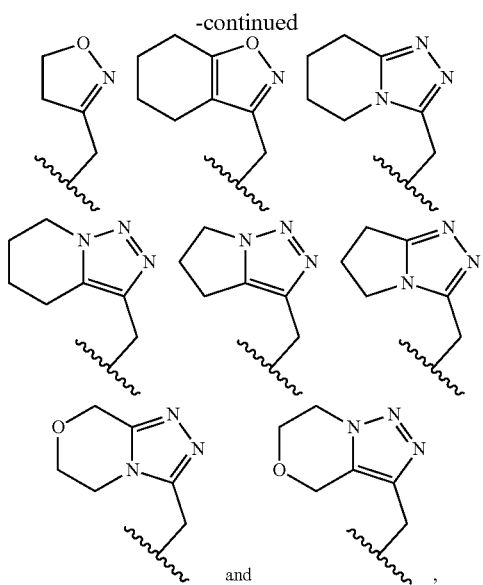

wherein ~~~ represents the point of attachment of the group to the oxygen atom of the rest of the compound and wherein each group is optionally substituted with one or more substituents independently selected from $C_{1-4}$alkyl, $C_{1-3}$haloalkyl, $C_{3-7}$cycloalkyl, $C_{1-4}$alkylene-$R^{30}$, halo, OH, $C_{1-3}$alkoxy, heterocycloalkyl and cyano;

(14) $R^1$ is selected from one of the following groups:

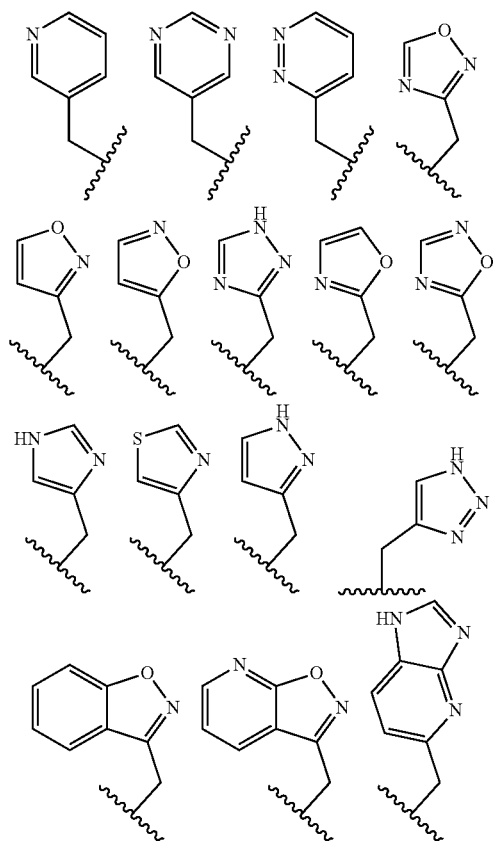

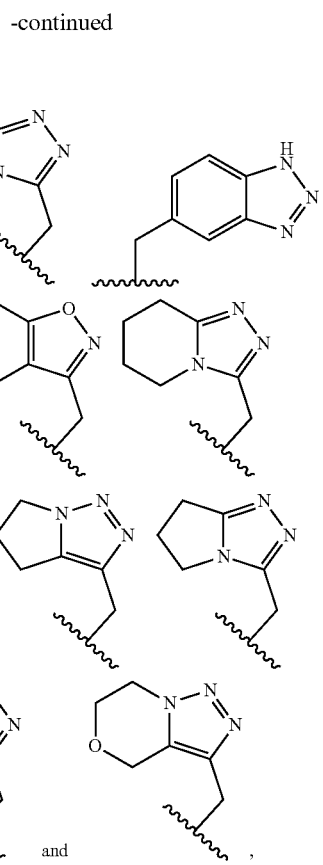

wherein ~~~ represents the point of attachment of the group to the oxygen atom of the rest of the compound and wherein each group is optionally substituted with one or more substituents independently selected from $C_{1-4}$alkyl, $C_{1-3}$haloalkyl, $C_{3-7}$cycloalkyl, $C_{1-4}$alkylene-$R^{30}$, $C_{1-3}$alkoxy and cyano;

(15) $R^1$ is selected from one of the following groups:

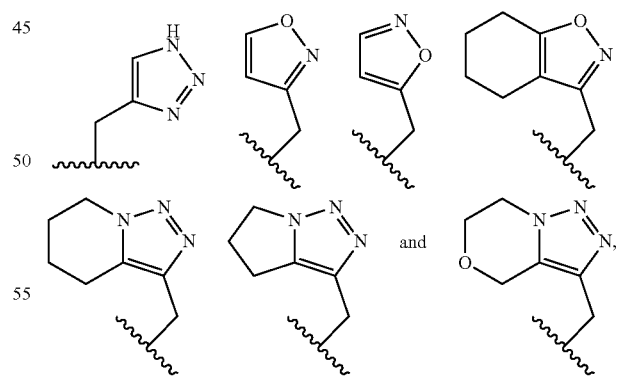

wherein ~~~ represents the point of attachment of the group to the oxygen atom of the rest of the compound and wherein each group is optionally substituted with one or more substituents independently selected from $C_{1-4}$alkyl, $C_{1-3}$haloalkyl, $C_{3-7}$cycloalkyl, $C_{1-4}$alkylene-$R^{30}$, halo, OH, $C_{1-3}$alkoxy, heterocycloalkyl and cyano;

17

(16) $R^1$ is selected from one of the following groups:

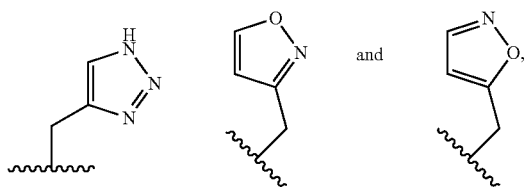 [SMILES: *Cc1c[nH]nn1 ; *Cc1ccon1 ; *Cc1ccno1]

wherein ~~~ represents the point of attachment of the group to the oxygen atom of the rest of the compound and wherein each group is optionally substituted with one or more substituents independently selected from $C_{1-4}$alkyl and $C_{1-3}$haloalkyl;

(17) $R^1$ is:

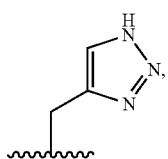 [SMILES: *Cc1c[nH]nn1]

wherein ~~~ represents the point of attachment of the group to the oxygen atom of the rest of the compound and wherein the group is optionally substituted with one or more substituents independently selected from $C_{1-4}$alkyl and $C_{1-3}$haloalkyl;

(18) $R^1$ is:

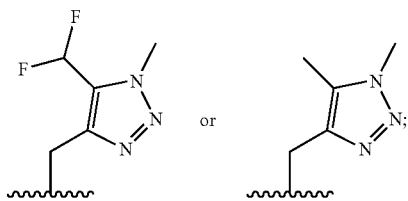

(19) $R^2$ is selected from hydrogen, fluoro and chloro;
(20) $R^2$ is hydrogen or fluoro;
(21) $R^3$ is selected from hydrogen, chloro, bromo, $C_{1-3}$alkoxy, $C_{1-3}$alkyl, $C_{1-3}$haloalkyl and cyano;
(22) $R^3$ is selected from hydrogen, chloro, bromo, methoxy, methyl, trifluoromethyl and cyano;
(23) $R^3$ is selected from hydrogen and chloro;
(24) $R^3$ is chloro;
(25) $R^4$ is hydrogen;
(26) $R^5$ is —C(O)—$C_{1-4}$alkyl or —C(O)-aryl, wherein said aryl group is optionally substituted with one or more substituents selected from $C_{1-4}$alkyl, halo, hydroxy, $C_{1-3}$alkoxy, $CO_2R^{15}$ and cyano;
(27) $R^4$ is hydrogen and $R^5$ is —C(O)—$C_{1-4}$alkyl or —C(O)-aryl, wherein said aryl group is optionally substituted with one or more substituents selected from $C_{1-4}$alkyl, halo, hydroxy, $C_{1-3}$alkoxy, $CO_2R^{15}$ and cyano;
(28) $R^4$ is hydrogen and $R^5$ is —C(O)—$C_{1-4}$alkyl or —C(O)-aryl, wherein said aryl group is optionally substituted with one or more substituents selected from halo, hydroxy and $CO_2R^{15}$;

18

(29) $R^4$ is hydrogen and $R^5$ is —C(O)-aryl, wherein said aryl group is phenyl optionally substituted with one or more substituents selected from fluoro, hydroxy and $CO_2R^{15}$;
(30) $R^4$ and $R^5$, taken together with the nitrogen atom to which they are attached, form a 4-, 5-, or 6-membered heteroaryl or heterocyclyl ring, wherein:
said heterocyclyl ring comprises one or more —C(O)— moieties attached to the nitrogen atom and is optionally fused to an aryl or heteroaryl ring, or optionally spiro-attached to a $C_{3-7}$cycloalkyl group; and
said heteroaryl and heterocyclyl rings are optionally substituted with one or more substituents independently selected from $C_{1-4}$alkyl, halo, OH, $C_{1-3}$alkoxy, $C_{1-3}$haloalkyl, cyano, $NR^{16}R^{17}$, $C(O)R^{18}$, $S(O)R^{19}$ and $SO_2R^{20}$;
(31) $R^4$ and $R^5$, taken together with the nitrogen atom to which they are attached, form a 5-membered heteroaryl or heterocyclyl ring, wherein:
said heterocyclyl ring comprises a —C(O)— moiety attached to the nitrogen atom and is optionally fused to an aryl or heteroaryl ring, or optionally spiro-attached to a $C_{3-7}$cycloalkyl group; and
said heteroaryl and heterocyclyl rings are optionally substituted with one or more substituents independently selected from $C_{1-4}$alkyl, halo, OH, $C_{1-3}$alkoxy and cyano;
(32) $R^4$ and $R^5$, taken together with the nitrogen atom to which they are attached, form a 5-membered heteroaryl ring, optionally substituted with one or more substituents independently selected from $C_{1-4}$alkyl, halo, OH, $C_{1-3}$alkoxy and cyano;
(33) $R^4$ and $R^5$, taken together with the nitrogen atom to which they are attached, form a 5-membered heteroaryl ring, optionally substituted with one or more substituents independently selected from $C_{1-4}$alkyl, halo and OH;
(34) $R^4$ and $R^5$, taken together with the nitrogen atom to which they are attached, form a pyrazolyl ring, optionally substituted with one or more substituents independently selected from $C_{1-4}$alkyl, halo and OH;
(35) $R^4$ and $R^5$, taken together with the nitrogen atom to which they are attached, form a 5- or 6-membered heterocyclyl ring, wherein said heterocyclyl ring comprises a —C(O)— moiety attached to the nitrogen atom and is optionally fused to an aryl or heteroaryl ring, or optionally spiro-attached to a $C_{3-7}$cycloalkyl group; and said heterocyclyl ring is optionally substituted with one or more substituents independently selected from $C_{1-4}$alkyl, halo and OH;
(36) $R^4$ and $R^5$, taken together with the nitrogen atom to which they are attached, form a 5-membered heterocyclyl ring, wherein said heterocyclyl ring comprises a —C(O)— moiety attached to the nitrogen atom and is optionally fused to a phenyl or heteroaryl ring, or optionally spiro-attached to a cyclopropyl group; and said heterocyclyl ring is optionally substituted with one or more substituents independently selected from methyl, fluoro and OH;
(37) $R^4$ and $R^5$, taken together with the nitrogen atom to which they are attached, form a heterocyclic moiety selected from one of the following:

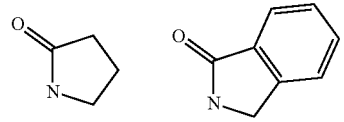

-continued

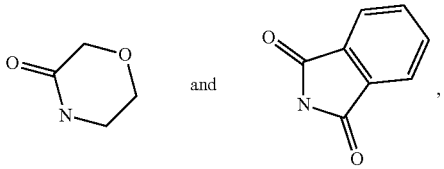
and wherein the saturated ring of the heterocyclic moiety is optionally spiro-attached to a $C_{3-7}$cycloalkyl group, and wherein said heterocyclic moiety is optionally substituted with one or more substituents independently selected from $C_{1-4}$alkyl, halo and OH;

(38) $R^4$ and $R^5$, taken together with the nitrogen atom to which they are attached, form a heterocyclic moiety selected from one of the following:

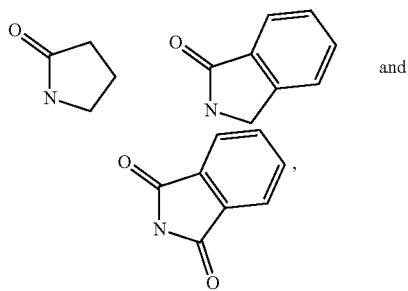
and wherein the saturated ring of the heterocyclic moiety is optionally spiro-attached to a cyclopropyl group, and wherein said heterocyclic moiety is optionally substituted with one or more substituents independently selected from methyl, fluoro and OH;

(39) $R^4$ and $R^5$, taken together with the nitrogen atom to which they are attached, form the following heterocyclic moiety:

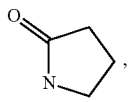

wherein the heterocyclic moiety is optionally spiro-attached to a cyclopropyl group and is optionally substituted with one or more substituents independently selected from methyl and fluoro;

(40) $R^4$ and $R^5$, taken together with the nitrogen atom to which they are attached, form the following heterocyclic moiety:

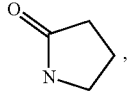

wherein the heterocyclic moiety is optionally spiro-attached to a cyclopropyl group, and is optionally substituted with $C_{1-3}$alkyl, wherein said cyclopropyl and/or $C_{1-3}$alkyl group is attached to the heterocyclic ring at a position either alpha or beta to the carbonyl group;

(41) $L^1$ and $L^2$ are independently selected from a bond and —$CH_2$—;
(42) $L^1$ is a bond and $L^2$ is —$CH_2$—;
(43) $L^1$ is $CH_2$— and $L^2$ is a bond;
(44) $L^1$ and $L^2$ are both bonds;
(45) $R^6$ and $R^7$ are independently selected from hydrogen and $C_{1-4}$alkyl;
(46) $R^6$ and $R^7$ are independently selected from hydrogen and methyl;
(47) $R^6$ and $R^7$, taken together with the carbon atom to which they are attached, form a 3-, 4-, 5-, or 6-membered cycloalkyl ring;
(48) $R^8$ is selected from $CO_2R^{23}$, $C(O)NHSO_2C_{1-3}$alkyl, tetrazolyl and 3-trifluoromethyl-1,2,4-triazol-5-yl;
(49) $R^8$ is selected from $CO_2R^{23}$, $C(O)NHSO_2C_{1-3}$alkyl and tetrazolyl;
(50) $R^8$ is selected from $CO_2H$, $C(O)NHSO_2Me$ and tetrazolyl;
(51) $R^8$ is $CO_2H$;
(52) $R^9$ is selected from hydrogen, $C_{1-4}$alkyl, $C_{1-3}$alkoxy and halo;
(53) $R^9$ is selected from hydrogen, methyl, methoxy and fluoro;
(54) $R^9$ is selected from $C_{1-4}$alkyl, $C_{1-3}$alkoxy and halo;
(55) $R^9$ is selected from methyl, methoxy and fluoro;
(56) $R^9$ is hydrogen or $C_{1-4}$alkyl;
(57) $R^9$ is hydrogen or methyl;
(58) $R^9$ is methyl;
(59) $R^{10}$ is selected from hydrogen and methyl;
(60) $R^9$ and $R^{10}$, taken together with the carbon atom to which they are attached, form a 3-, 4-, 5-, or 6-membered cycloalkyl ring;
(61) $L^2$ is a bond and $R^7$ and $R^{10}$, taken together with the atoms to which they are attached, form a 4-, 5- or 6-membered cycloalkyl or heterocyclyl ring, wherein:
said heterocyclyl ring contains 1 or 2 heteroatoms independently selected from nitrogen, oxygen and sulfur;
said cycloalkyl ring optionally comprises 1 or 2 carbon-carbon double bonds and is optionally bridged by a $C_{1-3}$alkylene group connecting two carbon atoms of the ring, or $R^9$ is optionally a $C_{1-3}$alkylene group connecting C* to a carbon atom of the ring; and
said cycloalkyl and heterocyclyl rings are optionally substituted with one or more substituents independently selected from $C_{1-4}$alkyl, halo, OH, $C_{1-3}$alkoxy and deuterium;
(62) $L^1$ and $L^2$ are both bonds and $R^7$ and $R^{10}$, taken together with the atoms to which they are attached, form a 4-, 5- or 6-membered cycloalkyl or heterocyclyl ring, wherein: said heterocyclyl ring contains 1 or 2 heteroatoms independently selected from nitrogen, oxygen and sulfur;
said cycloalkyl ring optionally comprises a carbon-carbon double bond and is optionally bridged by a $C_{1-3}$alkylene group connecting two carbon atoms of the ring, or $R^9$ is optionally a $C_{1-3}$alkylene group connecting C* to a carbon atom of the ring; and
said cycloalkyl and heterocyclyl rings are optionally substituted with one or more substituents independently selected from $C_{1-4}$alkyl, halo, OH, $C_{1-3}$alkoxy and deuterium;
(63) $L^2$ is a bond and $R^7$ and $R^{10}$, taken together with the atoms to which they are attached, form a 4-, 5- or 6-membered cycloalkyl ring, wherein said cycloalkyl ring is optionally bridged by a $C_{1-3}$alkylene group connecting two carbon atoms of the ring, or $R^9$ is optionally a $C_{1-3}$alkylene group connecting C* to a carbon atom of the ring, and said cycloalkyl ring is optionally substituted with one or more substituents independently selected from $C_{1-4}$alkyl, halo, OH, $C_{1-3}$alkoxy and deuterium;

(64) $L^2$ is a bond and $R^7$ and $R^{10}$, taken together with the atoms to which they are attached, form a cyclohexyl ring, wherein said cyclohexyl ring optionally comprises a carbon-carbon double bond and is optionally bridged by a $C_{1-3}$alkylene group connecting two carbon atoms of the ring, or $R^9$ is optionally a $C_{1-3}$alkylene group connecting C* to a carbon atom of the ring, and said cyclohexyl ring is optionally substituted with one or more substituents independently selected from $C_{1-4}$alkyl, halo, OH and deuterium;

(65) $R^{11}$ is selected from —C(O)—$R^{24}$, —$NR^{26}$C(O)—$R^{27}$ and heteroaryl wherein said heteroaryl is optionally substituted with one or more substituents independently selected from $C_{1-4}$alkyl, $C_{1-3}$haloalkyl, $C_{3-7}$cycloalkyl, $C_{1-4}$alkylene-$R^{30}$, halo, OH, $C_{1-3}$alkoxy, heterocyclyl and cyano;

(66) $R^{11}$ is —C(O)—$R^{24}$ and $R^{24}$ is selected from $NR^{40}R^{41}$ and $OR^{42}$;

(67) $R^{11}$ is —$NR^{26}$C(O)—$R^{27}$ and $R^{27}$ is selected from $C_{1-4}$alkyl, $C_{3-7}$cycloalkyl, heterocyclyl, aryl and heteroaryl, wherein said aryl and heteroaryl are optionally substituted with one or more substituents independently selected from $C_{1-4}$alkyl and $C_{3-7}$cycloalkyl;

(68) $R^{11}$ is heteroaryl optionally substituted with one or more substituents independently selected from $C_{1-4}$alkyl, $C_{1-3}$haloalkyl, $C_{3-7}$cycloalkyl, $C_{1-4}$alkylene-$R^{30}$, halo, OH, $C_{1-3}$alkoxy, heterocyclyl and cyano;

(69) $R^{11}$ is heteroaryl optionally substituted with one or more substituents independently selected from $C_{1-4}$alkyl, $C_{1-3}$haloalkyl, $C_{3-7}$cycloalkyl, $C_{1-4}$alkylene-$R^{30}$, $C_{1-3}$alkoxy, and cyano;

(70) $R^{11}$ is heteroaryl optionally substituted with one or more substituents independently selected from methyl, ethyl, isopropyl, difluoromethyl, trifluoromethyl, chloro, fluoro, cyclopropyl, methoxy, cyano, oxetanyl, $CH_2$—$R^{30}$ and $CH_2CH_2$—$R^{30}$;

(71) $R^{11}$ is pyridyl, pyrimidinyl, pyridazinyl, oxazolyl, isoxazolyl, 1,2,3-triazolyl, 1,2,4-oxadiazolyl, benzotriazolyl, benzisoxazolyl, isoxazolopyridinyl, imidazopyridinyl or triazolopyridinyl, each optionally substituted with one or more substituents independently selected from $C_{1-4}$alkyl, $C_{1-3}$haloalkyl, $C_{3-7}$cycloalkyl, $C_{1-4}$alkylene-$R^{30}$, halo, OH, $C_{1-3}$alkoxy, heterocyclyl and cyano;

(72) $R^{11}$ is heteroaryl selected from:

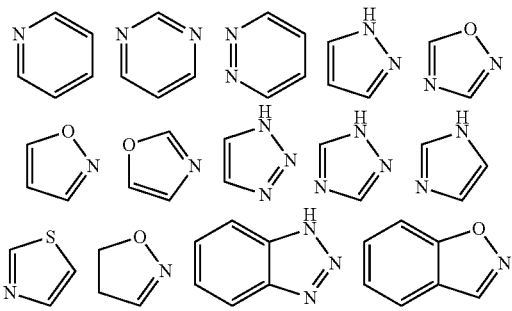

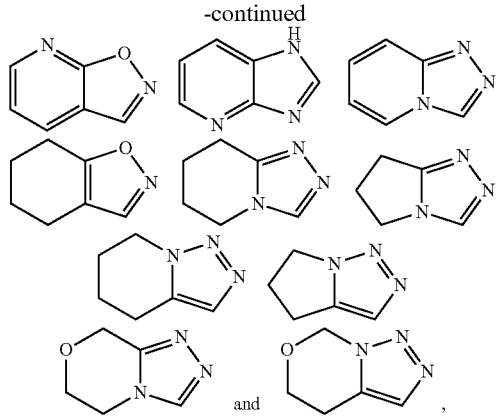

and each heteroaryl being optionally substituted with one or more substituents independently selected from $C_{1-4}$alkyl, $C_{1-3}$haloalkyl, $C_{3-7}$cycloalkyl, $C_{1-4}$alkylene-$R^{30}$, halo, OH, $C_{1-3}$alkoxy, heterocycloalkyl and cyano;

(73) $R^{11}$ is oxazolyl, isoxazolyl or 1,2,3-triazolyl, each optionally substituted with one or more substituents independently selected from $C_{1-4}$alkyl, $C_{1-3}$haloalkyl, $C_{3-7}$cycloalkyl, $C_{1-4}$alkylene-$R^{30}$, halo, OH, $C_{1-3}$alkoxy, heterocycloalkyl and cyano;

(74) $R^{11}$ is 1,2,3-triazolyl optionally substituted with one or more substituents independently selected from $C_{1-4}$alkyl, $C_{1-3}$haloalkyl, $C_{3-7}$cycloalkyl, $C_{1-4}$alkylene-$R^{30}$, halo, OH, $C_{1-3}$alkoxy, heterocycloalkyl and cyano;

(75) $R^{11}$ is heterocyclyl optionally substituted with one or more substituents independently selected from $C_{1-4}$alkyl, $C_{1-3}$haloalkyl, $C_{3-7}$cycloalkyl, $C_{1-4}$alkylene-$R^{30}$, halo, OH, $C_{1-3}$alkoxy, oxo and cyano;

(76) $R^{11}$ is heterocyclyl optionally substituted with one or more substituents independently selected from $C_{1-4}$alkyl, $C_{1-3}$haloalkyl, halo, OH and oxo;

(77) $R^{11}$ is dihydroisoxazolyl or dihydropyridinyl optionally substituted with one or more substituents independently selected from $C_{1-4}$alkyl, $C_{1-3}$haloalkyl, halo, OH and oxo;

(78) $R^{29}$ is selected from $C_{1-4}$alkyl, $C_{3-7}$cycloalkyl, $C_{1-3}$haloalkyl and heteroaryl, wherein said heteroaryl is optionally substituted with one or more substituents independently selected from $C_{1-4}$alkyl and $C_{1-3}$haloalkyl;

(79) $R^{29}$ is methyl, ethyl or cyclopropyl;

(80) $R^{30}$ is selected from hydroxy, $C_{1-3}$alkoxy, $C_{3-7}$cycloalkyl and cyano;

(81) $R^{30}$ is selected from hydroxy, methoxy, cyclopropyl and cyano;

(82) $R^{40}$ is selected from hydrogen and methyl;

(83) $R^{41}$ is selected from hydrogen, methyl, cyclopropyl, methoxy and phenyl;

(84) $R^{40}$ and $R^{41}$, taken together with the nitrogen atom to which they are attached, form 5-membered heteroaryl or heterocyclyl ring, wherein said heteroaryl and heterocyclyl rings are optionally substituted with one or more substituents independently selected from $C_{1-4}$alkyl, halo, OH, $C_{1-3}$alkoxy, $C_{3-7}$cycloalkyl and cyano;

(85) $R^{40}$ and $R^{41}$, taken together with the nitrogen atom to which they are attached, form 5-membered heterocyclyl ring, wherein said heterocyclyl ring is optionally substituted with one or more substituents independently selected from $C_{1-4}$alkyl, halo and OH;

(86) $R^{40}$ and $R^{41}$, taken together with the nitrogen atom to which they are attached, form 5-membered heterocyclyl ring, wherein said heterocyclyl ring is optionally substituted with one or more substituents independently selected from methyl, fluoro and OH.

Suitably, $R^1$ is as defined in any one of paragraphs (1) to (18) above. In an embodiment, $R^1$ is as defined in paragraph (2) above. In another embodiment, $R^1$ is as defined in paragraphs (7) to (9) above. In another embodiment, $R^1$ is as defined in any one of paragraphs (13) to (18) above. In a further embodiment, $R^1$ is as defined in paragraphs (16) to (18) above.

Suitably, $R^2$ is as defined in any one of paragraphs (19) to (20) above. In an embodiment, $R^2$ is as defined in paragraph (20) above.

Suitably, $R^3$ is as defined in any one of paragraphs (21) to (24) above. In another embodiment, $R^3$ is as defined in paragraphs (23) to (24) above.

Suitably, $R^4$ is as defined in paragraph (25) above.

Suitably, $R^5$ is as defined in paragraph (26) above.

Suitably, $R^4$ and $R^5$ are as defined in any one of paragraphs (27) to (29) above. In another embodiment, $R^4$ and $R^5$ are as defined in paragraph (29) above. In an embodiment, $R^4$ and $R^5$ are as defined in paragraphs (30) to (40) above. In another embodiment, $R^4$ and $R^5$ are as defined in paragraphs (37) to (40) above. In another embodiment, $R^4$ and $R^5$ are as defined in paragraph (34) above. In a further embodiment, $R^4$ and $R^5$ are as defined in paragraph (40) above.

Suitably, $L^1$ and $L^2$ are as defined in any one of paragraphs (41) to (44) above. In another embodiment, $L^1$ and $L^2$ are as defined in paragraph (44) above.

Suitably, $R^6$ and $R^7$ are as defined in any one of paragraphs (45) to (47) above. In another embodiment, $R^6$ and $R^7$ are as defined in paragraph (46) above.

Suitably, $R^8$ is as defined in any one of paragraphs (48) to (51) above. In another embodiment, $R^8$ is as defined in paragraphs (50) to (51) above. In an embodiment, $R^8$ is as defined in paragraph (51) above.

Suitably, $R^9$ is as defined in any one of paragraphs (52) to (58) above. In another embodiment, $R^9$ is as defined in paragraphs (57) to (58) above. In an embodiment, $R^9$ is as defined in paragraph (58) above.

Suitably, $R^{10}$ is as defined in paragraph (59) above.

Suitably, $R^9$ and $R^{19}$ are as defined in paragraph (60) above.

Suitably, $L^2$, $R^7$ and $R^{10}$ are as defined in any one of paragraphs (61) to (64) above. In another embodiment, $L^2$, $R^7$ and $R^{10}$ are as defined in paragraph (64) above.

Suitably, $R^{11}$ is as defined in any one of paragraphs (65) to (77) above. In another embodiment, $R^{11}$ is as defined in paragraphs (72) to (74) above. In another embodiment, $R^{11}$ is as defined in paragraphs (73) to (74) above. In a further embodiment, $R^1$ is as defined in paragraph (2) above and $R^{11}$ is as defined in paragraphs (72) to (74) above.

Suitably, $R^{29}$ is as defined in paragraphs (78) to (79) above. In an embodiment, $R^{29}$ is as defined in paragraph (79) above.

Suitably, $R^{30}$ is as defined in paragraphs (80) to (81) above. In an embodiment, $R^{30}$ is as defined in paragraph (81) above.

Suitably, $R^{40}$ is as defined in paragraph (82) above.

Suitably, $R^{41}$ is as defined in paragraph (83) above.

Suitably, $R^{40}$ and $R^{41}$ are as defined in any one of paragraphs (84) to (86) above. In another embodiment, $R^{40}$ and $R^{41}$ are as defined in paragraph (86) above.

In a further group of compounds, the compounds have the structural formula IA shown below:

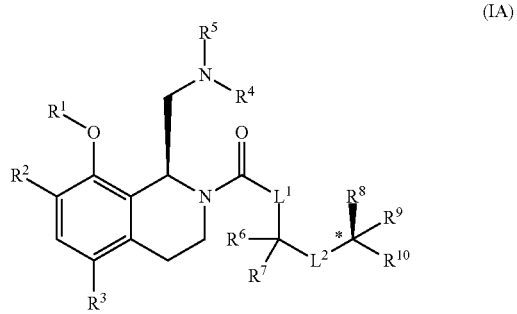

(IA)

wherein $L^1$ and $L^2$ and $R^1$ to $R^{10}$ are as defined hereinbefore.

In a further group of compounds, the compounds have the structural formula IA shown above, wherein $R^1$ is as defined in any one of paragraphs (7) to (18) above; $R^2$ is as defined in paragraph (20) above; $R^3$ is as defined in any one of paragraphs (23) to (24) above; $R^4$ and $R^5$ are as defined in any one of paragraphs (37) to (40) above; $L^1$ and $L^2$ are as defined in any one of paragraphs (41) to (44) above; $R^6$ and $R^7$ are as defined in any one of paragraphs (45) to (47) above; $R^8$ is as defined in any one of paragraphs (48) to (51) above; $R^9$ is as defined in any one of paragraphs (52) to (58) above; and $R^{10}$ is as defined in paragraph (59) above.

In a further group of compounds, the compounds have the structural formula IB shown below:

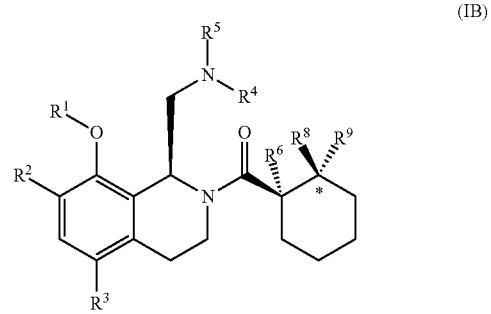

(IB)

wherein $R^1$ to $R^6$, $R^8$ and $R^9$ are as defined hereinbefore.

In a further group of compounds, the compounds have the structural formula IB shown above, wherein $R^1$ is as defined in any one of paragraphs (7) to (18) above; $R^2$ is as defined in paragraph (20) above; $R^3$ is as defined in any one of paragraphs (23) to (24) above; $R^4$ and $R^5$ are as defined in any one of paragraphs (37) to (40) above; $R^6$ is hydrogen or methyl; $R^8$ is as defined in any one of paragraphs (48) to (51) above; and $R^9$ is as defined in any one of paragraphs (52) to (58) above.

In a further group of compounds, the compounds have the structural formula IB shown above, wherein $R^1$ is as defined in any one of paragraphs (13) to (18) above; $R^2$ is as defined in paragraph (20) above; $R^3$ is as defined in any one of paragraphs (23) to (24) above; $R^4$ and $R^5$ are as defined in any one of paragraphs (37) to (40) above; $R^6$ is hydrogen or methyl; $R^8$ is as defined in any one of paragraphs (50) to (51) above; and $R^9$ is as defined in any one of paragraphs (57) to (58) above.

In a further group of compounds, the compounds have the structural formula IC shown below:

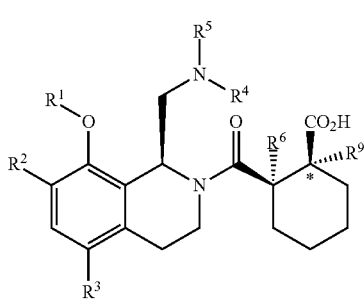

(IC)

wherein $R^1$ to $R^6$ and $R^9$ are as defined hereinbefore.

In a further group of compounds, the compounds have the structural formula IC shown above, wherein $R^1$ is as defined in any one of paragraphs (7) to (18) above; $R^2$ is as defined in paragraph (20) above; $R^3$ is as defined in any one of paragraphs (23) to (24) above; $R^4$ and $R^5$ are as defined in any one of paragraphs (37) to (40) above; $R^6$ is hydrogen or methyl; and $R^9$ is as defined in any one of paragraphs (57) to (58) above.

In a further group of compounds, the compounds have the structural formula ID shown below:

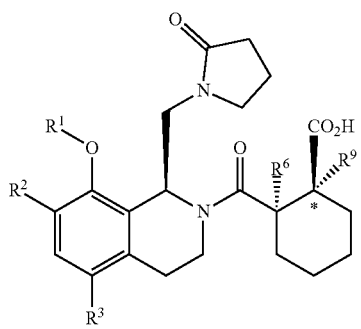

(ID)

wherein $R^1$ to $R^3$, $R^6$ and $R^9$ are as defined hereinbefore.

In a further group of compounds, the compounds have the structural formula ID shown above, wherein $R^1$ is as defined in any one of paragraphs (7) to (18) above; $R^2$ is as defined in paragraph (20) above; $R^3$ is as defined in any one of paragraphs (23) to (24) above; $R^6$ is hydrogen or methyl; and $R^9$ is as defined in any one of paragraphs (57) to (58) above.

In a further group of compounds, the compounds have the structural formula ID shown above, wherein $R^1$ is as defined in any one of paragraphs (9) and (13) to (18) above; $R^2$ is as defined in paragraph (20) above; $R^3$ is as defined in any one of paragraphs (23) to (24) above; $R^6$ is hydrogen; and $R^9$ is as defined in paragraph (58) above.

In a further group of compounds, the compounds have the structural formula IE shown below:

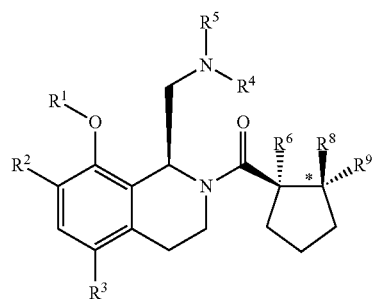

(IE)

wherein $R^1$ to $R^6$, $R^8$ and $R^9$ are as defined hereinbefore.

In a further group of compounds, the compounds have the structural formula IE shown above, wherein $R^1$ is as defined in any one of paragraphs (7) to (18) above; $R^2$ is as defined in paragraph (20) above; $R^3$ is as defined in any one of paragraphs (21) to (24) above; $R^4$ and $R^5$ are as defined in any one of paragraphs (37) to (40) above; $R^6$ is hydrogen or methyl; $R^8$ is as defined in any one of paragraphs (48) to (51) above; and $R^9$ is as defined in any one of paragraphs (52) to (58) above.

In a further group of compounds, the compounds have the structural formula IE shown above, wherein $R^1$ is as defined in any one of paragraphs (13) to (18) above; $R^2$ is as defined in paragraph (20) above; $R^3$ is as defined in any one of paragraphs (23) to (24) above; $R^4$ and $R^5$ are as defined in any one of paragraphs (37) to (40) above; $R^6$ is hydrogen or methyl; $R^8$ is as defined in any one of paragraphs (50) to (51) above; and $R^9$ is as defined in any one of paragraphs (57) to (58) above.

In a further group of compounds, the compounds have the structural formula IF shown below:

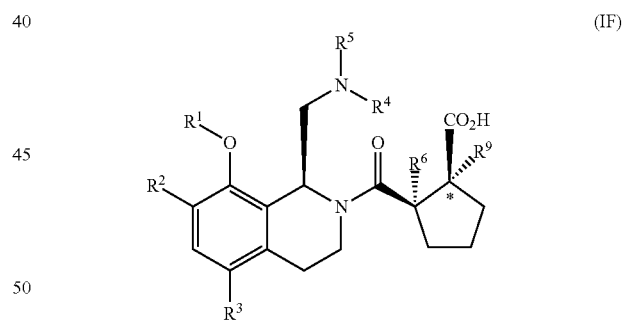

(IF)

wherein $R^1$ to $R^6$ and $R^9$ are as defined hereinbefore.

In a further group of compounds, the compounds have the structural formula IF shown above, wherein $R^1$ is as defined in any one of paragraphs (7) to (18) above; $R^2$ is as defined in paragraph (20) above; $R^3$ is as defined in any one of paragraphs (23) to (24) above; $R^4$ and $R^5$ are as defined in any one of paragraphs (37) to (40) above; $R^6$ is hydrogen or methyl; and $R^9$ is as defined in any one of paragraphs (57) to (58) above.

In a further group of compounds, the compounds have the structural formula IG shown below:

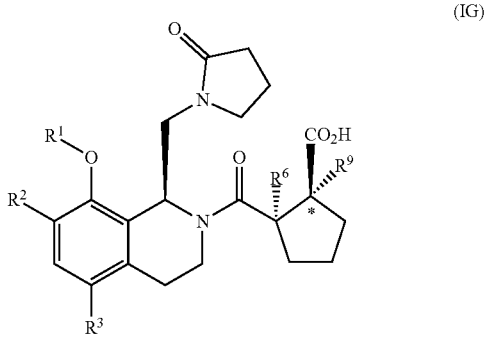

(IG)

wherein $R^1$ to $R^3$, $R^6$ and $R^9$ are as defined hereinbefore.

In a further group of compounds, the compounds have the structural formula IG shown above, wherein $R^1$ is as defined in any one of paragraphs (7) to (18) above; $R^2$ is as defined in paragraph (20) above; $R^3$ is as defined in any one of paragraphs (21) to (24) above; $R^6$ is hydrogen or methyl; and $R^9$ is as defined in any one of paragraphs (57) to (58) above.

In a further group of compounds, the compounds have the structural formula IG shown above, wherein $R^1$ is as defined in any one of paragraphs (9) and (13) to (18) above; $R^2$ is as defined in paragraph (20) above; $R^3$ is as defined in any one of paragraphs (23) to (24) above; $R^6$ is hydrogen; and $R^9$ is as defined in paragraph (58) above.

Particular compounds of the present invention include any one of the following:

(1S,2R)-2-((S)-1-((1,3-dioxoisoindolin-2-yl)methyl)-8-(2-(5-methylisoxazole-3-carboxamido)ethoxy)-1,2,3,4-tetrahydroisoquinoline-2-carbonyl)cyclohexane-1-carboxylic acid;

(1S,2R)-2-((S)-8-(2-(Benzo[d]oxazole-2-carboxamido)ethoxy)-1-((1,3-dioxoisoindolin-2-yl)methyl)-1,2,3,4-tetrahydroisoquinoline-2-carbonyl)cyclohexane-1-carboxylic acid;

(1S,2R)-2-((S)-8-(((S)-1-Acetylpyrrolidin-3-yl)oxy)-1-((1,3-dioxoisoindolin-2-yl)methyl)-1,2,3,4-tetrahydroisoquinoline-2-carbonyl)cyclohexane-1-carboxylic acid;

(1S,2R)-2-((S)-1-((1,3-dioxoisoindolin-2-yl)methyl)-8-(((S)-1-(5-methylisoxazole-3-carbonyl)pyrrolidin-3-yl)oxy)-1,2,3,4-tetrahydroisoquinoline-2-carbonyl)cyclohexane-1-carboxylic acid;

(1S,2R)-2-((S)-5-bromo-1-((1,3-dioxoisoindolin-2-yl)methyl)-8-(((S)-1-(thiazole-5-carbonyl)pyrrolidin-3-yl)oxy)-1,2,3,4-tetrahydroisoquinoline-2-carbonyl)cyclohexane-1-carboxylic acid;

(1S,2R)-2-((S)-1-((1,3-dioxoisoindolin-2-yl)methyl)-8-(((S)-1-(thiazole-5-carbonyl)pyrrolidin-3-yl)oxy)-1,2,3,4-tetrahydroisoquinoline-2-carbonyl)cyclohexane-1-carboxylic acid;

(1S,2R)-2-((S)-1-((1,3-dioxoisoindolin-2-yl)methyl)-8-(((S)-1-(2-methylthiazole-5-carbonyl)pyrrolidin-3-yl)oxy)-1,2,3,4-tetrahydroisoquinoline-2-carbonyl)cyclohexane-1-carboxylic acid;

(1S,2R)-2-((S)-1-((1,3-dioxoisoindolin-2-yl)methyl)-8-((1-methyl-1H-benzo[d][1,2,3]triazol-5-yl)methoxy)-1,2,3,4-tetrahydroisoquinoline-2-carbonyl)cyclohexane-1-carboxylic acid;

(1S,2R)-2-((S)-1-((1,3-dioxoisoindolin-2-yl)methyl)-8-((1-methyl-1H-1,2,3-triazol-4-yl)methoxy)-1,2,3,4-tetrahydroisoquinoline-2-carbonyl)cyclohexane-1-carboxylic acid;

(1S,2R)-2-((S)-1-((1,3-dioxoisoindolin-2-yl)methyl)-8-((1-methyl-1H-benzo[d]imidazol-5-yl)methoxy)-1,2,3,4-tetrahydroisoquinoline-2-carbonyl)cyclohexane-1-carboxylic acid;

(1S,2R)-2-((S)-8-(((S)-1-acetylpyrrolidin-3-yl)oxy)-5-bromo-1-((1,3-dioxoisoindolin-2-yl)methyl)-1,2,3,4-tetrahydroisoquinoline-2-carbonyl)cyclohexane-1-carboxylic acid;

(1S,2R)-2-((S)-8-(((S)-1-acetylpyrrolidin-3-yl)oxy)-5-chloro-1-((1,3-dioxoisoindolin-2-yl)methyl)-1,2,3,4-tetrahydroisoquinoline-2-carbonyl)cyclohexane-1-carboxylic acid;

(1S,2R)-2-((S)-8-(((S)-1-acetylpyrrolidin-3-yl)oxy)-5,7-dichloro-1-((1,3-dioxoisoindolin-2-yl)methyl)-1,2,3,4-tetrahydroisoquinoline-2-carbonyl)cyclohexane-1-carboxylic acid;

(1S,2R)-2-((S)-5-chloro-1-((1,3-dioxoisoindolin-2-yl)methyl)-8-(((S)-1-(thiazole-5-carbonyl)pyrrolidin-3-yl)oxy)-1,2,3,4-tetrahydroisoquinoline-2-carbonyl)cyclohexane-1-carboxylic acid;

(1S,2R)-2-((S)-1-((1-oxoisoindolin-2-yl)methyl)-8-(((S)-1-(thiazole-5-carbonyl)pyrrolidin-3-yl)oxy)-1,2,3,4-tetrahydroisoquinoline-2-carbonyl)cyclohexane-1-carboxylic acid;

(1S,2R)-2-((S)-8-([1,2,4]triazolo[4,3-a]pyridin-3-ylmethoxy)-5-bromo-1-((1-oxoisoindolin-2-yl)methyl)-1,2,3,4-tetrahydroisoquinoline-2-carbonyl)cyclohexane-1-carboxylic acid;

(1S,2R)-2-((S)-8-((1-isopropyl-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-8-((1-methyl-1H-benzo[d][1,2,3]triazol-5-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-8-(((S)-1-acetylpyrrolidin-3-yl)oxy)-5-bromo-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-(((S)-1-(2-methylthiazole-5-carbonyl)pyrrolidin-3-yl)oxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-(((S)-1-(5-methylthiazol-2-yl)pyrrolidin-3-yl)oxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-(((S)-1-(5-methylpyridazin-3-yl)pyrrolidin-3-yl)oxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-((4-methyl-4H-1,2,4-triazol-3-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-((5-methyl-1,2,4-oxadiazol-3-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-Bromo-8-((1-methyl-1H-imidazol-4-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-((5-methylisoxazol-3-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-((2-ethyl-2H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((1S)-5-bromo-8-((5-methylthiazol-2-yl)methoxy)-1-((1-oxo-1,3,3a,4,5,6-hexahydro-2H-isoindol-2-yl)methyl)-1,2,3,4-tetrahydroisoquinoline-2-carbonyl)cyclohexane-1-carboxylic acid;

(1S,2R)-2-((S)-5-bromo-8-((1-methyl-1H-1,2,4-triazol-5-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-1-((1-oxoisoindolin-2-yl)methyl)-8-(pyridazin-3-ylmethoxy)-1,2,3,4-tetrahydroisoquinoline-2-carbonyl)cyclohexane-1-carboxylic acid;

(1S,2R)-2-((S)-5-bromo-8-((1-(cyclopropylmethyl)-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-(imidazo[1,2-a]pyridin-7-ylmethoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-((1-methyl-1H-benzo[d]imidazol-5-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-((1-methyl-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-((1-isopropyl-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-((5-methyl-1,3,4-oxadiazol-2-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-((7-methoxy-1-methyl-1H-benzo[d][1,2,3]triazol-5-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-((1-methyl-1H-benzo[d][1,2,3]triazol-5-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-((1-methyl-1H-1,2,4-triazol-3-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-((1-isopropyl-1H-imidazol-2-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-((5-(difluoromethyl)-1-methyl-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-((4-ethyl-4H-1,2,4-triazol-3-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-((5-cyano-1-ethyl-1H-imidazol-4-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-1-((1-oxoisoindolin-2-yl)methyl)-8-((5,6,7,8-tetrahydro-[1,2,4]triazolo[4,3-a]pyridin-3-yl)methoxy)-1,2,3,4-tetrahydroisoquinoline-2-carbonyl)cyclohexane-1-carboxylic acid;

(1S,2R)-2-((1S)-5-bromo-8-(1-(1-methyl-1H-1,2,3-triazol-4-yl)ethoxy)-1-((1-oxoisoindolin-2-yl)methyl)-1,2,3,4-tetrahydroisoquinoline-2-carbonyl)cyclohexane-1-carboxylic acid;

(1S,2R)-2-((1S)-5-bromo-8-(1-(1-isopropyl-1H-1,2,3-triazol-4-yl)ethoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-chloro-8-((1-methyl-1H-benzo[d][1,2,3]triazol-5-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-chloro-8-((5-methylisoxazol-3-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-8-([1,2,4]triazolo[4,3-a]pyridin-3-ylmethoxy)-5-chloro-1-((1-oxoisoindolin-2-yl)methyl)-1,2,3,4-tetrahydroisoquinoline-2-carbonyl)cyclohexane-1-carboxylic acid;

(1S,2R)-2-((S)-5-chloro-1-((1-oxoisoindolin-2-yl)methyl)-8-((1-(2,2,2-trifluoroethyl)-1H-imidazol-2-yl)methoxy)-1,2,3,4-tetrahydroisoquinoline-2-carbonyl)cyclohexane-1-carboxylic acid;

(1S,2R)-2-((S)-5-chloro-8-((1-(2,2-difluoroethyl)-1H-imidazol-2-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-chloro-8-((5-(difluoromethyl)-1-methyl-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-chloro-8-((1-methyl-5-(trifluoromethyl)-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-chloro-8-((1-ethyl-1H-pyrazol-3-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-chloro-8-((5-(difluoromethyl)-1-methyl-1H-imidazol-4-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-chloro-8-((1-isopropyl-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-fluoro-8-((1-isopropyl-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-8-((1-isopropyl-1H-1,2,3-triazol-4-yl)methoxy)-5-methyl-1-((1-oxoisoindolin-2-yl)methyl)-1,2,3,4-tetrahydroisoquinoline-2-carbonyl)cyclohexane-1-carboxylic acid;

(1S,2R)-2-((S)-5-cyano-8-((1-isopropyl-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-8-((1-isopropyl-1H-1,2,3-triazol-4-yl)methoxy)-5-methoxy-1-((1-oxoisoindolin-2-yl)methyl)-1,2,3,4-tetrahydroisoquinoline-2-carbonyl)cyclohexane-1-carboxylic acid;

(1S,2R)-2-((S)-8-((1-isopropyl-1H-1,2,3-triazol-4-yl)methoxy)-1-((1-oxoisoindolin-2-yl)methyl)-5-(trifluoromethyl)-1,2,3,4-tetrahydroisoquinoline-2-carbonyl)cyclohexane-1-carboxylic acid;

(1S,2R)-2-((S)-5-bromo-1-((2-oxopyrrolidin-1-yl)methyl)-8-(((S)-1-(thiazole-5-carbonyl)pyrrolidin-3-yl)oxy)-1,2,3,4-tetrahydroisoquinoline-2-carbonyl)cyclohexane-1-carboxylic acid;

(1S,2R)-2-((S)-8-([1,2,4]triazolo[4,3-a]pyridin-3-ylmethoxy)-5-bromo-1-((2-oxopyrrolidin-1-yl)methyl)-1,2,3,4-tetrahydroisoquinoline-2-carbonyl)cyclohexane-1-carboxylic acid;

(1S,2R)-2-((S)-5-bromo-8-((5-methylthiazol-2-yl)methoxy)-1-((2-oxopyrrolidin-1-yl)methyl)-1,2,3,4-tetrahydroisoquinoline-2-carbonyl)cyclohexane-1-carboxylic acid;

(1S,2R)-2-((S)-5-bromo-8-((5-isopropyl-1,2,4-oxadiazol-3-yl)methoxy)-1-((2-oxopyrrolidin-1-yl)methyl)-1,2,3,4-tetrahydroisoquinoline-2-carbonyl)cyclohexane-1-carboxylic acid;

(1S,2R)-2-((S)-8-(benzo[d]isoxazol-3-ylmethoxy)-5-bromo-1-((2-oxopyrrolidin-1-yl)methyl)-1,2,3,4-tetrahydroisoquinoline-2-carbonyl)cyclohexane-1-carboxylic acid;

(1S,2R)-2-((S)-8-(benzo[d]isothiazol-3-ylmethoxy)-5-chloro-1-((2-oxopyrrolidin-1-yl)methyl)-1,2,3,4-tetrahydroisoquinoline-2-carbonyl)cyclohexane-1-carboxylic acid;

(1S,2R)-2-((S)-5-chloro-1-((2-oxopyrrolidin-1-yl)methyl)-8-(pyridin-2-ylmethoxy)-1,2,3,4-tetrahydroisoquinoline-2-carbonyl)cyclohexane-1-carboxylic acid;

(1S,2R)-2-((S)-5-chloro-8-((5-methylisothiazol-3-yl)methoxy)-1-((2-oxopyrrolidin-1-yl)methyl)-1,2,3,4-tetrahydroisoquinoline-2-carbonyl)cyclohexane-1-carboxylic acid;

(1S,2R)-2-((S)-5-chloro-8-(isothiazol-3-ylmethoxy)-1-((2-oxopyrrolidin-1-yl)methyl)-1,2,3,4-tetrahydroisoquinoline-2-carbonyl)cyclohexane-1-carboxylic acid;

(1S,2R)-2-((S)-8-(benzo[d]isoxazol-3-ylmethoxy)-5-chloro-1-((2-oxopyrrolidin-1-yl)methyl)-1,2,3,4-tetrahydroisoquinoline-2-carbonyl)cyclohexane-1-carboxylic acid (1S,2R)-2-((1S)-5-bromo-8-((1-isopropyl-1H-1,2,3-triazol-4-yl)methoxy)-1-((3-methyl-2-oxopyrrolidin-1-yl)methyl)-1,2,3,4-tetrahydroisoquinoline-2-carbonyl)cyclohexane-1-carboxylic acid;

(1S,2R)-2-((S)-5-bromo-8-((1-isopropyl-1H-1,2,3-triazol-4-yl)methoxy)-1-(((R)-4-methyl-2-oxopyrrolidin-1-yl)methyl)-1,2,3,4-tetrahydroisoquinoline-2-carbonyl)cyclohexane-1-carboxylic acid;

(1S,2R)-2-((S)-5-bromo-8-((1-isopropyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)cyclohexane-1-carboxylic acid;

(1S,2R)-2-((S)-5-bromo-8-((1-isopropyl-1H-1,2,3-triazol-4-yl)methoxy)-1-(((S)-4-methyl-2-oxopyrrolidin-1-yl)methyl)-1,2,3,4-tetrahydroisoquinoline-2-carbonyl)cyclohexane-1-carboxylic acid;

(1S,2R)-2-((S)-5-chloro-1-((2-oxopyrrolidin-1-yl)methyl)-8-(pyridin-3-ylmethoxy)-1,2,3,4-tetrahydroisoquinoline-2-carbonyl)cyclohexane-1-carboxylic acid;

(1S,2R)-2-((S)-5-chloro-8-((5-(difluoromethyl)-1-ethyl-1H-1,2,3-triazol-4-yl)methoxy)-1-((2-oxopyrrolidin-1-yl)methyl)-1,2,3,4-tetrahydroisoquinoline-2-carbonyl)cyclohexane-1-carboxylic acid;

(R)-4-((S)-8-(benzo[d]isoxazol-3-ylmethoxy)-5-chloro-1-((2-oxopyrrolidin-1-yl)methyl)-3,4-dihydroisoquinolin-2(1H)-yl)-3-methyl-4-oxobutanoic acid;

1-(((S)-2-((1R,2S)-2-(2H-tetrazol-5-yl)cyclohexane-1-carbonyl)-8-(benzo[d]isoxazol-3-ylmethoxy)-5-chloro-1,2,3,4-tetrahydroisoquinolin-1-yl)methyl)pyrrolidin-2-one;

(1S,2R)-2-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)cyclohexane-1-carboxylic acid;

(1S,2R)-2-((S)-5-chloro-8-((5-isopropyl-1,2,4-oxadiazol-3-yl)methoxy)-1-((2-oxopyrrolidin-1-yl)methyl)-1,2,3,4-tetrahydroisoquinoline-2-carbonyl)cyclohexane-1-carboxylic acid;

(1S,2R)-2-((S)-5-chloro-8-((5-(difluoromethyl)-1-methyl-1H-1,2,3-triazol-4-yl)methoxy)-1-((4-methyl-1H-pyrazol-1-yl)methyl)-1,2,3,4-tetrahydroisoquinoline-2-carbonyl)cyclohexane-1-carboxylic acid;

(1S,2R)-2-((S)-5-chloro-1-((2-oxopyrrolidin-1-yl)methyl)-8-(pyrimidin-5-ylmethoxy)-1,2,3,4-tetrahydroisoquinoline-2-carbonyl)cyclohexane-1-carboxylic acid;

(1S,2R)-2-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)cyclopentane-1-carboxylic acid;

(1R,2S)-2-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)cyclopentane-1-carboxylic acid;

(1S,2R)-2-((S)-5-chloro-1-((2-oxopyrrolidin-1-yl)methyl)-8-(pyridazin-3-ylmethoxy)-1,2,3,4-tetrahydroisoquinoline-2-carbonyl)cyclohexane-1-carboxylic acid;

(1S,2R)-2-((S)-5-chloro-8-((3-methyl-3H-imidazo[4,5-b]pyridin-6-yl)methoxy)-1-((2-oxopyrrolidin-1-yl)methyl)-1,2,3,4-tetrahydroisoquinoline-2-carbonyl)cyclohexane-1-carboxylic acid;

(1S,2R)-2-((S)-5-chloro-8-((1-methyl-1H-benzo[d][1,2,3]triazol-5-yl)methoxy)-1-((2-oxopyrrolidin-1-yl)methyl)-1,2,3,4-tetrahydroisoquinoline-2-carbonyl)cyclohexane-1-carboxylic acid;

(1S,2R)-2-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-(imidazo[1,2-a]pyrimidin-2-ylmethoxy)-1-((2-oxopyrrolidin-1-yl)methyl)-1,2,3,4-tetrahydroisoquinoline-2-carbonyl)cyclohexane-1-carboxylic acid;

(1S,2R)-2-((S)-5-chloro-8-(isoxazolo[5,4-b]pyridin-3-ylmethoxy)-1-((2-oxopyrrolidin-1-yl)methyl)-1,2,3,4-tetrahydroisoquinoline-2-carbonyl)cyclohexane-1-carboxylic acid;

(1S,2R)-2-((S)-8-([1,2,4]triazolo[4,3-a]pyridin-3-ylmethoxy)-5-chloro-1-((2-oxopyrrolidin-1-yl)methyl)-1,2,3,4-tetrahydroisoquinoline-2-carbonyl)cyclohexane-1-carboxylic acid;

(1S,2R)-2-((S)-5-chloro-8-((3-methylisoxazolo[5,4-b]pyridin-6-yl)methoxy)-1-((2-oxopyrrolidin-1-yl)methyl)-1,2,3,4-tetrahydroisoquinoline-2-carbonyl)cyclohexane-1-carboxylic acid;

3-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)bicyclo[2.2.1]heptane-2-carboxylic acid;

3-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)tetrahydrofuran-2-carboxylic acid;

(1S,2R)-2-((S)-5-chloro-8-((1-methyl-1H-indazol-3-yl)methoxy)-1-((2-oxopyrrolidin-1-yl)methyl)-1,2,3,4-tetrahydroisoquinoline-2-carbonyl)cyclohexane-1-carboxylic acid;

(1S,2R)-2-((S)-5-chloro-8-((3-methyl-3H-imidazo[4,5-b]pyridin-5-yl)methoxy)-1-((2-oxopyrrolidin-1-yl)methyl)-1,2,3,4-tetrahydroisoquinoline-2-carbonyl)cyclohexane-1-carboxylic acid;

(1S,2R)-2-((S)-8-(benzo[d]isoxazol-3-ylmethoxy)-5-chloro-1-((2-oxopyrrolidin-1-yl)methyl)-1,2,3,4-tetrahydroisoquinoline-2-carbonyl)-1-methylcyclohexane-1-carboxylic acid;

2-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)-4,4-difluorocyclopentane-1-carboxylic acid;

(1S,2R)-2-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)-1-methylcyclopentane-1-carboxylic acid;

(1S,2R)-2-((S)-5-chloro-8-((4,5-dimethyl-4H-1,2,4-triazol-3-yl)methoxy)-1-((2-oxopyrrolidin-1-yl)methyl)-1,2,3,4-tetrahydroisoquinoline-2-carbonyl)cyclohexane-1-carboxylic acid;

(1S,2R)-2-((S)-5-chloro-8-((1-methyl-1H-1,2,3-triazol-4-yl)methoxy)-1-((2-oxopyrrolidin-1-yl)methyl)-1,2,3,4-tetrahydroisoquinoline-2-carbonyl)cyclohexane-1-carboxylic acid;

(1R,2S)-2-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)-1-fluorocyclohexane-1-carboxylic acid;

(1S,2R)-2-((S)-5-chloro-8-((1-methyl-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((1,5-dimethyl-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((1-methyl-5-(trifluoromethyl)-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-methyl-1H-1,2,3-triazol-4-yl)methoxy)-1-(((R)-4-methyl-2-oxopyrrolidin-1-yl)methyl)-1,2,3,4-tetrahydroisoquinoline-2-carbonyl)-1-methylcyclopentane-1-carboxylic acid;

(1S,2R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclopentane-1-carboxylic acid;

(1S,2R)-2-((S)-5-chloro-8-((5-(difluoromethyl)-1-methyl-1H-1,2,3-triazol-4-yl)methoxy)-1-(((R)-4-methyl-2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-methyl-1H-1,2,3-triazol-4-yl)methoxy)-1-(((R)-3-methyl-2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-methyl-1H-1,2,3-triazol-4-yl)methoxy)-1-(((R)-3-methyl-2-oxopyrrolidin-1-yl)methyl)-1,2,3,4-tetrahydroisoquinoline-2-carbonyl)-1-methylcyclopentane-1-carboxylic acid;

(1S,2R)-2-((S)-5-chloro-8-((5-(difluoromethyl)-1-methyl-1H-1,2,3-triazol-4-yl)methoxy)-1-(((S)-3-methyl-2-oxopyrrolidin-1-yl)methyl)-1,2,3,4-tetrahydroisoquinoline-2-carbonyl)-1-methylcyclopentane-1-carboxylic acid;

(1S,2R)-2-((S)-5-chloro-8-((5-(difluoromethyl)-1-methyl-1H-1,2,3-triazol-4-yl)methoxy)-1-(((S)-3-methyl-2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-methyl-1H-1,2,3-triazol-4-yl)methoxy)-1-(((S)-4-methyl-2-oxopyrrolidin-1-yl)methyl)-1,2,3,4-tetrahydroisoquinoline-2-carbonyl)-1-methylcyclopentane-1-carboxylic acid;

(1S,2R)-2-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)-1-ethylcyclohexane-1-carboxylic acid;

(1S,2R)-2-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)-1-ethylcyclopentane-1-carboxylic acid;

(1S,2R)-2-((S)-5-chloro-8-((5-(difluoromethyl)-1-ethyl-1H-1,2,3-triazol-4-yl)methoxy)-1-((2-oxopyrrolidin-1-yl)methyl)-1,2,3,4-tetrahydroisoquinoline-2-carbonyl)-1-methylcyclopentane-1-carboxylic acid;

(1S,2R)-2-((S)-5-chloro-8-((5-(difluoromethyl)-1-ethyl-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-isopropyl-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-isopropyl-1H-1,2,3-triazol-4-yl)methoxy)-1-((2-oxopyrrolidin-1-yl)methyl)-1,2,3,4-tetrahydroisoquinoline-2-carbonyl)-1-methylcyclopentane-1-carboxylic acid;

(1S,2R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((4,5-dimethylisoxazol-3-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((4-chloro-5-methylisoxazol-3-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((4-methylisoxazol-5-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-(methoxymethyl)-1-methyl-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-(2-methoxyethyl)-1-methyl-1H-1,2,3-triazol-4-yl)methoxy)-1-((2-oxopyrrolidin-1-yl)

methyl)-1,2,3,4-tetrahydroisoquinoline-2-carbonyl)-1-methylcyclohexane-1-carboxylic acid;

(1S,2R)-2-((S)-5-chloro-8-((5-cyclopropyl-1-methyl-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-1-(((S)-3-methyl-2-oxopyrrolidin-1-yl)methyl)-8-((1-methyl-5-(trifluoromethyl)-1H-1,2,3-triazol-4-yl)methoxy)-1,2,3,4-tetrahydroisoquinoline-2-carbonyl)-1-methylcyclohexane-1-carboxylic acid;

(1S,2R)-2-((S)-5-chloro-1-(((R)-3-methyl-2-oxopyrrolidin-1-yl)methyl)-8-((1-methyl-5-(trifluoromethyl)-1H-1,2,3-triazol-4-yl)methoxy)-1,2,3,4-tetrahydroisoquinoline-2-carbonyl)-1-methylcyclohexane-1-carboxylic acid;

(1S,2R)-2-((S)-5-chloro-1-(((R)-4-methyl-2-oxopyrrolidin-1-yl)methyl)-8-((1-methyl-5-(trifluoromethyl)-1H-1,2,3-triazol-4-yl)methoxy)-1,2,3,4-tetrahydroisoquinoline-2-carbonyl)-1-methylcyclohexane-1-carboxylic acid;

(1S,2S)-2-((S)-5-chloro-1-(((R)-4-methyl-2-oxopyrrolidin-1-yl)methyl)-8-((1-methyl-5-(trifluoromethyl)-1H-1,2,3-triazol-4-yl)methoxy)-1,2,3,4-tetrahydroisoquinoline-2-carbonyl)-1-methylcyclohexane-1-carboxylic acid;

(1S,2R)-2-((S)-5-chloro-8-((1-cyclopropyl-5-(difluoromethyl)-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((4-(difluoromethyl)pyrimidin-5-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5,5-dimethyl-4,5-dihydroisoxazol-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((4-methylisoxazol-3-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-1-((2-oxopyrrolidin-1-yl)methyl)-8-((4,5,6,7-tetrahydrobenzo[d]isoxazol-3-yl)methoxy)-1,2,3,4-tetrahydroisoquinoline-2-carbonyl)-1-methylcyclohexane-1-carboxylic acid;

(1S,2R)-2-((S)-8-((2,5-bis(difluoromethyl)-2H-1,2,3-triazol-4-yl)methoxy)-5-chloro-1-((6-oxo-5-azaspiro[2.4]heptan-5-yl)methyl)-1,2,3,4-tetrahydroisoquinoline-2-carbonyl)-1-methylcyclohexane-1-carboxylic acid;

2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)tetrahydro-2H-pyran-3-carboxylic acid;

(R)-2-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)bicyclo[2.2.2]octane-1-carboxylic acid;

(1S,2R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic-4,4-d2 acid;

(1S,2R)-2-((S)-5-chloro-8-((1,5-dimethyl-1H-1,2,3-triazol-4-yl)methoxy)-7-fluoro-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-7-fluoro-1-((6-oxo-5-azaspiro[2.4]heptan-5-yl)methyl)-8-((4,5,6,7-tetrahydro-[1,2,3]triazolo[1,5-a]pyridin-3-yl)methoxy)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-(2-methoxyethyl)-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5,6-dihydro-4H-pyrrolo[1,2-c][1,2,3]triazol-3-yl)methoxy)-7-fluoro-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-methyl-1H-1,2,3-triazol-4-yl)methoxy)-7-fluoro-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((1-methyl-2-oxo-1,2-dihydropyridin-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2S)-2-((S)-5-chloro-8-((5-(difluoromethyl)-1-methyl-1H-1,2,3-triazol-4-yl)methoxy)-1-(((R)-4-methyl-2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((1-methyl-5-(trifluoromethyl)-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

1-(((S)-5-chloro-8-((5-(difluoromethyl)-1-methyl-1H-1,2,3-triazol-4-yl)methoxy)-2-((1R,2S)-2-methyl-2-(2H-tetrazol-5-yl)cyclohexane-1-carbonyl)-1,2,3,4-tetrahydroisoquinolin-1-yl)methyl)pyrrolidin-2-one;

(1S,2R)-2-((S)-5-chloro-8-((5-(difluoromethyl)-1-methyl-1H-1,2,3-triazol-4-yl)methoxy)-1-((4,4-dimethyl-2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((1-methyl-5-(trifluoromethyl)-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclopentane-1-carboxylic acid;

(1S,2R)-2-((S)-5-chloro-8-((5-methyl-4-(trifluoromethyl)isoxazol-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-(2,2,2-trifluoroethyl)-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((1,5-dimethyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((4-(difluoromethyl)-5-methylisoxazol-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5-cyclopropyl-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5-(methoxymethyl)-1-methyl-1H-1,2,3-triazol-4-yl)methoxy)-1-((6-oxo-5-azaspiro

[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((1-methyl-1H-1,2,3-triazol-4-yl)methoxy)-1-(((R)-4-methyl-2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-(methoxymethyl)-1-methyl-1H-1,2,3-triazol-4-yl)methoxy)-1-(((R)-4-methyl-2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-cyclopropyl-1-methyl-1H-1,2,3-triazol-4-yl)methoxy)-1-(((R)-4-methyl-2-oxopyrrolidin-1-yl)methyl)-1,2,3,4-tetrahydroisoquinoline-2-carbonyl)-1-methylcyclohexane-1-carboxylic acid;

(1S,2R)-2-((1S)-5-chloro-8-((7-fluoro-2,7a-dihydrobenzo[d]isoxazol-3-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((6,7-difluorobenzo[d]isoxazol-3-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-methylisoxazol-3-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((3-methyl-1,2,4-oxadiazol-5-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-methyl-1,2,4-oxadiazol-3-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2S)-2-((S)-5-chloro-8-((1-methyl-5-(trifluoromethyl)-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-1-((6-oxo-5-azaspiro[2.4]heptan-5-yl)methyl)-8-((4,5,6,7-tetrahydro-[1,2,3]triazolo[1,5-a]pyridin-3-yl)methoxy)-1,2,3,4-tetrahydroisoquinoline-2-carbonyl)-1-methylcyclohexane-1-carboxylic acid;

(1S,2R)-2-((S)-5-chloro-1-((6-oxo-5-azaspiro[2.4]heptan-5-yl)methyl)-8-((4-(trifluoromethyl)pyrimidin-5-yl)methoxy)-1,2,3,4-tetrahydroisoquinoline-2-carbonyl)-1-methylcyclohexane-1-carboxylic acid;

(1S,2R)-2-((S)-5-chloro-8-((1-cyclopropyl-5-(difluoromethyl)-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((1-(2-(dimethylamino)ethyl)-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-1-methyl-2-((S)-5-methyl-8-((1-methyl-5-(trifluoromethyl)-1H-1,2,3-triazol-4-yl)methoxy)-1-((2-oxopyrrolidin-1-yl)methyl)-1,2,3,4-tetrahydroisoquinoline-2-carbonyl)cyclohexane-1-carboxylic acid;

(1S,2R)-2-((S)-5-chloro-8-((4-methyl-4H-1,2,4-triazol-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5,6-dihydro-8H-[1,2,4]triazolo[3,4-c][1,4]oxazin-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((4-cyclopropyl-5-methyl-4H-1,2,4-triazol-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-fluoro-8-((1-methyl-5-(trifluoromethyl)-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((4,5-dimethyl-4H-1,2,4-triazol-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-1-((6-oxo-5-azaspiro[2.4]heptan-5-yl)methyl)-8-((4,5,6,7-tetrahydro-[1,2,3]triazolo[1,5-a]pyridin-3-yl)methoxy)-1,2,3,4-tetrahydroisoquinoline-2-carbonyl)-1-methylcyclopentane-1-carboxylic acid;

(1S,2R)-2-((S)-5-chloro-8-((5,6-dihydro-4H-pyrrolo[1,2-c][1,2,3]triazol-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-fluoro-1-((6-oxo-5-azaspiro[2.4]heptan-5-yl)methyl)-8-((4,5,6,7-tetrahydro-[1,2,3]triazolo[1,5-a]pyridin-3-yl)methoxy)-1,2,3,4-tetrahydroisoquinoline-2-carbonyl)-1-methylcyclohexane-1-carboxylic acid;

(1S,2R)-2-((S)-5-chloro-8-((6,7-dihydro-5H-pyrrolo[2,1-c][1,2,4]triazol-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5-cyclopropyl-4-methyl-4H-1,2,4-triazol-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((1-methyl-1H-imidazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-1-((6-oxo-5-azaspiro[2.4]heptan-5-yl)methyl)-8-((5,6,7,8-tetrahydro-[1,2,4]triazolo[4,3-a]pyridin-3-yl)methoxy)-1,2,3,4-tetrahydroisoquinoline-2-carbonyl)-1-methylcyclohexane-1-carboxylic acid;

(1S,2R)-2-((S)-5-chloro-8-(((S)-1-(methylsulfonyl)pyrrolidin-3-yl)oxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-8-(((S)-1-acetylpyrrolidin-3-yl)oxy)-5-chloro-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((6,7-dihydro-4H-[1,2,3]triazolo[5,1-c][1,4]oxazin-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-1-methyl-2-((S)-8-((1-methyl-5-(trifluoromethyl)-1H-1,2,3-triazol-4-yl)methoxy)-1-((2-oxopyrrolidin-1-yl)methyl)-1,2,3,4-tetrahydroisoquinoline-2-carbonyl)cyclohexane-1-carboxylic acid;

(1S,2R)-2-((S)-5-bromo-8-((1-methyl-5-(trifluoromethyl)-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-(oxetan-3-yl)-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-8-((1,5-bis(difluoromethyl)-1H-1,2,3-triazol-4-yl)methoxy)-5-chloro-1-((6-oxo-5-azaspiro[2.4]

heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-methyl-1H-1,2,3-triazol-4-yl)methoxy)-1-(((R)-2-methyl-5-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-methyl-1H-1,2,3-triazol-4-yl)methoxy)-1-(((S)-2-methyl-5-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-1-((3-oxomorpholino)methyl)-8-((4,5,6,7-tetrahydro-[1,2,3]triazolo[1,5-a]pyridin-3-yl)methoxy)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)cyclohexane-1-carboxylic acid;

(1S,2R)-2-((S)-5-bromo-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((1-methyl-5-(oxetan-3-yl)-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-methyl-1H-1,2,3-triazol-4-yl)methoxy)-1-((3-oxomorpholino)methyl)-1,2,3,4-tetrahydroisoquinoline-2-carbonyl)-1-methylcyclohexane-1-carboxylic acid;

(1S,6R)-6-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohex-3-ene-1-carboxylic acid;

5-(((S)-2-((1R,2S)-2-(1H-tetrazol-5-yl)cyclohexane-1-carbonyl)-5-chloro-8-((5-(difluoromethyl)-1-methyl-1H-1,2,3-triazol-4-yl)methoxy)-1,2,3,4-tetrahydroisoquinolin-1-yl)methyl)-5-azaspiro[2.4]heptan-6-one;

(1S,2R)-2-((S)-5-chloro-8-((5-(difluoromethyl)-1-methyl-1H-1,2,3-triazol-4-yl)methoxy)-7-fluoro-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)thiazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5-methylthiazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((2-methyl-2H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1R,3S,4R,6S)-4-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-3-methylbicyclo[4.1.0]heptane-3-carboxylic acid;

(1S,3S,4R,6R)-4-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-3-methylbicyclo[4.1.0]heptane-3-carboxylic acid;

(1S,2R)-2-((1S)-5-chloro-8-((6,7-dihydro-5H-pyrrolo[2,1-c][1,2,4]triazol-7-yl)oxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R,4S,5R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic-4,5-d2 acid;

(1S,2R)-2-((S)-5-chloro-8-((1-methyl-2-oxo-1,2-dihydropyridin-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((1S)-5-chloro-8-((5-(difluoromethyl)-1-methyl-1H-1,2,3-triazol-4-yl)methoxy)-1-((2-oxo-4-(trifluoromethyl)pyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((1-methyl-6-oxo-1,6-dihydropyridin-2-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((1S)-5-chloro-8-((1-methyl-1,4,5,6-tetrahydrocyclopenta[d][1,2,3]triazol-5-yl)oxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-4,4-difluoro-1-methylcyclohexane-1-carboxylic acid;

(1S,2R,4S)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-4-fluoro-1-methylcyclohexane-1-carboxylic acid;

(1S,2R,4R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic-4-d acid;

(1S,2R,4S)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-4-hydroxy-1-methylcyclohexane-1-carboxylic acid;

(1S,2R,5S)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-5-hydroxy-1-methylcyclohexane-1-carboxylic acid;

(1S,2R,5R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-5-hydroxy-1-methylcyclohexane-1-carboxylic acid;

(1S,2R,4R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-4-hydroxy-1-methylcyclohexane-1-carboxylic acid;

(2S,3R)-3-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)tetrahydro-2H-pyran-2-carboxylic acid;

(1R,2R,6S)-2-((S)-5-chloro-8-((5-(difluoromethyl)-1-methyl-1H-1,2,3-triazol-4-yl)methoxy)-1-((6-oxo-5- azaspiro[2.4]heptan-5-yl)methyl)-1,2,3,4-tetrahydroisoquinoline-2-carbonyl)-6-hydroxy-1-methylcyclohexane-1-carboxylic acid;

(1R,2R,6R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-6-hydroxy-1-methylcyclohexane-1-carboxylic acid;

(1S,2S,3R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-3-hydroxy-1-methylcyclohexane-1-carboxylic acid; and (1S,2S,3S)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-3-hydroxy-1-methylcyclohexane-1-carboxylic acid;

or a pharmaceutically acceptable salt thereof.

In an embodiment, the compound of formula I is selected from the following compounds:

(1S,2R)-2-((S)-5-bromo-1-((1,3-dioxoisoindolin-2-yl)methyl)-8-(((S)-1-(thiazole-5-carbonyl)pyrrolidin-3-yl)oxy)-1,2,3,4-tetrahydroisoquinoline-2-carbonyl)cyclohexane-1-carboxylic acid;

(1S,2R)-2-((S)-8-(((S)-1-acetylpyrrolidin-3-yl)oxy)-5-bromo-1-((1,3-dioxoisoindolin-2-yl)methyl)-1,2,3,4-tetrahydroisoquinoline-2-carbonyl)cyclohexane-1-carboxylic acid;

(1S,2R)-2-((S)-8-(((S)-1-acetylpyrrolidin-3-yl)oxy)-5-chloro-1-((1,3-dioxoisoindolin-2-yl)methyl)-1,2,3,4-tetrahydroisoquinoline-2-carbonyl)cyclohexane-1-carboxylic acid;

(1S,2R)-2-((S)-5-chloro-1-((1,3-dioxoisoindolin-2-yl)methyl)-8-(((S)-1-(thiazole-5-carbonyl)pyrrolidin-3-yl)oxy)-1,2,3,4-tetrahydroisoquinoline-2-carbonyl)cyclohexane-1-carboxylic acid;

(1S,2R)-2-((S)-8-([1,2,4]triazolo[4,3-a]pyridin-3-ylmethoxy)-5-bromo-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-(((S)-1-(5-methylthiazol-2-yl)pyrrolidin-3-yl)oxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-((1-(cyclopropylmethyl)-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-((1-methyl-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-((1-isopropyl-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-((5-(difluoromethyl)-1-methyl-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-1-((1-oxoisoindolin-2-yl)methyl)-8-((5,6,7,8-tetrahydro-[1,2,4]triazolo[4,3-a]pyridin-3-yl)methoxy)-1,2,3,4-tetrahydroisoquinoline-2-carbonyl)cyclohexane-1-carboxylic acid;

(1S,2R)-2-((S)-5-chloro-8-((1-methyl-1H-benzo[d][1,2,3]triazol-5-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-8-([1,2,4]triazolo[4,3-a]pyridin-3-ylmethoxy)-5-chloro-1-((1-oxoisoindolin-2-yl)methyl)-1,2,3,4-tetrahydroisoquinoline-2-carbonyl)cyclohexane-1-carboxylic acid;

(1S,2R)-2-((S)-5-chloro-8-((5-(difluoromethyl)-1-methyl-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-chloro-8-((1-methyl-5-(trifluoromethyl)-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-chloro-8-((5-(difluoromethyl)-1-methyl-1H-imidazol-4-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-chloro-8-((1-isopropyl-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-cyano-8-((1-isopropyl-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-8-(benzo[d]isoxazol-3-ylmethoxy)-5-bromo-1-((2-oxopyrrolidin-1-yl)methyl)-1,2,3,4-tetrahydroisoquinoline-2-carbonyl)cyclohexane-1-carboxylic acid;

(1S,2R)-2-((S)-8-(benzo[d]isoxazol-3-ylmethoxy)-5-chloro-1-((2-oxopyrrolidin-1-yl)methyl)-1,2,3,4-tetrahydroisoquinoline-2-carbonyl)cyclohexane-1-carboxylic acid;

(1S,2R)-2-((S)-5-bromo-8-((1-isopropyl-1H-1,2,3-triazol-4-yl)methoxy)-1-(((R)-4-methyl-2-oxopyrrolidin-1-yl)methyl)-1,2,3,4-tetrahydroisoquinoline-2-carbonyl)cyclohexane-1-carboxylic acid;

(1S,2R)-2-((S)-5-bromo-8-((1-isopropyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)cyclohexane-1-carboxylic acid;

(1S,2R)-2-((S)-5-bromo-8-((1-isopropyl-1H-1,2,3-triazol-4-yl)methoxy)-1-(((S)-4-methyl-2-oxopyrrolidin-1-yl)methyl)-1,2,3,4-tetrahydroisoquinoline-2-carbonyl)cyclohexane-1-carboxylic acid;

(1S,2R)-2-((S)-5-chloro-8-((5-(difluoromethyl)-1-ethyl-1H-1,2,3-triazol-4-yl)methoxy)-1-((2-oxopyrrolidin-1-yl)methyl)-1,2,3,4-tetrahydroisoquinoline-2-carbonyl)cyclohexane-1-carboxylic acid;

(1S,2R)-2-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)cyclohexane-1-carboxylic acid;

(1S,2R)-2-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)cyclopentane-1-carboxylic acid;

(1S,2R)-2-((S)-5-chloro-8-((3-methyl-3H-imidazo[4,5-b]pyridin-6-yl)methoxy)-1-((2-oxopyrrolidin-1-yl)methyl)-1,2,3,4-tetrahydroisoquinoline-2-carbonyl)cyclohexane-1-carboxylic acid;

(1S,2R)-2-((S)-5-chloro-8-((1-methyl-1H-benzo[d][1,2,3]triazol-5-yl)methoxy)-1-((2-oxopyrrolidin-1-yl)methyl)-1,2,3,4-tetrahydroisoquinoline-2-carbonyl)cyclohexane-1-carboxylic acid;

(1S,2R)-2-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-8-([1,2,4]triazolo[4,3-a]pyridin-3-ylmethoxy)-5-chloro-1-((2-oxopyrrolidin-1-yl)methyl)-1,2,3,4-tetrahydroisoquinoline-2-carbonyl)cyclohexane-1-carboxylic acid;

(1S,2R)-2-((S)-5-chloro-8-((3-methylisoxazolo[5,4-b]pyridin-6-yl)methoxy)-1-((2-oxopyrrolidin-1-yl)methyl)-1,2,3,4-tetrahydroisoquinoline-2-carbonyl)cyclohexane-1-carboxylic acid;

(1S,2R)-2-((S)-8-(benzo[d]isoxazol-3-ylmethoxy)-5-chloro-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)-1-methylcyclopentane-1-carboxylic acid;

(1S,2R)-2-((S)-5-chloro-8-((1-methyl-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((1,5-dimethyl-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((1-methyl-5-(trifluoromethyl)-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-methyl-1H-1,2,3-triazol-4-yl)methoxy)-1-(((R)-4-methyl-2-oxopyrrolidin-1-yl)methyl)-1,2,3,4-tetrahydroisoquinoline-2-carbonyl)-1-methylcyclopentane-1-carboxylic acid;

(1S,2R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclopentane-1-carboxylic acid;

(1S,2R)-2-((S)-5-chloro-8-((5-(difluoromethyl)-1-methyl-1H-1,2,3-triazol-4-yl)methoxy)-1-(((R)-4-methyl-2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-methyl-1H-1,2,3-triazol-4-yl)methoxy)-1-(((S)-3-methyl-2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-ethyl-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((4,5-dimethylisoxazol-3-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-(methoxymethyl)-1-methyl-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-(2-methoxyethyl)-1-methyl-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-cyclopropyl-1-methyl-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-1-(((R)-4-methyl-2-oxopyrrolidin-1-yl)methyl)-8-((1-methyl-5-(trifluoromethyl)-1H-1,2,3-triazol-4-yl)methoxy)-1,2,3,4-tetrahydroisoquinoline-2-carbonyl)-1-methylcyclohexane-1-carboxylic acid;

(1S,2R)-2-((S)-5-chloro-8-((1-cyclopropyl-5-(difluoromethyl)-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((4-(difluoromethyl)pyrimidin-5-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((4-methylisoxazol-3-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-1-((2-oxopyrrolidin-1-yl)methyl)-8-((4,5,6,7-tetrahydrobenzo[d]isoxazol-3-yl)methoxy)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic-4,4-d2 acid;

(1S,2R)-2-((S)-5-chloro-8-((1,5-dimethyl-1H-1,2,3-triazol-4-yl)methoxy)-7-fluoro-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-7-fluoro-1-((6-oxo-5-azaspiro[2.4]heptan-5-yl)methyl)-8-((4,5,6,7-tetrahydro-[1,2,3]triazolo[1,5-a]pyridin-3-yl)methoxy)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-(2-methoxyethyl)-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5,6-dihydro-4H-pyrrolo[1,2-c][1,2,3]triazol-3-yl)methoxy)-7-fluoro-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-methyl-1H-1,2,3-triazol-4-yl)methoxy)-7-fluoro-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((1-methyl-5-(trifluoromethyl)-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-methyl-1H-1,2,3-triazol-4-yl)methoxy)-1-((4,4-dimethyl-2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((1-methyl-5-(trifluoromethyl)-1H-1,2,3-triazol-4-yl)methoxy)-1-((6-oxo-5-azaspiro

[2.4]heptan-5-yl)methyl)-1,2,3,4-tetrahydroisoquinoline-2-carbonyl)-1-methylcyclopentane-1-carboxylic acid;

(1S,2R)-2-((S)-5-chloro-8-((5-(difluoromethyl)-1-(2,2,2-trifluoroethyl)-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((1,5-dimethyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((4-(difluoromethyl)-5-methylisoxazol-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5-cyclopropyl-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5-(methoxymethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5-(methoxymethyl)-1-methyl-1H-1,2,3-triazol-4-yl)methoxy)-1-(((R)-4-methyl-2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-cyclopropyl-1-methyl-1H-1,2,3-triazol-4-yl)methoxy)-1-(((R)-4-methyl-2-oxopyrrolidin-1-yl)methyl)-1,2,3,4-tetrahydroisoquinoline-2-carbonyl)-1-methylcyclohexane-1-carboxylic acid;

(1S,2R)-2-((1S)-5-chloro-8-((7-fluoro-2,7a-dihydrobenzo[d]isoxazol-3-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-1-((6-oxo-5-azaspiro[2.4]heptan-5-yl)methyl)-8-((4,5,6,7-tetrahydro-[1,2,3]triazolo[1,5-a]pyridin-3-yl)methoxy)-1,2,3,4-tetrahydroisoquinoline-2-carbonyl)-1-methylcyclohexane-1-carboxylic acid;

(1S,2R)-2-((S)-5-chloro-8-((1-cyclopropyl-5-(difluoromethyl)-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-1-methyl-2-((S)-5-methyl-8-((1-methyl-5-(trifluoromethyl)-1H-1,2,3-triazol-4-yl)methoxy)-1-((2-oxopyrrolidin-1-yl)methyl)-1,2,3,4-tetrahydroisoquinoline-2-carbonyl)cyclohexane-1-carboxylic acid;

(1S,2R)-2-((S)-5-chloro-8-((5,6-dihydro-8H-[1,2,4]triazolo[3,4-c][1,4]oxazin-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((4-cyclopropyl-5-methyl-4H-1,2,4-triazol-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((4,5-dimethyl-4H-1,2,4-triazol-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-1-((6-oxo-5-azaspiro[2.4]heptan-5-yl)methyl)-8-((4,5,6,7-tetrahydro-[1,2,3]triazolo[1,5-a]pyridin-3-yl)methoxy)-1,2,3,4-tetrahydroisoquinoline-2-carbonyl)-1-methylcyclopentane-1-carboxylic acid;

(1S,2R)-2-((S)-5-chloro-8-((5,6-dihydro-4H-pyrrolo[1,2-c][1,2,3]triazol-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-fluoro-1-((6-oxo-5-azaspiro[2.4]heptan-5-yl)methyl)-8-((4,5,6,7-tetrahydro-[1,2,3]triazolo[1,5-a]pyridin-3-yl)methoxy)-1,2,3,4-tetrahydroisoquinoline-2-carbonyl)-1-methylcyclohexane-1-carboxylic acid;

(1S,2R)-2-((S)-5-chloro-8-((6,7-dihydro-5H-pyrrolo[2,1-c][1,2,4]triazol-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5-cyclopropyl-4-methyl-4H-1,2,4-triazol-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-1-((6-oxo-5-azaspiro[2.4]heptan-5-yl)methyl)-8-((5,6,7,8-tetrahydro-[1,2,4]triazolo[4,3-a]pyridin-3-yl)methoxy)-1,2,3,4-tetrahydroisoquinoline-2-carbonyl)-1-methylcyclohexane-1-carboxylic acid;

(1S,2R)-2-((S)-8-(((S)-1-acetylpyrrolidin-3-yl)oxy)-5-chloro-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((6,7-dihydro-4H-[1,2,3]triazolo[5,1-c][1,4]oxazin-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-1-methyl-2-((S)-8-((1-methyl-5-(trifluoromethyl)-1H-1,2,3-triazol-4-yl)methoxy)-1-((2-oxopyrrolidin-1-yl)methyl)-1,2,3,4-tetrahydroisoquinoline-2-carbonyl)cyclohexane-1-carboxylic acid;

(1S,2R)-2-((S)-5-bromo-8-((1-methyl-5-(trifluoromethyl)-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-(oxetan-3-yl)-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-8-((1,5-bis(difluoromethyl)-1H-1,2,3-triazol-4-yl)methoxy)-5-chloro-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-methyl-1H-1,2,3-triazol-4-yl)methoxy)-1-(((S)-2-methyl-5-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-1-((3-oxomorpholino)methyl)-8-((4,5,6,7-tetrahydro-[1,2,3]triazolo[1,5-a]pyridin-3-yl)methoxy)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)cyclohexane-1-carboxylic acid;

(1S,2R)-2-((S)-5-bromo-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((1-methyl-5-(oxetan-3-yl)-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-methyl-1H-1,2,3-triazol-4-yl)methoxy)-1-((3-oxomorpholino)

methyl)-1,2,3,4-tetrahydroisoquinoline-2-carbonyl)-1-methylcyclohexane-1-carboxylic acid;

(1S,6R)-6-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohex-3-ene-1-carboxylic acid;

(1S,2R)-2-((S)-5-chloro-8-((5-(difluoromethyl)-1-methyl-1H-1,2,3-triazol-4-yl)methoxy)-7-fluoro-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1R,3S,4R,6S)-4-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-3-methylbicyclo[4.1.0]heptane-3-carboxylic acid;

(1S,2R,4S,5R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic-4,5-d2 acid;

(1S,2R)-2-((1S)-5-chloro-8-((5-(difluoromethyl)-1-methyl-1H-1,2,3-triazol-4-yl)methoxy)-1-((2-oxo-4-(trifluoromethyl)pyrrolidin-1-yl)methyl)-1,2,3,4-tetrahydroisoquinoline-2-carbonyl)-1-methylcyclohexane-1-carboxylic acid;

(1S,2R,4S)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-4-fluoro-1-methylcyclohexane-1-carboxylic acid; and (1S,2R,4R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic-4-d acid;

or a pharmaceutically acceptable salt thereof.

In an embodiment, the compound of formula I is selected from the following compounds:

(1S,2R)-2-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-1-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)-1-methylcyclopentane-1-carboxylic acid;

(1S,2R)-2-((S)-5-chloro-8-((1,5-dimethyl-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5-cyclopropyl-1-methyl-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((4-(difluoromethyl)pyrimidin-5-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-1-((2-oxopyrrolidin-1-yl)methyl)-8-((4,5,6,7-tetrahydrobenzo[d]isoxazol-3-yl)methoxy)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic-4,4-d2 acid;

(1S,2R)-2-((S)-5-chloro-8-((1,5-dimethyl-1H-1,2,3-triazol-4-yl)methoxy)-7-fluoro-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-7-fluoro-1-((6-oxo-5-azaspiro[2.4]heptan-5-yl)methyl)-8-((4,5,6,7-tetrahydro-[1,2,3]triazolo[1,5-a]pyridin-3-yl)methoxy)-1,2,3,4-tetrahydroisoquinoline-2-carbonyl)-1-methylcyclohexane-1-carboxylic acid;

(1S,2R)-2-((S)-5-chloro-8-((5,6-dihydro-4H-pyrrolo[1,2-c][1,2,3]triazol-3-yl)methoxy)-7-fluoro-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-methyl-1H-1,2,3-triazol-4-yl)methoxy)-7-fluoro-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((1-methyl-5-(trifluoromethyl)-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((1,5-dimethyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5-cyclopropyl-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5-(methoxymethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5-cyclopropyl-1-methyl-1H-1,2,3-triazol-4-yl)methoxy)-1-(((R)-4-methyl-2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-1-((6-oxo-5-azaspiro[2.4]heptan-5-yl)methyl)-8-((4,5,6,7-tetrahydro-[1,2,3]triazolo[1,5-a]pyridin-3-yl)methoxy)-1,2,3,4-tetrahydroisoquinoline-2-carbonyl)-1-methylcyclohexane-1-carboxylic acid;

(1S,2R)-2-((S)-5-chloro-8-((5,6-dihydro-4H-pyrrolo[1,2-c][1,2,3]triazol-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-fluoro-1-((6-oxo-5-azaspiro[2.4]heptan-5-yl)methyl)-8-((4,5,6,7-tetrahydro-[1,2,3]triazolo[1,5-a]pyridin-3-yl)methoxy)-1,2,3,4-tetrahydroisoquinoline-2-carbonyl)-1-methylcyclohexane-1-carboxylic acid;

(1S,2R)-2-((S)-5-chloro-8-((6,7-dihydro-4H-[1,2,3]triazolo[5,1-c][1,4]oxazin-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-1-((3-oxomorpholino)methyl)-8-((4,5,6,7-tetrahydro-[1,2,3]triazolo[1,5-a]pyridin-3-yl)methoxy)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)cyclohexane-1-carboxylic acid;

(1S,2R)-2-((S)-5-bromo-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((1-methyl-5-(oxetan-3-yl)-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,6R)-6-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohex-3-ene-1-carboxylic acid;

(1S,2R)-2-((S)-5-chloro-8-((5-(difluoromethyl)-1-methyl-1H-1,2,3-triazol-4-yl)methoxy)-7-fluoro-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1R,3S,4R,6S)-4-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-3-methylbicyclo[4.1.0]heptane-3-carboxylic acid;

(1S,2R,4S,5R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic-4,5-d2 acid;

(1S,2R,4S)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-4-fluoro-1-methylcyclohexane-1-carboxylic acid; and (1S,2R,4R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic-4-d acid;

or a pharmaceutically acceptable salt thereof.

In an embodiment, the compound of formula I is selected from the following compounds:

(1S,2R)-2-((S)-5-chloro-8-((1-methyl-5-(trifluoromethyl)-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-methyl-1H-1,2,3-triazol-4-yl)methoxy)-1-(((R)-4-methyl-2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic-4,4-d2 acid;

(1S,2R)-2-((S)-5-chloro-8-((1,5-dimethyl-1H-1,2,3-triazol-4-yl)methoxy)-7-fluoro-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-7-fluoro-1-((6-oxo-5-azaspiro[2.4]heptan-5-yl)methyl)-8-((4,5,6,7-tetrahydro-[1,2,3]triazolo[1,5-a]pyridin-3-yl)methoxy)-1,2,3,4-tetrahydroisoquinoline-2-carbonyl)-1-methylcyclohexane-1-carboxylic acid;

(1S,2R)-2-((S)-5-chloro-8-((5,6-dihydro-4H-pyrrolo[1,2-c][1,2,3]triazol-3-yl)methoxy)-7-fluoro-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-methyl-1H-1,2,3-triazol-4-yl)methoxy)-7-fluoro-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((1,5-dimethyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-methyl-1H-1,2,3-triazol-4-yl)methoxy)-7-fluoro-1-((6-oxo-5-azaspiro[2.4]heptan-5-yl)methyl)-1,2,3,4-tetrahydroisoquinoline-2-carbonyl)-1-methylcyclohexane-1-carboxylic acid; and (1S,2R,4R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic-4-d acid;

or a pharmaceutically acceptable salt thereof.

The various functional groups and substituents making up the compounds of the present invention are typically chosen such that the molecular weight of the compound does not exceed 1000. More usually, the molecular weight of the compound will be less than 750, for example less than 700, or less than 650.

Suitable or preferred features of any compounds of the present invention may also be suitable features of any other aspect.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric centre, for example, it is bonded to four different groups, a pair of enantiomers is possible. An enantiomer can be characterized by the absolute configuration of its asymmetric centre and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention typically possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers, diastereoisomers and mixtures, racemic or otherwise, thereof. The methods for the determination of stereochemistry and the separation of stereoisomers are well-known in the art (see discussion in Chapter 4 of "*Advanced Organic Chemistry*", 4th edition J. March, John Wiley and Sons, New York, 2001), for example by synthesis from optically active starting materials or by resolution of a racemic form. Some of the compounds of the invention may have geometric isomeric centres (E- and Z- isomers). It is to be understood that the present invention encompasses all optical, diastereoisomers and geometric isomers and mixtures thereof that possess Nrf2 activation activity.

The present invention also encompasses compounds of the invention as defined herein which comprise one or more isotopic substitutions. For example, H may be in any isotopic form, including $^{1}H$, $^{2}H$ (D) and $^{3}H$ (T); C may be in any isotopic form including $^{12}C$, $^{13}C$, and $^{14}C$; and O may be in any isotopic form, including $^{16}O$ and $^{18}O$; and the like.

It is also to be understood that certain compounds of the invention may exist in solvated as well as unsolvated forms such as, for example, hydrated forms. It is to be understood that the invention encompasses all such solvated forms that possess Nrf2 activation activity.

It is also to be understood that certain compounds of the invention may exhibit polymorphism, and that the invention encompasses all such forms that possess Nrf2 activation activity.

Compounds of the invention may exist in a number of different tautomeric forms and references to compounds of the invention include all such forms. For the avoidance of doubt, where a compound can exist in one of several tautomeric forms, and only one is specifically described or shown, all others are nevertheless embraced by compounds of the invention. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

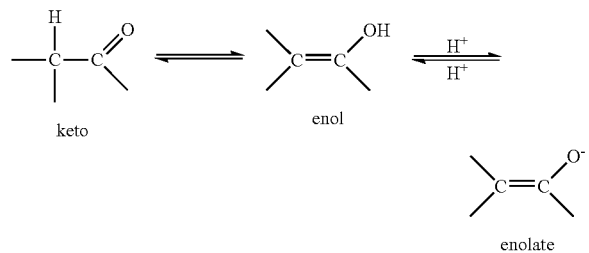

Compounds of the invention containing an amine function may also form N-oxides. A reference herein to a compound of the formula I that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4th Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

The compounds of the invention may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the invention and in-vivo cleavable amide derivatives that may be formed at a carboxy group or an amino group in a compound of the invention.

Accordingly, the present invention includes those compounds of the formula I as defined hereinbefore when made available by organic synthesis and when made available within the human or animal body by way of cleavage of a pro-drug thereof. Accordingly, the present invention includes those compounds of the formula I that are produced by organic synthetic means and also such compounds that are produced in the human or animal body by way of metabolism of a precursor compound, that is a compound of the formula I may be a synthetically-produced compound or a metabolically-produced compound.

A suitable pharmaceutically acceptable pro-drug of a compound of the formula I is one that is based on reasonable medical judgement as being suitable for administration to the human or animal body without undesirable pharmacological activities and without undue toxicity.

Various forms of pro-drug have been described, for example in the following documents:
a) *Methods in Enzymology*, Vol. 42, p. 309-396, edited by K. Widder, et al. (Academic Press, 1985);
b) *Design of Pro-drugs*, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", *A.C.S. Symposium Series*, Volume 14; and
h) E. Roche (editor), "*Bioreversible Carriers in Drug Design*", Pergamon Press, 1987.

A suitable pharmaceutically acceptable pro-drug of a compound of the formula I that possesses a carboxy group is, for example, an in vivo cleavable ester thereof. An in vivo cleavable ester of a compound of the formula I containing a carboxy group is, for example, a pharmaceutically acceptable ester which is cleaved in the human or animal body to produce the parent acid. Suitable pharmaceutically acceptable esters for carboxy include $C_{1-6}$alkyl esters such as methyl, ethyl and tert-butyl, $C_{1-6}$alkoxymethyl esters such as methoxymethyl esters, $C_{1-6}$alkanoyloxymethyl esters such as pivaloyloxymethyl esters, 3-phthalidyl esters, $C_{3-8}$cycloalkylcarbonyloxy-$C_{1-6}$alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and $C_{1-6}$alkoxycarbonyloxy-$C_{1-6}$alkyl esters such as methoxycarbonyloxymethyl and 1-methoxycarbonyloxyethyl esters.

A suitable pharmaceutically acceptable pro-drug of a compound of the formula I that possesses a hydroxy group is, for example, an in vivo cleavable ester or ether thereof. An in vivo cleavable ester or ether of a compound of the formula I containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_{1-10}$alkanoyl groups such as acetyl, benzoyl, phenylacetyl and substituted benzoyl and phenylacetyl groups, $C_{1-10}$alkoxycarbonyl groups such as ethoxycarbonyl, N,N—$(C_{1-6})_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable pro-drug of a compound of the formula I that possesses a carboxy group is, for example, an in vivo cleavable amide thereof, for example an amide formed with an amine such as ammonia, a $C_{1-4}$alkylamine such as methylamine, a $(C_{1-4}$alkyl$)_2$ amine such as dimethylamine, N-ethyl-N-methylamine or diethylamine, a $C_{1-4}$alkoxy-$C_{2-4}$alkylamine such as 2-methoxyethylamine, a phenyl-$C_{1-4}$alkylamine such as benzylamine and amino acids such as glycine or an ester thereof.

A suitable pharmaceutically acceptable pro-drug of a compound of the formula I that possesses an amino group is, for example, an in vivo cleavable amide derivative thereof. Suitable pharmaceutically acceptable amides from an amino group include, for example an amide formed with $C_{1-10}$alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl.

The in vivo effects of a compound of the formula I may be exerted in part by one or more metabolites that are formed within the human or animal body after administration of a compound of the formula I. As stated hereinbefore, the in vivo effects of a compound of the formula I may also be exerted by way of metabolism of a precursor compound (a pro-drug).

It shall also be appreciated that compounds of the formula I may also be covalently linked (at any suitable position) to other groups such as, for example, solubilising moieties (for example, PEG polymers), moieties that enable them to be bound to a solid support (such as, for example, biotin-containing moieties), and targeting ligands (such as antibodies or antibody fragments).

Synthesis

In the description of the synthetic methods described below and in the referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

Necessary starting materials may be obtained by standard procedures of organic chemistry. The preparation of such starting materials is described in conjunction with the following representative process variants and within the accompanying Examples. Alternatively, necessary starting materials are obtainable by analogous procedures to those illustrated which are within the ordinary skill of an organic chemist.

It will be appreciated that during the synthesis of the compounds of the invention in the processes defined below, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, "Protecting groups in Organic Synthesis ($3^{rd}$ Ed), John Wiley & Sons, NY (1999)", T. Greene & P. Wuts. Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively, an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example $BF_3 \cdot OEt_2$. A suitable alternative protecting group for a primary amino group is, for example, a phthaloyl group which may be removed by treatment with an alkylamine, for example dimethylaminopropylamine, or with hydrazine.

The person skilled in the art will recognise that the compounds of the invention may be prepared, in known manner, in a variety of ways. Compounds of formula I can be prepared by the methods given below, by the methods given in the experimental or by analogous methods. The routes described are merely illustrative of some of the methods that can be employed for the synthesis of compounds of formula I and the person skilled in the art will appreciate that the order of the reaction steps is not limited to those described. It will also be appreciated that the assignment of nucleophile and electrophile is not limited to that described herein and in some cases it may be appropriate for the assignment to be reversed. Different approaches to synthetic chemistry strategy are described in "Organic Synthesis: The Disconnection Approach", 2$^{nd}$ edition, S. Warren and P. Wyatt (2008).

General Method A

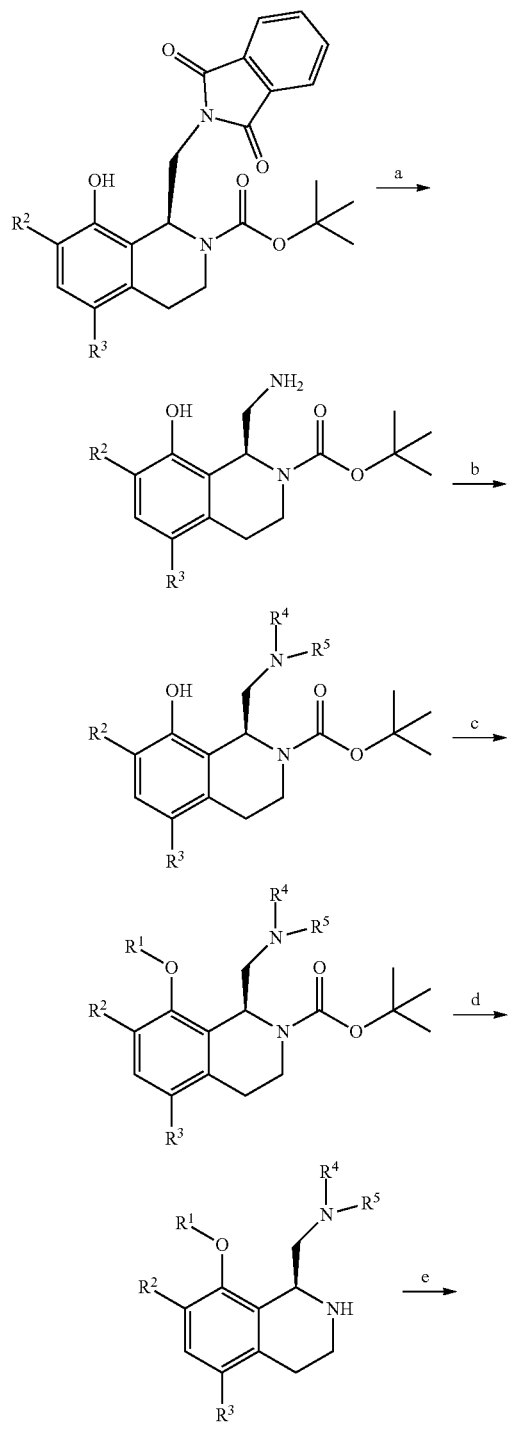

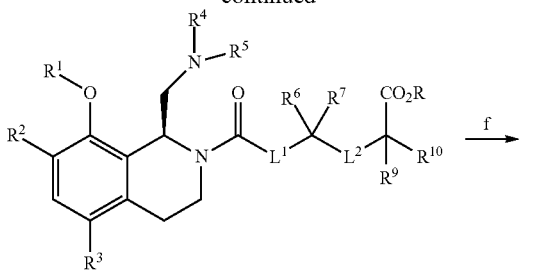

In a typical synthetic procedure the phthalimide, when used as a protecting group, is removed using typical reagents (e.g. hydrazine) and the amine is reacted with appropriate reagents to install the desired substitution NR$^4$R$^5$. A third step involves installation of the required ether through conventional methods such as alkylation with an alkyl halide or activated alcohol e.g. mesylate, triflate) or Mitsunobu reaction using reagents such as DBAD or DEAD and an appropriate phosphine. The Boc protecting group is then removed typically by treatment with HCl. The L$^1$C(R$^6$)(R$^7$)L$^2$C(R$^8$)(R$^9$)R$^{10}$ group may be introduced from the appropriately substituted and protected bis-acid derivative; ideally where one of the acid groups is activated for reaction with the amine of the tetrahydroisoquinoline (THIQ) scaffold and the other acid group is suitably protected, for example as a benzyl or dimethoxybenzyl ester, or by ring opening of an appropriate cyclic anhydride, or by reaction with an acid chloride. Typical amide coupling reagents such as HATU are used to effect acid activion. In a final step, the protecting group is removed from the carboxylic acid by the appropriate methodology such as hydrolysis, hydrogenolysis, strong acid such as HCl or TFA or lewis acid such as BBr$_3$.

General Method B

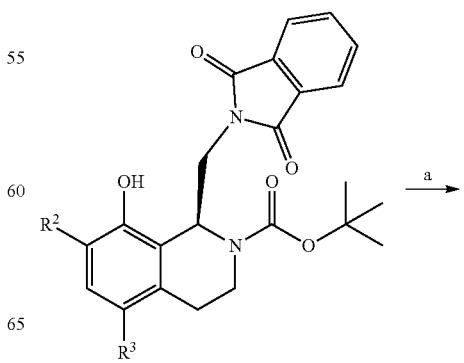

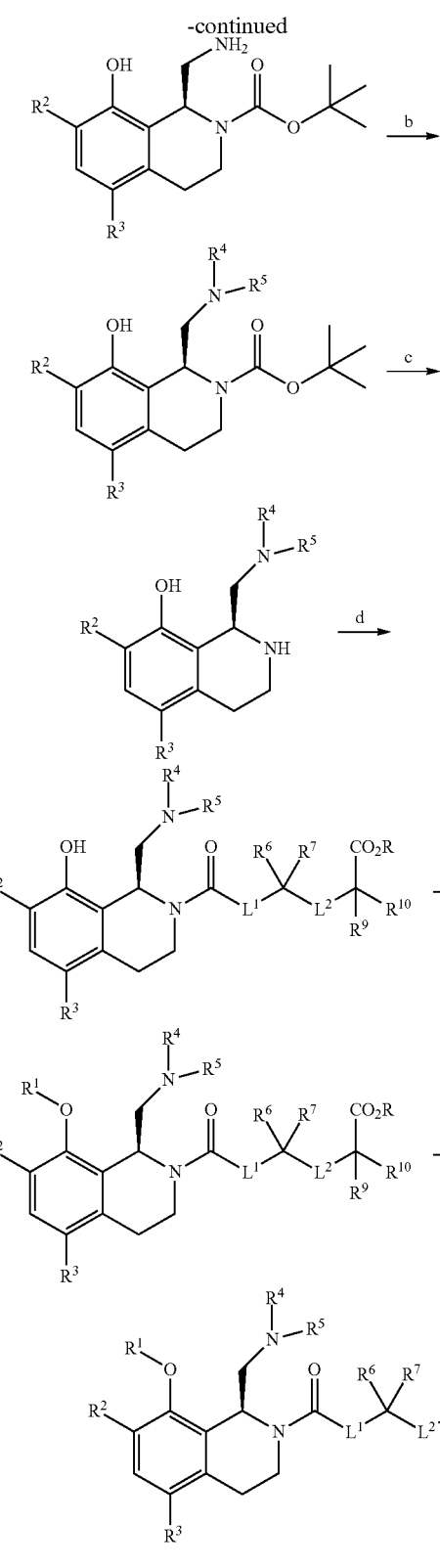

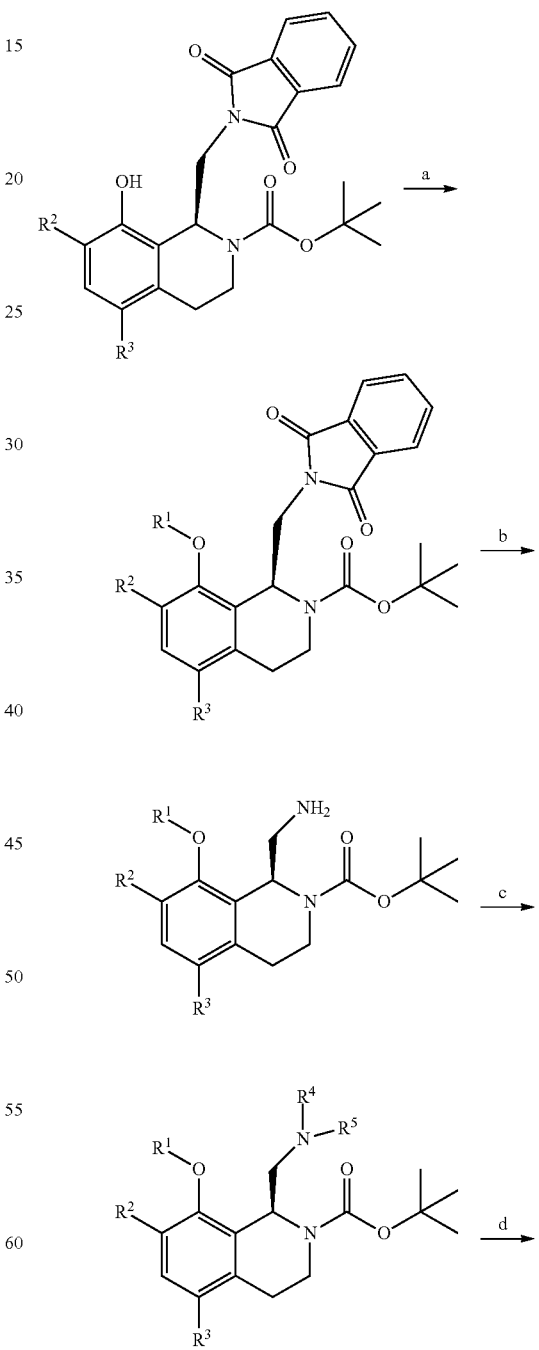

described in general method A, followed by installation of the required ether through conventional methods such as alkylation with an alkyl halide or activated alcohol e.g. mesylate, triflate) or Mitsunobu reaction using reagents such as DBAD or DEAD and an appropriate phosphine. In a final step, the protecting group is removed from the carboxylic acid by the appropriate methodology such as hydrolysis, hydrogenolysis, strong acid such as HCl or TFA or lewis acid such as $BBr_3$.

General Method C

In a further typical procedure, the order of steps can be altered compared with general method A. The first two steps are carried out as described in general method A. In a third step the Boc protecting group ($CO_2{}^tBu$) is then removed typically by treatment with HCl. The $L^1C(R^6)(R^7)L^2C(R^8)(R^9)R^{10}$ group may then be introduced in a fourth step as

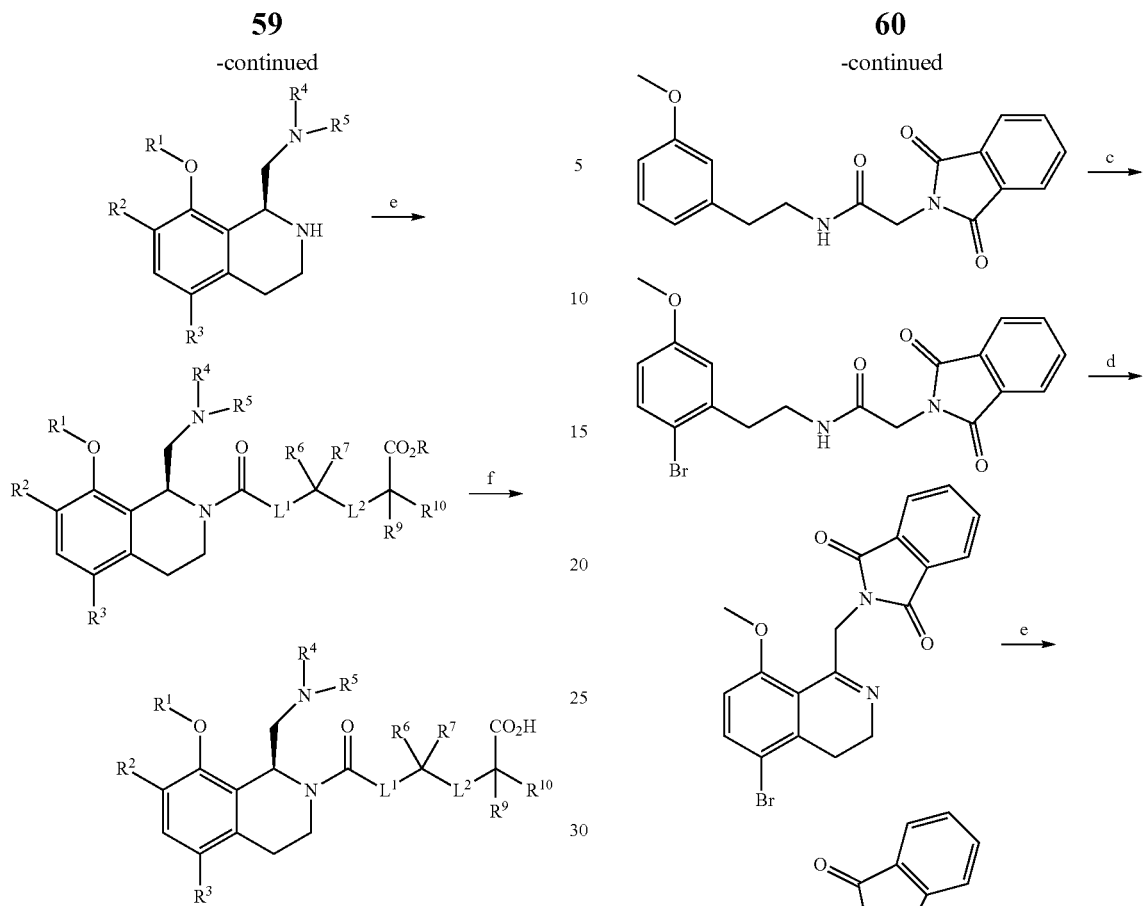

In a further typical procedure, the order of steps can be altered compared with general methods A and B. The required ether is installed in a first step, again through conventional methods as described in the above General Methods A and B. The phthalimide protecting group is removed in a second step and the amine is reacted with appropriate reagents to install the desired substitution NR⁴R⁵. The Boc protecting group is then removed and the L¹C(R⁶)(R⁷)L²C(R⁸)(R⁹)R¹⁰ group may then be introduced in a fifth step. The final step comprises removal of the carboxylic acid protecting group as described in the above general methods.

The THIQ scaffold, wherein R³ is bromo, may be constructed according to the route outlined in Scheme 1

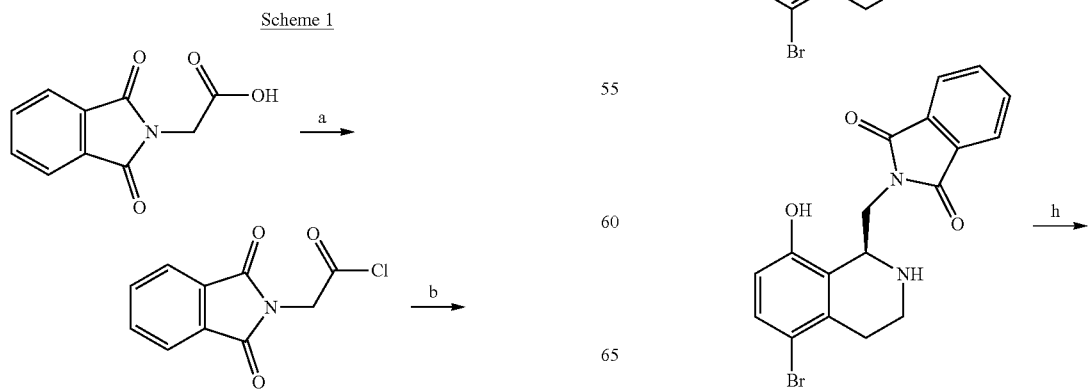

Scheme 1

-continued

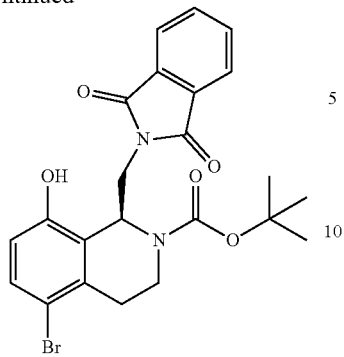

a) SOCl₂, EtOAc; b) 2-(3-methoxyphenyl)ethan-1-amine, Et₃N, DCM; c) NBS, DMF; d) P₂O₅, MeCN; e) benzeneruthenium(II) chloride dimer, (1S,2S)-(+)-N-p-tosyl-1,2-diphenylethylene-diamine, Et₃N, HCO₂H, MeCN; f) HCl, THF; g) BBr₃, DCM; h) Boc₂O, DCM.

Compounds where $R^8$ is —COOH can be converted to other groups as defined by $R^8$ in Formula 1 by commonly known methods, such as tetrazole via reaction of the appropriate nitrile with an azide, as shown in Scheme 2.

Scheme 2

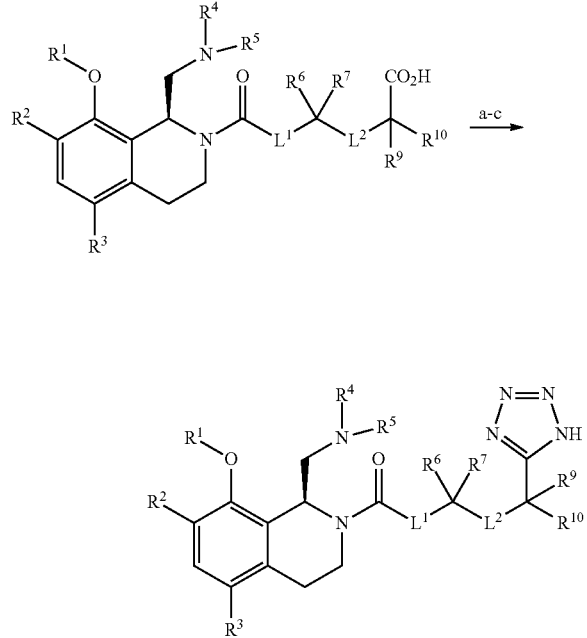

a) HATU, DIPEA, NH₄Cl, DMF; b) POCl₃, imidazole, pyridine; c) ⁿBu₃SnN₃, xylene.

Variations at the $R^3$ position can be conveniently prepared from compounds of the invention or intermediates thereof wherein $R^3$ is bromo from chemistry well known in the art, as illustrated in Schemes 3 and 4. Compounds of the invention wherein $R^3$ is H, or Cl may be prepared from intermediates where $R^3$ is Br according to the method outlined in Scheme 3.

Scheme 3

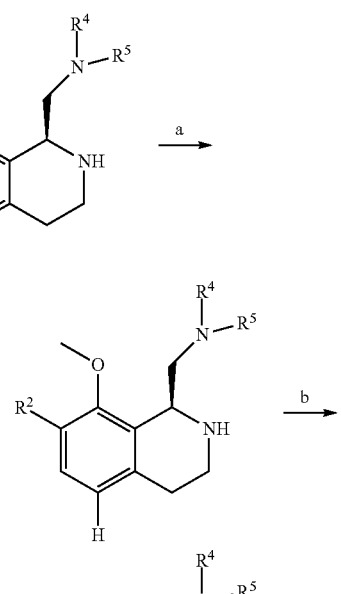

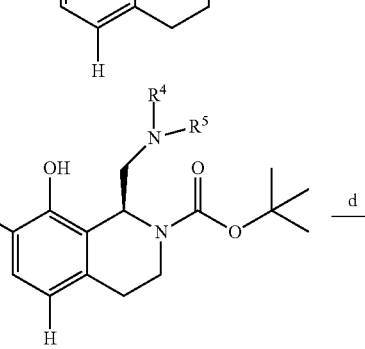

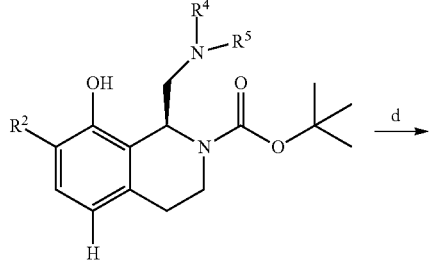

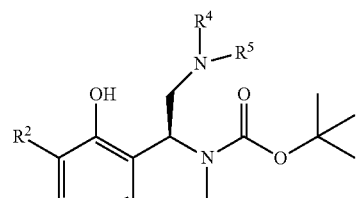

a) H₂, 10% Pd/C, THF, EtOH; b) BBr₃, DCM; c) Boc₂O, DCM; d) NCS, DMF.

As shown in Scheme 4, the conversion of the bromo $R^3$ substituent into a suitable boronate or boronic acid allows preparation of the fluoro and trifluoro derivatives. The bromo can be converted to an alkyl group through reaction with a suitable alkyl boronate with a suitable palladium catalyst; for example, where alkyl is methyl, a suitable boronate is 2,4,6-trimethyl-1,3,5,2,4,6-trioxatriborinane and a suitable palladium catalyst is Pd(dppf)Cl₂. Compounds wherein $R^3$ is cyano can be prepared from bromo derivatives by treatment with a cyanating agent such as Zn(CN)₂ with a palladium catalyst such as Pd(PPh₃)₄.

Scheme 4

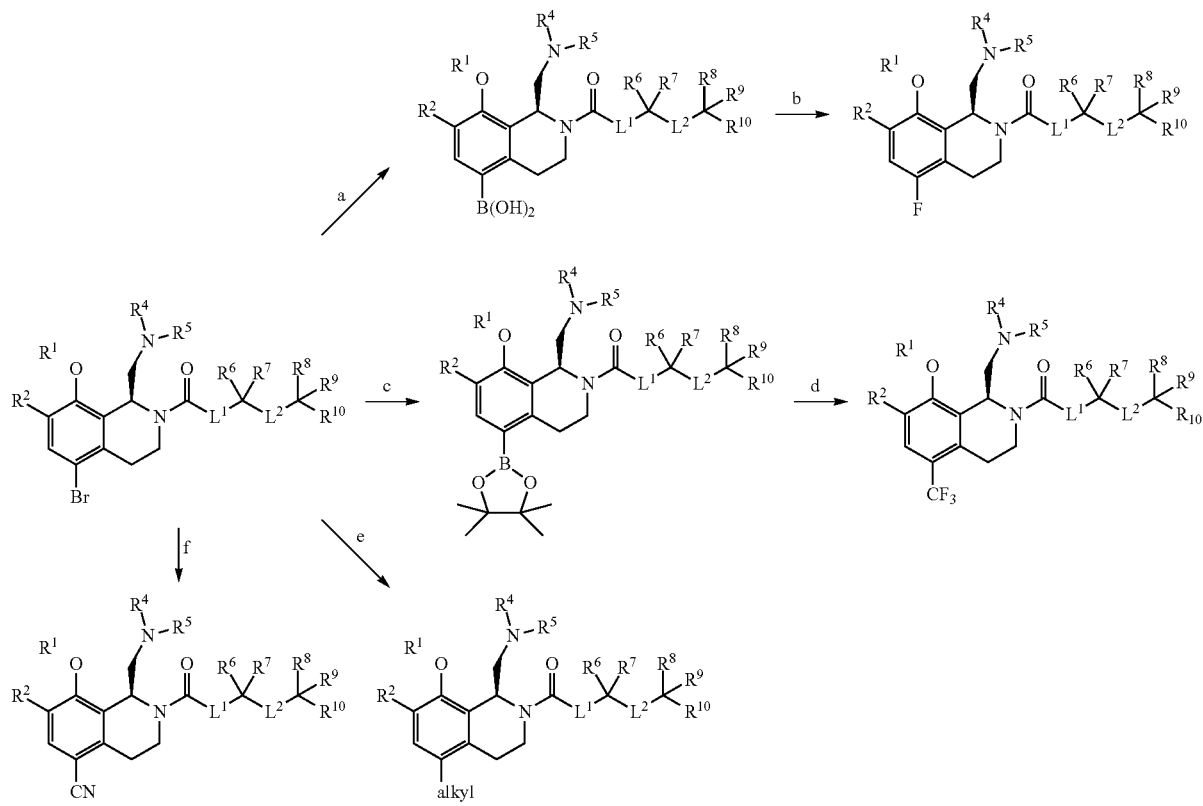

a) dicyclohexyl-[2-(2,4,6-triisopropylphenyl)phenyl]phosphane, X-phos PD, hypoboric acid; b) CF$_3$SO$_3$Ag, SelectFluor®; c) bis(pinacolato)diboron, Pd(dppf)Cl$_2$; d) potassium trimethoxy(trifluoromethyl)boranide, Cu(OAc)$_2$; e) Pd(dppf)Cl$_2$, alkyl borane; f) Zn(CN)$_2$, Pd(PPh$_3$)$_4$.

Compounds of the invention wherein —NR$^4$R$^5$ represents an indolinone may be prepared by reduction of the corresponding phthalimide sequentially with sodium borohydride and then triethylsilane, according to Scheme 5.

Scheme 5

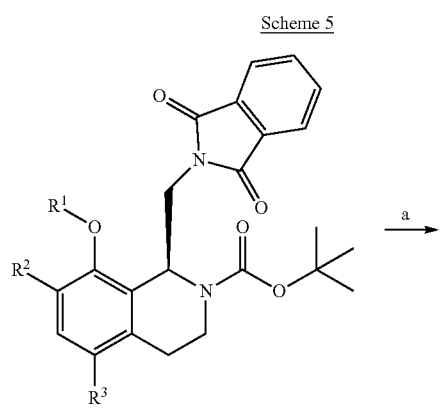

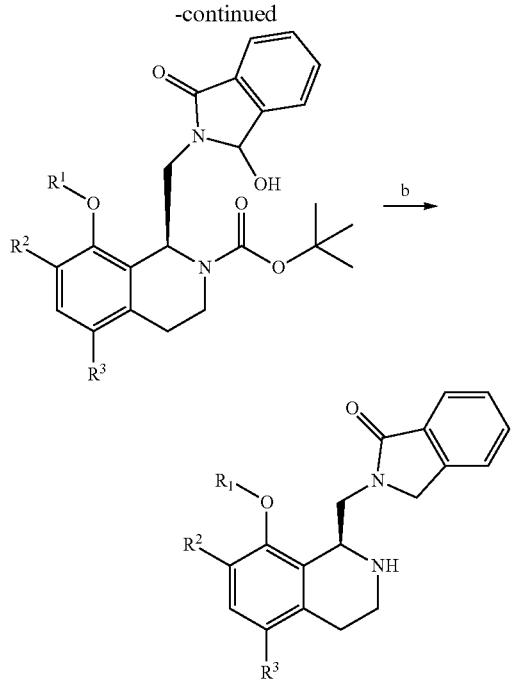

a) NaBH$_4$, MeOH; b) TFA, Et$_3$SiH.

Compounds of the invention wherein the group —NR⁴R⁵ represents a pyrrolidinone may be prepared from intermediates wherein —NR⁴R⁵ represents a phthalimide group by removal of the phthalimide group with hydrazine, followed by conversion of the resulting primary amine to a pyrrolidinone by reaction with an appropriate lactone or co-halo ester, or to an indolinone according to the routes outlined in Scheme 6.

Scheme 6

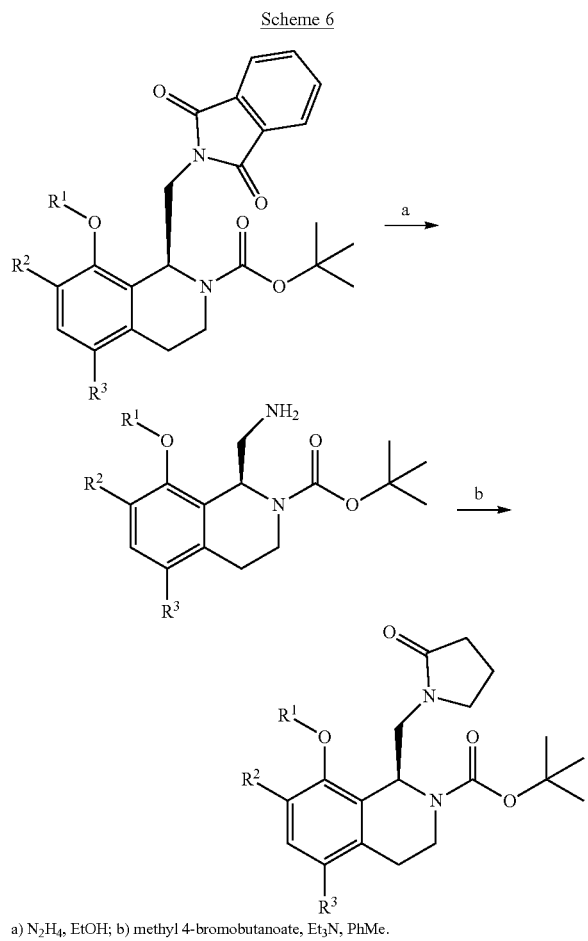

a) N₂H₄, EtOH; b) methyl 4-bromobutanoate, Et₃N, PhMe.

Compounds of the invention wherein R² is a halo substituent may be prepared from intermediates or Examples of the invention wherein R² is hydrogen by treatment with a suitable halogenating agent, such as N-chlorosuccinimide, as shown in Scheme 7.

Scheme 7

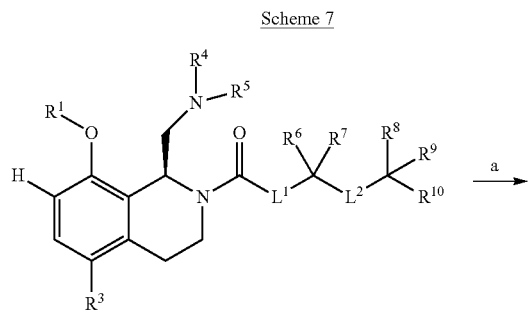

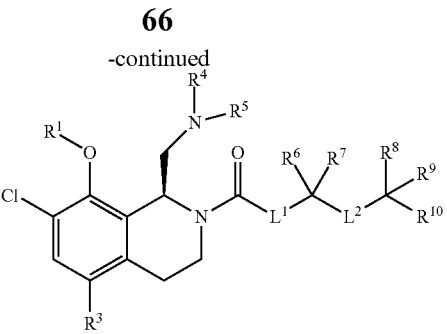

a) NCS, DCM/DMF.

Pharmaceutical Compositions

The compounds of the invention will normally, but not necessarily, be formulated into pharmaceutical compositions prior to administration to a patient. Therefore, according to a further aspect of the invention there is provided a pharmaceutical composition which comprises a compound of the invention as defined hereinbefore, or a pharmaceutically acceptable salt thereof, and one or more pharmaceutically acceptable excipients, diluent or carrier.

The pharmaceutical compositions of the invention may be prepared and packaged in bulk form wherein a safe and effective amount of a compound of the invention can be extracted and then given to the patient such as with powders or syrups. Alternatively, the pharmaceutical compositions of the invention may be prepared and packaged in unit dosage form wherein each physically discrete unit contains a safe and effective amount of a compound of the invention. When prepared in unit dosage form, the pharmaceutical compositions of the invention typically contain from 1 mg to 1000 mg.

The compositions of the invention may be in a form suitable for oral use (for example as tablets, capsules, caplets, pills, troches, powders, syrups, elixirs, suspensions, solutions, emulsions, sachets, and cachets), for topical use (for example as creams, ointments, lotions, solutions, pastes, sprays, foams, and gels), for transdermal administration such as via transdermal patches, for administration by inhalation (for example as a dry powders, aerosols, suspensions, and solutions), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must be of sufficiently high purity to render it pharmaceutically-acceptable.

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting of the compound or compounds of the invention once administered to the patient from one organ, or portion of the body, to another organ, or portion of the body. Certain pharmaceutically-acceptable excipients may be chosen for their ability to enhance patient compliance.

Suitable pharmaceutically-acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. The person skilled in the art will appreciate that certain pharmaceutically-acceptable excipients may serve more than one function and may serve alternative functions depending on how much of the excipient is present in the formulation and what other ingredients are present in the formulation.

Persons skilled in the art possess the knowledge and skill to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the formula I will naturally vary according to the nature and severity of the conditions, the age and sex of the animal or patient and the route of administration, according to well-known principles of medicine.

In using a compound of the invention for therapeutic or prophylactic purposes it will generally be administered so that a daily dose in the range, for example, 0.1 mg/kg to 75 mg/kg body weight is received, given if required in divided doses. In general, lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Routes of Administration

The compounds of the invention or pharmaceutical composition comprising the active compound may be administered to a subject by any convenient route of administration, whether systemically/peripherally or topically (i.e. at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

In a preferred embodiment, a compound of the invention as defined herein, or a pharmaceutically acceptable salt thereof, or a pharmaceutical composition as defined herein, is administered orally or via inhalation.

Therapeutic Uses and Applications

The compounds of the invention are activators of Nrf2. As a consequence, they are potentially useful therapeutic agents for the treatment of diseases or conditions mediated by Nrf2 activation.

Thus, in one aspect, the present invention relates to a compound of the invention as defined herein, or a pharmaceutically acceptable salt thereof, or a pharmaceutical composition as defined herein, for use in therapy.

In another aspect, the present invention relates to a compound of the invention as defined herein, or a pharmaceutically acceptable salt thereof, or a pharmaceutical composition as defined herein, for use in the treatment of diseases or disorders mediated by Nrf2 activation.

In another aspect, the present invention relates to the use of a compound of the invention as defined herein, or a pharmaceutically acceptable salt thereof, in the manufacture of a medicament for use in the treatment of diseases or disorders mediated by Nrf2 activation.

In another aspect, the present invention relates to a method of treating a disease or disorders mediated by Nrf2 activation, said method comprising administering to a subject in need of such treatment a therapeutically effective amount of a compound of the invention as defined herein, or a pharmaceutically acceptable salt thereof, or a pharmaceutical composition as defined herein.

Examples of particular diseases or conditions that the compounds of formula (I) and their pharmaceutically acceptable salts may be used to treat include, but are not limited to, any one of the following: chronic obstructive pulmonary disease, acute, chronic and severe asthma, acute lung injury/acute respiratory distress syndrome with or without accompanying multi organ dysfunction syndrome, pulmonary fibrosis including idiopathic pulmonary fibrosis, cystic fibrosis, diabetes, atherosclerosis, hypertension, heart failure, myocardial infarction and repair, cardiac remodelling, cardiac arrhythmias, cardiac hypertrophy, heart failure with preserved ejection fraction, diabetic cardiomyopathy, obesity, metabolic syndrome, diabetes mellitus, insulin resistance, pulmonary arterial hypertension, subarachnoid haemorrhage, intracerebral haemorrhage, ischemic stroke, beta-thalassemia, sickle cell disease, rheumatoid arthritis, irritable bowel disorder, ulcerative colitis, Crohn's disease, psoriasis, radiation-induced dermatitis, atopic dermatitis, non-alcoholic fatty liver disease, non-alcoholic steatohepatitis, toxin-induced liver disease, viral hepatitis and cirrhosis, chronic kidney disease, diabetic nephropathy, autosomal dominant polycystic kidney disease, CKD associated with type 1 diabetes (T1D), IgA nephropathy (IgAN), Alport Syndrome, focal segmental glomerulosclerosis, Huntington's disease, Parkinson's disease, Alzheimer's disease, amyotrophic lateral sclerosis, frontotemporal dementia, multiple sclerosis, Friedreich's ataxia, lung cancer, breast cancer, colon cancer, age related macular degeneration (AMD), Fuchs Endothelial Corneal Dystrophy or uveitis.

In particular, the compounds of the invention (including pharmaceutically acceptable salts) may be used in the treatment of chronic obstructive pulmonary disease, asthma, pulmonary arterial hypertension, diabetes mellitus, chronic kidney disease, Friedreich's ataxia, sickle cell disease or non-alcoholic steatohepatitis.

In another aspect, the present invention provides a compound, or a pharmaceutically acceptable salt thereof, or a pharmaceutical composition as defined herein, for use in the treatment of chronic obstructive pulmonary disease, acute, chronic and severe asthma, acute lung injury/acute respiratory distress syndrome with or without accompanying multi organ dysfunction syndrome, pulmonary fibrosis including idiopathic pulmonary fibrosis, cystic fibrosis, diabetes, atherosclerosis, hypertension, heart failure, myocardial infarction and repair, cardiac remodelling, cardiac arrhythmias, cardiac hypertrophy, heart failure with preserved ejection fraction, diabetic cardiomyopathy, obesity, metabolic syndrome, diabetes mellitus, insulin resistance, pulmonary arterial hypertension, subarachnoid haemorrhage, intracerebral haemorrhage, ischemic stroke, beta-thalassemia, sickle cell disease, rheumatoid arthritis, irritable bowel disorder, ulcerative colitis, Crohn's disease, psoriasis, radiation-induced dermatitis, atopic dermatitis, non-alcoholic fatty liver disease, non-alcoholic steatohepatitis, toxin-induced liver disease, viral hepatitis and cirrhosis, chronic kidney disease, diabetic nephropathy, autosomal dominant polycystic kidney disease, CKD associated with type 1 diabetes (T1D), IgA nephropathy (IgAN), Alport Syndrome, focal segmental glomerulosclerosis, Huntington's disease, Parkinson's disease, Alzheimer's disease, amyotrophic lateral sclerosis, frontotemporal dementia, multiple sclerosis, Friedreich's ataxia, lung cancer, breast cancer, colon cancer, age related macular degeneration (AMD), Fuchs Endothelial Corneal Dystrophy or uveitis.

In another aspect, the present invention provides a compound, or a pharmaceutically acceptable salt thereof, or a pharmaceutical composition as defined herein, for use in the treatment of chronic obstructive pulmonary disease, asthma, pulmonary arterial hypertension, diabetes mellitus, chronic kidney disease, Friedreich's ataxia, sickle cell disease or non-alcoholic steatohepatitis.

In another aspect, the present invention provides the use of a compound, or a pharmaceutically acceptable salt thereof, in the manufacture of a medicament for use in the treatment of chronic obstructive pulmonary disease, acute, chronic and severe asthma, acute lung injury/acute respiratory distress syndrome with or without accompanying multi organ dysfunction syndrome, pulmonary fibrosis including idiopathic pulmonary fibrosis, cystic fibrosis, diabetes, atherosclerosis, hypertension, heart failure, myocardial infarction and repair, cardiac remodelling, cardiac arrhythmias, cardiac hypertrophy, heart failure with preserved ejection fraction, diabetic cardiomyopathy, obesity, metabolic syndrome, diabetes mellitus, insulin resistance, pulmonary arterial hypertension, subarachnoid haemorrhage, intracerebral haemorrhage, ischemic stroke, beta-thalassemia, sickle cell disease, rheumatoid arthritis, irritable bowel disorder, ulcerative colitis, Crohn's disease, psoriasis, radiation-induced dermatitis, atopic dermatitis, non-alcoholic fatty liver disease, non-alcoholic steatohepatitis, toxin-induced liver disease, viral hepatitis and cirrhosis, chronic kidney disease, diabetic nephropathy, autosomal dominant polycystic kidney disease, CKD associated with type 1 diabetes (T1D), IgA nephropathy (IgAN), Alport Syndrome, focal segmental glomerulosclerosis, Huntington's disease, Parkinson's disease, Alzheimer's disease, amyotrophic lateral sclerosis, frontotemporal dementia, multiple sclerosis, Friedreich's ataxia, lung cancer, breast cancer, colon cancer, age related macular degeneration (AMD), Fuchs Endothelial Corneal Dystrophy or uveitis.

In another aspect, the present invention provides the use of a compound, or a pharmaceutically acceptable salt thereof, in the manufacture of a medicament for use in the treatment of chronic obstructive pulmonary disease, asthma, pulmonary arterial hypertension, diabetes mellitus, chronic kidney disease, Friedreich's ataxia, sickle cell disease or non-alcoholic steatohepatitis.

In another aspect, the present invention provides a method of treating chronic obstructive pulmonary disease, acute, chronic and severe asthma, acute lung injury/acute respiratory distress syndrome with or without accompanying multi organ dysfunction syndrome, pulmonary fibrosis including idiopathic pulmonary fibrosis, cystic fibrosis, diabetes, atherosclerosis, hypertension, heart failure, myocardial infarction and repair, cardiac remodelling, cardiac arrhythmias, cardiac hypertrophy, heart failure with preserved ejection fraction, diabetic cardiomyopathy, obesity, metabolic syndrome, diabetes mellitus, insulin resistance, pulmonary arterial hypertension, subarachnoid haemorrhage, intracerebral haemorrhage, ischemic stroke, beta-thalassemia, sickle cell disease, rheumatoid arthritis, irritable bowel disorder, ulcerative colitis, Crohn's disease, psoriasis, radiation-induced dermatitis, atopic dermatitis, non-alcoholic fatty liver disease, non-alcoholic steatohepatitis, toxin-induced liver disease, viral hepatitis and cirrhosis, chronic kidney disease, diabetic nephropathy, autosomal dominant polycystic kidney disease, CKD associated with type 1 diabetes (T1D), IgA nephropathy (IgAN), Alport Syndrome, focal segmental glomerulosclerosis, Huntington's disease, Parkinson's disease, Alzheimer's disease, amyotrophic lateral sclerosis, frontotemporal dementia, multiple sclerosis, Friedreich's ataxia, lung cancer, breast cancer, colon cancer, age related macular degeneration (AMD), Fuchs Endothelial Corneal Dystrophy or uveitis, said method comprising administering to a subject in need of such treatment a therapeutically effective amount of a compound, or a pharmaceutically acceptable salt thereof, or a pharmaceutical composition as defined herein.

In another aspect, the present invention provides a method of treating chronic obstructive pulmonary disease, asthma, pulmonary arterial hypertension, diabetes mellitus, chronic kidney disease, Friedreich's ataxia, sickle cell disease or non-alcoholic steatohepatitis, said method comprising administering to a subject in need of such treatment a therapeutically effective amount of a compound, or a pharmaceutically acceptable salt thereof, or a pharmaceutical composition as defined herein.

In another aspect, the present invention provides a method of activating Nrf2 in vitro, said method comprising administering an effective amount of a compound, or a pharmaceutically acceptable salt thereof.

In another aspect, the present invention provides a method of activating Nrf2 in vivo, said method comprising administering an effective amount of a compound, or a pharmaceutically acceptable salt thereof.

In another aspect, the present invention provides a method of activating Nrf2 in vitro and/or in vivo, said method comprising contacting a cell with an effective amount of a compound as defined herein, or a pharmaceutically acceptable salt thereof.

Combination Therapies

The compounds of the invention may be administered alone as a monotherapy or may administered in combination with one or more additional therapeutic agents. The selection of the one or more additional therapeutic agents will of course vary depending on the disease or condition to be treated and its severity.

It is commonplace to use combination therapies to treat certain medical conditions.

According to a particular aspect of the invention there is provided a combination suitable for use in the treatment of a disease or condition in which Nrf2 activation is implicated, comprising a compound of the invention as defined hereinbefore, or a pharmaceutically acceptable salt thereof, and another therapeutic agent.

According to this aspect of the invention there is provided a combination suitable for use in the prevention or treatment of chronic obstructive pulmonary disease, acute, chronic and severe asthma, acute lung injury/acute respiratory distress syndrome with or without accompanying multi organ dysfunction syndrome, pulmonary fibrosis including idiopathic pulmonary fibrosis, cystic fibrosis, diabetes, atherosclerosis, hypertension, heart failure, myocardial infarction and repair, cardiac remodelling, cardiac arrhythmias, cardiac hypertrophy, heart failure with preserved ejection fraction, diabetic cardiomyopathy, obesity, metabolic syndrome, diabetes mellitus, insulin resistance, pulmonary arterial hypertension, subarachnoid haemorrhage, intracerebral haemorrhage, ischemic stroke, beta-thalassemia, sickle cell disease, rheumatoid arthritis, irritable bowel disorder, ulcerative colitis, Crohn's disease, psoriasis, radiation-induced dermatitis, atopic dermatitis, non-alcoholic fatty liver disease, non-alcoholic steatohepatitis, toxin-induced liver disease, viral hepatitis and cirrhosis, chronic kidney disease, diabetic nephropathy, autosomal dominant polycystic kidney disease, CKD associated with type 1 diabetes (T1D), IgA nephropathy (IgAN), Alport Syndrome, focal segmental glomerulosclerosis, Huntington's disease, Parkinson's disease, Alzheimer's disease, amyotrophic lateral sclerosis, frontotemporal dementia, multiple sclerosis, Friedreich's ataxia, lung cancer, breast cancer, colon cancer, age related macular degeneration (AMD), Fuchs Endothelial Corneal Dystrophy or uveitis, the combination comprising a compound of the invention as defined hereinbefore, or a pharmaceutically acceptable salt thereof, and one or more additional therapeutic agents.

In a further aspect of the invention there is provided a compound of the invention or a pharmaceutically acceptable salt thereof, in combination with one or more additional therapeutic agents.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided a pharmaceutical composition which comprises a compound of the invention, or a pharmaceutically acceptable salt thereof in combination with one or more additional therapeutic agents in association with a pharmaceutically acceptable diluent or carrier.

The one or more additional therapeutic agents may comprise a further compound of the present invention. Therefore, in an embodiment, there is provided a pharmaceutical composition which comprises two compounds of the invention, or pharmaceutically acceptable salts thereof, in association with a pharmaceutically acceptable diluent or carrier.

According to a particular aspect of the invention there is provided a combination suitable for use in the prevention or treatment of allergic disease, inflammatory disease or autoimmune disease (e.g. asthma or COPD); a cardiovascular or metabolic disease (e.g. diabetes); a neurodegenerative disease; a chronic kidney or liver disease; sickle cell disease; pulmonary arterial hypertension; cancer; or for aiding transplantation.

According to a particular aspect of the invention there is provided a combination suitable for use in the prevention or treatment of chronic obstructive pulmonary disease, asthma, pulmonary arterial hypertension, diabetes mellitus, chronic kidney disease, Friedreich's ataxia, sickle cell disease or non-alcoholic steatohepatitis.

Examples of other therapeutic agents that may be used as part of a combination therapy with a compound of the present invention (e.g. as one of two or more active agents as part of double or triple combinations) include, but are not limited to, the following:

(i) beta2-adrenoreceptor agonists (which may be a racemate or a single enantiomer) including salmeterol, salbutamol, formoterol, salmefamol, fenoterol, carmoterol, etanterol, naminterol, clenbuterol, pirbuterol, flerbuterol, reproterol, bambuterol, indacaterol, terbutaline, vilanterol, olodaterol and salts thereof;

(ii) anticholinergic agents that act as antagonists at the muscarinic receptors that include ipratropium (for example, as the bromide, CAS 22254-24-6, sold under the name Atrovent), oxitropium and tiotropium (for example, as the bromide, CAS 136310-93-5, sold under the name Spiriva), revatropate, LAS-34273, Aclidinium, Glycopyrronium, Umeclidinium and salts thereof;

(iii) Corticosteroid anti-inflammatory agents. Examples include methyl prednisolone, prednisolone, dexamethasone, fluticasone propionate, fluticasone furoate, beclomethasone esters (for example the 17-propionate ester or the 17,21-dipropionate ester), budesonide, flunisolide, mometasone esters (for example mometasone furoate), triamcinolone acetonide, rofleponide, ciclesonide, butixocort propionate, RPR-106541, and ST-126;

(iv) Anti-inflammatory agents including non-steroidal anti-inflammatory drugs (NSAIDs). Examples of NSAID's include sodium cromoglycate, nedocromil sodium, phosphodiesterase (PDE) inhibitors (for example, theophylline, PDE4 inhibitors or mixed PDE3/PDE4 inhibitors), leukotriene antagonists, JAK inhibitors, Pi3K inhibitors, inhibitors of leukotriene synthesis (for example montelukast), iNOS inhibitors, tryptase and elastase inhibitors, beta-2 integrin antagonists and adenosine receptor agonists or antagonists (e.g. adenosine 2a agonists), cytokine antagonists (for example chemokine antagonists, such as a CCR3 antagonist) or inhibitors of cytokine synthesis, or 5-lipoxygenase inhibitors;

(v) Vasodilator and anti-proliferative agents (e.g. prostanoids and PDE5 inhibitors) including Epoprostenol (Flolan), Treprostinil (Remodulin), Iloprost (Ventavis), Treprostinil (Tyvaso), Bosentan (Tracleer), Ambrisentan (Letairis), Sildenafil (Revatio), Tadalafil (Adcirca);

(vi) Anti-diabetic medications including insulins, biguanides (e.g. metformin), sulfonylureas (e.g. glimepiride), meglitinides (e.g. repaglinide), thiazolidinediones (e.g., pioglitazone), dipeptidyl peptidase IV inhibitors (e.g. sitagliptin), incretin mimetics/GLP-1 analogues (e.g. liraglutide, exenatide, dulaglutide), sodium glucose co-transporter-2 (SGLT2) inhibitors (e.g. canagliflozin, dapagliflozin and empagliflozin) and α-glucosidase inhibitors (e.g. acarbose);

(vii) Hydroxyurea and other agents used to treat sickle cell disease such as L-glutamine, NCX1443, GBT440 (voxelotor), pan-Selectin antagonists (GMI-1070, rivipansel), humanized anti-P-Selectin antibody (SelG1, crinalizumab), P-selectin aptamers, sevuparin, Regadenoson, Ticagrelor, N-Acetyl-Cysteine (NAC), phosphodiesterase 9 inhibitors (e.g. PF-04447943, IMR-687, BAY 73-6691, BAY 41-2271); and (viii) ASK1 inhibitors such as selonsertib, FXR agonists such as obeticholic acid, GS-9674, Px-102, ACC inhibitors such as GS-0976 and PPARα/δ agonists such as Elafibranor.

The combinations referred to above may conveniently be presented for use in the form of a pharmaceutical formulation and thus pharmaceutical formulations comprising a combination as defined above together with a pharmaceutically acceptable diluent or carrier represent a further aspect of the invention.

Such conjoint/combination treatment may be achieved by way of the simultaneous, sequential or separate dosing of the individual components of the treatment. In one embodiment, the individual compounds will be administered simultaneously in a combined pharmaceutical formulation.

Such combination therapies employ the compounds of this invention within the dosage range described herein and the other pharmaceutically active agent within approved dosage ranges and/or the dosage such as described in the relevant publication reference.

EXAMPLES

General Procedures:

Methods for preparing the compounds of this invention are illustrated in the following Examples. Starting materials are made according to procedures known in the art, or as illustrated herein, or are available commercially. Commercial reagents were used without further purification. Where no reaction temperature is included, the reaction was performed at ambient temperature which is typically 18-27° C.

Where compounds described in the invention are characterized by $^1$H NMR spectroscopy, spectra were recorded on 500 MHz Bruker, 400 MHz Bruker, 250 MHz Bruker, 300 MHz JEOL or 400 MHz JEOL instruments. Where no temperature is included, the spectra were recorded at ambient temperature. Chemical shift values are expressed in parts per million (ppm). Where NMR spectra are complex due to the presence of interconverting isomers, approximate partial integrations of signals are reported, or characterisation for the major isomer only is reported. The following abbreviations are used for the multiplicity of the NMR signals: s=singlet, b=broad, t=triplet, q=quartet, m=multiplet, d=doublet.

Analytical LCMS

Where compounds described in the invention are characterized by LCMS data, retention time and molecular weight are determined using the methods listed in the table below. In cases where compounds of the invention appear as slowly interconverting stereoisomers, multiple retention times are reported.

| Method | Instrument | Column | | Eluents | Gradient |
|---|---|---|---|---|---|
| 1 | HP1100 (quaternary pump with PDA detector) and ZQ Mass Spectrometer | Phenomenex Luna C18(2) (3 μm, 4.6 × 30 mm) | 40° C. | A: 0.1% formic acid in water B: MeCN (containing 0.1% formic acid) | 5-95% B from 0.3 to 4.3 min |
| 1a | HP1100 (quaternary pump with PDA detector) and ZQ Mass Spectrometer | Gemini NX-C18 (3 μm, 4.6 × 30 mm) | 40° C. | A: 0.1% ammonia in water B: 0.1% ammonia in acetonitrile | 5-95% B from 0.3 to 4.3 min |
| 2 | Acquity H-Class (quaternary pump with PDA detector) and QDa Mass Spectrometer | Acquity UPLC CSH C18 (1.7 μm, 2.1 × 50 mm) | 50° C. | A: 0.1% aq. formic acid in water B: MeCN (containing 0.1% formic acid) | 3-99% B from 0.0 to 1.5 min |
| 3 | Acquity UPLC (binary pump with PDA detector) and ZQ Mass Spectrometer | Acquity UPLC BEH C18 (1.7 μm, 2.1 × 100 mm) | 40° C. | A: 0.1% formic acid in water B: MeCN (containing 0.1% formic acid) | 5-95% B from 0.4 to 6.0 min |
| 3a | Acquity UPLC (binary pump with PDA detector) and ZQ Mass Spectrometer | Acquity UPLC BEH C18 (1.7 μm, 2.1 × 100 mm) | 40° C. | A: 0.03% aq. ammonia B: MeCN (containing 0.03% ammonia) | 5-95% from 0.4 min to 6.0 min |

| Method | Instrument | Column | | Eluents | Gradient |
|---|---|---|---|---|---|
| 4 | Waters Acquity UPLC (diode array 210-350 nm) and SQD mass detector | XBridge BEH C18 (2.5 μm, 2.1 × 50 mm) | 40° C. | A: 10 mM ammonium bicarbonate pH 10<br>B: MeCN | 2-98% B from 0.0 to 0.8 min |
| 4a | Waters Acquity UPLC (diode array 210-350 nm) and SQD mass detector | XBridge BEH C18 (2.5 μm, 2.1 × 50 mm) | 40° C. | A: 10 mM ammonium bicarbonate pH 10<br>B: MeCN | 2-98% B from 0.0 to 4.0 min |
| 5 | Waters Alliance 2795 HPLC System (diode array 215-350 nm) and ZQ2000 mass detector | XBridge IS C18 (2.5 μm, 2.1 × 20 mm) | 40° C. | A: 10 mM ammonium bicarbonate pH 10<br>B: MeCN | 0-95% B from 0.18 to 2.0 min |
| 6 | Waters Acquity UPLC1 (diode array 210-350 nm) and QDa mass detector | Acquity UPLC CSH C18 (1.7 μm, 2.1 × 50 mm) | 40° C. | A: 0.1% formic acid in water<br>B: 0.1% formic acid in MeCN | 2-50% B from 0.0 to 1.0 min, 50% B to 1.8 min |
| 6a | Waters Acquity UPLC1 (diode array 210-350 nm) and QDa mass detector | Acquity UPLC CSH C18 (1.7 μm, 2.1 × 50 mm) | 40° C. | A: 0.1% formic acid in water<br>B: 0.1% formic acid in MeCN | 2-95% B from 0.0 to 1.2 min, 95% B to 1.4 min |
| 6b | Waters Acquity UPLC1 (diode array 210-350 nm) and QDa mass detector | Acquity UPLC CSH C18 (1.7 μm, 2.1 × 50 mm) | 40° C. | A: 0.1% formic acid in water<br>B: 0.1% formic acid in MeCN | 2-95% B from 0.0 to 4.0 min |
| 7 | Waters Acquity UPLC2 (diode array 210-350 nm) and QDa mass detector | XBridge C18 (2.5 μm, 2.1 × 50 mm) | 40° C. | A: 10 mM ammonium bicarbonate pH 10<br>B: MeCN | 2-98% B from 0.0 to 4.0 min, 98% B to 4.60 min |
| 7a | Waters Acquity UPLC2 (diode array 210-350 nm) and QDa mass detector | XBridge C18 (2.5 μm, 2.1 × 50 mm) | 40° C. | A: 2% ammonia in water<br>B: MeCN | 2-95% B from 0.0 to 4.0 min, 95% B to 4.60 min |
| 8 | Waters Acquity UPLC3 (diode array 210-350 nm) and SQD mass detector | XBridge C18 (2.5 μm, 2.1 × 50 mm) | 40° C. | A; water<br>C: MeCN<br>D: 2% ammonia in water | 2-95% C in A (5% D throughout) from 0.0 to 4.50 min, 95% C to 5.00 min |
| 9 | Waters Acquity UPLC H-Class system (Quaternary pump with PDA 210-350 nm) and QDa mass detector | BEH C18 (1.7 μm, 2.1 × 50 mm) | 40° C. | A: water<br>B: MeCN<br>C: 2% ammonia in water | 2-95% B with A (5% C throughout) from 0.0 to 1.2 min, 95% B 5% C to 1.40 min |
| 9a | Waters Acquity UPLC H-Class system (Quaternary pump with PDA 210-350 nm) and QDa mass detector | BEH C18 (1.7 μm, 2.1 × 50 mm) | 40° C. | A: water<br>B: MeCN<br>C: 2% ammonia in water | 2-95% B with (5% C throughout) from 0.0 to 4.0 min, 95% B 5% C to 4.60 min |
| 9b | Waters Acquity UPLC H-Class system (Quaternary pump with PDA 210-350 nm) and QDa mass detector | BEH C18 (1.7 μm, 2.1 × 50 mm) | 40° C. | A: water<br>B: MeCN<br>C: 2% ammonia in water | 2-50% B with A (5% C throughout) 0.0 to 3.0 min, to 95% B with 5% C at 4.0 min, 95% B 5% C to 4.60 min |

-continued

| Method | Instrument | Column | | Eluents | Gradient |
|---|---|---|---|---|---|
| 9c | Waters Acquity UPLC H-Class system (Quaternary pump with PDA 210-350 nm) and QDa mass detector | BEH C18 (1.7 μm, 2.1 × 50 mm) | 40° C. | A: water B: MeCN C: 2% ammonia in water | 2-50% B with A (5% C throughout) from 0.0 to 1.0 min, to 95% B with 5% C at 1.8 min, 95% B 5% C to 2.0 min |
| 9d | Waters Acquity UPLC H-Class system (Quaternary pump with PDA 210-350 nm) and QDa mass detector | BEH C18 (1.7 μm, 2.1 × 50 mm) | 40° C. | A: water B: MeCN C: 2% ammonia in water | 2-20% B with A (5% C throughout) 0.0 to 1.0 min, to 95% B with 5% C at 1.8 min, 95% B 5% C to 2.0 min |
| 10 | Waters Acquity UPLC H-Class system (Quaternary pump with PDA 210-350 nm) and QDa mass detector | CSH C18 (1.7 μm, 2.1 × 50 mm) | 40° C. | A: water B: MeCN C: 2% formic acid in water | 2-95% B with A (5% D throughout) from 0.0 to 4.0 min, 95% B 5% D to 4.60 min |
| 10a | Waters Acquity UPLC H-Class system (Quaternary pump with PDA 210-350 nm) and QDa mass detector | CSH C18 (1.7 μm, 2.1 × 50 mm) | 40° C. | A: water B: MeCN C: 2% formic acid in water | 2-50% B with A (5% D throughout) from 0.0 to 3.0 min, to 95% B with 5% D at 4.0 min, 95% B 5% D to 4.60 min |
| 10b | Waters Acquity UPLC H-Class system (Quaternary pump with PDA 210-350 nm) and QDa mass detector | CSH C18 (1.7 μm, 2.1 × 50 mm) | 40° C. | A: water B: MeCN C: 2% formic acid in water | 2-95% B with A (5% D throughout) from 0.0 to 1.2 min, 95% B 5% D to 1.40 min |
| 10c | Waters Acquity UPLC H-Class system (Quaternary pump with PDA 210-350 nm) and QDa mass detector | CSH C18 (1.7 μm, 2.1 × 50 mm) | 40° C. | A: water B: MeCN C: 2% formic acid in water | 2-50% B with A (5% D throughout) from 0.0 to 1.0 min, to 95% B with 5% D at 1.8 min, 95% B 5% D to 2.0 min |
| 11 | UPLC + Waters DAD + Waters SQD2, single quadrapole UPLC-MS | Acquity UPLC HSS $C_{18}$ (1.8 μm, 2.1 × 100 mm) | 40° C. | A: 0.1% formic acid in water B: MeCN (containing 0.1% formic acid) | 5-95% B from 0.4 to 6.0 min |
| 12 | UPLC + Waters DAD + Waters SQD2, single quadrapole UPLC-MS | Acquity UPLC BEH Shield RP18 (1.7 μm 2.1 × 100 mm) | 40° C. | A: 10 mM ammonium bicarbonate pH 10 B: MeCN | 5-95% B from 0.4 to 6.0 min |
| 13 | Waters Acquity Sample manager (Quaternary pump with PDA 210-350 nm and ELS and SQD mass detector) | BEH C18 (1.7 μm, 2.1 × 50 mm) | 40° C. | A: water B: MeCN C: 2% formic acid in water | 2% B with 5% C and 93% A to 95% B and 5% C from 0.0 to 4.50 min, 95% B 5% C to 5.00 min |
| 13a | Waters Acquity Sample manager (Quaternary pump with PDA 210-350 nm and ELS and SQD mass detector) | CSH C18 (1.7 μm 2.1 × 50 mm) | 40° C. | A: water B: MeCN C: 2% formic acid in water | 2% B with 5% C and 93% A to 95% B and 5% C from 0.0 to 4.50 min, 95% B 5% C to 5.00 min |
| 14 | Waters Acquity Sample manager (Quaternary pump with PDA 210- | BEH C18 (1.7 μm, 2.1 × 50 mm) | 40° C. | A: water B: MeCN C: 2% ammonia in water | 2% B with 5% C and 93% A to 95% B and 5% C from 0.0 |

-continued

| Method | Instrument | Column | | Eluents | Gradient |
|---|---|---|---|---|---|
| | 350 nm and ELS and SQD mass detector) | | | | to 4.50 min, 95% B 5% C to 5.00 min |
| 14a | Waters Acquity Sample manager (Quaternary pump with PDA 210-350 nm and ELS and SQD mass detector) | CSH C18 (1.7 µm 2.1 × 50 mm) | 40° C. | A: water B: MeCN C: 2% ammonia in water | 2% B with 5% C and 93% A to 95% B and 5% C from 0.0 to 4.50 min, 95% B 5% C to 5.00 min |
| 15 | Acquity H-Class (quaternary pump with PDA detector) and QDa Mass Spectrometer | XBridge BEH C18 (2.5 µm, 2.1 × 50 mm) | 40° C. | A: 0.1% aq. ammonia B: MeCN (containing 0.1% ammonia) | 3-95% B from 0.2 to 2.2 min, 95% B to 2.7 min |
| 16 | HP1100 (quaternary pump with PDA detector) and ZQ Mass Spectrometer | Gemini NX-C18 (3 µm, 4.6 × 30 mm) | 40° C. | A: 0.03% ammonia in water B: 0.03% ammonia in acetonitrile | 5-95% B from 0.3 to 4.3 min, 95% B to 5.3 min |
| 17 | Waters Acquity Classic (996 PDA detector) and Waters ZMD Mass Spectrometer | Acquity UPLC CSH C18 (1.7 µm, 2.1 × 50 mm) | 40° C. | A: 0.1% formic acid in water B: MeCN (containing 0.1% formic acid) | 3%-99% B from 0.3 to 2.3 min, 99% B to 2.4 min |
| 18 | HP1100 (quaternary pump with PDA detector) and ZQ Mass Spectrometer | XBridge BEH C18 (3.5 µm, 4.6 × 30 mm). | 40° C. | A: 0.1% ammonia in water B: 0.1% ammonia in MeCN | 5% to 95% B from 0.0 to 4.3 min, 95% B to 5.3 min |

Preparative HPLC

Preparative HPLC was performed using a variety of preparative systems with variable wavelength UV detection or Mass Directed AutoPrep (MDAP) systems as listed in the table below. Collection was triggered by UV, MS or a combination of the two. The UV detection was at a selected wavelength generally 210 nm, 230 nm or 280 nm. Mass spectra were recorded on a mass spectrometer using an alternate-scan positive and negative electrospray ionization.

| Method | Instrument | Column | | Eluents | Gradient |
|---|---|---|---|---|---|
| 1 | Agilent 1260 infinity purifications system. Agilent 6100 series single Quadrupole LC/MS | XSELECT CSH Prep C18 (5 µm OBD, 21 × 250 mm) | rt | A: 0.1% formic acid in water B: MeCN (containing 0.1% formic acid) | 10% to 95% B over 22 min, centered around a specific focused gradient |
| 2 | Agilent 1260 infinity purifications system. Agilent 6100 series single Quadrupole LC/MS | XBridge Prep C18 (5 µm OBD, 21 × 250 mm) | rt | A: 0.1% ammonia in water B: MeCN (containing 0.1% ammonia) | 10% to 95% B over 22 min, centered around a specific focused gradient |
| 3 | Waters Fractionlynx preparative HPLC system (2525 pump, 2996/2998 UV/VIS detector, 2767 liquid handler) with Waters Acquity systems with Waters SQD LCMS detection | Waters Sunfire OBD Phenomenex Luna Phenyl Hexyl (10 µm, 19 × 150 mm) | rt | A: MeOH B: MeCN (containing 0.1% formic acid) | Gradient as specified |
| 4 | Waters Fractionlynx preparative HPLC system (2525 pump, 2996/2998 UV/VIS detector, 2767 liquid handler) with Waters Acquity systems with Waters SQD LCMS detection | Waters Sunfire OBD Phenomenex Luna Phenyl Hexyl (10 µm, 19 × 150 mm) | rt | A: MeOH B: MeCN (containing 10 mM ammonium bicarbonate) | Gradient as specified |
| 5 | Waters mass directed automated purification | XBridge C18 (5 µm, 19 × | rt | A: MeOH B: MeCN | Gradient as specified, run |

| Method | Instrument | Column | | Eluents | Gradient |
|---|---|---|---|---|---|
| | system (MDAP) | 100 mm) | | C: 0.1% formic acid in water<br>D: 10 nM ammonium bicarbonate (pH 10) | time 14.0 min. |
| 6 | Waters automated purification system (HPLC) | XBridge C18 (5 μm, 19 × 100 mm) | rt | A: MeOH<br>B: MeCN<br>C: 0.1% formic acid in water<br>D: 10 nM ammonium bicarbonate (pH 10) | Gradient as specified |
| 7 | Gilson HPLC system (321 Pump, 151/152/155/156 UV/VIS detector) | Phenomenex Kinetex® 5 μm XB-C18 100 Å, AXIA (50 × 21.2 mm and 250 × 21.2 mm) | rt | A: MeOH<br>B: 0.1% formic acid in MeCN | Gradient as specified |
| 7a | Gilson HPLC system (321 Pump, 151/152/155/156 UV/VIS detector) | Phenomenex Kinetex® 5 μm EVO C18 100 Å, AXIA (50 × 21.2 mm and 250 × 21.2 mm). | rt | A: MeOH<br>B: 0.1% ammonia in MeCN | Gradient as specified |
| 8 | Waters Fractionlynx preparative HPLC system (2525 pump, 2996/2998 UV/VIS detector, 2767 liquid handler) with Waters Acquity systems with Waters SQD LCMS detection | Phenomenex Luna Phenyl Hexyl (10 μm 21.2 × 150 mm) | rt | A: MeOH<br>B: MeCN (containing 0.1% formic acid) | Gradient as specified |
| 9 | Waters Fractionlynx preparative HPLC system (2525 pump, 2996/2998 UV/VIS detector, 2767 liquid handler) with Waters Acquity systems with Waters SQD LCMS detection | Phenomenex Luna Phenyl Hexyl (10 μm 21.2 × 150 mm) | rt | A: MeOH<br>B: MeCN (containing 10 mM ammonium bicarbonate) | Gradient as specified |

Preparative Chiral SFC

Preparative chiral SFC was performed using one of the methods outlined below.

Method 1:

Waters Thar Prep100 preparative SFC system (P200 $CO_2$ pump, 2545 modifier pump, 2998 UV/VIS detector, 2767 liquid handler with Stacked Injection Module). Column: Diacel Chiralpak IA/IB/IC, YMC Amylose/Cellulose C (5 μm, 20-21.2×250 mm), maintained at 40° C. Conditions: supercritical fluid $CO_2$ and eluents chosen from MeOH, EtOH, IPA, MeCN, EtOAc, THF with modifiers chosen from $Me_2NH$, formic acid as specified. Gradient/isocratic as specified.

Method 2:

Waters Thar Prep100 preparative SFC system (P200 $CO_2$ pump, 2545 modifier pump, 2998 UV/VIS detector, 2767 liquid handler with Stacked Injection Module). Column: Phenomenex Lux Cellulose-4 (5 μm, 20-21.2×250 mm), maintained at 40° C. Conditions: supercritical fluid $CO_2$ and eluents chosen from MeOH, EtOH, IPA, MeCN, EtOAc, THF with modifiers chosen from $Me_2NH$, formic acid as specified. Gradient/isocratic as specified.

Method 3:

Waters Thar Prep100 preparative SFC system (P200 CO2 pump, 2545 modifier pump, 2998 UV/VIS detector, 2767 liquid handler with Stacked Injection Module). Column: YMC Amylose-C/Amylose-SA/Cellulose-C/Cellulose-SB/Cellulose-SC (5 μm, 20×250 mm), maintained at 40° C. Conditions: supercritical fluid $CO_2$ and eluents chosen from MeOH, EtOH, IPA, MeCN, EtOAc, THF with formic acid. Gradient/isocratic as specified.

Method 3a:

Waters Thar Prep100 preparative SFC system (P200 CO2 pump, 2545 modifier pump, 2998 UV/VIS detector, 2767 liquid handler with Stacked Injection Module). Column: YMC Amylose-C/Amylose-SA/Cellulose-C/Cellulose-SB/Cellulose-SC (5 μm, 20×250 mm), maintained at 40° C. Conditions: supercritical fluid CO2 and eluents chosen from MeOH, EtOH, IPA, MeCN, EtOAc, THF with $Me_2NH$. Gradient/isocratic as specified.

Method 4:

Waters Thar Prep100 preparative SFC system (P200 CO2 pump, 2545 modifier pump, 2998 UV/VIS detector, 2767 liquid handler with Stacked Injection Module). Column: Phenomenex Lux Cellulose-3 (5 μm, 20-21.2×250 mm), maintained at 40° C. Conditions: supercritical fluid $CO_2$ and eluents chosen from MeOH, EtOH, IPA, MeCN, EtOAc, THF with modifiers chosen from $Me_2NH$, formic acid as specified. Gradient/isocratic as specified.

Abbreviations:

| | |
|---|---|
| AcOH | Acetic acid |
| AIBN | 2,2'-Azobis(2-methylpropionitrile) |
| DAST | (Diethylamino)sulfur trifluoride |
| DBAD | Di-tert-butyl azodicarboxylate |
| DBU | 1,8-Diazabicyclo[5.4.0]undec-7-ene |
| DCM | Dichloromethane |
| DIPEA | N,N-Diisopropylethylamine |
| DMF | N,N-Dimethylformamide |
| DMSO | Dimethylsulfoxide |
| EDTA | Ethylenediaminetetraacetic acid |
| Et$_2$O | Diethyl ether |
| EtOAc | Ethyl acetate |
| EtOH | Ethanol |
| h | Hour(s) |
| HATU | N-[(Dimethylamino)-1H-1,2,3-triazolo-[4,5-b]pyridin-1-ylmethylene]-N-methylmethanaminium hexafluorophosphate N-oxide |
| HMPA | Hexamethylphosphoramide |
| HPLC | High Performance Liquid Chromatography |
| IMS | Industrial methylated spirits |
| IPA | Isopropyl alcohol |
| LCMS | Liquid Chromatography Mass Spectrometry |
| LDA | Lithium diisopropylamine |
| MDAP | Mass Directed Auto Purification |
| MeCN | Acetonitrile |
| MeOH | Methanol |
| 2-MeTHF | 2-Methyl tetrahydrofuran |
| min | Minute(s) |
| NBS | N-bromosuccinimide |
| NCS | N-chlorosuccinimide |
| NMR | Nuclear Magnetic Resonance |
| Pd/C | Palladium on carbon |
| rt | Room Temperature |
| SCX | Strong Cation Exchange |
| SFC | Supercritical fluid chromatography |
| T$_3$P ® | Propylphosphonic anhydride solution |
| TFA | Trifluoroacetic acid |
| THF | Tetrahydrofuran |
| XPhos | 2-Dicyclohexylphosphino-2',4',6'-triisopropylbiphenyl |

Synthesis of Intermediates

Intermediate 1: 2-(1,3-Dioxoisoindolin-2-yl)acetyl chloride

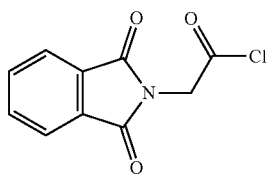 [SMILES: O=C(Cl)CN1C(=O)c2ccccc2C1=O]

To a stirred suspension of 2-(1,3-dioxoisoindolin-2-yl) acetic acid (555 g, 2.71 mol; CAS: 4702-13-0) in EtOAc (958 mL) at rt was added thionyl chloride (1039 mL, 14.24 mol). The mixture was heated at reflux for 1.5 h, then cooled to rt. The reaction mixture was concentrated in vacuo to give the title compound (605 g, 99%), used without further purification. $^1$H NMR (300 MHz, CDCl$_3$) δ 7.96-7.87 (m, 2H), 7.85-7.74 (m, 2H), 4.81 (d, 2H).

Intermediate 2: 2-(1,3-Dioxoisoindolin-2-yl)-N-(3-methoxyphenethyl)acetamide

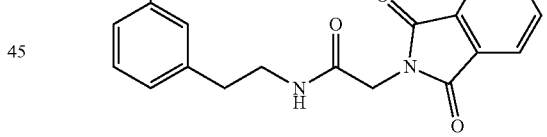

To a stirred solution of 2-(3-methoxyphenyl)ethan-1-amine (160 g, 1.06 mol, CAS: 2039-67-0) and triethylamine (248 mL, 2.04 mol) in DCM (2.4 L) at 5° C. was added a solution of Intermediate 1 (232 g, 1.04 mol) in DCM (1.2 L). The reaction mixture was stirred at rt for 18 h, then hydrochloric acid (2M; 2.4 L) was added and the mixture stirred for 1 h. The mixture was filtered, and the precipitate washed with water, then dried in vacuo. The residue was dissolved in DCM (10.0 L) and washed with saturated aqueous NaHCO$_3$ and the organics dried over MgSO$_4$, filtered and concentrated in vacuo to give a white solid (267 g). The organic layer from the first separation was washed with water, saturated aqueous NaHCO$_3$ and the organics dried over MgSO$_4$, filtered and concentrated in vacuo to give a further portion of white solid (61.4 g). The isolated solids were combined to give the title compound as a white solid (328 g, 82%), used without further purification. LCMS (Method 7): 1.68 min, 339.1 [M+H]$^+$.

Intermediate 3: N-(2-Bromo-5-methoxyphenethyl)-2-(1,3-dioxoisoindolin-2-yl)acetamide

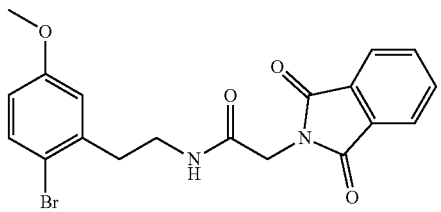 [SMILES: COc1ccc(Br)c(CCNC(=O)CN2C(=O)c3ccccc3C2=O)c1]

To a stirred solution of Intermediate 2 (328 g, 970 mmol) in DMF (3.2 L) was added NBS (173 g, 970 mmol) in portions over 0.5 h. The reaction mixture was heated at 40° C., then cooled to rt and allowed to stand at rt for 18 h. The reaction mixture was poured into water (5.0 L) and the resultant precipitate collected by filtration and washed with water. The residue was diluted with DCM, the aqueous phase separated and the combined organics concentrated in vacuo to give the title compound (314 g, 76%), used without further purification. $^1$H NMR (300 MHz, CDCl$_3$) δ 7.90-7.73 (m, 4H), 7.37 (dd, 1H), 6.78 (d, 1H), 6.64 (td, 1H), 5.80 (s, 1H), 4.31 (d, 2H), 3.79-3.75 (m, 3H), 3.59-3.54 (m, 2H), 2.94 (dd, 2H).

Intermediate 4: 2-((5-Bromo-8-methoxy-3,4-dihydroisoquinolin-1-yl)methyl)isoindoline-1,3-dione

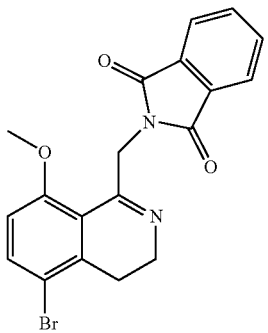 [SMILES: COc1ccc(Br)c2c1C(CN1C(=O)c3ccccc3C1=O)=NCC2]

To a suspension of Intermediate 3 (312 g, 748 mmol) in MeCN (5.0 L) was added phosphorus pentoxide (630 g, 4.44 mol). The reaction mixture was heated at 60° C. for 4 h, cooled to rt and allowed to stand at rt for 18 h. The reaction mixture was filtered and the filtrate concentrated in vacuo to a volume of 500 mL. The filtered solids were dissolved in water (4.0 L) and combined with the organic layer. The combined mixture was heated at 40° C. for 1 h, cooled to rt and to the stirred mixture was added saturated aqueous NaHCO$_3$ to adjust to pH 8. The precipitated solid was collected by filtration and washed with water (1.0 L). The residue was dried in vacuo at 40° C. to give the title compound (293 g, 92%), used without further purification. LCMS (Method 7): 2.34 min, 401.1 [M+H]$^+$.

Intermediate 5: (S)-5-Bromo-1-((1,3-dioxoisoindolin-2-yl)methyl)-8-methoxy-3,4-dihydroisoquinoline-2(1H)-carbaldehyde

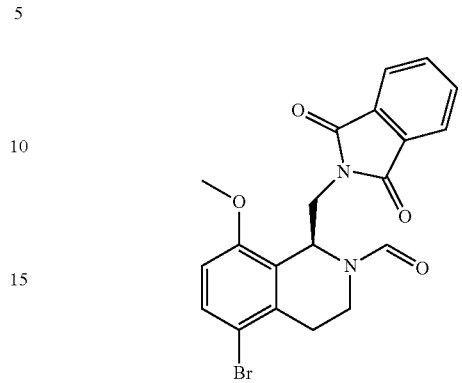

A solution of benzeneruthenium(II) chloride dimer (3.78 g, 7.6 mmol, CAS: 37366-09-9) and (1S,2S)-(+)-N-p-tosyl-1,2-diphenylethylenediamine (6.78 g, 18.5 mmol, CAS: 167316-27-0) in MeCN (300 mL) under argon was stirred at rt for 1 h. To this was added MeCN (2.1 L) and DCM (300 mL) followed by Intermediate 4 (205 g, 457 mmol) and MeCN (1.4 L). To the reaction mixture was added a solution of formic acid and triethylamine (1:1; 760 mL) and the reaction mixture was stirred at rt under argon for 72 h. The reaction mixture was diluted with water (2.0 L) and to this was added NaHCO$_3$ to adjust to pH 8.0. The mixture was diluted with DCM (3.0 L) and the organics washed with water, dried over MgSO$_4$ and filtered. The organics were passed through a silica plug, eluting with 66% EtOAc in DCM and the combined organics concentrated in vacuo to give the title compound (215 g, 99%), used without further purification. LCMS (Method 4): 0.91 min, 431.1 [M+H]$^+$.

Intermediate 6: (S)-2-((5-Bromo-8-methoxy-1,2,3,4-tetrahydroisoquinolin-1-yl)methyl)isoindoline-1,3-dione

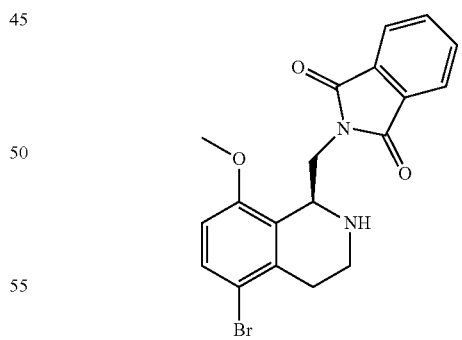

To a suspension of Intermediate 5 (215 g, 451 mmol) in THF (1.5 L) was added HCl (2 M aqueous; 2.14 L, 4.33 mol) and the mixture heated at reflux for 18 h. The reaction mixture was cooled to rt and saturated aqueous NaHCO$_3$ was added slowly to adjust to pH 8. The mixture was extracted with DCM (2×2.0 L) and the combined organics dried over MgSO$_4$ and filtered. The solution was concentrated in vacuo and the residue recrystallised twice from MeCN (1.0 L+250 mL). The resulting precipitate was filtered and dried in vacuo to give the title compound (113 g, 59%), used without further purification. LCMS (Method 7a): 2.30 min, 401.1 [M+H]$^+$; $^1$H NMR (300 MHz, CDCl$_3$) δ 7.86 (dt, 2H), 7.76-7.69 (m, 2H), 7.43 (d, 1H), 6.64 (d, 1H), 4.53 (dd, 1H), 4.12-3.92 (m, 2H), 3.91-3.81 (m, 3H), 3.64 (s, OH), 3.43-3.32 (m, 1H), 3.06 (qd, 1H), 2.56-2.82 (m, 2H).

Intermediate 7: (S-2-((5-Bromo-8-hydroxy-1,2,3,4-tetrahydroisoquinolin-1-yl)methyl)isoindoline-1,3-dione

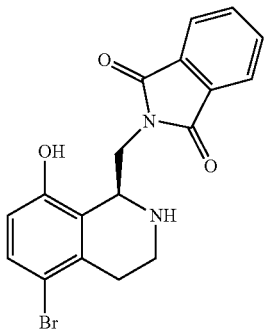 [SMILES: O=C1c2ccccc2C(=O)N1C[C@H]1NCCc2c(Br)ccc(O)c21]

To a solution of Intermediate 6 (141 g, 351 mmol) in DCM (2.5 L) at 0° C. was added boron tribromide (1 M in DCM; 1.34 L, 1.44 mol) dropwise over 1 h and the reaction mixture was stirred at rt for 18 h. The reaction mixture was cooled to 0° C., MeOH (150 mL) was added slowly and the mixture stirred for 1.5 h. The resultant precipitate was isolated by filtration, washed with DCM and dried in vacuo at 50° C. to give the title compound (Intermediate 7-HBr) (129 g, 71%). To the combined organics was added hydrochloric acid (2 M aqueous; 3.0 L) and the mixture stirred for 1 h. The resultant precipitate was isolated by filtration and dried in vacuo at 50° C. to give the title compound (Intermediate 7-HCl) (44.1 g, 27%). The acidic aqueous phase was separated and adjusted to pH 8 by the addition of Na$_2$CO$_3$ and extracted with DCM. The organic phase was dried over MgSO$_4$, filtered and concentrated in vacuo to give the title compound (3.67 g, 2%), used without further purification. LCMS (Method 9a): 1.87 min, 389.1 [M+H]$^+$.

Intermediate 8: tert-Butyl (S)-5-bromo-1-((1,3-dioxoisoindolin-2-yl)methyl)-8-hydroxy-3,4-dihydroisoquinoline-2(1H)-carboxylate

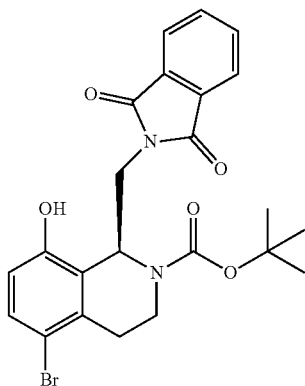 [SMILES: CC(C)(C)OC(=O)N1CCc2c(Br)ccc(O)c2[C@H]1CN1C(=O)c2ccccc2C1=O]

To a stirred suspension of Intermediate 7-HBr (129 g, 251 mmol) in DCM (1 L) was added triethylamine (89 mL, 636 mmol) and di-tert-butyl dicarbonate (41.5 g, 190 mmol). Additional di-tert-butyl dicarbonate (7.3 g, 33.5 mmol) was added and the mixture stirred for 2 h. A final portion of di-tert-butyl dicarbonate (3.37 g, 15.45 mmol) was added and the mixture stirred at rt for 18 h. The reaction mixture was diluted with water and the mixture was extracted with DCM. The combined organics were dried over MgSO$_4$, filtered and concentrated in vacuo to give the title compound (145 g, assumed quantitative), used without further purification. LCMS (Method 9a): 2.54 min, 487.1 [M–H]$^-$.

Intermediate 9: (S)-2-((8-Methoxy-1,2,3,4-tetrahydroisoquinolin-1-yl)methyl)isoindoline-1,3-dione

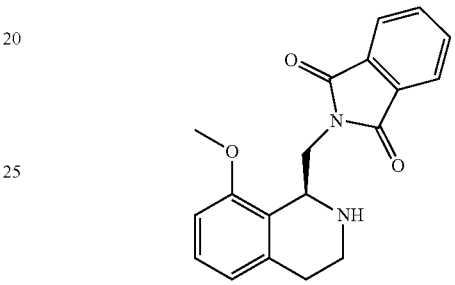

To a solution of Intermediate 6 (250 mg, 0.62 mmol) in THF (6 mL) and EtOH (6 mL) was added Pd/C (10%; 25 mg). The mixture was stirred at rt under an atmosphere of hydrogen for 48 h at atmospheric pressure. A further portion of Pd/C (10%; 10 mg) was added and the mixture was stirred under an atmosphere of hydrogen for 72 h. The mixture was then filtered through a pad of Celite® washing with EtOH (10 mL) and MeOH (10 mL). The filtrate was concentrated in vacuo. Purification by flash column chromatography (19% EtOAc in DCM with 1% 7 M NH$_3$ in MeOH, to 16% EtOAc in DCM with 4% 7M NH$_3$ in MeOH) gave the title compound (153 mg, 76%). LCMS (Method 4): 0.76 min, 323.23 [M+H]$^+$.

Intermediate 10: (S)-2-((8-Hydroxy-1,2,3,4-tetrahydroisoquinolin-1-yl)methyl)isoindoline-1,3-dione

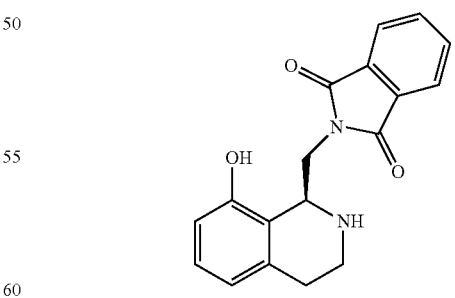

To a solution of Intermediate 9 (200 mg, 0.62 mmol) in DCM (2 mL) at −10° C. under argon, was added boron tribromide (1M in DCM; 3.1 mL, 3.1 mmol). The reaction mixture was warmed to rt and stirred for 1 h. The reaction mixture was cooled to 0° C. and MeOH (1 mL) was added. The mixture was warmed to rt, concentrated in vacuo and the residue stirred in saturated aqueous NaHCO$_3$ (10 mL) and EtOAc (10 mL) for 15 minutes. The layers were separated, and the aqueous phase extracted with EtOAc (15 mL). The combined organics were washed with brine (10 mL), dried over Na$_2$SO$_4$ and concentrated in vacuo to give the title compound (130 mg, 68%), used without further purification. LCMS (Method 4): 0.66 min, 309.19 [M+H]$^+$.

Intermediate 11: tert-Butyl (S)-1-((1,3-dioxoisoindolin-2-yl)methyl)-8-hydroxy-3,4-dihydroisoquinoline-2(1H)-carboxylate

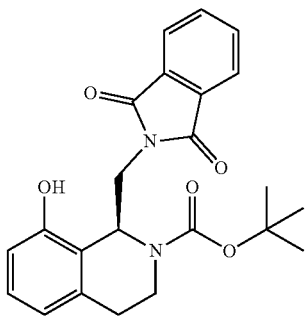 [SMILES: CC(C)(C)OC(=O)N1CCc2cccc(O)c2[C@H]1CN1C(=O)c2ccccc2C1=O]

To a solution of Intermediate 10 (3.4 g, 11.03 mmol) in DCM (400 mL) was added di-tert-butyl dicarbonate (2.9 g, 13.23 mmol). The reaction mixture was stirred at rt for 2 h. Saturated aqueous NaHCO$_3$ (150 mL) was added and mixture stirred for 15 min. The layers were separated, and the organic layer was washed with water (100 mL), dried over MgSO$_4$, filtered and concentrated in vacuo. The residue was diluted with a 1:1 mixture of IPA and heptanes (50 mL) and the mixture stirred for 1 h. The solid was filtered and washed with pentane (50 mL) to give the title compound (3.8 g, 85%), used without further purification. LCMS (Method 4): 0.82 min, 407.4 [M−H]$^-$.

Intermediate 12: tert-Butyl (S)-5-chloro-1-((1,3-dioxoisoindolin-2-yl)methyl)-8-hydroxy-3,4-dihydroisoquinoline-2(1H)-carboxylate

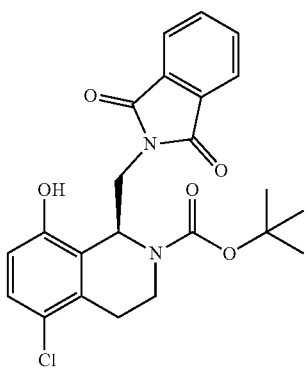 [SMILES: CC(C)(C)OC(=O)N1CCc2c(Cl)ccc(O)c2[C@H]1CN1C(=O)c2ccccc2C1=O]

Method 1: To a solution of Intermediate 11 (77.72 g, 188 mmol) in DMF (1.50 L) was added N-chlorosuccinimide (27.5 g, 206 mmol). The mixture was heated at 50° C. for 72 h then concentrated in vacuo. The residue was partitioned between EtOAc and water. The organic phase was washed with water (×2), brine, dried over MgSO$_4$, filtered and concentrated in vacuo. The residue was combined with an additional batch of crude material (70.97 mmol) which was dissolved into DCM (750 mL) and allowed to crystallise. The resulting precipitate was collected by filtration, washed with DCM and dried in vacuo to give the title compound (80 g, 65%), used without further purification. LCMS (Method 9a): 2.57 min, 441.2 [M−H]$^-$.

Method 2: To a suspension of Intermediate 55-HBr (57.3 g, 135.2 mmol) in DCM (1000 mL) was added DIPEA (59.7 mL, 343 mmol) followed by di-tert-butyl dicarbonate (22.1 g, 101 mmol; CAS: 24424-99-5). The reaction mixture was stirred at rt for 66 h. An additional portion of di-tert-butyl dicarbonate (3.56 g, 16.31 mmol) was added and the mixture stirred for 2 h followed by further di-tert-butyl dicarbonate (1.6 g, 7.33 mmol) and the mixture was stirred for an additional 1 h. The reaction mixture was washed with water and the organics separated, dried (MgSO$_4$) and filtered. The organics were concentrated in vacuo (to ~500 mL) and the mixture stood at rt for 18 h. The precipitate was isolated by filtration, washed with Et$_2$O, and dried in vacuo (50° C.) giving the title compound (43.3 g, 72%). LCMS (Method 9a): 2.33 min, 441.1 [M−H]$^-$. $^1$H NMR (300 MHz, CDCl$_3$) d 7.91-7.85 (m, 2H), 7.74 (dq, 2H), 7.23-7.18 (m, 1H), 6.80-6.76 (m, 1H), 5.49-5.78 (1H), 4.08 (dd, 1H), 3.83-4.00 (1H), 3.22-3.54 (1H), 2.87-3.04 (1H), 2.61-2.84 (1H), 1.20 (s, 4H), 1.03 (d, 5H). The organics were concentrated in vacuo and combined with the crude material from the following experiment (Method 3) for further purification.

Method 3: To a suspension of Intermediate 55-HCl (49.3 g, 130 mmol) in DCM (1.0 L) was added DIPEA (57.36 mL, 329 mmol) followed by di-tert-butyl dicarbonate (22.49 g, 103.05 mmol; CAS: 24424-99-5). The reaction mixture was allowed to stir at rt for 66 h. An additional portion of di-tert-butyl dicarbonate (0.46 g, 2.12 mmol) was added and the mixture stirred for 2 h followed by further di-tert-butyl dicarbonate (0.5 g, 2.29 mmol) and the mixture stirred for an additional 1 h. The reaction mixture was washed with water and the organics separated, dried (MgSO$_4$) and filtered. The organics were concentrated in vacuo (to ~500 mL) and the mixture stood at rt for 18 h. The precipitate was isolated by filtration, washed with Et$_2$O, and dried in vacuo (50° C.) to give the title compound (26.95 g, 46%). LCMS (Method 9a): 2.38 min, 441.1 [M−H]$^-$. The organics were concentrated in vacuo and combined with concentrated organics from Method 2 for further purification by flash column chromatography (silica; 40% EtOAc in heptane) to give a further batch of the title compound (32.4 g, 72.7 mmol). LCMS (Method 9): 2.56 min, 441.1 [M−H]−.

Intermediate 13: tert-Butyl (1S)-8-hydroxy-1-((1-hydroxy-3-oxoisoindolin-2-yl)methyl)-3,4-dihydroisoquinoline-2(1H)-carboxylate

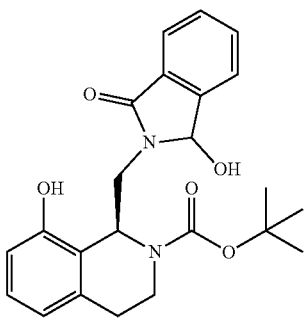 [SMILES: CC(C)(C)OC(=O)N1CCc2cccc(O)c2[C@H]1CN1C(=O)c2ccccc2C1O]

To a stirred suspension of Intermediate 11 (400 mg, 0.98 mmol) in MeOH (8 mL) was added NaBH₄ (148 mg, 3.9 mmol) under argon at rt. The reaction mixture was stirred at rt for 72 h then quenched with saturated aqueous NH₄Cl (~15 mL) and acidified by addition of 10% aqueous citric acid solution. The product was collected by filtration, washed with water and dried in vacuo. The residue was azeotroped with MeCN to give the title compound (343 mg, 85%), used without further purification. LCMS (Method 5): 1.86, 1.99 min, 409.1 [M−H]⁺.

Intermediate 14: (S)-2-((8-Hydroxy-1,2,3,4-tetrahydroisoquinolin-1-yl)methyl)isoindolin-1-one

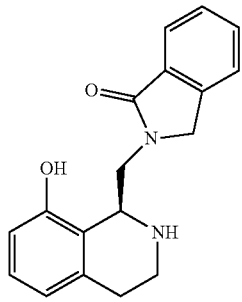 [SMILES: O=C1c2ccccc2CN1C[C@H]1NCCc2cccc(O)c21]

To a solution of Intermediate 13 (50 mg, 0.122 mmol) in TFA (1 mL) was added triethylsilane (0.03 mL, 0.18 mmol). The reaction mixture was stirred at rt for 3 h and then concentrated in vacuo. The residue was partitioned between DCM (2 mL) and saturated aqueous NaHCO₃ (5 mL). The layers were separated and the aqueous layer washed with DCM (10 mL). The combined organics were dried over Na₂SO₄, filtered and concentrated in vacuo to give the title compound (30 mg, 84%), used without further purification. ¹H NMR (400 MHz, CDCl₃) δ 7.88 (m, 1H), 7.61-7.41 (m, 3H), 7.06 (t, 1H), 6.77 (d, 1H), 6.62 (d, 1H), 4.83 (d, 1H), 4.52 (d, 1H), 4.41 (d, 1H), 3.90 (d, 1H), 3.58 (dd, 1H), 3.22-3.03 (m, 2H), 2.83-2.61 (m, 2H).

Intermediate 15: tert-Butyl (1S)-5-bromo-8-hydroxy-1-((1-hydroxy-3-oxoisoindolin-2-yl)methyl)-3,4-dihydroisoquinoline-2(1H)-carboxylate

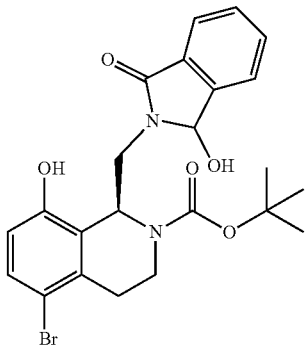 [SMILES: CC(C)(C)OC(=O)N1CCc2c(Br)ccc(O)c2[C@H]1CN1C(=O)c2ccccc2C1O]

To a stirred solution of Intermediate 8 (4.58 g, 9.4 mmol) in anhydrous THF (130 mL) cooled in ice/brine bath under a nitrogen atmosphere, was added NaBH₄ (0.53 g, 14.1 mmol) and MeOH (15 mL). The solution was warmed to rt and stirred for 30 min. A second portion of NaBH₄ (0.53 g, 14.1 mmol) was added and stirring continued for 45 min. A further portion of NaBH₄ (0.36 g, 9.4 mmol) was added and the mixture stirred at rt for 15 h. The reaction mixture was diluted with water, acidified to pH 3-4 with 10% citric acid and the extracted with EtOAc. The combined organics were washed with water, brine, dried over Na₂SO₄, filtered and concentrated in vacuo to give the title compound (4.4 g, 97%), used without further purification. LCMS (Method 2): 1.46 min, 511.2/513.2 [M+Na]⁺.

Intermediate 16: (S)-2-((5-Bromo-8-hydroxy-1,2,3,4-tetrahydroisoquinolin-1-yl)methyl)isoindolin-1-one

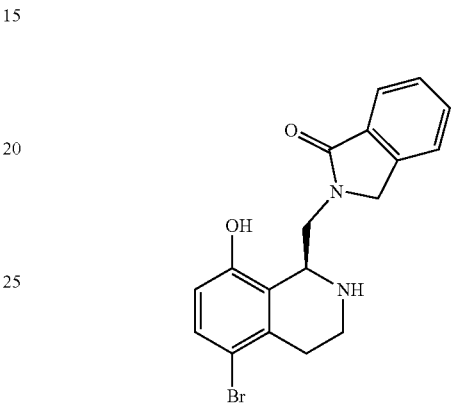

To a stirred solution of Intermediate 15 (4.44 g, 9.07 mmol) in TFA (50 mL, 652 mmol) was added triethylsilane (2.5 mL, 15.65 mmol). The mixture was stirred at rt for 90 mins, then diluted with DCM (200 mL). Saturated aqueous NaHCO₃ was added carefully, followed by ammonia (aqueous 30-33 wt %; 100 mL). The aqueous layer was extracted with DCM, and the combined organics were washed with brine (100 mL), dried over Na₂SO₄, filtered and concentrated in vacuo. MeCN (40 mL) and DCM (10 mL) were added to the residue, and the resulting suspension sonicated for 5 min. The solid was collected by filtration, rinsed with MeCN/DCM (4:1; 10 mL) and concentrated in vacuo to give the title compound (1.92 g, 56%). LCMS (Method 2): 0.86 min, 373.1/375.1 [M+H]⁺.

Intermediate 17: tert-Butyl (1S)-5-chloro-8-hydroxy-1-((1-hydroxy-3-oxoisoindolin-2-yl)methyl)-3,4-dihydroisoquinoline-2(1H)-carboxylate

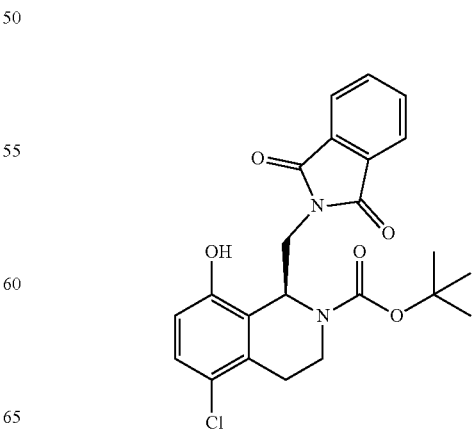

To a stirred solution of Intermediate 12 (2.18 g, 4.92 mmol) in anhydrous THF (72 mL) under argon at 0° C. was added NaBH₄ (0.28 g, 7.38 mmol) followed by anhydrous MeOH (8 mL). The mixture was stirred at 0° C. for 5 min warmed to rt and stirred for 75 min. An additional portion of NaBH₄ (0.28 g, 7.38 mmol) was added and the mixture was stirred at rt for a further 2 h. Further NaBH₄ (0.19 g, 4.92 mmol) was added and the mixture stirred at rt for a further 19 h. The mixture was quenched with saturated aqueous NaHCO₃ solution (120 mL), then acidified to pH 5 with 10% aqueous citric acid (220 mL). The mixture was extracted into EtOAc (3×100 mL). The combined organics were washed with brine (100 mL), dried over Na₂SO₄, filtered and concentrated in vacuo to give the title compound (2.18 g, assumed quantitative), used without further purification. LCMS (Method 2): 1.44 min, 467.2/469.2 [M+Na]⁺.

Intermediate 18: (S)-2-((5-Chloro-8-hydroxy-1,2,3,4-tetrahydroisoquinolin-1-yl)methyl)isoindolin-1-one

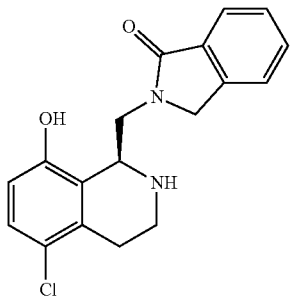 [SMILES: O=C1c2ccccc2CN1C[C@H]1NCCc2c(Cl)ccc(O)c21]

To a stirred solution of Intermediate 17 (1.98 g, 4.45 mmol) in TFA (33.6 mL, 436.2 mmol) under argon was added triethylsilane (1.07 mL, 6.68 mmol) and the resulting solution was stirred at rt for 2 h. The mixture was diluted with DCM (300 mL) and saturated aqueous NaHCO₃ solution (440 mL) was added carefully with stirring to bring pH to 8-9. The aqueous layer was extracted further with DCM (2×300 mL) and the combined organics were dried over Na₂SO₄, filtered and concentrated in vacuo. The residue was triturated with diethyl ether (30 mL) and the solid was collected by filtration, washed with diethyl ether (×3) and dried in vacuo at 40° C. Purification by flash column chromatography (Puriflash 40 g, 0-5% MeOH in DCM) gave the title compound (420 mg, 35%). LCMS (Method 1): 0.79 min, m/z 329.1 [M+H]⁺.

Intermediate 19: tert-Butyl (S)-1-(aminomethyl)-5-bromo-8-hydroxy-3,4-dihydroisoquinoline-2(1H)-carboxylate

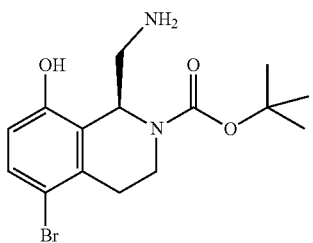 [SMILES: CC(C)(C)OC(=O)N1CCc2c(Br)ccc(O)c2[C@H]1CN]

To a stirred suspension of Intermediate 8 (3.41 g, 7 mmol) in EtOH (100 mL) was added hydrazine hydrate (1.7 mL, 34.95 mmol) and the resulting red mixture heated at 65° C. for 7 h forming a colourless precipitate. The mixture was cooled to rt and the precipitated solid was removed by filtration, and the solids washed with EtOH (20 mL). The filtrates were concentrated in vacuo to give the title compound (3.24 g, assumed quantitative), used without further purification. LCMS (Method 2): 1.01 min, 357.1 [M+H]⁺.

Intermediate 20: tert-Butyl (S)-5-bromo-8-hydroxy-1-((2-oxopyrrolidin-1-yl)methyl)-3,4-dihydroisoquinoline-2(1H)-carboxylate

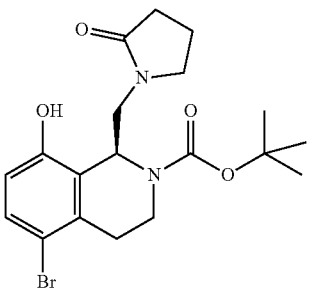 [SMILES: CC(C)(C)OC(=O)N1CCc2c(Br)ccc(O)c2[C@H]1CN1CCCC1=O]

A stirred solution of methyl 4-bromobutanoate (1.52 g, 8.4 mmol; CAS: 4897-84-1), Intermediate 19 (3.24 g, 7 mmol) and triethylamine (1.47 mL, 10.55 mmol) in toluene (70 mL) was heated at reflux for 18 h. A second portion of methyl 4-bromobutanoate (250 mg, 1.38 mmol) was added and the mixture heated at reflux for a further 5 h. The mixture was cooled to rt, diluted with EtOAc and washed with 10% aqueous citric acid, water, brine, dried over Na₂SO₄, filtered and concentrated in vacuo Purification by flash column chromatography on the Teledyne ISCO CombiFlash® Rf+ (100 g silica column, Biotage SNAP, 0-100% EtOAc in DCM, then 0-100% MeOH iN DCM) gave the title compound (1.41 g, 47%). LCMS (Method 2): 1.48 min, 447.2 [M+Na]⁺.

Intermediate 21: (S)-1-((5-Bromo-8-hydroxy-1,2,3,4-tetrahydroisoquinolin-1-yl)methyl)pyrrolidin-2-one

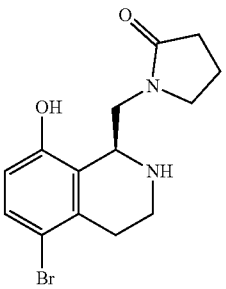 [SMILES: O=C1CCCN1C[C@H]1NCCc2c(Br)ccc(O)c21]

A stirred solution of Intermediate 20 (826 mg, 1.94 mmol) in DCM (60 mL) was treated with TFA (3 mL, 39.2 mmol) and the resulting solution stirred at rt for 2 h. The mixture was diluted with DCM (50 mL) and water (50 mL) and basified to pH 8 by addition of saturated aqueous NaHCO₃. The organic layer was washed with brine, dried over Na₂SO₄, filtered and concentrated in vacuo to give the title compound (593 mg, 94%) used without further purification. LCMS (Method 2): 0.74 min, 325.1 [M+H]⁺ with Br isotope.

Intermediate 22: tert-Butyl (S)-1-(aminomethyl)-5-chloro-8-hydroxy-3,4-dihydroisoquinoline-2(1H)-carboxylate

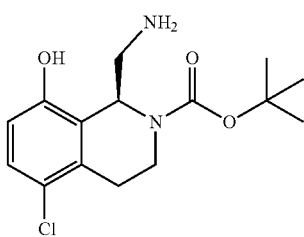 [SMILES: CC(C)(C)OC(=O)N1CCc2c(Cl)ccc(O)c2[C@H]1CN]

Method 1: To a solution of Intermediate 12 (2.35 g, 5.31 mmol) in EtOH (50 mL) was added hydrazine hydrate (1.29 mL, 26.5 mmol) and mixture heated at reflux for 24 h. The reaction was cooled to rt and filtered. The filtrate was concentrated in vacuo. Purification by flash column chromatography on the Teledyne ISCO CombiFlash® Rf+ (120 g silica column Puriflash HC/Biotage SNAP, 0-30% EtOAc in MeOH) gave the title compound (1.49 g, 90%). LCMS (Method 2): 1.01 min, 313.0 [M+H]⁺.

Method 2: To a stirred suspension of Intermediate 12 (40.0 g, 90.3 mmol) in EtOH (150 mL) was added hydrazine monohydrate (16.9 mL, 226 mmol, CAS: 7803-57-8) and the resulting mixture heated to 75° C. and stirred for 1 h. The reaction mixture was cooled to rt, diluted with additional IMS and filtered. The filter cake was washed with cold EtOH and the combined filtrates were concentrated in vacuo to 400 mL. The solution was allowed to stand for 18 h then filtered to remove precipitate and the precipitate was washed with cold EtOH. The filtrates were concentrated in vacuo and to the residue was added EtOH (100 mL) and MeCN (100 mL). The suspension was filtered and concentrated in vacuo to give the title compound (24.5 g, 82% yield).

Intermediate 23: tert-Butyl (S)-5-chloro-8-hydroxy-1-((2-oxopyrrolidin-1-yl)methyl)-3,4-dihydroisoquinoline-2(1H)-carboxylate

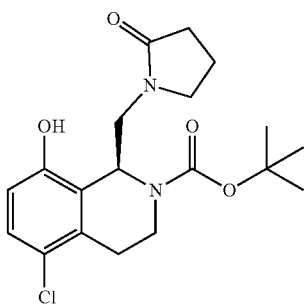 [SMILES: CC(C)(C)OC(=O)N1CCc2c(Cl)ccc(O)c2[C@H]1CN1CCCC1=O]

To a solution of Intermediate 22 (1.65 g, 5.28 mmol) in toluene (40 mL) was added methyl 4-bromobutanoate (1.24 g, 6.86 mmol; CAS: 4897-84-1) and triethylamine (1.1 mL, 7.93 mmol). The reaction heated at reflux for 24 h after which time, additional portions of methyl 4-bromobutanoate (1.24 g, 6.86 mmol) in toluene (1 mL) and triethylamine (1.1 mL, 7.93 mmol) were added and the reaction heated at reflux for an additional 6.5 h. The mixture was concentrated in vacuo, the residue dissolved in EtOAc, and washed sequentially with brine (20 mL), water (20 mL), dried over MgSO₄ and concentrated in vacuo. Purification by flash column chromatography on the Teledyne ISCO CombiFlash® Rf+ (200 g silica column Puriflash HC/Biotage SNAP, 0-100% EtOAc in cyclohexane) gave the title compound (1.29 g, 64%). LCMS (Method 2): 1.43 min, 403 [M+Na]⁺.

Intermediate 24: (S)-1-((5-Chloro-8-hydroxy-1,2,3,4-tetrahydroisoquinolin-1-yl)methyl)pyrrolidin-2-one

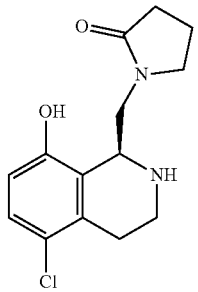 [SMILES: O=C1CCCN1C[C@H]1NCCc2c(Cl)ccc(O)c21]

To a stirred mixture of Intermediate 23 (203 mg, 0.530 mmol) in anhydrous DCM (8 mL) under argon was added TFA (0.82 mL, 10.66 mmol) dropwise and the resulting solution was stirred at rt for 1.5 h. The reaction mixture was diluted with water (5 mL) and adjusted to pH 8-9 by the addition of saturated aqueous NaHCO₃ solution (~8 mL). The aqueous layer was extracted with DCM (3×10 mL). The combined organics were dried over Na₂SO₄, filtered and concentrated in vacuo to give the title compound (173 mg, assumed quantitative), used without further purification. LCMS (Method 2): 0.75 min, 281.1 [M+H]⁺.

Intermediate 25: (1R,2S)-2-((Benzyloxy)carbonyl)cyclohexane-1-carboxylic acid

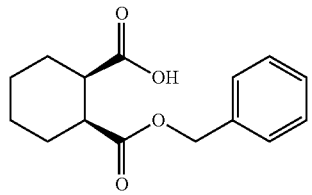 [SMILES: O=C(OCc1ccccc1)[C@H]1CCCC[C@H]1C(=O)O]

To a suspension of cis-1,2-cyclohexanedicarboxylic anhydride (10 g, 65.0 mmol, CAS: 13149-00-3) and quinidine (23 g, 71.4 mmol) in toluene (200 mL) at −10° C. was added benzyl alcohol (21 g, 195 mmol) dropwise over 30 min under argon. The reaction mixture was then stored in the refrigerator at 0° C. for 5 days. After warming to rt, the mixture was diluted with EtOAc (150 mL) and toluene (150 mL). The solution was washed with aqueous HCl (1M; 2×200 mL), then brine (200 mL). The organic layer was dried over Na₂SO₄ and concentrated in vacuo to 350 mL and a solution of (R)-alpha methylbenzylamine (7.86 g, 65 mmol) in toluene (75 mL) was added. The resulting mixture was stirred at rt for 30 min, before seeding with a small crystal of the pure ammonium salt (prepared by taking a small aliquot of the solution and concentrating to dryness) and stirring for a further 18 h. The solids were then collected by filtration and washed with toluene (50 mL) then dried in vacuo. The solids were then partitioned between EtOAc (250 mL) and 1M aqueous HCl (200 mL). The EtOAc layer was collected, washed with brine (100 mL), dried over MgSO$_4$, and concentrated in vacuo to give the title compound (10 g, 58%, >99% ee). Chiral HPLC (Chiralpak IA 4.6×250 mm, 90:10 hep/IPA+0.1% TFA, flowrate 1 ml/min); Rt=6.2 min. LCMS (Method 4): 0.51 min, 236.3 [M+H]$^+$. $^1$H NMR (400 MHz, CDCl$_3$) δ 7.38-7.26 (m, 5H), 5.20-5.04 (m, 2H), 2.92-2.85 (m, 2H), 2.09-1.99 (m, 2H), 1.85-1.75 (m, 2H), 1.61-1.35 (m, 4H).

Intermediate 26: Benzyl (1S,2R)-2-(chlorocarbonyl)cyclohexane-1-carboxylate

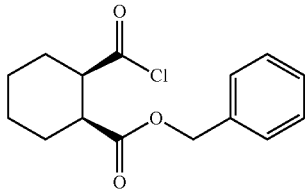 [SMILES: O=C(OCc1ccccc1)[C@H]1CCCC[C@H]1C(=O)Cl]

To a solution of Intermediate 25 (0.50 g, 1.90 mmol) in DCM (5 mL) was added oxalyl chloride (0.82 mL, 9.53 mmol). The reaction mixture was stirred at rt for 3 h, then the reaction mixture was concentrated in vacuo and the residue azeotroped in vacuo with toluene (2×20 mL) to give the title compound (0.57 g, 100%) used without further purification. $^1$H NMR (400 MHz, CDCl$_3$) δ 7.42-7.20 (m, 5H), 5.19-5.08 (m, 2H), 3.22-3.00 (m, 2H), 2.17-2.01 (m, 2H), 1.92-1.77 (2H, m), 1.60-1.37 (m, 4H).

Intermediate 27: (1R,2S)-2-[(2,4-Dimethoxyphenyl)methoxycarbonyl]cyclohexanecarboxylic acid; (1R)-1-phenylethanamine

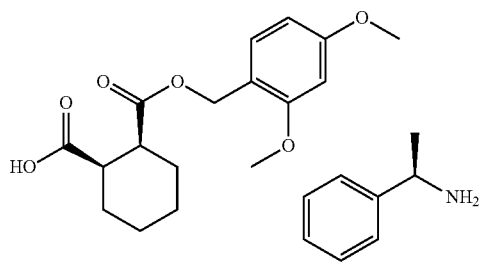

A solution of (2,4-dimethoxyphenyl)methanol (32.7 g, 195 mmol, CAS: 7314-44-5) in toluene (50 ml) was added dropwise to a suspension of cis-1,2-cyclohexanedicarboxylic anhydride (10.0 g, 64.9 mmol, CAS: 13149-00-3) and (S)-(6-methoxy-4-quinolyl)-[(2R,4S,5R)-5-vinylquinuclidin-2-yl]methanol (23.2 g, 71.4 mmol, CAS: 56-54-2) in toluene (150 ml) at −5° C. over 1 h. The solution was then transferred to a fridge and allowed to stand for 12 days. The reaction mixture was washed with 1M aqueous HCl (200 mL), brine (100 mL) and the organic layer dried over MgSO$_4$ and filtered. A portion (ca. 2 mL) of the filtrate was concentrated in vacuo and ether (2 mL) was added to the residue followed by (1R)-1-phenylethanamine (1 drop; CAS 3886-69-9). The resulting solid was collected by trituration. (1R)-1-Phenylethanamine (8.4 mL, 64.9 mmol) was added to the remaining filtrate whilst stirring. The solid collected from previous trituration was added to this solution and left stirring at rt for 18 h. The solid precipitated was collected by filtration, washed with ether (200 mL) and dried to give the title compound (16.4 g, 57%), used without further purification. $^1$H NMR (300 MHz, MeOD) δ 7.42-7.20 (m, 6H), 6.49-6.44 (m, 2H), 5.11-4.90 (m, 2H), 4.32 (q, 1H), 3.78 (s, 3H), 3.76 (s, 3H), 2.76-2.65 (m, 2H), 2.13-1.33 (m, 11H). The above reaction was repeated with 10 g of cis-1,2-cyclohexanedicarboxylic anhydride to give 20.6 g of the title compound (68%).

Intermediate 28: (1R,2S)-2-(((2,4-Dimethoxybenzyl)oxy)carbonyl)cyclohexane-1-carboxylic acid

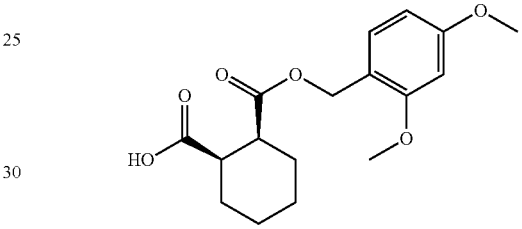

Intermediate 27 (16.4 g, 36.98 mmol) was partitioned between citric acid (10% aqueous; 80 mL) and EtOAc (400 mL). The organic layer was washed with brine, dried over Na$_2$SO$_4$, filtered and concentrated in vacuo to provide the title compound (11.5 g, 99%), used without further purification. $^1$H NMR (300 MHz, MeOD) δ 7.17 (d, 1H), 6.51-6.44 (m, 2H), 5.02 (dd, 2H), 3.78 (s, 3H), 3.76 (s, 3H), 2.81-2.79 (m, 2H), 2.01-1.99 (m, 2H), 1.75-1.71 (m, 2H), 1.47-1.41 (m, 4H).

Intermediate 29: (1R,2S)-2-(((2,4-Dimethoxybenzyl)oxy)carbonyl)-2-methylcyclohexane-1-carboxylic acid

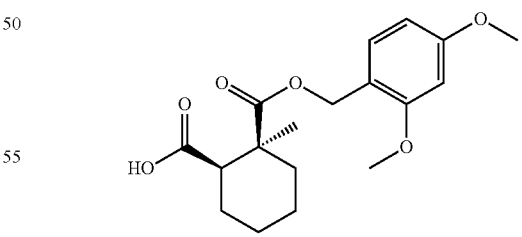

To a stirred solution of Intermediate 28 (11.5 g, 35.68 mmol) in anhydrous THF (92 mL) was added LDA (2M in THF/heptane/ethyl benzene; 44.6 mL, 89.19 mmol) dropwise at −25° C. under argon for over 2 h. The mixture was stirred at −25° C. for 30 min then iodomethane (6.66 mL, 107.03 mmol) was added dropwise, and the reaction stirred at −25° C. for 1 h. The reaction was quenched with saturated aqueous NH$_4$Cl and extracted with EtOAc. The organic layer was washed with 10% aqueous citric acid solution, the aqueous layer was further extracted with EtOAc and the combined organics were washed with brine, dried over Na₂SO₄, filtered and concentrated in vacuo. Purification by flash column chromatography (eluting 2-5% MeOH in DCM) gave the title compound (2.1 g, 13%). ¹H NMR (400 MHz, MeOD) δ 7.20-7.16 (m, 1H), 6.51-6.44 (m, 2H), 5.07-4.94 (m, 2H), 3.82-3.74 (m, 6H), 2.57-2.49 (m, 1H), 2.14-1.79 (m, 3H), 1.57-1.21 (m, 8H).

Intermediate 30: (1R,2S)-2-[(2,4-Dimethoxyphenyl)methoxycarbonyl]cyclopentane-carboxylic acid; (1R)-1-phenylethanamine

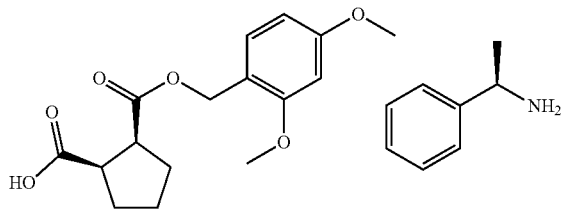

To a stirred suspension of (3aR,6aS)-4,5,6,6a-tetrahydro-3aH-cyclopenta-[c]furan-1,3-dione (10. g, 71.36 mmol, CAS: 35878-28-5) and (S)-(6-methoxy-4-quinolyl)-[(2R,4S,5R)-5-vinylquinuclidin-2-yl]methanol (25.46 g, 78.49 mmol, CAS: 56-54-2) in toluene (150 mL) was added (2,4-dimethoxyphenyl)methanol (37.82 mL, 214.07 mmol) in toluene (50 mL) dropwise at −5° C. over 1 h. The solution was then transferred to a fridge and allowed to stand for 5 days. The solution was washed with 1M aqueous HCl (400 mL) and brine (100 mL). The organic layer was dried over MgSO₄ and filtered. A portion (ca. 2 mL) of the filtrate was concentrated in vacuo and ether (2 mL) was added to the residue followed by (1R)-1-phenylethanamine (1 drop; CAS 3886-69-9). The resulting solid was collected by trituration. (1R)-1-Phenylethanamine (9.2 mL, 71.36 mmol) was then added to the bulk of the filtrate whilst stirring. The solid collected from previous trituration was added to this solution and left stirring at rt for 18 h. The solid precipitated was collected by filtration, washed with ether (200 mL) and dried to give the title compound (18.6 g, 58%), used without further purification. ¹H NMR (300 MHz, DMSO-d₆) δ 7.37-7.10 (m, 6H), 6.53-6.45 (m, 2H), 5.02-4.77 (m, 2H), 4.81-4.59 (m, 2H), 4.04-3.97 (m, 1H), 3.73 (d, 6H), 2.94-2.70 (m, 2H), 1.85-1.19 (m, 9H).

Intermediate 31: (1R,2S)-2-(((2,4-Dimethoxybenzyl)oxy)carbonyl)cyclopentane-1-carboxylic acid

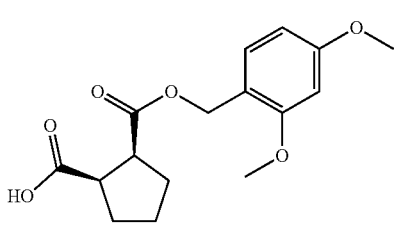 [SMILES: COc1ccc(COC(=O)[C@H]2CCC[C@H]2C(=O)O)c(OC)c1]

Intermediate 30 (18.6 g, 43.4 mmol) was partitioned between 10% aqueous citric acid solution (72 mL) and EtOAc (300 mL). The organic layer was washed with brine, dried over Na₂SO₄, filtered and concentrated in vacuo to provide the title compound (13.2 g, 95%), used without further purification. ¹H NMR (300 MHz, MeOD) δ 7.18 (d, 1H), 6.56-6.44 (m, 2H), 5.07-4.91 (m, 2H), 3.82-3.77 (m, 6H), 3.09-3.00 (m, 2H), 2.01-1.55 (m, 6H).

Intermediate 32: (1R,2S)-2-(((2,4-Dimethoxybenzyl)oxy)carbonyl)-2-methylcyclopentane-1-carboxylic acid

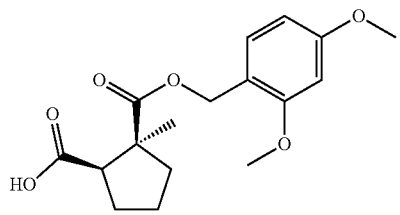 [SMILES: COc1ccc(COC(=O)[C@@]2(C)CCC[C@H]2C(=O)O)c(OC)c1]

To a stirred solution of Intermediate 31 (13.2 g, 42.8 mmol) in anhydrous THF (120 mL) was added LDA (2 M in THF/heptane/ethylbenzene; 53.5 mL, 107 mmol) dropwise at −25° C. under argon over 45 min. The mixture was stirred at −25° C. for 30 min then iodomethane (2.67 mL, 42.81 mmol) was added dropwise. The reaction was stirred for 30 min and then quenched with saturated aqueous NH₄Cl. EtOAc was added and the aqueous layer was extracted with EtOAc. The combined organics were washed with 10% citric acid solution, brine, dried over Na₂SO₄, filtered and concentrated in vacuo. Purification by flash column chromatography (2-5% MeOH in DCM) gave the title compound (1.9 g, 14%). ¹H NMR (300 MHz, MeOD) δ 7.21-7.16 (m, 1H), 6.51-6.44 (m, 2H), 4.98 (s, 2H), 3.78 (d, 6H), 2.69-2.59 (m, 1H), 2.21-1.29 (m, 9H).

Intermediate 33: 2-(3H-[1,2,3]triazolo[4,5-b]pyridin-3-yl) 1-(2,4-dimethoxybenzyl) (1S,2R)-1-methylcyclohexane-1,2-dicarboxylate

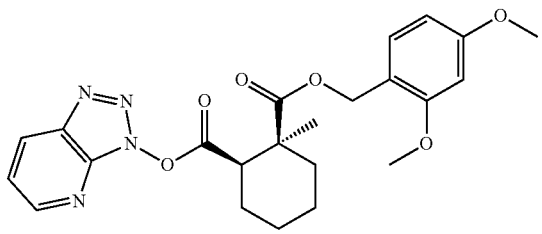 [SMILES: COc1ccc(COC(=O)[C@@]2(C)CCCC[C@H]2C(=O)On2nnc3cccnc32)c(OC)c1]

To a stirred solution of crude Intermediate 29 (13.5 g, 40.0 mmol) in DMF (72 mL) at rt under argon was added HATU (19.8 g, 52.0 mmol; CAS: 148893-10-1) and the reaction mixture was stirred for 5 min. To the mixture was added DIPEA (7.67 mL, 44.0 mmol) and the mixture was stirred at rt for 3.5 h. The reaction was diluted with water, extracted with EtOAc and the combined organics were washed with water, brine, dried over Na₂SO₄, filtered and concentrated in vacuo. Purification on the Teledyne ISCO CombiFlash® Rf+ (330 g silica column Puriflash HC, 0-75% EtOAc in cyclohexane) gave the title compound (14.4 g, 79%). LCMS (Method 16): 1.59 min, 477.3 [M+Na]⁺. ¹H NMR (400 MHz, CDCl₃) δ: 8.70 (dd, 1H), 8.40 (dd, 1H), 7.41 (dd, 1H), 7.25-7.22 (m, 1H), 6.43-6.40 (m, 2H), 5.16 (dd, 2H), 3.78 (d, 6H), 3.11 (dd, 1H), 2.32-2.13 (m, 3H), 1.73-1.52 (m, 5H), 1.47 (s, 3H).

Intermediate 34: 2-(3H-[1,2,3]triazolo[4,5-b]pyridin-3-yl) 1-(2,4-dimethoxybenzyl) (1S,2R)-1-methylcyclopentane-1,2-dicarboxylate

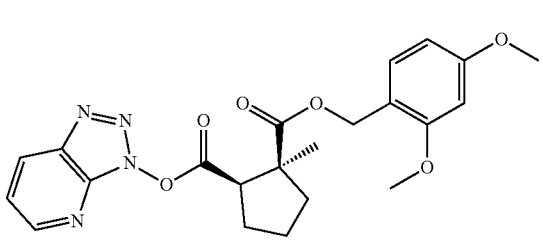 [SMILES: COc1ccc(COC(=O)[C@@]2(C)CCC[C@H]2C(=O)On2nnc3cccnc32)c(OC)c1]

To a stirred solution of Intermediate 32 (1.5 g, 4.65 mmol) in DMF (8 mL) was added HATU (2.3 g, 6.05 mmol) and the resulting mixture was stirred at rt under argon for 5 min. DIPEA (0.89 mL, 5.12 mmol) was added and the resulting mixture was stirred for 4 h. The reaction mixture was diluted with water and extracted with EtOAc. The combined organics were washed with water, brine, dried over $Na_2SO_4$, filtered and concentrated in vacuo. The crude product was purified by flash column chromatography on the Teledyne ISCO CombiFlash® Rf+ (80 g silica column Puriflash HC, 0-50% EtOAc in cyclohexane) to provide the title compound (771 mg, 38%). LCMS (Method 16): 1.49 min, 463.3 $[M+Na]^+$. $^1$H NMR (400 MHz, $CDCl_3$) δ: 8.71 (dd, 1H), 8.40 (dd, 1H), 7.42 (dd, 1H), 7.27-7.24 (m, 1H), 6.42 (d, 2H), 5.24 (s, 2H), 3.78 (d, 6H), 3.15 (dd, 1H), 2.44-2.28 (m, 3H), 1.93-1.71 (m, 3H), 1.58 (d, 3H).

Intermediate 35: tert-butyl (S)-5-chloro-8-hydroxy-1-((6-oxo-5-azaspiro[2.4]heptan-5-yl)methyl)-3,4-dihydroisoquinoline-2(1H)-carboxylate

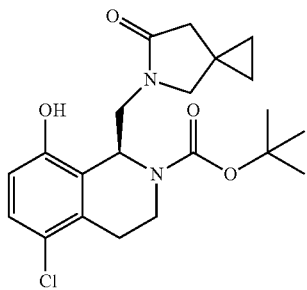 [SMILES: CC(C)(C)OC(=O)N1CCc2c(Cl)ccc(O)c2[C@H]1CN1CC2(CC2)CC1=O]

To a stirred solution of Intermediate 22 (2.70 g, 8.63 mmol) in toluene (30 mL) was added methyl 2-(1-(bromomethyl)cyclopropyl)acetate (2.14 g, 10.4 mmol; CAS: 855473-50-6) and triethylamine (1.8 mL, 13.0 mmol) in toluene (30 mL) and the reaction mixture was heated under reflux for 30 h. The reaction mixture was allowed to cool to rt and concentrated in vacuo. To this was added brine and the mixture extracted with DCM. The combined organics were washed with brine, dried over $MgSO_4$ and concentrated in vacuo. The crude product was purified by flash column chromatography on the Teledyne ISCO CombiFlash® Rf+ (80 g silica column Puriflash HC, 5-80% EtOAc in cyclohexane) to provide the title compound (2.89 g, 82%). LCMS (Method 17): 1.66 min, 407.1 $[M+H]^+$. The above reaction was repeated with 24.0 g of Intermediate 22 and yielded 24.8 g (79%).

Intermediate 36: (S)-5-((5-chloro-8-hydroxy-1,2,3,4-tetrahydroisoquinolin-1-yl)methyl)-5-azaspiro[2.4]heptan-6-one hydrochloride

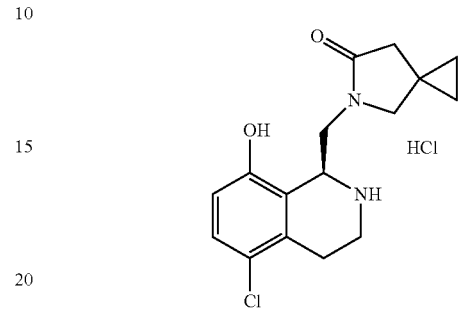

A solution of Intermediate 35 (2.35 g, 5.78 mmol) in HCl (4 M in dioxane; 29 mL, 116 mmol) was stirred at rt for 1 h. The reaction mixture was concentrated in vacuo and azeotroped with toluene (×2) to give the title compound (1.98 g, assumed quantitative) used without further purification. LCMS (Method 17): 0.79 min, 307.1 $[M+H]^+$.

Intermediate 37: 2,4-Dimethoxybenzyl (1S,2R)-2-((S)-5-chloro-8-hydroxy-1-((6-oxo-5-azaspiro[2.4]heptan-5-yl)methyl)-1,2,3,4-tetrahydroisoquinoline-2-carbonyl)-1-methylcyclohexane-1-carboxylate

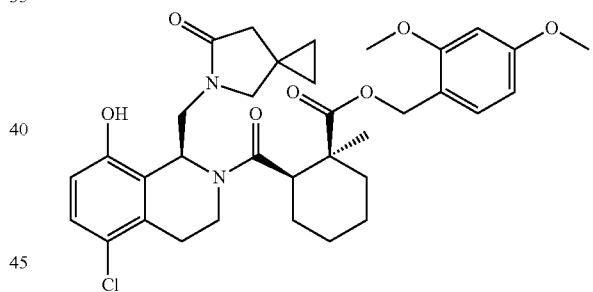

To a stirred solution of Intermediate 36 (4.50 m g, 13.1 mmol) in DMF (39 mL) was added Intermediate 33 (5.96 g, 13.1 mmol) and DIPEA (4.57 mL, 26.22 mmol) and the reaction mixture was stirred under nitrogen for 5 d. The reaction was diluted with brine, extracted with EtOAc and concentrated in vacuo. The residue was redissolved in EtOAc (75 mL) and cooled to 0° C. and a precipitate formed. The solid was removed by filtration to give the title compound (5.05 g, 62%). LCMS (Method 16): 1.52 min, 647.4 $[M+Na]^+$.

Intermediate 38: Ethyl (R)-4-iodo-3-methylbutanoate

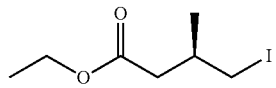

To a stirred solution of (R)-4-methyldihydrofuran-2(3H)-one (13.4 g, 134 mmol, CAS: 65284-00-6) in EtOH (250 mL) at −20° C. was added trimethylsilyl iodide (38.1 mL, 268 mmol) dropwise. The solution was stirred at −20° C. for 30 min. Triethyl orthoformate (22.3 mL, 134 mmol) was then added and the reaction stirred at reflux for 18 h. The reaction mixture was cooled to rt and concentrated in vacuo. The crude was product purified by flash column chromatography (silica, 5% EtOAc in heptane) to give the title compound (24.3 g, 71%). ¹H NMR (300 MHz, CDCl₃) δ: 4.15 (q, 2H), 3.32-3.23 (m, 2H), 2.46 (dd, 1H), 2.24 (dd, 1H), 2.07-1.99 (m, 1H), 1.30-1.25 (t, 3H), 1.06 (d, 3H).

Intermediate 39: (1R,6S)-6-(methoxycarbonyl)-6-methylcyclohex-3-ene-1-carboxylic acid

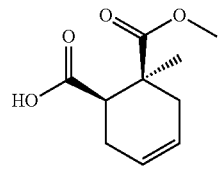

To a stirred solution of (1R,6S)-6-methoxycarbonylcyclohex-3-ene-1-carboxylic acid (10.5 g, 57.01 mmol; CAS: 88335-93-7) in anhydrous THF (150 mL), cooled to −25° C. under argon, was added dropwise lithium diisopropylamide solution (1.0 M in THF/hexanes; 143 mL, 143 mmol) and the resulting solution was stirred at −25° C. for 30 min. To this was added dropwise iodomethane (10.65 mL, 171.0 mmol) and the solution was allowed to slowly warm to rt over 4 h. The mixture was quenched with saturated aqueous NH₄Cl (200 mL) then partitioned between EtOAc (200 mL) and 10% aqueous citric acid (200 mL). The aqueous layer was extracted further with EtOAc (2×200 mL) and the combined organics were washed with brine, dried over Na₂SO₄, filtered and concentrated in vacuo give the title compound (11.4 g, quantitative). ¹H NMR (400 MHz, CDCl₃) δ 5.67-5.59 (m, 2H), 3.71 (s, 3H), 3.02-2.98 (m, 1H), 2.78-2.72 (m, 1H), 2.61-2.55 (m, 1H), 2.48-2.36 (m, 1H), 2.09-2.01 (m, 1H), 1.26 (s, 3H).

Intermediate 40: 2-(3H-[1,2,3]triazolo[4,5-b]pyridin-3-yl) 1-methyl (1S,2R)-1-methylcyclohex-4-ene-1,2-dicarboxylate

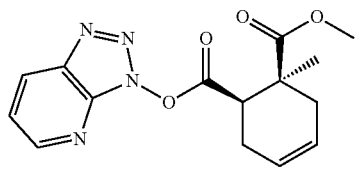 [SMILES: COC(=O)[C@@]1(C)CC=CC[C@H]1C(=O)On1nnc2cccnc21]

To a stirred solution of Intermediate 39 (2.15 g, 10.9 mmol) in DMF (50 mL) at rt under argon was added HATU (4.54 g, 11.9 mmol; CAS: 148893-10-1) and the reaction mixture stirred at rt for 5 minutes. DIPEA (2.08 mL, 11.9 mmol) was added and the reaction mixture was stirred for a further 4 h. The reaction mixture was diluted with water, extracted with EtOAc and the combined organics were washed with water, brine, dried over MgSO₄, filtered and concentrated in vacuo. The crude product was purified by flash column chromatography on the Teledyne ISCO CombiFlash® Rf+ (80 g silica column Puriflash HC/Biotage SNAP, 0-10% MeOH in DCM) to give the title compound (2.30 mg, 67%). LCMS (Method 16): 1.29 min, 339.0 [M+Na]⁺.

Intermediate 41: (E)-1-fluoro-2-methoxy-4-(2-nitrovinyl)benzene

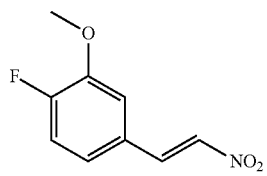

A solution of 4-fluoro-3-methoxybenzaldehyde (57 g, 370 mmol; CAS: 128495-46-5), ammonium acetate (14.25 g, 185 mmol), and nitromethane (100.14 mL, 1850 mmol) in acetic acid (150 mL) was heated at 100° C. for 5 h. The reaction mixture was allowed to cool to rt overnight. The resulting solid was collected by filtration, washed with diethyl ether and the solid dried in vacuo. The solid was suspended in DCM (1 L) and washed with water. The organic layer was filtered to remove precipitate, dried (Na₂SO₄), filtered and concentrated in vacuo to give the title compound (42 g, 200 mmol, 54%). The precipitate was dissolved in 2-MeTHF, and the organic layer was washed with water, brine, dried (Na₂SO₄) and evaporated to give further product (11 g, 55.2 mmol, 15% yield) as a yellow solid. The acetic acid mother liquors were evaporated and diluted with IMS. The resulting solid was collected by filtration and washed with IMS to provide another batch of the product (1.5 g). These batches were combined to give the title compound (54.5 g, 74%) used without further purification. ¹H NMR (300 MHz; CDCl₃) δ: 7.95 (d, 1H), 7.52 (d, 1H), 7.16-7.08 (m, 3H), 3.95 (s, 3H).

Intermediate 42: 2-(4-fluoro-3-methoxyphenyl)ethan-1-amine

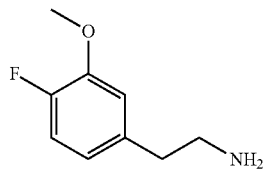

Sulfuric acid (8.92 mL, 167.38 mmol) was added dropwise under nitrogen to a stirred solution of lithium aluminium hydride in THF (2M; 12.7 g, 335 mmol) pre-cooled in an ice-salt bath. The mixture was stirred for 15 min until all gas evolution had subsided. A solution of Intermediate 41 (22 g, 111.6 mmol) in 2-methyltetrahydrofuran (660 mL) was added dropwise, ensuring that the temperature remained <20° C. The cooling bath was removed and the mixture was heated under reflux for 5 min, then cooled in an ice salt bath. IPA (57 mL) was added dropwise followed by sodium hydroxide (2M, 39 mL). Magnesium sulphate was added and the mixture was stirred for 30 min then filtered through Celite®. The filter cake was washed with 2-MeTHF/IPA ~98:2 (~1.5 L) followed by 10% MeOH in DCM (~1.5 L). The filtrate was concentrated in vacuo to give the title compound (18.8 g, 99%) used without further purification. $^1$H NMR (400 MHz, CDCl$_3$) 7.02-6.97 (m, 1H), 6.80 (dd, 1H), 6.74-6.68 (m, 1H), 3.89-3.88 (s, 3H), 2.96 (t, 2H), 2.71 (t, 2H), 1.24-1.18 (m, 2H).

Intermediate 43: 2-(1,3-dioxoisoindolin-2-yl)-N-(4-fluoro-3-methoxyphenethyl)acetamide

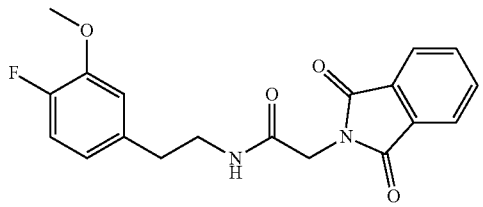 [SMILES: COc1cc(CCNC(=O)CN2C(=O)c3ccccc3C2=O)ccc1F]

To a solution of Intermediate 42 (49.3 g, 291 mmol) and DIPEA (101.5 mL, 583 mmol) in DCM (250 mL) under nitrogen cooled in an ice-salt bath was added a solution of Intermediate 1 (65.2 g, 291 mmol) in DCM (1.25 L) dropwise. The mixture was stirred warming from 0° C. to room temperature over 2 h. The resulting precipitate was isolated by filtration and washed thoroughly with DCM. The solid was dried in vacuo to give the title compound (83 g, 80%) used without further purification. $^1$H NMR (400 MHz, CDCl$_3$) d 7.89-7.86 (m, 2H), 7.77-7.74 (m, 2H), 6.90 (dd, 1H), 6.78 (dd, 1H), 6.66 (ddd, 1H), 5.75 (s, 1H), 4.29 (s, 2H), 3.88 (s, 3H), 3.52 (q, 2H), 2.79 (t, 2H).

Intermediate 44: N-(2-chloro-4-fluoro-5-methoxyphenethyl)-2-(1,3-dioxoisoindolin-2-yl)acetamide

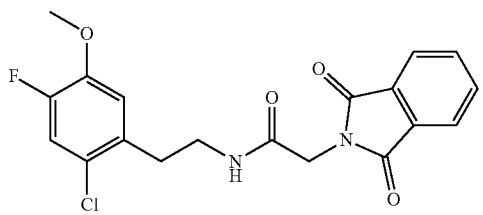 [SMILES: COc1cc(CCNC(=O)CN2C(=O)c3ccccc3C2=O)c(Cl)cc1F]

A mixture of Intermediate 43 (82.6 g, 232 mmol) and NCS (34.05 g, 254.97 mmol) in DMF (780 mL) was heated to 50° C. and stirred for 1 h at 50° C., then cooled and concentrated in vacuo. To the resulting residue was added water (~2 L) and the resulting precipitate stirred for 1 h. The solid was isolated by filtration, washed with water, Et$_2$O, air dried and dried in vacuo to give the title compound (85.8 g, 94%) used without further purification. LCMS (Method 15): 1.43 min, 391.3 [M+H]$^+$.

Intermediate 45: 2-((5-chloro-7-fluoro-8-methoxy-3,4-dihydroisoquinolin-1-yl)methyl)isoindoline-1,3-dione

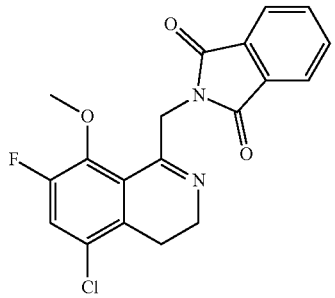 [SMILES: COc1c(F)cc(Cl)c2c1C(CN1C(=O)c3ccccc3C1=O)=NCC2]

A solution of Intermediate 44 (5 g, 12.79 mmol) in nitromethane (200 mL) was stirred under nitrogen at 108° C. and poured onto a suspension of phosphorus pentoxide (10.9 g, 76.77 mmol) in nitromethane, also at 108° C. and the resulting mixture was stirred at 108° C. for 1 h. The mixture was cooled to rt and the solvent was decanted into a flask and concentrated in vacuo. The combined residues were diluted with water 500 mL and the resulting mixture heated at 40° C. for 30 min. The mixture was cooled and neutralised with solid sodium carbonate portionwise, then extracted with DCM (3×200 mL). The combined extracts were washed with brine, dried (MgSO$_4$) and concentrated in vacuo. The residue was suspended in diethyl ether and to this was added EtOAc. The resulting precipitate was isolated by filtration and dried in vacuo to give the title compound (4.1 g, 86% yield) used without further purification. LCMS (Method 15): 1.64 min, 373.2 [M+H]$^+$.

Intermediate 46: 2-((5-chloro-7-fluoro-8-methoxy-1,2,3,4-tetrahydroisoquinolin-1-yl)methyl)isoindoline-1,3-dione

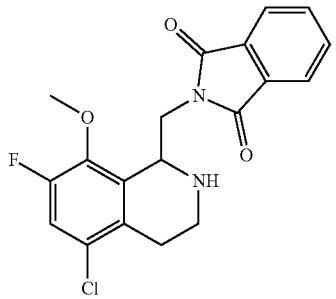 [SMILES: COc1c(F)cc(Cl)c2c1C(CN1C(=O)c3ccccc3C1=O)NCC2]

A stirred suspension of Intermediate 45 (37.1 g, 99.5 mmol) in DCM (450 mL) was cooled in an ice bath. To this was added acetic acid (6.27 mL, 109 mmol) and sodium triacetoxyborohydride (42.2 g, 199 mmol) was added portionwise over 30 min. The mixture was stirred overnight warming to rt. The mixture was diluted with water and neutralised with solid sodium carbonate. The mixture extracted with DCM and the combined organics washed with brine, dried (MgSO$_4$) and concentrated in vacuo. The residue was triturated in EtOAc to give the title compound (16.8 g, 43% yield). The mother liquors were concentrated in vacuo and the residue triturated in a mixture of Et$_2$O and Intermediate 47: 2-((5-chloro-7-fluoro-8-hydroxy-1,2,3,4-tetrahydroisoquinolin-1-yl)methyl)isoindoline-1,3-dione hydrobromide

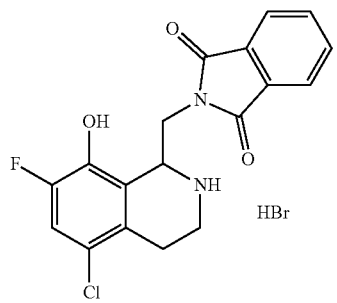 [SMILES: O=C1c2ccccc2C(=O)N1CC1NCCc2c(Cl)cc(F)c(O)c21 ; Br]

To a stirred solution of Intermediate 46 (12.3 g, 32.8 mmol) in DCM (246 mL) cooled in an ice bath under argon was added boron tribromide in DCM (1 M; 131 mL, 131 mmol) dropwise over 1.5 h. The reaction mixture was allowed to warm to rt and stirred for 20 h. The reaction was quenched by dropwise addition onto ice-water (130 mL) over 1 h and the resulting mixture was stirred for 1 h. The solid was collected by filtration, washed with water and dried in vacuo at 50° C. for 18 h to provide the title compound (8.6 g, 60%) used without further purification. LCMS (Method 2): 0.96 min, 361.0 [M+H]$^+$.

Intermediate 48: tert-butyl (S)-5-chloro-1-((1,3-dioxoisoindolin-2-yl)methyl)-7-fluoro-8-hydroxy-3,4-dihydroisoquinoline-2(1H)-carboxylate

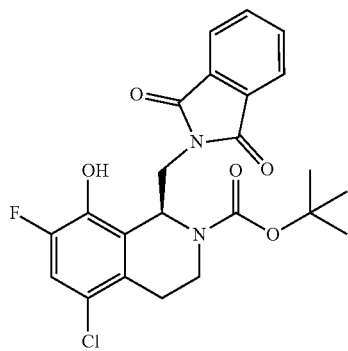 [SMILES: CC(C)(C)OC(=O)N1CCc2c(Cl)cc(F)c(O)c2[C@H]1CN1C(=O)c2ccccc2C1=O]

To a suspension of Intermediate 47 (16 g, 36.2 mmol) in DCM (280 mL) was added DIPEA (15.69 mL, 90.56 mmol) followed by di-tert-butyl dicarbonate (7.12 g, 32.6 mmol) and the resulting mixture was stirred at rt under argon for 1 h. The reaction mixture was diluted with water and the organic layer separated. The aqueous layer was extracted with DCM and the combined organics washed with brine, dried (Na$_2$SO$_4$) and concentrated in vacuo. The residue was triturated in 10% MeOH/DCM and the resulting solid collected by filtration to provide the title compound (8.50 g). The filtrate was purified by flash column chromatography on the Teledyne ISCO CombiFlash® Rf+ (120 g silica column Puriflash HC, 0-10% EtOAc in DCM) to provide a further batch of the title compound (2.5 g); combined yield (11 g, 66%; racemic mixture) Purification of a 2.0 g portion by chiral SFC (Method 1; YMC Amylose-C 20/80 EtOH (0.1% diethylamine)/CO$_2$, 100 ml/min, 120 bar, 40° C.) gave the title compound (first eluting enantiomer; 0.99 g, 47%). Absolute stereochemistry confirmed by small molecule X-ray crystallography of the carboxylic acid final compound arising from enantiomer 2. LCMS (Method 15): 1.41 min, 483.1 [M+Na]$^+$. $^1$H NMR (400 MHz; DMSO-d$_6$) δ 7.95-7.80 (m, 4H), 7.42-7.37 (m, 1H), 5.60-5.45 (m, 1H), 4.19-3.75 (m, 3H), 3.45-3.35 (m, 1H), 2.83-2.79 (m, 1H), 2.63-2.53 (m, 1H), 1.03-0.95 (m, 9H).

Intermediate 49: tert-Butyl (S)-1-(aminomethyl)-5-chloro-7-fluoro-8-hydroxy-3,4-dihydroisoquinoline-2(1H)-carboxylate

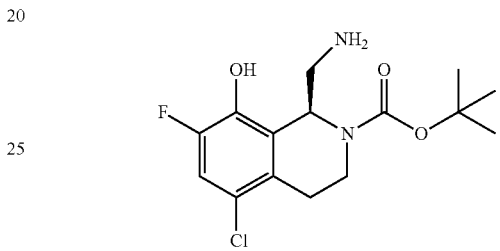

To a stirred suspension of Intermediate 48 (970 mg, 2.1 mmol) In EtOH (10.7 mL) was added hydrazine monohydrate (0.39 mL, 5.26 mmol; CAS: 7803-57-8) and the reaction mixture heated at 75° C. for 1 h. The reaction mixture was allowed to cool to rt, diluted with cold MeCN, filtered and the filtrate concentrated in vacuo. The residue was taken up in IMS (5 mL) and stirred at rt for 18 h. The solution was filtered, the solid washed with cold IMS and the filtrate concentrated in vacuo to provide the title compound (700 mg, 96% yield) used without further purification. LCMS (Method 15): 1.34 min, 331.2 [M+H]$^+$.

Intermediate 50: tert-butyl (S)-5-chloro-7-fluoro-8-hydroxy-1-((6-oxo-5-azaspiro[2.4]heptan-5-yl)methyl)-3,4-dihydroisoquinoline-2(1H)-carboxylate

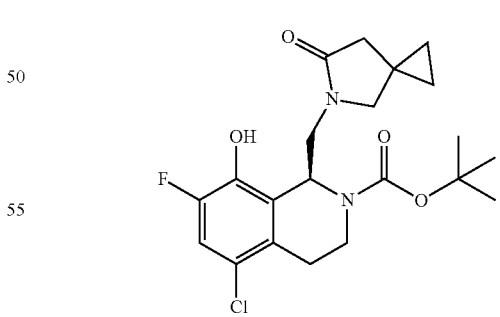

A stirred solution of Intermediate 49 (500 mg, 1.51 mmol), methyl 2-(1-(bromomethyl)cyclopropyl)acetate (344 mg, 1.66 mmol; CAS: 855473-50-6) and triethylamine (0.32 mL, 2.27 mmol) in toluene (7 mL) was heated under reflux for 18 h. A further portion of methyl 2-(1-(bromomethyl)cyclopropyl)acetate (156 mg, 0.75 mmol) and triethylamine (0.16 mL, 1.14 mmol) were added and the mixture heated under reflux for 3 h. The reaction mixture was cooled to rt and concentrated in vacuo. The residue was partitioned diluted with brine, extracted with DCM and the combined organics washed with brine, dried over Na$_2$SO$_4$ and concentrated in vacuo. The crude product was purified by flash column chromatography on the Teledyne ISCO Combi-Flash® Rf+ (40 g silica column Puriflash HC, 0-100% EtOAc in cyclohexane) to provide the title compound (426 mg, 66%). LCMS (Method 2): 1.64 min, 447.1 [M+Na]$^+$.

Intermediate 51: N-(2-chloro-5-methoxyphenethyl)-2-(1,3-dioxoisoindolin-2-yl)acetamide

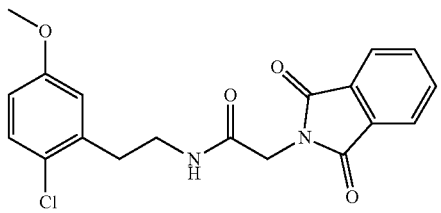 [SMILES: COc1ccc(Cl)c(CCNC(=O)CN2C(=O)c3ccccc3C2=O)c1]

To a stirred solution of Intermediate 2 (870 g, 2.573 mol) in DMF (13.0 L) divided between 4 flasks was added N-chlorosuccinimide (361 g, 2.701 mol; 128-09-6) divided equally between each reaction. The reaction mixtures were heated to 80° C. for 2 h, cooled to rt and combined into two batches. Each batch was concentrated in vacuo to approximately 1 L. The mixtures were left to stand for 18 h and the resulting precipitates collected by filtration. The organics were each diluted with DCM (2.5 L) and washed with water (2 L). The organics were concentrated in vacuo and the resulting slurry combined with the previously isolated solid and filtered (both batches treated separately). The solids were washed with Et$_2$O and concentrated in vacuo to give the title compound in two batches (435.5 g and 419.2 g, 79%) used without further purification. LCMS (Method 9a): 2.02 min, 373.4 [M+H]$^+$. $^1$H NMR (300 MHz, CDCl$_3$) δ 7.85-7.90 (m, 2H), 7.73-7.78 (m, 2H), 7.19 (d, 1H), 6.76-6.80 (m, 1H), 6.70 (dd, 1H), 5.78 (s, 1H), 4.29 (d, 2H), 3.75-3.80 (m, 3H), 3.56 (q, 2H), 2.94 (d, 2H).

Intermediate 52: 2-((5-chloro-8-methoxy-3,4-dihydroisoquinolin-1-yl)methyl)isoindoline-1,3-dione

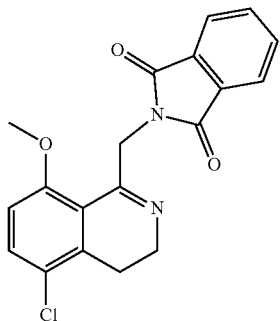 [SMILES: COc1ccc(Cl)c2c1C(CN1C(=O)c3ccccc3C1=O)=NCC2]

To a suspension of Intermediate 51 (419 g, 965 mmol) in MeCN (7.5 L) divided between over 3 flasks was added phosphorus pentoxide (813 g, 5.73 mol; CAS: 1314-56-3). The mixture was heated to 60° C. for 20 h. The organic phase (approximately 1.5 L) was decanted away from the precipitate and concentrated in vacuo. Water (2.5 L) was added to the remaining solids. The acetonitrile concentrate was washed into this solution with water (500 mL) and the mixture heated to 40° C. for 1 h. The resulting solution was allowed to cool to rt and split between two flasks. To these was added saturated aqueous sodium carbonate solution with stirring until the pH was around pH 9. The precipitated solid was collected by filtration and washed with water (500 mL). The combined was dried in vacuo at 40° C. to give the title compound (353 g, 93%) used without further purification. LCMS (Method 9a): 2.42 min, 355.0 [M+H]$^+$.

Intermediate 53: (S)-5-chloro-1-((1,3-dioxoisoindolin-2-yl)methyl)-8-methoxy-3,4-dihydroisoquinoline-2(1H)-carbaldehyde

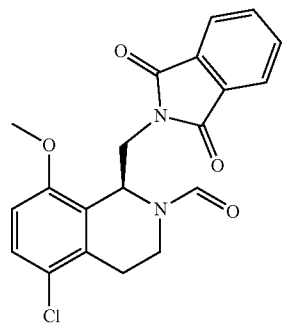 [SMILES: COc1ccc(Cl)c2c1[C@@H](CN1C(=O)c3ccccc3C1=O)N(C=O)CC2]

A solution of benzeneruthenium(II) chloride dimer (4.67 g, 9.35 mmol; CAS: 37366-09-9) and (1S,2S)-(+)-N-p-tosyl-1,2-diphenylethylenediamine (8.38 g, 22.88 mmol; CAS: 167316-27-0) in MeCN (300 mL) under argon was stirred at rt for 1 h. The mixture was divided into two flasks and each added to a flask containing MeCN (520 mL). To each mixture was added MeCN (520 mL) and DCM (150 mL). To each flask was added Intermediate 52 (201 g, 565 mmol) followed by MeCN (520 mL). A 1:1 mixture of formic acid (470 mL, 12.6 mol; CAS: 64-18-6) and triethylamine (470 mL, 3.370 mol) was divided into two and added to the two reaction flasks. The mixtures were stirred at rt under argon for 3 days. To each was added water (1 L) and solid sodium hydrogen carbonate added until the mixture was pH 8-9. DCM (1.5 L) was added to each reaction and the aqueous layers separated. The organics were washed further with water and combined. The organic phase was filtered and passed through a plug of silica, eluted with a 2:1 mixture of EtOAc in DCM (approximately 4 L). The organics were concentrated in vacuo to give the title compound (192.3 g, 76%; mixture with Intermediate 54), used without further purification. LCMS (Method 9a): 2.28 min, 385.4 [M+H]$^+$.

Intermediate 54: (S)-2-((5-chloro-8-methoxy-1,2,3,4-tetrahydroisoquinolin-1-yl)methyl)isoindoline-1,3-dione

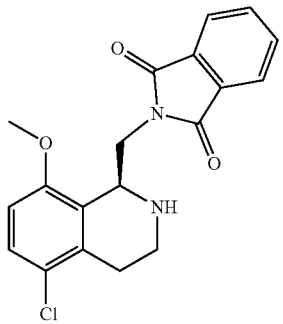 [SMILES: COc1ccc(Cl)c2c1[C@@H](CN1C(=O)c3ccccc3C1=O)NCC2]

To a suspension of hydrochloric acid (2 M; 0.11 L, 221 mmol) in THF (1.4 L) was added Intermediate 53 (192 g, 500 mmol) and the mixture heated at reflux for 18 h. The reaction mixture was cooled to rt and saturated sodium hydrogen carbonate solution added gradually until pH 8-9 was reached. The mixture was extracted with DCM (5 L) and the combined organics dried over MgSO$_4$, filtered and concentrated in vacuo. Recrystallisation from acetonitrile gave a solid that was dried in vacuo (50° C.) to give the title compound (100.5 g, 55%), used without further purification. LCMS (Method 9a): 2.36 min, 357.4 [M+H]$^+$.

Intermediate 55: (S)-2-((5-chloro-8-hydroxy-1,2,3,4-tetrahydroisoquinolin-1-yl)methyl)isoindoline-1,3-dione

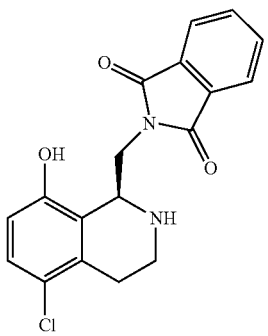 [SMILES: O=C1c2ccccc2C(=O)N1C[C@H]1NCCc2c(Cl)ccc(O)c21]

To a solution of Intermediate 54 (95.5 g, 268 mmol) in DCM (2 L) at 0° C. was added boron tribromide (1M in DCM; 1.02 L, 1.02 mol; CAS: 10294-33-4) dropwise over 1 h. The reaction mixture was allowed to warm to rt and stirred for 48 h. The reaction was cooled to 0° C. and quenched with MeOH (200 mL). The mixture was stood for 2 h and the precipitate isolated by filtration. The precipitate was washed with DCM and dried in vacuo (50° C.) to give (S)-2-((5-chloro-8-hydroxy-1,2,3,4-tetrahydroisoquinolin-1-yl)methyl)-isoindoline-1,3-dione hydrobromide (57.3 g, 51%). To a stirred solution of the DCM filtrate was added aqueous hydrochloric acid (2 M; 2 L) and the mixture stirred for 1 h. The precipitate was isolated by filtration and dried in vacuo (50° C.) to give (S)-2-((5-chloro-8-hydroxy-1,2,3,4-tetrahydroisoquinolin-1-yl)methyl)isoindoline-1,3-dione (49.3 g, ~45%) as a mixture of hydrobromide and hydrochloride salts. The acidic aqueous phase was separated and adjusted to pH 8-9 by the addition of solid sodium bicarbonate and extracted with DCM. The organics were dried (MgSO$_4$), filtered and concentrated in vacuo to give the title compound (2.53 g, 2%). 2-[[(1S)-5-chloro-8-hydroxy-1,2,3,4-tetrahydroisoquinolin-1-yl]methyl]isoindoline-1,3-dione hydrobromide: LCMS (Method 10): 0.99 min, 343.0 [M+H]$^+$. 2-[[(1S)-5-chloro-8-hydroxy-1,2,3,4-tetrahydroisoquinolin-1-yl]methyl]isoindoline-1,3-dione hydrochloride: (Method 9a): 1.84 min, 343.3 [M+H]$^+$. 2-[[(1S)-5-chloro-8-hydroxy-1,2,3,4-tetrahydroisoquinolin-1-yl]methyl]isoindoline-1,3-dione: LCMS (Method 9a): 1.93 min, 343.3 [M+H]$^+$.

Intermediate 56: tert-butyl (S)-5-chloro-1-((1,3-dioxoisoindolin-2-yl)methyl)-8-methoxy-3,4-dihydroisoquinoline-2(1H)-carboxylate

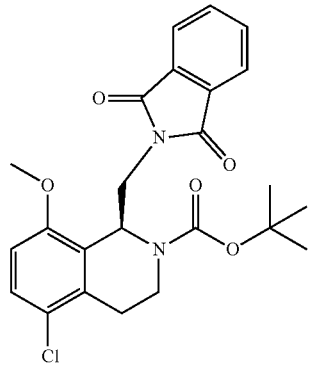 [SMILES: COc1ccc(Cl)c2c1[C@@H](CN1C(=O)c3ccccc3C1=O)N(C(=O)OC(C)(C)C)CC2]

To a suspension of Intermediate 54 (5.0 g, 14.01 mmol) in DCM (100 mL) was added triethylamine (2.93 mL, 21.02 mmol) followed by di-tert-butyl dicarbonate (3.06 g, 14.0 mmol; CAS: 24424-99-5). The reaction mixture was stirred at rt for 72 h, concentrated in vacuo and the residue purified by flash column chromatography (silica; 0-60% EtOAc in heptane) to give the title compound (6.37 g, 99%). LCMS (Method 9a): 3.04 min, 357.4 [M+H–CO$_2$$^t$Bu]$^+$. $^1$H NMR (300 MHz, CDCl$_3$) δ 7.88-7.82 (m, 2H), 7.70 (dq, 2H), 7.29 (d, 1H), 6.73 (dd, 1H), 5.43-5.90 (1H), 4.18-4.13 (m, 2H), 3.95-3.86 (m, 4H), 3.30-3.62 (1H), 3.12-2.77 (m, 2H), 1.08 (d, 9H).

Intermediate 57: tert-butyl (S)-1-(aminomethyl)-5-chloro-8-methoxy-3,4-dihydroisoquinoline-2(1H)-carboxylate

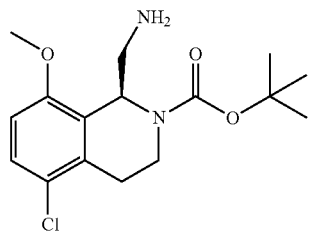 [SMILES: COc1ccc(Cl)c2c1[C@@H](CN)N(C(=O)OC(C)(C)C)CC2]

To a stirred solution of Intermediate 56 (6.3 g, 13.8 mmol) in EtOH (200 mL) was added hydrazine hydrate (3.35 mL, 68.9 mmol) and the reaction mixture was heated at 65° C. for 32 h. The mixture was cooled to rt, filtered and the filter cake washed with EtOH. The filtrate was concentrated in vacuo and the residue triturated with Et$_2$O. The mixture was filtered and the filter cake washed with Et$_2$O. The filtrate was concentrated in vacuo to give the title compound (4.5 g, 99%) used without further purification. LCMS (Method 9): 0.95 min, 327.1 [M+H]$^+$.

R$^1$ Method A: 3-(chloromethyl)-5-methylisothiazole

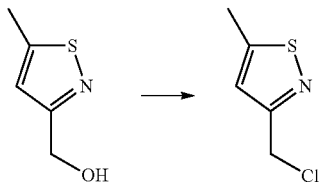

To a stirred solution of (5-methylisothiazol-3-yl)methanol (203 mg, 1.57 mmol, CAS: 1803598-19-7) in chloroform (2 mL) under argon was added thionyl chloride (0.23 mL, 3.14 mmol) dropwise and the resulting solution was stirred at rt for 75 min. The reaction mixture was concentrated in vacuo to give 3-(chloromethyl)-5-methylisothiazole (224 mg, 97%), used without further purification. $^1$H NMR (400 MHz; DMSO-d$_6$) δ 7.21 (d, 1H), 4.76 (s, 2H), 2.56 (d, 3H).

R$^1$ Method B: 4-(chloromethyl)-5-(difluoromethyl)-1-methyl-1H-1,2,3-triazole

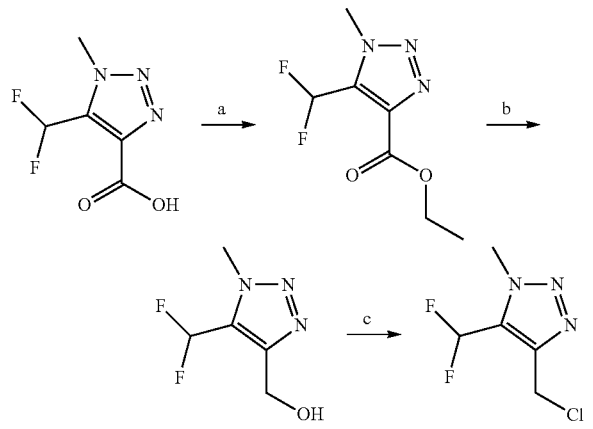

Step a. 5-(Difluoromethyl)-1-methyl-triazole-4-carboxylic acid (8.0 g, 45.2 mmol; CAS: 1423028-04-9) was suspended in EtOH (200 mL) and sulfuric acid (4.8 mL, 90.3 mmol) was added. The resulting solution was heated at 80° C. for 12 h. The reaction mixture was concentrated in vacuo and the residue diluted with water and adjusted to pH 8 with saturated aqueous sodium bicarbonate. The mixture was extracted with EtOAc (2×100 mL) and the combined organics were washed with brine, dried (MgSO$_4$) and concentrated in vacuo to give ethyl 5-(difluoromethyl)-1-methyl-triazole-4-carboxylate (7.3 g, 79%), used without further purification. LCMS (Method 16): 1.20 min, 206.1 [M+H]$^+$. $^1$H NMR (400 MHz, CDCl$_3$) δ 7.51 (t, 1H), 4.47 (q, 2H), 4.29-4.28 (m, 3H), 1.45 (t, 3H).

Step b. Ethyl 5-(difluoromethyl)-1-methyl-triazole-4-carboxylate (7.2 g, 35.1 mmol) was dissolved in THF (50 mL) and the resulting solution cooled to 0° C. under an argon atmosphere. To this was added lithium aluminium hydride (1M in THF; 17.6 mL, 17.6 mmol) dropwise and the reaction mixture stirred for 1 h from 0° C. to rt. Additional lithium aluminium hydride (1M in THF; 3 mL, 3 mmol) was added and the mixture was stirred for 30 min. The mixture was cooled in ice water, water (0.7 mL) was added dropwise, followed by NaOH (3M, 0.7 mL) and water (2 mL) and the resulting suspension was stirred for 30 min. The mixture was filtered through Celite® and the filtrate was concentrated in vacuo to give (5-(difluoromethyl)-1-methyl-1H-1,2,3-triazol-4-yl)methanol (5.7 g, 100%). LCMS (Method 15): 0.68 min, 164.1 [M+H]$^+$. $^1$H NMR (400 MHz; DMSO-d$_6$,) δ 7.45 (t, 1H), 5.42 (t, 1H), 4.62 (d, 2H), 4.13 (s, 3H).

Step c. The above intermediate (6.16 g, 37.8 mmol) was dissolved in DCM (76 mL) and the mixture sonicated. The solution was cooled in ice water and to this was added thionyl chloride (5.5 mL, 75.5 mmol) dropwise under nitrogen. The reaction mixture stirred for 2 h from 0° C. to rt and concentrated in vacuo. The residue was diluted in chloroform and concentrated in vacuo to give the title compound (7.08 g, 39.0 mmol, quantitative), used without further purification. LCMS (Method 2) 0.90 min, 181.9 [M+H]$^+$.

R$^1$ Method C: 4-(Chloromethyl)-5-(methoxymethyl)-1-methyl-1H-1,2,3-triazole hydrochloride

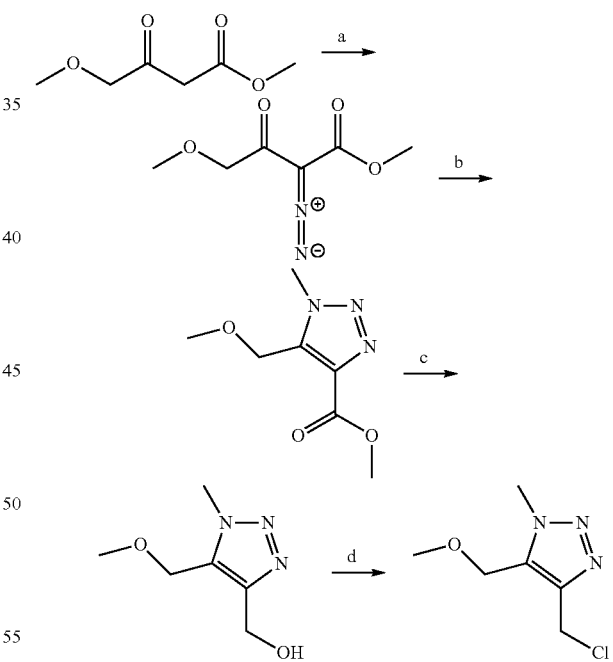

R$^1$ Step a. To a stirred solution of methyl 4-methoxy acetoacetate (0.78 mL, 6 mmol) and 4-acetamidobenzenesulfonyl azide (1.59 g, 6.6 mmol, CAS: 2158-14-7) in dry acetonitrile (80 mL) at 0° C. under argon, was added dry triethylamine (2.51 mL, 18 mmol) dropwise over 5 min. The mixture was stirred for 10 min then stirred at rt for 18 h. The reaction mixture was filtered through Celite®, washed with DCM and the filtrate concentrated in vacuo. The residue was taken up in DCM, filtered through Celite® and the filtrate washed with water. The aqueous layer was extracted with DCM and the combined organic layers were dried over Na₂SO₄, filtered and concentrated in vacuo. Purification by flash silica chromatography (50 g silica, 25-60% EtOAc in heptane) gave methyl 2-diazo-4-methoxy-3-oxobutanoate (0.96 g, 91%). $^1$H NMR (300 MHz, CDCl₃) δ: 4.53 (s, 2H), 3.84 (s, 3H), 3.47 (s, 3H).

R$^1$ Step b. Methylamine (2 M in THF; 5.2 mL, 11.6 mmol) was added dropwise to acetic acid (5 mL) and a solution of the above intermediate (0.5 g, 2.9 mmol) in THF (2.5 mL) was added under argon. The mixture was heated at 95° C. for 3 days. The reaction mixture was concentrated in vacuo, diluted with water and the crude product extracted into EtOAc. The combined organics were washed with saturated sodium bicarbonate, dried over Na₂SO₄, filtered and concentrated in vacuo. The crude product was purified by flash column chromatography (20 g silica, 40 to 100% EtOAc in heptane) to provide methyl 5-(methoxymethyl)-1-methyl-1H-1,2,3-triazole-4-carboxylate (218 mg, 40%). $^1$H NMR (300 MHz, CDCl₃) δ: 4.90 (s, 2H), 4.12 (s, 3H), 3.96 (s, 3H), 3.38 (s, 3H).

R$^1$ Step c. To a stirred solution of the above intermediate (218 mg, 1.18 mmol) in THF (1.5 mL) and EtOH (6 mL) under argon was added sodium borohydride (134 mg, 3.54 mmol) then lithium chloride (0.5M in THF; 5.9 mL, 2.94 mmol) and the mixture was heated at 40° C. for 18 h. The mixture was allowed to cool and hydrolysed with 10% citric acid, then the volatiles were removed in vacuo. The residue was diluted with water and extracted with 2:1 IPA/chloroform. The combined organic layer was washed with 1:1 brine/saturated sodium bicarbonate, then brine, dried over Na₂SO₄, filtered and concentrated in vacuo to provide (5-(methoxymethyl)-1-methyl-1H-1,2,3-triazol-4-yl)methanol (89 mg, 51%). $^1$H NMR (300 MHz; CDCl₃) δ: 4.73 (s, 2H), 4.56 (s, 2H), 4.02 (s, 3H), 3.35 (s, 3H).

R$^1$ Step d. To a stirred suspension of the above intermediate (360 mg, 0.38 mmol) in chloroform (18 mL) was added thionyl chloride (0.33 mL, 0.760 mmol) and the mixture was stirred at rt for 3 h. The reaction mixture was concentrated in vacuo to give 4-(chloromethyl)-5-(methoxymethyl)-1-methyl-1H-1,2,3-triazole hydrochloride (420 mg, 84%) used without further purification. $^1$H NMR (300 MHz, CDCl₃) δ: 4.74 (s, 2H), 4.58 (s, 2H), 4.07 (s, 3H), 3.39 (s, 3H).

R$^1$ Method D: 3-(chloromethyl)-5-methyl-4-(trifluoromethyl)isoxazole

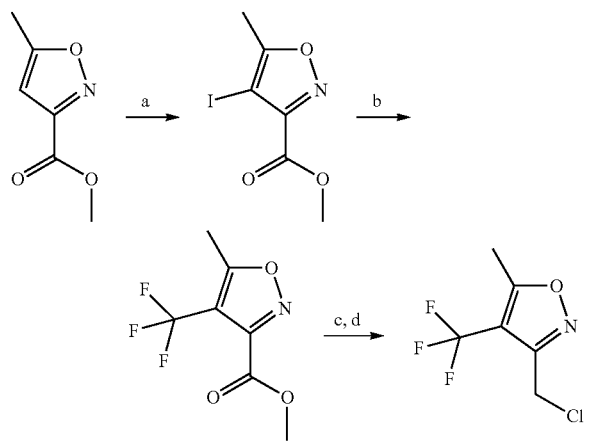

R$^1$ Step a. To a stirred solution of methyl 5-methylisoxazole-3-carboxylate (500 mg, 3.54 mmol, CAS: 19788-35-3) in TFA (8.0 mL, 105 mmol) was added N-iodosuccinimide (956 mg, 4.25 mmol) and the reaction mixture was stirred at rt for 72 h. Water was added and the mixture extracted with EtOAc. The combined organics were washed with water, saturated aqueous NaHCO₃, water and Na₂S₂O₃, dried over MgSO₄, filtered and concentrated in vacuo. The residue was triturated with IPA to give 4-iodo-3-(methoxymethyl)-5-methylisoxazole (542 mg, 57%). $^1$H NMR (300 MHz, CDCl₃) δ: 3.99 (s, 3H), 2.56 (s, 3H).

R$^1$ Step b. Copper (I) iodide (71 mg, 0.37 mmol) was added to a solution of the above intermediate (500 mg, 1.9 mmol) and HMPA (1.0 mL, 5.8 mmol) in DMF (8 mL). Methyl 2,2-difluoro-2-(fluorosulfonyl)acetate (0.95 mL, 7.5 mmol, CAS: 680-15-9) was added dropwise and the reaction mixture was heated under microwave irradiation for 1 h at 85° C. The reaction mixture was partitioned between EtOAc and a saturated aqueous solution of ammonium chloride and the aqueous extracted with EtOAc. The combined organics were washed with water, brine, dried over MgSO₄, filtered and concentrated in vacuo. The residue was purified by flash silica chromatography (80% DCM in heptane) to give methyl 5-methyl-4-(trifluoromethyl)isoxazole-3-carboxylate (240 mg, 55%). $^1$H NMR (300 MHz, CDCl₃) δ: 4.01 (s, 3H), 2.64 (s, 3H). $^{19}$F-NMR (283 MHz, CDCl₃) δ: −56.72 (s, 3F).

R$^1$ Steps c,d. The title compound was prepared from the above intermediate using R$^1$ method B and used without further purification. $^1$H NMR (300 MHz, CDCl₃) δ: 5.49 (dd, 2H), 2.61 (q, 3H).

R$^1$ Method E: 3-(chloromethyl)-4-(difluoromethyl)-5-methylisoxazole hydrochloride

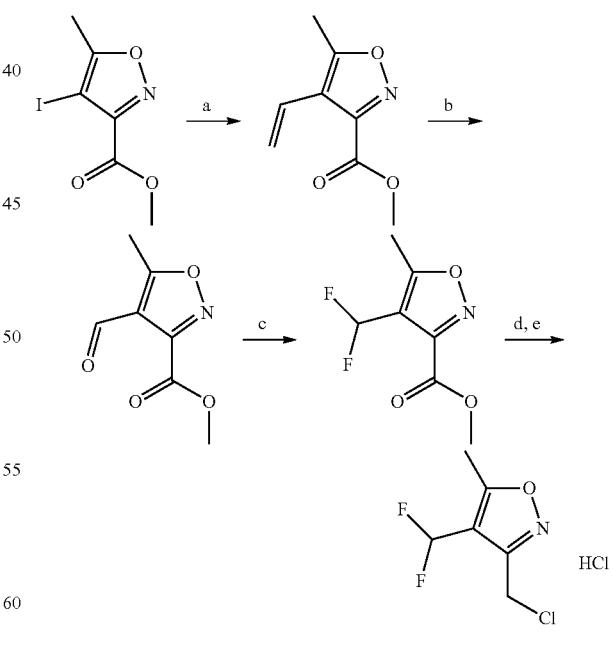

R$^1$ Step a. To a stirred solution of methyl 4-iodo-5-methylisoxazole-3-carboxylate (700 mg, 2.62 mmol, Example 154, R$^1$ step a), potassium vinyltrifluoroborate (1.053 g, 7.86 mmol, CAS: 13682-77-4) and triethylamine (1.1 mL, 7.86 mmol) in IPA (28 mL) and THF (28 mL)

degassed with nitrogen was added [1,1'-bis(diphenylphosphino)-ferrocene]dichloropalladium(II) complex with DCM (214 mg, 0.26 mmol) and the reaction mixture was heated at 90° C. for 16 h, cooled to rt and concentrated in vacuo. The residue was partitioned between water and DCM and the aqueous extracted with DCM. The combined organics were washed with brine, dried over $MgSO_4$, filtered and concentrated. The residue was purified by flash column chromatography (silica, 33% EtOAc in heptane) to give methyl 5-methyl-4-vinylisoxazole-3-carboxylate (321 mg, 66%). $^1$H NMR (300 MHz, $CDCl_3$) δ 6.80 (dd, 1H), 5.52-5.44 (m, 2H), 3.98 (s, 3H), 2.55 (s, 3H).

$R^1$ Step b. To a solution of the above intermediate (321 mg, 1.92 mmol) in THF (27 mL) at rt was added osmium tetroxide (49 mg, 0.19 mmol, CAS: 20816-12-0) and the reaction mixture stirred for 5 min. To this was added sodium periodate (10% on silica, 12.5 g, 5.84 mmol) and the reaction mixture was stirred at rt for 2 h. The reaction mixture was filtered and the silica washed with THF. The filtrate was concentrated in vacuo and purified by flash column chromatography (silica, 100% DCM) to give methyl 4-formyl-5-methylisoxazole-3-carboxylate (286 mg, 79%). $^1$H NMR (300 MHz, $CDCl_3$) δ: 10.32 (s, 1H), 4.06 (s, 3H), 2.78 (s, 3H).

$R^1$ Step c. To a stirred solution of the above intermediate (286 mg, 1.69 mmol) and ethanol (0.1 mL, 1.69 mmol) in DCM (15 mL) was added bis(2-methoxyethyl)aminosulfur trifluoride solution (50% in THF; 1.44 mL, 3.38 mmol, CAS: 202289-38-1) and the reaction mixture was stirred at rt for 16 h. To this was added DCM and the organics washed with a saturated aqueous solution of sodium bicarbonate. The aqueous was extracted with DCM and the combined organics were washed with brine, dried over $MgSO_4$, filtered and concentrated in vacuo. The residue was purified by flash column chromatography (silica, 100% DCM) to give methyl 4-(difluoromethyl)-5-methylisoxazole-3-carboxylate (214 mg, 59%). $^1$H NMR (300 MHz, $CDCl_3$) δ: 7.09 (t, 1H), 4.07-3.95 (m, 3H), 2.70-2.60 (m, 3H).

$R^1$ Steps d-e. The title compound (283 mg) was prepared from the above intermediate using $R^1$ method B and used without further purification. $^1$H NMR (300 MHz, $CDCl_3$) δ 6.89-6.53 (m, 1H), 4.81-4.61 (m, 2H), 2.54-2.52 (m, 3H).

The intermediates in Table 1 were prepared according to methods analogous to $R^1$ Methods A-E, for use in the synthesis of the Examples referred to.

TABLE 1

| Example | Method | Structure | Name | Characterisation |
|---|---|---|---|---|
| 71 | A | 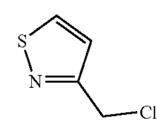 | 3-(chloromethyl) isothiazole | $^1$H NMR (400 MHz, DMSO-$d_6$) δ 8.67 (d, 1H), 7.36 (d, 1H), 4.73 (s, 2H) |
| 89 | A | 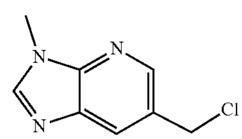 | 6-(chloromethyl)-3-methyl-3H-imidazo[4,5-b]pyridine | LCMS (Method 2): 0.74 min, 181.9 [M + H]$^+$ |
| 95 | B | 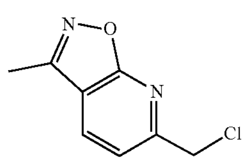 | 6-(chloromethyl)-3-methylisoxazolo[5,4-b]pyridine hydrochloride | LCMS (Method 2): 1.05 min, 182.9 [M + H]$^+$ |
| 124 | B | 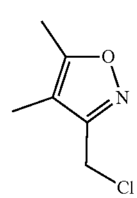 | 3-(chloromethyl)-4,5-dimethylisoxazole | LCMS (Method 2): 1.05 min, 145.9 [M + H]$^+$ |
| 125 | B | 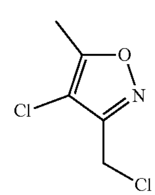 | 4-chloro-3-(chloromethyl)-5-methylisoxazole | $^1$H NMR (400 MHz, $CDCl_3$) δ 4.56 (s, 2H), 2.43 (s, 3H) |

TABLE 1-continued

| Example | Method | Structure | Name | Characterisation |
|---|---|---|---|---|
| 128 | C | 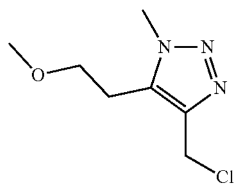 | 4-(chloromethyl)-5-(2-methoxyethyl)-1-methyl-1H-1,2,3-triazole | $^1$H NMR (300 MHz, CDCl$_3$) δ 4.73 (s, 2H), 4.01 (s, 3H), 3.60 (t, 2H), 3.30 (s, 3H), 2.99 (t, 2H) |
| 129 | C | 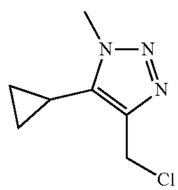 | 4-(chloromethyl)-5-cyclopropyl-1-methyl-1H-1,2,3-triazole | $^1$H NMR (300 MHz, CDCl$_3$) δ 4.71 (s, 2H), 4.03 (s, 3H), 1.69 (m, 1H), 1.13 (m, 2H), 0.86 (m, 2H) |
| 139 | A From Example 193 step d | 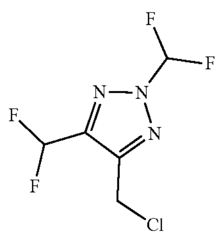 [SMILES: FC(F)c1nn(C(F)F)nc1CCl] | 4-(chloromethyl)-2,5-bis(difluoromethyl)-2H-1,2,3-triazole | $^1$H NMR (400 MHz, CDCl$_3$) δ 7.32 (t, 1H), 6.90 (t, 1H), 5.26 (dd, 2H) |
| 155 | C | 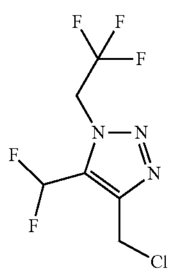 [SMILES: FC(F)c1c(CCl)nnn1CC(F)(F)F] | 4-(chloromethyl)-5-(difluoromethyl)-1-(2,2,2-trifluoroethyl)-1H-1,2,3-triazole | $^1$H NMR (300 MHz, CDCl$_3$) δ 7.05 (t, 1H), 5.10 (q, 2H), 4.77 (s, 2H) |
| 156 | C | 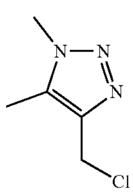 | 4-(chloromethyl)-1,5-dimethyl-1H-1,2,3-triazole hydrochloride | $^1$H NMR (300 MHz, CDCl$_3$) δ 7.88 (br, 1H), 4.84 (s, 2H), 4.14 (s, 3H), 2.49 (s, 3H) |
| 181 | A | 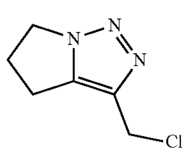 | 3-(chloromethyl)-5,6-dihydro-4H-pyrrolo[1,2-c]triazole | LCMS (Method 16): 0.79 min, 158.0 [M + H]$^+$ |
| 204 | E | 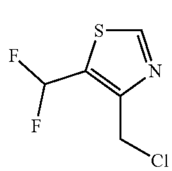 | 4-(chloromethyl)-5-(difluoromethyl)thiazole | $^1$H NMR (300 MHz, CDCl$_3$) δ 8.86 (s, 1H), 7.07 (t, 1H), 4.80 (s, 2H) |

121

(R)-1-(5-methylpyridazin-3-yl)pyrrolidin-3-yl methanesulfonate

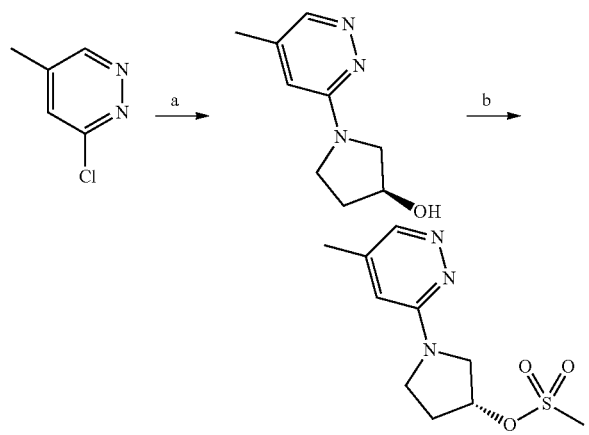

Step a. A mixture of 3-chloro-5-methyl-pyridazine (206 mg, 1.61 mmol, CAS: 89283-31-8) and (3R)-pyrrolidin-3-ol (0.16 mL, 1.93 mmol, CAS: 2799-21-5) in anhydrous 1,4-dioxane (3 mL) under argon was heated at 120° C. for 21 h. The mixture was diluted with aqueous NaHCO$_3$ solution/brine (1:1; 50 mL) and extracted with ethyl acetate (5×50 mL), DCM (50 mL) and IPA/DCM (1:10; 8×50 mL). The combined organics were dried over Na$_2$SO$_4$, filtered and concentrated in vacuo. The crude product was purified by flash column chromatography on the Teledyne ISCO CombiFlash® Rf200 (12 g silica column Puriflash HC, eluting 0 to 10% MeOH in DCM) to give (R)-1-(5-methylpyridazin-3-yl)pyrrolidin-3-yl methanesulfonate (123 mg, 43%). $^1$H NMR (400 MHz, CDCl$_3$) δ 8.37 (d, 1H), 6.43-6.41 (m, 1H), 4.69-4.64 (m, 1H), 3.72-3.60 (m, 4H), 2.24 (d, 3H), 2.20-2.12 (m, 2H).

Step b. To a stirred solution of the above intermediate (121 mg, 0.67 mmol) in DCM (5 mL) under argon at 0° C., was added triethylamine (0.14 mL, 1.01 mmol) then dropwise methanesulfonyl chloride (0.06 mL, 0.810 mmol). The mixture was stirred at 0° C. for 5 min then at rt for 1.75 h. The mixture was diluted with water (10 mL) and extracted with DCM (5×10 mL). The combined organics were dried over Na$_2$SO$_4$, filtered and concentrated in vacuo to provide (R)-1-(5-methylpyridazin-3-yl)pyrrolidin-3-yl methanesulfonate (154 mg, 88%), used without further purification. $^1$H NMR (400 MHz, CDCl$_3$) δ 8.45 (s, 1H), 6.47 (s, 1H), 5.48-5.44 (m, 1H), 4.00 (d, 1H), 3.84 (dd, 1H), 3.75-3.63 (m, 2H), 3.05 (s, 3H), 2.54-2.47 (m, 1H), 2.39-2.30 (m, 1H), 2.28 (s, 3H).

5-(Chloromethyl)-3-methyl-3H-imidazo[4,5-b]pyridine

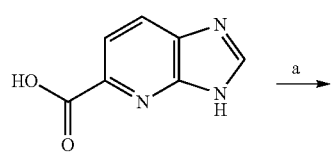

122

-continued

Step a. To a stirred solution of 3H-imidazo[4,5-b]pyridine-5-carboxylic acid (200 mg, 1.23 mmol, CAS: 1019108-05-4) in MeOH (5 mL) was added sulfuric acid (0.5 mL, 8.9 mmol) and the reaction mixture heated at reflux for 16 h. A solution of NaHCO3 was added slowly and the resulting precipitate filtered and washed with water. The residue was dried in vacuo to give methyl 3H-imidazo[4,5-b]pyridine-5-carboxylate (234 mg, assumed quantitative), used without further purification. $^1$H NMR (400 MHz, DMSO-d$_6$) δ 8.84 (s, 1H), 8.2 (bs, 1H), 7.97 (d, 1H), 3.95 (s, 3H).

Step b. To a stirred solution of the above intermediate (287 mg, 1.6 mmol) in DMF (2 mL) was added potassium carbonate (448 mg, 3.2 mmol) and methyl iodide (0.20 mL, 3.2 mmol) and the reaction mixture stirred at room temperature for 2 h. The mixture was diluted with water (20 mL) and extracted with 2-methyl tetrahydrofuran (3×10 mL) and DCM (2×10 mL). The combined organic extracts were dried over MgSO$_4$ and concentrated in vacuo to give methyl 3-methyl-3H-imidazo[4,5-b]pyridine-5-carboxylate (305 mg, assumed quantitative; 2:1 mixture with regioisomer methyl 1-methyl-1H-imidazo[4,5-b]pyridine-5-carboxylate). LCMS (Method 2): 0.77 and 0.78 min, 192.1 [M+H]$^+$.

Step c. To a solution of the above intermediate (305 mg, 1.6 mmol; 2:1 mixture with methyl 1-methyl-1H-imidazo[4,5-b]pyridine-5-carboxylate) in tetrahydrofuran (10 mL) at 0° C. was added LiAlH$_4$ (0.8 mL, 1.6 mmol, 2M in THF). The mixture was stirred at 0° C. for 30 min, then diluted with EtOAc and quenched with few drops of saturated aqueous NH$_4$Cl. The mixture was stirred at rt for 10 mins and the organics dried over Na$_2$SO$_4$, filtered and concentrated in vacuo. Purification by flash column chromatography (40 g column, 0-100% 10% 2M methanolic ammonia (2M; 10%) in DCM in DCM) gave (3-methyl-3H-imidazo[4,5-b]pyridin-5-yl)methanol (60 mg, 23%), used without further purification. LCMS (Method 2) 0.17 min, 164.1 [M+H]$^+$ Step d. To a stirred solution of the above intermediate (60 mg, 0.37 mmol) in chloroform (1 mL) under argon was added thionyl chloride (0.054 mL, 0.74 mmol) dropwise and the reaction mixture stirred at rt for 2 h. The reaction mixture was concentrated in vacuo and azeotroped with toluene (3×5 mL) to give the title compound (67 mg, assumed quantitative), used without further purification. LCMS (Method 2) 0.93 min, 182.1 [M+H]$^+$

5-(Chloromethyl)-4-(difluoromethyl)pyrimidine

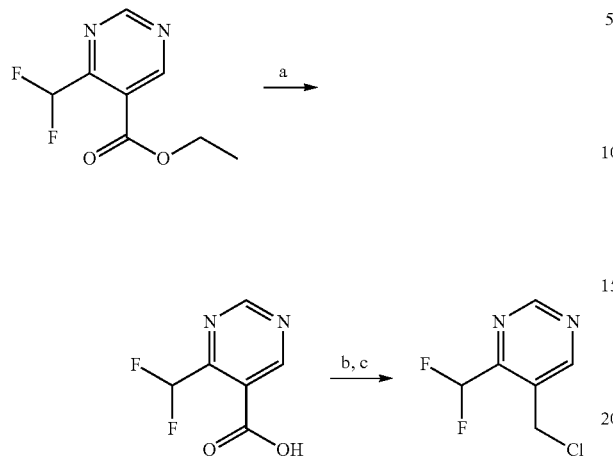

Step a. To a stirred solution of ethyl 4-(difluoromethyl) pyrimidine-5-carboxylate (1.0 g, 4.95 mmol; CAS: 1600338-90-6) in THF (8 mL) and water (2 mL) was added lithium hydroxide monohydrate (0.23 g, 5.44 mmol) and the mixture stirred at rt for 18 h. The mixture was concentrated in vacuo and the residue diluted to pH 4 with aqueous HCl (6M). The precipitate was collected by filtration and dried in vacuo to give a white solid (88 mg). The filtrate was further extracted with 2-methyl tetrahydrofuran, dried (MgSO$_4$), filtered and concentrated to give product (105 mg). The filtrate was further extracted with n-butanol dried (MgSO$_4$), filtered and concentrated to give further product (219 mg). Both batches gave 4-(difluoromethyl)pyrimidine-5-carboxylic acid (0.50 g, 58%). LCMS (Method 10c): 0.50 min, 174.9 [M+H]$^+$.

Step b. To a stirred solution of the above intermediate (219 mg, 1.26 mmol) in THF (11 mL) was added 4-methylmorpholine (0.19 mL, 1.76 mmol) and isobutyl chloroformate (0.22 mL, 1.70 mmol) dropwise at −5° C. under argon. The reaction mixture was stirred at −5° C. for 1.5 h, rt for 1.5 h. The mixture was cooled to −5° C. and to this was added a solution of sodium borohydride (71 mg, 1.89 mmol) in water (0.5 mL) dropwise and the reaction mixture was stirred for 45 min. The reaction mixture was diluted with water and extracted with DCM and the combined organics were washed with brine, dried (Na$_2$SO$_4$), filtered and concentrated in vacuo. The residue was purified by flash column chromatography (3% MeOH in DCM) to give (4-(difluoromethyl)pyrimidin-5-yl)methanol (11 mg, 4%). LCMS (Method 10c): 0.40 min, 161.0 [M+H]$^+$.

Step c. To a solution of the above intermediate (11 mg, 0.070 mmol) in 1,4-dioxane (0.15 mL) was added phosphorus oxychloride (0.07 mL, 0.70 mmol) and the reaction was stirred at 100° C. for 2 h. The reaction mixture was cooled to rt and concentrated in vacuo. The residue was diluted with saturated aqueous sodium bicarbonate solution and extracted with DCM. The combined organics were dried (Na$_2$SO$_4$), filtered and concentrated in vacuo to give 5-(chloromethyl)-4-(difluoromethyl)pyrimidine (31 mg, assume quantitative), used without further purification. $^1$H NMR (300 MHz, CD$_3$OH) δ 9.21 (s, 1H), 9.05 (s, 1H), 6.90 (t, 1H), 4.89 (s, 2H).

3-(Chloromethyl)-5,5-dimethyl-4,5-dihydroisoxazole

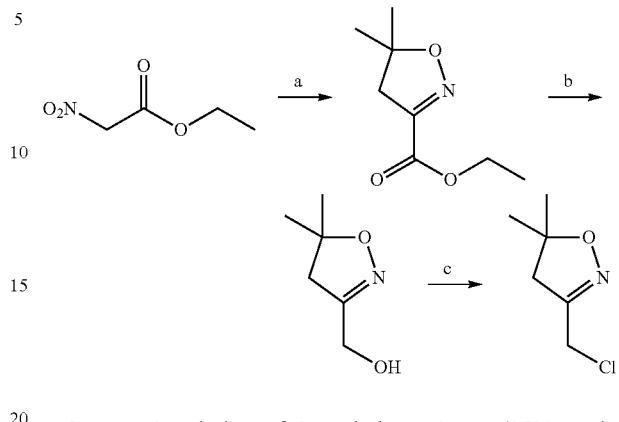

Step a. A solution of 2-methylprop-1-ene (15% wt in THF; 2.0 g, 35.6 mmol; CAS: 115-11-7), ethyl 2-nitroacetate (7.9 mL, 71.3 mmol) and 1,4-diazabicyclo[2.2.2]octane (0.4 g, 3.56 mmol; CAS: 280-57-9) in EtOH (145 mL) in an autoclave was heated at 80° C. for 7 days. The reaction mixture was concentrated in vacuo and purified by flash column chromatography (silica, 15% EtOAc in heptane) followed by automated reverse phase column chromatography on the Isolera (Biotage C18 SNAP 30 g; 5-80% MeCN in water+0.1% ammonia) to give ethyl 5,5-dimethyl-4,5-dihydroisoxazole-3-carboxylate (174 mg, 3%). $^1$H NMR (300 MHz, CDCl$_3$) δ 4.37-4.34 (m, 2H), 2.95 (s, 2H), 1.47 (s, 6H), 1.38 (t, 3H).

Step b. To a stirred suspension of sodium borohydride (100 mg, 2.64 mmol) in EtOH (1 mL) was added a solution of the above intermediate (174 mg, 1.02 mmol) in EtOH (2 mL) dropwise at 0° C. The reaction mixture was warmed to rt and stirred for 3 h. The reaction mixture was concentrated in vacuo, diluted with water and made acidic to pH 6 using acetic acid. The aqueous was extracted with EtOAc and the combined organics washed with water, brine, dried over Na$_2$SO$_4$, filtered and concentrated in vacuo to provide (5,5-dimethyl-4,5-dihydroisoxazol-3-yl)methanol (100 mg, 53%). $^1$H NMR (300 MHz, CDCl$_3$) δ 4.41 (s, 2H), 2.76-2.79 (m, 3H), 1.45 (s, 6H).

Step c. To a stirred solution of the above intermediate (92 mg, 0.71 mmol) in anhydrous DCM (1.5 mL) was added thionyl chloride (0.1 mL, 1.42 mmol) slowly at 0° C. The reaction was warmed to rt and stirred at rt for 18 h. The reaction mixture was concentrated in vacuo and co-evaporated several times with toluene to give the title compound (72 mg, 48%), used in the next step without purification. $^1$H NMR (300 MHz, CDCl$_3$) δ 4.29 (s, 2H), 2.84 (s, 2H), 1.42 (s, 6H).

4-(Chloromethyl)-1,5-dimethyl-1H-1,2,3-triazole

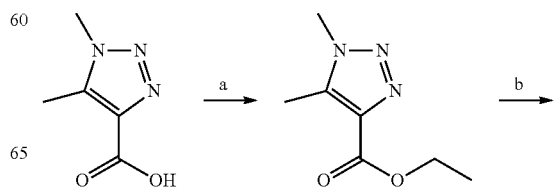

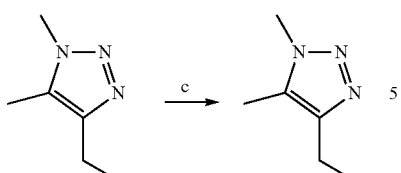 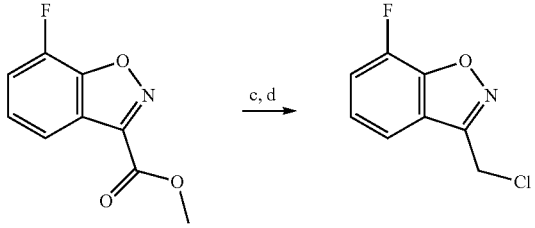

Step a. To a stirred solution of 1,5-dimethyltriazole-4-carboxylic acid (5.0 g, 35.4 mmol; CAS: 329064-07-5) in EtOH (21 mL, 354 mmol) was added sulfuric acid (1.89 mL, 35.4 mmol) and the solution heated at 70° C. for 24 h. Further sulfuric acid (1.89 mL, 35.4 mmol) was added and the solution heated at 70° C. for 4 h then allowed to cool to rt. The reaction mixture was concentrated in vacuo, and the residue was diluted with water (10 mL), adjusted to pH 8 with saturated sodium hydrogen carbonate solution and extracted with EtOAc. The organics were separated, dried (MgSO$_4$) and concentrated in vacuo to give ethyl 1,5-dimethyl-1H-1,2,3-triazole-4-carboxylate (4.66 g, 78%). $^1$H NMR (300 MHz, CDCl$_3$) δ 4.46-4.39 (q, 2H), 4.00 (s, 3H), 2.58 (s, 3H), 1.44-1.39 (t, 3H).

Step b. To a stirred solution of the above intermediate (4.66 g, 27.6 mmol) in THF (41 mL) at 0° C. under an argon atmosphere was added lithium aluminium hydride solution (1M in THF; 27.56 mL, 27.56 mmol) dropwise and the reaction mixture stirred for 1 h from 0° C. to rt. The mixture was cooled in ice water, water (1.0 mL) was added dropwise, followed by NaOH (3M, 1.0 mL) and water (2 mL) and the resulting suspension stirred for 30 min. The mixture was filtered through Celite® and the filtrate was concentrated in vacuo to give (1,5-dimethyl-1H-1,2,3-triazol-4-yl)methanol (3.35 g, 96%). $^1$H NMR (300 MHz, CDCl$_3$) δ 7.33 (s, 1H), 4.64 (s, 2H), 3.90 (s, 3H), 2.30 (s, 3H).

Step c. To a stirred solution of the above intermediate (3.35 g, 26.4 mmol) in DCM (40 mL) cooled in ice water was added thionyl chloride (3.84 mL, 52.7 mmol) dropwise under nitrogen. The reaction mixture was stirred for 1 h from 0° C. to rt and concentrated in vacuo. The residue was diluted with chloroform and concentrated in vacuo to give the title compound (3.32 g, 87%). LCMS (Method 2) 1.14 min, 146.2 [M+H]$^+$.

3-(Chloromethyl)-7-fluorobenzo[d]isoxazole

Step a. To a stirred solution of methyl 2-(2,3-difluorophenyl)acetate (1.67 g, 8.97 mmol, CAS: 1036273-31-0) in diethyl ether (18 mL) was added a solution of isopentyl nitrite (2.65 mL, 19.7 mmol) in diethyl ether (10 mL) and then sodium methoxide (0.78 g, 14.35 mmol) in methanol (11.7 mL) and the mixture was stirred at rt for 18 h. Water was added and the mixture was acidified using hydrochloric acid (aqueous 1 M). The mixture was extracted with diethyl ether (×3), the combined organics were dried over sodium sulfate Na$_2$SO$_4$ and concentrated in vacuo. The residue was purified by flash column chromatography on the Teledyne ISCO CombiFlash® Rf+ (120 g silica column Puriflash HC, 0-50% EtOAc in cyclohexane) to provide methyl (E)-2-(2,3-difluorophenyl)-2-(hydroxyimino)acetate (1.05 g, 54%). $^1$H NMR (400 MHz, CDCl$_3$) δ: 9.08 (br. s, 1H), 7.31-7.04 (m, 2H), 3.90 (s, 3H).

Step b. To a stirred solution of the above intermediate (950 mg, 4.42 mmol) in DMSO (9.5 mL) was added potassium carbonate (854 mg, 6.18 mmol) and the resulting mixture was heated at 75° C. for 0.5 h. The reaction mixture was cooled to rt, diluted with water and the crude extracted EtOAc. The combined organics were washed with water, brine, dried over Na$_2$SO$_4$, filtered and concentrated in vacuo to provide methyl 7-fluorobenzo[d]isoxazole-3-carboxylate (683 mg, 79%). LCMS (Method 2): 1.17 min, 194.0 [M−H]$^−$. $^1$H NMR (400 MHz, CDCl$_3$) δ: 7.92 (dd, 1H), 7.43-7.33 (m, 2H), 4.11 (s, 3H).

Steps c-d. The title compound (502 mg) was prepared from the above intermediate using R$^1$ method B and used without further purification. $^1$H NMR (400 MHz, CDCl$_3$) δ: 7.64-7.62 (m, 1H), 7.34-7.30 (m, 2H), 4.92 (s, 2H).

3-(Chloromethyl)-6,7-difluorobenzo[d]isoxazole

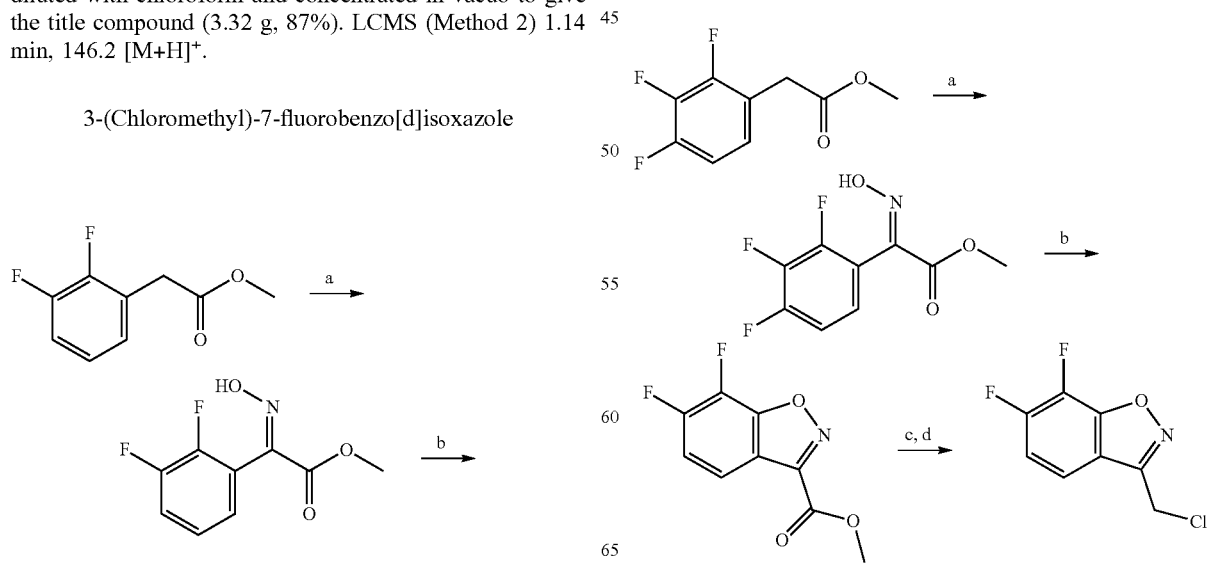

The title compound (894 mg) was prepared from methyl 2-(2,3,4-trifluorophenyl)acetate (CAS: 1443340-20-2) using methods analogous to 3-(chloromethyl)-7-fluorobenzo[d]isoxazole (Example 164). ¹H NMR (400 MHz, CDCl₃) δ: 7.57 (ddd, 1H), 7.28-7.21 (m, 1H), 4.89 (s, 2H).

3-(Chloromethyl)-4,5,6,7-tetrahydrotriazolo[1,5-a]pyridine

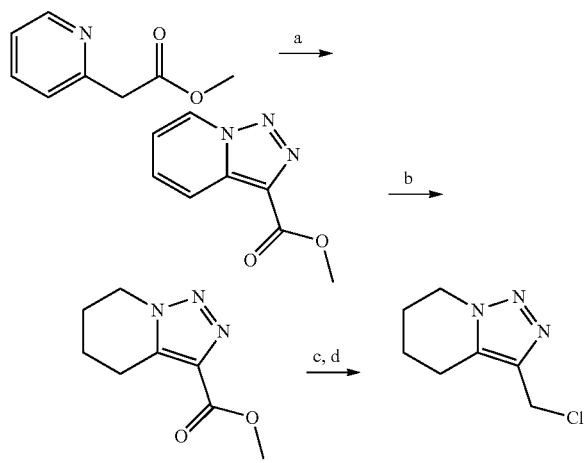

Step a. To a stirred solution of methyl 2-(pyridin-2-yl)acetate (5.0 g, 33.1 mmol, CAS: 1658-42-0) in MeCN (83 mL) was added 4-acetamidobenzenesulfonyl azide (7.95 g, 33.1 mmol, CAS: 2158-14-7) and the reaction mixture was cooled to 0° C. under argon. To this was added DBU (3.97 mL, 33.1 mmol) dropwise over 10 min. The reaction mixture was allowed to warm to rt and stirred 3 h. To this was added of saturated ammonium chloride solution and the mixture extracted with EtOAc. The combined organics were washed with brine, dried over Na₂SO₄, filtered and concentrated in vacuo. Purification by flash column chromatography on the Interchim 4125 (120 g silica column Puriflash HP, 0-15% EtOAc in DCM) gave methyl [1,2,3]triazolo[1,5-a]pyridine-3-carboxylate (5.48 g, 89%). ¹H NMR (400 MHz, CDCl₃) δ 8.86-8.83 (m, 1H), 8.31-8.28 (m, 1H), 7.56 (ddd, 1H), 7.19-7.15 (m, 1H), 4.06 (s, 3H).

Step b. To a stirred solution of the above intermediate (2.0 g, 11.3 mmol) in EtOH (455 mL) was added Pd/C (10%; 1.20 g, 11.3 mmol) and the reaction mixture was degassed and backfilled with hydrogen (×3). The reaction mixture was stirred under a hydrogen atmosphere at atmospheric pressure for 3 h. The mixture was filtered through Celite® and concentrated in vacuo to provide methyl 4,5,6,7-tetrahydro-[1,2,3]triazolo[1,5-a]pyridine-3-carboxylate (1.98 g, 99%). ¹H NMR (400 MHz, CDCl₃) δ: 4.41 (t, 2H), 3.94 (s, 3H), 3.11 (t, 2H), 2.13-2.06 (m, 2H), 1.98-1.91 (m, 2H).

Step c. To a stirred suspension of the above intermediate (1.96 g, 11.1 mmol) in THF (88 mL) was added lithium borohydride (2M in THF; 10.0 mL, 19.9 mmol) dropwise over 10 min. The reaction was stirred at rt under argon for 20 h. The reaction mixture was cooled to 0° C. and diluted with 10% citric acid (33 mL) then extracted with DCM. The combined organics were washed with water and concentrated in vacuo. The crude product was purified by flash column chromatography on the Interchim Puriflash® 4100 (80 g silica column Puriflash HP, 0-30% EtOAc in DCM) to give (4,5,6,7-tetrahydro-[1,2,3]triazolo[1,5-a]pyridin-3-yl)methanol (620 mg, 35%). ¹H NMR (400 MHz, CDCl₃) δ 4.76 (s, 2H), 4.38 (t, 2H), 2.92-2.88 (m, 3H), 2.17-2.10 (m, 2H), 2.05-1.95 (m, 2H).

Step d. Thionyl chloride (0.59 mL, 8.1 mmol) was added to Int 170-C (620 mg, 4.1 mmol). Chloroform (6.5 mL) was added and the mixture and stirred at rt for 16 h. The reaction mixture was concentrated in vacuo, azeotroped with toluene (×2) and concentrated in vacuo to provide the title compound (702 mg, assumed quantitative) used without further purification. LCMS (Method 2): 0.90 min, 171.9 [M+H]⁺.

5-(Bromomethyl)-4-(trifluoromethyl)pyrimidine

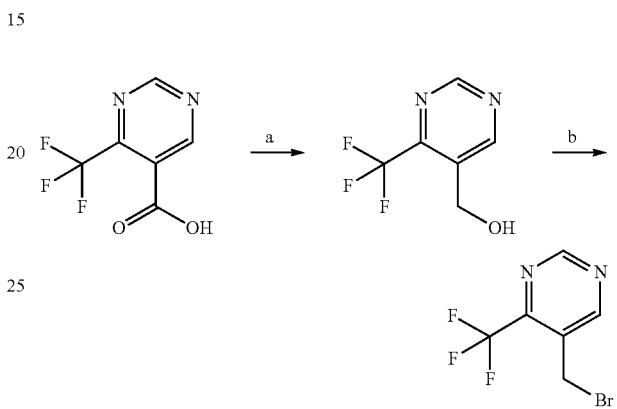

Step a. To a stirred suspension of 4-(trifluoromethyl)pyrimidine-5-carboxylic acid (2.5 g, 13.0 mmol, CAS: 220880-12-6) in THF (124 mL) at −5° C. under argon was added 4-methylmorpholine (1.65 mL, 15.0 mmol, CAS: 109-02-4) followed by isobutyl chloroformate (1.86 mL, 14.32 mmol, CAS: 543-27-1) dropwise. The reaction mixture was stirred at −5° C. for 1.5 h and then at rt for 1.5 h. The mixture was cooled to −5° C. and to this was added additional 4-methylmorpholine (0.43 mL, 3.90 mmol) and isobutyl chloroformate (0.42 mL, 3.25 mmol). The reaction mixture was stirred at −5° C. for 30 min then stirred at rt for 45 min and cooled again to −5° C. To this was added a solution of sodium borohydride (738 mg, 19.5 mmol) in water (6 mL) dropwise over 25 min and the reaction mixture was stirred for 20 min. Water was added, the mixture was extracted with DCM and the combined organics were dried (Na₂SO₄), filtered and concentrated in vacuo. The crude product was purified by flash column chromatography on the Interchim Puriflash® 4100 (120 g silica column HP, 0-50% EtOAc in cyclohexane) to provide (4-(trifluoromethyl)pyrimidin-5-yl)methanol (334 mg, 17%). LCMS (Method 2): 0.74 min, 178.9 [M+H]⁺.

Step b. To a stirred solution of the above intermediate (334 mg, 1.88 mmol) in DCM (9 mL) was added triphenylphosphine (492 mg, 1.88 mmol) and the reaction mixture was cooled to 0° under argon. To this was added a solution of carbon tetrabromide (622 mg, 1.88 mmol) in DCM (2 mL) and the reaction mixture was stirred at rt for 18 h and concentrated in vacuo. The crude product was purified by flash column chromatography on the Interchim Puriflash® 4100 (40 g silica column Puriflash HP, 0-30% EtOAc in DCM) to provide the title compound (273 mg, 60%). ¹H NMR (400 MHz, CDCl₃) δ: 9.29 (1H, s), 9.06 (1H, s), 4.60 (2H, s).

3-(Bromomethyl)-6,7-dihydro-4H-[1,2,3]triazolo[5,1-c][1,4]oxazine

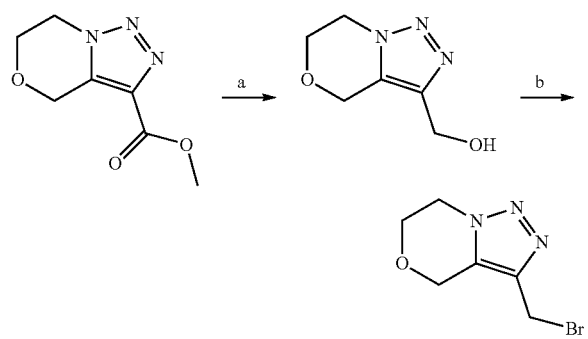

Step a. To a suspension of methyl 6,7-dihydro-4H-triazolo[5,1-c][1,4]oxazine-3-carboxylate (28 mg, 0.15 mmol, CAS: 2115637-63-1) in THF (1 mL) at 0° C. under argon was added lithium aluminium hydride (1M in THF; 0.15 mL, 0.15 mmol) dropwise and the resulting mixture was stirred for 1 h. The reaction mixture was treated with water (7 μL), 3M NaOH (7 μL) and water (14 μL) dropwise. The resulting mixture was stirred for 1 h. The reaction mixture was diluted with THF and filtered through a pad of Celite®. The Celite® was washed with THF and DCM and the filtrate concentrated in vacuo to provide (6,7-dihydro-4H-[1,2,3]triazolo[5,1-c][1,4]oxazin-3-yl)methanol (22 mg, 88%) used without further purification. LCMS (Method 2): 0.18 min, 156.0 [M+H]+

Step b. To a solution of the above intermediate (120 mg, 0.73 mmol) in DCM (4.8 mL) at 0° C. under argon was added triphenylphosphine (206 mg, 0.79 mmol) followed by dropwise addition of a solution of carbon tetrabromide (261 mg, 0.79 mmol) in DCM (3.2 mL). The reaction mixture was warmed to rt over 1 h, then stirred at rt for 16 h. Additional triphenylphosphine (96 mg, 0.37 mmol) was added, followed by dropwise addition of a solution of carbon tetrabromide (122 mg, 0.37 mmol) in DCM (3.2 mL). The reaction mixture was stirred for 3 h at rt then concentrated in vacuo. Purification by flash column chromatography on the Interchim Puriflash® 4100 (40 g silica column InterChim HP, 0-30% EtOAc in DCM) gave the title compound (89 mg, 55%). ¹H NMR (400 MHz, CDCl₃) δ 4.93 (s, 2H), 4.55 (s, 2H), 4.44 (t, 2H), 4.11 (t, 2H).

(5-(difluoromethyl)-1-(oxetan-3-yl)-1H-1,2,3-triazol-4-yl)methyl methanesulfonate

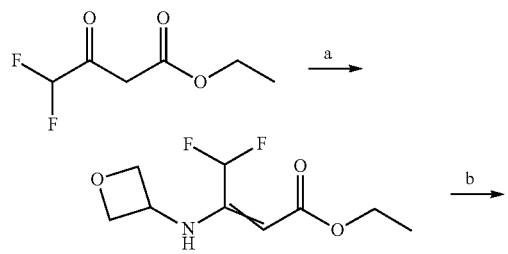

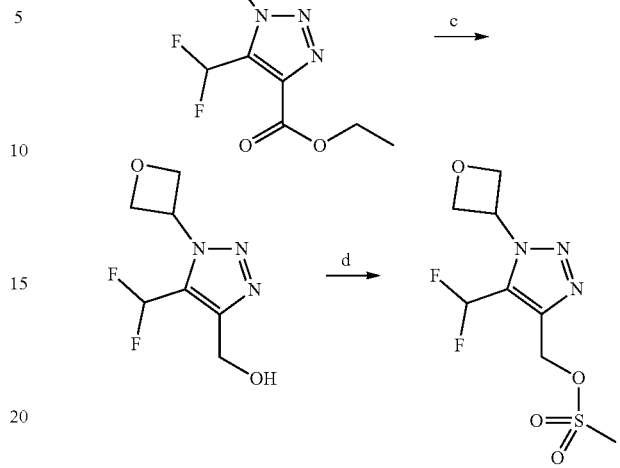

Step a. To a stirred solution of ethyl 4,4-difluoro-3-oxobutanoate (4.0 g, 24.1 mmol, CAS: 352-24-9) and AcOH (1.4 mL, 24.1 mmol) in anhydrous chloroform (50 mL) under argon, at 0° C. was added oxetan-3-amine (1.8 mg, 24.1 mmol, CAS: 21635-88-1) dropwise maintaining the temperature below 10° C. The resulting solution was heated at reflux for 48 h then cooled to rt. The reaction mixture was poured into saturated aqueous NaHCO₃ solution, diluted with water and extracted into DCM. The combined organics were washed with saturated aqueous NaHCO₃, water and the layers separated using a phase separator cartridge. The combined organics were concentrated in vacuo to give ethyl 4,4-difluoro-3-(oxetan-3-ylamino)but-2-enoate (5.3 g, 99%) which was used without further purification. LCMS (Method 18): 1.24 min, 222.1 [M+H]+

Step b. To a stirred solution of the above intermediate(2.0 g, 9.0 mmol) in MeCN (75 mL) at -20° C. was added DBU (3.38 mL, 22.6 mmol), followed by the dropwise addition of methanesulfonyl azide (2.74 g, 22.6 mmol, CAS: 1516-70-7) in MeCN (25 mL) maintaining the temperature below -19° C. The mixture was allowed to warm to rt and stirred for 72 h. The reaction mixture was partitioned between EtOAC and saturated aqueous NaHSO₄. The aqueous layer was extracted with EtOAc and the combined organics washed with saturated aqueous NaHSO₄ (×2), dried over MgSO₄, filtered and concentrated in vacuo. Purification by flash column chromatography on the Interchim Puriflash® 4100 (80 g silica column Puriflash HC, 0-50% EtOAc in cyclohexane) gave ethyl 5-(difluoromethyl)-1-(oxetan-3-yl)-1H-1,2,3-triazole-4-carboxylate (1.52 g, 68%). LCMS (Method 17): 1.10 min, 248.1 [M+H]+

Step c. To a solution of the above intermediate (1.3 g, 5.3 mmol) in THF (18 mL) at -5° C. was added lithium aluminium hydride (2M in THF; 2.6 mL, 5.3 mmol) dropwise and the reaction mixture was stirred for 1 h. The reaction mixture was quenched with water (10 mL) and extracted into DCM (2×100 mL). The combined organics were dried over MgSO₄ and concentrated in vacuo to give the title compound (882 mg, 82%) used without further purification. LCMS (Method 16): 0.60 min, 206.1 [M+H]+

Step d. To a solution of the above intermediate (400 mg, 1.95 mmol) in DCM (5 mL) was added triethylamine (0.54 mL, 3.9 mmol). The reaction was cooled to 0° C. and methanesulfonyl chloride (0.15 mL, 1.9 mmol) was added dropwise. The reaction was allowed to warm to rt and stirred for 18 h. The reaction was partitioned between distilled water (50 mL) and DCM (3×50 mL). The organic layer was separated, dried over Na$_2$SO$_4$ and concentrated in vacuo to give the title compound (462 mg, as a 1:1 mixture with 4-(chloromethyl)-5-(difluoromethyl)-1-(oxetan-3-yl)-1H-1,2,3-triazole). $^1$H NMR (400 MHz, CDCl$_3$) δ 6.89-7.15 (t, 1H), 5.73-5.80 (m, 1H), 5.28-5.31 (m, 2H), 5.05-5.09 (m, 2H), 4.77-4.78 (m, 2H), 3.15 (s, 1.5H).

4-(Chloromethyl)-1,5-bis(difluoromethyl)-1H-1,2,3-triazole

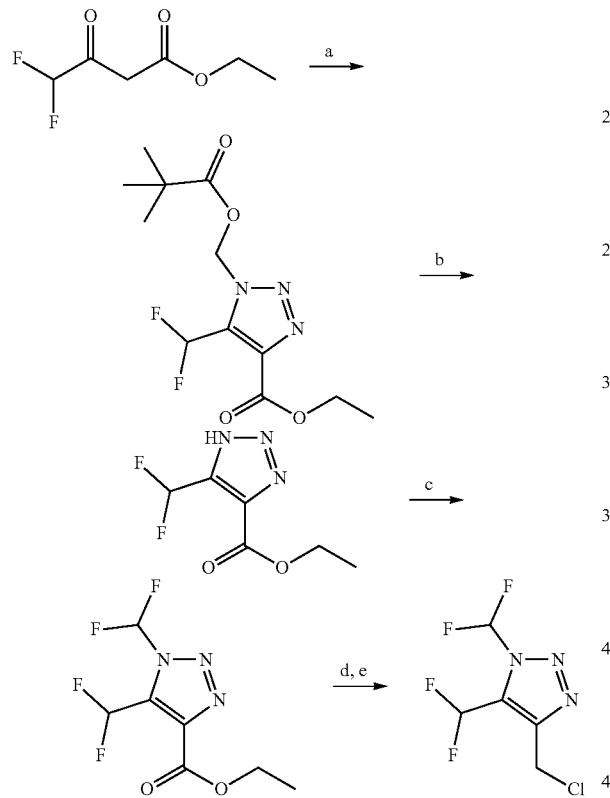

Step a. To a solution of ethyl 4,4-difluoro-3-oxo-butanoate (1. mL, 7.64 mmol, CAS: 352-24-9) and azidomethyl pivalate (1.17 mL, 7.64 mmol, CAS: 872700-68-0) in DMSO (13 mL) was added triethylamine (3.2 mL, 22.9 mmol) and the reaction mixture was heated at 70° C. for 4 h then at rt for 18 h. The mixture diluted with water and extracted with EtOAc. The combined organics were washed with water, brine and dried (Na$_2$SO$_4$), filtered and concentrated in vacuo. The crude product was purified by flash column chromatography (75 g silica column, 30-40% EtOAc in heptane) to provide ethyl 5-(difluoromethyl)-1-(2,2-dimethylpropanoyloxymethyl)triazole-4-carboxylate (1.15 g, 48%). $^1$H NMR (300 MHz, CDCl$_3$) δ: 7.53 (t, 1H), 6.45 (s, 2H), 4.49 (q, 2H), 1.45 (t, 3H), 1.20 (s, 9H).

Step b. To a stirred solution of the above intermediate (0.87 g, 2.85 mmol) in methyl alcohol (40 mL) was added triethylamine (0.4 mL, 2.87 mmol) and the solution was stirred at 70° C. for 8 days. The reaction mixture was concentrated in vacuo then azeotroped with toluene. This was partitioned between hydrochloric acid (2 M) and EtOAc. The combined organics were washed with water, dried (Na$_2$SO$_4$), filtered and concentrated in vacuo. The crude product was purified by flash column chromatography (25 g silica column, 60-100% EtOAc in heptane) to provide methyl 5-(difluoromethyl)-1H-triazole-4-carboxylate (345 mg, 59%). Mixed fractions were re-purified by flash column chromatography (10 g silica column, 20-100% EtOAc in heptane) to provide a further batch (145 mg, 19%). LCMS (Method 10b): 0.48 min, 175.9 [M–H]$^-$.

Step c. A mixture of methyl 5-(difluoromethyl)-1H-triazole-4-carboxylate (360 mg, 1.83 mmol), Sodium chlorodifluoroacetate (700 mg, 4.6 mmol) and caesium carbonate (894 mg, 2.74 mmol) in DMF (15 mL) was stirred at 70° C. for 2 h then cooled to rt. The mixture was poured into water and extracted with ethyl acetate. The organics were washed with water, brine, dried (Na$_2$SO$_4$), filtered and the filtrate concentrated in vacuo to provide methyl 1,5-bis(difluoromethyl)triazole-4-carboxylate (417 mg, quantitative) as a 7:3 mixture with ethyl 1,4-bis(difluoromethyl)-1H-1,2,3-triazole-5-carboxylate. $^1$H NMR (300 MHz; CDCl3, 298 K) δ: 7.68 (t, 0.3H), 7.55 (t, 0.3H), 7.40 (t, 0.7H), 7.17 (t, 0.7H), 4.09 (m, 2H), 4.04 (s, 3H), 1.45 (m, 3H).

Step d. To a stirred solution of sodium borohydride (106 mg, 2.8 mmol) in EtOH (13 mL) under nitrogen was added lithium chloride (0.5 M in THF; 4.59 mL, 2.3 mmol) and the above intermediate (417 mg, 1.84 mmol). The reaction mixture was heated at 60° C. for 5 h then stirred at rt for 18 h. The reaction mixture was diluted with water and the crude product extracted into IPA/chloroform (2:1). The combined organics were washed with brine, dried (Na$_2$SO$_4$), filtered and concentrated in vacuo. The crude product was purified by flash column chromatography (25 g silica column, 40-60% EtOAc in heptane) to provide [2,5-bis(difluoromethyl)triazol-4-yl]methanol (158 mg, 42%) and the desired compound [1,5-bis(difluoromethyl)triazol-4-yl]methanol (47 mg, 11%). $^1$H NMR (300 MHz, CDCl$_3$) δ: 7.63 (t, 1H), 7.19 (t, 1H), 4.98 (s, 2H), 1.96 (br s, OH).

Step e. To a stirred solution of [1,5-bis(difluoromethyl)triazol-4-yl]methanol (60 mg, 0.300 mmol) in chloroform (3 mL) was added thionyl chloride (0.07 mL, 0.900 mmol) and the mixture was stirred at rt for 21 h. The reaction mixture was concentrated in vacuo to give the title compound (76 mg, 89%) used without further purification. $^1$H NMR (300 MHz, CDCl$_3$) δ: 7.64 (t, 1H), 7.11 (t, 1H), 4.81 (s, 2H).

4-(Chloromethyl)-1-methyl-5-(oxetan-3-yl)-1H-1,2,3-triazole

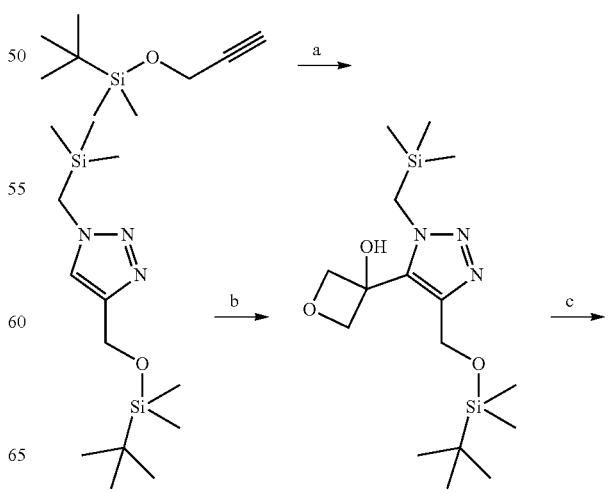

-continued

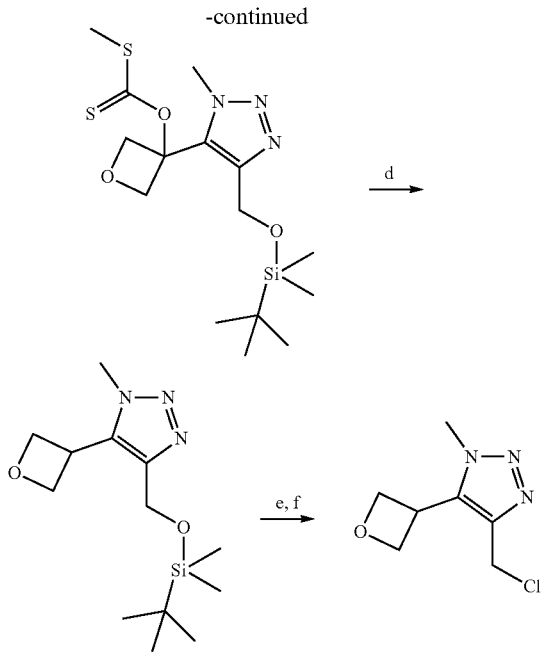

Step a. To a suspension of azidomethyl(trimethyl)silane (1.0 g, 7.7 mmol, CAS: 87576-94-1) and tert-butyldimethyl (2-propynyloxy)silane (1449.6 mg, 8.5 mmol, CAS: 76782-82-6) in 2-methyl-2-propanol (20 mL) was added (+)-sodium L-ascorbate (1.5 g, 7.7 mmol) in water (10 mL) followed by copper sulfate (386.4 mg, 1.55 mmol) in water (10 mL) dropwise over 20 mins and the reaction mixture was stirred vigorously at rt overnight. The reaction was diluted with EtOAc and water and extracted into EtOAc. The organic phase was washed with aqueous ammonia, brine, dried over sodium sulphate, filtered and concentration in vacuo. Purification by flash column chromatography on the Interchim Puriflash® 4100 (80 g silica column InterChim HP, 0-50% EtOAc in isohexane) gave 4-(((tert-butyldimethylsilyl)oxy)methyl)-1-((trimethylsilyl)methyl)-1H-1,2,3-triazole (2.23 g, 95%). $^1$H NMR (400 MHz, CDCl$_3$) δ 7.35 (s, 1H), 4.85 (s, 2H), 3.91 (s, 2H), 0.92 (s, 9H), 0.15 (s, 9H), 0.10 (s, 6H).

Step b. To a solution of the above intermediate (200 mg, 0.67 mmol) in THF (2.6 mL) at −78° C. under argon was added n-butyllithium (2.5 M in hexanes; 0.32 mL, 0.8 mmol) dropwise. The mixture was stirred at −78° C. for 1.25 h then to warmed to −60° C. and stirred for 15 mins then cooled back to −78° C. Oxetan-3-one (241 mg, 3.34 mmol, CAS: 6704-31-0) was added dropwise and the mixture stirred at −78° C. for 1 h before warming to rt and stirring for a further 1 h. The reaction mixture was cooled to 0° C. and quenched by the dropwise addition of saturated NH$_4$Cl. The reaction mixture was diluted with EtOAc and extracted into EtOAc. The organic layer was washed with water, brine, dried over Na$_2$SO$_4$, filtered and concentrated in vacuo. Purification by flash column chromatography on the Interchim Puriflash® 4100 (40 g silica column Puriflash InterChim HP, 0-50% EtOAc in cyclohexane) gave 3-(4-(((tert-butyldimethylsilyl)oxy)methyl)-1-((trimethylsilyl)methyl)-1H-1,2,3-triazol-5-yl)oxetan-3-ol (116 mg, 44%). $^1$H NMR (400 MHz, CDCl$_3$) δ 5.06 (d, 2H), 4.94 (dd, 2H), 4.85 (s, 2H), 4.41-4.39 (m, 1H), 3.81 (s, 2H), 0.89 (s, 9H), 0.23 (s, 9H), 0.11 (s, 6H).

Step c. To a solution of the above intermediate (94 mg, 0.250 mmol) in THF (3.8 mL) at 0° C. under argon was added sodium hydride (25 mg, 0.63 mmol). The mixture stirred at 0° C. for 30 mins then carbon disulfide (0.13 mL, 0.63 mmol) was added and the reaction mixture was stirred at 0° C. for 15 mins then warmed to rt and stirred for 1 h. Saturated aqueous NH$_4$Cl was added and the mixture diluted with EtOAc and the layers separated. The organics were washed with water, brine, dried over Na$_2$SO$_4$, filtered and concentrated in vacuo. Purification by flash column chromatography on the Interchim Puriflash® 4100 (12 g silica column InterChim HP, 0-50% EtOAc in cyclohexane) gave O-(3-(4-(((tert-butyldimethylsilyl)oxy)methyl)-1-methyl-1H-1,2,3-triazol-5-yl)oxetan-3-yl) S-methyl carbonodithioate (92 mg, 89%). $^1$H NMR (400 MHz, CDCl$_3$) δ 5.37 (d, 2H), 5.22 (dd, 2H), 4.92-4.91 (m, 2H), 3.96 (s, 3H), 2.52 (s, 3H), 0.90 (m, 9H), 0.11 (m, 6H).

Step d. To a solution of the above intermediate (92 mg, 0.24 mmol) in toluene (1.3 mL) was added AIBN (7.8 mg, 0.05 mmol) followed by tributyltin hydride (0.08 mL, 0.28 mmol) and the reaction mixture was heated in a sealed vial to 120° C. and stirred for 4 h. The reaction mixture was concentrated in vacuo. Purification by flash column chromatography using the Interchim Puriflash® 4100 (25 g silica column Puriflash InterChim, 0-30% EtOAc in cyclohexane) gave 4-(((tert-butyldimethylsilyl)oxy)methyl)-1-methyl-5-(oxetan-3-yl)-1H-1,2,3-triazole (55 mg, 76%). LCMS (Method 15): 1.51 min, 284.2 [M+H]$^+$ Step e. To a solution of the above intermediate (50 mg, 0.18 mmol) in THF (2 mL) under argon was added triethylamine trihydrofluoride (0.14 mL, 0.88 mmol) and the mixture was stirred at rt for 16 h. The reaction mixture was concentrated in vacuo, and the residue diluted with EtOAc and water and the crude product extracted into EtOAc. The organic layer was washed further with water, brine and dried over Na$_2$SO$_4$, filtered and concentrated in vacuo. Purification by flash column chromatography using the Interchim Puriflash® 4100 (12 g silica column, 0-10% MeOH in DCM) gave (1-methyl-5-(oxetan-3-yl)-1H-1,2,3-triazol-4-yl)methanol (16 mg, 51%). $^1$H NMR (400 MHz, CDCl$_3$) δ 5.11 (dd, 2H), 4.95-4.87 (m, 4H), 4.49-4.40 (m, 1H), 4.03 (s, 3H), 2.20 (s, 1H).

Step f. To a solution of the above intermediate (16 mg, 0.09 mmol) in DCM (1 mL) was added triethylamine (26.4 μL, 0.19 mmol). The mixture was cooled to 0° C. and methanesulfonyl chloride (7.3 μL, 0.09 mmol) was added dropwise. The reaction was warmed to rt and stirred for 18 h. The reaction mixture was partitioned between distilled water and DCM. The organic layer was separated, dried over Na$_2$SO$_4$, filtered and concentrated in vacuo to give the title compound (11 mg, 59%). $^1$H NMR (300 MHz, CDCl$_3$) δ 5.14 (dd, 2H), 4.92 (t, 2H), 4.85 (s, 2H), 4.49-4.41 (m, 1H), 4.06 (s, 3H).

(S)-6,7-dihydro-5H-pyrrolo[2,1-c][1,2,4]triazol-7-yl methanesulfonate

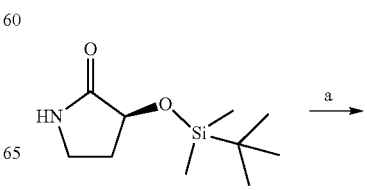

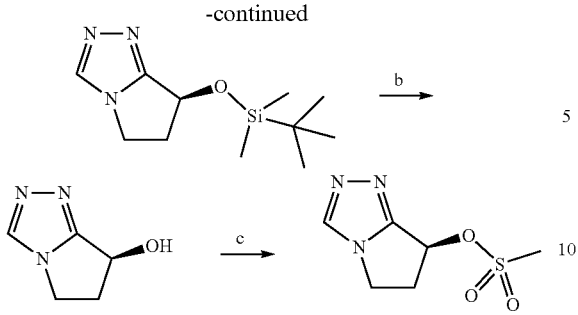

Step a. Trimethyloxonium tetrafluoroborate (0.69 g, 4.64 mmol; CAS: 420-37-1) was added to a solution of (3S)-3-[tert-butyl(dimethyl)silyl]oxypyrrolidin-2-one (1 g, 4.64 mmol; CAS: 130403-91-7) in DCM (10 mL) and the reaction mixture was stirred at rt for 16 h. To the reaction mixture was added formyl hydrazine (0.28 g, 4.64 mmol; CAS: 624-84-0) and the reaction mixture was stirred for 3 h at rt then concentrated in vacuo. The residue was dissolved in MeOH (10 mL), transferred to a microwave vial and heated under microwave irradiation at 100° C. for 4 h. The reaction mixture was concentrated in vacuo and purified by flash column chromatography (silica, 10% MeOH in DCM) to give (S)-7-((tert-butyldimethylsilyl)oxy)-6,7-dihydro-5H-pyrrolo[2,1-c][1,2,4]triazole (75 mg, 6%). $^1$H NMR (300 MHz, CDCl$_3$) δ 8.18 (s, 1H), 5.20 (q, 1H), 4.27-4.18 (m, 1H), 4.03-3.95 (m, 1H), 3.03-2.91 (m, 1H), 2.66-2.57 (m, 1H), 0.92-0.89 (s, 9H), 0.24 (s, 3H), 0.16 (s, 3H).

Step b. To a solution of the above intermediate (75 mg, 0.31 mmol) in THF (2 mL), cooled in an ice bath, was added tetrabutylammonium fluoride solution (1M in THF; 82 mg, 0.31 mmol; CAS: 429-41-4). The reaction mixture was stirred at rt for 3 h and concentrated in vacuo. The crude product was purified by flash column chromatography (silica, 10% MeOH in DCM) to give (S)-6,7-dihydro-5H-pyrrolo[2,1-c][1,2,4]triazol-7-ol (35 mg, 71%). $^1$H NMR (300 MHz, CDCl$_3$) δ 8.07 (s, 1H), 5.87 (br, 1H), 5.54-5.29 (m, 1H), 4.31-4.22 (m, 1H), 4.03-3.95 (m, 1H), 3.10-2.98 (m, 1H), 2.81-2.71 (m, 1H).

Step c. To a stirred solution of the above intermediate (35 mg, 0.28 mmol) and triethylamine (0.06 mL, 0.420 mmol) in DCM (2 mL) cooled in an ice bath was added methanesulfonyl chloride (0.03 mL, 0.340 mmol). The reaction mixture was stirred at rt for 4 h and then diluted with water and extracted with DCM. The organics were dried over MgSO$_4$ and concentrated in vacuo to give the title compound (19 mg, 23%) used without further purification. $^1$H NMR (300 MHz, CDCl$_3$) δ 8.37 (s, 1H), 6.02 (dd, 1H), 4.34-4.15 (m, 2H), 3.35-3.27 (m, 2H), 3.24 (s, 3H).

1-Methyl-1,4,5,6-tetrahydrocyclopenta[d][1,2,3]triazol-5-yl methanesulfonate

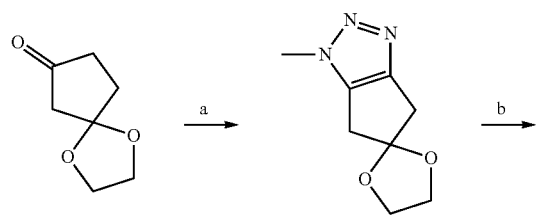

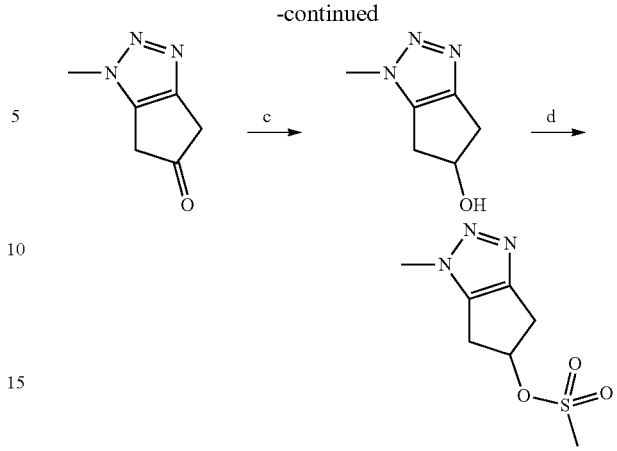

Step a. To a stirring solution of 1,4-dioxaspiro[4.4]nonan-7-one (760. mg, 5.35 mmol; CAS: 109459-59-8) in DMF (15 mL) were added 1-azido-4-nitro-benzene (1.22 g, 7.5 mmol; CAS: 1516-60-5) and methylamine (2M in THF; 13.5 mL, 26.6 mmol). The reaction was stirred at 80° C. for 5 days. The reaction mixture concentrated in vacuo and the crude was purified by flash column chromatography (silica, 1:2 EtOAc:heptane) followed by (5% MeOH in DCM) to give 1-methyl-4,6-dihydro-1H-spiro[cyclopenta[d][1,2,3]triazole-5,2'-[1,3]dioxolane] (760 mg, 60%). LCMS (Method 9): 0.42 min, 182.1 [M+H]$^+$.

Step b. To a stirred solution of the above intermediate (468 mg, 2.58 mmol) in acetone (10 mL) was added Amberlyst® 15 hydrogen form (1000. mg, 2.58 mmol, CAS: 39389-20-3) and the reaction was stirred at rt for 18 h. The reaction was filtered through Celite® and the filter cake washed with acetone followed by MeOH. The filtrate was concentrated in vacuo to give 1-methyl-4,6-dihydrocyclopenta[d][1,2,3]triazol-5(1H)-one (104 mg, 26%), used in the next step without purification. $^1$H NMR (300 MHz, CDCl$_3$-$_D$) δ 4.17 (s, 3H), 3.05-3.18 (m, 4H), 3.74 (s, 1H).

Step c. To a stirred solution of the above intermediate (169 mg, 1.98 mmol) in anhydrous THF (6.5 mL) was added lithium aluminium hydride solution (1M in THF; 1.85 mL, 1.85 mmol) dropwise at 0° C. The reaction mixture stirred at rt for 1 h, cooled back to 0° C. and to this was added sodium sulfate decahydrate. The reaction was warmed to rt and stirred for 30 min, filtered and the filtrate concentrated in vacuo to give 1-methyl-1,4,5,6-tetrahydrocyclopenta[d][1,2,3]triazol-5-ol (158 mg, 93%), used in the next step without further purification. LCMS (Method 9-2-20% B with A and 5% C in 1.0 mins, to 95% B with 5% C at 1.8 mins): 0.38 min, 140.0 [M+H]$^+$.

Step d. To a solution of the above intermediate (50 mg, 0.36 mmol) in DCM (1.5 mL) cooled in an ice bath was added triethylamine (0.07 mL, 0.470 mmol) and methane sulfonyl chloride (0.03 mL, 0.400 mmol). The reaction mixture was stirred at rt for 3 h. The reaction mixture was diluted with DCM and washed with a saturated aqueous solution of sodium bicarbonate. The mixture was extracted with DCM and the combined organics dried over MgSO$_4$ and concentrated in vacuo to give the title compound (50 mg, 48%), used without further purification. $^1$H NMR (300 MHz, CDCl$_3$) δ 5.40-5.24 (m, 1H), 4.07 (s, 3H), 3.82-2.12 (m, 7H).

137

Tetrahydro-2H-furo[3,4-b]pyran-5,7-dione

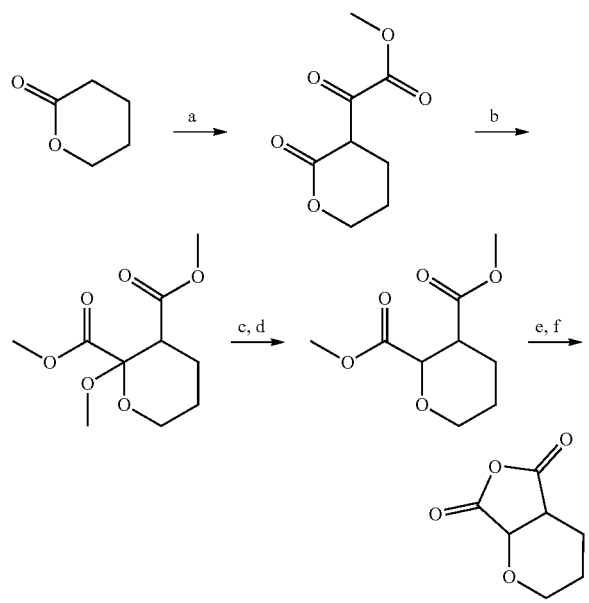

Step a. Sodium metal in kerosene (6.89 g, 300 mmol; CAS: 7440-23-5) was added to a solution of MeOH (4 drops) in Et₂O (75 mL). The mixture was stirred at rt for 2 h. A solution of tetrahydropyran-2-one (30.0 g, 300 mmol; CAS: 542-28-9) and dimethyl oxalate (35.4 g, 300 mmol; CAS: 553-90-2) in Et₂O (100 mL) was added dropwise, and the mixture stirred at rt for 2 days. The reaction mixture was poured onto ice-water and extracted with Et₂O. The aqueous phase was acidified with 10% sulphuric acid solution to pH 3 and extracted with Et₂O. The combined organics were washed with brine, dried over MgSO₄ and concentrated in vacuo to give methyl 2-oxo-2-(2-oxotetrahydro-2H-pyran-3-yl)acetate (13.3 g, 24%) used without further purification. $^1$H NMR (400 MHz, CDCl$_3$) δ 4.42-4.39 (t, 2H), 3.90 (s, 3H), 2.86-2.83 (t, 2H), 1.96-1.92 (m, 2H).

Step b. A solution of the above intermediate (13.3 g, 71.4 mmol) in hydrochloric acid in MeOH (1.25 M; 103 mL, 129 mmol) was stirred at reflux for 20 h, cooled to rt and stirred at rt overnight. The reaction mixture was neutralised with saturated sodium hydrogen carbonate solution, extracted with Et₂O and the combined organics washed with brine, dried over MgSO₄ and concentrated in vacuo to give dimethyl 2-methoxytetrahydro-2H-pyran-2,3-dicarboxylate (11.5 g, 55%) as a mixture of diastereoisomers. $^1$H NMR (300 MHz, CDCl$_3$) δ 4.00 (td, 1H), 3.88 (s, 3H), 3.70-3.63 (m, 6H), 3.14-3.08 (m, 1H), 2.37 (t, 1H), 2.10-1.99 (m, 2H).

Step c. 3 drops of sulphuric acid were added to the above intermediate (9.6 g, 41.34 mmol) in a Kugelrohr and the mixture was subjected to slow bulb-to-bulb distillation, heating to 160° C. at 2.2 mbar. The second fraction collected (5.1 g) was purified using an Isolera (Biotage Silica ZIPSphere 45 g, 0-50% EtOAc in heptane) to give dimethyl 3,4-dihydro-2H-pyran-5,6-dicarboxylate (289 mg, 3%). A third fraction collected (1.07 g) was purified using the Isolera (Silicycle Siliaprep Silica 120 g, 0-50% EtOAc in heptane) to give dimethyl 3,4-dihydro-2H-pyran-5,6-dicarboxylate (2.18 g, 9.801 mmol, 24%). $^1$H NMR (400 MHz, CDCl$_3$) δ 4.16 (t, 2H), 3.86 (s, 3H), 3.73 (s, 3H), 2.37 (t, 2H), 1.96-1.90 (m, 2H).

138

Step d. A solution of the above intermediate (2.47 g, 12.34 mmol) and Pd/C (10%; 131 mg, 1.23 mmol) in EtOH (200 mL) was stirred under a hydrogen atmosphere at ambient pressure at rt for 3 days. The reaction mixture was filtered through Celite® and concentrated to give dimethyl tetrahydro-2H-pyran-2,3-dicarboxylate (2.04 g, 70%), used without further purification. $^1$H NMR (400 MHz, CDCl$_3$) δ 4.23 (d, 1H), 4.08-4.04 (m, 1H), 3.81 (s, 3H), 3.71 (s, 3H), 3.58 (td, 1H), 3.12 (q, 1H), 2.32 (m, 1H), 1.87-1.73 (m, 3H).

Step e. Potassium hydroxide (1.13 g, 20.2 mmol) was added to a solution of the above intermediate (2.04 g, 10.1 mmol) in water (15 mL) and the reaction mixture was stirred at rt for 18 h. The reaction mixture was acidified to pH~2 with concentrated hydrochloric acid and extracted with chloroform:IPA (7:3). The combined organics were washed with brine, dried over MgSO₄ and concentrated in vacuo. The residue was purified using the Biotage Isolera (Silicycle Siliaprep 25 g, 0-10% MeOH in DCM) to give tetrahydro-2H-pyran-2,3-dicarboxylic acid (1.01 g, 46%). $^1$H NMR (400 MHz, CDCl$_3$) δ 8.23 (br s, 2H), 4.17-4.08 (m, 2H), 3.65-3.57 (m, 1H), 3.24 (m, 1H), 2.41-2.34 (m, 1H), 1.91-1.54 (m, 3H).

Step f. DMF (1 drop) was added to a solution of the above intermediate (1.0 g, 5.74 mmol) and oxalyl chloride (0.58 mL, 6.89 mmol) in toluene (30 mL). The reaction was stirred at reflux for 3 h, cooled to rt and stood at rt for 18 h. The liquid was decanted from the residue in the flask and the liquors concentrated in vacuo to give an oil (815 mg). Half of this purified using the Biotage Isolera (Biotage Silica ZIPSphere 10 g, 0-100% EtOAc in heptane) to give tetrahydro-2H-furo[3,4-b]pyran-5,7-dione (249 mg, 23%), used in the next step without further purification. $^1$H NMR (400 MHz, CDCl$_3$) complex mixture including characteristic peaks for the title compound: δ 4.73 (d, 1H), 3.11 (q, 1H).

2-(3H-[1,2,3]triazolo[4,5-b]pyridin-3-yl) 1-methyl (1S,2R)-1-methylcyclohexane-1,2-dicarboxylate-4,4-d$_2$

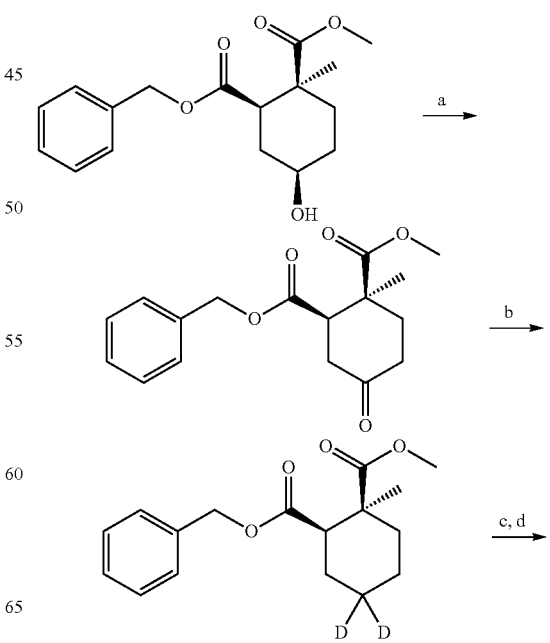

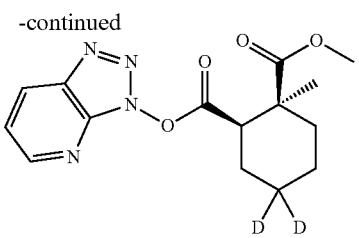

Step a. To a solution of 2-benzyl 1-methyl (1S,2R,4R)-4-hydroxy-1-methylcyclohexane-1,2-dicarboxylate (325 mg, 1.06 mmol, Example 219 step d) in DCM (10 mL) was added Dess-Martin periodinane (585 mg, 1.38 mmol; CAS: 87413-09-0) and the resulting mixture was stirred at rt under argon for 1 h. The reaction mixture was quenched with sodium thiosulfate solution and the crude product extracted with EtOAc. The combined organics were washed with water and brine, dried over $Na_2SO_4$, filtered and concentrated in vacuo. The crude product was purified by flash column chromatography on the Teledyne ISCO Combi-Flash® Rf+ (40 g silica column Puriflash HC, 0-50% EtOAc in cyclohexane) to give 2-benzyl 1-methyl (1S,2R)-1-methyl-4-oxocyclohexane-1,2-dicarboxylate (284 mg, 88%). $^1$H NMR (400 MHz; $CDCl_3$) δ 7.37-7.32 (m, 5H), 5.12 (s, 2H), 3.60 (s, 3H), 2.98-2.84 (m, 2H), 2.68-2.50 (m, 2H), 2.44-2.30 (m, 2H), 1.88-1.80 (m, 1H), 1.48 (s, 3H).

Step b. To a solution of the above intermediate (50 mg, 0.160 mmol) in methanol-$d_4$ (2. mL) was added p-toluenesulfonyl hydrazide (31 mg, 0.16 mmol, CAS: 1576-35-8) and the resulting mixture was stirred at rt under argon for 1.5 h. The reaction mixture was treated with sodium borodeuteride (21 mg, 0.49 mmol; CAS: 15681-89-7) and the resulting mixture stirred for a further 1.5 h. The mixture was heated at 60° C. for 1.5 h. The mixture was allowed to cool to rt, diluted with water and extracted with EtOAc. The combined organics were dried over $Na_2SO_4$, filtered and concentrated in vacuo. The crude product was purified by flash column chromatography on the Teledyne ISCO CombiFlash® Rf+ (12 g silica column Puriflash HC, 0-20% EtOAc in cyclohexane) to give 2-benzyl 1-methyl (1S,2R)-1-methylcyclohexane-1,2-dicarboxylate-4,4-$d_2$ (32 mg, 66%). $^1$H NMR (400 MHz, $CDCl_3$) δ 7.38-7.29 (m, 5H), 5.11 (s, 2H), 3.57 (s, 3H), 2.66-2.61 (m, 1H), 2.15-2.06 (m, 1H), 1.97 (dd, 1H), 1.84 (dd, 1H), 1.53-1.40 (m, 3H), 1.30 (s, 3H).

Step c. To a solution of the above intermediate (154 mg, 0.53 mmol) in EtOH (4 mL) was added Pd/C (10%; 50 mg, 0.47 mmol) and the resulting mixture was stirred under a hydrogen atmosphere at atmospheric pressure for 7 h. The reaction mixture was diluted with IMS and filtered through Celite®. The filtrate was concentrated in vacuo to give (1R,2S)-2-(methoxycarbonyl)-2-methylcyclohexane-1-carboxylic-5,5-$d_2$ acid (101 mg, 95%). $^1$H NMR (300 MHz, $CDCl_3$) δ 3.70 (s, 3H), 2.58 (dd, 1H), 2.18-2.05 (m, 1H), 1.95-1.88 (m, 2H), 1.57-1.41 (m, 3H), 1.33 (s, 3H).

Step d. To a stirred solution of the above intermediate (101 mg, 0.50 mmol) in DMF (1.1 mL) was added HATU (209 mg, 0.55 mmol; CAS: 148893-10-1) and the resulting mixture was stirred at rt under argon for 5 min. DIPEA (0.1 mL, 0.55 mmol) was added and the mixture stirred for 1 h. The reaction mixture was diluted with water and extracted with EtOAc. The combined organics were washed with water, brine, dried over $Na_2SO_4$, filtered and concentrated in vacuo. The crude product was purified by flash column chromatography on the Teledyne ISCO CombiFlash® Rf+ (25 g silica column Puriflash HC, 0-50% EtOAc in cyclohexane) to provide the title compound (130 mg, 81%). LCMS (Method 2): 1.34 min, 321.0 $[M+H]^+$. $^1$H NMR (300 MHz, $CDCl_3$) δ 8.74-8.71 (m, 1H), 8.41 (dd, 1H), 7.43 (dd, 1H), 3.76 (s, 3H), 3.16-3.10 (m, 1H), 2.30-2.12 (m, 3H), 1.66-1.54 (m, 3H), 1.48 (s, 3H).

Synthesis of Example Compounds

Example 1

(1S,2R)-2-((S)-1-((1,3-Dioxoisoindolin-2-yl)methyl)-8-(2-(5-methylisoxazole-3-carboxamido)ethoxy)-1,2,3,4-tetrahydroisoquinoline-2-carbonyl)cyclohexanecarboxylic acid

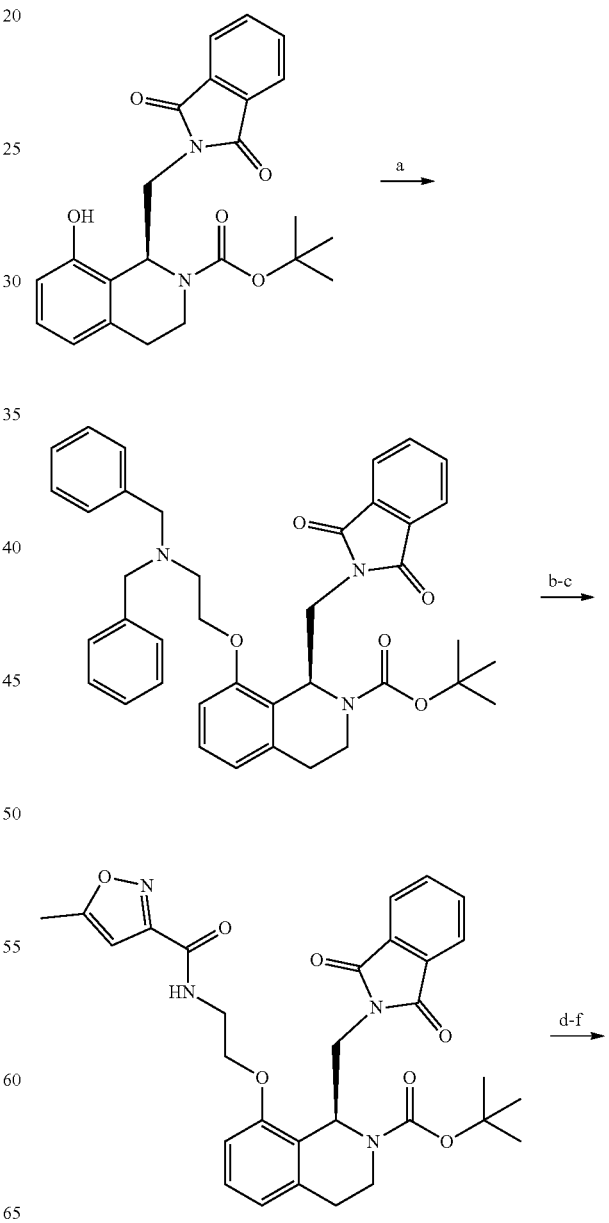

141

-continued

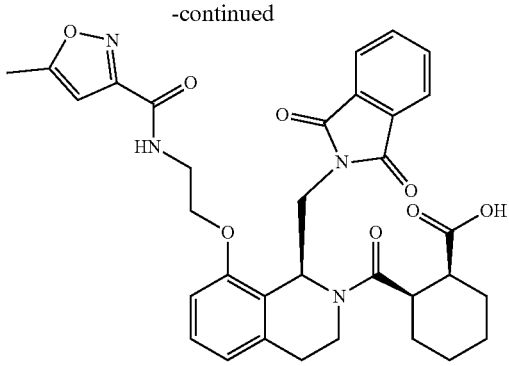

Step a. To a stirred suspension of Intermediate 11 (0.45 g, 1.1 mmol) and caesium carbonate (1.44 g, 4.4 mmol) in DMF (6 mL) at rt was added N-(2-chloroethyl)-dibenzylamine hydrochloride (0.46 g, 1.5 mmol, CAS: 55-43-6) and the reaction was heated 100° C. for 18 h. The reaction mixture was concentrated in vacuo, diluted with water (25 mL) and extracted with DCM (25 mL). The organic layer was washed with further water (50 mL), dried over $Na_2SO_4$ and concentrated in vacuo to give tert-butyl (S)-8-(2-(dibenzylamino)ethoxy)-1-((1,3-dioxoisoindolin-2-yl)methyl)-3,4-dihydroisoquinoline-2(1H)-carboxylate (1.10 g, assumed quantitative). $^1$H NMR (400 MHz, DMSO-$d_6$, rotamers observed, both reported) δ 7.98-7.75 (m, 4H), 7.44-7.03 (m, 11H), 6.83-6.72 (m, 2H), 5.54 (dd, 0.3H), 5.45 (dd, 0.7H), 4.42-3.90 (m, 4H), 3.81-3.64 (m, 5H), 3.63-3.45 (m, 2H), 3.15-2.95 (m, 2H), 2.85-2.70 (m, 1H), 1.03 (s, 2.7H), 0.84 (s, 6.3H).

Step b. To a solution of the above intermediate (1 g, 1.6 mmol) in IMS (20 mL) was added 1-methyl-1,4-cyclohexadiene (1.8 g, 15.8 mmol) and Pd/C (20%; 0.11 g, 0.16 mmol) and the reaction mixture was heated at 60° C. for 18 h. Further 1-methyl-1,4-cyclohexadiene (3.6 g, 31.6 mmol) was added and the mixture heated at 60° C. for a further 36 h. The mixture was filtered through a pad of Celite® and washed with IMS (20 mL) and THF (20 mL) and the filtrate was concentrated in vacuo. Purification by flash column chromatography (10% MeOH in DCM) gave tert-butyl (S)-8-(2-aminoethoxy)-1-((1,3-dioxoisoindolin-2-yl)methyl)-3,4-dihydroisoquinoline-2(1H)-carboxylate (352 mg, 49%). LCMS (Method 4): 0.81 min, 452.4 [M+H]$^+$.

Step c. To a stirred solution of 5-methylisoxazole-3-carboxylic acid (19 mg, 0.15 mmol, CAS: 3405-77-4) in DMF (2 mL) was added 1,1'-carbonyldiimidazole (24 mg, 0.15 mmol, CAS: 530-62-1). After 5 min, a solution of the above intermediate (60 mg, 0.13 mmol) in DMF (1 mL) was added. The reaction mixture stirred at rt for 3 h, diluted with water (10 mL) and extracted with EtOAc (2×10 mL). The combined organics were washed with water (20 mL), dried over $MgSO_4$, filtered and concentrated in vacuo. Purification by flash column chromatography (EtOAc) gave tert-butyl (S)-1-((1,3-dioxoisoindolin-2-yl)methyl)-8-(2-(5-methyl-isoxazole-3-carboxamido)ethoxy)-3,4-dihydroisoquinoline-2(1H)-carboxylate (67 mg, 80%). LCMS (Method 4): 0.93 min, 561.3 [M+H]$^+$.

Step d. A solution of the above intermediate (67 mg, 0.12 mmol) in HCl (4M in dioxane; 2 mL) was stirred at rt for 1 h. The reaction mixture was concentrated in vacuo to give (S)-N-(2-((1-((1,3-dioxoisoindolin-2-yl)methyl)-1,2,3,4-tetrahydroisoquinolin-8-yl)oxy)ethyl)-5-methylisoxazole-3-carboxamide hydrochloride (59 mg, 100%), used without further purification. LCMS (Method 4): 0.76 min, 461.3 [M+H]$^+$.

142

Step e. To a stirred solution of the above intermediate (59 mg, 0.12 mmol) and triethylamine (82 μL, 0.59 mmol) in DCM (5 mL) at 0° C. was added a solution of Intermediate 26 (50 mg, 0.18 mmol) in DCM (1 mL). The reaction mixture was stirred at 0° C. for 15 min. DCM (6 mL) and saturated aqueous NaHCO3 (12 mL) were added. The layers were separated by passing through a phase separation cartridge and the organic layer was concentrated in vacuo. Purification by flash column chromatography (40-80% EtOAc in heptanes) gave benzyl (1S,2R)-2-((S)-1-((1,3-dioxoisoindolin-2-yl)methyl)-8-(2-(5-methylisoxazole-3-carboxamido)ethoxy)-1,2,3,4-tetrahydroisoquinoline-2-carbonyl)cyclohexane-1-carboxylate (78 mg, 92%). LCMS (Method 4): 0.98 min, 705.4 [M+H]$^+$.

Step f. To a solution of the above intermediate (78 mg, 0.11 mmol) in THF (5 mL) was added Pd/C (10%; 50 mg). The reaction mixture was stirred under a hydrogen atmosphere at rt under atmospheric pressure for 18 h. The mixture was filtered through a pad of Celite®, washed with THF (15 mL) and the filtrate was concentrated in vacuo. Purification by reverse phase column chromatography (12 g spherical bead C18 cartridge, 15-80% MeCN in pH10 ammonium hydrogen carbonate aqueous buffer solution) gave the title compound (15 mg, 22%). LCMS (Method 4a): 1.7 min, 615.1 [M+H]$^+$. $^1$H NMR (400 MHz, DMSO-$d_6$) δ 11.68 (bs, 1H), 8.76 (t, 1H), 7.91-7.78 (m, 4H), 7.19 (t, 1H), 6.89 (d, 1H), 6.80 (d, 1H), 6.54 (m, 1H), 6.04 (dd, 1H), 4.28-4.03 (m, 3H), 4.01-3.73 (m, 4H), 3.66 (m, 1H), 3.27 (m, 1H), 2.94-2.72 (m, 2H), 2.35 (m, 3H), 2.21 (m, 1H), 1.83 (m, 1H), 1.60-1.42 (m, 2H), 1.41-1.18 (m, 2H), 0.94 (m, 1H), 0.82 (m, 1H), 0.15 (m, 1H).

Example 2

(1S,2R)-2-((S)-8-(2-(Benzo[d]oxazole-2-carboxamido)ethoxy)-1-((1,3-dioxoisoindolin-2-yl)methyl)-1,2,3,4-tetrahydroisoquinoline-2-carbonyl)cyclohexane-1-carboxylic acid

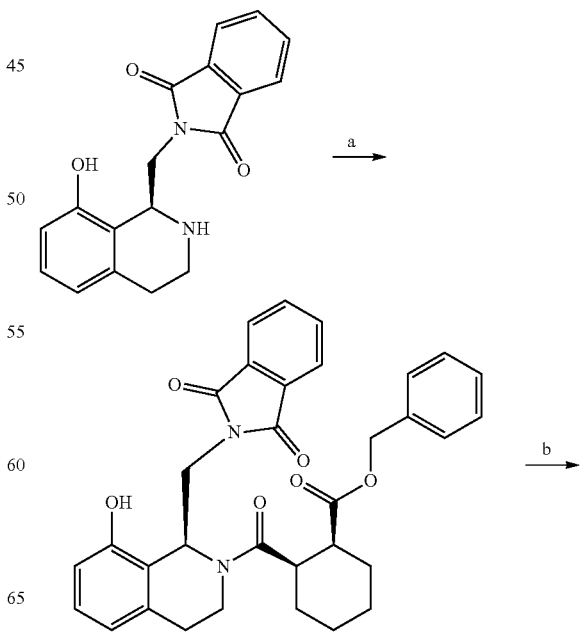

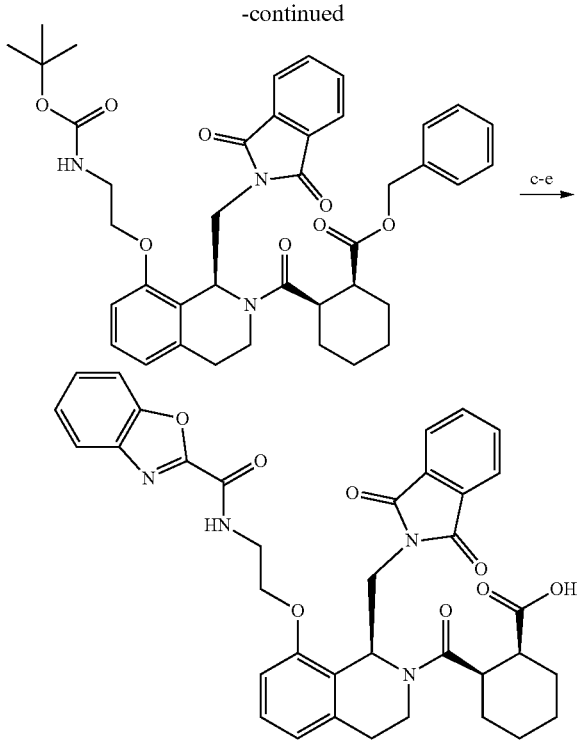

Step a. Benzyl (1S,2R)-2-((S)-1-((1,3-dioxoisoindolin-2-yl)methyl)-8-hydroxy-1,2,3,4-tetrahydroisoquinoline-2-carbonyl)cyclohexane-1-carboxylate (370 mg, 59%) was prepared from Intermediate 10 (350 mg, 1.14 mmol) and Intermediate 26 (351 mg, 1.25 mmol) using a procedure similar to that described for Example 1, step e. LCMS (Method 4a): 2.86 min, 553.4 [M+H]$^+$. 1H NMR (400 MHz, DMSO-d$_6$) 9.86 (br s, 1H), 7.86-7.79 (m, 4H), 7.19-7.00 (m, 5H), 6.73 (d, 1H), 6.60 (d, 1H), 5.98 (dd, 1H), 4.77 (q, 2H), 4.22 (dd, 1H), 3.80 (d, 1H), 3.75-3.60 (m, 2H), 3.29-3.24 (m, 1H), 2.73-2.69 (m, 1H), 2.40 (dt, 1H), 1.84 (q, 1H), 1.68-1.60 (m, 1H), 1.50 (d, 1H), 1.36-1.23 (m, 3H), 1.00-0.76 (m, 3H), 0.15 (q, 1H).

Step b. Benzyl (1S,2R)-2-((S)-8-(2-((tert-butoxycarbonyl)amino)ethoxy)-1-((1,3-dioxoisoindolin-2-yl)methyl)-1,2,3,4-tetrahydroisoquinoline-2-carbonyl)cyclohexane-1-carboxylate (380 mg, 43%) was prepared from the above intermediate and tert-butyl (2-bromoethyl)carbamate using a procedure similar to that described for Example 1, step a. LCMS (Method 4): 1.05 min, 713.6 [M+NH$_4$]$^+$.

Step c. Benzyl (1S,2R)-2-((S)-8-(2-((tert-butoxycarbonyl)amino)ethoxy)-1-((1,3-dioxoisoindolin-2-yl)methyl)-1,2,3,4-tetrahydroisoquinoline-2-carbonyl)cyclohexane-1-carboxylate was prepared from the above intermediate using a procedure similar to that described for Example 1, step d. LCMS (Method 4): 0.93 min, 596.5 [M+H]$^+$.

Step d. To a solution of the above intermediate (105 mg, 0.16 mmol) and triethylamine (0.11 mL, 0.80 mmol) in DCM (2 mL) was added a solution of benzo[d]oxazole-2-carbonyl chloride (43 mg, 0.26 mmol, CAS: 408538-63-6) in DCM (0.5 mL). The reaction mixture was stirred at rt for 20 min then quenched with saturated aqueous NaHCO$_3$ (2 mL) and the mixture passed through a phase separator. The DCM layer was concentrated in vacuo. Purification by flash column chromatography (30-60% EtOAc in heptanes) gave benzyl (1S,2R)-2-((S)-8-(2-(benzo[d]oxazole-2-carboxamido)-ethoxy)-1-((1,3-dioxoisoindolin-2-yl)methyl)-1,2,3,4-tetrahydroisoquinoline-2-carbonyl)cyclohexane-1-carboxylate (104 mg, 88%). LCMS (Method 4): 1.02 min, 741.6 [M+H]$^+$.

Step e. To a solution of the above intermediate (104 mg, 0.14 mmol) in DCM (2 mL) cooled to −10° C. was added boron tribromide (1 M in DCM; 1 mL) and the reaction mixture was allowed to warm to rt. After 2 h, saturated aqueous NaHCO$_3$ (2 mL) was added and the reaction mixture concentrated in vacuo. Purification by preparative HPLC (Method 6; 25-50% MeCN in aq. NH$_4$CO$_3$H (pH 10)) gave the title compound (42 mg, 53%). LCMS (Method 4a): 1.80 min, 651.5 [M+H]$^+$. $^1$H NMR (400 MHz, DMSO-d$_6$) δ 11.67 (bs, 1H), 9.31 (t, 1H), 7.88-7.77 (m, 4H), 7.72 (m, 1H), 7.44 (m, 1H), 7.35-7.27 (m, 2H), 7.20 (t, 1H), 6.91 (d, 1H), 6.80 (d, 1H), 6.09 (dd, 1H), 4.30-4.10 (m, 3H), 4.02 (m, 1H), 3.95-3.75 (m, 3H), 3.63 (m, 1H), 3.27 (m, 1H), 2.94-2.71 (m, 2H), 2.20 (m, 1H), 1.80 (m, 1H), 1.59-1.41 (m, 2H), 1.40-1.16 (m, 2H), 0.93 (m, 1H), 0.79 (m, 1H), 0.14 (m, 1H).

Example 3

(1S,2R)-2-((S)-8-(((S)-1-Acetylpyrrolidin-3-yl)oxy)-1-((1,3-dioxoiso-indolin-2-yl)methyl)-1,2,3,4-tetrahydroisoquinoline-2-carbonyl)cyclohexane-1-carboxylic acid

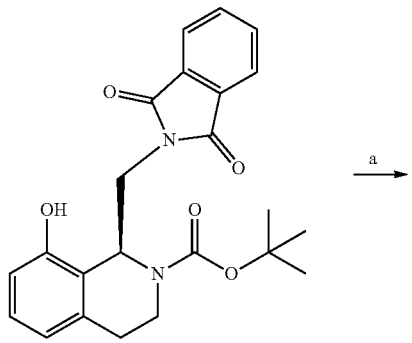

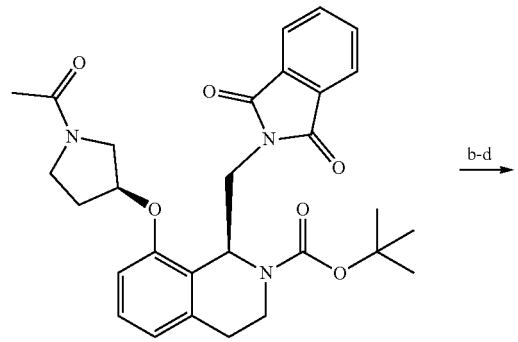

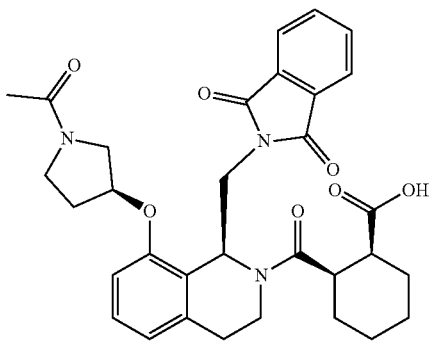

Step a. A solution of DBAD (120 mg, 0.52 mmol, CAS: 870-50-8) in THF (2.0 mL) was added slowly over 10 min to a stirred solution of Intermediate 11 (180 mg, 0.40 mmol), (R)-1-(3-hydroxypyrrolidin-1-yl)ethan-1-one (67.0 mg, 0.52 mmol, CAS: 916733-17-0) and triphenyl phosphine (136 mg, 0.52 mmol) in THF (3.0 mL) at it After stirring for 2 h the reaction was concentrated in vacuo. Purification by flash column chromatography gave tert-butyl (S)-8-(((S)-1-acetylpyrrolidin-3-yl)oxy)-1-((1,3-dioxoisoindolin-2-yl)methyl)-3,4-dihydroisoquinoline-2(1H)-carboxylate (171 mg, 63%). LCMS (Method 4a): 2.38 min, 520.4 [M+H]$^+$.

Steps b-d. The title compound was synthesised from the above intermediate using procedures similar to those described for Example 1, steps d,e,f. LCMS (Method 4a): 1.47 and 1.57 min (rotamers), 574.3 [M+H]$^+$. $^1$H NMR (400 MHz, DMSO-d$_6$; rotamers observed, both reported) δ 11.67 (bs, 1H), 7.89-7.76 (m, 4H), 7.21 (m, 1H), 6.88 (d, 1H), 6.80 (d, 1H), 5.98-5.89 (m, 1H), 5.15 (m, 0.5H), 5.11 (m, 0.5H), 4.11 (m, 1H), 3.98-3.71 (m, 4H), 3.71-3.52 (m, 3H), 3.25 (m, 1H), 2.94-2.71 (m, 2H), 2.54-2.09 (m, 3H), 2.03 (s, 1.5H), 2.01 (s, 1.5H), 1.82 (m, 1H), 1.59-1.40 (m, 2H), 1.40-1.19 (m, 2H), 0.93 (m, 1H), 0.76 (m, 1H), 0.10 (m, 1H).

Example 4

(1S,2R)-2-((S)-1-((1,3-Dioxoisoindolin-2-yl)methyl)-8-(((S)-1-(5-methylisoxazole-3-carbonyl)pyrrolidin-3-yl)oxy)-1,2,3,4-tetrahydroisoquinoline-2-carbonyl)cyclohexane-1-carboxylic acid

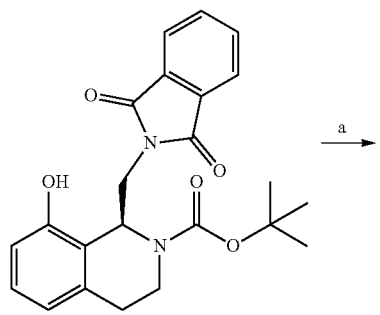

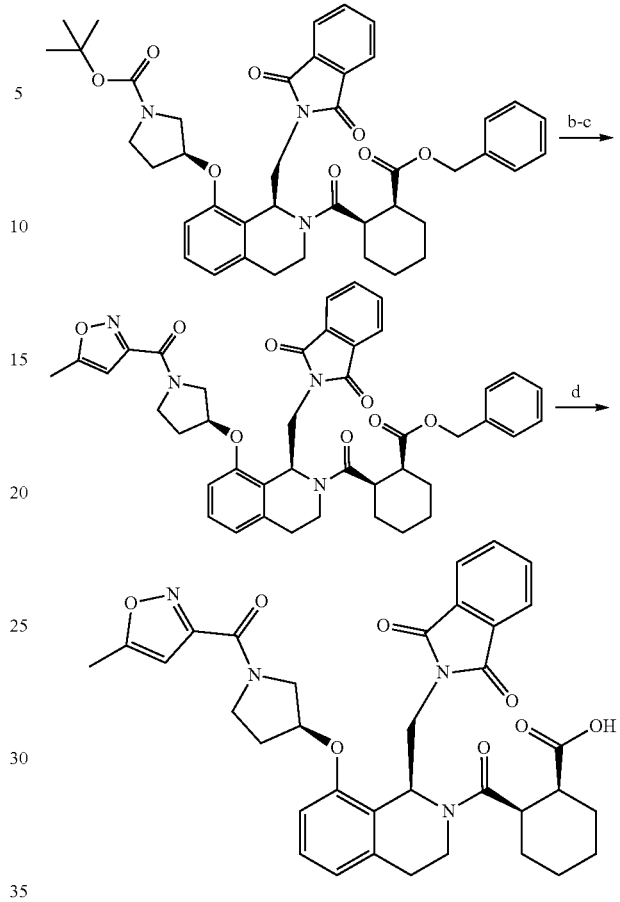

Step a. tert-Butyl (S)-3-(((S)-2-((1R,2S)-2-((benzyloxy)carbonyl)-cyclohexane-1-carbonyl)-1-((1,3-dioxoisoindolin-2-yl)methyl)-1,2,3,4-tetrahydroisoquinolin-8-yl)oxy)pyrrolidine-1-carboxylate (4.3 g, 93%) was prepared from (R)-tert-butyl 3-hydroxypyrrolidine-1-carboxylate (1.78 g, 9.50 mmol, CAS: 103057-44-9) and benzyl (1S,2R)-2-((S)-1-((1,3-dioxoisoindolin-2-yl)methyl)-8-hydroxy-1,2,3,4-tetrahydroisoquinoline-2-carbonyl)cyclohexane-1-carboxylate (from Example 2 step a, 3.56 g, 6.40 mmol) using a procedure similar to that described for Example 3, step a. The crude product was purified by flash column chromatography (50-100% EtOAc in heptanes). LCMS (Method 4): 1.07 min, 722.6 [M+H]$^+$.

Step b. Benzyl (1S,2R)-2-((S)-1-((1,3-dioxoisoindolin-2-yl)methyl)-8-(((S)-pyrrolidin-3-yl)oxy)-1,2,3,4-tetrahydroisoquinoline-2-carbonyl)cyclohexane-1-carboxylate (1.8 g, 48%) was prepared from the above intermediate using a procedure similar to that described for Example 1, step d. LCMS (Method 4a): 2.85 min, 622.4 [M+H]$^+$.

Step c. To a suspension of 5-methylisoxazole-3-carboxylic acid (130 mg, 0.89 mmol, CAS: 3405-77-4) in DCM (5 mL) was added oxalyl chloride (0.5 mL) and THF (0.1 mL). After 30 min, to the reaction mixture was added oxalyl chloride (0.5 mL) and DMF (0.05 mL). After a further 30 min the reaction mixture was concentrated in vacuo, azeotroping twice with toluene to give 5-methylisoxazole-3-carbonyl chloride (150 mg, 100%). To a stirred solution of benzyl (1S,2R)-2-((S)-1-((1,3-dioxoisoindolin-2-yl)methyl)-8-(((S)-pyrrolidin-3-yl)oxy)-1,2,3,4-tetrahydroisoquinoline-2-carbonyl)cyclohexane-1-carboxylate (92 mg, 0.14 mmol) and triethylamine (0.10 mL, 0.70 mmol) in DCM (1 mL) was added portionwise a solution of 5-methylisoxazole-3-carbonyl chloride (150 mg, 0.91 mmol) in DCM (2 mL). After 30 min saturated aqueous NaHCO$_3$ (2 mL) was added and the organic layer separated and dried over MgSO$_4$, filtered and concentrated in vacuo. The residue was passed through an SCX-2 cartridge (1 g, methanolic ammonia) and concentrated in vacuo to give (1S,2R)-benzyl 2-((S)-1-((1,3-dioxoisoindolin-2-yl)methyl)-8-(((S)-1-(5-methyl isoxazole-3-carbonyl)pyrrolidin-3-yl)oxy)-1,2,3,4-tetrahydroisoquinoline-2-carbonyl)cyclohexanecarboxylate (34 mg, 33%), used without further purification. LCMS (Method 4a): 3.07 min, 748.6 [M+NH$_4$]$^+$.

Step d. The title compound (5 mg, 17%) was prepared from the above intermediate (34 mg, 0.05 mmol) using a procedure similar to that described for Example 1, step f. The crude product was purified by preparative HPLC (Method 6; 20-45% MeCN in aq. NH$_4$CO$_3$H (pH 10)). LCMS (Method 4a): 1.62 & 1.76 min, 641.5 [M+H]$^+$. $^1$H NMR (400 MHz, DMSO-d$_6$; rotamers observed, both reported) δ 11.50 (bs, 1H), 7.88-7.76 (m, 4H), 7.26-7.16 (m, 1H), 6.93 (d, 0.5H), 6.88 (d, 0.5H), 6.81 (m, 1H), 6.54 (m, 0.5H), 6.53 (m, 0.5H), 5.92 (m, 1H), 5.19 (m, 1H), 4.20-4.00 (m, 3H), 3.99-3.73 (m, 4H), 3.65 (m, 1H), 3.25 (m, 1H), 2.95-2.71 (m, 2H), 2.60-2.24 (m, 5H), 2.19 (m, 1H), 1.82 (m, 1H), 1.60-1.40 (m, 2H), 1.39-1.16 (m, 2H), 0.93 (m, 1H), 0.77 (m, 1H), 0.12 (m, 1H).

Examples 5 and 6

(1S,2R)-2-((S)-1-((1,3-dioxoisoindolin-2-yl)methyl)-8-(((S)-1-(thiazole-5-carbonyl)pyrrolidin-3-yl)oxy)-1,2,3,4-tetrahydroisoquinoline-2-carbonyl)cyclohexane-1-carboxylic acid and (1S,2R)-2-((S)-1-((1,3-dioxoisoindolin-2-yl)methyl)-8-(((S)-1-(thiazole-5-carbonyl)pyrrolidin-3-yl)oxy)-1,2,3,4-tetrahydroisoquinoline-2-carbonyl)cyclohexane-1-carboxylic acid

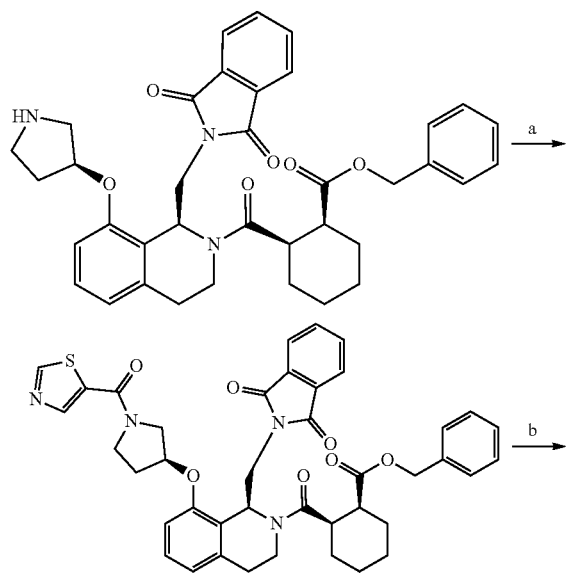

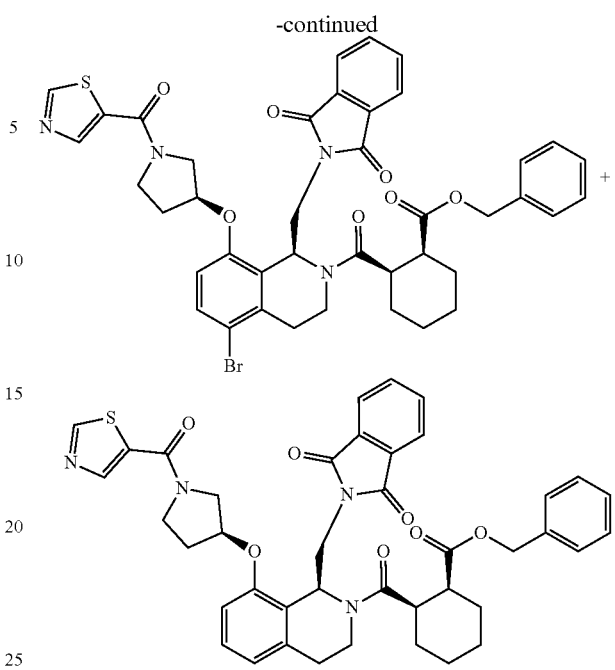

Step a. To a solution of benzyl (1S,2R)-2-((S)-1-((1,3-dioxoisoindolin-2-yl)methyl)-8-(((S)-pyrrolidin-3-yl)oxy)-1,2,3,4-tetrahydroisoquinoline-2-carbonyl)cyclohexane-1-carboxylate (Example 4 step b; 320 mg, 0.51 mmol) and triethylamine (0.27 mL, 2.06 mmol) in DCM (6 mL) was added thiazole-5-carboxylic acid (75 mg, 0.61 mmol CAS: 14527-41-4]) and HATU (194 mg, 0.53 mmol; CAS: 148893-10-1). The mixture was stirred at rt for 8 h, then diluted with water (10 mL). The product was extracted with DCM (3×15 mL). The combined organic layers were washed with saturated aqueous of NaHCO$_3$ (4 mL), dried over Na$_2$SO$_4$, filtered and concentrated in vacuo. Purification by flash column chromatography (5-10% MeOH in EtOAc) gave benzyl (1S,2R)-2-((S)-1-((1,3-dioxoisoindolin-2-yl)methyl)-8-(((S)-1-(thiazole-5-carbonyl)pyrrolidin-3-yl)oxy)-1,2,3,4-tetrahydroisoquinoline-2-carbonyl)cyclohexane-1-carboxylate (120 mg, 32%). LCMS (Method 4): 0.92 min, 733.5 [M+H]$^+$.

Step b. The title compounds Example 5 (1S,2R)-2-((S)-5-bromo-1-((1,3-dioxoisoindolin-2-yl)methyl)-8-(((S)-1-(thiazole-5-carbonyl)pyrrolidin-3-yl)oxy)-1,2,3,4-tetrahydroisoquinoline-2-carbonyl)cyclohexane-1-carboxylic acid (6.1 mg, 5%) and Example 6 (1S,2R)-2-((S)-1-((1,3-dioxoisoindolin-2-yl)methyl)-8-(((S)-1-(thiazole-5-carbonyl)pyrrolidin-3-yl)oxy)-1,2,3,4-tetrahydroisoquinoline-2-carbonyl)cyclohexane-1-carboxylic acid (20 mg, 19%) were prepared from the above intermediate (120 mg, 0.16 mmol) using a procedure similar to that described for Example 2, step e. The crude products were separated by preparative HPLC (Method 6; 20-40% MeCN in aq. NH$_4$CO$_3$H (pH 10)).

Example 5

LCMS (Method 4a): 1.70 min, 721.3 & 723.3 [M+H]$^+$. $^1$H NMR (400 MHz, DMSO-d$_6$) δ 11.63 (bs, 1H), 9.27 (s, 0.6H), 9.23 (s, 0.4H), 8.45 (s, 0.6H), 8.40 (s, 0.4H), 7.90-7.71 (m, 4H), 7.54 (m, 1H), 6.99 (m, 1H), 5.94 (m, 1H), 5.23 (bm, 1H), 4.44-3.54 (m, 7H), 3.53-3.11 (m, 2H), 2.90-2.61

(bm, 2H), 2.61-2.10 (m, 3H), 1.78 (bm, 1H), 1.59-1.38 (bm, 2H), 1.38-1.17 (bm, 2H), 1.00-0.65 (bm, 2H), 0.11 (bm, 1H).

Example 6

LCMS (Method 4a): 1.52 min, 643.3 [M+H]$^+$. $^1$H NMR (400 MHz, DMSO-d$_6$, rotamers observed both reported) δ 11.51 (bs, 1H), 9.27 (s, 0.5H), 9.24 (s, 0.5H), 8.45 (s, 0.5H), 8.40 (s, 0.5H), 7.87-7.75 (m, 4H), 7.26-7.16 (m, 1H), 6.98-6.88 (m, 1H), 6.85-6.75 (m, 1H), 5.96 (dd, 0.5H), 5.91 (dd, 0.5H), 5.21 (m, 1H), 4.33 (dd, 0.5H), 4.26-3.55 (m, 7.5H), 3.24 (m, 1H), 2.97-2.69 (m, 2H), 2.56-2.34 (m, 1H), 2.17 (m, 1H), 1.80 (m, 1H), 1.58-1.39 (m, 2H), 1.38-1.17 (m, 2H), 0.91 (m, 1H), 0.76 (m, 1H), 0.11 (m, 1H).

Example 8

(1S,2R)-2-((S)-1-((1,3-Dioxoisoindolin-2-yl)methyl)-8-((1-methyl-1H-benzo[d][1,2,3]triazol-5-yl)methoxy)-1,2,3,4-tetrahydroisoquinoline-2-carbonyl)cyclohexane-1-carboxylic acid

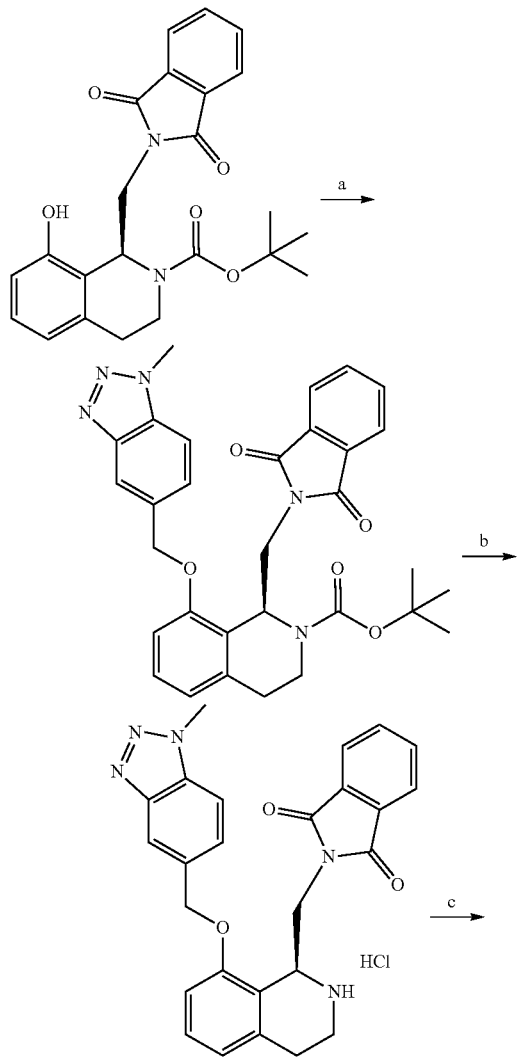

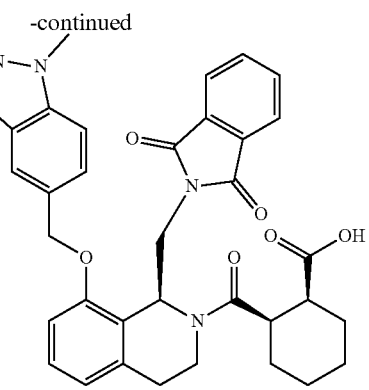

Step a. tert-Butyl (S)-1-((1,3-Dioxoisoindolin-2-yl)methyl)-8-((1-methyl-1H-benzo[d][1,2,3]triazol-5-yl)methoxy)-3,4-dihydroisoquinoline-2(1H)-carboxylate (264 mg, 97%) was prepared from Intermediate 11 (200 mg, 0.45 mmol) and 1-methyl-1H-benzo[d][1,2,3]triazol-5-yl)methanol (104 mg, 0.64 mmol, CAS: 120321-72-4) using a procedure similar to that described for Example 3, step a. The crude product was purified by flash column chromatography (0-100% EtOAc in cyclohexane). LCMS (Method 2): 1.61 min, 576.3 [M+Na]$^+$.

Step b. (S)-2-((8-((1-Methyl-1H-benzo[d][1,2,3]triazol-5-yl)methoxy)-1,2,3,4-tetrahydroisoquinolin-1-yl)methyl)isoindoline-1,3-dione hydrochloride (234 mg, assumed quantitative) was prepared from the above intermediate (264 mg, 0.48 mmol) using a procedure similar to that described for Example 1, step d. The crude product was used without further purification. LCMS (Method 2): 0.90 min, 454.0 [M+H]$^+$.

Step c. To a stirred solution of the above intermediate (233 mg, 0.48 mmol) and cis-cyclohexane dicarboxylic anhydride (81 mg, 0.52 mmol, CAS: 85-42-7) in DCM (6 mL) was added triethylamine (0.17 mL, 1.19 mmol) and the reaction mixture stirred at rt for 24 h. The reaction mixture was concentrated in vacuo and purification by preparative HPLC (Method 1) gave the title compound (31 mg, 11%). LCMS (Method 3) 4.65 min, 608.3 [M+H]$^+$. $^1$H NMR (400 MHz, DMSO-d$_6$) δ 11.62 (bs, 1H), 8.27 (m, 1H), 7.92 (d, 2H), 7.88-7.77 (m, 4H), 7.20 (t, 1H), 7.07 (d, 1H), 6.81 (d, 1H), 6.15 (dd, 1H), 5.45 (d, 1H), 5.40 (d, 1H), 4.33 (s, 3H), 4.20 (dd, 1H), 3.90-3.75 (m, 2H), 3.69 (m, 1H), 3.50-3.14 (m, 1H), 2.99-2.72 (m, 2H), 2.19 (m, 1H), 1.87 (m, 1H), 1.59 (m, 1H), 1.48-1.19 (m, 3H), 0.92 (m, 1H), 0.67 (m, 1H), 0.12 (m, 1H).

Example 11

(1S,2R)-2-((S)-8-(((S)-1-Acetylpyrrolidin-3-yl)oxy)-5-bromo-1-((1,3-dioxoisoindolin-2-yl)methyl)-1,2,3,4-tetrahydroisoquinoline-2-carbonyl)cyclohexane-1-carboxylic acid

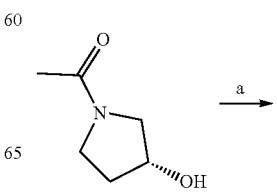

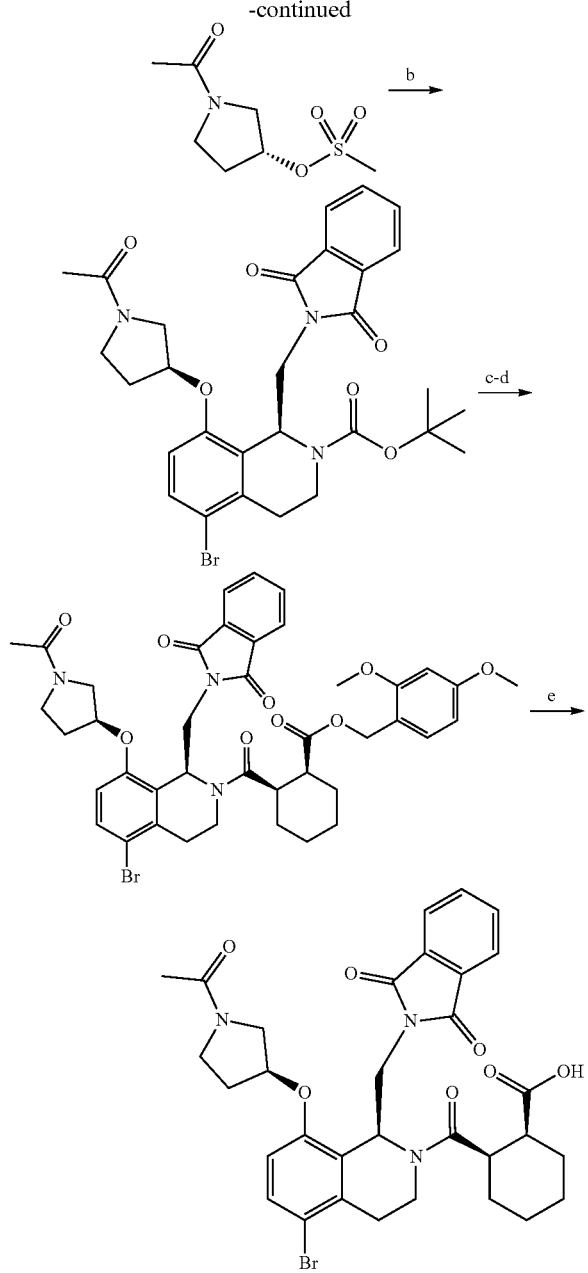

Step a. To a solution of (R)-1-(3-hydroxypyrrolidin-1-yl)ethan-1-one (3.40 g, 26.3 mmol, CAS: 916733-17-0) in DCM (100 mL) was added triethylamine (7.34 mL, 52.7 mmol) at rt. The reaction was cooled to 0° C. and methanesulfonyl chloride (4.23 mL, 52.7 mmol) was added dropwise. The reaction was allowed to warm to rt and stirred for 18 h. The reaction was diluted with water (50 mL) and extracted with DCM (3×50 mL). The combined organic layers were separated, dried over Na$_2$SO$_4$, filtered and concentrated in vacuo. Purification by flash column chromatography on the Biotage Companion™ (Puriflash cartridge 220 g, 80-100% MeOH in EtOAc) gave (R)-1-acetylpyrrolidin-3-yl methanesulfonate (4.09 g, 75%). $^1$H NMR (400 MHz, CDCl$_3$) δ 5.38-5.28 (m, 1H), 3.96-3.52 (m, 4H), 3.05 (m, 3H), 2.50-2.13 (m, 2H), 2.10 (m, 3H).

Step b. To a stirred solution of Intermediate 8 (6.41 g, 13.2 mmol) and (R)-1-acetylpyrrolidin-3-yl methanesulfonate (4.09 g, 19.7 mmol) in anhydrous DMF (100 mL) under argon was added caesium carbonate (21.4 g, 65.8 mmol) and the mixture stirred at rt for 18 h, then at 40° C. for 7.5 h. The reaction mixture was diluted with water (400 mL) and the crude product extracted into ethyl acetate [400+(2×300 mL)]. The combined organic layers were washed with brine (250 mL), dried over Na$_2$SO$_4$, filtered and concentrated in vacuo. Purification by flash column chromatography on the Teledyne ISCO CombiFlash® Rf200 (220 g silica column Puriflash HC, 0-20% MeOH in EtOAc) gave tert-butyl (S)-8-(((S)-1-acetylpyrrolidin-3-yl)oxy)-5-bromo-1-((1,3-dioxoisoindolin-2-yl)methyl)-3,4-dihydroisoquinoline-2 (1H)-carboxylate (7.33 g, 93%). LCMS (Method 2): 1.62 min, 620.2 [M+Na]$^+$.

Step c. To a solution of the above intermediate (7.32 g, 12.23 mmol) in DCM (33 mL) under argon was added TFA (33 mL, 428 mmol) and the resulting solution was stirred at rt for 1 h. The reaction mixture was concentrated in vacuo, dissolved in DCM (100 mL) and stirred rapidly. Saturated NaHCO$_3$ solution (48 mL) was then added portion wise until the aqueous layer was pH 9. The phases were separated and the aqueous layer extracted with DCM (4×100 mL). The combined organics were dried over Na$_2$SO$_4$, filtered and concentrated in vacuo. The residue was dissolved in DCM (300 mL) and washed with water/saturated NaHCO$_3$ solution (10:1, 55 mL) and the aqueous layer (pH 9) was extracted further with DCM (2×100 mL). The combined organics were dried over Na$_2$SO$_4$, filtered and concentrated in vacuo to provide 2-(((S)-8-(((S)-1-acetylpyrrolidin-3-yl)oxy)-5-bromo-1,2,3,4-tetrahydroisoquinolin-1-yl)methyl)isoindoline-1,3-dione (4.94 g, 81%). LCMS (Method 2): 0.97 min, 498.2 [M+H]$^+$ Step d. To a solution of Intermediate 28 (4.15 g, 12.9 mmol) in anhydrous DMF (66 mL) under argon was added HATU (4.9 g, 12.9 mmol; CAS: 148893-10-1) then DIPEA (2.24 mL, 12.9 mmol) and the resulting solution was stirred for 10 min. The solution was then added dropwise by dropping funnel over 10 min to a solution of the above intermediate (4.94 g, 9.91 mmol) in anhydrous DMF (33 mL) under argon and stirred at rt for 48 h then at 40° C. for 48 h. The mixture was partitioned between water/brine solution (400 mL/50 mL) and EtOAc (400 mL). The aqueous layer was extracted with further EtOAc (2×200 mL) and the combined organic extracts washed with saturated NaHCO$_3$ solution (250 mL), brine (100 mL), dried over Na$_2$SO$_4$, filtered and concentrated in vacuo. Purification by flash column chromatography on the Teledyne ISCO CombiFlash® Rf200 (300 g silica column Puriflash HC, 0 to 20% MeOH in EtOAc) gave 2,4-dimethoxybenzyl (1S,2R)-2-((S)-8-(((S)-1-acetylpyrrolidin-3-yl)oxy)-5-bromo-1-((1,3-dioxoisoindolin-2-yl)methyl)-1,2,3,4-tetrahydroisoquinoline-2-carbonyl)cyclohexane-1-carboxylate (4.71 g, 59%). LCMS (Method 2): 1.74 min, 802.3 [M+H]$^+$.

Step e. To a stirred solution of the above intermediate (4.56 g, 5.68 mmol) in anhydrous DCM (100 mL) under argon was added triethylsilane (4.54 mL, 28.4 mmol) then TFA (4.38 mL, 56.8 mmol) and the resulting solution was stirred at rt for 0.5 h. The mixture was poured into pH 5.2 buffer (100 mL) and the crude product was extracted into DCM (250 mL). The combined organics were dried over Na$_2$SO$_4$, filtered and concentrated in vacuo. Purification by preparative HPLC (Method below) gave the title compound (2.09 g, 55%). [Unique MDAP Method: PMIG1-AUV-Quick40-60, 250 mAU threshold for collection. 40-60% gradient of ACN in H2O with 0.1% formic acid buffer, over 12 minutes on an XSelect 5 um PhenylHexyl column. Compound dissolved in formic acid]. LCMS (Method 3):

4.61 min, 652.1 [M+H]⁺. ¹H NMR (400 MHz, DMSO-d₆; rotamers observed, both reported) δ 11.65 (bs, 1H), 7.90-7.77 (m, 4H), 7.53 (m, 1H), 6.92 (d, 1H), 5.94 (m, 1H), 5.17 (m, 0.5H), 5.12 (m, 0.5H), 4.09 (m, 1H), 4.03-3.80 (m, 3.5H), 3.79-3.46 (m, 3.5H), 3.43-3.20 (m, 1H), 2.82 (dt, 1H), 2.69 (m, 1H), 2.57-2.42 (m, 0.5H), 2.41-2.27 (m, 1H), 2.27-2.12 (m, 1.5H), 2.03 (s, 1.5H), 2.01 (s, 1.5H), 1.82 (m, 1H), 1.54 (m, 1H), 1.45 (m, 1H), 1.39-1.20 (m, 2H), 0.94 (m, 1H), 0.75 (m, 1H), 0.13 (m, 1H).

Example 12

(1S,2R)-2-((S)-8-(((S)-1-Acetylpyrrolidin-3-yl)oxy)-5-chloro-1-((1,3-dioxoisoindolin-2-yl)methyl)-1,2,3,4-tetrahydroisoquinoline-2-carbonyl)cyclohexane-1-carboxylic acid

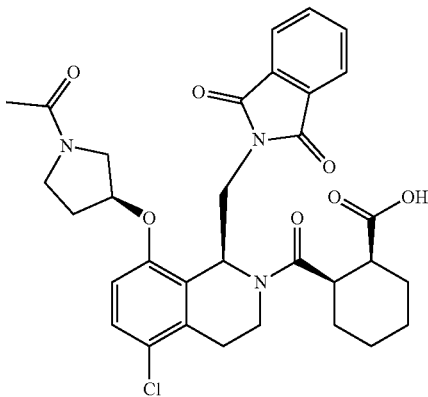 [SMILES: CC(=O)N1CC[C@H](Oc2ccc(Cl)c3c2[C@@H](CN2C(=O)c4ccccc4C2=O)N(C(=O)[C@@H]2CCCC[C@@H]2C(=O)O)CC3)C1]

To a stirred solution of Example 3 (182 mg, 0.32 mmol) in DMF (2 mL) was added N-chlorosuccinimide (45 mg, 0.34 mmol) and the reaction mixture was stirred at rt for 4 days. The reaction mixture was diluted with DCM (20 mL) and washed with water (2×5 mL), brine (5 mL), dried over MgSO₄, filtered and concentrated in vacuo. A portion of the residue (94 mg) was purified by preparative HPLC (Method 1) to give the title compound (46 mg, 24%). LCMS (Method 3): 4.57 min, 608.3 [M+H]⁺. ¹H NMR (400 MHz, DMSO-d₆; rotamers observed, both reported) δ 11.65 (bs, 1H), 7.90-7.77 (m, 4H), 7.37 (m, 1H), 6.97 (m, 1H), 5.94 (m, 1H), 5.17 (m, 0.5H), 5.12 (m, 0.5H), 4.16-4.04 (m, 1H), 4.03-3.50 (m, 7H), 3.42-3.19 (m, 1H), 2.86 (dt, 1H), 2.73 (m, 1H), 2.54-2.09 (m, 3H), 2.03 (s, 1.5H), 2.01 (s, 1.5H), 1.82 (m, 1H), 1.54 (m, 1H), 1.45 (m, 1H), 1.38-1.20 (m, 2H), 0.94 (m, 1H), 0.75 (m, 1H), 0.13 (m, 1H).

Example 13

(1S,2R)-2-((S)-8-(((S)-1-Acetylpyrrolidin-3-yl)oxy)-5,7-dichloro-1-((1,3-dioxoisoindolin-2-yl)methyl)-1,2,3,4-tetrahydroisoquinoline-2-carbonyl)cyclohexane-1-carboxylic acid

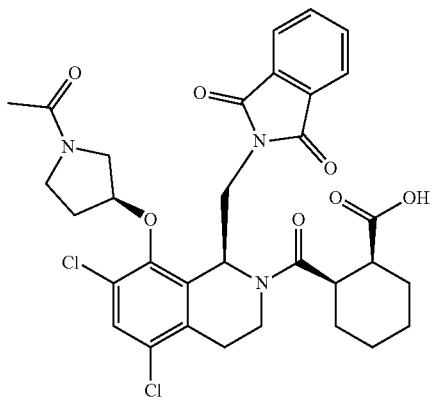 [SMILES: CC(=O)N1CC[C@H](Oc2c(Cl)cc(Cl)c3c2[C@@H](CN2C(=O)c4ccccc4C2=O)N(C(=O)[C@@H]2CCCC[C@@H]2C(=O)O)CC3)C1]

To a stirred solution of Example 3 (40 mg, 0.07 mmol) in DCM (3 mL) and DMF (2 mL) was added N-chlorosuccinimide (19 mg, 0.14 mmol) and the reaction mixture heated at reflux for 24 h. An additional portion of N-chlorosuccinimide (19 mg, 0.14 mmol) was added and the mixture heated at reflux for 8 h. Further N-chlorosuccinimide (19 mg, 0.14 mmol) was added and the mixture heated at reflux for 16 h. The reaction mixture was concentrated in vacuo and purified by preparative HPLC (Method 1) to give the title compound (8 mg, 18%). LCMS (Method 3): 5.21 min, 642.4 [M+H]⁺. ¹H NMR (400 MHz, DMSO-d₆; rotamers observed, both reported) δ 11.60 (bs, 1H), 7.91-7.79 (m, 4H), 7.69 (s, 0.5H), 7.65 (s, 0.5H), 6.11 (m, 1H), 5.24 (m, 0.5H), 4.99 (m, 0.5H), 4.10-3.50 (m, 8H), 3.50-3.12 (m, 1H), 2.91 (m, 1H), 2.75 (m, 1H), 2.60-2.43 (m, 0.5H), 2.37-2.08 (m, 2.5H), 1.94 (s, 3H), 1.88 (m, 1H), 1.57 (m, 1H), 1.46-1.18 (m, 3H), 0.94 (m, 1H), 0.65 (m, 1H), 0.19 (m, 1H).

Example 15

(1S,2R)-2-((S)-1-((1-Oxoisoindolin-2-yl)methyl)-8-(((S)-1-(thiazole-5-carbonyl)pyrrolidin-3-yl)oxy)-1,2,3,4-tetrahroisoquinoline-2-carbonyl)cyclohexane-1-carboxylic acid

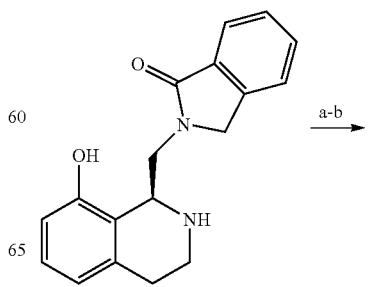

-continued

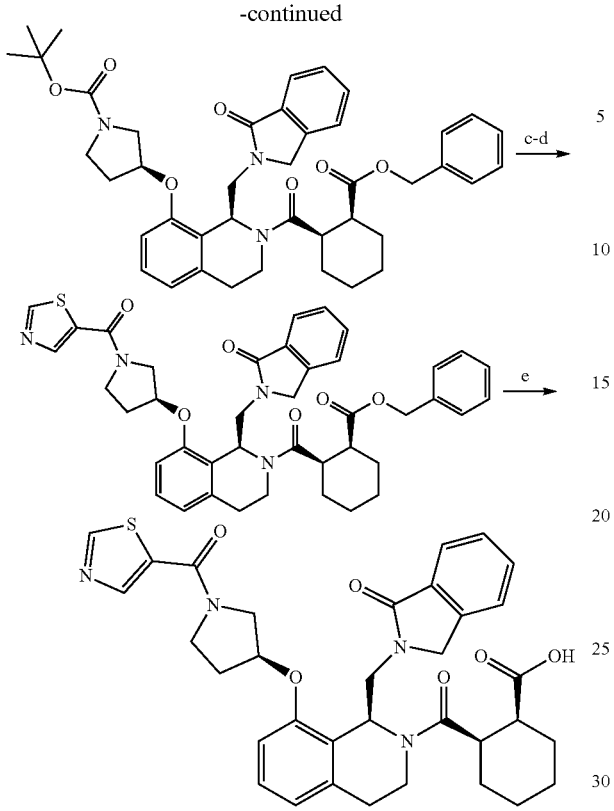

Step a. Benzyl (1S,2R)-2-((S)-8-hydroxy-1-((1-oxoisoindolin-2-yl)methyl)-1,2,3,4-tetrahydroisoquinoline-2-carbonyl)cyclohexane-1-carboxylate (269 mg, 72%) was prepared from Intermediate 14 (173 mg, 0.59 mmol) and Intermediate 26 (250 mg, 0.88 mmol) using a procedure similar to that described for Example 1, step e. The crude product was purified by flash column chromatography (75% EtOAc in heptanes, followed by 10% MeOH in EtOAc). LCMS (Method 5): 2.18 min, 539.1 [M+H]+

Step b. tert-Butyl (S)-3-(((S)-2-((1R,2S)-2-((benzyloxy)carbonyl)-cyclohexane-1-carbonyl)-1-((1-oxoisoindolin-2-yl)methyl)-1,2,3,4-tetrahydroisoquinolin-8-yl)oxy)pyrrolidine-1-carboxylate (344 mg, 99%) was prepared from the above intermediate (265 mg, 0.49 mmol) and tert-butyl (R)-3-hydroxypyrrolidine-1-carboxylate (111 mg, 0.59 mmol, CAS: 103057-44-9) using a procedure similar to that described for Example 3, step a. The crude product was purified by flash column chromatography (20-75% EtOAc in heptanes). LCMS (Method 5): 2.49 min, 708.2 [M+H]+

Step c. A solution of the above intermediate (344 mg, 0.486 mmol) in HCl (4 M in dioxane; 5 mL) was stirred at rt for 3 h. The reaction mixture was concentrated in vacuo to give benzyl (1S,2R)-2-((S)-1-((1-oxoisoindolin-2-yl)methyl)-8-(((S)-pyrrolidin-3-yl)oxy)-1,2,3,4-tetrahydroisoquinoline-2-carbonyl)cyclohexane-1-carboxylate hydrochloride (313 mg, 100%), used without further purification. LCMS (Method 5): 2.19 min, 608.2 [M+H]+

Step d. Benzyl (1S,2R)-2-((S)-1-((1-oxoisoindolin-2-yl)methyl)-8-(((S)-1-(thiazole-5-carbonyl)pyrrolidin-3-yl)oxy)-1,2,3,4-tetrahydroisoquinoline-2-carbonyl)cyclohexane-1-carboxylate (210 mg, 60%) was prepared from the above intermediate (313 mg, 0.48 mmol) and thiazole-5-carboxylic acid (75 mg, 0.58 mmol, CAS: 14527-41-4) using a procedure similar to that described for Example 5, step a. The crude product was purified by flash column chromatography (0-10% MeOH in EtOAc). LCMS (Method 5): 2.13 min, 719.1 [M+H]+.

Step e. The title compound (30 mg, 16%) was prepared from the above intermediate (210 mg, 0.29 mmol) using a procedure similar to that described for Example 2, step e. The crude product was purified by flash column chromatography (0-20% MeOH in EtOAc). LCMS (Method 4a): 1.34 min, 629.4 [M+H]+. $^1$H NMR (400 MHz, DMSO-$d_6$; rotamers observed, both reported) δ 11.61 (bs, 1H), 9.33 (s, 0.5H), 9.23 (s, 0.5H), 8.51 (s, 1H), 7.64-7.34 (m, 4H), 7.22 (m, 1H), 6.95 (m, 1H), 6.82 (m, 1H), 5.93 (m, 1H), 5.23 (d, 0.5H), 5.16 (d, 0.5H), 4.66 (d, 0.5H), 4.57 (d, 0.5H), 4.29 (dd, 0.5H), 4.24-3.99 (m, 3.5H), 3.98-3.82 (m, 2H), 3.82-3.62 (m, 2H), 3.52-3.20 (m, 2H), 2.92-2.72 (m, 2H), 2.43 (m, 1H), 2.31 (m, 1H), 2.17 (m, 1H), 1.83 (m, 1H), 1.60-1.37 (m, 2H), 1.33-1.15 (m, 2H), 0.88 (m, 1H), 0.60 (m, 1H), 0.04 (m, 1H).

Example 16

(1S,2R)-2-((S)-8-([1,2,4]triazolo[4,3-a]pyridin-3-ylmethoxy)-5-bromo-1-((1-oxoisoindolin-2-yl)methyl)-1,2,3,4-tetrahydroisoquinoline-2-carbonyl)cyclohexane-1-carboxylic acid

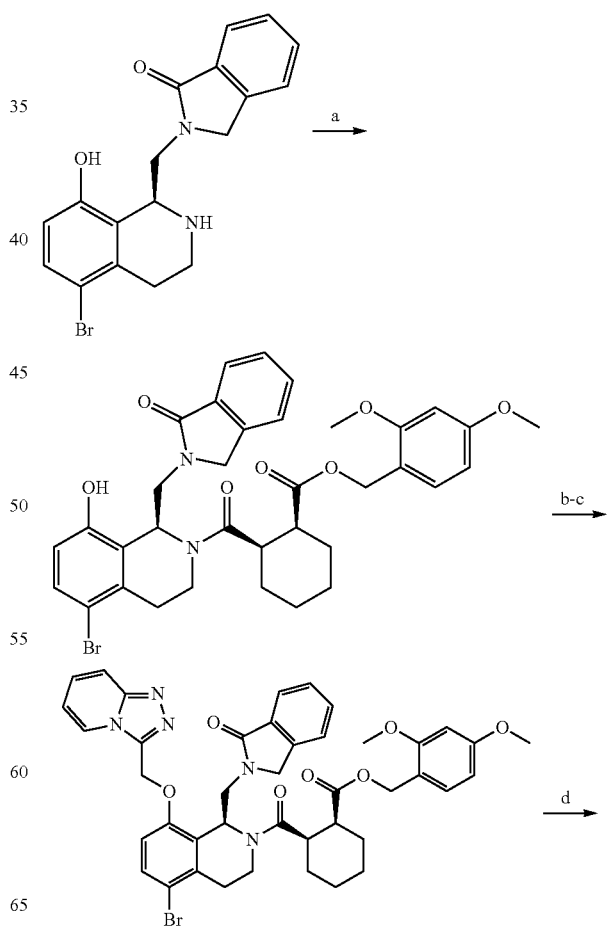

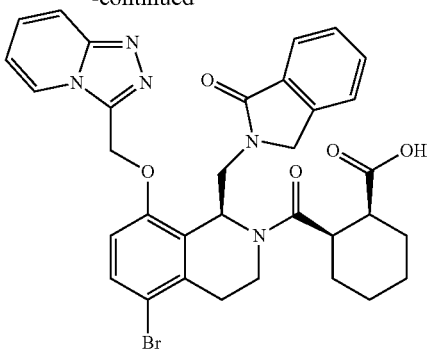

Step a. A mixture of Intermediate 27 (2.51 g, 5.66 mmol in EtOAc (70 mL) and citric acid (10 wt % aqueous; 25 mL, 5.14 mmol) was shaken until all a clear two-phase mixture was obtained. The organic layer was separated, washed with brine (10 mL) dried ($Na_2SO_4$), filtered and concentrated in vacuo. The residue was dissolved in DMF (50 mL), and to this was added Intermediate 16 (1.92 g, 5.14 mmol?, followed by DIPEA (2.64 mL, 15.43 mmol) and HATU (2.15 g, 5.66 mmol; CAS: 148893-10-1). The resulting solution was stirred at rt for 17 h, diluted with water and extracted with EtOAc. The combined organic layers were washed with water, brine (50 mL), dried ($Na_2SO_4$), filtered and concentrated in vacuo. Purification by flash column chromatography on the Teledyne ISCO CombiFlash® Rf+ (100 g silica column Biotage SNAP, 0-100% EtOAc in DCM) gave 2,4-dimethoxybenzyl (1S,2R)-2-((S)-5-bromo-8-hydroxy-1-((1-oxoisoindolin-2-yl)methyl)-1,2,3,4-tetrahydroisoquinoline-2-carbonyl)cyclohexane-1-carboxylate (1.34 g, 1.98 mmol, 38% yield). LCMS (Method 2): 1.64 min, 699.3 [M+Na]⁺.

Step b. To a solution of 1H-pyridin-2-one hydrazone (1.0 g, 9.2 mmol, CAS: 4930-98-7) in ethanol (15 mL) was added 2-chloro-1,1,1-trimethoxy-ethane (2.47 mL, 18.3 mmol, CAS: 74974-54-2) and the reaction was heated at reflux for 4 h. The reaction mixture was cooled, concentrated in vacuo and purified by flash column chromatography on the Biotage Companion™ (Puriflash cartridge 80 g, 0-30% IPA in EtOAc) to give 3-(chloromethyl)-[1,2,4]triazolo[4,3-a]pyridine (128 mg, 8%). LCMS (Method 2): 0.77 min, 168.1 [M+H]⁺.

Step c. To a stirred solution of 2,4-dimethoxybenzyl (1S,2R)-2-((S)-5-bromo-8-hydroxy-1-((1-oxoisoindolin-2-yl)methyl)-1,2,3,4-tetrahydroisoquinoline-2-carbonyl)-cyclohexane-1-carboxylate (80 mg, 0.12 mmol) in DMF (2 mL) at 0° C. was added sodium hydride (5.2 mg, 0.13 mmol; 60% dispersion in mineral oil) and the reaction mixture stirred for 5 min. To this was added 3-(chloromethyl)-[1,2,4]triazolo[4,3-a]pyridine (22 mg, 0.13 mmol) and the reaction stirred at 0° C. for 0.5 h, then at rt for 1 h. Water (10 mL) was added and the mixture concentrated in vacuo to give 2,4-Dimethoxybenzyl (1S,2R)-2-((S)-8-([1,2,4]triazolo[4,3-a]pyridin-3-ylmethoxy)-5-bromo-1-((1-oxoisoindolin-2-yl)methyl)-1,2,3,4-tetrahydroisoquinoline-2-carbonyl)cyclohexane-1-carboxylate (95 mg, assumed quantitative), used without further purification. LCMS (Method 2): 1.56 min, 808.4 [M+H]⁺.

Step d. To a stirred solution of the above intermediate (95 mg, 0.12 mmol) in DCM (2 mL) was added TFA (200 μL, 2.7 mmol) and anisole (13 μL, 0.12 mmol). The crude product was azeotroped in vacuo with toluene and purified by preparative HPLC (Method 1) to give the title compound (35 mg, 44%). LCMS (Method 3): 3.92 min, 658.4 [M+H]⁺. ¹H NMR (400 MHz, DMSO-d₆) δ 11.65 (bs, 1H), 8.81 (dt, 1H), 7.93 (dt, 1H), 7.61 (d, 1H), 7.58-7.49 (m, 3H), 7.42 (t, 1H), 7.37 (d, 1H), 7.26 (d, 1H), 7.15 (td, 1H), 5.94-5.79 (m, 3H), 4.19 (d, 1H), 4.13 (dd, 1H), 3.99 (dd, 1H), 3.70 (m, 1H), 3.54 (d, 1H), 3.40-3.25 (m, 2H), 2.83 (dd, 1H), 2.67 (m, 1H), 2.18 (m, 1H), 1.83 (m, 1H), 1.54 (m, 1H), 1.41 (m, 1H), 1.31-1.17 (m, 2H), 0.89 (m, 1H), 0.60 (m, 1H), 0.06 (m, 1H).

Example 17

(1S,2R)-2-((S)-8-((1-Isopropyl-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid

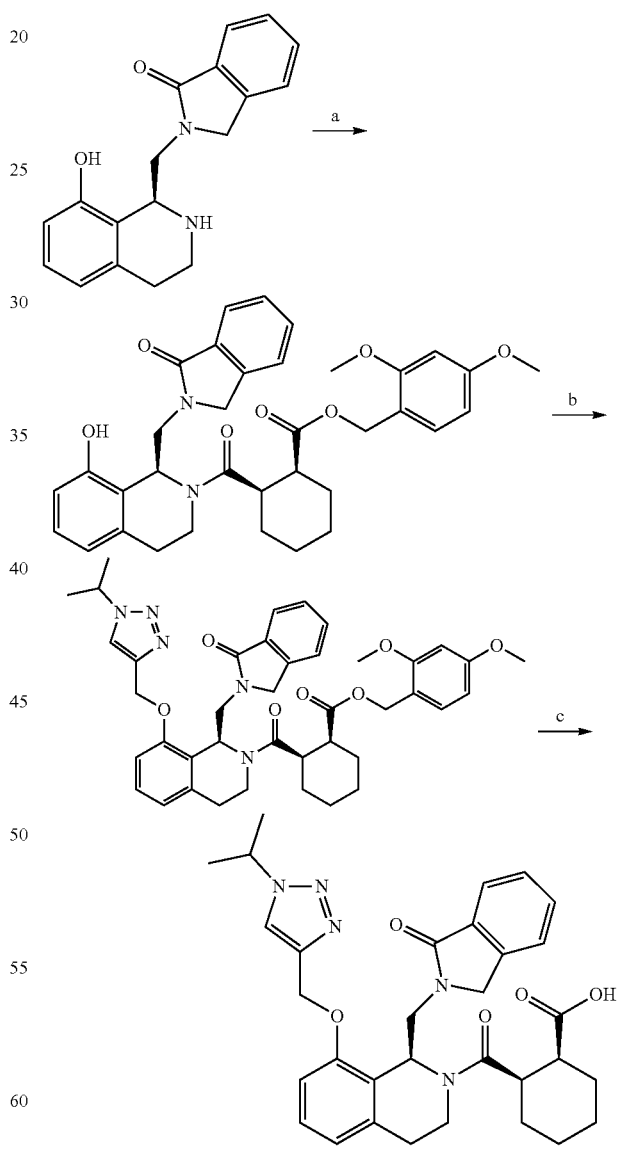

Step a. 2,4-Dimethoxybenzyl (1S,2R)-2-((S)-8-hydroxy-1-((1-oxoisoindolin-2-yl)methyl)-1,2,3,4-tetrahydroisoquinoline-2-carbonyl)cyclohexane-1-carboxylate (331 mg, 94%) was prepared from Intermediate 28 (216 mg, 0.62 mmol) and Intermediate 14 (174 mg, 0.59 mmol) using a procedure similar to that described for Example 11, step d. The crude product was purified by flash column chromatography on the CombiFlash Rf 200™ (25 g silica column, 20-100% EtOAc in cyclohexane, then 0-10% MeOH in DCM). LCMS (Method 2): 1.56 min, 621.4 [M+Na]+.

Step b. 2,4-Dimethoxybenzyl (1S,2R)-2-((S)-8-((1-isopropyl-1H-1,2,3-triazol-4-yl)methoxy)-1-((1-oxoisoindolin-2-yl)methyl)-1,2,3,4-tetrahydroisoquinoline-2-carbonyl)-cyclohexane-1-carboxylate (74 mg, 61%) was prepared from the above intermediate (100 mg, 0.17 mmol) and 4-(bromomethyl)-1-isopropyl-triazole (64 mg, 0.32 mmol, CAS: 1248068-91-8) using a procedure similar to that described for Example 1, step a. The crude product was purified by flash column chromatography on the CombiFlash Rf 200™ (12 g silica column, 0-100% EtOAc in DCM). LCMS (Method 2): 1.63 min, 722.5 [M+H]+

Step c. The title compound (47 mg, 81%) was prepared from the above intermediate (70 mg, 0.10 mmol) using a procedure similar to that described for Example 16, step d. The crude product was purified by flash column chromatography on the CombiFlash Rf 200™ (12 g silica column, 0-10% MeOH in DCM) gave a colourless solid. The residue was dissolved in MeCN—H$_2$O (3:2, 5 mL) and freeze-dried to provide the title compound. LCMS (Method 3): 4.11 min, 572.4 [M+H]+. $^1$H NMR (400 MHz, DMSO-d$_6$) δ 11.63 (bs, 1H), 8.48 (s, 1H), 7.60 (m, 1H), 7.56 (td, 1H), 7.50 (m, 1H), 7.44 (m, 1H), 7.23 (t, 1H), 7.09 (d, 1H), 6.83 (d, 1H), 5.96 (dd, 1H), 5.29-5.17 (m, 2H), 4.91 (m, 1H), 4.56 (d, 1H), 4.16-4.05 (m, 2H), 3.90 (m, 1H), 3.70 (m, 1H), 3.53 (dd, 1H), 3.42-3.21 (m, 1H), 2.93-2.76 (m, 2H), 2.17 (m, 1H), 1.85 (m, 1H), 1.59-1.41 (m, 8H), 1.33-1.18 (m, 2H), 0.89 (m, 1H), 0.61 (m, 1H), 0.07 (m, 1H).

Example 22

(1S,2R)-2-((S)-5-bromo-8-(((S)-1-(5-methylpyridazin-3-yl)pyrrolidin-3-yl)oxy)-1-((1-oxoisoindolin-2-yl)methyl)-1,2,3,4-tetrahydroisoquinoline-2-carbonyl)cyclohexane-1-carboxylic acid

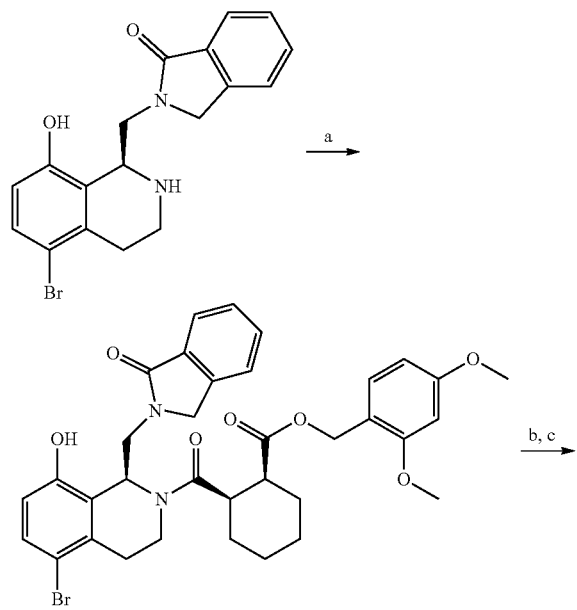

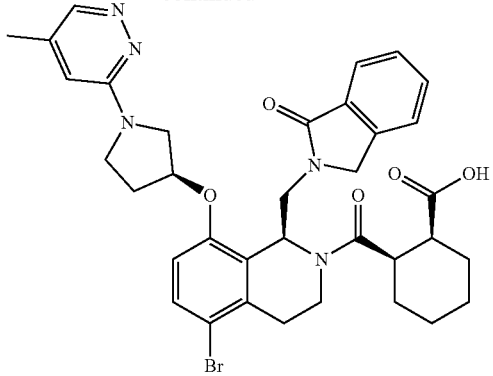

Step a. A mixture of Intermediate 27 (2.51 g, 5.66 mmol) in EtOAc (70 mL) and citric acid (10 wt % aqueous; 25 mL, 5.14 mmol) was shaken until all a clear two-phase mixture was obtained. The organic layer was separated, washed with brine (10 mL) dried (Na$_2$SO$_4$), filtered and concentrated in vacuo. The residue was dissolved in DMF (50 mL), and to this was added Intermediate 16 (1.92 g, 5.14 mmol), followed by DIPEA (2.64 mL, 15.43 mmol) and HATU (2.15 g, 5.66 mmol). The resulting solution was stirred at rt for 17 h, diluted with water and extracted with EtOAc. The combined organic layers were washed with water, brine (50 mL), dried (Na$_2$SO$_4$), filtered and concentrated in vacuo. Purification by flash column chromatography on the Teledyne ISCO CombiFlash® Rf+ (100 g silica column Biotage SNAP, 0-100% EtOAc in DCM) gave the title compound (1.339 g, 38%). LCMS (Method 2): 1.64 min, 699.3 [M+Na]+. Step b. To a stirred solution of the above intermediate (81 mg, 0.12 mmol) and (R)-1-(5-methylpyridazin-3-yl)pyrrolidin-3-yl methanesulfonate (46 mg, 0.18 mmol) in anhydrous DMF (1 mL) under argon was added caesium carbonate (194 mg, 0.59 mmol) and the mixture stirred at rt for 72 h, then at 40° C. for 24 h. Further (R)-1-(5-methylpyridazin-3-yl)pyrrolidin-3-yl methanesulfonate (15 mg, 0.06 mmol) was added and the reaction mixture stirred at 40° C. for 24 h. The mixture was diluted with water (20 mL) and extracted with ethyl acetate (3×20 mL). The combined organics were dried over Na$_2$SO$_4$, filtered and concentrated in vacuo. The crude product was purified by flash column chromatography on the Teledyne ISCO CombiFlash® Rf200 (12 g silica column Puriflash HC, 0-20% MeOH in EtOAc) gave 2,4-dimethoxybenzyl (1S,2R)-2-((S)-5-bromo-8-(((S)-1-(5-methylpyridazin-3-yl)pyrrolidin-3-yl)oxy)-1-((1-oxoisoindolin-2-yl)methyl)-1,2,3,4-tetrahydroisoquinoline-2-carbonyl)cyclohexane-1-carboxylate (68 mg, 68%). LCMS (Method 2): 1.30 min, 838.5/840.2 [M+H]+, 860.4 [M+Na]+.

Step c. To a stirred solution of the above intermediate (66 mg, 0.080 mmol) in anhydrous DCM (2 mL) under argon was added triethylsilane (0.06 mL, 0.390 mmol) then TFA (0.06 mL, 0.780 mmol) and the resulting solution was stirred at rt for 30 min. The mixture was diluted with pH 5.2 buffer (5 mL) and the crude product was extracted into DCM (3×10 mL). The combined organics were dried over Na$_2$SO$_4$, filtered and concentrated in vacuo. Purification by MDAP (Method 1) gave the title compound (32 mg, 59%). LCMS (Method 3): 3.50 min, 688.0 [M+H]+. $^1$H NMR (400 MHz, DMSO-d$_6$) δ 8.42 (d, 1H), 7.59-7.51 (m, 3H), 7.41 (t, 1H), 7.24 (d, 1H), 7.01 (d, 1H), 6.86 (m, 1H), 5.89 (dd, 1H), 5.28 (bm, 1H), 4.38 (d, 1H), 4.16 (dd, 1H), 4.04-3.90 (m, 2H), 3.82 (dd, 1H), 3.78-3.60 (m, 4H), 3.57-3.10 (m, 2H), 2.83

(dd, 1H), 2.72-2.57 (m, 1H), 2.46-2.31 (m, 2H), 2.21 (s, 3H), 2.18 (m, 1H), 1.79 (m, 1H), 1.58-1.40 (m, 2H), 1.32-1.13 (m, 2H), 0.88 (m, 1H), 0.63 (m, 1H), 0.05 (m, 1H).

Example 29

(1S,2R)-2-((S)-5-Bromo-8-((1-methyl-1H-1,2,4-triazol-5-yl)methoxy)-1-((1-oxoisoindolin-2-yl)methyl)-1,2,3,4-tetrahydroisoquinoline-2-carbonyl)cyclohexane-1-carboxylic acid

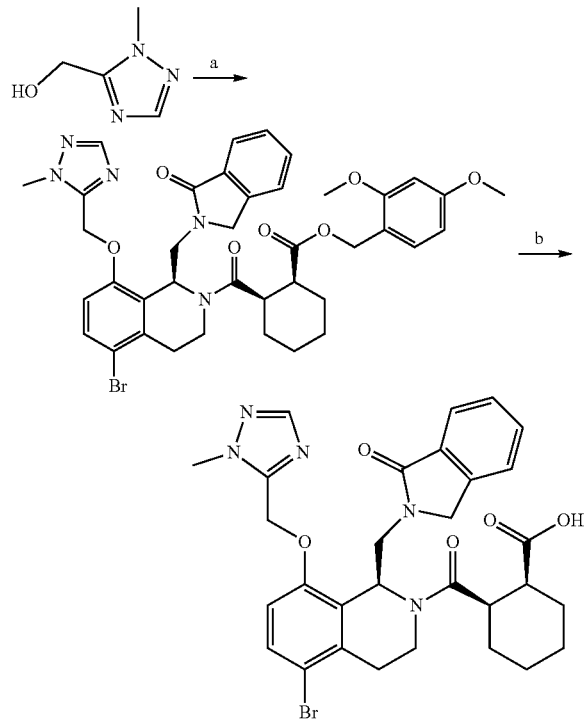

Step a. To a stirred solution of (1-methyl-1H-1,2,4-triazol-5-yl)methanol (16 mg, 0.14 mmol, CAS: 91616-36-3) in anhydrous DMF (1 mL) at 0° C. under argon was added triethylamine (0.02 mL, 0.14 mmol) and methanesulfonic anhydride (0.01 mL, 0.14 mmol) and the reaction mixture stirred at 0° C. for 0.5 h. This solution was added dropwise to a stirred solution of 2,4-dimethoxybenzyl (1S,2R)-2-((S)-5-bromo-8-hydroxy-1-((1-oxoisoindolin-2-yl)methyl)-1,2,3,4-tetrahydroisoquinoline-2-carbonyl)cyclohexane-1-carboxylate (80 mg, 0.12 mmol) and caesium carbonate (96 mg, 0.29 mmol) in anhydrous DMF (1 mL) at 0° C. under argon, and the reaction mixture stirred for 0.5 h, then at rt for 18 h. To an additional portion of (1-methyl-1H-1,2,4-triazol-5-yl)methanol (16 mg, 0.14 mmol) in anhydrous DMF (1 mL) at 0° C. under argon was added triethylamine (0.02 mL, 0.14 mmol) and methanesulfonyl chloride (0.01 mL, 0.12 mmol) and the mixture stirred for 0.5 h at 0° C. This was added to the bulk reaction mixture and the mixture stirred at rt for an additional 18 h. The mixture was concentrated in vacuo, diluted with water (10 mL) and extracted with DCM (30 mL). The organics were washed with water (5 mL), brine (5 mL), dried over Na$_2$SO$_4$, filtered and concentrated in vacuo to give 2,4-dimethoxybenzyl (1S,2R)-2-((S)-5-bromo-8-((1-methyl-1H-1,2,4-triazol-5-yl)methoxy)-1-((1-oxoisoindolin-2-yl)methyl)-1,2,3,4-tetrahydroisoquinoline-2-carbonyl)cyclohexane-1-carboxylate (88 mg, 96%). LCMS (Method 2): 1.59 min, 772.4 [M+H]$^+$.

Step b. The title compound was synthesised from the above intermediate using a procedure similar to that described for Example 22, step d. LCMS (Method 3): 4.01 min, 622.2 [M+H]$^+$. $^1$H NMR (400 MHz, DMSO-d$_6$) δ 11.65 (bs, 1H), 8.03 (s, 1H), 7.64-7.53 (m, 4H), 7.44 (m, 1H), 7.12 (d, 1H), 6.01 (dd, 1H), 5.50-5.40 (m, 2H), 4.54 (d, 1H), 4.23-4.12 (m, 2H), 4.06-3.93 (m, 4H), 3.75 (m, 1H), 3.52 (dd, 1H), 3.44-3.22 (m, 1H), 2.85 (dd, 1H), 2.75-2.61 (m, 1H), 2.20 (m, 1H), 1.86 (m, 1H), 1.55 (m, 1H), 1.42 (m, 1H), 1.33-1.19 (m, 2H), 0.90 (m, 1H), 0.59 (m, 1H), 0.09 (m, 1H).

Example 45

(1S,2R)-2-((1S)-5-bromo-8-(1-(1-methyl-1H-1,2,3-triazol-4-yl)ethoxy)-1-((1-oxoisoindolin-2-yl)methyl)-1,2,3,4-tetrahydroisoquinoline-2-carbonyl)cyclohexane-1-carboxylic acid

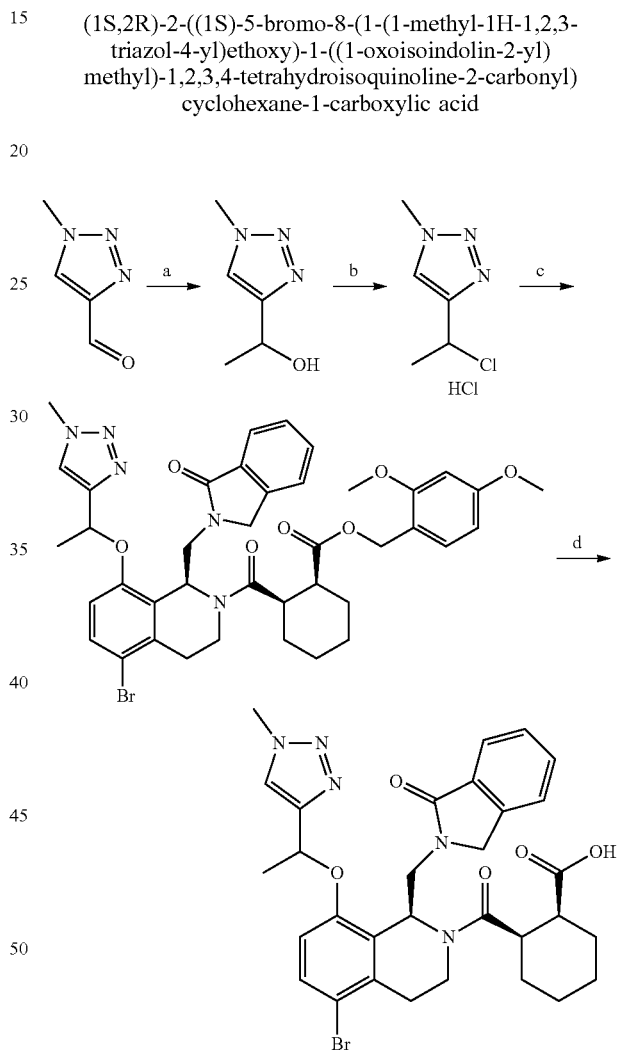

Step a. To a stirred solution of 1-methyltriazole-4-carbaldehyde (1.0 g, 9 mmol, CAS: 16681-69-9) and in THF (20 mL) at 0° C. was added bromo(methyl)magnesium (1.4 M toluene/THF 3:1; 7.72 mL, 10.8 mmol) dropwise over 5 min. The reaction mixture was stirred at 0 oC for 0.5 h, allowed to warm to rt and stirred at rt for 1.5 h. The reaction mixture was diluted with saturated aqueous NH$_4$Cl solution (15 mL) and extracted with EtOAc (2×50 mL). The combined organics were dried over MgSO$_4$, filtered and concentrated in vacuo. Purification by flash column chromatography on the Biotage Companion™ (Puriflash cartridge 40 g, 0-10% MeOH in EtOAc) gave 1-(1-methyltriazol-4-yl)

ethanol (467 mg, 41%). ¹H NMR (400 MHz, CDCl₃) δ 7.46 (s, 1H), 5.12-5.06 (m, 1H), 4.09 (s, 3H), 2.63 (d, 1H), 1.59 (d, 3H).

Step b. To a stirred solution of the above intermediate (140 mg, 1.1 mmol) in chloroform (2 mL) at rt was added thionyl chloride (0.16 mL, 2.2 mmol) and the reaction stirred at rt for 3 h. The reaction mixture was concentrated in vacuo and the residue was triturated with diethyl ether (3 mL). The resulting solid was collected by filtration and dried in vacuo to give 4-(1-chloroethyl)-1-methyl-triazole hydrochloride (142 mg, 71%). ¹H NMR (400 MHz, DMSO-d₆) δ 8.17 (s, 1H), 5.45 (q, 1H), 4.03 (s, 3H), 1.83 (d, 3H).

Steps c-d. The title compound was prepared using a procedure similar to those described for Example 22, steps c,d. LCMS (Method 3): 4.18 min, 636.4 [M+H]⁺. ¹H NMR (400 MHz, DMSO-d₆) δ 11.73 (bs, 1H), 8.25 (s, 1H), 7.67-7.60 (m, 2H), 7.58 (m, 1H), 7.49-7.41 (m, 2H), 6.99 (d, 1H), 6.05 (dd, 1H), 5.76 (m, 1H), 4.72 (d, 1H), 4.37 (d, 1H), 4.11 (dd, 1H), 4.04-3.94 (m, 4H), 3.71 (m, 1H), 3.57 (dd, 1H), 3.51-3.11 (m, 1H), 2.79 (dd, 1H), 2.73-2.58 (m, 1H), 2.18 (m, 1H), 1.87 (m, 1H), 1.79 (d, 3H), 1.56 (m, 1H), 1.45 (m, 1H), 1.34-1.19 (m, 2H), 0.90 (m, 1H), 0.62 (m, 1H), 0.10 (m, 1H).

Example 49

(1S,2R)-2-((S)-5-chloro-8-((5-methylisoxazol-3-yl)methoxy)-1-((1-oxoisoindolin-2-yl)methyl)-1,2,3,4-tetrahydroisoquinoline-2-carbonyl)cyclohexane-1-carboxylic acid

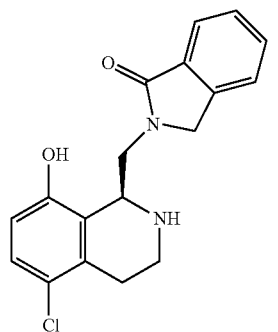

+

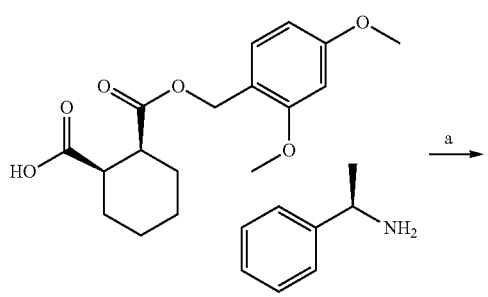

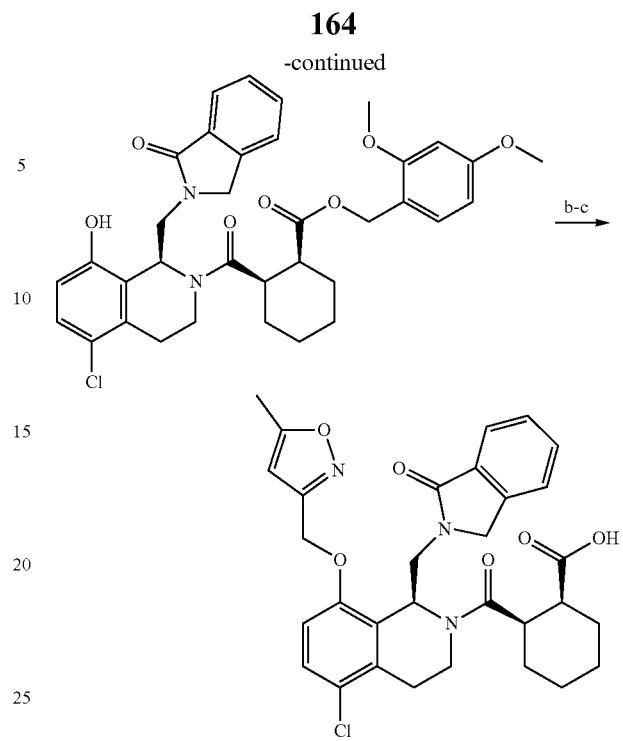

Step a. 2,4-Dimethoxybenzyl (1S,2R)-2-((S)-5-chloro-8-hydroxy-1-((1-oxoisoindolin-2-yl)methyl)-1,2,3,4-tetrahydroisoquinoline-2-carbonyl)cyclohexane-1-carboxylate (1.4 g, 50%) was prepared from Intermediate 27 (2.11 g, 4.76 mmol) and Intermediate 18 (1.49 g, 4.53 mmol) using a procedure similar to that described for Example 16, step a. LCMS (Method 2): 1.70 min, 655.4 [M+Na]⁺

Steps b-c. The title compound (23 mg, 31%) was prepared from the above intermediate (80 mg, 0.126 mmol) and 3-(chloromethyl)-5-methyl-isoxazole (25 mg, 0.19 mmol, CAS: 35166-37-1) using procedures similar to that described for Example 22, steps c and d. LCMS (Method 3): 4.62 min, 578.1 [M+H]⁺. ¹H NMR (400 MHz, DMSO-d₆) δ 11.66 (bs, 1H), 7.64-7.53 (m, 3H), 7.45 (m, 1H), 7.40 (d, 1H), 7.09 (d, 1H), 6.54 (m, 1H), 6.02 (dd, 1H), 5.31 (d, 1H), 5.23 (d, 1H), 4.62 (d, 1H), 4.27 (d, 1H), 4.19 (dd, 1H), 4.01 (dd, 1H), 3.76 (m, 1H), 3.54 (dd, 1H), 3.36-3.26 (m, 3H), 2.89 (dd, 1H), 2.69 (m, 1H), 2.52-2.47 (m, 1H), 2.20 (m, 1H), 1.87 (m, 1H), 1.56 (m, 1H), 1.42 (m, 1H), 1.33-1.18 (m, 2H), 0.90 (m, 1H), 0.58 (m, 1H), 0.08 (m, 1H).

Example 56

(1S,2R)-2-((S)-5-Chloro-8-((5-(difluoromethyl)-1-methyl-1H-imidazol-4-yl)methoxy)-1-((1-oxoisoindolin-2-yl)methyl)-1,2,3,4-tetrahydroisoquinoline-2-carbonyl)cyclohexane-1-carboxylic acid

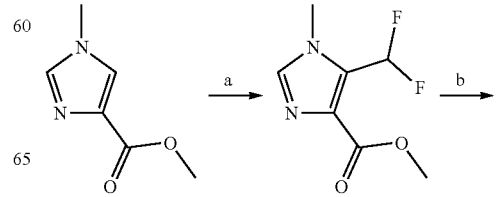

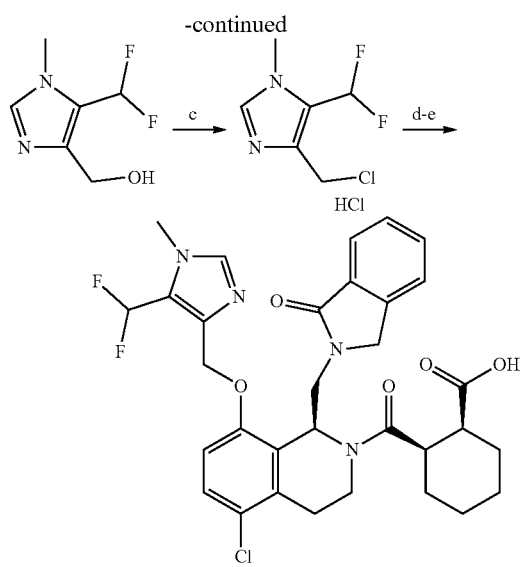

Step a. To a rapidly stirred solution of methyl 1-methyl-imidazole-4-carboxylate (500 mg, 3.57 mmol, CAS: 17289-19-9) and zinc difluoromethanesulfinate (1475 mg, 4.99 mmol) in DMSO (65 mL) was added tert-butyl hydroperoxide (70% in water; 1.62 mL, 11.8 mmol) in one portion and the resulting solution was stirred at rt for 21 h. A further portion of zinc difluoromethanesulfinate (1476 mg, 4.99 mmol) was added, followed by tert-butyl hydroperoxide (70% in water; 1.62 mL, 11.8 mmol) and the mixture was stirred at rt for a further 72 h. The mixture was carefully poured into saturated $NaHCO_3$-EDTA solution (200 mL) and the crude product extracted into EtOAc (3×300 mL). The combined organics were washed with water (2×200 mL), brine (200 mL), dried over $Na_2SO_4$, filtered and concentrated in vacuo. Purification by flash column chromatography on the Teledyne ISCO CombiFlash® Rf200 (25 g silica column Puriflash HC, 0-10% MeOH in EtOAc) gave methyl 5-(difluoromethyl)-1-methyl-1H-imidazole-4-carboxylate (137 mg, 20%). $^1$H NMR (400 MHz, $CDCl_3$) δ 7.57 (t, 1H), 7.50 (s, 1H), 3.94 (s, 3H), 3.87 (s, 3H).

Step b. To a stirred solution of the above intermediate (130 mg, 0.68 mmol) in EtOH (2 mL) and THF (1 mL) under argon was added lithium chloride (64 mg, 1.5 mmol) and $NaBH_4$ (57 mg, 1.5 mmol) and the resulting mixture was stirred at rt for 18 h. The mixture was diluted with 10% aqueous citric acid (5 mL) and extracted with DCM (3×10 mL). The aqueous layer was adjusted to pH 8 by the addition of saturated $NaHCO_3$ solution (5 mL) and extracted further with DCM (9×10 mL). The combined organics were dried over $Na_2SO_4$, filtered and concentrated in vacuo to give (5-(difluoromethyl)-1-methyl-1H-imidazol-4-yl)methanol (96.6 mg, 87%), used without further purification. $^1$H NMR (400 MHz, $CDCl_3$) δ 7.44 (s, 1H), 6.96 (t, 1H), 4.69 (t, 2H), 3.78 (s, 3H), 2.59 (br s, 1H).

Step c. To a stirred mixture of the above intermediate (96.4 mg, 0.59 mmol) in chloroform (2 mL) under argon was added thionyl chloride (0.08 mL, 1.05 mmol) dropwise and the resulting solution was stirred at rt for 1.5 h. The reaction mixture was concentrated in vacuo to give 4-(chloromethyl)-5-(difluoromethyl)-1-methyl-1H-imidazole hydrochloride (135 mg, assumed quantitative), used without further purification. $^1$H NMR (400 MHz, $CDCl_3$) δ 8.13 (s, 1H), 7.42 (t, 1H), 4.81 (s, 2H), 3.76 (s, 3H).

Steps d-e. The title compound (47 mg, 71%) was prepared from 2,4-dimethoxybenzyl (1S,2R)-2-((S)-5-chloro-8-hydroxy-1-((1-oxoisoindolin-2-yl)methyl)-1,2,3,4-tetrahydroisoquinoline-2-carbonyl)cyclohexane-1-carboxylate (Example 45 step a; 80 mg, 0.13 mmol) and the above intermediate (41 mg, 0.19 mmol) using procedures similar to that described for Example 22, steps c and d. LCMS (Method 3): 4.15 min, 627.0 [M+H]$^+$. $^1$H NMR (400 MHz, DMSO-$d_6$) δ 11.66 (bs, 1H), 7.91 (s, 1H), 7.63-7.52 (m, 3H), 7.47 (t, 1H), 7.44 (m, 1H), 7.38 (d, 1H), 7.17 (d, 1H), 5.92 (dd, 1H), 5.20 (d, 1H), 5.14 (d, 1H), 4.50 (d, 1H), 4.14 (dd, 1H), 4.06-3.94 (m, 2H), 3.79 (s, 3H), 3.71 (m, 1H), 3.51 (dd, 1H), 3.44-3.18 (m, 1H), 2.87 (dd, 1H), 2.67 (m, 1H), 2.19 (m, 1H), 1.84 (m, 1H), 1.55 (m, 1H), 1.42 (m, 1H), 1.32-1.18 (m, 2H), 0.89 (m, 1H), 0.61 (m, 1H), 0.09 (m, 1H).

Example 58

(1S,2R)-2-((S)-5-fluoro-8-((1-isopropyl-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid

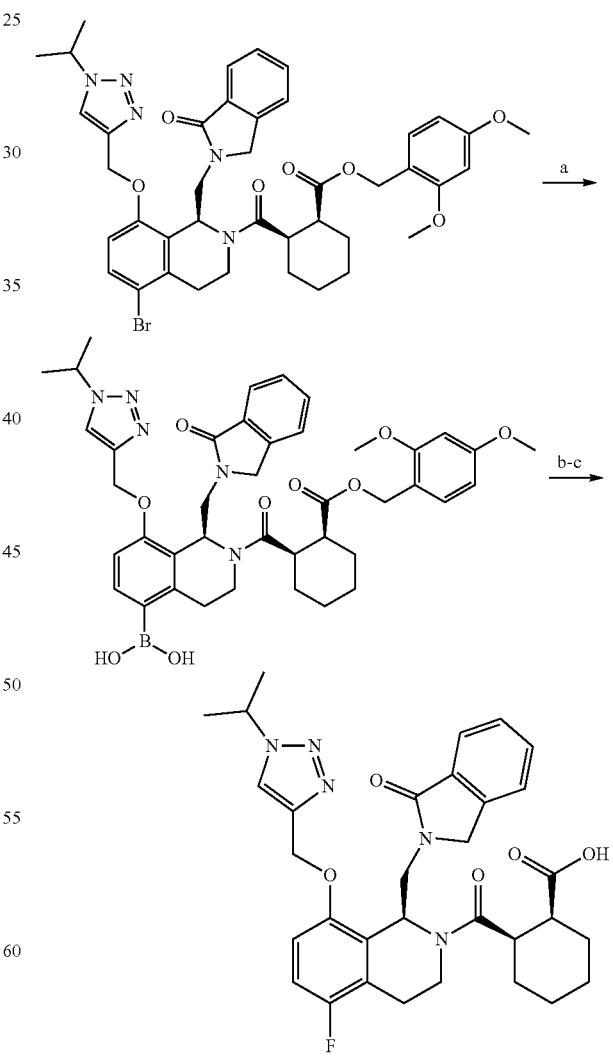

Step a. A microwave tube was charged with 2,4-dimethoxybenzyl (1S,2R)-2-((S)-5-bromo-8-((1-isopropyl-1H-1, 2,3-triazol-4-yl)methoxy)-1-((1-oxoisoindolin-2-yl)
methyl)-1,2,3,4-tetrahydroisoquinoline-2-carbonyl)
cyclohexane-1-carboxylate (From Example 35; 200 mg,
0.25 mmol), potassium acetate (0.05 mL, 0.75 mmol),
dicyclohexyl-[2-(2,4,6-triisopropylphenyl)-phenyl]phosphane (5 mg, 0.010 mmol), X-Phos Pd G2 (4 mg, 0.005 mmol) and hypoboric acid (67 mg, 0.750 mmol). The tube was sealed and EtOH (2.5 mL) added. The reaction mixture was degassed with argon for 10 min, heated at 60° C. for 4 h, cooled to rt and concentrated in vacuo. The residue was dissolved in EtOAc (5 mL) and filtered through a plug of Celite®. The filtrate was washed with water (10 mL) and the aqueous phase extracted with EtOAc (3×10 mL). The combined organics were washed with water, brine, dried over $Na_2SO_4$, filtered and concentrated in vacuo to provide a 1:1 mixture of ((S)-2-((1R,2S)-2-(((2,4-dimethoxybenzyl)oxy)carbonyl)-cyclohexane-1-carbonyl)-8-((1-isopropyl-1H-1,2,3-triazol-4-yl)methoxy)-1-((1-oxoisoindolin-2-yl)methyl)-1,2,3,4-tetrahydroisoquinolin-5-yl)boronic acid and 2,4-dimethoxybenzyl (1S,2R)-2-((S)-8-((1-isopropyl-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylate (170 mg), used in the next step without further purification. LCMS (Method 2) 1.45 min, 766.5 $[M+H]^+$.

Step b. A mixture of the above intermediate (85 mg, 0.06 mmol) and sodium hydroxide (2.2 mg, 0.06 mmol) in MeOH (1 mL) was stirred at rt for 15 min then cooled to 0° C. and silver trifluoromethanesulfonate (43 mg, 0.17 mmol) was added in a single portion. The mixture was stirred for at 0° C. for 30 min, then acetone (2 mL) was added and the reaction mixture concentrated in vacuo at 0° C. The residue was azeotroped in vacuo at 0° C. with acetone (2×1 mL). The residue was dissolved in acetone (0.5 mL) and powdered 3 Å molecular sieves (50 mg) were added followed by SelectFluor® (20.65 mg, 0.06 mmol). The mixture was stirred at rt for 3 h then diluted with water and extracted into DCM. The combined organics were washed with water, brine, dried over $Na_2SO_4$, filtered and concentrated in vacuo to provide a mixture of 2,4-dimethoxybenzyl (1S,2R)-2-((S)-5-fluoro-8-((1-isopropyl-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylate and 2,4-dimethoxybenzyl (1S,2R)-2-((S)-8-((1-isopropyl-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylate (67 mg), used in the next step without further purification. LCMS (Method 2): 1.62 min, 740.5 $[M+H]^+$.

Step c. The title compound (10 mg, 37%) was prepared from the above crude reaction mixture (1:1 mixture with dehalogenated material) (67 mg, 0.045 mmol) using the method described for Example 22, step d. The crude product was purified by preparative HPLC (Method 1). LCMS (Method 3), 4.18 min, 590.2 $[M+H]^+$. $^1H$ NMR (400 MHz, DMSO-$d_6$) δ 11.69 (bs, 1H), 8.48 (s, 1H), 7.61 (m, 1H), 7.56 (td, 1H), 7.50 (m, 1H), 7.44 (m, 1H), 7.17-7.07 (m, 2H), 5.96 (dd, 1H), 5.28-5.18 (m, 2H), 4.91 (m, 1H), 4.54 (d, 1H), 4.20-4.05 (m, 2H), 3.98 (dd, 1H), 3.69 (m, 1H), 3.53 (dd, 1H), 3.48-3.15 (m, 1H), 2.84 (m, 1H), 2.69 (m, 1H), 2.17 (m, 1H), 1.85 (m, 1H), 1.65-1.48 (m, 7H), 1.43 (m, 1H), 1.34-1.17 (m, 2H), 0.89 (m, 1H), 0.60 (m, 1H), 0.09 (m, 1H).

Example 59

(1S,2R)-2-((S)-8-((1-isopropyl-1H-1,2,3-triazol-4-yl)methoxy)-5-methyl-1-((1-oxoisoindolin-2-yl)methyl)-1,2,3,4-tetrahydroisoquinoline-2-carbonyl)cyclohexane-1-carboxylic acid

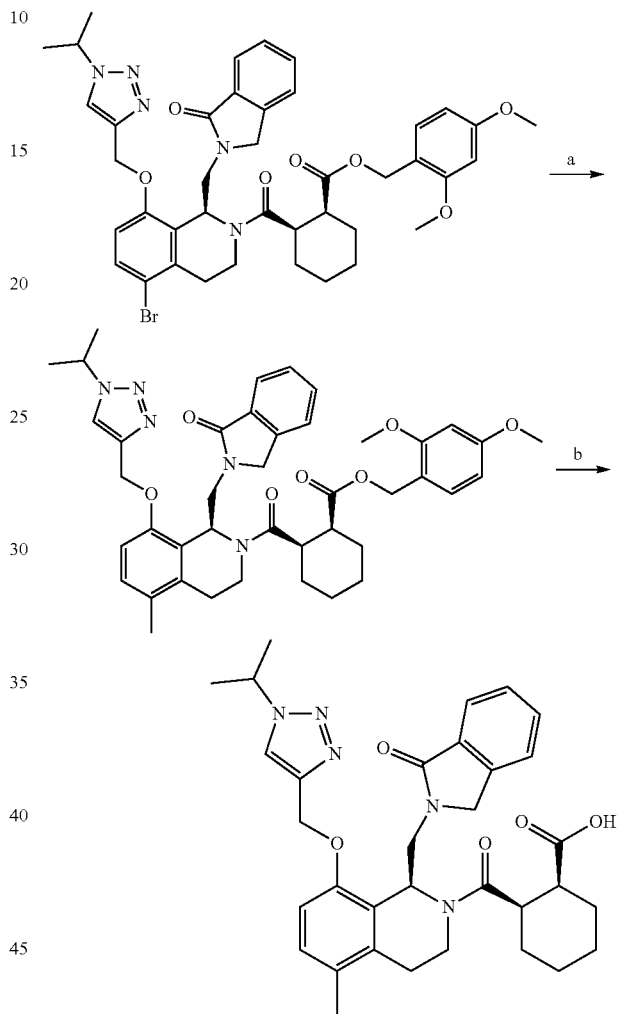

Step a. A microwave vial was charged with 2,4-dimethoxybenzyl (1S,2R)-2-((S)-5-bromo-8-((1-isopropyl-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylate (From Example 35; 80 mg, 0.1 mmol), trimethylboroxine (0.02 mL, 0.15 mmol), caesium carbonate (65.1 mg, 0.2 mmol), $Pd(dppf)Cl_2 \cdot DCM$ (4.1 mg, 0.005 mmol) and flushed with argon. The tube was sealed and 1,4-dioxane (0.7 mL) and water (0.1 mL) were added. The mixture was heated at 80° C. for 18 h then was cooled to rt diluted with water and extracted into EtOAc. The combined organics were washed with water, brine, dried over $Na_2SO_4$, filtered and concentrated in vacuo to give 2,4-dimethoxybenzyl (1S,2R)-2-((S)-8-((1-isopropyl-1H-1,2,3-triazol-4-yl)methoxy)-5-methyl-1-((1-oxoisoindolin-2-yl)methyl)-1,2,3,4-tetrahydroisoquinoline-2-carbonyl)cyclohexane-1-carboxylate (67 mg, 91%) used without further purification. LCMS (Method 2): 1.67 min, 736.5 $[M+H]^+$.

Step b. The title compound (15 mg, 26%) was prepared from the above intermediate (67 mg, 0.091 mmol) using the method described for Example 22, step d. The crude product was purified by preparative HPLC (Method 1). LCMS (Method 3): 4.24 min, 586.5 [M+H]$^+$. $^1$H NMR (400 MHz, DMSO-d$_6$) δ 11.59 (bs, 1H), 8.47 (s, 1H), 7.60 (m, 1H), 7.55 (td, 1H), 7.49 (m, 1H), 7.44 (m, 1H), 7.10 (d, 1H), 7.00 (d, 1H), 5.95 (dd, 1H), 5.25-5.13 (m, 2H), 4.90 (m, 1H), 4.55 (d, 1H), 4.13 (dd, 1H), 4.07 (d, 1H), 3.97 (dd, 1H), 3.71 (m, 1H), 3.51 (dd, 1H), 3.46-3.23 (m, 1H), 2.78-2.56 (m, 2H), 2.21-2.10 (m, 4H), 1.84 (m, 1H), 1.59-1.50 (m, 7H), 1.45 (m, 1H), 1.32-1.17 (m, 2H), 0.88 (m, 1H), 0.60 (m, 1H), 0.08 (m, 1H).

Example 60

(1S,2R)-2-((S)-5-cyano-8-((1-isopropyl-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid

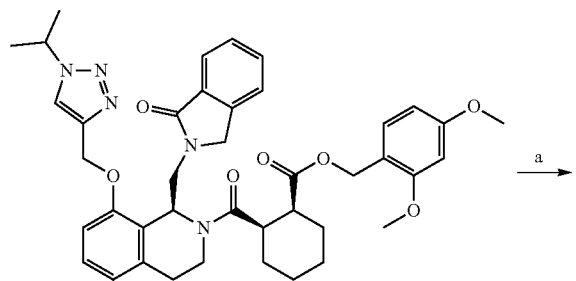

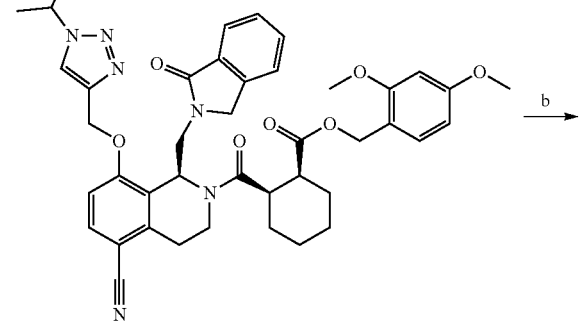

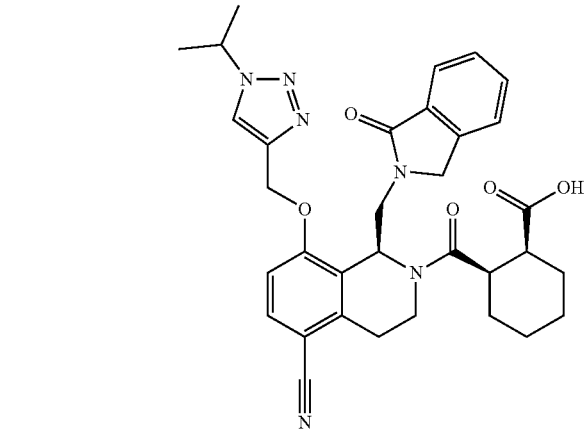

Step a. A microwave vial was charged with 2,4-dimethoxybenzyl (1S,2R)-2-((S)-5-bromo-8-((1-isopropyl-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylate (From Example 35; 80 mg, 0.1 mmol), palladium-tetrakis(triphenylphosphine) (23 mg, 0.02 mmol) and zinc cyanide (0.02 mL, 0.3 mmol) and flushed with argon. DMF (0.75 mL) was added, the tube sealed and the mixture heated at 100° C. for 18 h. The mixture was cooled to rt and concentrated in vacuo. The residue was diluted with water and extracted into EtOAc. The combined organics were washed with water, brine, dried over Na$_2$SO$_4$, filtered and concentrated in vacuo. Purification by flash column chromatography on the Companion™ (4 g silica column, 0-100% DCM in EtOAc) gave 2,4-dimethoxybenzyl (1S,2R)-2-((S)-5-cyano-8-((1-isopropyl-1H-1,2,3-triazol-4-yl)methoxy)-1-((1-oxoiso-indolin-2-yl)methyl)-1,2,3,4-tetrahydroisoquinoline-2-carbonyl)cyclohexane-1-carboxylate (35 mg, 46%). LCMS (Method 2): 1.59 min, 747.5 [M+H]$^+$.

Step b. The title compound (12 mg, 97%) was prepared from the above intermediate (35 mg, 0.05 mmol) using the method described for Example 22, step d. The crude product was purified by preparative HPLC (Method 1). LCMS (Method 3): 4.02 min, 597.2 [M+H]$^+$. $^1$H NMR (400 MHz, DMSO-d$_6$) δ 11.66 (bs, 1H), 8.52 (s, 1H), 7.82 (d, 1H), 7.66-7.53 (m, 2H), 7.50 (m, 1H), 7.44 (m, 1H), 7.32 (d, 1H), 5.94 (dd, 1H), 5.45-5.29 (m, 2H), 4.91 (m, 1H), 4.50 (d, 1H), 4.16 (dd, 1H), 4.11-3.98 (m, 2H), 3.77 (m, 1H), 3.50 (dd, 1H), 3.39-3.27 (m, 1H), 3.06-2.81 (m, 2H), 2.20 (m, 1H), 1.84 (m, 1H), 1.62-1.48 (m, 7H), 1.43 (m, 1H), 1.33-1.16 (m, 2H), 0.90 (m, 1H), 0.62 (m, 1H), 0.09 (m, 1H).

Example 61 and 62

(1S,2R)-2-((S)-8-((1-isopropyl-1H-1,2,3-triazol-4-yl)methoxy)-5-methoxy-1-((1-oxoisoindolin-2-yl)methyl)-1,2,3,4-tetrahydroisoquinoline-2-carbonyl)cyclohexane-1-carboxylic acid (61) and (1S,2R)-2-((S)-8-((1-isopropyl-1H-1,2,3-triazol-4-yl)methoxy)-1-((1-oxoisoindolin-2-yl)methyl)-5-(trifluoromethyl)-1,2,3,4-tetrahydroisoquinoline-2-carbonyl)cyclohexane-1-carboxylic acid (62)

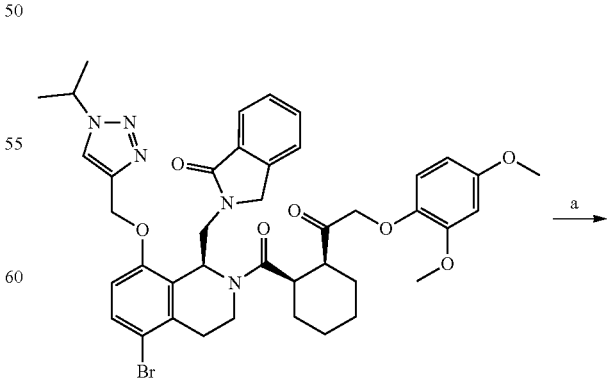

-continued

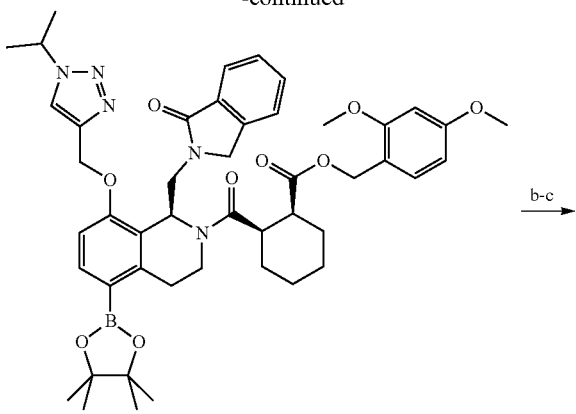

↓ b-c

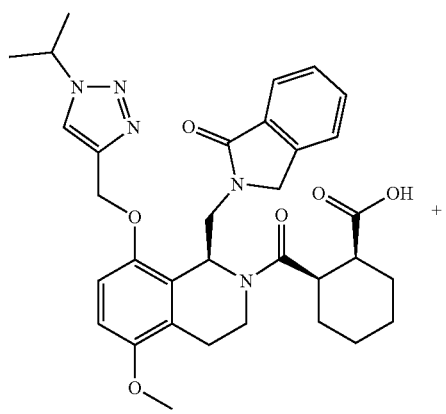

+

Step a. A microwave tube was charged with 2,4-dimethoxybenzyl (1S,2R)-2-((S)-5-bromo-8-((1-isopropyl-1H-1,2,3-triazol-4-yl)methoxy)-1-((1-oxoisoindolin-2-yl)methyl)-1,2,3,4-tetrahydroisoquinoline-2-carbonyl)

cyclohexane-1-carboxylate (From Example 35; 400 mg, 0.5 mmol), potassium acetate (147 mg, 1.5 mmol), bis(pinacolato)diboron (165 mg, 0.65 mmol) and Pd(dppf)Cl₂) (21 mg, 0.02 mmol) and the tube was sealed, evacuated then back-filled with argon. Anhydrous 1,4-dioxane (4 mL) was added and the mixture heated at 80° C. for 14 h. The mixture was cooled to rt, then an additional portion of bis(pinacolato)diboron (127 mg, 0.5 mmol) and Pd(dppf)Cl₂ (21 mg, 0.02 mmol) were added under nitrogen. The flask was resealed and heated for a further 8 h at 100° C. before cooling to rt. The reaction mixture was filtered through a pad of Celite® washing with DCM (50 mL). The filtrate was partitioned with water (50 mL) and the phases separated. The aqueous layer was washed with DCM (25 mL) and the organic phases combined and passed through a phase separator then concentrated in vacuo. Purification by flash column chromatography on the Teledyne ISCO CombiFlash® Rf+ (24 g silica column Puriflash HC, 0-100% EtOAc in isohexane) gave 2,4-dimethoxybenzyl (1S,2R)-2-((S)-8-((1-isopropyl-1H-1,2,3-triazol-4-yl)methoxy)-1-((1-oxoisoindolin-2-yl)methyl)-5-(4,4,5,5-tetramethyl-1,3,2-dioxaborolan-2-yl)-1,2,3,4-tetrahydroisoquinoline-2-carbonyl)cyclohexane-1-carboxylate (397 mg, 94%). LCMS (Method 2): 1.10 min, 848.5 [M+H]⁺.

Step b. A microwave vial was charged with the above intermediate (150 mg, 0.180 mmol), copper(II) acetate (32 mg, 0.18 mmol) and potassium trimethoxy(trifluoromethyl)boranuide (75 mg, 0.35 mmol). The flask was sealed and purged with oxygen gas. Anhydrous DMSO was added and the reaction mixture heated at 60° C. for 18 h. The reaction was cooled to rt, diluted with water and extracted into EtOAc/diethyl ether (1:1). The combined organics were filtered through a pad of Celite® washed with water, brine, dried over Na₂SO₄, filtered and concentrated in vacuo. Purification by flash column chromatography on the Biotage Companion™ (12 g silica column, 0-100% DCM in EtOAc) gave a mixture of 2,4-dimethoxybenzyl (1S,2R)-2-((S)-8-((1-isopropyl-1H-1,2,3-triazol-4-yl)methoxy)-5-methoxy-1-((1-oxoisoindolin-2-yl)methyl)-1,2,3,4-tetrahydroisoquinoline-2-carbonyl)cyclohexane-1-carboxylate and 2,4-dimethoxybenzyl (1S,2R)-2-((S)-8-((1-isopropyl-1H-1,2,3-triazol-4-yl)methoxy)-1-((1-oxoisoindolin-2-yl)methyl)-5-(trifluoromethyl)-1,2,3,4-tetrahydroisoquinoline-2-carbonyl)cyclohexane-1-carboxylate (16 mg, 11%), which was used without further purification. 2,4-Dimethoxybenzyl (1S,2R)-2-((S)-8-((1-isopropyl-1H-1,2,3-triazol-4-yl)methoxy)-5-methoxy-1-((1-oxoisoindolin-2-yl)methyl)-1,2,3,4-tetrahydroisoquinoline-2-carbonyl)cyclohexane-1-carboxylate: LCMS (Method 2): 1.67 min, 774.5 [M+Na]⁺. 2,4-Dimethoxybenzyl (1S,2R)-2-((S)-8-((1-isopropyl-1H-1,2,3-triazol-4-yl)methoxy)-1-((1-oxoisoindolin-2-yl)methyl)-5-(trifluoromethyl)-1,2,3,4-tetrahydroisoquinoline-2-carbonyl)cyclohexane-1-carboxylate: LCMS (Method 2): 1.73 min, 812.4 [M+Na]⁺.

Step c. The title compounds Example 61 (12 mg, 59%) and Example 62 (10 mg, 46%) were prepared from the above mixture (52 mg, 0.035 mmol) using the method described for Example 22, step d. The crude products were purified and separated by preparative HPLC (Method 1).

Example 61

(1S,2R)-2-((S)-8-((1-isopropyl-1H-1,2,3-triazol-4-yl)methoxy)-5-methoxy-1-((1-oxoisoindolin-2-yl)methyl)-1,2,3,4-tetrahydroisoquinoline-2-carbonyl)cyclohexane-1-carboxylic acid. LCMS (Method 3): 4.19 min, 602.13 [M+H]$^+$. $^1$H NMR (400 MHz, MeOD) δ 8.30 (s, 1H), 7.69 (m, 1H), 7.58 (td, 1H), 7.51-7.42 (m, 2H), 6.99 (d, 1H), 6.84 (d, 1H), 6.06 (dd, 1H), 5.24 (d, 1H), 5.19 (d, 1H), 4.94 (m, 1H), 4.72 (d, 1H), 4.27 (dd, 1H), 4.15 (d, 1H), 4.03 (dd, 1H), 3.88-3.75 (m, 4H), 3.67 (dd, 1H), 3.41 (m, 1H), 2.90 (dd, 1H), 2.74 (m, 1H), 2.33 (m, 1H), 1.97 (m, 1H), 1.83-1.56 (m, 8H), 1.47-1.30 (m, 2H), 1.02 (m, 1H), 0.80 (m, 1H), 0.23 (m, 1H)

Example 62

(1S,2R)-2-((S)-8-((1-isopropyl-1H-1,2,3-triazol-4-yl)methoxy)-1-((1-oxoiso-indolin-2-yl)methyl)-5-(trifluoromethyl)-1,2,3,4-tetrahydroisoquinoline-2-carbonyl)-cyclohexane-1-carboxylic acid. LCMS (Method 3): 4.52 min, 640.11 [M+H]$^+$. $^1$H NMR (400 MHz, MeOD) δ 8.36 (s, 1H), 7.70 (m, 1H), 7.66 (d, 1H), 7.59 (m, 1H), 7.51-7.42 (m, 2H), 7.21 (d, 1H), 6.13 (dd, 1H), 5.39 (d, 1H), 5.34 (d, 1H), 4.96 (m, 1H), 4.69 (d, 1H), 4.31 (dd, 1H), 4.13 (d, 1H), 4.08 (m, 1H), 3.90 (m, 1H), 3.67 (dd, 1H), 3.41 (m, 1H), 3.15-3.05 (m, 2H), 2.34 (m, 1H), 1.96 (m, 1H), 1.78-1.57 (m, 8H), 1.48-1.32 (m, 2H), 1.02 (m, 1H), 0.82 (m, 1H), 0.23 (m, 1H)

Compounds in Table 2 were synthesised by methods analogous to the above Examples.

TABLE 2

| Ex. | Structure | Name | Analogous Example | 1H NMR δ ppm | LCMS |
|---|---|---|---|---|---|
| 7 | 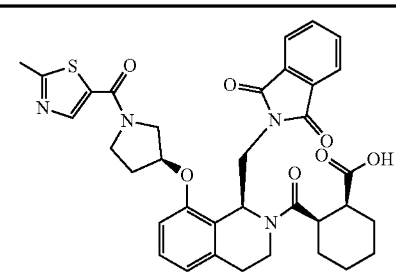 | (1S,2R)-2-((S)-1-((1,3-dioxoisoindolin-2-yl)methyl)-8-(((S)-1-(2-methylthiazole-5-carbonyl)pyrrolidin-3-yl)oxy)-1,2,3,4-tetrahydroisoquinoline-2-carbonyl)cyclohexane-1-carboxylic acid | 5 | (400 MHz, DMSO-d$_6$; rotamers observed, both reported) δ 8.14 (s, 1H), 7.88-7.71 (m, 4H), 7.20 (m, 1H), 6.91 (m, 1H), 6.78 (m, 1H), 5.94 (m, 1H), 5.21 (m, 0.5H), 5.17 (m, 0.5H), 4.34-3.98 (m, 3H), 3.97-3.70 (m, 4H), 3.60 (m, 1H), 3.21 (m, 1H), 3.01 (m, 1H), 2.80-2.20 (m, 6H), 1.96-1.72 (m, 2H), 1.52 (m, 1H), 1.38 (m, 1H), 1.30-1.13 (m, 2H), 0.87 (m, 1H), 0.66 (m, 1H), 0.15 (m, 1H). | Method 4a: 1.60 min, 657.4 [M + H]$^+$ |
| 9 | 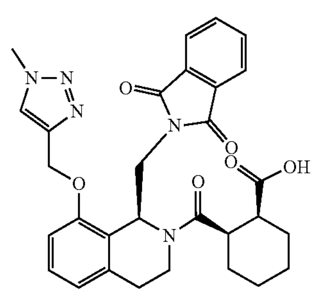 [SMILES: Cn1cc(COc2cccc3c2[C@@H](CN2C(=O)c4ccccc4C2=O)N(C(=O)[C@@H]2CCCC[C@@H]2C(=O)O)CC3)nn1] | (1S,2R)-2-((S)-1-((1,3-dioxoisoindolin-2-yl)methyl)-8-((1-methyl-1H-1,2,3-triazol-4-yl)methoxy)-1,2,3,4-tetrahydroisoquinoline-2-carbonyl)cyclohexane-1-carboxylic acid | 8 | (400 MHz, DMSO-d$_6$) δ 11.65 (bs, 1H), 8.45 (s, 1H), 7.91-7.75 (m, 4H), 7.22 (t, 1H), 7.09 (d, 1H), 6.82 (d, 1H), 6.03 (dd, 1H), 5.33 (d, 1H), 5.25 (d, 1H), 4.18-4.04 (m, 4H), 3.84 (m, 1H), 3.76 (dd, 1H), 3.67 (m, 1H), 3.47-3.14 (m, 1H), 2.95-2.75 (m, 2H), 2.19 (m, 1H), 1.85 (m, 1H), 1.54 (m, 1H), 1.41 (m, 1H), 1.37-1.20 (m, 2H), 0.92 (m, 1H), 0.68 (m, 1H), 0.09 (m, 1H). | Method 3: 4.26 min, 558.2 [M + H]$^+$. |

TABLE 2-continued

| Ex. | Structure | Name | Analogous Example | 1H NMR δ ppm | LCMS |
|---|---|---|---|---|---|
| 10 | 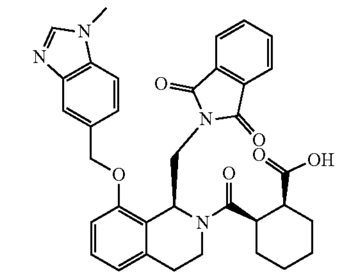 [SMILES: Cn1cnc2cc(COc3cccc4c3[C@@H](CN3C(=O)c5ccccc5C3=O)N(C(=O)[C@@H]3CCCC[C@@H]3C(=O)O)CC4)ccc21] | (1S,2R)-2-((S)-1-((1,3-dioxoisoindolin-2-yl)methyl)-8-((1-methyl-1H-benzo[d]imidazol-5-yl)methoxy)-1,2,3,4-tetrahydroisoquinoline-2-carbonyl)cyclohexane-1-carboxylic acid | 3 step a, 8 steps b,c | (400 MHz, DMSO-$d_6$) δ 11.69 (bs, 1H), 8.19 (s, 1H), 7.87-7.79 (m, 5H), 7.67-7.58 (m, 2H), 7.16 (t, 1H), 7.03 (d, 1H), 6.77 (d, 1H), 6.14 (dd, 1H), 5.44-5.34 (m, 2H), 4.21 (dd, 1H), 3.88-3.74 (m, 5H), 3.68 (m, 1H), 3.39-3.20 (m, 1H), 2.95-2.77 (m, 2H), 2.20 (m, 1H), 1.87 (m, 1H), 1.54 (m, 1H), 1.44 (m, 1H), 1.39-1.21 (m, 2H), 0.93 (m, 1H), 0.70 (m, 1H), 0.14 (m, 1H). | Method 3: 3.68 min, 607.4 [M + H]$^+$ |
| 14 | 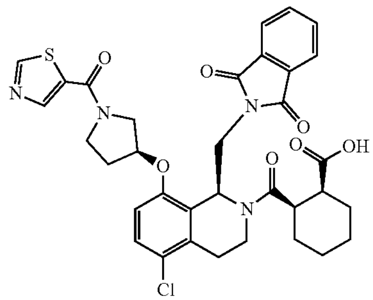 [SMILES: O=C(O)[C@H]1CCCC[C@H]1C(=O)N1CCc2c(Cl)ccc(O[C@H]3CCN(C(=O)c4cncs4)C3)c2[C@H]1CN1C(=O)c2ccccc2C1=O] | (1S,2R)-2-((S)-5-chloro-1-((1,3-dioxoisoindolin-2-yl)methyl)-8-(((S)-1-(thiazole-5-carbonyl)pyrrolidin-3-yl)oxy)-1,2,3,4-tetrahydroisoquinoline-2-carbonyl)cyclohexane-1-carboxylic acid | 12 (from Example 6) | (400 MHz, DMSO-$d_6$; rotamers observed, both reported) δ 11.64 (bs, 1H), 9.26 (s, 0.6H), 9.23 (s, 0.4H), 8.44 (s, 0.6H), 8.39 (s, 0.4H), 7.88-7.73 (m, 4H), 7.38 (m, 1H), 7.04 (m, 1H), 5.97 (dd, 0.4H), 5.92 (dd, 0.6H), 5.23 (m, 1H), 4.33 (m, 0.6H), 4.24-3.58 (m, 7.4H), 3.48-3.17 (m, 1H), 2.86 (m, 1H), 2.73 (m, 1H), 2.62-2.24 (m, 2H), 2.19 (m, 1H), 1.81 (m, 1H), 1.60-1.39 (m, 2H), 1.38-1.19 (m, 2H), 0.92 (m, 1H), 0.75 (m, 1H), 0.13 (m, 1H). | Method 3: 4.59 min, 677.3 [M + H]$^+$ |
| 18 | 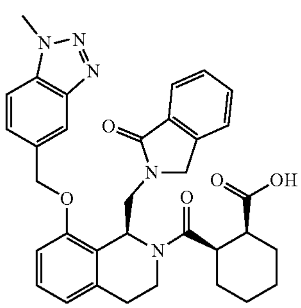 [SMILES: Cn1nnc2cc(COc3cccc4c3[C@@H](CN3Cc5ccccc5C3=O)N(C(=O)[C@@H]3CCCC[C@@H]3C(=O)O)CC4)ccc21] | (1S,2R)-2-((S)-8-((1-methyl-1H-benzo[d][1,2,3]triazol-5-yl)methoxy)-1-((1-oxoisoindolin-2-yl)methyl)-1,2,3,4-tetrahydroisoquinoline-2-carbonyl)cyclohexane-1-carboxylic acid | 17 | (400 MHz, DMSO-$d_6$) δ 11.63 (bs, 1H), 8.28 (m, 1H), 8.00 (dd, 1H), 7.82 (dd, 1H), 7.61-7.51 (m, 2H), 7.46-7.39 (m, 2H), 7.24 (t, 1H), 7.05 (d, 1H), 6.83 (d, 1H), 6.07 (dd, 1H), 5.40 (d, 1H), 5.31 (d, 1H), 4.53 (d, 1H), 4.36 (s, 3H), 4.16 (dd, 1H), 4.03 (d, 1H), 3.91 (m, 1H), 3.80-3.66 (m, 1H), 3.56 (dd, 1H), 3.42-3.20 (m, 1H), 2.95-2.76 (m, 2H), 2.17 (m, 1H), 1.85 (m, 1H), 1.54 (m, 1H), 1.44 (m, 1H), 1.32-1.17 (m, 2H), 0.88 (m, 1H), 0.58 (m, 1H), 0.06 (m, 1H). | Method 3: 4.15 min, 594.5 [M + H]$^+$ |
| 19 | 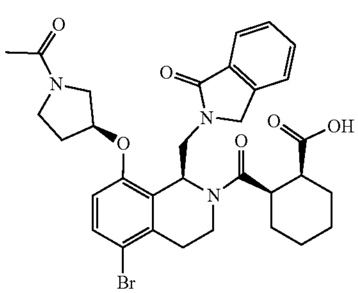 [SMILES: CC(=O)N1CC[C@H](Oc2ccc(Br)c3c2[C@@H](CN2Cc4ccccc4C2=O)N(C(=O)[C@@H]2CCCC[C@@H]2C(=O)O)CC3)C1] | (1S,2R)-2-((S)-8-(((S)-1-acetylpyrrolidin-3-yl)oxy)-5-bromo-1-((1-oxoisoindolin-2-yl)methyl)-1,2,3,4-tetrahydroisoquinoline-2-carbonyl)cyclohexane-1-carboxylic acid | 15 | (400 MHz, DMSO-$d_6$; rotamers observed, both reported) δ 11.65 (bs, 1H), 7.64-7.50 (m, 4H), 7.45 (m, 1H), 6.96 (d, 0.5H), 6.93 (d, 0.5H), 5.95 (m, 1H), 5.19 (m, 0.5H), 5.09 (m, 0.5H), 4.67 (m, 1H), 4.31 (d, 0.5H), 4.25 (d, 0.5H), 4.19 (dd, 1H), 4.01 (dd, 1H), 3.86 (dd, 0.5H), 3.80-3.58 (m, 4H), 3.52-3.37 (m, 1.5H), 3.37-3.26 (m, 1H), 2.83 (m, 1H), 2.73-2.60 (m, 1H), 2.41-2.29 (m, 1H), 2.27-2.13 (m, 2H), 2.06 (s, 1.5H), 2.01 (s, 1.5H), 1.86 (m, 1H), 1.55 (m, 1H), | Method 3: 4.02 min, 638.3 [M + H]$^+$ |

TABLE 2-continued

| Ex. | Structure | Name | Analogous Example | 1H NMR δ ppm | LCMS |
|---|---|---|---|---|---|
| | | | | 1.47 (m, 1H), 1.34-1.18 (m, 2H), 0.91 (m, 1H), 0.63 (m, 1H), 0.10 (m, 1H). | |
| 20 | 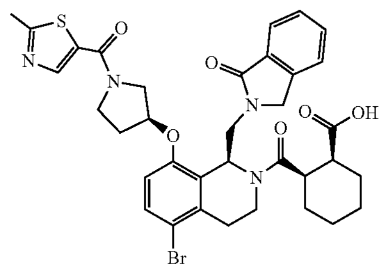 [SMILES: Cc1ncc(C(=O)N2CC[C@H](Oc3ccc(Br)c4c3[C@@H](CN3Cc5ccccc5C3=O)N(C(=O)[C@@H]3CCCC[C@@H]3C(=O)O)CC4)C2)s1] | (1S,2R)-2-((S)-5-Bromo-8-(((S)-1-(2-methylthiazole-5-carbonyl)-pyrrolidin-3-yl)oxy)-1-((1-oxoisoindolin-2-yl)methyl)-1,2,3,4-tetrahydroisoquinoline-2-carbonyl)cyclohexane-1-carboxylic acid | 15 | (400 MHz, DMSO-d$_6$; rotamers observed, both reported) δ 11.63 (bs, 1H), 8.21 (s, 1H), 7.64-7.51 (m, 3H), 7.50-7.39 (m, 2H), 7.00 (m, 1H), 5.94 (m, 1H), 5.25 (m, 0.5H), 5.17 (m, 0.5H), 4.62 (d, 0.5H), 4.55 (d, 0.5H), 4.31-3.82 (m, 6H), 3.81-3.64 (m, 2H), 3.50-3.17 (m, 2H), 2.83 (m, 1H), 2.77-2.58 (m, 4H), 2.42 (m, 1H), 2.36-2.24 (m, 1H), 2.18 (m, 1H), 1.83 (m, 1H), 1.54 (m, 1H), 1.45 (m, 1H), 1.33-1.14 (m, 2H), 0.89 (m, 1H), 0.61 (m, 1H), 0.07 (m, 1H). | Method 3: 4.17 min, 721.3 [M + H]$^+$ |
| 21 | 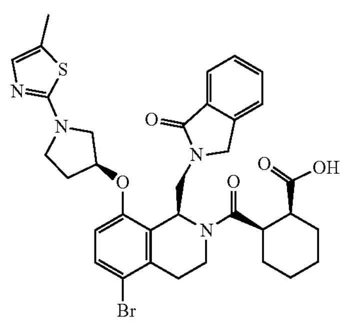 [SMILES: Cc1cnc(N2CC[C@H](Oc3ccc(Br)c4c3[C@@H](CN3Cc5ccccc5C3=O)N(C(=O)[C@@H]3CCCC[C@@H]3C(=O)O)CC4)C2)s1] | (1S,2R)-2-((S)-5-bromo-8-(((S)-1-(5-methylthiazol-2-yl)pyrrolidin-3-yl)oxy)-1-((1-oxoisoindolin-2-yl)methyl)-1,2,3,4-tetrahydroisoquinoline-2-carbonyl)cyclohexane-1-carboxylic acid | 15 | NMR (400 MHz, DMSO-d$_6$) δ 11.66 (bs, 1H), 7.61-7.51 (m, 3H), 7.42 (t, 1H), 7.38 (d, 1H), 6.98 (d, 1H), 6.87 (m, 1H), 5.90 (dd, 1H), 5.22 (m, 1H), 4.44 (d, 1H), 4.17 (dd, 1H), 3.99 (dd, 1H), 3.87-3.63 (m, 4H), 3.60-3.44 (m, 2H), 3.41-3.21 (m, 2H), 2.83 (dd, 1H), 2.72-2.58 (m, 1H), 2.44-2.34 (m, 2H), 2.22 (d, 3H), 2.19 (m, 1H), 1.82 (m, 1H), 1.54 (m, 1H), 1.45 (m, 1H), 1.34-1.14 (m, 2H), 0.89 (m, 1H), 0.62 (m, 1H), 0.05 (m, 1H) | Method 3: 3.68 min, 692.9 [M + H]$^+$ |
| 23 | 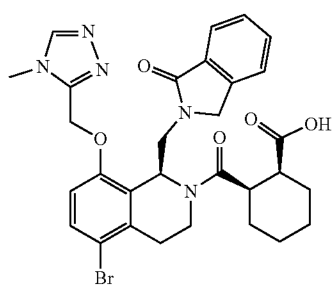 [SMILES: Cn1cnnc1COc1ccc(Br)c2c1[C@@H](CN1Cc3ccccc3C1=O)N(C(=O)[C@@H]1CCCC[C@@H]1C(=O)O)CC2] | (1S,2R)-2-((S)-5-bromo-8-((4-methyl-4H-1,2,4-triazol-3-yl)methoxy)-1-((1-oxoisoindolin-2-yl)methyl)-1,2,3,4-tetrahydroisoquinoline-2-carbonyl)cyclohexane-1-carboxylic acid | 22 | (400 MHz, DMSO-d$_6$) δ 11.63 (bs, 1H), 8.60 (s, 1H), 7.64-7.53 (m, 4H), 7.44 (m, 1H), 7.18 (d, 1H), 5.99 (dd, 1H), 5.48 (d, 1H), 5.43 (d, 1H), 4.51 (d, 1H), 4.17 (dd, 1H), 4.10 (d, 1H), 4.00 (dd, 1H), 3.84 (s, 3H), 3.74 (m, 1H), 3.44 (dd, 1H), 3.41-3.21 (m, 1H), 2.85 (dd, 1H), 2.69 (m, 1H), 2.20 (m, 1H), 1.86 (m, 1H), 1.55 (m, 1H), 1.41 (m, 1H), 1.33-1.19 (m, 2H), 0.90 (m, 1H), 0.59 (m, 1H), 0.09 (m, 1H). | Method 3: 3.72 min, 622.3 [M + H]$^+$ |
| 24 | 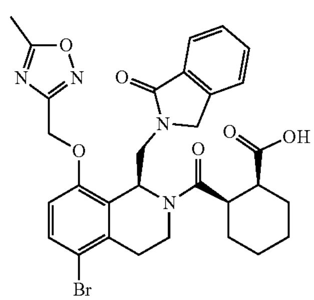 [SMILES: Cc1nc(COc2ccc(Br)c3c2[C@@H](CN2Cc4ccccc4C2=O)N(C(=O)[C@@H]2CCCC[C@@H]2C(=O)O)CC3)no1] | (1S,2R)-2-((S)-5-Bromo-8-((5-methyl-1,2,4-oxadiazol-3-yl)methoxy)-1-((1-oxoisoindolin-2-yl)methyl)-1,2,3,4-tetrahydroisoquinoline-2-carbonyl)cyclohexane-1-carboxylic acid | 16 step c, 22 step d | (400 MHz, DMSO-d$_6$) δ 11.57 (bs, 1H), 7.64-7.53 (m, 4H), 7.44 (m, 1H), 7.08 (d, 1H), 6.05 (dd, 1H), 5.45-5.33 (m, 2H), 4.68 (d, 1H), 4.35 (d, 1H), 4.20 (dd, 1H), 4.00 (dd, 1H), 3.75 (m, 1H), 3.63 (dd, 1H), 3.44-3.21 (m, 1H), 2.84 (dd, 1H), 2.76-2.63 (m, 4H), 2.18 (m, 1H), 1.86 (m, 1H), 1.55 (m, 1H), 1.42 (m, 1H), 1.32-1.18 (m, 2H), 0.89 (m, 1H), 0.58 (m, 1H), 0.07 (m, 1H). | Method 2: 1.46 min, 623.3 [M + H]$^+$ |

TABLE 2-continued

| Ex. | Structure | Name | Analogous Example | 1H NMR δ ppm | LCMS |
|---|---|---|---|---|---|
| 25 | 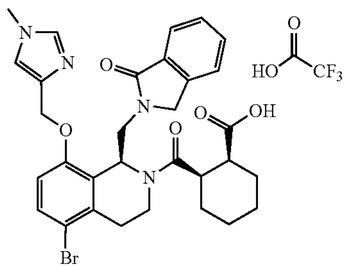 | (1S,2R)-2-((S)-5-Bromo-8-((1-methyl-1H-imidazol-4-yl)methoxy)-1-((1-oxoisoindolin-2-yl)methyl)-1,2,3,4-tetrahydroisoquinoline-2-carbonyl)cyclohexane-1-carboxylic acid 2,2,2-trifluoroacetic acid | 22 | (400 MHz, DMSO-d$_6$) δ 11.61 (bs, 1H), 8.97 (s, 1H), 7.84 (m, 1H), 7.65-7.52 (m, 4H), 7.45 (m, 1H), 7.10 (d, 1H), 5.97 (dd, 1H), 5.27 (d, 1H), 5.20 (d, 1H), 4.56 (d, 1H), 4.23-4.08 (m, 2H), 4.00 (dd, 1H), 3.90 (s, 3H), 3.74 (m, 1H), 3.52 (dd, 1H), 3.31 (m, 1H), 2.84 (dd, 1H), 2.68 (m, 1H), 2.21 (m, 1H), 1.85 (m, 1H), 1.56 (m, 1H), 1.44 (m, 1H), 1.35-1.17 (m, 2H), 0.91 (m, 1H), 0.62 (m, 1H), 0.09 (m, 1H). | Method 3: 3.36 min, 621.3 [M + H]$^+$ |
| 26 | 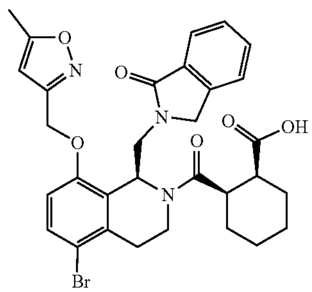 [SMILES: Cc1cc(COc2ccc(Br)c3c2[C@@H](CN2Cc4ccccc4C2=O)N(C(=O)[C@@H]2CCCC[C@@H]2C(=O)O)CC3)no1] | (1S,2R)-2-((S)-5-Bromo-8-((5-methylisoxazol-3-yl)methoxy)-1-((1-oxoisoindolin-2-yl)methyl)-1,2,3,4-tetrahydroisoquinoline-2-carbonyl)cyclohexane-1-carboxylic acid | 16 step c, 22 step d | (400 MHz, DMSO-d$_6$) δ 11.65 (s, 1H), 7.64-7.52 (m, 4H), 7.44 (m, 1H), 7.04 (d, 1H), 6.54 (m, 1H), 6.02 (dd, 1H), 5.31 (d, 1H), 5.23 (d, 1H), 4.62 (d, 1H), 4.27 (d, 1H), 4.19 (d, 1H), 4.00 (dd 1H), 3.76 (m, 1H), 3.53 (dd, 1H), 3.38-3.25 (m, 1H), 2.84 (dd, 1H), 2.75-2.61 (m, 1H), 2.53-2.47 (m, 3H), 2.20 (m, 1H), 1.87 (m, 1H), 1.55 (m, 1H), 1.42 (m, 1H), 1.33-1.18 (m, 2H), 0.90 (m, 1H), 0.58 (m, 1H), 0.08 (m, 1H). | Method 3: 4.71 min, 622.2 [M + H]$^+$ |
| 27 | 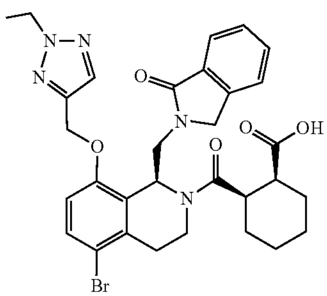 [SMILES: CCn1ncc(COc2ccc(Br)c3c2[C@@H](CN2Cc4ccccc4C2=O)N(C(=O)[C@@H]2CCCC[C@@H]2C(=O)O)CC3)n1] | (1S,2R)-2-((S)-5-bromo-8-((2-ethyl-2H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid | 22 | (400 MHz, DMSO-d$_6$) δ 11.65 (bs, 1H), 8.00 (s, 1H), 7.63-7.52 (m, 4H), 7.44 (m, 1H), 7.10 (d, 1H), 5.98 (dd, 1H), 5.31 (d, 1H), 5.25 (d, 1H), 4.58-4.46 (m, 3H), 4.16 (dd, 1H), 4.13 (d, 1H), 3.99 (dd, 1H), 3.74 (m, 1H), 3.50 (dd, 1H), 3.44-3.19 (m, 1H), 2.83 (dd, 1H), 2.74-2.61 (m, 1H), 2.18 (m, 1H), 1.85 (m, 1H), 1.55 (m, 1H), 1.48 (t, 3H), 1.41 (m, 1H), 1.31-1.18 (m, 2H), 0.89 (m, 1H), 0.59 (m, 1H), 0.08 (m, 1H). | Method 3: 4.68 min, 636.3 [M + H]$^+$ |
| 28 | 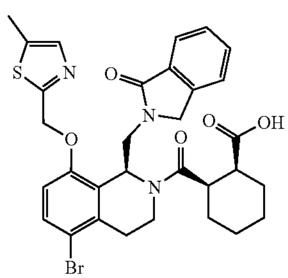 [SMILES: Cc1cnc(COc2ccc(Br)c3c2[C@@H](CN2Cc4ccccc4C2=O)N(C(=O)[C@@H]2CCCC[C@@H]2C(=O)O)CC3)s1] | (1S,2R)-2-((S)-5-Bromo-8-((5-methylthiazol-2-yl)methoxy)-1-((1-oxoisoindolin-2-yl)methyl)-1,2,3,4-tetrahydroisoquinoline-2-carbonyl)cyclohexane-1-carboxylic acid | 22 | (400 MHz, DMSO-d$_6$) δ 11.67 (bs, 1H), 7.65-7.53 (m, 5H), 7.45 (m, 1H), 7.07 (d, 1H), 6.10 (dd, 1H), 5.51 (d, 1H), 5.42 (d, 1H), 4.67 (d, 1H), 4.29 (d, 1H), 4.22 (dd, 1H), 4.00 (dd, 1H), 3.78 (m, 1H), 3.58 (dd, 1H), 3.37-3.28 (m, 1H), 2.86 (dd, 1H), 2.69 (m, 1H), 2.53 (d, 3H), 2.20 (m, 1H), 1.88 (m, 1H), 1.56 (m, 1H), 1.38 (m, 1H), 1.25 (m, 2H), 0.90 (m, 1H), 0.54 (m, 1H), 0.06 (m, 1H). | Method 3: 4.75 min, 638.1 [M + H]$^+$. |
| 30 | 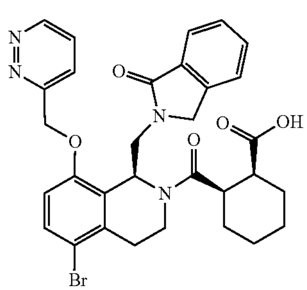 [SMILES: O=C(O)[C@H]1CCCC[C@H]1C(=O)N1CCc2c(Br)ccc(OCc3cccnn3)c2[C@H]1CN1Cc2ccccc2C1=O] | (1S,2R)-2-((S)-5-Bromo-1-((1-oxoisoindolin-2-yl)methyl)-8-(pyridazin-3-yl)methoxy)-1,2,3,4-tetrahydroisoquinoline-2-carbonyl)cyclohexane-1-tetrahydroisoquinoline-2-carbonyl)cyclohexane-1-carboxylic acid | 22 | (400 MHz, DMSO-d$_6$) δ 11.66 (bs, 1H), 9.31 (dd, 1H), 8.03 (dd, 1H), 7.93 (dd, 1H), 7.65-7.51 (m, 4H), 7.44 (m, 1H), 7.09 (d, 1H), 6.08 (dd, 1H), 5.56 (d, 1H), 5.49 (d, 1H), 4.57 (d, 1H), 4.29-4.11 (m, 2H), 4.01 (dd, 1H), 3.78 (m, 1H), 3.62 (dd, 1H), 3.32 (m, 1H), 2.86 (dd, 1H), 2.70 (m, 1H), 2.20 (m, 1H), 1.86 (m, 1H), 1.56 (m, 1H), 1.42 (m, 1H), 1.34-1.16 (m, 2H), 0.91 (m, 1H), 0.57 (m, 1H), 0.06 (m, 1H). | Method 3: 4.03 min, 619.4 [M+ H]$^+$. |

TABLE 2-continued

| Ex. | Structure | Name | Analogous Example | 1H NMR δ ppm | LCMS |
|---|---|---|---|---|---|
| 31 | 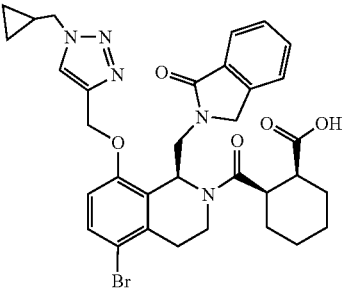 [SMILES: O=C(O)[C@H]1CCCC[C@H]1C(=O)N1CCc2c(Br)ccc(OCc3cn(CC4CC4)nn3)c2[C@H]1CN1Cc2ccccc2C1=O] | (1S,2R)-2-((S)-5-bromo-8-((1-(cyclopropylmethyl)-1 1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid | 22 | (400 MHz, CDCl$_3$) δ 7.79 (s, 1H), 7.70 (m, 1H), 7.48 (td, 1H), 7.46 (d, 1H), 7.39 (t, 1H), 7.33 (d, 1H), 6.86 (d, 1H), 6.14 (dd, 1H), 5.28 (d, 1H), 5.21 (d, 1H), 4.68 (d, 1H), 4.33 (dd, 1H), 4.26 (d, 2H), 4.12 (d, 1H), 4.04 (m, 1H), 3.86 (dd, 1H), 3.62 (dd, 1H), 3.09-2.91 (m, 2H), 2.79 (m, 1H), 2.50 (m, 1H), 2.16 (m, 1H), 1.64-1.14 (m, 6H), 1.12-0.81 (m, 2H), 0.72 (m, 2H), 0.46 (m, 2H). | Method 3: 4.54 min. 662.5 [M + H]$^+$. |
| 32 | 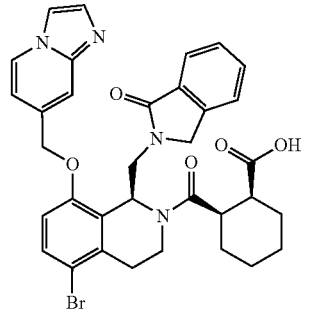 [SMILES: O=C(O)[C@H]1CCCC[C@H]1C(=O)N1CCc2c(Br)ccc(OCc3ccn4ccnc4c3)c2[C@H]1CN1Cc2ccccc2C1=O] | (1S,2R)-2-((S)-5-bromo-8-(imidazo[1,2-a]pyridin-7-yl)methoxy)-1-((1-oxoisoindolin-2-yl)methyl)-1,2,3,4-tetrahydroisoquinoline-2-carbonyl)cyclohexane-1-carboxylic acid | 22 | (400 MHz, DMSO-d$_6$) δ 11.73 (bs, 1H), 8.67 (d, 1H), 8.01 (s, 1H), 7.78 (s, 1H), 7.66-7.51 (m, 4H), 7.50-7.40 (m, 2H), 7.12 (dd, 1H), 7.05 (d, 1H), 6.10 (dd, 1H), 5.31 (d, 1H), 5.23 (d, 1H), 4.60 (d, 1H), 4.29-4.13 (m, 2H), 4.01 (dd, 1H), 3.78 (m, 1H), 3.58 (dd, 1H), 3.48-3.18 (m, 1H), 2.86 (dd, 1H), 2.69 (m, 1H), 2.20 (m, 1H), 1.86 (m, 1H), 1.55 (m, 1H), 1.43 (m, 1H), 1.34-1.18 (m, 2H), 0.90 (m, 1H), 0.59 (m, 1H), 0.08 (m, 1H). | Method 3: 3.40 min, 657.2 [M + H]$^+$. |
| 33 | 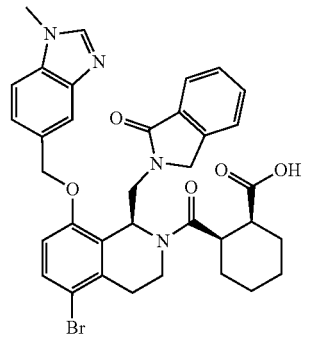 [SMILES: Cn1cnc2cc(COc3ccc(Br)c4c3[C@@H](CN3Cc5ccccc5C3=O)N(C(=O)[C@@H]3CCCC[C@@H]3C(=O)O)CC4)ccc21] | (1S,2R)-2-((S)-5-bromo-8-((1-methyl-1H-benzo[d]imidazol-5-yl)methoxy)-1-((1-oxoisoindolin-2-yl)methyl)-1,2,3,4-tetrahydroisoquinoline-2-carbonyl)cyclohexane-1-carboxylic acid | 22 | (400 MHz, DMSO-d$_6$) δ 11.70 (bs, 1H), 8.26 (s, 1H), 7.92 (s, 1H), 7.70 (d, 1H), 7.60-7.50 (m, 4H), 7.42 (t, 1H), 7.36 (d, 1H), 7.08 (d, 1H), 6.03 (dd, 1H), 5.36 (d, 1H), 5.27 (d, 1H), 4.44 (d, 1H), 4.19 (dd, 1H), 4.00 (dd, 1H), 3.91 (d, 1H), 3.89 (s, 3H), 3.74 (m, 1H), 3.50 (dd, 1H), 3.45-3.20 (m, 1H), 2.84 (dd, 1H), 2.67 (m, 1H), 2.19 (m, 1H), 1.83 (m, 1H), 1.54 (m, 1H), 1.44 (m, 1H), 1.32-1.16 (m, 2H), 0.89 (m, 1H), 0.62 (m, 1H), 0.09 (m, 1H). | Method 3: 3.60 min, 671.5 [M + H]$^+$. |
| 34 | 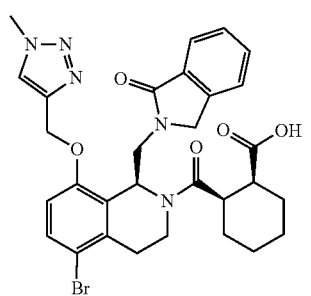 [SMILES: Cn1cc(COc2ccc(Br)c3c2[C@@H](CN2Cc4ccccc4C2=O)N(C(=O)[C@@H]2CCCC[C@@H]2C(=O)O)CC3)nn1] | (1S,2R)-2-((S)-5-bromo-8-((1-methyl-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid | 22 | (400 MHz, DMSO-d$_6$) δ 11.66 (bs, 1H), 8.32 (s, 1H), 7.64-7.51 (m, 4H), 7.44 (m, 1H), 7.12 (d, 1H), 5.97 (dd, 1H), 5.35-5.22 (m, 2H), 4.54 (d, 1H), 4.21-4.05 (m, 5H), 3.99 (dd, 1H), 3.73 (m, 1H), 3.51 (dd, 1H), 3.43-3.23 (m, 1H), 2.83 (dd, 1H), 2.66 (m, 1H), 2.19 (m, 1H), 1.85 (m, 1H), 1.55 (m, 1H), 1.42 (m, 1H), 1.33-1.17 (m, 2H), 0.90 (m, 1H), 0.60 (m, 1H), 0.09 (m, 1H). | Method 3: 4.08 min, 622.4 [M + H]$^+$. |

TABLE 2-continued

| Ex. | Structure | Name | Analogous Example | 1H NMR δ ppm | LCMS |
|-----|-----------|------|-------------------|--------------|------|
| 35 | 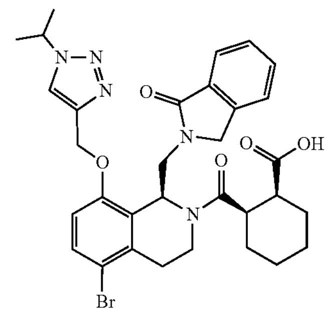 [SMILES: CC(C)n1cc(COc2ccc(Br)c3c2[C@@H](CN2Cc4ccccc4C2=O)N(C(=O)[C@@H]2CCCC[C@@H]2C(=O)O)CC3)nn1] | (1S,2R)-2-((S)-5-Bromo-8-((1-isopropyl-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid | 22 | (400 MHz, DMSO-$d_6$) δ 11.66 (bs, 1H), 8.49 (s, 1H), 7.58 (m, 3H), 7.49 (d, 1H), 7.44 (t, 1H), 7.13 (d, 1H), 5.95 (dd, 1H), 5.32-5.21 (m, 2H), 4.91 (m, 1H), 4.52 (d, 1H), 4.16 (dd, 1H), 4.07 (d, 1H), 4.00 (dd, 1H), 3.73 (m, 1H), 3.51 (dd, 1H), 3.39-3.24 (m, 1H), 2.83 (dd, 1H), 2.67 (m, 1H), 2.19 (m, 1H), 1.84 (m, 1H), 1.60-1.50 (m, 7H), 1.44 (m, 1H), 1.33-1.18 (m, 2H), 0.89 (m, 1H), 0.62 (m, 1H), 0.09 (m, 1H) | Method 3: 4.42 min, 650.4 [M + H]$^+$ |
| 36 | 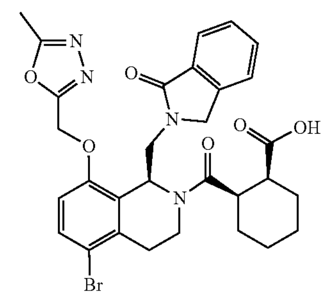 [SMILES: Cc1nnc(COc2ccc(Br)c3c2[C@@H](CN2Cc4ccccc4C2=O)N(C(=O)[C@@H]2CCCC[C@@H]2C(=O)O)CC3)o1] | (1S,2R)-2-((S)-5-bromo-8-((5-methyl-1,3,4-oxadiazol-2-yl)methoxy)-1-((1-oxoisoindolin-2-yl)methyl)-1,2,3,4-tetrahydroisoquinoline-2-carbonyl)cyclohexane-1-carboxylic acid | 22 | (400 MHz, DMSO-$d_6$) δ 11.67 (bs, 1H), 7.64-7.54 (m, 4H), 7.45 (td, 1H), 7.11 (d, 1H), 6.04 (dd, 1H), 5.55 (d, 1H), 5.49 (d, 1H), 4.66 (d, 1H), 4.33 (d, 1H), 4.21 (dd, 1H), 4.01 (dd, 1H), 3.76 (m, 1H), 3.55 (dd, 1H), 3.44-3.21 (m, 1H), 2.85 (dd, 1H), 2.76-2.62 (m, 1H), 2.59 (s, 3H), 2.20 (m, 1H), 1.87 (m, 1H), 1.56 (m, 1H), 1.42 (m, 1H), 1.33-1.18 (m, 2H), 0.90 (m, 1H), 0.59 (m, 1H), 0.08 (m, 1H) | Method 3: 4.13 min, 623.3 [M + H]$^+$. |
| 37 | 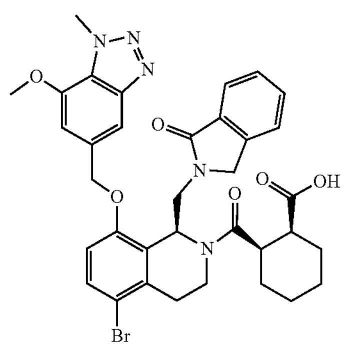 [SMILES: COc1cc(COc2ccc(Br)c3c2[C@@H](CN2Cc4ccccc4C2=O)N(C(=O)[C@@H]2CCCC[C@@H]2C(=O)O)CC3)cc2nnn(C)c12] | (1S,2R)-2-((S)-5-bromo-8-((7-methoxy-1-methyl-1H-benzo[d][1,2,3]triazol-5-yl)methoxy)-1-((1-oxoisoindolin-2-yl)methyl)-1,2,3,4-tetrahydroisoquinoline-2-carbonyl)cyclohexane-1-carboxylic acid | 22 | (400 MHz, DMSO-$d_6$) δ 11.67 (bs, 1H), 7.82 (m, 1H), 7.61-7.51 (m, 3H), 7.43 (m, 1H), 7.38 (m, 1H), 7.18 (d, 1H), 7.07 (d, 1H), 6.10 (dd, 1H), 5.38 (d, 1H), 5.31 (d, 1H), 4.51 (d, 1H), 4.43 (s, 3H), 4.21 (dd, 1H), 4.09-3.95 (m, 5H), 3.77 (m, 1H), 3.57 (dd, 1H), 3.44-3.19 (m, 1H), 2.85 (dd, 1H), 2.76-2.61 (m, 1H), 2.20 (m, 1H), 1.85 (m, 1H), 1.55 (m, 1H), 1.43 (m, 1H), 1.33-1.18 (m, 2H), 0.90 (m, 1H), 0.61 (m, 1H), 0.10 (m, 1H). | Method 3: 4.72 min, 702.5 [M + H]$^+$. |
| 38 | 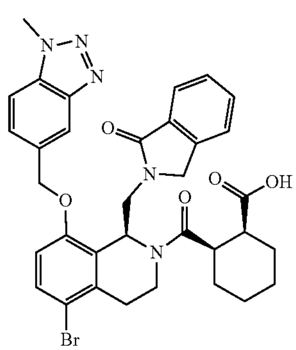 [SMILES: Cn1nnc2cc(COc3ccc(Br)c4c3[C@@H](CN3Cc5ccccc5C3=O)N(C(=O)[C@@H]3CCCC[C@@H]3C(=O)O)CC4)ccc21] | (1S,2R)-2-((S)-5-bromo-8-((1-methyl-1H-benzo[d][1,2,3]triazol-5-yl)methoxy)-1-((1-oxoisoindolin-2-yl)methyl)-1,2,3,4-tetrahydroisoquinoline-2-carbonyl)cyclohexane-1-carboxylic acid | 22 | (400 MHz, DMSO-$d_6$) δ 11.64 (bs, 1H), 8.29 (s, 1H), 8.00 (d, 1H), 7.82 (dd, 1H), 7.62-7.51 (m, 3H), 7.46-7.36 (m, 2H), 7.09 (d, 1H), 6.05 (dd, 1H), 5.42 (d, 1H), 5.33 (d, 1H), 4.47 (d, 1H), 4.36 (s, 3H), 4.20 (dd, 1H), 4.06-3.94 (m, 2H), 3.75 (m, 1H), 3.54 (dd, 1H), 3.46-3.18 (m, 1H), 2.85 (dd, 1H), 2.76-2.62 (m, 1H), 2.17 (m, 1H), 1.83 (m, 1H), 1.54 (m, 1H), 1.42 (m, 1H), 1.32-1.17 (m, 2H), 0.89 (m, 1H), 0.59 (m, 1H), 0.08 (m, 1H). | Method 3: 4.52 min, 672.5 [M + H]$^+$. |

TABLE 2-continued

| Ex. | Structure | Name | Analogous Example | 1H NMR δ ppm | LCMS |
|---|---|---|---|---|---|
| 39 | 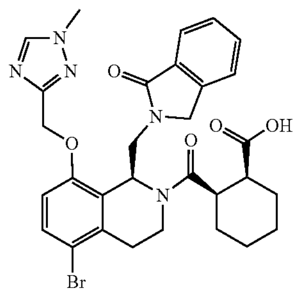 [SMILES: Cn1cnc(COc2ccc(Br)c3c2[C@@H](CN2Cc4ccccc4C2=O)N(C(=O)[C@@H]2CCCC[C@@H]2C(=O)O)CC3)n1] | (1S,2R)-2-((S)-5-bromo-8-((1-methyl-1H-1,2,4-triazol-3-yl)methoxy)-1-((1-oxoisoindolin-2-yl)methyl)-1,2,3,4-tetrahydroisoquinoline-2-carbonyl)cyclohexane-1-carboxylic acid | 22 | (400 MHz, DMSO-$d_6$) δ 11.66 (bs, 1H), 8.55 (s, 1H), 7.62-7.55 (m, 3H), 7.54 (d, 1H), 7.44 (td, 1H), 7.10 (d, 1H), 6.00 (dd, 1H), 5.30-5.16 (m, 2H), 4.61 (d, 1H), 4.26 (d, 1H), 4.17 (dd, 1H), 3.99 (dd, 1H), 3.92 (s, 3H), 3.73 (m, 1H), 3.64 (dd, 1H), 3.42-3.22 (m, 1H), 2.83 (dd, 1H), 2.67 (m, 1H), 2.19 (m, 1H), 1.85 (m, 1H), 1.55 (m, 1H), 1.43 (m, 1H), 1.33-1.17 (m, 2H), 0.90 (m, 1H), 0.60 (m, 1H), 0.08 (m, 1H). | Method 3: 4.03 min, 622.2 [M + H]+. |
| 40 | 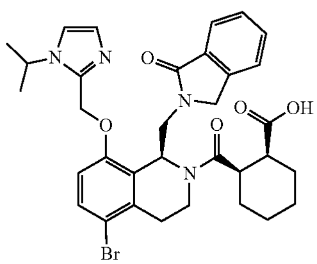 [SMILES: CC(C)n1ccnc1COc1ccc(Br)c2c1[C@@H](CN1Cc3ccccc3C1=O)N(C(=O)[C@@H]1CCCC[C@@H]1C(=O)O)CC2] | (1S,2R)-2-((S)-5-bromo-8-((1-isopropyl-1H-imidazol-2-yl)methoxy)-1-((1-oxoisoindolin-2-yl)methyl)-1,2,3,4-tetrahydroisoquinoline-2-carbonyl)cyclohexane-1-carboxylic acid | 22 | (400 MHz, DMSO-$d_6$) δ 11.67 (bs, 1H), 7.62-7.51 (m, 4H), 7.49-7.39 (m, 2H), 7.22 (d, 1H), 7.00 (d, 1H), 5.95 (dd, 1H), 5.35 (d, 1H), 5.24 (d, 1H), 4.71 (m, 1H), 4.48 (d, 1H), 4.17 (dd, 1H), 4.04-3.88 (m, 2H), 3.71 (m, 1H), 3.42 (dd, 1H), 3.38-3.20 (m, 1H), 2.83 (dd, 1H), 2.73-2.60 (m, 1H), 2.19 (m, 1H), 1.84 (m, 1H), 1.54 (m, 1H), 1.48 (d, 3H), 1.46-1.37 (m, 4H), 1.32-1.19 (m, 2H), 0.90 (m, 1H), 0.61 (m, 1H), 0.11 (m, 1H). | Method 3: 3.62 min, 649.2 [M + H]+ |
| 41 | 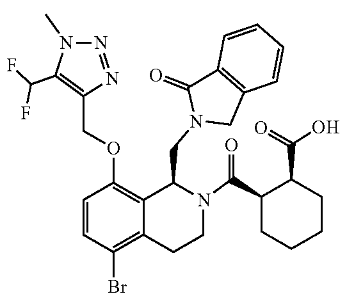 [SMILES: Cn1nnc(COc2ccc(Br)c3c2[C@@H](CN2Cc4ccccc4C2=O)N(C(=O)[C@@H]2CCCC[C@@H]2C(=O)O)CC3)c1C(F)F] | (1S,2R)-2-((S)-5-bromo-8-((5-(difluoromethyl)-1-methyl-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid | 22 | (400 MHz, DMSO-$d_6$) δ 11.66 (bs, 1H), 7.63 (t, 1H), 7.62-7.52 (m, 4H), 7.44 (m, 1H), 7.15 (d, 1H), 5.93 (dd, 1H), 5.43-5.30 (m, 2H), 4.49 (d, 1H), 4.22 (s, 3H), 4.15 (dd, 1H), 4.06-3.92 (m, 2H), 3.72 (m, 1H), 3.45 (dd, 1H), 3.40-3.22 (m, 1H), 2.83 (dd, 1H), 2.67 (m, 1H), 2.18 (m, 1H), 1.84 (m, 1H), 1.54 (m, 1H), 1.39 (m, 1H), 1.31-1.17 (m, 2H), 0.89 (m, 1H), 0.57 (m, 1H), 0.06 (m, 1H). | Method 3: 4.49 min, 672.0 [M + H]+ |
| 42 | 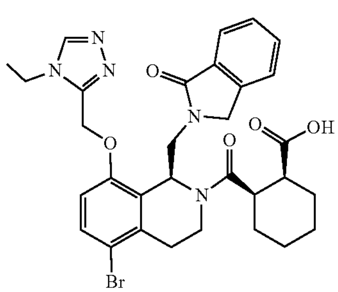 [SMILES: CCn1cnnc1COc1ccc(Br)c2c1[C@@H](CN1Cc3ccccc3C1=O)N(C(=O)[C@@H]1CCCC[C@@H]1C(=O)O)CC2] | (1S,2R)-2-((S)-5-bromo-8-((4-ethyl-4H-1,2,4-triazol-3-yl)methoxy)-1-((1-oxoisoindolin-2-yl)methyl)-1,2,3,4-tetrahydroisoquinoline-2-carbonyl)cyclohexane-1-carboxylic acid | 22 | (400 MHz, DMSO-$d_6$) δ 11.65 (bs, 1H), 8.70 (s, 1H), 7.64-7.52 (m, 4H), 7.48-7.40 (m, 1H), 7.19 (d, 1H), 5.97 (dd, 1H), 5.50-5.40 (m, 2H), 4.50 (d, 1H), 4.28-4.12 (m, 3H), 4.06 (d, 1H), 3.99 (dd, 1H), 3.73 (m, 1H), 3.44 (dd, 1H), 3.38-3.24 (m, 1H), 2.84 (dd, 1H), 2.68 (m, 1H), 2.19 (m, 1H), 1.85 (m, 1H), 1.55 (m, 1H), 1.49-1.35 (m, 4H), 1.32-1.19 (m, 2H), 0.89 (m, 1H), 0.58 (m, 1H), 0.08 (m, 1H). | Method 3: 3.82 min, 636.1 [M + H]+ |

TABLE 2-continued

| Ex. | Structure | Name | Analogous Example | 1H NMR δ ppm | LCMS |
|---|---|---|---|---|---|
| 43 | 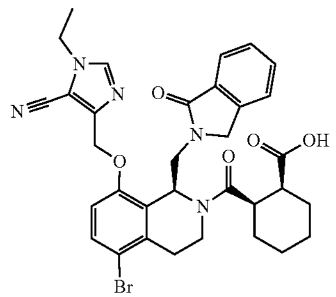 [SMILES: CCn1cnc(COc2ccc(Br)c3c2[C@@H](CN2Cc4ccccc4C2=O)N(C(=O)[C@@H]2CCCC[C@@H]2C(=O)O)CC3)c1C#N] | (1S,2R)-2-((S)-5-bromo-8-((5-cyano-1-ethyl-1H-imidazol-4-yl)methoxy)-1-((1-oxoisoindolin-2-yl)methyl)-1,2,3,4-tetrahydro-isoquinoline-2-carbonyl)cyclohexane-1-carboxylic acid | 22 | (400 MHz, DMSO-d$_6$) δ 11.65 (bs, 1H), 8.18 (s, 1H), 7.60 (m, 1H), 7.56 (m, 3H), 7.44 (m, 1H), 7.10 (d, 1H), 5.97 (dd, 1H), 5.22 (s, 2H), 4.59 (d, 1H), 4.28-4.10 (m, 4H), 3.99 (dd, 1H), 3.73 (m, 1H), 3.57 (dd, 1H), 3.41-3.23 (m, 1H), 2.83 (dd, 1H), 2.67 (m, 1H), 2.19 (m, 1H), 1.84 (m, 1H), 1.54 (m, 1H), 1.49-1.35 (m, 4H), 1.33-1.18 (m, 2H), 0.89 (m, 1H), 0.58 (m, 1H), 0.07 (m, 1H). | Method 3: 4.44 min, 660.0 [M + H]$^+$ |
| 44 | 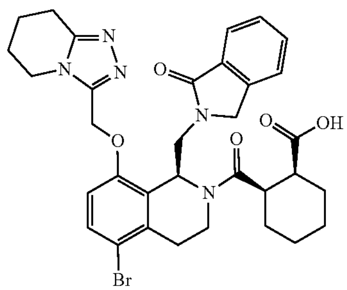 [SMILES: O=C(O)[C@H]1CCCC[C@H]1C(=O)N1CCc2c(Br)ccc(OCc3nnc4n3CCCC4)c2[C@H]1CN1Cc2ccccc2C1=O] | (1S,2R)-2-((S)-5-bromo-1-((1-oxoisoindolin-2-yl)methyl)-8-((5,6,7,8-tetrahydro-[1,2,4]triazolo[4,3-a]pyridin-3-yl)methoxy)-1,2,3,4-tetrahydroisoquinoline-2-carbonyl)cyclohexane-1-carboxylic acid | 22 | (400 MHz, DMSO-d$_6$) δ 11.55 (bs, 1H), 7.61 (m, 1H), 7.59-7.53 (m, 3H), 7.45 (m, 1H), 7.19 (d, 1H), 5.99 (dd, 1H), 5.42 (d, 1H), 5.37 (d, 1H), 4.53 (d, 1H), 4.22-4.05 (m, 4H), 3.99 (dd, 1H), 3.75 (m, 1H), 3.46 (dd, 1H), 3.42-3.16 (m, 1H), 2.97-2.77 (m, 3H), 2.69 (m, 1H), 2.18 (m, 1H), 2.06-1.76 (m, 5H), 1.55 (m, 1H), 1.41 (m, 1H), 1.32-1.17 (m, 2H), 0.90 (m, 1H), 0.59 (m, 1H), 0.10 (m, 1H). | Method 3: 3.75 min, 662.0 [M + H]$^+$ |
| 46 | 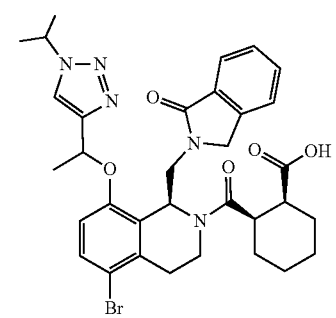 [SMILES: CC(Oc1ccc(Br)c2c1[C@@H](CN1Cc3ccccc3C1=O)N(C(=O)[C@@H]1CCCC[C@@H]1C(=O)O)CC2)c1cn(C(C)C)nn1] | (1S,2R)-2-((1S)-5-bromo-8-(1-(1-isopropyl-1H-1,2,3-triazol-4-yl)ethoxy)-1-((1-oxoisoindolin-2-yl)methyl)-1,2,3,4-tetrahydroisoquinoline-2-carbonyl)cyclohexane-1-carboxylic acid (isomer 1) | 45 | (400 MHz, DMSO-d$_6$) δ 11.68 (bs, 1H), 8.41 (s, 1H), 7.64-7.54 (m, 3H), 7.50-7.41 (m, 2H), 7.03 (d, 1H), 6.03 (dd, 1H), 5.75 (m, 1H), 4.79 (m, 1H), 4.68 (d, 1H), 4.25 (d, 1H), 4.10 (dd, 1H), 3.99 (dd, 1H), 3.71 (m, 1H), 3.65-3.35 (m, 1H), 3.31 (bm, 1H), 2.80 (dd, 1H), 2.64 (m, 1H), 2.20 (m, 1H), 1.86 (m, 1H), 1.78 (d, 3H), 1.56 (m, 1H), 1.52-1.41 (m, 7H), 1.34-1.19 (m, 2H), 0.90 (m, 1H), 0.62 (m, 1H), 0.08 (m, 1H). | Method 3: 4.52 min, 664.1 [M + H]$^+$ |
| 47 | 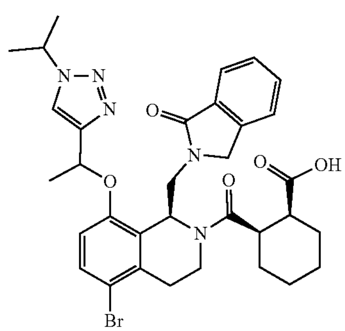 [SMILES: CC(Oc1ccc(Br)c2c1[C@@H](CN1Cc3ccccc3C1=O)N(C(=O)[C@@H]1CCCC[C@@H]1C(=O)O)CC2)c1cn(C(C)C)nn1] | (1S,2R)-2-((1S)-5-bromo-8-(1-(1-isopropyl-1H-1,2,3-triazol-4-yl)ethoxy)-1-((1-oxoisoindolin-2-yl)methyl)-1,2,3,4-tetrahydroisoquinoline-2-carbonyl)cyclohexane-1-carboxylic acid (isomer 2) | 45 | (400 MHz, DMSO-d$_6$) δ 11.62 (bs, 1H), 8.40 (s, 1H), 7.62 (m, 1H), 7.60-7.55 (m, 2H), 7.52-7.40 (m, 2H), 7.11 (d, 1H), 5.96 (dd, 1H), 5.76 (m, 1H), 4.82 (m, 1H), 4.64 (d, 1H), 4.40 (d, 1H), 4.20 (dd, 1H), 3.99 (dd, 1H), 3.85-3.42 (m, 2H), 3.30 (m, 1H), 2.82 (dd, 1H), 2.63 (m, 1H), 2.19 (m, 1H), 1.85 (m, 1H), 1.78 (d, 3H), 1.60-1.40 (m, 8H), 1.34-1.17 (m, 2H), 0.90 (m, 1H), 0.61 (m, 1H), 0.08 (m, 1H). | Method 3: 4.61 min, 664.1 [M + H]$^+$ |

TABLE 2-continued

| Ex. | Structure | Name | Analogous Example | 1H NMR δ ppm | LCMS |
|---|---|---|---|---|---|
| 48 | 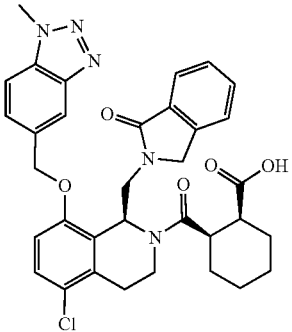 [SMILES: Cn1nnc2cc(COc3ccc(Cl)c4c3[C@@H](CN3Cc5ccccc5C3=O)N(C(=O)[C@@H]3CCCC[C@@H]3C(=O)O)CC4)ccc21] | (1S,2R)-2-((S)-5-chloro-8-((1-methyl-1H-benzo[d][1,2,3]triazol-5-yl)methoxy)-1-((1-oxoisoindolin-2-yl)methyl)-1,2,3,4-tetrahydroisoquinoline-2-carbonyl)cyclohexane-1-carboxylic acid | 12 (from Example 18) | (400 MHz, DMSO-d$_6$) δ 11.65 (bs, 1H), 8.29 (s, 1H), 8.00 (d, 1H), 7.82 (dd, 1H), 7.58 (d, 1H), 7.55 (td, 1H), 7.46-7.36 (m, 3H), 7.14 (d, 1H), 6.05 (dd, 1H), 5.43 (d, 1H), 5.33 (d, 1H), 4.48 (d, 1H), 4.36 (s, 3H), 4.21 (dd, 1H), 4.07-3.95 (m, 2H), 3.76 (m, 1H), 3.54 (dd, 1H), 3.49-3.22 (m, 1H), 2.89 (m, 1H), 2.77-2.63 (m, 1H), 2.20 (m, 1H), 1.84 (m, 1H), 1.54 (m, 1H), 1.43 (m, 1H), 1.33-1.17 (m, 2H), 0.89 (m, 1H), 0.60 (m, 1H), 0.07 (m, 1H). | Method 3: 4.45 min, 628.4 [M + H]$^+$ |
| 50 | 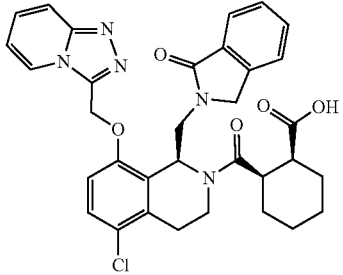 [SMILES: O=C(O)[C@H]1CCCC[C@H]1C(=O)N1CCc2c(Cl)ccc(OCc3nnc4ccccn34)c2[C@H]1CN1Cc2ccccc2C1=O] | (1S,2R)-2-((S)-8-([1,2,4]triazolo[4,3-a]pyridin-3-yl)methoxy)-5-chloro-1-((1-oxoisoindolin-2-yl)methyl)-1,2,3,4-tetrahydroisoquinoline-2-carbonyl)cyclohexane-1-carboxylic acid | 22 | (400 MHz, DMSO-d$_6$) δ 11.66 (bs, 1H), 8.81 (dt, 1H), 7.93 (dt, 1H), 7.58-7.49 (m, 3H), 7.47-7.35 (m, 3H), 7.31 (d, 1H), 7.16 (td, 1H), 5.95-5.77 (m, 3H), 4.20 (d, 1H), 4.13 (dd, 1H), 4.00 (dd, 1H), 3.70 (m, 1H), 3.55 (d, 1H), 3.39-3.25 (m, 1H), 2.87 (dd, 1H), 2.68 (m, 1H), 2.55-2.45 (m, 1H), 2.19 (m, 1H), 1.83 (m, 1H), 1.54 (m, 1H), 1.41 (m, 1H), 1.31-1.15 (m, 2H), 0.89 (m, 1H), 0.60 (m, 1H), 0.06 (m, 1H). | Method 3: 1.23 min, 614 [M + H]$^+$. |
| 51 | 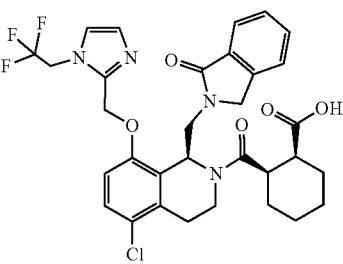 [SMILES: O=C(O)[C@H]1CCCC[C@H]1C(=O)N1CCc2c(Cl)ccc(OCc3nccn3CC(F)(F)F)c2[C@H]1CN1Cc2ccccc2C1=O] | (1S,2R)-2-((S)-5-chloro-1-((1-oxoisoindolin-2-yl)methyl)-8-((1-(2,2,2-trifluoroethyl)-1H-imidazol-2-yl)methoxy)-1,2,3,4-tetrahydroisoquinoline-2-carbonyl)cyclohexane-1-carboxylic acid | 22 | (400 MHz, DMSO-d$_6$) δ 11.66 (bs, 1H), 7.63-7.49 (m, 3H), 7.47-7.37 (m, 3H), 7.21 (d, 1H), 7.12 (d, 1H), 5.93 (dd, 1H), 5.36-5.19 (m, 4H), 4.47 (d, 1H), 4.15 (dd, 1H), 4.00 (dd, 1H), 3.92 (d, 1H), 3.71 (m, 1H), 3.46 (dd, 1H), 3.38-3.25 (m, 1H), 2.87 (dd, 1H), 2.70 (m, 1H), 2.19 (m, 1H), 1.84 (m, 1H), 1.55 (m, 1H), 1.45 (m, 1H), 1.34-1.18 (m, 2H), 0.90 (m, 1H), 0.64 (m, 1H), 0.12 (m, 1H). | Method 3: 4.01 min, 645 [M + H]$^+$. |
| 52 | 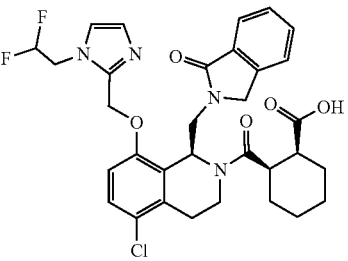 [SMILES: O=C(O)[C@H]1CCCC[C@H]1C(=O)N1CCc2c(Cl)ccc(OCc3nccn3CC(F)F)c2[C@H]1CN1Cc2ccccc2C1=O] | (1S,2R)-2-((S)-5-chloro-8-((1-(2,2-difluoroethyl)-1H-imidazol-2-yl)methoxy)-1-((1-oxoisoindolin-2-yl)methyl)-1,2,3,4-tetrahydroisoquinoline-2-carbonyl)cyclohexane-1-carboxylic acid | 22 | (400 MHz, DMSO-d$_6$) δ 11.70 (bs, 1H), 7.64-7.50 (m, 3H), 7.48-7.33 (m, 3H), 7.23 (d, 1H), 7.06 (d, 1H), 6.42 (m, 1H), 5.95 (dd, 1H), 5.34-5.22 (m, 2H), 4.75 (m, 2H), 4.48 (d, 1H), 4.16 (dd, 1H), 4.06-3.93 (m, 2H), 3.72 (m, 1H), 3.45 (dd, 1H), 3.41-3.22 (m, 1H), 2.88 (dd, 1H), 2.69 (m, 1H), 2.20 (m, 1H), 1.85 (m, 1H), 1.55 (m, 1H), 1.45 (m, 1H), 1.33-1.18 (m, 2H), 0.90 (m, 1H), 0.63 (m, 1H), 0.11 (m, 1H). | Method 3: 3.52 min, 627.1 [M + H]$^+$. |

TABLE 2-continued

| Ex. | Structure | Name | Analogous Example | 1H NMR δ ppm | LCMS |
|---|---|---|---|---|---|
| 53 | 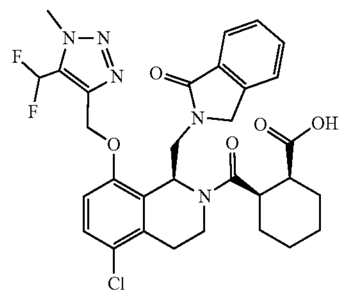 [SMILES: Cn1nnc(COc2ccc(Cl)c3c2[C@@H](CN2Cc4ccccc4C2=O)N(C(=O)[C@@H]2CCCC[C@@H]2C(=O)O)CC3)c1C(F)F] | (1S,2R)-2-((S)-5-chloro-8-((5-(difluoromethyl)-1-methyl-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid | 22 | (400 MHz, DMSO-$d_6$) δ 11.66 (bs, 1H), 7.63 (t, 1H), 7.60 (m, 1H), 7.57-7.53 (m, 2H), 7.47-7.37 (m, 2H), 7.20 (d, 1H), 5.93 (dd, 1H), 5.41-5.31 (m, 2H), 4.49 (d, 1H), 4.22 (s, 3H), 4.15 (dd, 1H), 4.07-3.92 (m, 2H), 3.72 (m, 1H), 3.45 (dd, 1H), 3.41-3.22 (m, 1H), 2.87 (dd, 1H), 2.68 (m, 1H), 2.19 (m, 1H), 1.85 (m, 1H), 1.54 (m, 1H), 1.39 (m, 1H), 1.32-1.16 (m, 2H), 0.89 (m, 1H), 0.57 (m, 1H), 0.06 (m, 1H). | Method 3: 4.44 min, 628.0 [M + H]$^+$ |
| 54 | 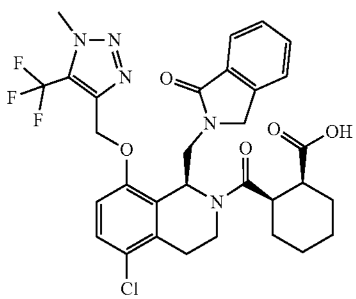 [SMILES: Cn1nnc(COc2ccc(Cl)c3c2[C@@H](CN2Cc4ccccc4C2=O)N(C(=O)[C@@H]2CCCC[C@@H]2C(=O)O)CC3)c1C(F)(F)F] | (1S,2R)-2-((S)-5-Chloro-8-((1-methyl-5-(trifluoromethyl)-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid | 22 | (400 MHz, DMSO-$d_6$) δ 11.66 (bs, 1H), 7.63-7.52 (m, 3H), 7.48-7.38 (m, 2H), 7.21 (d, 1H), 5.93 (dd, 1H), 5.43 (d, 1H), 5.36 (d, 1H), 4.52 (d, 1H), 4.28 (d, 3H), 4.17 (dd, 1H), 4.07 (d, 1H), 3.98 (dd, 1H), 3.73 (m, 1H), 3.44 (dd, 1H), 3.39-3.23 (m, 1H), 2.87 (dd, 1H), 2.69 (m, 1H), 2.19 (m, 1H), 1.85 (m, 1H), 1.55 (m, 1H), 1.37 (m, 1H), 1.31-1.16 (m, 2H), 0.88 (m, 1H), 0.54 (m, 1H), 0.04 (m, 1H). | Method 3: 4.68 min, 646.0 [M + H]$^+$ |
| 55 | 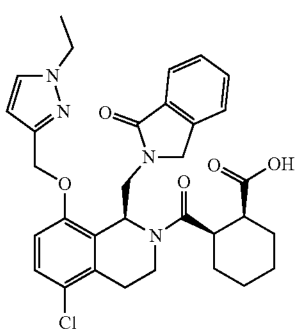 [SMILES: CCn1ccc(COc2ccc(Cl)c3c2[C@@H](CN2Cc4ccccc4C2=O)N(C(=O)[C@@H]2CCCC[C@@H]2C(=O)O)CC3)n1] | (1S,2R)-2-((S)-5-chloro-8-((1-ethyl-1H-pyrazol-3-yl)methoxy)-1-((1-oxoisoindolin-2-yl)methyl)-1,2,3,4-tetrahydroisoquinoline-2-carbonyl)cyclohexane-1-carboxylic acid | 22 | (400 MHz, DMSO-$d_6$) δ 11.67 (bs, 1H), 7.80 (d, 1H), 7.64-7.50 (m, 3H), 7.44 (m, 1H), 7.37 (d, 1H), 7.13 (d, 1H), 6.47 (d, 1H), 5.99 (dd, 1H), 5.16 (d, 1H), 5.11 (d, 1H), 4.55 (d, 1H), 4.22-4.06 (m, 4H), 4.00 (dd, 1H), 3.73 (m, 1H), 3.50 (dd, 1H), 3.43-3.20 (m, 1H), 2.87 (dd, 1H), 2.69 (m, 1H), 2.19 (m, 1H), 1.85 (m, 1H), 1.55 (m, 1H), 1.47-1.32 (m, 4H), 1.32-1.18 (m, 2H), 0.90 (m, 1H), 0.60 (m, 1H), 0.09 (m, 1H). | Method 3: 4.52 min, 591.1 [M + H]$^+$ |
| 57 | 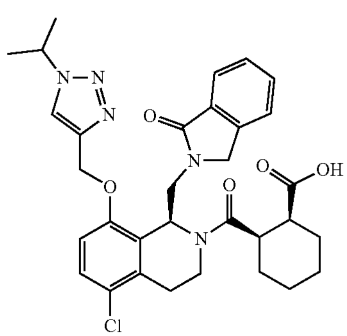 [SMILES: CC(C)n1cc(COc2ccc(Cl)c3c2[C@@H](CN2Cc4ccccc4C2=O)N(C(=O)[C@@H]2CCCC[C@@H]2C(=O)O)CC3)nn1] | (1S,2R)-2-((S)-5-chloro-8-((1-isopropyl-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid | 22 | (400 MHz, DMSO-$d_6$) δ 11.60 (bs, 1H), 8.49 (s, 1H), 7.60 (d, 1H), 7.57 (td, 1H), 7.49 (d, 1H), 7.44 (t, 1H), 7.40 (d, 1H), 7.18 (d, 1H), 5.95 (dd, 1H), 5.32-5.20 (m, 2H), 4.91 (m, 1H), 4.52 (d, 1H), 4.16 (dd, 1H), 4.07 (d, 1H), 4.01 (dd, 1H), 3.73 (m, 1H), 3.51 (dd, 1H), 3.43-3.23 (m, 1H), 2.88 (dd, 1H), 2.68 (m, 1H), 2.20 (m, 1H), 1.84 (m, 1H), 1.61-1.50 (m, 7H), 1.45 (m, 1H), 1.33-1.16 (m, 2H), 0.90 (m, 1H), 0.62 (m, 1H), 0.08 (m, 1H). | Method 3: 4.38 min, 606.1 [M + H]$^+$ |

Example 63

(1S,2R)-2-((S)-5-bromo-1-((2-oxopyrrolidin-1-yl)methyl)-8-(((S)-1-(thiazole-5-carbonyl)pyrrolidin-3-yl)oxy)-1,2,3,4-tetrahydroisoquinoline-2-carbonyl)cyclohexane-1-carboxylic acid

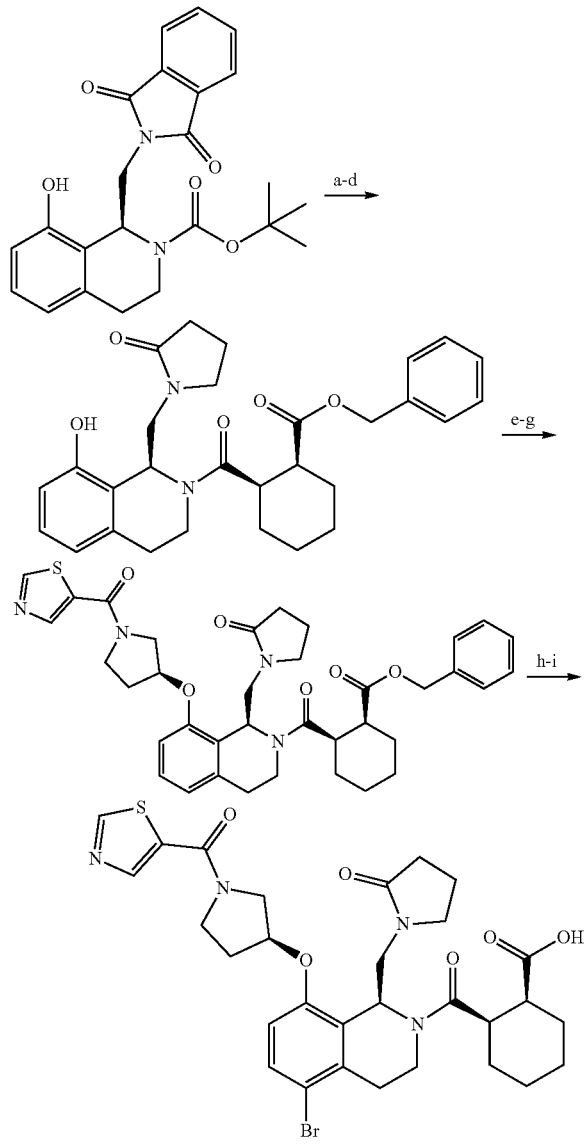

Step a. A solution of Intermediate 11 (3.30 g, 8.10 mmol) and hydrazine hydrate (5.4 ml, 110.2 mmol) in IMS (45 mL) was stirred at rt for 18 h. The reaction mixture was cooled at 0° C., filtered and rinsed with IMS (10 mL). The filtrate was concentrated in vacuo to give (S)-tert-butyl 1-(aminomethyl)-8-hydroxy-3,4-dihydroisoquinoline-2(1H)-carboxylate (2.25 g, quantitative), used without further purification. LCMS (Method 2): 0.92 min, 301.2 [M+Na]+.

Step b. A solution of the above intermediate (2.25 g, 8.10 mmol), Et$_3$N (2.80 mL, 20.2 mmol) and methyl 4-bromobutanoate (CAS: 4897-84-1; 1.61 g, 8.90 mmol) in DMF (35 mL) was heated at 70° C. for 18 h. The reaction mixture was partitioned between EtOAc (25 mL) and water (25 mL) and the aqueous was further extracted with EtOAc (2×25 mL). The combined organic layers were washed with water (50 mL), dried over MgSO$_4$, filtered and concentrated in vacuo. Purification by flash column chromatography (25-85% EtOAc in heptanes) gave (S)-tert-butyl 8-hydroxy-1-((2-oxopyrrolidin-1-yl)methyl)-3,4-dihydroisoquinoline-2(1H)-carboxylate (1.30 g, 46%). LCMS (Method 4a): 1.84 min, 347.2 [M−H]−.

Step c. A solution of the above intermediate (600 mg, 1.70 mmol) in HCl in dioxane (4M; 5 mL) was stirred at rt for 4 h. The reaction mixture was concentrated in vacuo to give (S)-1-((8-hydroxy-1,2,3,4-tetrahydroisoquinolin-1-yl)methyl)pyrrolidin-2-one hydrochloride (0.49 g, quantitative), used without further purification. LCMS (Method 4): 0.49 min, 247.1 [M+H]+.

Step d. To a solution of the above intermediate (490 mg, 1.70 mmol) and Et$_3$N (1.20 mL, 8.70 mmol) in DCM (6 mL) was added dropwise at 0° C. under an atmosphere of argon, a solution of intermediate 26 (490 mg, 1.70 mmol) in DCM (2 mL). The reaction mixture was allowed to warm to rt, stirred for 0.5 h and diluted with saturated aqueous NaHCO$_3$ solution (6 mL). The organic layer was separated by phase separator cartridge and concentrated in vacuo. Purification by flash column chromatography (50-100% EtOAc in heptanes) gave (1S,2R)-benzyl 2-((S)-8-hydroxy-1-((2-oxopyrrolidin-1-yl)methyl)-1,2,3,4-tetrahydroisoquinoline-2-carbonyl)cyclo hexanecarboxylate (579 mg, 69%). LCMS (Method 4): 0.77 min, 491.3 [M+H]+.

Step e. (S)-tert-butyl 3-(((S)-2-((1R,2S)-2-((benzyloxy)carbonyl)cyclohexanecarbonyl)-1-((2-oxopyrrolidin-1-yl)methyl)-1,2,3,4-tetrahydroisoquinolin-8-yl)oxy)-pyrrolidine-1-carboxylate (436 mg, 56%) was synthesised from the above intermediate (504 mg, 0.91 mmol) and (R)-tert-butyl 3-hydroxypyrrolidine-1-carboxylate (CAS: 103057-44-9; 331 mg, 1.33 mmol) using a procedure similar to that described for Example 3, step a. LCMS (Method 4): 0.93 min, 660.5 [M+H]+.

Step f. (1S,2R)-benzyl 2-((S)-1-((2-oxopyrrolidin-1-yl)methyl)-8-((S)-pyrrolidin-3-yloxy)-1,2,3,4-tetrahydroisoquinoline-2-carbonyl)cyclohexanecarboxylate hydrochloride (390 mg, quantitative) was synthesised from the above intermediate (436 mg 0.66 mmol) using a procedure similar to that described for Example 4, step b. LCMS (Method 4a): 0.80 min, 560.3 [M+H]+.

Step g. (1S,2R)-Benzyl 2-((S)-1-((2-oxopyrrolidin-1-yl)methyl)-8-(((S)-1-(thiazole-5-carbonyl)pyrrolidin-3-yl)oxy)-1,2,3,4-tetrahydroisoquinoline-2-carbonyl)cyclohexanecarboxylate (316 mg, 72%) was synthesised from the above intermediate (390 mg, 0.65 mmol) and 2-methylthiazole-5-carboxylic acid (CAS: 20485-41-0; 100 mg, 0.78 mmol) using a procedure similar to that described for Example 5, step a. LCMS (Method 4a): 0.78 min, 671.2 [M+H]+

Step h. (1S,2R)-2-((S)-1-((2-oxopyrrolidin-1-yl)methyl)-8-(((S)-1-(thiazole-5-carbonyl)pyrrolidin-3-yl)oxy)-1,2,3,4-tetrahydroisoquinoline-2-carbonyl)cyclohexanecarboxylic acid (83 mg, 30%) was synthesised from the above intermediate (316 mg, 0.47 mmol) using a procedure similar to that described for Example 2, step e. LCMS (Method 4a): 1.10 min, 581.3 [M+H]+.

Step i. To a stirred solution of the above intermediate (35 mg, 0.060 mmol) in DMF (2 mL) was added NBS (11 mg, 0.064 mmol, CAS: 128-08-5) and the reaction mixture stirred at rt for 24 h. An additional portion of NBS (6 mg, 0.03 mmol) was added and stirring continued for another 24 h. Brine was added and extracted with DCM. The organic was separated, washed with water, dried over MgSO$_4$, filtered and concentrated in vacuo. Purification by MDAP (Method 3) provided the title compound (22 mg, 55%). LCMS (Method 3) 3.69 min, 661.2 [M+H]$^+$. $^1$H NMR (400 MHz, DMSO-d$_6$; rotamers observed, both reported) δ 11.70 (bs, 1H), 9.26 (m, 1H), 8.46 (s, 0.5H), 8.42 (s, 0.5H), 7.51 (m, 1H), 6.95 (d, 1H), 5.80 (m, 1H), 5.19 (m, 0.5H), 5.13 (m, 0.5H), 4.25 (dd, 0.5H), 4.08-3.80 (m, 4.5H), 3.75 (m, 0.5H), 3.68-3.50 (m, 2H), 3.50-3.14 (m, 1.5H), 3.04 (m, 1H), 2.95 (dd, 0.5H), 2.88 (dd, 0.5H), 2.83-2.57 (m, 2H), 2.44-1.94 (m, 6H), 1.94-1.59 (m, 5H), 1.58-1.33 (m, 2H), 1.28-0.94 (m, 2H).

Example 64

(1S,2R)-2-((S)-8-[(1,2,4]triazolo[4,3-a]pyridin-3-ylmethoxy)-5-bromo-1-((2-oxopyrrolidin-1-yl)methyl)-1,2,3,4-tetrahydroisoquinoline-2-carbonyl)cyclohexane-1-carboxylic acid

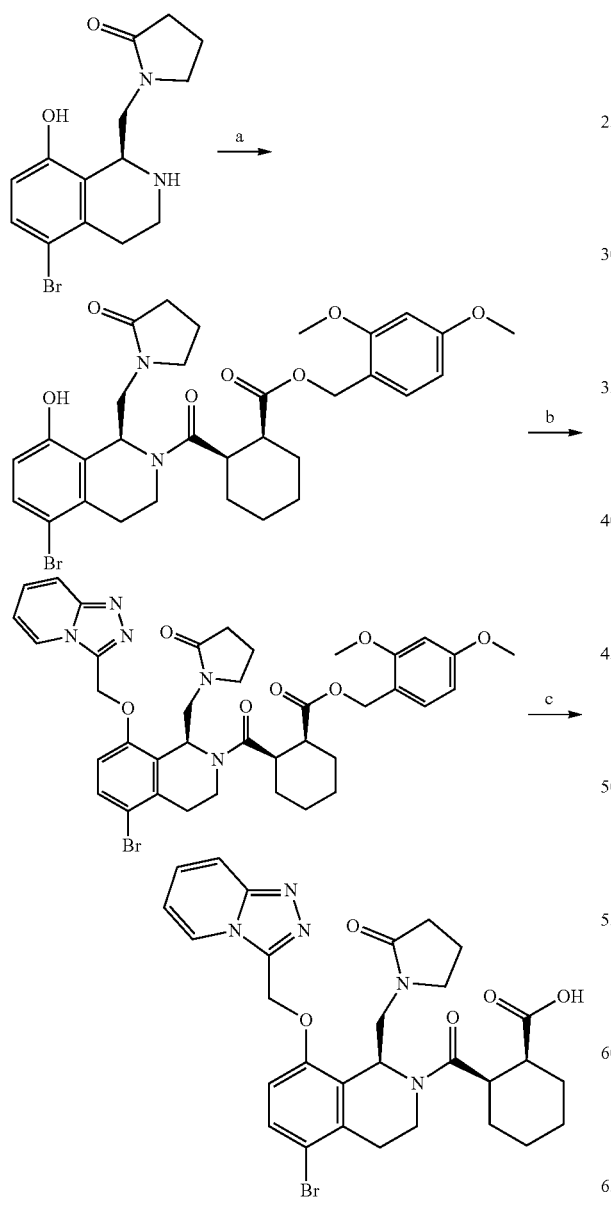

Step a. 2,4-Dimethoxybenzyl (1S,2R)-2-((S)-5-bromo-8-hydroxy-1-((2-oxopyrrolidin-1-yl)methyl)-1,2,3,4-tetrahydroisoquinoline-2-carbonyl)cyclohexane-1-carboxylate (1.097 g, 78%) was prepared from Intermediate 21 (730 mg, 2.24 mmol) and Intermediate 28 (872 mg, 2.71 mmol) using a procedure similar to that described for Example 11, step d. The crude product was purified by flash column chromatography on the Teledyne ISCO CombiFlash® Rf+ (80 g silica column Puriflash HC, 0-100% EtOAc in DCM). LCMS (Method 2): 1.62 min, 651.3 [M+Na]$^+$.

Step b. 2,4-Dimethoxybenzyl (1S,2R)-2-((S)-8-([1,2,4]triazolo[4,3-a]pyridin-3-ylmethoxy)-5-bromo-1-((2-oxopyrrolidin-1-yl)methyl)-1,2,3,4-tetrahydroisoquinoline-2-carbonyl)cyclohexane-1-carboxylate (121 mg, assumed quantitative) was prepared from the above intermediate (100 mg, 0.16 mmol) and (3-(chloromethyl)-[1,2,4]triazolo[4,3-a]pyridine (from Example 16 step b; 40 mg, 0.24 mmol) using a procedure similar to that described for Example 11, step b. LCMS (Method 2): 1.45 min, 759 [M+H]$^+$.

Step c. The title compound (14 mg, 14%) was prepared from the above intermediate (121 mg, 0.16 mmol) using a procedure similar to that described for Example 11, step e. The crude product was purified by preparative HPLC (Method 1). LCMS (Method 3): 3.42 min, 610.2 [M+H]$^+$. $^1$H NMR (400 MHz, DMSO-d$_6$) δ 11.70 (bs, 1H), 8.71 (dt, 1H), 7.87 (dt, 1H), 7.58 (d, 1H), 7.48 (m, 1H), 7.20 (d, 1H), 7.12 (td, 1H), 5.91-5.69 (m, 3H), 3.94 (dd, 1H), 3.81 (dd, 1H), 3.57 (m, 1H), 3.41-3.23 (m, 1H), 3.05 (m, 1H), 2.87-2.73 (m, 2H), 2.73-2.61 (m, 1H), 2.42-2.27 (m, 2H), 2.21-2.01 (m, 2H), 1.99-1.87 (m, 1H), 1.76-1.54 (m, 5H), 1.53-1.42 (m, 1H), 1.38 (m, 1H), 1.28-0.95 (m, 2H).

Example 68

(1S,2R)-2-((S)-8-(Benzo[d]isothiazol-3-ylmethoxy)-5-chloro-1-((2-oxopyrrolidin-1-yl)methyl)-1,2,3,4-tetrahydroisoquinoline-2-carbonyl)cyclohexane-1-carboxylic acid

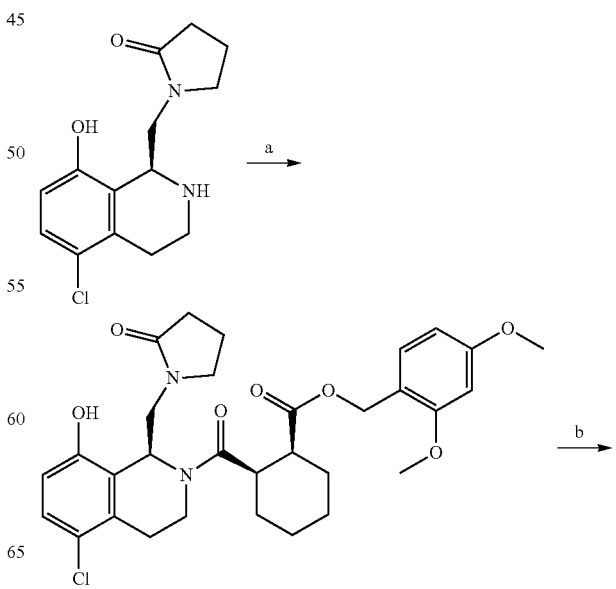

197
-continued

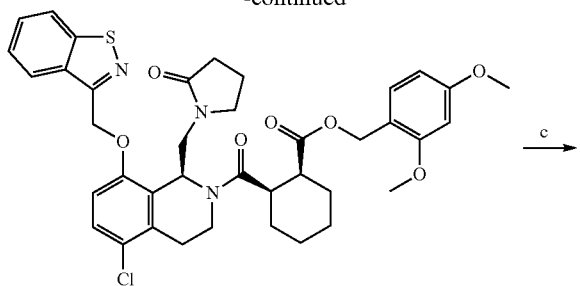

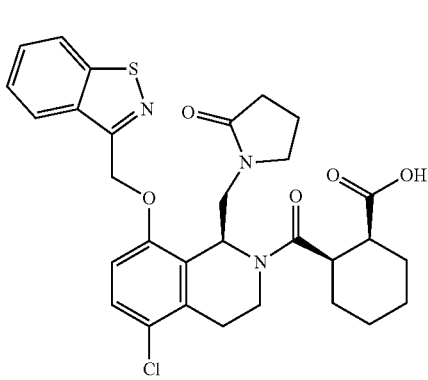

Step a. 2,4-Dimethoxybenzyl (1S,2R)-2-((S)-5-chloro-8-hydroxy-1-((2-oxopyrrolidin-1-yl)methyl)-1,2,3,4-tetrahydroisoquinoline-2-carbonyl)cyclohexane-1-carboxylate (169 mg, 54%) was prepared from Intermediate 28 (180 mg, 0.56 mmol) and Intermediate 24 (150 mg, 0.53 mmol) using the method described for Example 11, step d. The crude product was purified by flash column chromatography on the Teledyne ISCO CombiFlash Rf 200™ (25 g silica column, 0-10% MeOH in DCM) then triturated with MeCN-diethylether. LCMS (Method 2): 1.57 min, 607.4 [M+Na]⁺.

Step b. 2,4-Dimethoxybenzyl (1S,2R)-2-((S)-8-(benzo[d]isothiazol-3-ylmethoxy)-5-chloro-1-((2-oxopyrrolidin-1-yl)methyl)-1,2,3,4-tetrahydroisoquinoline-2-carbonyl)-cyclohexane-1-carboxylate (100 mg, 100%) was prepared from the above intermediate (81 mg, 0.14 mmol) and 3-(bromomethyl)-1,2-benzothiazole (47 mg, 0.21 mmol, CAS: 59057-83-9) using a procedure similar to that described for Example 11, step b. The crude product was purified by flash column chromatography on the Teledyne ISCO Combi-Flash® Rf200 (12 g silica column Puriflash HC, 20-100% EtOAc in cyclohexane). LCMS (Method 2): 1.79 min, 754.3 [M+Na]⁺.

Step c. The title compound (48 mg, 62%) was prepared from the above intermediate (98 mg, 0.13 mmol) using a procedure similar to that described for Example 11, step e. The crude product was purified by preparative HPLC (Method 1). LCMS (Method 3): 4.71 min, 582.1 [M+H]⁺.
¹H NMR (400 MHz, DMSO-d₆) δ 11.70 (bs, 1H), 8.33 (m, 1H), 8.28 (m, 1H), 7.67 (m, 1H), 7.58 (m, 1H), 7.40 (d, 1H), 7.19 (d, 1H), 5.83 (dd, 1H), 5.68 (d, 1H), 5.61 (d, 1H), 3.94 (dd, 1H), 3.84 (dd, 1H), 3.60 (m, 1H), 3.40-3.21 (m, 1H), 3.16 (m, 1H), 2.98 (dd, 1H), 2.83 (dd, 1H), 2.69 (m, 1H), 2.54-2.44 (m, 1H), 2.33 (m, 1H), 2.20-2.01 (m, 2H), 1.94 (m, 1H), 1.80-1.56 (m, 5H), 1.49 (m, 1H), 1.39 (m, 1H), 1.27-0.97 (m, 2H).

198
Example 73

(1S,2R)-2-((1S)-5-Bromo-8-((1-isopropyl-1H-1,2,3-triazol-4-yl)methoxy)-1-((3-methyl-2-oxopyrrolidin-1-yl)methyl)-1,2,3,4-tetrahydroisoquinoline-2-carbonyl)cyclohexane-1-carboxylic acid (Isomer 1) and Example 74: (1S,2R)-2-((1S)-5-Bromo-8-((1-isopropyl-1H-1,2,3-triazol-4-yl)methoxy)-1-((3-methyl-2-oxopyrrolidin-1-yl)methyl)-1,2,3,4-tetrahydroisoquinoline-2-carbonyl)cyclohexane-1-carboxylic acid (Isomer 2)

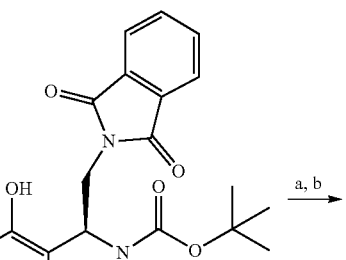

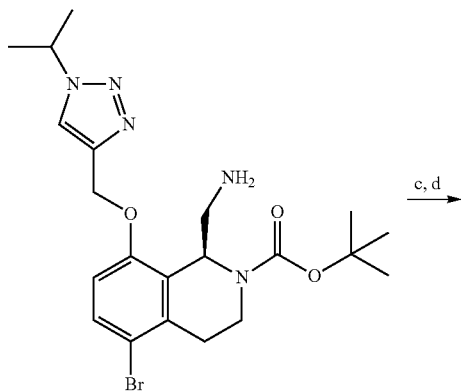

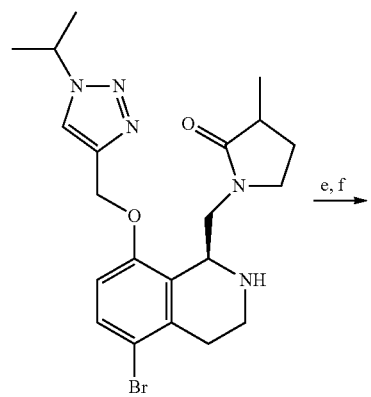

-continued

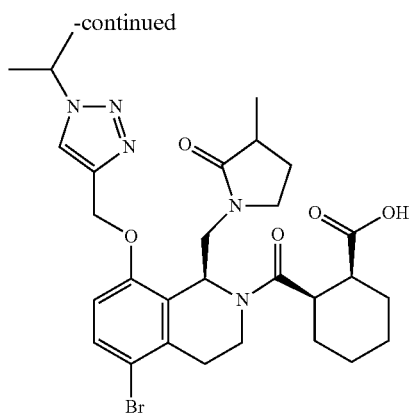

Step a. tert-Butyl (S)-5-bromo-1-((1,3-dioxoisoindolin-2-yl)methyl)-8-((1-isopropyl-1H-1,2,3-triazol-4-yl)methoxy)-3,4-dihydroisoquinoline-2(1H)-carboxylate (1.02 g, 81%) was synthesised from Intermediate 8 (1.0 g, 2.05 mmol) and (1-isopropyltriazol-4-yl)methanol (377 mg, 2.67 mmol) using a procedure similar to that described for Example 3, step a. LCMS (Method 2): 1.74 min, 610.2 [M+H]$^+$.

Step b. tert-Butyl (S)-1-(aminomethyl)-5-bromo-8-((1-isopropyl-1H-1,2,3-triazol-4-yl)methoxy)-3,4-dihydroisoquinoline-2(1H)-carboxylate (462 mg, 51%) was synthesised from the above intermediate using a procedure similar to that described for Intermediate 19. LCMS (Method 2): 1.15 min, 480.3 [M+H]$^+$.

Step c. To a stirred solution of the above intermediate (20 mg, 0.420 mmol) in toluene (5 mL) was added methyl 4-bromo-2-methyl-butanoate (106 mg, 0.540 mmol; CAS: 58029-83-7) and triethylamine (0.087 mL, 0.62 mmol). The reaction mixture was heated at reflux for 24 h, cooled to rt and concentrated in vacuo. The mixture was diluted with water, extracted with ethyl acetate, separated and the combined organics dried over MgSO$_4$, filtered and concentrated in vacuo. Purification by flash column chromatography on the Teledyne ISCO CombiFlash® Rf+ (24 g silica column Puriflash HC/Biotage SNAP, 0-100% EtOAc in cyclohexane) gave tert-butyl (1S)-5-bromo-8-((1-isopropyl-1H-1,2,3-triazol-4-yl)methoxy)-1-((3-methyl-2-oxopyrrolidin-1-yl)methyl)-3,4-dihydroisoquinoline-2(1H)-carboxylate (176 mg, 76%) as a mixture of diastereoisomers. LCMS (Method 2): 1.61 min, 562.3 [M+H]$^+$.

Step d. 1-(((S)-5-Bromo-8-((1-isopropyl-1H-1,2,3-triazol-4-yl)methoxy)-1,2,3,4-tetrahydroisoquinolin-1-yl)methyl)-3-methylpyrrolidin-2-one (mixture of diastereoisomers; 1.02 g, 81%) was synthesised from the above intermediate using a procedure similar to that described for Example 11, step c. LCMS (Method 2): 0.92 & 0.94 min, 462.3 [M+H]$^+$.

Step e. 2,4-Dimethoxybenzyl (1S,2R)-2-((1S)-5-bromo-8-((1-isopropyl-1H-1,2,3-triazol-4-yl)methoxy)-1-((3-methyl-2-oxopyrrolidin-1-yl)methyl)-1,2,3,4-tetrahydroisoquinoline-2-carbonyl)cyclohexane-1-carboxylate (mixture of diastereoisomers; 237 mg, 98%) was prepared from the above intermediate (145 mg, 0.31 mmol) and Intermediate 28 (121 mg, 0.38 mmol) using a procedure similar to that described for Example 11, step d. LCMS (Method 2): 1.64 & 1.67 min, 766 [M+H]$^+$.

Step f. (1S,2R)-2-((1S)-5-Bromo-8-((1-isopropyl-1H-1,2,3-triazol-4-yl)methoxy)-1-((3-methyl-2-oxopyrrolidin-1-yl)methyl)-1,2,3,4-tetrahydroisoquinoline-2-carbonyl)-cyclohexane-1-carboxylic acid (mixture of diastereoisomers; 64 mg, 33%) was prepared from the above intermediate (237 mg, 0.31 mmol) using a procedure similar to that described for Example 11, step e. The crude product was purified by MDAP (Method 1). LCMS (Method 3): 4.20 min, 616.1 [M+H]$^+$.

The mixture of isomers was separated by SFC (YMC Cellulose-SC 35/65 MeOH (0.1% DEA)/CO2, 15 mL/min, 120 bar, 40° C., System 185 bar, DAD 215 nM. Prep.: 1 47 mg in 1.5 mL MeOH, 1 vial, approximately 31 mg/mL, injections 300 uL×6; CT 3.75/0.5 mins. Post Prep: SFC4 YMC Cellulose-SC 35/65 MeOH (0.1% DEA)/CO2, 0.95 mL/min, 120 bar, 40° C. Isomers observed at 2.4 and 3.1 min post run. Purification gave Example 73 (isomer 1; 13 mg, 20%) and Example 74 (isomer 2; 15 mg, 23%).

Example 73

LCMS (Method 3): 4.19 min, 616.1 [M+H]$^+$. $^1$H NMR (400 MHz, DMSO-d$_6$) δ 8.43 (s, 1H), 7.52 (d, 1H), 7.08 (d, 1H), 5.77 (dd, 1H), 5.25-5.11 (m, 2H), 4.87 (m, 1H), 3.94 (dd, 1H), 3.86 (dd, 1H), 3.58 (m, 1H), 3.47-3.19 (m, 2H), 3.02 (dd, 1H), 2.83-2.60 (m, 3H), 2.33 (m, 1H), 2.20-1.97 (m, 3H), 1.77-1.61 (m, 3H), 1.57-1.30 (m, 9H), 1.25-1.09 (m, 2H), 0.99 (d, 3H).

Example 74

LCMS (Method 3): 4.20 min, 616.1 [M+H]$^+$. $^1$H NMR (400 MHz, DMSO-d$_6$) δ 8.43 (s, 1H), 7.52 (d, 1H), 7.07 (d, 1H), 5.82 (dd, 1H), 5.23-5.12 (m, 2H), 4.86 (m, 1H), 3.97 (m, 1H), 3.80 (dd, 1H), 3.59 (m, 1H), 3.50-3.14 (m, 2H), 3.01 (dd, 1H), 2.87-2.63 (m, 3H), 2.36 (m, 1H), 2.26 (m, 1H), 2.14-1.99 (m, 2H), 1.76-1.61 (m, 3H), 1.59-1.44 (m, 7H), 1.42-1.10 (m, 4H), 0.97 (d, 3H).

Example 79

(1S,2R)-2-((S)-5-Chloro-8-((5-(difluoromethyl)-1-ethyl-1H-1,2,3-triazol-4-yl)methoxy)-1-((2-oxopyrrolidin-1-yl)methyl)-1,2,3,4-tetrahydroisoquinoline-2-carbonyl)cyclohexane-1-carboxylic acid

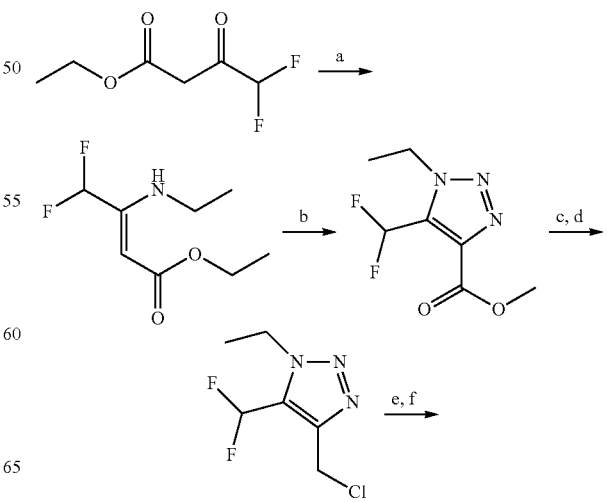

201

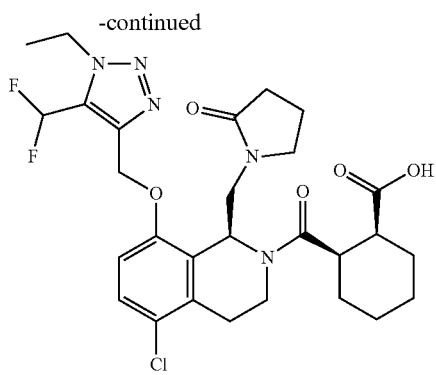

Step a. To a stirred solution of ethyl 4,4-difluoro-3-oxo-butanoate (4.01 g, 24.1 mmol, CAS: 352-24-9) and AcOH (1.38 mL, 24.1 mmol) in anhydrous chloroform (50 mL) under argon at 0° C., was added ethanamine (2.0 M in THF; 12.1 mL, 24.1 mmol) dropwise, maintaining a temperature of <10° C. The resulting solution was then heated at reflux for 21 h. The mixture was allowed to cool to rt, then poured carefully into saturated aqueous NaHCO$_3$ solution (80 mL). The mixture was diluted with water extracted into EtOAc. The organic layer was washed with 5% aqueous NaHCO$_3$ (30 mL), water (30 mL), brine (30 mL), dried over Na$_2$SO$_4$, filtered and concentrated in vacuo to provide ethyl (Z)-3-(ethylamino)-4,4-difluorobut-2-enoate (4.42 g, 95%), used without further purification. $^1$H NMR (400 MHz; CDCl$_3$; mixture of imine and enamine tautomers) δ 7.96 (s, 0.6H), 7.50 (t, 0.4H), 5.99 (t, 0.6H), 4.75 (s, 1.2H), 4.17-4.10 (m, 2H), 3.41-3.33 (m, 1.2H), 3.06 (m, 0.8H), 1.30-1.22 (m, 6H).

Step b. To a stirred solution of the above intermediate (0.44 g, 2.27 mmol) in anhydrous MeCN (95 mL) under argon, at −20° C. was added DBU (1 mL, 6.8 mmol) followed by dropwise addition of a solution of methanesulfonyl azide (0.82 g, 6.8 mmol, CAS: 1516-70-7) in anhydrous MeCN (2 mL) over 15 min, maintaining a temperature of <−19° C. The resulting solution was allowed to warm slowly to rt over 2 h then stirred at rt for 18 h. The mixture was concentrated in vacuo and the residue partitioned between EtOAc (15 mL) and saturated aqueous KHSO$_4$ (10 mL). The aqueous layer was extracted with EtOAc (15 mL) and the combined organics were washed with saturated aqueous KHSO$_4$ (4×10 mL), water (10 mL), brine (10 mL), dried over Na$_2$SO$_4$, filtered and concentrated in vacuo. Purification by flash column chromatography on the Teledyne ISCO CombiFlash® Rf 200 (40 g silica column Puriflash HC, 0-100% EtOAc in isohexane) gave ethyl 5-(difluoromethyl)-1-ethyl-1H-1,2,3-triazole-4-carboxylate (0.26 g, 53%). $^1$H NMR (400 MHz; CDCl$_3$) δ 7.53 (t, 1H), 4.64 (q, 2H), 4.47 (q, 2H), 1.62 (t, 3H), 1.45 (t, 3H).

Step c. To a stirred solution of the above intermediate (257 mg, 1.17 mmol) in EtOH (3 mL) and THF (1.5 mL) under argon was added lithium chloride (110 mg, 2.58 mmol) and sodium borohydride (98 mg, 2.58 mmol) and the resulting mixture was stirred at rt for 22 h. The mixture was diluted with citric acid (10% aqueous; 5 mL) and extracted with DCM (5×10 mL). The combined organics were dried over Na$_2$SO$_4$, filtered and concentrated in vacuo to give (5-(difluoromethyl)-1-ethyl-1H-1,2,3-triazol-4-yl)methanol (205 mg, 98%), used without further purification. $^1$H NMR (400 MHz; CDCl$_3$) δ 7.10 (t, 1H), 4.92 (s, 2H), 4.55 (q, 2H), 2.20 (br s, 1H), 1.59 (t, 3H).

Step d. To a stirred solution of the above intermediate (204 mg, 1.15 mmol) in chloroform (5 mL) under argon was added thionyl chloride (0.17 mL, 2.31 mmol) dropwise and the resulting mixture was stirred at rt for 2 h. The reaction mixture was concentrated in vacuo to give 4-(chloromethyl)-5-(difluoromethyl)-1-ethyl-1H-1,2,3-triazole (235 mg, assumed quantitative), used without further purification. $^1$H NMR (400 MHz; CDCl$_3$) δ 7.00 (t, 1H), 4.76 (s, 2H), 4.53 (q, 2H), 1.60 (t, 3H).

Steps e,f. The title compound (29 mg, 35%) was prepared from the above intermediate (69 mg, 0.35 mmol) and 2,4-dimethoxybenzyl (1S,2R)-2-((S)-5-chloro-8-hydroxy-1-((2-oxopyrrolidin-1-yl)methyl)-1,2,3,4-tetrahydroisoquinoline-2-carbonyl)cyclohexane-1-carboxylate (from Example 68 step a; 81 mg, 0.14 mmol) using procedures similar to those described for Example 68, steps b,c. LCMS (Method 3): 4.13 min, 594.1 [M+H]$^+$. $^1$H NMR (400 MHz, DMSO-d$_6$) δ 11.66 (bs, 1H), 7.63 (t, 1H), 7.38 (d, 1H), 7.15 (d, 1H), 5.76 (dd, 1H), 5.38-5.22 (m, 2H), 4.56 (m, 2H), 3.95 (dd, 1H), 3.84 (dd, 1H), 3.59 (m, 1H), 3.45-3.20 (m, 2H), 2.93 (dd, 1H), 2.88-2.61 (m, 3H), 2.33 (m, 1H), 2.21-2.04 (m, 2H), 1.99 (m, 1H), 1.89-1.61 (m, 5H), 1.56-1.34 (m, 5H), 1.15 (m, 2H).

Example 80

(R)-4-((S)-8-(Benzo[d]isoxazol-3-ylmethoxy)-5-chloro-1-((2-oxopyrrolidin-1-yl)methyl)-3,4-dihydroisoquinolin-2(1H)-yl)-3-methyl-4-oxobutanoic acid

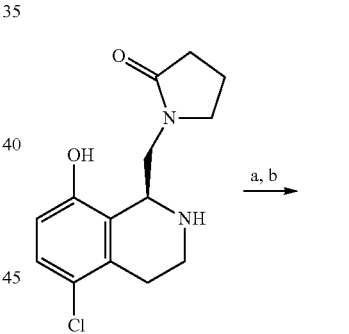

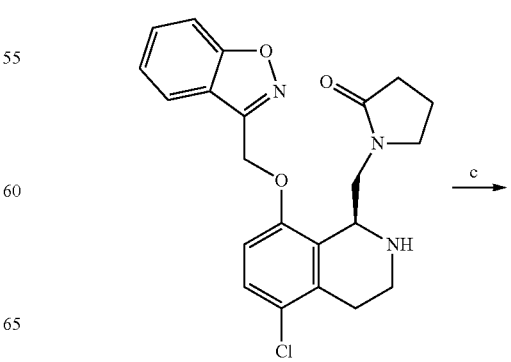

-continued

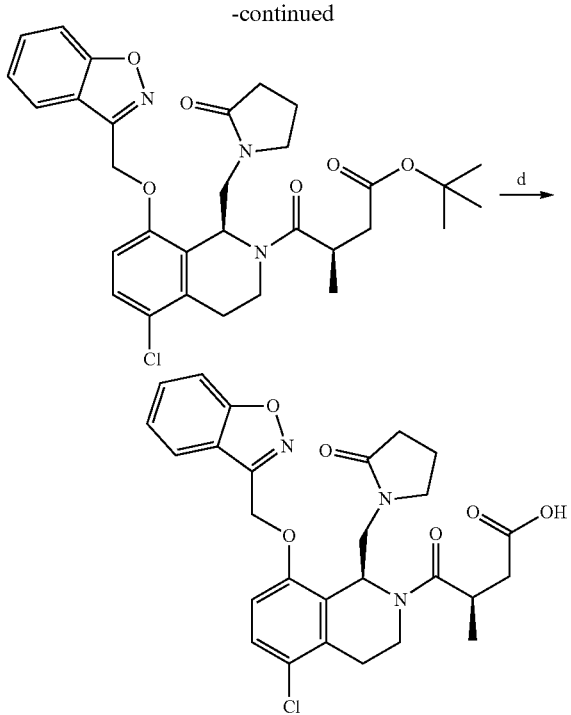

Step a. tert-Butyl (S)-8-(benzo[d]isoxazol-3-ylmethoxy)-5-chloro-1-((2-oxopyrrolidin-1-yl)methyl)-3,4-dihydroisoquinoline-2(1H)-carboxylate (1.58 g, 64%) was prepared from Intermediate 23 (1.85 g, 4.86 mmol) and 3-(bromomethyl)-1,2-benzoxazole (1.24 g, 5.83 mmol, CAS: 37924-85-9) using a procedure similar to that described for Example 68 step b. The crude product was purified by flash column chromatography on the Teledyne ISCO CombiFlash® Rf+ (80 g silica column Puriflash HC, 10-90% EtOAc in isohexane). LCMS (Method 2): 1.62 min, 534.3 [M+Na]+.

Step b. (S)-1-((8-(Benzo[d]isoxazol-3-ylmethoxy)-5-chloro-1,2,3,4-tetrahydro-isoquinolin-1-yl)methyl)pyrrolidin-2-one hydrochloride (1.41 g, assumed quantitative) was prepared from the above intermediate (1.58 g, 3.09 mmol) using a procedure similar to that described for Example 1, step d and used without further purification. LCMS (Method 2): 0.93 min, 412.2 [M−H]−.

Step c. tert-Butyl (R)-4-((S)-8-(benzo[d]isoxazol-3-ylmethoxy)-5-chloro-1-((2-oxopyrrolidin-1-yl)methyl)-3,4-dihydroisoquinolin-2(1H)-yl)-3-methyl-4-oxobutanoate (153 mg, 82%) was prepared from the above intermediate (144 mg, 0.32 mmol) and (R)-4-(tert-butoxy)-2-methyl-4-oxobutanoic acid (79 mg, 0.42 mmol, CAS: 185836-75-3) using a procedure similar to that described for Example 11, step d. The crude product was purified by flash column on the Teledyne ISCO CombiFlash® Rf+ (24 g silica column Puriflash HC, 0-5% MeOH in DCM). LCMS (Method 2): 1.56 min, 582.4 [M+H]+.

Step d. To a solution of the above intermediate (153 mg, 0.26 mmol) in DCM (5 mL) was added TFA (0.5 mL, 6.53 mmol) and the reaction mixture stirred at rt for 2.5 h. The solvent was removed in vacuo, and the residue azeotroped in vacuo with toluene. Purification by preparative HPLC (Method 1) gave the title compound (79 mg, 56%). LCMS (Method 3): 4.04 min, 526.1 [M+H]+. 1H NMR (400 MHz, DMSO-d6) δ 11.97 (bs, 1H), 8.04 (dt, 1H), 7.83 (dt, 1H), 7.72 (m, 1H), 7.47 (m, 1H), 7.43 (d, 1H), 7.20 (d, 1H), 5.87 (dd, 1H), 5.71 (d, 1H), 5.62 (d, 1H), 4.05 (dd, 1H), 3.89 (dd, 1H), 3.64 (m, 1H), 3.42-3.21 (m, 1H), 3.16 (m, 1H), 3.01 (dd, 1H), 2.91-2.71 (m, 2H), 2.62-2.45 (m, 2H), 2.22 (dd, 1H), 2.07 (m, 1H), 1.93 (m, 1H), 1.64 (m, 2H), 0.93 (d, 3H).

Example 81

1-(((S)-2-((1R,2S)-2-(2H-tetrazol-5-yl)cyclohexane-1-carbonyl)-8-(benzo[d]isoxazol-3-ylmethoxy)-5-chloro-1,2,3,4-tetrahydroisoquinolin-1-yl)methyl)pyrrolidin-2-one

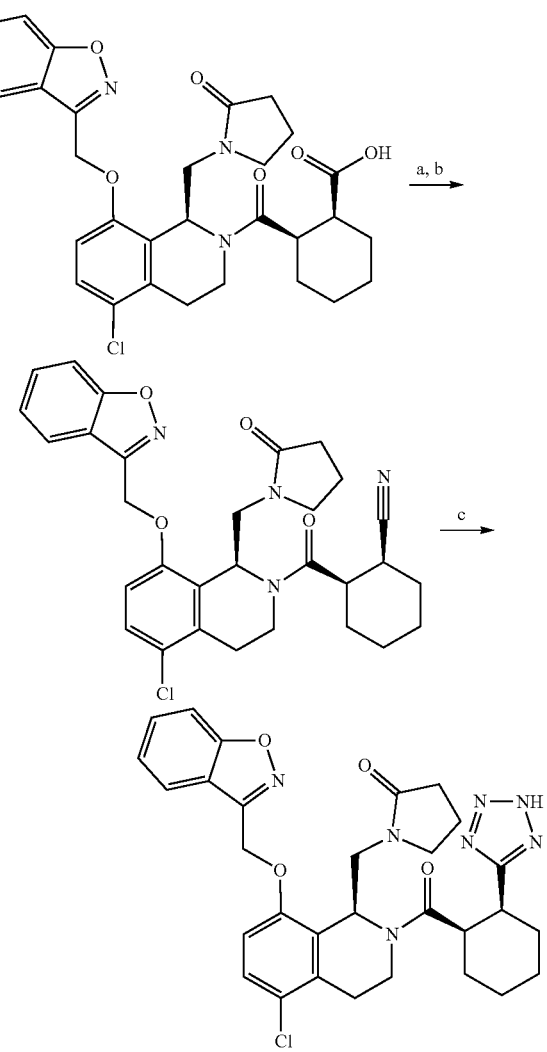

Step a. To a stirred solution of Example 72 (372 mg, 0.66 mmol) in DMF (9 mL) was added DIPEA (0.57 mL, 3.29 mmol) and HATU (275 mg, 0.72 mmol; CAS: 148893-10-1) and the reaction mixture was stirred at rt for 10 min. To this was added ammonium chloride (105 mg, 1.97 mmol) and the reaction mixture stirred at rt under argon for 18 h. The reaction mixture was partitioned between saturated aqueous NaHCO3 solution (40 mL) and EtOAc (40 mL), water (20 mL) and brine (20 mL). The aqueous layer was extracted further with EtOAc (2×40 mL) and the combined organics washed with brine (40 mL), dried over Na2SO4, filtered and concentrated in vacuo. The crude product was purified by flash column chromatography on the Teledyne ISCO CombiFlash® Rf200 (25 g silica column, 0-10% MeOH in DCM) to provide (1S,2R)-2-((S)-8-(benzo[d]isoxazol-3-ylmethoxy)-5-chloro-1-((2-oxopyrrolidin-1-yl)methyl)-1,2,3,4-tetrahydroisoquinoline-2-carbonyl)cyclohexane-1-carboxamide (356 mg, 0.63 mmol). LCMS (Method 2): 1.23 min, 587.3 [M+Na]$^+$.

Step b. To a stirred solution of the above intermediate (295 mg, 0.52 mmol) and imidazole (39 mg, 0.57 mmol) in pyridine (2 mL) under argon cooled to −20° C. was added dropwise phosphorous oxychloride (0.12 mL, 1.31 mmol) and the resulting mixture stirred at −20° C. for 35 min. The mixture was concentrated in vacuo and the residue partitioned between 10% citric acid (20 mL) and DCM (50 mL). The aqueous layer was extracted further with DCM (30 mL) and the combined organics washed with brine (40 mL), dried over Na$_2$SO$_4$, filtered and concentrated in vacuo. The crude product was purified by flash column chromatography on the Teledyne ISCO CombiFlash® Rf200 (4 g silica column, 0-10% MeOH in DCM) to provide (1S,2R)-2-((S)-8-(benzo[d]isoxazol-3-ylmethoxy)-5-chloro-1-((2-oxopyrrolidin-1-yl)methyl)-1,2,3,4-tetrahydroisoquinoline-2-carbonyl)cyclohexane-1-carbonitrile (193 mg, 68%). LCMS (Method 2): 1.38 min, 547.3 [M+H]$^+$.

Step c. To a solution of the above intermediate (61 mg, 0.11 mmol) in m-xylene (3 mL) in a reaction tube was added azidotri-n-butyltin(IV) (0.15 mL, 0.56 mmol; CAS: 17846-68-3). The tube was sealed and the mixture was heated at 140° C. for 19 h. Additional azidotri-n-butyltin(IV) (0.09 mL, 0.33 mmol) was added and the mixture was heated at 140° C. for a further 23 h. The reaction mixture was poured into water (15 mL) and the crude product was extracted into DCM (2×20 mL). The combined organics were dried over MgSO$_4$, filtered and concentrated in vacuo. Purification by flash column chromatography on the Teledyne ISCO CombiFlash® Rf200 (4 g silica column Puriflash HC, 0-10% MeOH in DCM) followed by purification by preparative HPLC (Method 3) gave the title compound (43 mg, 65%). LCMS (Method 12): 2.96 min, 590.4 [M+H]$^+$. $^1$H NMR (400 MHz, DMSO-d$_6$) δ 7.98 (m, 1H), 7.81 (m, 1H), 7.70 (m, 1H), 7.44-7.38 (m, 2H), 7.16 (d, 1H), 5.77-5.62 (m, 2H), 5.57 (d, 1H), 4.01 (dd, 1H), 3.83 (dd, 1H), 3.61 (m, 1H), 3.53 (m, 1H), 3.15 (m, 2H), 2.97-2.70 (m, 3H), 2.60-2.42 (m, 1H), 2.26 (m, 1H), 2.09 (m, 1H), 2.02-1.76 (m, 4H), 1.69-1.54 (m, 3H), 1.48 (m, 1H), 1.43-1.32 (m, 2H).

Example 84

(1S,2R)-2-((S)-5-chloro-8-((5-(difluoromethyl)-1-methyl-1H-1,2,3-triazol-4-yl)methoxy)-1-((4-methyl-1H-pyrazol-1-yl)methyl)-1,2,3,4-tetrahydroisoquinoline-2-carbonyl)cyclohexane-1-carboxylic acid

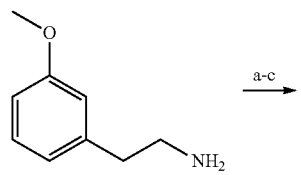

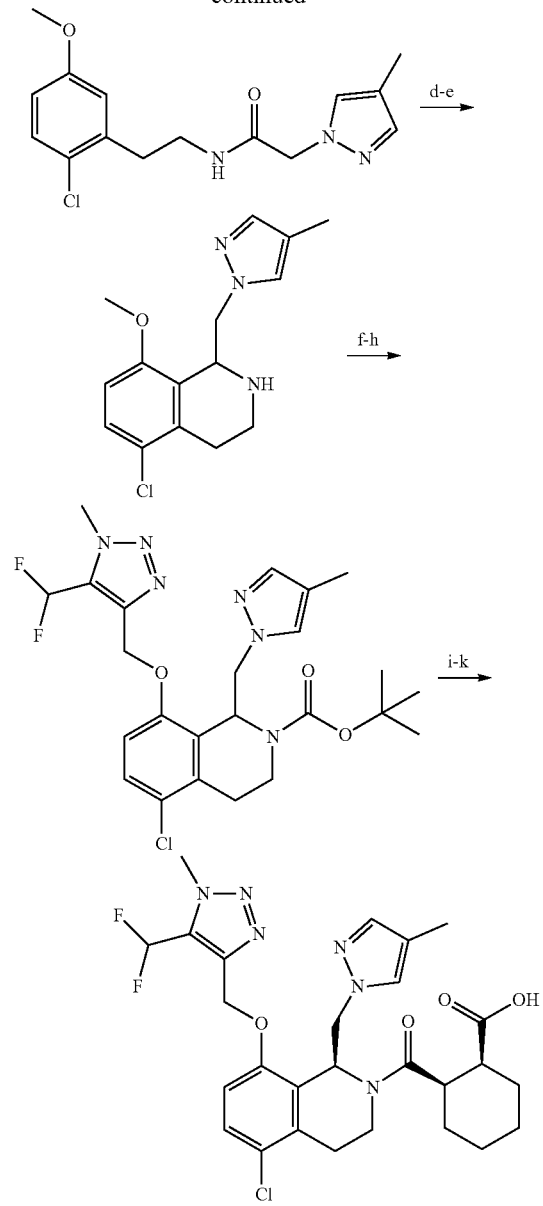

Step a. To a stirred solution of 2-(3-methoxyphenyl)ethan-1-amine (5.0 g, 33.1 mmol, CAS: 2039-67-0) in acetic acid (50 mL) at rt was added sulfuryl chloride (4.0 mL, 49.6 mmol) dropwise and the reaction mixture stirred at rt for 4 h. The mixture was concentrated in vacuo, the residue diluted with NaHCO$_3$ (100 mL) and extracted with EtOAc (3×100 mL). The combined organic extracts were washed with brine (100 mL) and dried (Na$_2$SO$_4$). The crude product was purified by flash column chromatography on the Teledyne ISCO CombiFlash® Rf+ (40 g silica column Puriflash HC/Biotage SNAP, 0-100% methanolic ammonia in DCM (2M; 20:1) in DCM) to give 2-(2-chloro-5-methoxyphenyl)ethan-1-amine (3.83 g, 62%). LCMS (Method 2): 0.74 min, 168.9 [M+H]$^+$.

Step b. To a stirred solution of the above intermediate (3.79 g, 20.4 mmol) in DCM (30 mL) at 0° C. was added triethylamine (5.7 mL, 40.8 mmol) and 2-chloroacetyl chloride (1.63 mL, 20.4 mmol CAS: 79-04-9) dropwise and the mixture stirred at rt for 2 h. The reaction mixture was diluted with saturated ammonium chloride solution (200 mL), extracted with DCM (100 mL), and the organics dried over MgSO$_4$ and concentrated in vacuo. Purification by flash column chromatography on the Biotage Companion (Puriflash cartridge 220 g, 0-70% EtOAc in cyclohexane) gave 2-chloro-N-(2-chloro-5-methoxyphenethyl)acetamide (2.66 g, 50%). LCMS (Method 2): 1.26 min, 261.9 [M+H]$^+$.

Step c. To a stirred solution of the above intermediate (2.66 g, 10.2 mmol) in DMF (50 mL) was added 4-methyl-1H-pyrazole (0.78 mL, 10.2 mmol, CAS: 7554-65-6) and caesium carbonate (16.5 g, 50.7 mmol) and the reaction mixture stirred at rt for 1 h. The mixture was diluted with water (50 mL) and extracted with EtOAc (3×50 mL) and the combined organics dried over MgSO$_4$ and concentrated in vacuo. Purification by flash column chromatography on the Teledyne ISCO CombiFlash® Rf+ (120 g silica column Puriflash HC/Biotage SNAP, 0-80% EtOAc in isohexane) gave N-(2-chloro-5-methoxyphenethyl)-2-(4-methyl-1H-pyrazol-1-yl)acetamide (1.59 g, 51%). LCMS (Method 2): 1.39 min, 307.9 [M+H]$^+$.

Step d. 5-Chloro-8-methoxy-1-((4-methyl-1H-pyrazol-1-yl)methyl)-3,4-dihydroisoquinoline (1.37 g, 94%) was prepared from the above intermediate (1.55 g, 5.04 mmol) using a procedure similar to that described for Intermediate 4. The crude product was used without further purification. LCMS (Method 2): 0.87 min, 289.9 [M+H]$^+$ Step e. 5-Chloro-8-methoxy-1-((4-methyl-1H-pyrazol-1-yl)methyl)-1,2,3,4-tetrahydroisoquinoline (1.03 g, 74%; mixture with 5-chloro-8-methoxy-1-((4-methyl-1H-pyrazol-1-yl)methyl)-3,4-dihydroisoquinoline-2(1H)-carbaldehyde) was prepared from the above intermediate (1.37 g, 4.73 mmol) using a procedure similar to that described for Intermediate 5. The crude product was purified by flash column chromatography (80 g silica column, 0-100% methanolic ammonia in DCM (2M; 20:1) in DCM). LCMS (Method 2): 0.92 min, 291.9 [M+H]$^+$.

Step f. 5-Chloro-1-((4-methyl-1H-pyrazol-1-yl)methyl)-1,2,3,4-tetrahydro-isoquin-olin-8-ol (1.01 g, assumed quantitative) was prepared from the above intermediate (1.03 g, 3.52 mmol) using a procedure similar to that described for Intermediate 10. The crude product was used without further purification. LCMS (Method 2): 0.83 min, 277.9 [M−H]$^−$ Step g. tert-Butyl 5-chloro-8-hydroxy-1-((4-methyl-1H-pyrazol-1-yl)methyl)-3,4-dihydroisoquinoline-2(1H)-carboxylate (316 mg, 37%) was prepared from the above intermediate (627 mg, 2.26 mmol) and di-tert-butyl dicarbonate (493 mg, 2.26 mmol) using a procedure similar to that described for Intermediate 8. The crude product was purified by flash column chromatography on the Interchim Puriflash® 4100 (25 g silica column Puriflash HC/Biotage SNAP, 0-100% EtOAc in DCM). LCMS (Method 2): 1.53 min, 376.1 [M−H]$^−$.

Steps h-j. 2,4-Dimethoxybenzyl (1S,2R)-2-(5-chloro-8-((5-(difluoromethyl)-1-methyl-1H-1,2,3-triazol-4-yl)methoxy)-1-((4-methyl-1H-pyrazol-1-yl)methyl)-1,2,3,4-tetrahydroisoquinoline-2-carbonyl)cyclohexane-1-carboxylate (276 mg, mixture of diastereoisomers) was prepared from the above intermediate (316 mg, 0.84 mmol), 4-(chloromethyl)-5-(difluoromethyl)-1-methyl-triazole (190 mg, 1.05 mmol, CAS: 2138555-23-2) and Intermediate 27 (221 mg, 0.50 mmol) using procedures similar to those described for Example 11, steps b, c, d. The crude product was purified by flash column chromatography on the Biotage Companion™ (12 g silica column, 0-60% EtOAc in DCM). LCMS (Method 2): 1.64 and 1.68 min, 727.2 [M+H]$^+$.

Step k. The title compound (30 mg, 13%) was prepared from the above intermediate (276 mg, 0.38 mmol) using a procedure similar to that described for Example 11, step e. The crude product was purified by preparative HPLC (Method 1), followed by SFC (Method 1). LCMS (Method 3): 4.65 min, 577.3 [M+H]$^+$. $^1$H NMR (400 MHz, DMSO-d$_6$) δ 7.63 (t, 1H), 7.40 (d, 1H), 7.18 (d, 1H), 7.08 (m, 2H), 5.91 (dd, 1H), 5.36 (s, 2H), 4.37 (dd, 1H), 4.23 (dd, 1H), 4.19 (s, 3H), 3.97 (m, 1H), 3.58 (m, 1H), 3.52-3.18 (m, 1H), 2.80-2.63 (m, 2H), 2.23 (m, 1H), 2.06-1.87 (m, 4H), 1.70-1.51 (m, 3H), 1.40 (m, 1H), 1.23 (m, 1H), 1.09 (m, 1H), 0.77 (m, 1H).

Example 86

(1S,2R)-2-((S)-5-Chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)cyclopentane-1-carboxylic acid

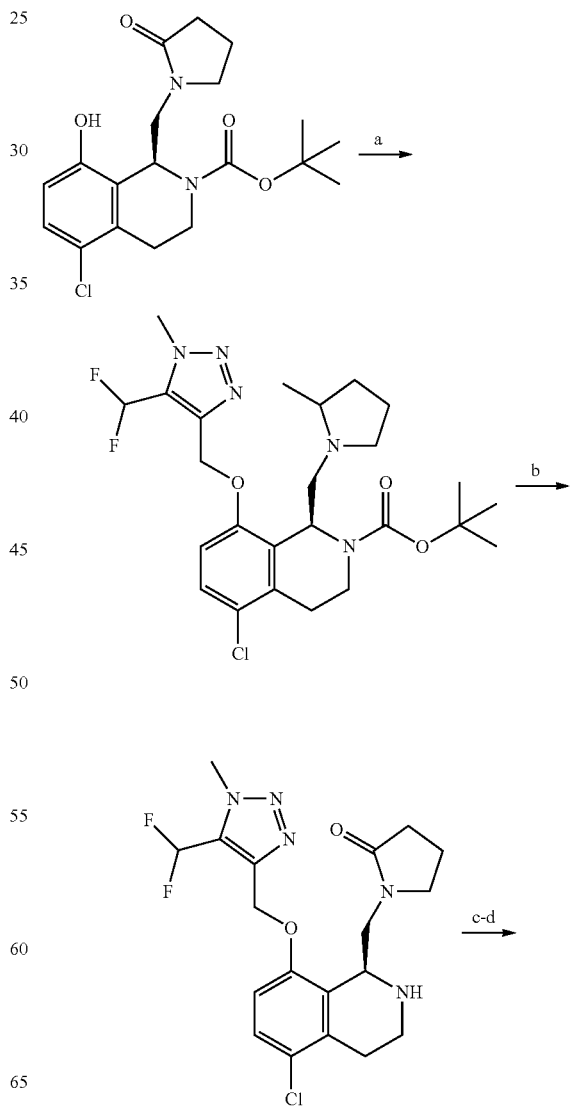

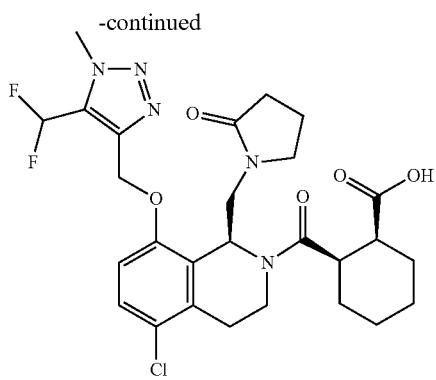

Step a. To a stirred solution of Intermediate 23 (2.6 g, 6.83 mmol) in DMF (59 mL) was added 4-(chloromethyl)-5-(difluoromethyl)-1-methyl-triazole (1.29 g, 7.09 mmol, CAS: 2138555-23-2) and caesium carbonate (8.01 g, 24.6 mmol) and the reaction mixture stirred under argon at rt for 19 h. The reaction was filtered and the solid washed with EtOAc (20 ml) and the filtrate concentrated in vacuo. The residue was partitioned between EtOAc and water, the organics washed with brine, dried (MgSO$_4$) and concentrated in vacuo. The crude product was purified by flash column chromatography on the Teledyne ISCO CombiFlash® Rf+ (80 g silica column Puriflash HC, 0-10% MeOH in DCM) to provide the title compound (0.63 g). The caesium carbonate residue was partitioned between DCM/H$_2$O, and the aqueous extracted with DCM, the combined organics dried over Mg$_2$SO$_4$, filtered and concentrated in vacuo to give another crop of the title compound (2.35 g). The batches were combined to give tert-butyl (S)-5-chloro-8-((5-(difluoromethyl)-1-methyl-1H-1,2,3-triazol-4-yl)methoxy)-1-((2-oxopyrrolidin-1-yl)methyl)-3,4-dihydroisoquinoline-2(1H)-carboxylate (2.98 g, 83%). LCMS (Method 2): 1.42 min, 548.3 [M+Na]$^+$.

Step b. (S)-1-((5-Chloro-8-((5-(difluoromethyl)-1-methyl-1H-1,2,3-triazol-4-yl)methoxy)-1,2,3,4-tetrahydroisoquinolin-1-yl)methyl)pyrrolidin-2-one hydrochloride (2.46 g, assumed quantitative) was prepared from the above intermediate (2.35 g, 4.47 mmol) using a procedure similar to that described for Example 1, step d and used without further purification. LCMS (Method 2): 0.80 min, 426.2 [M+H]$^+$.

Step c. 2,4-Dimethoxybenzyl (1S,2R)-2-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)cyclopentane-1-carboxylate (155 mg, assumed quantitative) was prepared from the above intermediate (100 mg, 0.22 mmol) and Intermediate 31 (67 mg, 0.22 mmol) using a procedure similar to that described for Example 11, step d and used without further purification. LCMS (Method 2): 1.46 min, 738.3 [M+Na]$^+$.

Step d. (1S,2R)-2-((S)-5-Chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)-cyclopentane-1-carboxylic acid (33 mg, 27%) was prepared from the above intermediate (155 mg, 0.22 mmol) using a procedure similar to that described for Example 22, step d. The crude product was purified by preparative chiral SFC (Method 3). LCMS (Method 3): 3.73 min, 566.2 [M+H]+. $^1$H NMR (400 MHz, DMSO-d$_6$; rotamers observed, both reported) δ 7.75-7.43 (m, 1H), 7.39 (d, 0.8H), 7.31 (d, 0.2H), 7.15 (d, 0.8H), 7.08 (d, 0.2H), 5.72 (dd, 0.8H), 5.39-5.20 (m, 2H), 5.15 (dd, 0.2H), 4.38 (m, 0.2H), 4.21-4.14 (m, 3H), 4.12-3.95 (m, 1H), 3.84 (dd, 0.8H), 3.77-2.40 (m, 8H), 2.36-1.36 (m, 10H).

Example 87

(1R,2S)-2-((S)-5-Chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)cyclopentane-1-carboxylic acid

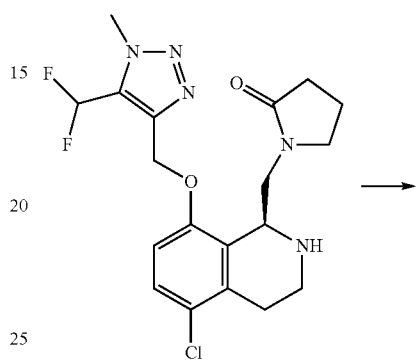

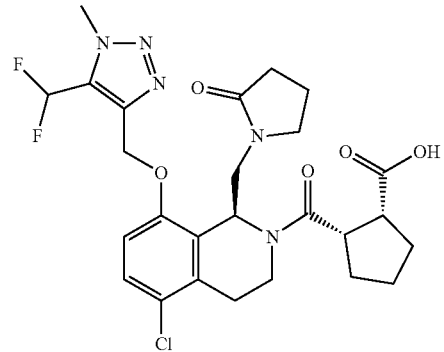

To a solution of (S)-1-((5-chloro-8-((5-(difluoromethyl)-1-methyl-1H-1,2,3-triazol-4-yl)methoxy)-1,2,3,4-tetrahydroisoquinolin-1-yl)methyl)pyrrolidin-2-one hydrochloride (from Example 86 step b; 0.10 g, 0.22 mmol) in DCM (2.5 mL) was added triethylamine (0.12 mL, 0.87 mmol) and (3aR,6aS)-tetrahydro-1H-cyclopenta[c]furan-1,3(3aH)-dione (0.03 g, 0.24 mmol, CAS: 35878-28-5). The reaction mixture was stirred at rt for 18 h. The reaction mixture partitioned between water and DCM, and the aqueous layer was acidified with dilute HCl and extracted with DCM. The combined organics were dried and concentrated in vacuo. A portion of the crude compound (40 mg) was purified by preparative HPLC (Method 3) to give the title compound (6 mg, 5%) and Example 86 (3 mg, 2%). LCMS: (Method 1) 4.09 min, 566.2 [M+H]$^+$. $^1$H NMR (400 MHz, DMSO-d$_6$; rotamers observed, both reported) δ 7.69 (t, 0.3H), 7.57 (t, 0.7H), 7.37 (d, 0.7H), 7.32 (d, 0.3H), 7.18-7.08 (m, 1H), 5.74 (dd, 0.7H), 5.40-5.20 (m, 2.3H), 4.44 (dd, 0.3H), 4.17 (s, 2.1H), 4.16 (s, 0.9H), 4.02 (m, 0.7H), 3.88-3.54 (m, 2H), 3.50-2.40 (m, 7H), 2.37-1.38 (m, 10H).

Example 91

(1S,2R)-2-((S)-5-Chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid

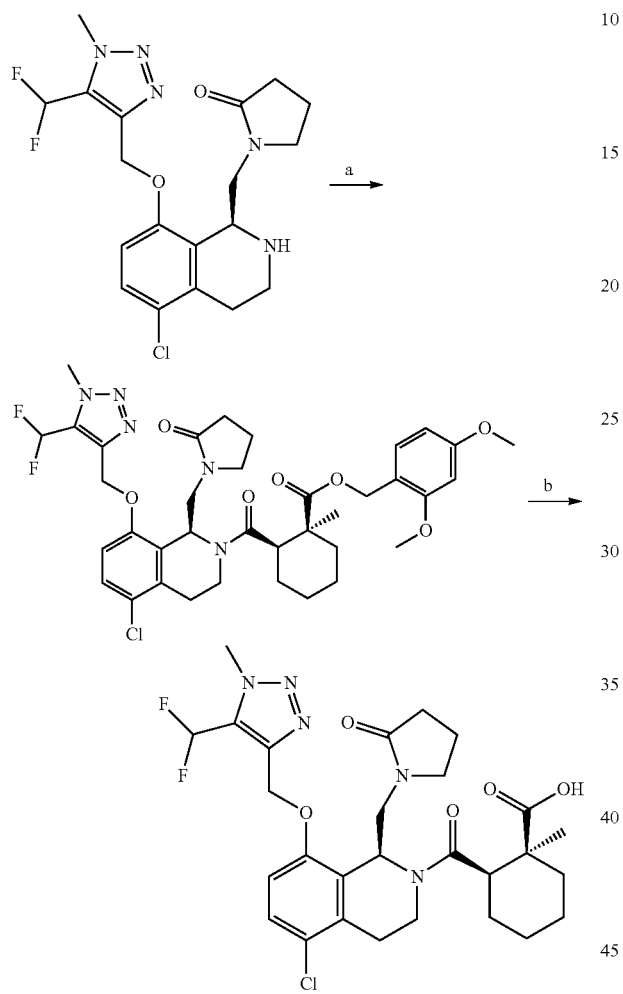

Step a. 2,4-Dimethoxybenzyl (1S,2R)-2-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylate (136 mg, 60%) was prepared from (S)-1-((5-chloro-8-((5-(difluoromethyl)-1-methyl-1H-1,2,3-triazol-4-yl)methoxy)-1,2,3,4-tetrahydroisoquinolin-1-yl)methyl)pyrrolidin-2-one hydrochloride (Example 86 step b; 131 mg, 0.31 mmol) and Intermediate 29 (117 mg, 0.34 mmol) using a procedure similar to that described for Example 11, step d. The crude product was purified by flash column chromatography on the on the Teledyne ISCO CombiFlash® Rf200 (12 g silica column Puriflash HC, 0-10% MeOH in EtOAc). LCMS (Method 2): 1.54 min, 744.4/746.3 [M+H]$^+$.

Step b. The title compound (19 mg, 54%) was prepared from the above intermediate (130 mg, 0.17 mmol) using a procedure similar to that described for Example 22, step d. The crude product was purified by preparative HPLC (Method 3). LCMS (Method 3): 4.34 min, 594.2 [M+H]+, 616.2 [M+Na]$^+$. $^1$H NMR (400 MHz, DMSO-d$_6$) δ 11.83 (bs, 1H), 7.58 (t, 1H), 7.37 (d, 1H), 7.14 (d, 1H), 5.77 (dd, 1H), 5.29 (s, 2H), 4.18 (s, 3H), 3.93 (dd, 1H), 3.83 (dd, 1H), 3.57 (m, 1H), 3.47-3.15 (m, 1H), 3.00-2.93 (m, 2H), 2.91-2.65 (m, 3H), 2.28-2.10 (m, 2H), 1.97 (m, 1H), 1.90-1.69 (m, 2H), 1.68-1.46 (m, 3H), 1.44-1.26 (m, 3H), 1.19 (bm, 1H), 1.08 (s, 3H).

Example 96

3-((S)-5-Chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)bicyclo[2.2.1]heptane-2-carboxylic acid

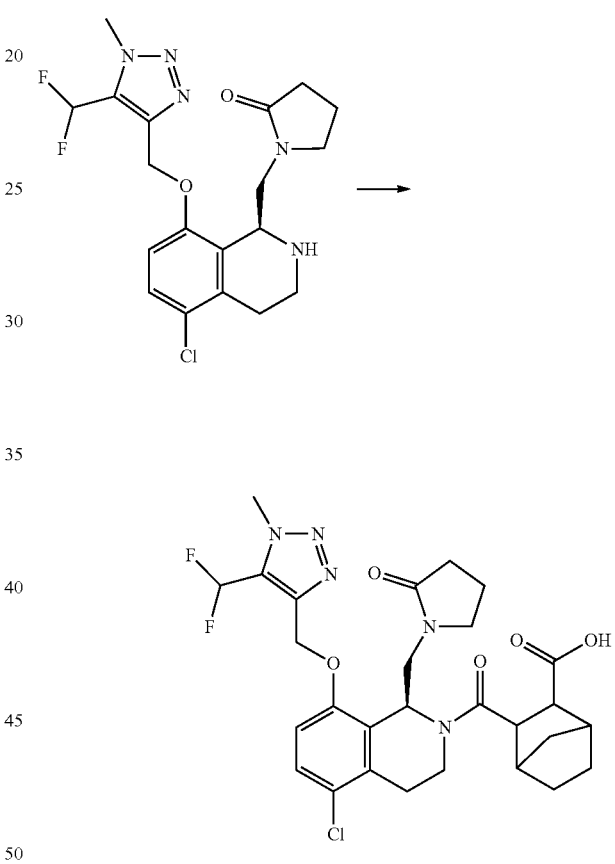

A solution of (S)-1-((5-chloro-8-((5-(difluoromethyl)-1-methyl-1H-1,2,3-triazol-4-yl)methoxy)-1,2,3,4-tetrahydroisoquinolin-1-yl)methyl)pyrrolidin-2-one hydrochloride (Example 86 step b; 100 mg, 0.22 mmol) and (3aR,4S,7R,7aS)-hexahydro-4,7-methanoisobenzofuran-1,3-dione (35.9 mg, 0.22 mmol, CAS: 14166-28-0) in DIPEA (0.08 mL, 0.43 mmol) and THF (2 mL) was stirred at rt for 20 h. The mixture was diluted with water and extracted with DCM (×2). The combined organics were dried over MgSO$_4$ and concentrated in vacuo. Purification by preparative HPLC (Method 3) then flash column chromatography on the Puriflash (4 g, 0-75% methanolic ammonia in DCM) and preparative HPLC (Method 7; 5-20% MeCN in water (0.1% NH$_4$OH)) gave the title compound (5 mg, 3%, mixture of diastereoisomers). LCMS (Method 3) 4.06 min, 592.3 [M+H]$^+$.

Example 101

2-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)-4,4-difluorocyclopentane-1-carboxylic acid

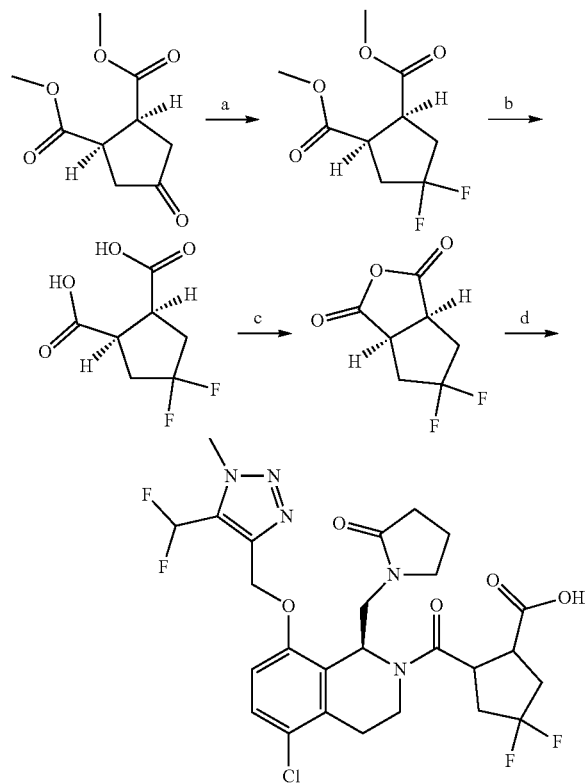

Step a. To a solution of 4-oxo-cyclopentane-cis-1,2-dicarboxylic acid dimethyl ester (0.5 g, 2.31 mmol, CAS: 28269-02-5) in anhydrous DCM (20 mL) was added DAST (0.76 mL, 5.78 mmol, CAS: 38078-09-0) and the reaction mixture was stirred at 40° C. for 24 h. A further portion of DAST (0.76 mL, 5.78 mmol) was added and the mixture stirred at 40° C. for further 48 h. The reaction mixture was cooled to rt and poured in water and extracted with DCM. The organic layer was dried over (MgSO$_4$) and concentrated in vacuo to give dimethyl 4,4-difluorocyclopentane-cis-1,2-dicarboxylate (450 mg, 88%), used without further purification. $^1$H NMR (CDCl$_3$) 3.70 (s, 6H), 3.28 (m, 2H), 2.60 (m, 2H), 2.44 (m, 2H).

Step b. To a solution of the above intermediate (200 mg, 0.9 mmol) in MeOH (5 mL) at 0° C. was added NaOH (108 mg, 2.7 mmol) and water (5 mL) and the mixture stirred for 10 min at 0° C., then warmed to rt and stirred for 18 h. The mixture was concentrated in vacuo to remove the volatile solvent, and the residue was cooled to 0° C., acidified with HCl and concentrated in vacuo. 5% MeOH in chloroform was added to the residue which was then filtered and concentrated in vacuo to give 4,4-difluorocyclopentane-cis-1,2-dicarboxylic acid (180 mg, assumed quantitative), used without further purification. LCMS (Method 2): 1.13 min, 217.1 [M+Na]$^+$.

Step c. A solution of the above intermediate (0.64 mL, 8.96 mmol) in acetyl chloride (0.6 mL) was heated at reflux for 3 h. The solvent was concentrated in vacuo and the residue was azeotroped in vacuo with toluene twice and dried under high vacuum to provide cis-5,5-difluorotetrahydro-1H-cyclopenta[c]furan-1,3(3aH)-dione (150 mg, 95%), used without further purification. $^1$H NMR (400 MHz; CDCl$_3$) δ: 3.12-3.33 (m, 2H), 2.22-2.62 (m, 4H).

Step d. To a solution of (S)-1-((5-chloro-8-((5-(difluoromethyl)-1-methyl-1H-1,2,3-triazol-4-yl)methoxy)-1,2,3,4-tetrahydroisoquinolin-1-yl)methyl)pyrrolidin-2-one hydrochloride (Example 86 step b; 150 mg, 0.35 mmol) in DCM (3.5 mL) at 0° C. was added triethylamine (0.25 mL, 1.76 mmol) and the above intermediate (124 mg, 0.7 mmol) and the mixture stirred at 0° C. for 1 h, then warmed to rt and stirred for 18 h. The reaction mixture partitioned between water (50 mL) and DCM (15 mL) and the layers was separated. The aqueous layer was acidified with dilute HCl and extracted with DCM. The combined organic layers were dried over Na$_2$SO$_4$, filtered and concentrated in vacuo to give the crude material (155 mg). A portion of the crude material (55 mg) was purified by preparative HPLC (Method 3) to give the title compound (4.1 mg, 2%) and an alternative diastereoisomer (4.3 mg, 2%). LCMS (Method 3): 4.22 min, 602.21 [M+H]$^+$. $^1$H NMR (400 MHz, DMSO-d$_6$) δ 7.58 (t, 1H), 7.39 (d, 1H), 7.16 (d, 1H), 5.79 (dd, 1H), 5.30 (s, 2H), 4.17 (s, 3H), 4.14 (m, 1H), 3.82 (dd, 1H), 3.68-3.54 (m, 2H), 3.53-3.15 (m, 1H), 3.07 (m, 1H), 3.01 (dd, 1H), 2.94-2.78 (m, 2H), 2.78-2.63 (m, 1H), 2.60-1.95 (m, 6H), 1.88-1.64 (m, 2H).

Example 102

(1S,2R)-2-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)-1-methylcyclopentane-1-carboxylic acid

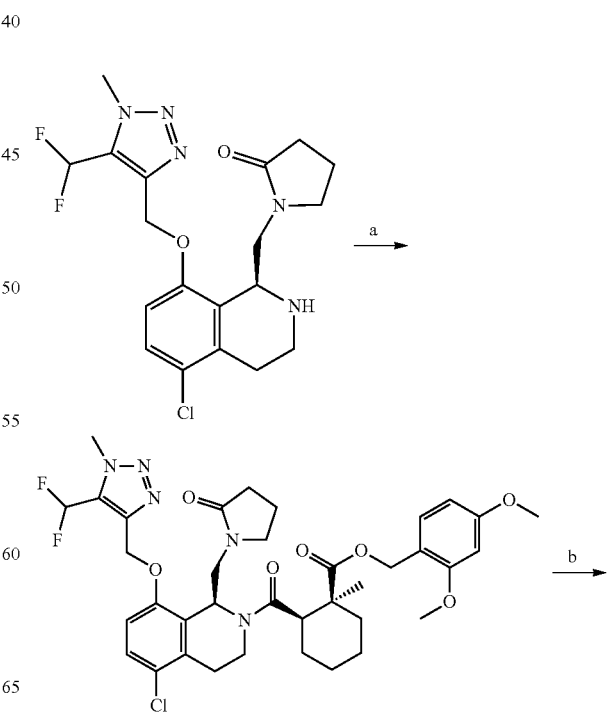

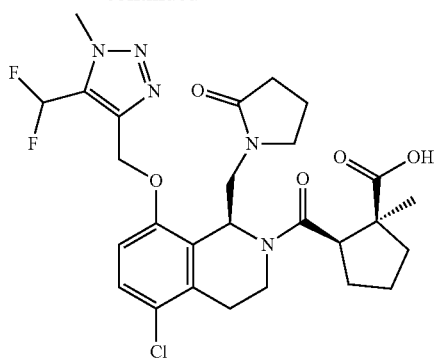

Step a. 2,4-Dimethoxybenzyl (1S,2R)-2-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)-1-methylcyclopentane-1-carboxylate (136.4 mg, 61%) was prepared from (S)-1-((5-chloro-8-((5-(difluoromethyl)-1-methyl-1H-1,2,3-triazol-4-yl)methoxy)-1,2,3,4-tetrahydroisoquinolin-1-yl)methyl)pyrrolidin-2-one hydrochloride (Example 86 step b; 141 mg, 0.31 mmol) and Intermediate 32 (98 mg, 0.31 mmol) using a procedure similar to that described for Example 11, step d. The crude product was purified by flash column chromatography on the Teledyne ISCO CombiFlash® Rf200 (12 g silica column Puriflash HC, 0-5% MeOH in DCM). LCMS (Method 2): 1.51 min, 730.3 [M+H]$^+$ Step b. The title compound (12 mg, 7%) was prepared from the above intermediate (200 mg, 0.27 mmol) using a procedure similar to that described for Example 11, step e. The crude product was purified by preparative HPLC (method 9). LCMS (Method 3): 2.69 min, 580.5 [M+H]$^+$. $^1$H NMR (400 MHz, DMSO-d$_6$) δ 10.77 (bs, 1H), 7.58 (t, 1H), 7.38 (d, 1H), 7.15 (d, 1H), 5.72 (dd, 1H), 5.29 (s, 2H), 4.18 (s, 3H), 3.98 (dd, 1H), 3.84 (dd, 1H), 3.56 (m, 1H), 3.40 (m, 1H), 3.03 (m, 1H), 2.93 (dd, 1H), 2.89-2.76 (m, 2H), 2.69 (m, 1H), 2.30 (m, 1H), 2.16 (m, 1H), 2.10-1.51 (m, 7H), 1.39 (m, 1H), 1.13 (s, 3H).

Example 104

(1S,2R)-2-((S)-5-Chloro-8-((1-methyl-1H-1,2,3-triazol-4-yl)methoxy)-1-((2-oxopyrrolidin-1-yl)methyl)-1,2,3,4-tetrahydroisoquinoline-2-carbonyl)cyclohexane-1-carboxylic acid

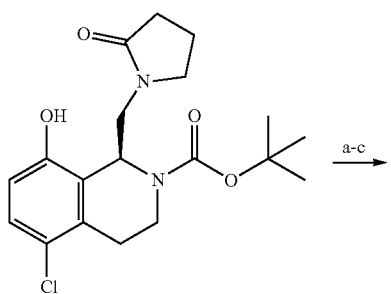

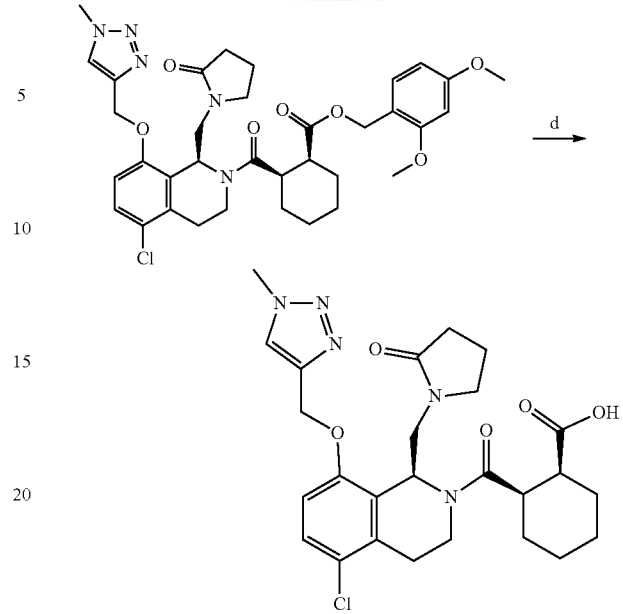

Step a. tert-Butyl (S)-5-chloro-8-((1-methyl-1H-1,2,3-triazol-4-yl)methoxy)-1-((2-oxopyrrolidin-1-yl)methyl)-3,4-dihydroisoquinoline-2(1H)-carboxylate (240 mg, 87%) was prepared from Intermediate 23 (220 mg, 0.58 mmol) and 4-(chloromethyl)-1-methyl-triazole hydrochloride (58 mg, 0.35 mmol, CAS: 327985-63-7) using a procedure similar to that described for Example 11, step b. Further portions of caesium carbonate (355 mg, 1.09 mmol) and 4-(chloromethyl)-1-methyl-triazole hydrochloride (58 mg, 0.35 mmol) were added, and the reaction mixture was stirred at rt for 5 days. The crude product was used without further purification. LCMS (Method 1a): 2.84 min, 476 [M+H]$^+$.

Step b. (S)-1-((5-Chloro-8-((1-methyl-1H-1,2,3-triazol-4-yl)methoxy)-1,2,3,4-tetrahydroisoquinolin-1-yl)methyl)pyrrolidin-2-one hydrochloride (210 mg, assumed quantitative) was prepared from the above intermediate (240 mg, 0.5 mmol) using a procedure similar to that described for Example 1, step d and was used without further purification. LCMS (Method 2): 0.71 min, 376.2 [M+H]$^+$.

Step c. 2,4-Dimethoxybenzyl (1S,2R)-2-((S)-5-chloro-8-((1-methyl-1H-1,2,3-triazol-4-yl)methoxy)-1-((2-oxopyrrolidin-1-yl)methyl)-1,2,3,4-tetrahydroisoquinoline-2-carbonyl)cyclohexane-1-carboxylate (40 mg, 77%) was prepared from the above intermediate (110. mg, 0.270 mmol) and Intermediate 31 (100 mg, 0.32 mmol) using a procedure similar to that described for Example 11, step d. The crude product was purified by flash column chromatography on the Interchim Puriflash 4100 (25 g column, 0-2.5% MeOH in DCM). LCMS (Method 2): 1.42 min, 680 [M+H]$^+$.

Step d. The title compound (30 mg, 27%) was prepared from the above intermediate (140 mg, 0.21 mmol) using a procedure similar to that described for Example 29, step d. The crude product was purified by preparative HPLC (Method 7; 10-70% MeCN (with 0.1% HCO$_2$H) in 0.1% aqueous formic acid). LCMS (Method 1): 3.55 min, 528.3 [M−H]$^−$. $^1$H NMR (400 MHz, DMSO-d$_6$) δ 11.73 (bs, 1H), 8.24 (s, 1H), 7.35 (d, 1H), 7.12 (d, 1H), 5.81 (dd, 1H), 5.26-5.15 (m, 2H), 4.07 (s, 3H), 3.95 (dd, 1H), 3.83 (dd, 1H), 3.60 (m, 1H), 3.48-3.13 (m, 2H), 3.03 (dd, 1H), 2.97 (m, 1H), 2.82 (dd, 1H), 2.69 (m, 1H), 2.34 (m, 1H), 2.27-1.95 (m, 3H), 1.95-1.62 (m, 5H), 1.50 (m, 1H), 1.42 (m, 1H), 1.28-1.05 (m, 2H).

Example 105

(1R,2S)-2-((S)-5-Chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)-1-fluorocyclohexane-1-carboxylic acid

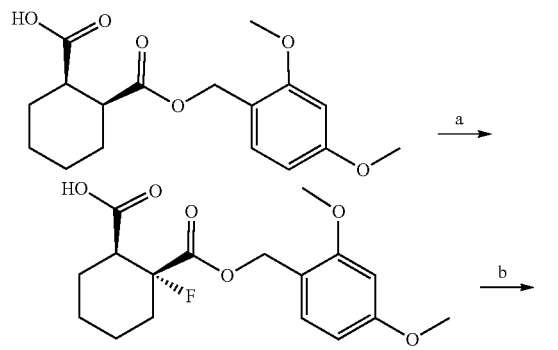

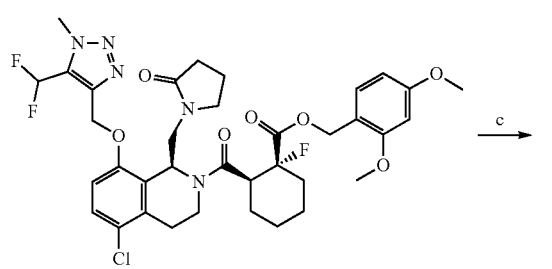

Step a. To a stirred solution of Intermediate 28 (193.4 mg, 0.6 mmol) in anhydrous THF (0.5 mL), cooled to −55° C. under argon, was added lithium diisopropylamide solution (1.0 M in THF/hexanes; 1.5 mL, 1.5 mmol) dropwise over 5 min. The solution was stirred at −45 to −25° C. for 30 min, then was treated dropwise with a solution of N-fluorobenzenesulfonimide (567.6 mg, 1.8 mmol) in anhydrous THF (2 mL). The reaction mixture was allowed to slowly warm to 5° C. over 2 h then quenched with saturated aqueous NaHCO₃ then extracted with EtOAc. The aqueous layer was acidified with 10% aqueous citric acid (20 mL) and extracted with EtOAc. The combined organic extracts were washed with brine, dried over Na₂SO₄, filtered, and concentrated in vacuo to give (1S,2R)-2-(((2,4-dimethoxybenzyl)oxy)carbonyl)-2-fluorocyclohexane-1-carboxylic acid (204 mg, assumed quantitative) used without further purification. LCMS (Method 2): 1.34, 363.2 [M+Na]⁺.

Step b. 2,4-Dimethoxybenzyl (1R,2S)-2-((S)-5-chloro-8-((5-(difluoromethyl)-1-methyl-1H-1,2,3-triazol-4-yl) methoxy)-1-((2-oxopyrrolidin-1-yl)methyl)-1,2,3,4-tetrahydroisoquinoline-2-carbonyl)-1-fluorocyclohexane-1-carboxylate (130 mg, assumed quantitative) was prepared from (S)-1-((5-Chloro-8-((5-(difluoromethyl)-1-methyl-1H-1,2,3-triazol-4-yl)methoxy)-1,2,3,4-tetrahydroisoquinolin-1-yl)methyl)pyrrolidin-2-one hydrochloride (Example 86 step b; 70 mg, 0.16 mmol) and the above intermediate (84 mg, 0.25 mmol) using a procedure similar to that described for Example 11, step d and used without further purification. LCMS (Method 2): 1.52 m/z 748.3 [M+H]⁺.

Step c. The title compound was prepared from the above intermediate (176 mg, 0.24 mmol) using a procedure similar to that described for Example 29, step d. The crude product was purified by preparative HPLC (Method 6) then further purified by SFC (Method 3) and freeze-dried to afford the title compound (3 mg, 8%). LCMS (Method 1): 4.00 min, m/z 598.4 [M+H]⁺. ¹H NMR (400 MHz, DMSO-d₆) δ 7.58 (t, 1H), 7.37 (d, 1H), 7.15 (d, 1H), 5.75 (dd, 1H), 5.36-5.22 (m, 2H), 4.18 (s, 3H), 3.96 (m, 1H), 3.82 (dd, 1H), 3.55 (m, 1H), 3.47-3.13 (m, 2H), 2.95 (dd, 1H), 2.90-2.72 (m, 3H), 2.15 (m, 2H), 1.98 (m, 1H), 1.88-1.70 (bm, 3H), 1.69-1.50 (bm, 3H), 1.49-1.30 (bm, 3H).

Example 108

(1S,2R)-2-((S)-5-Chloro-8-((1-methyl-5-(trifluoromethyl)-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid

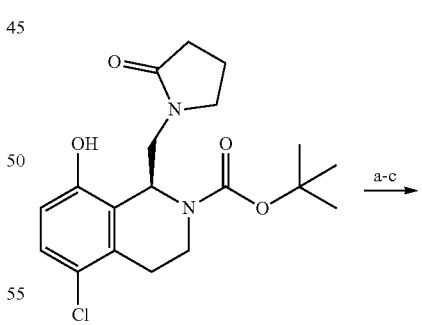

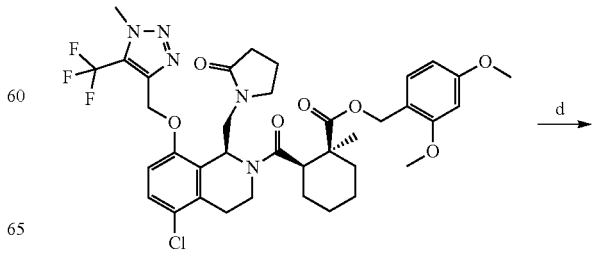

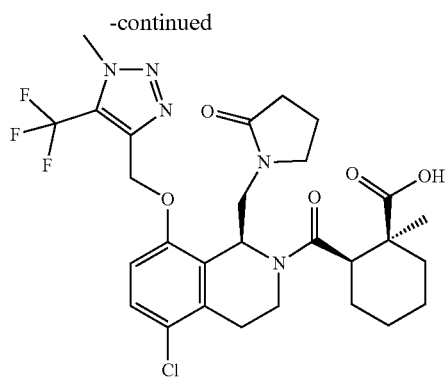

Step a. tert-Butyl (S)-5-chloro-8-((1-methyl-5-(trifluoromethyl)-1H-1,2,3-triazol-4-yl)methoxy)-1-((2-oxopyrrolidin-1-yl)methyl)-3,4-dihydroisoquinoline-2(1H)-carboxylate (157 mg, 99%) was prepared from Intermediate 23 (100 mg, 0.26 mmol) and 4-(chloromethyl)-1-methyl-5-(trifluoromethyl)triazole (63 mg, 0.32 mmol, CAS: 2169203-94-3) using a procedure similar to that described for Example 11, step b. The crude product was purified by flash column chromatography (4% MeOH in DCM). LCMS (Method 4): 0.99 min, 444.2 [M−CO$_2$$^t$Bu+H]$^+$. $^1$H NMR (300 MHz, CDCl$_3$) δ 7.23-7.26 (m, 1H), 6.95 (d, 1H), 5.49-5.53 (m, 1H), 5.26-5.32 (m, 2H), 4.22 (s, 3H), 3.98-4.16 (m, 2H), 3.77-3.85 (m, 1H), 3.37-3.55 (m, 1H), 3.04-3.18 (m, 2H), 2.71-2.88 (m, 2H), 2.17-2.35 (m, 2H), 1.93-2.06 (m, 2H), 1.43 (s, 9H).

Step b. (S)-1-((5-Chloro-8-((1-methyl-5-(trifluoromethyl)-1H-1,2,3-triazol-4-yl)methoxy)-1,2,3,4-tetrahydroisoquinolin-1-yl)methyl)pyrrolidin-2-one hydrochloride (143 mg, 97%) was prepared from the above intermediate (157 mg, 0.26 mmol) using a procedure similar to that described for Example 1, step d and was used without further purification. LCMS (Method 4): 0.73 min, 444.2 [M+H]$^+$. $^1$H NMR (300 MHz, DMSO-d$_6$) δ 9.67 (s, 1H), 8.73 (d, 1H), 7.50 (d, 1H), 7.24 (d, 1H), 5.35 (dd, 2H), 4.60 (d, 1H), 4.10-4.22 (m, 4H), 3.93 (dd, 1H), 3.53-3.63 (m, 1H), 3.48-3.35 (m, 1H), 2.82-3.12 (m, 4H), 2.12-2.33 (m, 2H), 1.80-1.97 (m, 2H).

Step c. 2,4-Dimethoxybenzyl (1S,2R)-2-((S)-5-chloro-8-((1-methyl-5-(trifluoromethyl)-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylate (42 mg, 30%) was prepared from the above intermediate (86 mg, 0.15 mmol) and Intermediate 29 (56 mg, 0.17 mmol) using a procedure similar to that described for Example 11, step d. The crude product was purified by reverse phase column chromatography on the Biotage Isolera (60 g column, C18, 30-90% MeCN in pH 10 ammonium carbonate buffer). LCMS (Method 4): 1.06 min, 762.4 [M+H]$^+$. $^1$H NMR (300 MHz, CDCl$_3$) δ 6.99 (d, 1H), 6.86-6.91 (m, 1H), 6.45 (q, 1H), 6.31 (d, 1H), 6.22 (dd, 1H), 5.94 (dd, 1H), 5.22-5.32 (m, 2H), 5.03-5.10 (m, 2H), 4.69 (d, 1H), 4.22 (s, 3H), 3.93-4.01 (m, 1H), 3.81 (t, 2H), 3.78 (s, 3H), 3.70 (s, 3H), 3.04-3.14 (m, 2H), 2.82-2.86 (m, 2H), 2.58 (s, 1H), 2.17-2.36 (m, 4H), 1.91 (t, 2H), 1.63-1.70 (m, 2H), 1.23-1.34 (m, 4H), 1.18 (s, 3H).

Step c Method 2. 2,4-Dimethoxybenzyl (1S,2R)-2-((S)-5-chloro-8-((1-methyl-5-(trifluoromethyl)-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylate (5.3 g, 66%) was prepared from the above intermediate (4.69 g, 10.6 mmol) and Intermediate 33 (4.80 g, 10.6 mmol) using a procedure similar to that described for Example 143 step c.

Step d. The title compound (24 mg, 84%) was prepared from the above intermediate (42 mg, 0.05 mmol) using a procedure similar to that described for Example 29, step b. The crude product was purified by flash column chromatography twice (4% MeOH in DCM). LCMS (Method 8): 1.35 min, 612.4 [M+H]$^+$. $^1$H NMR (300 MHz, CDCl$_3$) δ 7.30 (d, 1H), 7.02 (d, 1H), 5.97 (m, 1H), 5.29 (m, 2H), 4.22 (s, 3H), 4.11-3.61 (m, 4H), 3.24-2.98 (m, 3H), 2.74 (m, 1H), 2.56 (d, 1H), 2.46-2.08 (m, 3H), 2.04-1.18 (m, 8H), 1.17-0.87 (m, 4H). The above reaction was repeated with 4.5 g of the above intermediate and yielded 1.25 g (35%).

Example 109

(1S,2R)-2-((S)-5-Chloro-8-((5-(difluoromethyl)-1-methyl-1H-1,2,3-triazol-4-yl)methoxy)-1-(((R)-4-methyl-2-oxopyrrolidin-1-yl)methyl)-1,2,3,4-tetrahydroisoquinoline-2-carbonyl)-1-methylcyclopentane-1-carboxylic acid

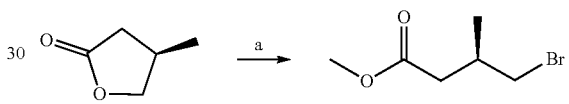

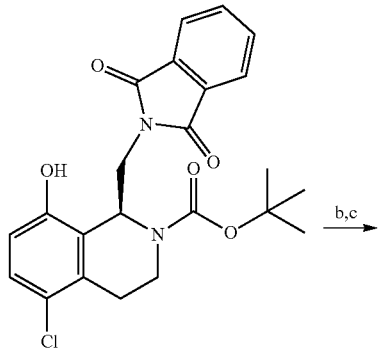

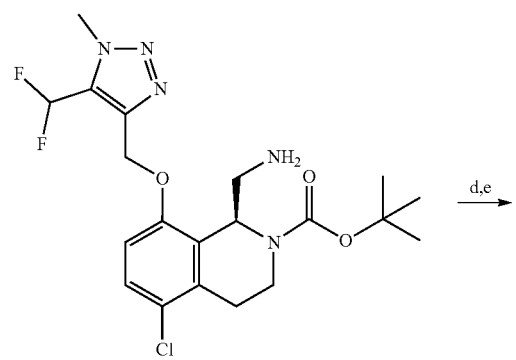

-continued

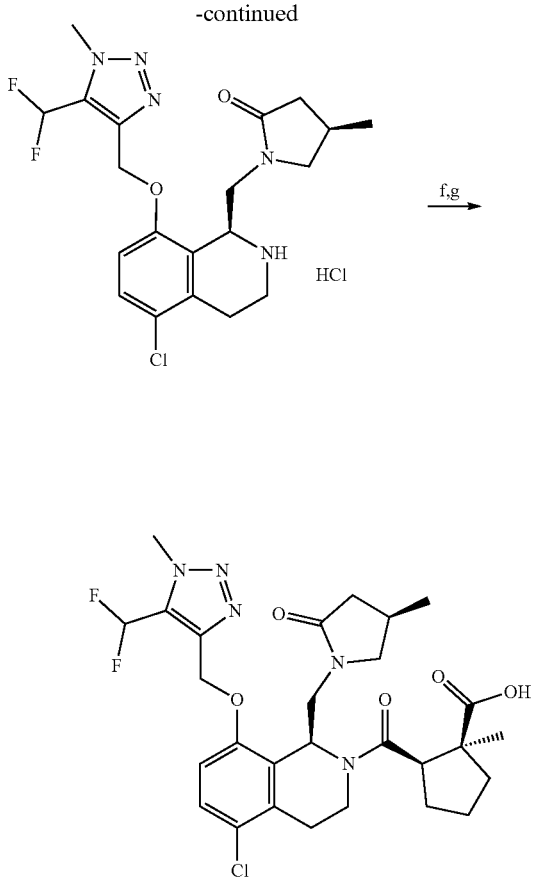

Step a. A solution of (4R)-4-methyltetrahydrofuran-2-one (875 mg, 8.74 mmol, CAS: 65284-00-6) in hydrogen bromide (33% in acetic acid; 6.1 mL, 35 mmol) was heated at 80° C. for 16 h. The mixture was cooled to rt and MeOH (5 mL) was added. The reaction mixture was stirred at rt for 16 h and concentrated in vacuo. The residue was partitioned between EtOAc and a saturated aqueous NaHCO$_3$. The aqueous layer was extracted with ethyl acetate (×2). The combined organic layers were washed with a saturated aqueous solution of sodium bicarbonate, brine, dried over MgSO$_4$, filtered and concentrated in vacuo to give methyl (R)-4-bromo-3-methylbutanoate (790 mg, 44%). $^1$H NMR (300 MHz, CDCl$_3$) δ 3.64-3.72 (m, 3H), 3.36-3.50 (m, 2H), 2.45-2.69 (m, 1H), 2.19-2.42 (m, 2H), 1.02-1.12 (m, 3H).

Step b. tert-Butyl (S)-5-chloro-8-((5-(difluoromethyl)-1-methyl-1H-1,2,3-triazol-4-yl)methoxy)-1-((1,3-dioxoisoindolin-2-yl)methyl)-3,4-dihydroisoquinoline-2(1H)-carboxylate (2.95 g, 97%) was prepared from Intermediate 12 (2.2 g, 4.97 mmol) and 4-(chloromethyl)-5-(difluoromethyl)-1-methyl-triazole (1.07 g, 5.51 mmol, CAS: 2138555-23-2) using a procedure similar to that described for Example 11 step b and used without further purification. LCMS (Method 4): 1.08 min, 488.2 [M-CO$_2^t$Bu+H]$^+$.

Step c. To a solution of the above intermediate (2.9 g, 4.74 mmol) in EtOH (98 mL) was added hydrazine hydrate (1.61 mL, 33.15 mmol). The reaction mixture was heated at 65° C. for 18 h. The suspension was filtered and the solid rinsed with ice cold EtOAc. The filtrate was concentrated in vacuo. The residue was washed with diethyl ether and filtered. The filtrate was concentrated in vacuo to give tert-butyl (S)-1-(aminomethyl)-5-chloro-8-((5-(difluoromethyl)-1-methyl-1H-1,2,3-triazol-4-yl)methoxy)-3,4-dihydroisoquinoline-2 (1H)-carboxylate (2.2 g, 93%). LCMS (Method 4): 0.90 min, 458.2 [M+H]$^+$.

Step d. A mixture of tert-butyl (S)-1-(aminomethyl)-5-chloro-8-((5-(difluoromethyl)-1-methyl-1H-1,2,3-triazol-4-yl)methoxy)-3,4-dihydroisoquinoline-2(1H)-carboxylate (step c; 520 mg, 1.14 mmol), methyl (R)-4-bromo-3-methylbutanoate (step a; 300 mg, 1.48 mmol) and triethylamine (0.24 mL, 1.7 mmol) in MeCN (10.6 mL) was heated at reflux for 16 h. Additional portions of methyl (R)-4-bromo-3-methylbutanoate (100 mg, 0.5 mmol) and triethylamine (0.08 mL, 0.57 mmol) were added and the reaction stirred at rt for 24 h. The reaction mixture was concentrated in vacuo and the residue was dissolved in EtOAc. The solution was washed with water, brine, dried over Na$_2$SO$_4$, filtered and concentrated in vacuo. Purification by flash column chromatography (66% EtOAc in hexanes) gave tert-butyl (S)-5-chloro-8-((5-(difluoromethyl)-1-methyl-1H-1,2,3-triazol-4-yl)methoxy)-1-(((R)-4-methyl-2-oxopyrrolidin-1-yl) methyl)-3,4-dihydroisoquinoline-2(1H)-carboxylate (252 mg, 41%). LCMS (Method 6a): 0.98 min; 537.75 [M-H]$^+$. $^1$H NMR (400 MHz, DMSO-d$_6$) δ 7.55 (t, 1H), 7.34-7.42 (m, 1H), 7.12 (d, 1H), 5.18-5.33 (m, 3H), 3.70-4.15 (m, 5H), 3.19-3.37 (m, 2H), 2.46-3.06 (m, 4H), 2.21-2.33 (m, 2H), 1.63-1.70 (m, 1H), 0.93-1.39 (m, 12H).

Step e. (R)-1-(((S)-5-chloro-8-((5-(difluoromethyl)-1-methyl-1H-1,2,3-triazol-4-yl)methoxy)-1,2,3,4-tetrahydroisoquinolin-1-yl)methyl)-4-methylpyrrolidin-2-one hydrochloride (237 mg, assumed quantitative) was prepared from the above intermediate (252 mg, 0.47 mmol) using a procedure similar to that described for Example 1, step d. The crude product was triturated with diethyl ether and used without further purification. LCMS (Method 6a): 0.44 min; 439.87 [M+H]$^+$.

Step f. 2,4-Dimethoxybenzyl (1S,2R)-2-((S)-5-chloro-8-((5-(difluoromethyl)-1-methyl-1H-1,2,3-triazol-4-yl) methoxy)-1-(((R)-4-methyl-2-oxopyrrolidin-1-yl)methyl)-1,2,3,4-tetrahydroisoquinoline-2-carbonyl)-1-methylcyclopentane-1-carboxylate (14 mg, 7%) was prepared from the above intermediate (119 mg, 0.24 mmol) and Intermediate 32 (132 mg, 0.29 mmol, 70% purity) using a procedure similar to that described for Example 11, step d. Further portions of Intermediate 32 (60 mg, 0.13 mmol, 70% purity) and HATU (50 mg, 0.13 mmol; CAS: 148893-10-1) were added and the mixture was stirred for a further 4 h at rt. The crude product was purified by reverse phase column chromatography (30 g C18 column, e20-100% MeCN in pH10 0.1M NH$_4$HCO$_3$ buffer solution) then further purified by flash column chromatography (40-66% EtOAc in heptanes). LCMS (Method 9): 1.01 min, 744.4 [M+H]$^+$.

Step g. The title compound (2.5 mg, 21%) was prepared from the above intermediate (14 mg, 0.02 mmol) using a procedure similar to that described for Example 11, step e. The crude product was purified by reverse phase chromatography (10-45% MeCN in 0.1% formic acid in water) then triturated with diethyl ether. LCMS (Method 10a): 2.74 min, 594.3 [M+H]$^+$. $^1$H NMR (400 MHz, DMSO-d$_6$) δ 11.42 (bs, 1H), 7.59 (t, 1H), 7.38 (d, 1H), 7.14 (d, 1H), 5.69 (m, 1H), 5.29 (s, 2H), 4.18 (s, 3H), 3.97 (dd, 1H), 3.86 (dd, 1H), 3.57 (m, 1H), 3.37-3.19 (m, 1H), 3.09-2.96 (m, 2H), 2.91-2.79 (m, 3H), 2.75-2.17 (m, 4H), 2.12-1.97 (m, 1H), 1.68-1.59 (m, 3H), 1.40 (m, 1H), 1.14 (s, 3H), 1.01-0.94 (d, 3H).

Example 110

(1S,2R)-2-((S)-5-Chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclopentane-1-carboxylic acid

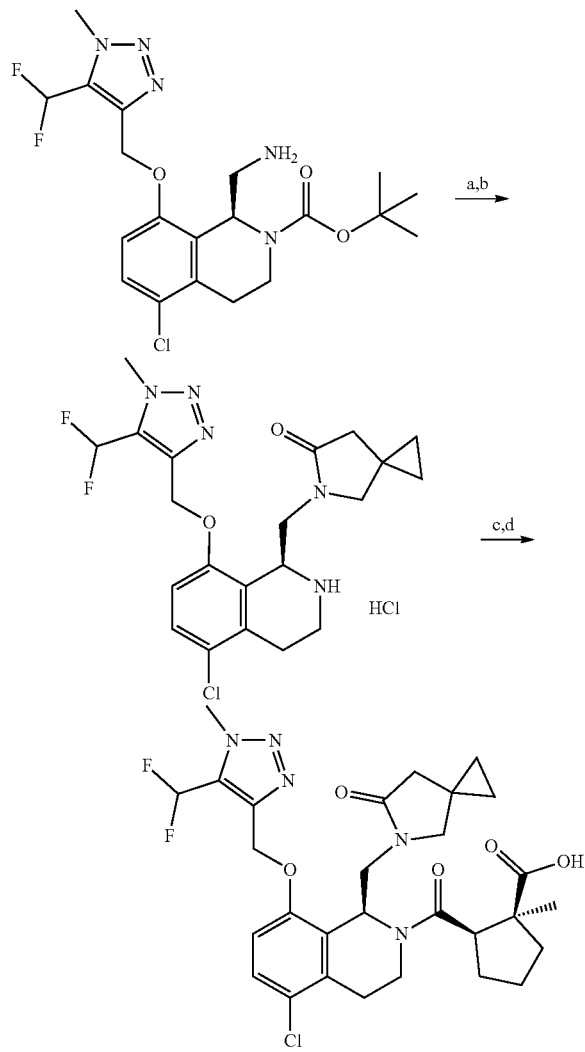

Step a. A mixture of tert-butyl (S)-1-(aminomethyl)-5-chloro-8-((5-(difluoromethyl)-1-methyl-1H-1,2,3-triazol-4-yl)methoxy)-3,4-dihydroisoquinoline-2(1H)-carboxylate (Example 109 step c; 320 mg, 0.7 mmol), triethylamine (0.15 mL, 1.05 mmol) and methyl 2-(1-(bromomethyl)cyclopropyl)acetate (376 mg, 0.91 mmol, CAS: 855473-50-6) in MeCN (6.5 mL) was heated at reflux for 72 h. The mixture was concentrated in vacuo. Purification by reverse phase column chromatography (30 g C18 column, 10-80% MeCN in pH10 0.1 M NH$_4$HCO$_3$ buffer solution) gave tert-butyl (S)-5-chloro-8-((5-(difluoromethyl)-1-methyl-1H-1,2,3-triazol-4-yl)methoxy)-1-((6-oxo-5-azaspiro[2.4]heptan-5-yl)methyl)-3,4-dihydroisoquinoline-2(1H)-carboxylate (223 mg, 58%). LCMS (Method 4): 0.97 min, 452.2 [M−CO$_2$$^t$Bu+H]$^+$.

Step b. (S)-5-((5-Chloro-8-((5-(difluoromethyl)-1-methyl-1H-1,2,3-triazol-4-yl)methoxy)-1,2,3,4-tetrahydroisoquinolin-1-yl)methyl)-5-azaspiro[2.4]heptan-6-one hydrochloride (198 mg, 99%) was prepared from the above intermediate (223 mg, 0.4 mmol) using a procedure similar to that described for Example 1, step d and was used without further purification. LCMS (Method 4): 0.73 min, 452.2 [M+H]$^+$.

Step c. 2,4-Dimethoxybenzyl (1S,2R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclopentane-1-carboxylate (94 mg, 23% yield) was prepared from the above intermediate (198 mg, 0.4 mmol) and Intermediate 32 (220 mg, 0.48 mmol, 70% purity) using a procedure similar to that described for Example 11, step d. The crude product was purified by flash column chromatography (40 g Zip sphere column, 0-80% EtOAc in heptanes). LCMS (Method 9): 1.02 min, 756.4 [M+H]$^+$.

Step d. The title compound (16 mg, 21%) was prepared from the above intermediate (94 mg, 0.12 mmol) using a procedure similar to that described for Example 29, step b. The crude product was purified by reverse phase column chromatography (30-60% MeCN in 0.1% formic acid in water). LCMS (Method 9a): 0.99 min, 606.3 [M+H]$^+$. $^1$H NMR (300 MHz, DMSO-d$_6$) δ 11.42 (bs, 1H), 7.57 (t, 1H), 7.38 (d, 1H), 7.14 (d, 1H), 5.70 (m, 1H), 5.28 (s, 2H), 4.17 (s, 3H), 4.09-3.88 (m, 2H), 3.56 (m, 1H), 3.36 (d, 1H), 3.06 (m, 1H), 2.98-2.77 (m, 2H), 2.67 (m, 1H), 2.58-2.43 (m, 1H), 2.42-2.23 (m, 1H), 2.23-1.96 (m, 3H), 1.64 (m, 3H), 1.40 (m, 1H), 1.14 (s, 3H), 0.63-0.37 (m, 4H).

Example 111

(1S)-2-((S)-5-Chloro-8-((5-(difluoromethyl)-1-methyl-1H-1,2,3-triazol-4-yl)methoxy)-1-1-(((R)-4-methyl-2-oxopyrrolidin-1-yl)methyl)-1,2,3,4-tetrahydroisoquinoline-2-carbonyl)-1-methylcyclohexane-1-carboxylic acid

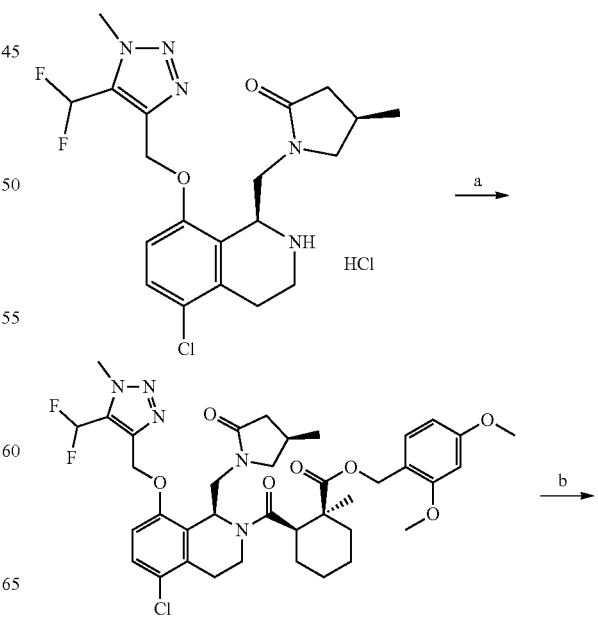

225
-continued

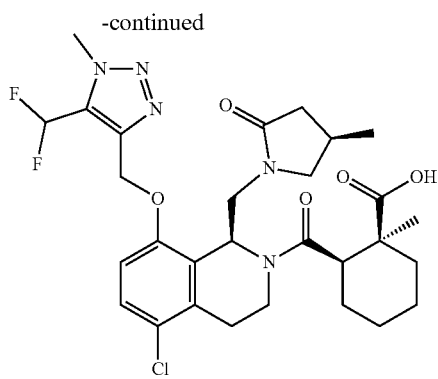

Step a. 2,4-Dimethoxybenzyl (1S,2R)-2-((S)-5-chloro-8-((5-(difluoromethyl)-1-methyl-1H-1,2,3-triazol-4-yl)methoxy)-1-(((R)-4-methyl-2-oxopyrrolidin-1-yl)methyl)-1,2,3,4-tetrahydroisoquinoline-2-carbonyl)-1-methylcyclohexane-1-carboxylate (84 mg, 18%) was prepared from (R)-1-(((S)-5-chloro-8-((5-(difluoromethyl)-1-methyl-1H-1,2,3-triazol-4-yl)methoxy)-1,2,3,4-tetrahydroisoquinolin-1-yl)methyl)-4-methylpyrrolidin-2-one hydrochloride (Example 109 step e, 119 mg, 0.24 mmol) and Intermediate 29 (120.5 mg, 0.29 mmol, 80% purity) using a procedure similar to that described for Example 11 step d. Additional portions of Intermediate 29 (60 mg, 0.14 mmol, 80% purity) and HATU (50 mg, 0.13 mmol; CAS: 148893-10-1) were added and the mixture stirred at rt for a further 16 h. The crude product was purified by reverse phase column chromatography (30 g C18 column, 20-75% MeCN in pH10 0.1 M $NH_4HCO_3$ buffer solution) then further purified by flash column chromatography (10 g Zip sphere column, 0-80% EtOAc in heptanes). LCMS (Method 9): 1.06-1.09 min, 758.4 $[M+H]^+$.

Step b. The title compound (4.9 mg, 18%) was prepared from the above intermediate (82 mg, 0.04 mmol) using a procedure similar to that described for Example 11 step d. The crude product was purified by preparative HPLC (Method 5; 60% MeOH in 0.1% formic acid in water). The isolated fractions were concentrated in vacuo and partitioned between DCM (5 mL) and HCl (2M aq., 5 mL) and the mixture passed through a phase separator (repeated twice more) and the organic layer concentrated in vacuo. LCMS (Method 9a): 1.04 min, 608.3 $[M+H]^+$. $^1$H NMR (400 MHz, DMSO-$d_6$) δ 11.92 (bs, 1H), 7.58 (t, 1H), 7.37 (d, 1H), 7.14 (d, 1H), 5.75 (m, 1H), 5.30 (s, 2H), 4.16 (s, 3H), 3.94 (dd, 1H), 3.86 (dd, 1H), 3.60 (m, 1H), 3.03-2.86 (m, 4H), 2.85-2.63 (m, 2H), 2.38-2.13 (m, 3H), 1.75-1.17 (m, 8H), 1.14-1.08 (m, 3H), 0.97 (d, 3H).

Step b Method 2. The title compound (641 mg, 48%) was prepared from the above intermediate (1.65 mg, 1.06 mmol) using a procedure similar to that described for Example 135 step b. The reaction mixture was concentrated in vacuo, triturated with MeOH and the supernatant concentrated in vacuo. The crude product was then subjected to purification on Isolera (Biotage C18 SNAP 120 g, 5-30% MeCN in water, 0.1 ammonia). Fractions containing the product were combined, freeze dried and re-purified on Isolera (Silicycle Silica SiliaPrep 120 g, 0-4% MeOH in DCM) to give the title compound (391 mg, 30%). LCMS (Method 13): 2.48 min, 608.1 $[M+H]^+$.

226
Example 112

(1S,2R)-2-((S)-5-Chloro-8-((5-(difluoromethyl)-1-methyl-1H-1,2,3-triazol-4-yl)methoxy)-1-(((R)-3-methyl-2-oxopyrrolidin-1-yl)methyl)-1,2,3,4-tetrahydroisoquinoline-2-carbonyl)-1-methylcyclohexane-1-carboxylic acid

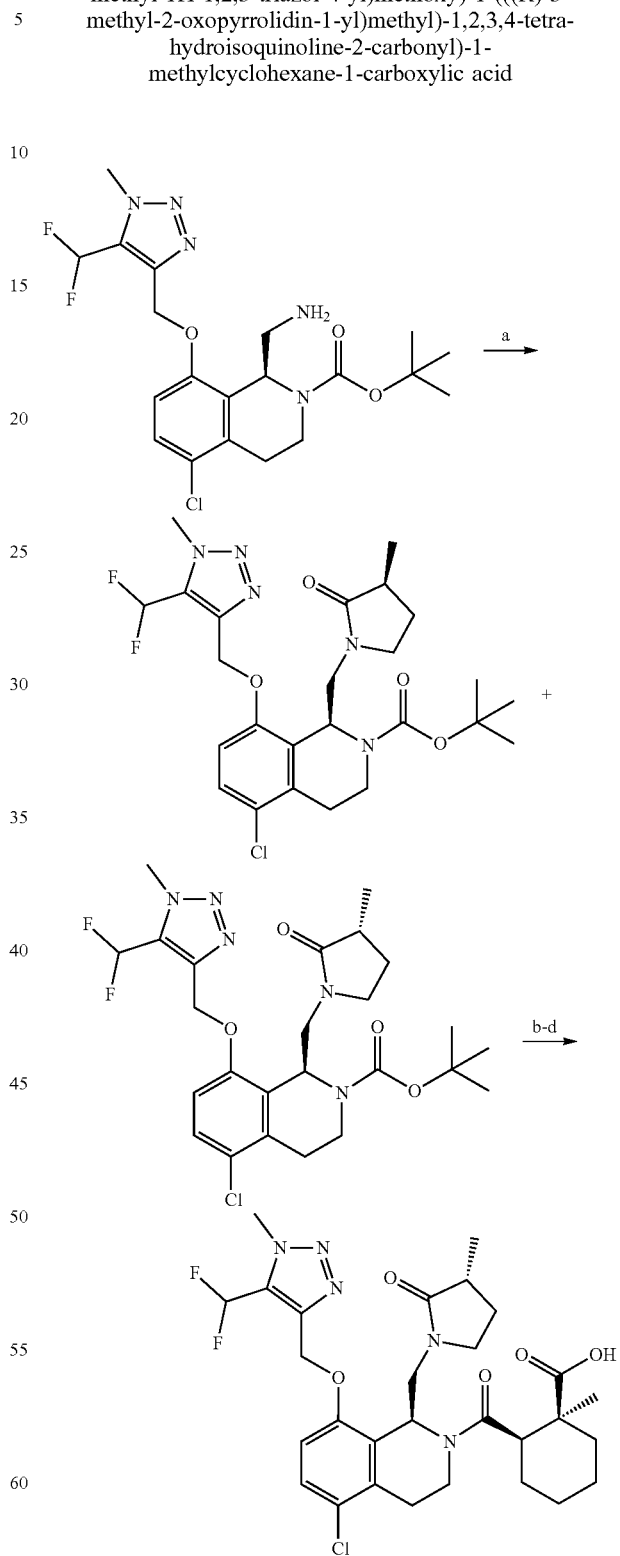

Step a. To a stirred solution of tert-butyl (S)-1-(aminomethyl)-5-chloro-8-((5-(difluoromethyl)-1-methyl-1H-1,2,3-triazol-4-yl)methoxy)-3,4-dihydroisoquinoline-2(1H)-carboxylate (Example 109 step c; 1.04 g, 2.27 mmol) and methyl 4-bromo-2-methyl-butanoate (0.71 g, 3.63 mmol, CAS: 58029-83-7) in MeCN (45 mL) was added triethylamine (0.6 mL, 4.32 mmol). The solution was heated at reflux and stirred for 18 h. The reaction mixture was concentrated in vacuo and the residue was dissolved in EtOAc. The solution was washed with water and the aqueous was extracted with EtOAc. The combined organics were washed with water, brine, dried over Na₂SO₄, filtered and concentrated in vacuo. Purification by flash column chromatography (66% EtOAc in heptanes) followed by purification by chiral flash column chromatography (Chiralpak IC, 15% EtOH in heptanes and 0.1% diethylamine) gave tert-butyl (S)-5-chloro-8-((5-(difluoromethyl)-1-methyl-1H-1,2,3-triazol-4-yl)methoxy)-1-(((S)-3-methyl-2-oxopyrrolidin-1-yl)methyl)-3,4-dihydroisoquinoline-2(1H)-carboxylate (200 mg, 16%) and tert-butyl (S)-5-chloro-8-((5-(difluoromethyl)-1-methyl-1H-1,2,3-triazol-4-yl)methoxy)-1-(((R)-3-methyl-2-oxopyrrolidin-1-yl)methyl)-3,4-dihydroisoquinoline-2(1H)-carboxylate (218 mg, 18%).

tert-butyl (S)-5-chloro-8-((5-(difluoromethyl)-1-methyl-1H-1,2,3-triazol-4-yl)methoxy)-1-(((S)-3-methyl-2-oxopyrrolidin-1-yl)methyl)-3,4-dihydroisoquinoline-2(1H)-carboxylate: $^1$H NMR (400 MHz, CDCl₃) δ 7.25-7.15 (m, 1H), 7.02-6.89 (m, 2H), 5.49-5.22 (m, 3H), 4.19-4.08 (m, 4H), 3.91 (dd, 1H), 3.63-3.35 (m, 3H), 3.21-2.68 (m, 4H), 2.40 (q, 1H), 2.18-2.10 (m, 1H), 1.43 (s, 9H), 1.18-1.14 (m, 3H).

tert-butyl (S)-5-chloro-8-((5-(difluoromethyl)-1-methyl-1H-1,2,3-triazol-4-yl)methoxy)-1-(((R)-3-methyl-2-oxopyrrolidin-1-yl)methyl)-3,4-dihydroisoquinoline-2(1H)-carboxylate: $^1$H NMR (400 MHz, CDCl₃) δ 7.25-7.15 (m, 1H), 7.02-6.89 (m, 2H), 5.49-5.22 (m, 3H), 4.19-3.91 (m, 5H), 3.70-3.45 (m, 3H), 3.14-3.01 (m, 2H), 2.86-2.71 (m, 2H), 2.36-2.16 (m, 2H), 1.42 (s, 9H), 1.20-1.14 (m, 3H).

Step b. (R)-1-(((S)-5-chloro-8-((5-(difluoromethyl)-1-methyl-1H-1,2,3-triazol-4-yl)methoxy)-1,2,3,4-tetrahydroisoquinolin-1-yl)methyl)-3-methylpyrrolidin-2-one hydrochloride (188 mg, 92%) was prepared from the above intermediate tert-butyl (S)-5-chloro-8-((5-(difluoromethyl)-1-methyl-1H-1,2,3-triazol-4-yl)methoxy)-1-(((R)-3-methyl-2-oxopyrrolidin-1-yl)methyl)-3,4-dihydroisoquinoline-2(1H)-carboxylate (218 mg, 0.4 mmol) using a procedure similar to that described for Example 1, step d and was used without further purification. LCMS (Method 6): 0.63 min, 439.8 [M+H]⁺.

Step c. 2,4-Dimethoxybenzyl (1S,2R)-2-((S)-5-chloro-8-((5-(difluoromethyl)-1-methyl-1H-1,2,3-triazol-4-yl)methoxy)-1-(((R)-3-methyl-2-oxopyrrolidin-1-yl)methyl)-1,2,3,4-tetrahydroisoquinoline-2-carbonyl)-1-methylcyclohexane-1-carboxylate (91 mg, 23%) was prepared from the above intermediate (94 mg, 0.2 mmol) and Intermediate 29 (122 mg, 0.25 mmol) using a procedure similar to that described for Example 11 step d. The crude product was purified by flash column chromatography (2-4% MeOH in DCM). LCMS (Method 6b): 2.86 min, 757.7 [M–H]⁻.

Step d. The title compound (15.4 mg, 56%) was prepared from the above intermediate (91 mg, 0.04 mmol) using a procedure similar to that described for Example 29, step b. The crude product was purified by flash column chromatography (2% MeOH in DCM). LCMS (Method 10): 2.50 min, 608.5 [M+H]⁺. $^1$H NMR (400 MHz, CDCl₃) δ 7.30 (d, 1H), 6.98 (d, 1H), 6.94 (t, 1H), 5.94 (m, 1H), 5.31 (d, 1H), 5.26 (d, 1H), 4.20 (s, 3H), 4.10-3.92 (m, 2H), 3.90-3.80 (m, 1H), 3.60 (m, 1H), 3.17 (dd, 1H), 3.11-2.98 (m, 2H), 2.81-2.69 (m, 1H), 2.55 (m, 1H), 2.40 (m, 1H), 2.28-2.10 (m, 2H), 1.82 (m, 2H), 1.68-1.19 (m, 5H), 1.13-1.08 (m, 6H), 1.01 (m, 1H).

Example 117

(1S,2R)-2-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)-1-ethylcyclohexane-1-carboxylic acid

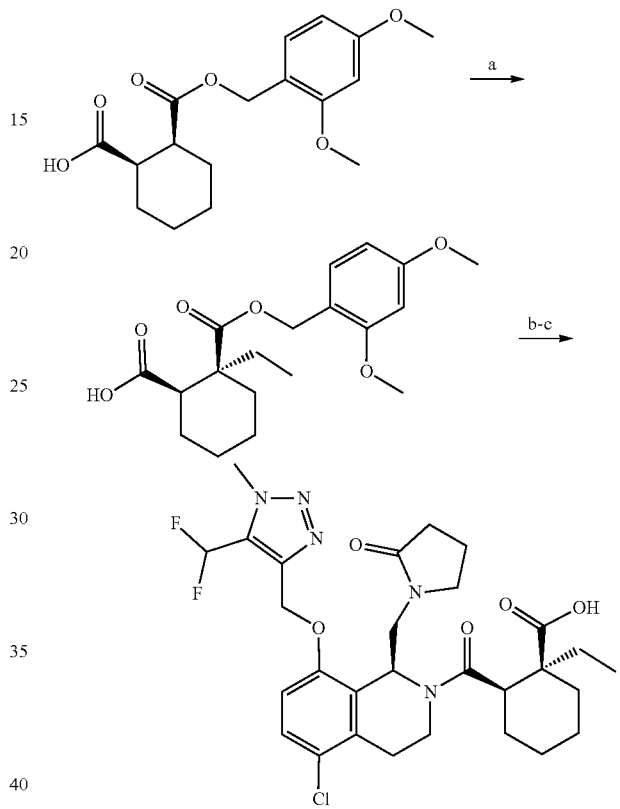

Step a. To a stirred solution of Intermediate 28 (400 mg, 1.24 mmol) in THF (10 mL) at −30° C. under argon was added LDA (2M in THF, heptane, ethylbenzene) (1.61 mL, 3.23 mmol) over 5 min. The resulting solution was stirred for 0.5 h and allowed to warm to −20° C. To this solution was added iodoethane (0.3 mL, 3.72 mmol) and the resulting solution was stirred for 2 h maintaining internal temperature at 10° C. The solution was stirred for another 1 h, diluted with saturated aqueous ammonium chloride solution. The mixture was partitioned between EtOAc and water and further extracted with EtOAc. The combined organics were dried (Na₂SO₄), filtered and concentrated in vacuo to give (1R,2S)-2-(((2,4-dimethoxybenzyl)oxy)carbonyl)-2-ethylcyclohexane-1-carboxylic acid (300 mg, 69%, ~70% purity), used without further purification. LCMS (Method 15): 1.65 min, m/z 373.1 [M+Na]⁺.

Steps b-c. The title compound (25 mg, 13%) was prepared from the above intermediate (148 mg, 0.42 mmol) using procedures similar to that described for Example 91 steps a, b. LCMS (Method 3): 4.52 min, 606.1 [M+H]⁺. $^1$H NMR (400 MHz, DMSO-d₆) δ 11.93 (bs, 1H), 7.59 (t, 1H), 7.38 (d, 1H), 7.15 (d, 1H), 5.78 (dd, 1H), 5.29 (s, 2H), 4.17 (s, 3H), 3.95 (dd, 1H), 3.85 (dd, 1H), 3.59 (m, 1H), 3.41-3.26 (m, 1H), 3.03 (m, 1H), 2.98 (dd, 1H), 2.92-2.77 (m, 2H), 2.76-2.62 (m, 1H), 2.33-2.10 (m, 2H), 2.04-1.93 (m, 1H), 1.92-1.60 (m, 4H), 1.55-1.35 (m, 5H), 1.33-1.05 (m, 2H), 0.72 (t, 3H).

Example 123

(1S,2R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid

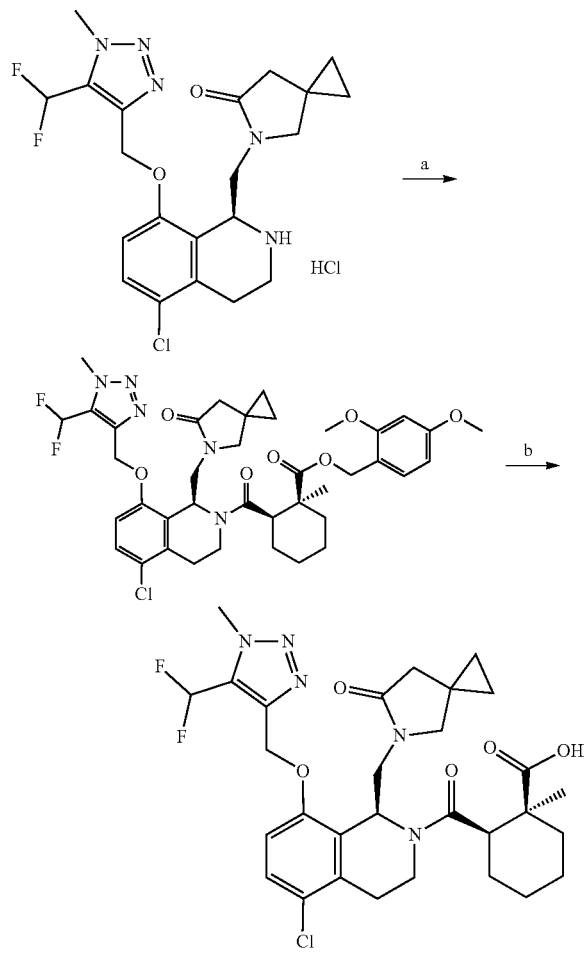

Step a. 2,4-Dimethoxybenzyl (1S,2R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylate (501 mg, 20%) was prepared from (S)-5-((5-chloro-8-((5-(difluoromethyl)-1-methyl-1H-1,2,3-triazol-4-yl)methoxy)-1,2,3,4-tetrahydroisoquinolin-1-yl)methyl)-5-azaspiro[2.4]heptan-6-one hydrochloride (1.92 g, 3.26 mmol; Example 110 step b) and Intermediate 29 (1.65 g, 5.00 mmol) using a procedure similar to that described for Example 11, step d. The crude product was purified by flash column chromatography on the Biotage Isolera (45 g column, 0-4% MeOH in DCM), followed by a further purification (60 g column, 20-80% 0.1% formic acid in MeCN). LCMS (Method 9a): 2.85 min, 770.3 [M+H]⁺. This purification also yielded Example 123 directly (155 mg, 7%).

Step a Method 2. A mixture of (S)-5-((5-chloro-8-((5-(difluoromethyl)-1-methyl-1H-1,2,3-triazol-4-yl)methoxy)-1,2,3,4-tetrahydroisoquinolin-1-yl)methyl)-5-azaspiro[2.4]heptan-6-one hydrochloride (12.4 g, 25.4 mmol; Example 110 step b), Intermediate 33 (17.3 g, 38.1 mmol) and DIPEA (8.85 mL, 50.8 mmol), in DMF (30 mL) was stirred under nitrogen at rt for 6 days. The mixture was diluted with water (120 mL) and extracted with ethyl acetate. The combined organics were dried (MgSO₄), filtered and concentrated in vacuo. The crude product was purified by flash column chromatography on the Teledyne ISCO CombiFlash® Rf+ (330 g silica column Puriflash HC, 0-5% MeOH in DCM) followed by another purification on the Teledyne ISCO CombiFlash® Rf+ (330 g silica column Puriflash HC, 0-5% MeOH in DCM) to give 2,4-dimethoxybenzyl (1S,2R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylate (14.7 g, 75%). LCMS (Method 15): 1.71 min, 770.5 [M+H]⁺.

Step b. A solution of the above intermediate (500 mg, 0.65 mmol) in hydrogen chloride in dioxane (4 M; 25 mL, 100 mmol) was stirred at rt for 10 mins and concentrated in vacuo to provide the title compound (160 mg, 39%). LCMS (Method 10): 2.52 min, 620.3 [M+H]⁺. ¹H NMR (300 MHz, DMSO-d₆) δ 11.84 (bs, 1H), 7.57 (t, 1H), 7.38 (d, 1H), 7.14 (d, 1H), 5.77 (m, 1H), 5.28 (s, 2H), 4.16 (s, 3H), 4.04-3.86 (m, 2H), 3.59 (m, 1H), 3.38-3.24 (m, 1H), 3.06-2.90 (m, 2H), 2.84 (m, 1H), 2.77-2.65 (m, 1H), 2.61 (d, 1H), 2.37-2.15 (m, 2H), 2.10 (d, 1H), 1.75-1.16 (m, 7H), 1.10 (s, 3H), 0.67-0.32 (m, 4H).

Step b Method 2. To a stirred solution of the above intermediate (14.7 g, 19.1 mmol) in DCM (92 mL) was added triethylsilane (3.05 mL, 19.1 mmol) followed by dropwise addition of TFA (1.76 mL, 22.9 mmol). The resulting solution was stirred for 1.5 h. The precipitate was removed by filtration, and the filtrate was concentrated in vacuo to 5 mL. The residue was purified by flash column chromatography on the Teledyne ISCO CombiFlash® Rf⁺ (220 g silica column Puriflash HC, 0-3% MeOH in DCM). The product was then dissolved in 10 mL of warm EtOH and left to cool to rt and the resulting precipitate was collected by filtration and the precipitate was washed with cold EtOH. The material was then slurried in MeCN (30 mL) and collected by filtration to provide the title compound (9.45 g, 15.0 mmol, 78%). LCMS (Method 3): 4.57 min, 620.4 [M+H]⁺.

Example 123A (1S,2R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid; potassium salt

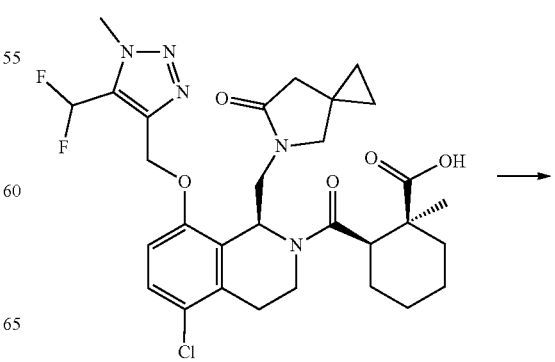

231
-continued

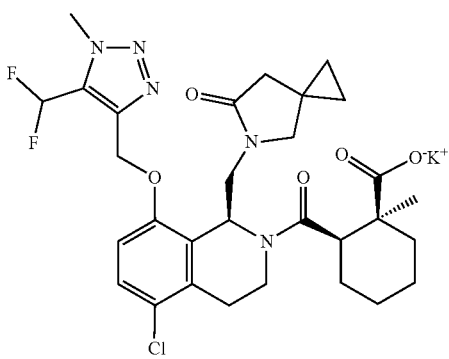

Example 123 (1.2 g, 1.94 mmol) was dissolved in 1,4-dioxane (100 mL) and potassium hydroxide (3.84 mL, 1.94 mmol) was added to give a clear solution. Water (100 mL) was added to the solution and the resulting solution was filtered through a coarse frit. The solution was freeze dried overnight, suspended in water and freeze-dried overnight again to remove the residual dioxane, providing the title compound (1.2 g, 94%). LCMS (Method 3): 4.56 min, 620.4 [M+H]$^+$. $^1$H NMR (400 MHz, DMSO-d$_6$) δ 7.59 (t, 1H), 7.34 (d, 1H), 7.11 (d, 1H), 5.75 (dd, 1H), 5.25 (m, 2H), 4.16 (s, 3H), 4.00-3.81 (m, 2H), 3.53-3.23 (m, 2H), 3.03 (m, 1H), 2.96-2.86 (m, 2H), 2.69 (m, 1H), 2.56-2.45 (m, 1H), 2.36-2.20 (m, 1H), 2.11 (m, 2H), 1.63-1.06 (m, 7H), 0.93 (s, 3H), 0.61-0.45 (m, 3H), 0.41 (m, 1H).

Example 135

(1S,2R)-2-((S)-5-chloro-8-((4-(difluoromethyl)pyrimidin-5-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid 232
-continued

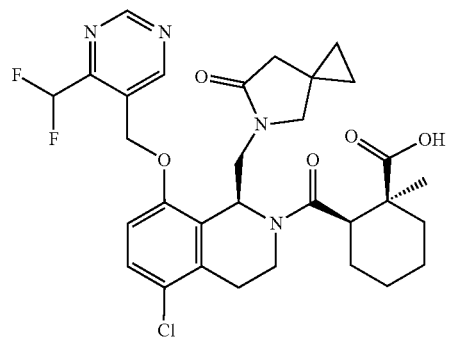

Step a. 2,4-Dimethoxybenzyl (1S,2R)-2-((S)-5-chloro-8-((4-(difluoromethyl)-pyrimidin-5-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylate (17 mg, 6%) was prepared from 5-(chloromethyl)-4-(difluoromethyl)pyrimidine (31 mg, 0.17 mmol) and Intermediate 37 (71 mg, 0.11 mmol) using a procedure similar to that described for Example 11, step b, used without further purification. LCMS (Method 9c): 1.54 min, 767.4 [M+H]$^+$.

Step b. A solution of 2,4-dimethoxybenzyl (1S,2R)-2-((S)-5-chloro-8-((4-(difluoromethyl)pyrimidin-5-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylate (17.4 mg, 0.020 mmol) in HCl in dioxane (4M; 0.46 mL, 1.83 mmol) was stirred at rt for 10 mins. The reaction mixture was concentrated in vacuo and the crude was purified by MDAP (Method 10-35% acetonitrile in 0.1% ammonium hydroxide) and selected fractions freeze dried to give the title compound (1.4 mg, 10%). LCMS (Method 9b): 1.51 min, 617.2 [M+H]$^+$. $^1$H NMR (300 MHz, CDCl$_3$) δ 9.27 (s, 1H), 9.09 (s, 1H), 7.33 (d, 1H), 6.82 (d, 1H), 6.66 (t, 1H), 6.10 (dd, 1H), 5.43 (m, 1H), 5.32 (m, 1H), 4.20 (dd, 1H), 4.11-3.84 (m, 2H), 3.49 (d, 1H), 3.19-3.05 (m, 2H), 3.01 (d, 1H), 2.79 (m, 1H), 2.62 (m, 1H), 2.48-2.36 (m, 2H), 2.12 (d, 1H), 1.90-1.76 (m, 2H), 1.71-1.22 (m, 4H), 1.15 (s, 3H), 1.04 (m, 1H), 0.73-0.47 (m, 4H).

Example 140

(2R,3S)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)tetrahydro-2H-pyran-3-carboxylic acid

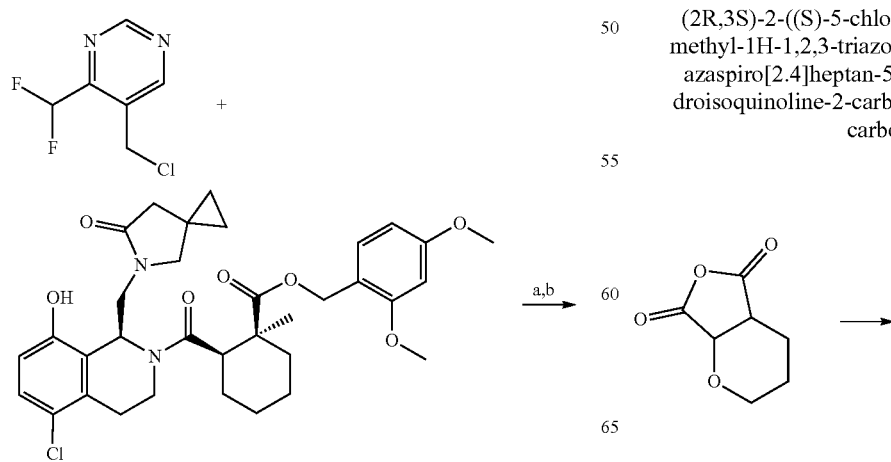

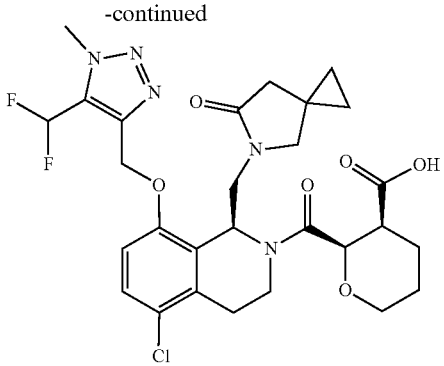

To a stirred solution of (S)-5-((5-chloro-8-((5-(difluoromethyl)-1-methyl-1H-1,2,3-triazol-4-yl)methoxy)-1,2,3,4-tetrahydroisoquinolin-1-yl)methyl)-5-azaspiro[2.4]heptan-6-one hydrochloride (389 mg, 0.80 mmol; Example 110 step b) and DIPEA (0.69 mL, 3.98 mmol) in MeCN (8.943 mL) was added tetrahydro-2H-furo[3,4-b]pyran-5,7-dione (Example 140 Intermediate; 249 mg, 0.80 mmol) in DCM. The reaction mixture was stirred at rt for 30 mins, concentrated in vacuo and purified using the Isolera (Biotage C18 SNAP 30 g, 5-30% MeCN in water, 0.1% ammonia), followed by preparative HPLC (Method 6) to give the title compound (23 mg, 5%). LCMS (Method 13): 2.19 min, 608.1 [M+H]$^+$. $^1$H NMR (400 MHz, CDCl$_3$; rotamers observed, both reported) δ 7.40-6.82 (m, 3H), 5.83 (dd, 0.7H), 5.74 (dd, 0.3H), 5.37-5.16 (m, 2H), 4.78 (m, 0.3H), 4.72-4.61 (m, 1H), 4.33 (dd, 0.7H), 4.18 (s, 0.9H), 4.14 (s, 2.1H), 4.08 (dd, 0.7H), 3.84-3.09 (m, 5.3H), 3.06 (d, 0.3H), 3.01 (d, 0.7H), 2.97-2.83 (m, 1H), 2.82-2.65 (m, 2H), 2.45-2.33 (m, 1H), 2.32-2.10 (m, 2H), 2.01-1.40 (m, 3H), 0.68-0.42 (m, 4H).

Example 141

(R)-2-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)bicyclo[2.2.2]octane-1-carboxylic acid

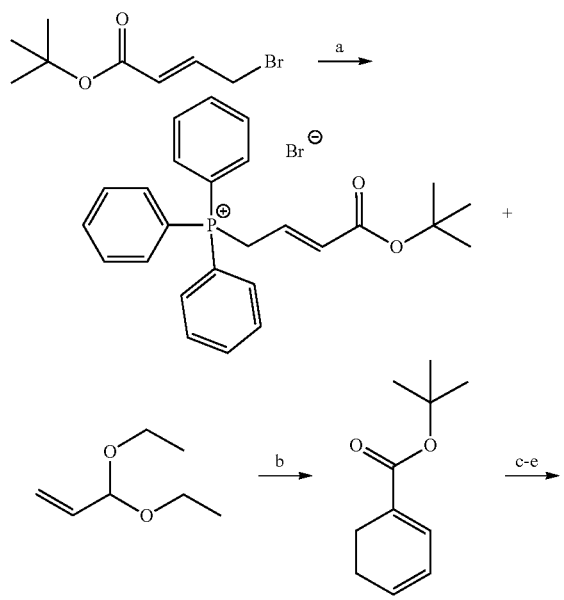

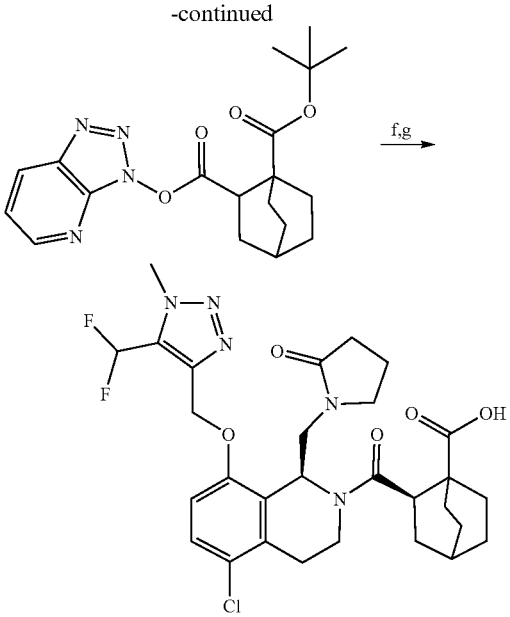

Step a. To a solution of triphenylphosphine (749 mg, 2.85 mmol) in toluene (4 mL) was added tert-butyl (E)-4-bromobut-2-enoate (631 mg, 2.85 mmol, CAS: 86606-04-4) dropwise and the resulting mixture was stirred at rt for 66 h. The resulting precipitate was collected by filtration, washed with toluene and dried in vacuo at 50° C. for 5 h to give (E)-(4-(tert-butoxy)-4-oxobut-2-en-1-yl)triphenylphosphonium bromide (874 mg, 63%). $^1$H NMR (300 MHz, CDCl$_3$) δ 7.92-7.77 (m, 9H), 7.74-7.65 (m, 6H), 6.70-6.44 (m, 2H), 5.30-5.21 (m, 2H), 1.42 (s, 9H).

Step b. To a stirred solution of 3,3-diethoxyprop-1-ene (0.28 mL, 1.81 mmol, CAS: 3054-95-3) in water (0.40 mL) was added (+)-camphor-10-sulfonic acid (14 mg, 0.06 mmol, CAS: 3144-16-9) and the resulting mixture was stirred for 0.5 h to produce acrolein. To a solution of the above intermediate (873 mg, 1.81 mmol) in DCM (14 mL) was added saturated aqueous sodium bicarbonate solution (11 mL, 1.81 mmol) followed by the above solution containing acrolein and the resulting mixture was stirred at rt under argon for 48 h. The organic phase was separated and the aqueous layer was extracted with DCM. The combined organics were dried over Na$_2$SO$_4$ and concentrated in vacuo. The crude product was purified by flash column chromatography on the Teledyne ISCO CombiFlash® Rf+ (40 g silica column, 100% DCM) to provide tert-butyl cyclohexa-1,3-diene-1-carboxylate (191 mg, 59%). $^1$H NMR (400 MHz, CDCl$_3$) δ 6.91 (dd, 1H), 6.13-6.01 (m, 2H), 2.44-2.37 (m, 2H), 2.28-2.21 (m, 2H), 1.50 (s, 9H).

Step c. A sealed vial containing tert-butyl prop-2-enoate (0.35 mL, 2.39 mmol, CAS: 2495-35-4) and the above intermediate (220 mg, 1.59 mmol) under argon was heated at 140° C. for 18 h. The reaction mixture was cooled to rt, diluted with DCM and purified by flash column chromatography on the Teledyne ISCO CombiFlash® Rf+ (25 g silica, 0-10% EtOAc in cyclohexane) to provide 2-benzyl 1-(tert-butyl)-bicyclo[2.2.2]oct-5-ene-1,2-dicarboxylate (146 mg, 53%). $^1$H NMR (400 MHz, CDCl$_3$) δ 7.35-7.29 (m, 5H), 6.63-6.47 (m, 1H), 6.29-6.14 (m, 1H), 5.14-4.99 (m, 2H), 3.14-3.00 (m, 1H), 2.78-2.61 (m, 1H), 2.06-1.99 (m, 1H), 1.90-1.23 (m, 14H).

Step d. A solution of the above intermediate (146 mg, 0.43 mmol) and Pd/C (10%; 12 mg, 0.11 mmol) in EtOAc (4 mL)

was stirred under hydrogen at atmospheric pressure at rt for 18 h. The catalyst was removed by filtration through Celite® and the filtrate concentrated in vacuo to provide the title compound (101 mg, 93%) as a mixture of 1-(tert-butoxycarbonyl)bicyclo[2.2.2]octane-2-carboxylic acid and 4-(tert-butoxycarbonyl)-bicyclo[2.2.2]octane-2-carboxylic acid. ¹H NMR (400 MHz, CDCl₃) δ 2.99 (m, 0.6H), 2.71-2.65 (m, 0.4H), 2.16-1.49 (m, 11H), 1.42 (s, 3.6H), 1.41 (s, 5.4H).

Step e. To a stirred solution of the above intermediate (101 mg, 0.40 mmol) and HATU (166 mg, 0.44 mmol; CAS: 148893-10-1) in DMF (1 mL) was added DIPEA (0.08 mL, 0.48 mmol) and the reaction mixture stirred at rt under argon for 1 h. The reaction mixture was diluted with saturated sodium bicarbonate solution and extracted with EtOAc. The combined organics were washed with water, brine, dried over Na₂SO₄, filtered and concentrated in vacuo. Purification by flash column chromatography on the Teledyne ISCO CombiFlash® Rf+ (25 g silica column, 0-100% EtOAc in cyclohexane) gave 2-(3H-[1,2,3]triazolo[4,5-b]pyridin-3-yl) 1-(tert-butyl) bicyclo[2.2.2]octane-1,2-dicarboxylate (69 mg, 47%). LCMS (Method 16): 1.54 min, 373.3 [M+H]⁺. ¹H NMR (400 MHz, CDCl₃) δ 8.71 (dd, 1H), 8.40 (dd, 1H), 7.42 (dd, 1H), 3.49 (ddd, 1H), 2.33-2.20 (m, 2H), 2.11-2.05 (m, 1H), 1.93-1.80 (m, 4H), 1.73-1.61 (m, 4H), 1.46 (s, 9H).

Step f. To a stirred solution of (S)-1-((5-chloro-8-((5-(difluoromethyl)-1-methyl-1H-1,2,3-triazol-4-yl)methoxy)-1,2,3,4-tetrahydroisoquinolin-1-yl)methyl)pyrrolidin-2-one hydrochloride (Example 86 step b; 94 mg, 0.20 mmol) and the above intermediate (69 mg, 0.19 mmol) in DMF (1.3 mL) was added DIPEA (0.04 mL, 0.22 mmol) and the reaction mixture was stirred at rt under argon for 18 h. The reaction mixture was diluted with saturated sodium bicarbonate solution and extracted with EtOAc. The combined organics were washed with water, brine, dried over Na₂SO₄, filtered and concentrated in vacuo. Purification by flash column chromatography on the Teledyne ISCO CombiFlash® Rf+ (12 g silica column, 0-100% EtOAc in cyclohexane) gave tert-butyl 2-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)bicyclo[2.2.2]octane-1-carboxylate as a mixture of diastereoisomers (101 mg, 82%). LCMS (Method 16): 1.50 min, 684.5 [M+Na]⁺ and 1.56 min, 684.5 [M+Na]⁺.

Step g. To a stirred solution of the above intermediate (101 mg, 0.15 mmol) in DCM (1 mL) was added TFA (0.01 mL, 0.15 mmol) and the resulting mixture stirred at rt for 18 h. A further aliquot of TFA (0.01 mL, 0.15 mmol) was added and the resulting mixture was stirred at rt for an additional 30 min. The reaction mixture was concentrated in vacuo and purification by flash column chromatography on the Teledyne ISCO CombiFlash® Rf+ (12 g silica column, 0-5% MeOH in DCM) followed by reverse phase prep HPLC (X-Select CSH 5 um C18 19×250 mm, 10-98% MeCN in 0.1% aqueous formic acid) gave the title compound (13 mg, 14%). LCMS (Method 3): 4.16 min, 606.3 [M+H]⁺. ¹H NMR (400 MHz, DMSO-d₆) δ 7.59 (t, 1H), 7.38 (d, 1H), 7.15 (d, 1H), 5.75 (dd, 1H), 5.29 (s, 2H), 4.18 (s, 3H), 4.03 (dd, 1H), 3.84 (dd, 1H), 3.54 (m, 1H), 3.46-3.26 (m, 1H), 3.10 (m, 1H), 2.94 (dd, 1H), 2.89-2.77 (m, 2H), 2.68 (m, 1H), 2.58-2.36 (m, 1H), 2.18 (m, 1H), 2.05-1.43 (m, 11H), 1.37 (m, 1H), 1.21 (m, 1H).

Example 142

(1S,2R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic-4,4-d₂ acid

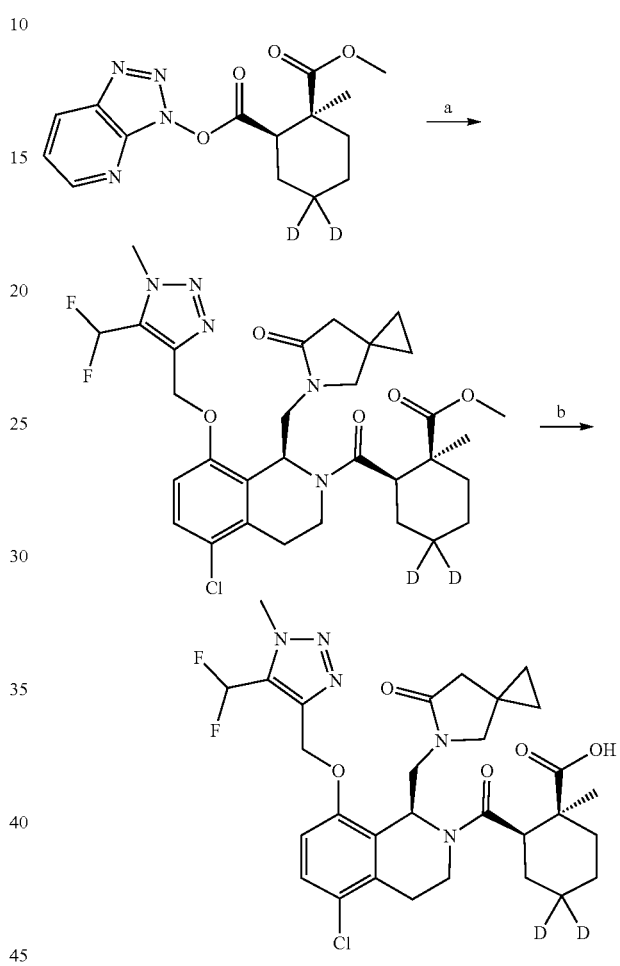

Step a. To a stirred solution of (S)-5-((5-Chloro-8-((5-(difluoromethyl)-1-methyl-1H-1,2,3-triazol-4-yl)methoxy)-1,2,3,4-tetrahydroisoquinolin-1-yl)methyl)-5-azaspiro[2.4]heptan-6-one hydrochloride (165 mg, 0.340 mmol; Example 110 step b) and 2-(3H-[1,2,3]triazolo[4,5-b]pyridin-3-yl) 1-methyl (1S,2R)-1-methylcyclohexane-1,2-dicarboxylate-4,4-d₂ (130 mg, 0.41 mmol) in DMF (1.4 mL) was added DIPEA (0.12 mL, 0.680 mmol) and the resulting mixture stirred at rt under argon for 2 days. The reaction mixture was diluted with saturated sodium bicarbonate solution and extracted with EtOAc. The combined organics were washed with water and brine, dried over Na₂SO₄, filtered and concentrated in vacuo. The crude product was purified by flash column chromatography on the Teledyne ISCO CombiFlash® Rf+ (40 g silica column Puriflash HC, 0-100% EtOAc in cyclohexane) to provide methyl (1S,2R)-2-((S)-5-chloro-8-((5-(difluoromethyl)-1-methyl-1H-1,2,3-triazol-4-yl)methoxy)-1-((6-oxo-5-azaspiro[2.4]heptan-5-yl) methyl)-1,2,3,4-tetrahydroisoquinoline-2-carbonyl)-1-methylcyclohexane-1-carboxylate-4,4-d₂ (112 mg, 52%). LCMS (Method 2): 1.45 min, 636.3 [M+H]⁺.

Step b. To a solution of the above intermediate (105 mg, 0.17 mmol) in MeOH (2.4 mL) was added a solution of sodium hydroxide (3 M; 0.55 mL, 1.65 mmol) and the resulting mixture was heated at 100° C. under microwave irradiation for 15 h. The solution was cooled and concentrated in vacuo. The residue was diluted with water, acidified to pH 4 using 5% citric acid solution and the aqueous was extracted with EtOAc. The combined organics were washed with water, brine, dried (Na$_2$SO$_4$) and concentrated in vacuo. The crude product was purified by reverse phase flash column chromatography on the InterChim 4125 (80 g C18 InterChim HP, 5-70% MeCN in water+0.1% HCOOH buffer) to provide the title compound (50 mg, 47%). LCMS (Method 3): 4.56 min, 622.5 [M+H]$^+$. $^1$H NMR (400 MHz, CDCl$_3$) δ 15.23 (bs, 1H), 7.30 (d, 1H), 6.98 (d, 1H), 6.92 (t, 1H), 5.95 (dd, 1H), 5.36-5.20 (m, 2H), 4.17 (m, 3H), 4.11 (dd, 1H), 4.00 (m, 1H), 3.88 (m, 1H), 3.44 (d, 1H), 3.15 (m, 1H), 3.11-3.01 (m, 2H), 2.75 (m, 1H), 2.59 (dd, 1H), 2.46-2.35 (m, 2H), 2.12 (d, 1H), 1.82 (m, 1H), 1.70-1.40 (m, 3H), 1.13 (s, 3H), 1.02 (m, 1H), 0.74-0.45 (m, 4H).

Example 143

(1S,2R)-2-((S)-5-chloro-8-((1,5-dimethyl-1H-1,2,3-triazol-4-yl)methoxy)-7-fluoro-1-((6-oxo-5-azaspiro[2.4]heptan-5-yl)methyl)-1,2,3,4-tetrahydroisoquinoline-2-carbonyl)-1-methylcyclohexane-1-carboxylic acid

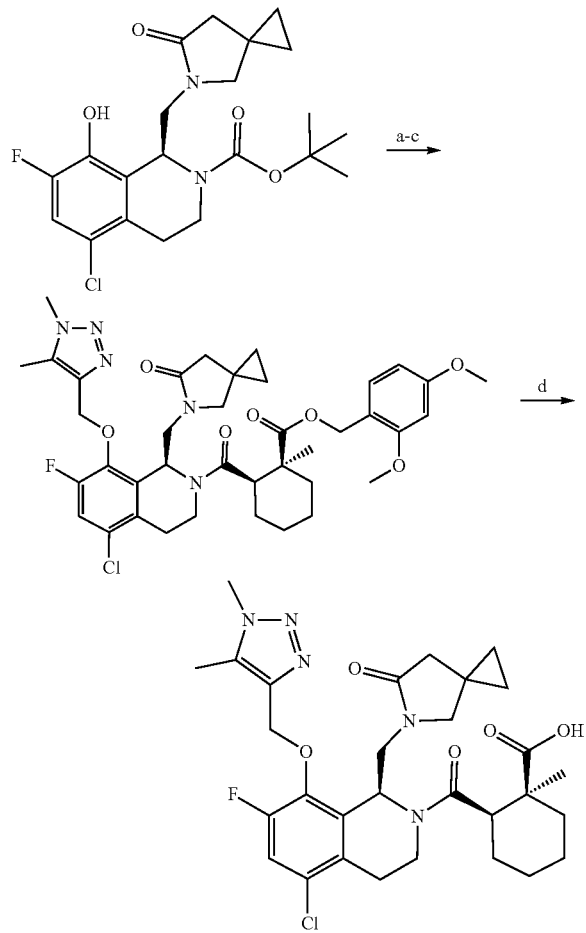

Step a. A mixture of Intermediate 50 (142 mg, 0.33 mmol), 4-(chloromethyl)-1,5-dimethyl-1H-1,2,3-triazole (63 mg, 0.430 mmol) and caesium carbonate (327 mg, 1 mmol) in DMF (1 mL) was stirred under nitrogen at rt for 18 h. A further amount of 4-(chloromethyl)-1,5-dimethyl-1H-1,2,3-triazole (32 mg, 0.22 mmol) and caesium carbonate (163 mg, 0.5 mmol) was added and the mixture stirred for a further 5 h. The reaction mixture was diluted with water and extracted with EtOAc. The combined organics were washed with water, brine, dried over Na$_2$SO$_4$, filtered and concentrated in vacuo. Purification by flash column chromatography on the Teledyne ISCO CombiFlash® Rf+ (12 g silica column Puriflash HC, 0-100% EtOAc in cyclohexane) gave tert-butyl (S)-5-chloro-8-((1,5-dimethyl-1H-1,2,3-triazol-4-yl)methoxy)-7-fluoro-1-((6-oxo-5-azaspiro[2.4]heptan-5-yl)methyl)-3,4-dihydroisoquinoline-2(1H)-carboxylate (150 mg, 84%). LCMS (Method 2): 1.64 min, 534.2 [M+H]$^+$.

Step b. Hydrochloric acid (4M in dioxane; 1.4 mL, 5.62 mmol) was added to the above intermediate (150 mg, 0.28 mmol) and the resulting reaction mixture left to stir at rt for 0.5 h. The reaction mixture was concentrated in vacuo and azeotroped with toluene to give (S)-5-((5-chloro-8-((1,5-dimethyl-1H-1,2,3-triazol-4-yl)methoxy)-7-fluoro-1,2,3,4-tetrahydroisoquinolin-1-yl)methyl)-5-azaspiro[2.4]heptan-6-one hydrochloride (146 mg, assumed quantitative). LCMS (Method 2): 0.97 min, 434.1 [M+H]$^+$.

Step c. To a stirred solution of the above intermediate (132 mg, 0.280 mmol) and Intermediate 33 (113 mg, 0.250 mmol) in DMF (1 mL) was added DIPEA (0.1 mL, 0.560 mmol) and the resulting mixture was stirred at rt under argon for 4 days. The reaction mixture was diluted with EtOAc and saturated sodium bicarbonate solution and extracted with EtOAc. The combined organics were washed with water and brine, dried over Na$_2$SO$_4$, filtered and concentrated in vacuo. The crude product was purified by flash column chromatography on the Teledyne ISCO CombiFlash® Rf+ (12 g silica column Puriflash HC, 0 to 100% EtOAc in cyclohexane) to provide 2,4-dimethoxybenzyl (1S,2R)-2-((S)-5-chloro-8-((1,5-dimethyl-1H-1,2,3-triazol-4-yl)methoxy)-7-fluoro-1-((6-oxo-5-azaspiro-[2.4]heptan-5-yl)methyl)-1,2,3,4-tetrahydroisoquinoline-2-carbonyl)-1-methylcyclohexane-1-carboxylate (119 mg, 56%). LCMS (Method 2): 1.77 min, 752.4 [M+H]$^+$.

Step d. To a stirred solution of the above intermediate (119 mg, 0.16 mmol) in DCM (1.5 mL) was added triethylsilane (0.03 mL, 0.160 mmol), followed by TFA (0.01 mL, 0.160 mmol) and the resulting mixture was stirred at rt for 30 min. The reaction mixture was concentrated in vacuo and the residue purified by flash column chromatography on the Teledyne ISCO CombiFlash® Rf+ (12 g silica column Puriflash HC, 15 um, 0-5% MeOH in DCM). Fractions containing the desired product were combined and concentrated in vacuo. The residue was taken up in MeCN/water (1:1) and freeze dried to provide the title compound (72 mg, 73%). LCMS (Method 3a): 3.01 min, 602.4 [M+H]$^+$. $^1$H NMR (400 MHz, DMSO-d$_6$) δ 11.88 (bs, 1H), 7.52 (d, 1H), 5.46 (dd, 1H), 5.27 (d, 1H), 5.08 (dd, 1H), 4.00-3.82 (m, 5H), 3.53 (m, 1H), 3.06 (m, 1H), 2.97 (t, 1H), 2.92 (dd, 1H), 2.83-2.71 (m, 2H), 2.62 (m, 1H), 2.38-2.16 (m, 2H), 2.13 (s, 3H), 2.05 (d, 1H), 1.71-1.49 (m, 3H), 1.48-1.14 (m, 4H), 1.11 (s, 3H), 0.65-0.40 (m, 4H).

Example 144

(1S,2R)-2-((S)-5-chloro-7-fluoro-1-((6-oxo-5-azaspiro[2.4]heptan-5-yl)methyl)-8-((4,5,6,7-tetrahydro-[1,2,3]triazolo[1,5-a]pyridin-3-yl)methoxy)-1,2,3,4-tetrahydroisoquinoline-2-carbonyl)-1-methylcyclohexane-1-carboxylic acid

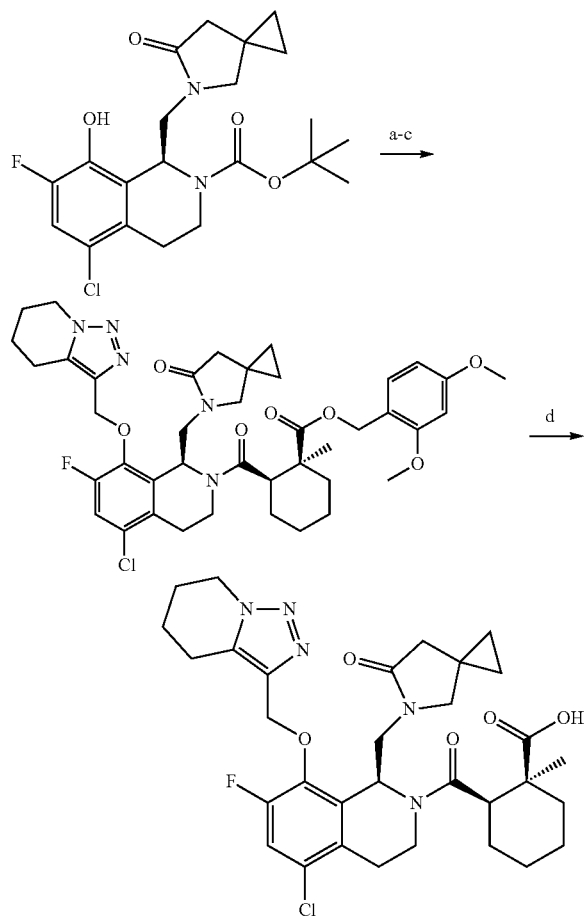

Step a. A mixture of Intermediate 50 (142 mg, 0.33 mmol), 3-(chloromethyl)-4,5,6,7-tetrahydro-[1,2,3]triazolo[1,5-a]pyridine (75 mg, 0.430 mmol) and caesium carbonate (327 mg, 1 mmol) in DMF (1 mL) was stirred under nitrogen at rt for 18 h. A further amount of 3-(chloromethyl)-4,5,6,7-tetrahydro-[1,2,3]triazolo[1,5-a]pyridine (38 mg, 0.22 mmol) and caesium carbonate (163 mg, 0.5 mmol) was added and the mixture stirred for a further 5 h. The reaction mixture was diluted with water and extracted with EtOAc. The combined organics were washed with water, brine, dried over Na$_2$SO$_4$, filtered and concentrated in vacuo. Purification by flash column chromatography on the Teledyne ISCO CombiFlash® Rf+ (12 g silica column Puriflash HC, 0-100% EtOAc in cyclohexane) gave tert-butyl (S)-5-chloro-7-fluoro-1-((6-oxo-5-azaspiro[2.4]heptan-5-yl)methyl)-8-((4,5,6,7-tetrahydro-[1,2,3]triazolo[1,5-a]pyridin-3-yl)methoxy)-3,4-dihydroisoquinoline-2(1H)-carboxylate (139 mg, 74%). LCMS (Method 2): 1.71 min, 560.3 [M+H]$^+$.

Step b. Hydrochloric acid (4M in dioxane; 1.2 mL, 4.96 mmol) was added to the above intermediate (139 mg, 0.25 mmol) and the resulting reaction mixture left to stir at rt for 0.5 h. The reaction mixture was concentrated in vacuo and azeotroped with toluene to give (S)-5-((5-chloro-7-fluoro-8-((4,5,6,7-tetrahydro-[1,2,3]triazolo[1,5-a]pyridin-3-yl)methoxy)-1,2,3,4-tetrahydroisoquinolin-1-yl)methyl)-5-azaspiro[2.4]heptan-6-one (136 mg, assumed quantitative). LCMS (Method 2): 1.02 min, 460.2 [M+H]$^+$.

Step c. To a stirred solution of the above intermediate (123 mg, 0.250 mmol) and Intermediate 33 (169 mg, 0.37 mmol) in DMF (1 mL) was added DIPEA (0.09 mL, 0.50 mmol) and the resulting mixture was stirred at rt under argon for 4 days. The reaction mixture was diluted with EtOAc and saturated sodium bicarbonate solution and extracted with EtOAc. The combined organics were washed with water and brine, dried over Na$_2$SO$_4$, filtered and concentrated in vacuo. The crude product was purified by flash column chromatography on the Teledyne ISCO CombiFlash® Rf+ (12 g silica column Puriflash HC, 0 to 100% EtOAc in cyclohexane) to provide 2,4-dimethoxybenzyl (1S,2R)-2-((S)-5-chloro-7-fluoro-1-((6-oxo-5-azaspiro[2.4]heptan-5-yl)methyl)-8-((4,5,6,7-tetrahydro-[1,2,3]triazolo[1,5-a]pyridin-3-yl)methoxy)-1,2,3,4-tetrahydroisoquinoline-2-carbonyl)-1-methylcyclohexane-1-carboxylate (103 mg, 53%). LCMS (Method 2): 1.81 min, 778.4 [M+H]$^+$.

Step d. To a stirred solution of the above intermediate (103 mg, 0.13 mmol) in DCM (1.2 mL) was added triethylsilane (0.02 mL, 0.13 mmol), followed by TFA (0.01 mL, 0.13 mmol) and the resulting mixture was stirred at rt for 30 min. The reaction mixture was concentrated in vacuo and the residue purified by flash column chromatography on the Teledyne ISCO CombiFlash® Rf+ (12 g silica column Puriflash HC, 15 um, 0-5% MeOH in DCM). Fractions containing the desired product were combined and concentrated in vacuo. The residue was taken up in MeCN/water (1:1) and freeze dried to provide the title compound (56 mg, 73%). LCMS (Method 3a): 3.25 min, 628.5 [M+H]$^+$. $^1$H NMR (400 MHz, DMSO-d$_6$) δ 11.88 (bs, 1H), 7.51 (d, 1H), 5.58 (dd, 1H), 5.26 (dd, 1H), 5.09 (dd, 1H), 4.28 (m, 2H), 4.00-3.84 (m, 2H), 3.55 (m, 1H), 3.13 (d, 1H), 3.06-2.56 (m, 7H), 2.35-2.16 (m, 2H), 2.08 (d, 1H), 2.03-1.92 (m, 2H), 1.88-1.72 (m, 2H), 1.70-1.48 (m, 3H), 1.47-1.19 (m, 4H), 1.10 (s, 3H), 0.65-0.42 (m, 4H).

Example 146

(1S,2R)-2-((S)-5-chloro-8-((5,6-dihydro-4H-pyrrolo[1,2-c][1,2,3]triazol-3-yl)methoxy)-7-fluoro-1-((6-oxo-5-azaspiro[2.4]heptan-5-yl)methyl)-1,2,3,4-tetrahydroisoquinoline-2-carbonyl)-1-methylcyclohexane-1-carboxylic acid

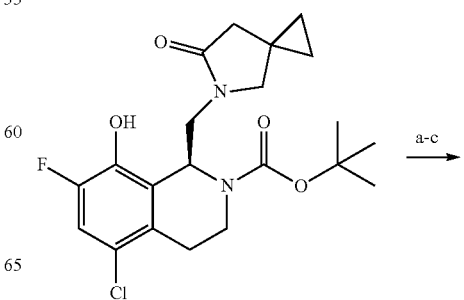

-continued

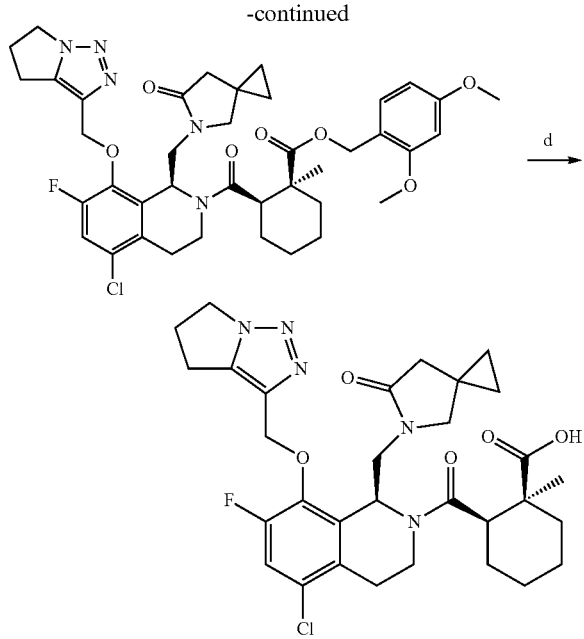

Step a. A mixture of Intermediate 50 (133 mg, 0.31 mmol), 3-(chloromethyl)-5,6-dihydro-4H-pyrrolo[1,2-c]triazole (64 mg, 0.41 mmol) and caesium carbonate (306 mg, 0.94 mmol) in DMF (1 mL) was stirred under nitrogen at rt for 3.5 h. A further amount of 3-(chloromethyl)-5,6-dihydro-4H-pyrrolo[1,2-c]triazole (47 mg, 0.30 mmol) and caesium carbonate (153 mg, 0.47 mmol) was added and the mixture stirred for a further 66 h. The reaction mixture was diluted with water and extracted with EtOAc. The combined organics were washed with water, brine, dried over $Na_2SO_4$, filtered and concentrated in vacuo. Purification by flash column chromatography on the Teledyne ISCO CombiFlash® Rf+ (12 g silica column Puriflash HC, 0-100% EtOAc in cyclohexane) gave tert-butyl (S)-5-chloro-8-((5,6-dihydro-4H-pyrrolo[1,2-c][1,2,3]triazol-3-yl)methoxy)-7-fluoro-1-((6-oxo-5-azaspiro[2.4]heptan-5-yl)methyl)-3,4-dihydroisoquinoline-2(1H)-carboxylate (128 mg, 75%). LCMS (Method 2): 1.65 min, 546.2 [M+H]$^+$.

Step b. Hydrochloric acid (4 M in dioxane; 1.2 mL, 4.69 mmol) was added to the above intermediate (128 mg, 0.23 mmol) and the resulting reaction mixture left to stir at rt for 0.5 h. The reaction mixture was concentrated in vacuo and azeotroped with toluene to give (S)-5-((5-chloro-8-((5,6-dihydro-4H-pyrrolo[1,2-c][1,2,3]triazol-3-yl)methoxy)-7-fluoro-1,2,3,4-tetrahydroisoquinolin-1-yl)methyl)-5-azaspiro[2.4]heptan-6-one hydrochloride (128 mg, assumed quantitative). LCMS (Method 2): 0.97 min, 446.2 [M+H]$^+$.

Step c. To a stirred solution of the above intermediate (113 mg, 0.23 mmol) and Intermediate 33 (160 mg, 0.35 mmol) in DMF (1 mL) was added DIPEA (0.08 mL, 0.47 mmol) and the resulting mixture was stirred at rt under argon for 4 days. The reaction mixture was diluted with EtOAc and saturated sodium bicarbonate solution and extracted with EtOAc. The combined organics were washed with water and brine, dried over $Na_2SO_4$, filtered and concentrated in vacuo. The crude product was purified by flash column chromatography on the Teledyne ISCO CombiFlash® Rf+ (12 g silica column Puriflash HC, 0 to 100% EtOAc in cyclohexane) to provide 2,4-dimethoxybenzyl (1S,2R)-2-((S)-5-chloro-8-((5,6-dihydro-4H-pyrrolo[1,2-c][1,2,3]triazol-3-yl)methoxy)-7-fluoro-1-(((6-oxo-5-azaspiro[2.4]heptan-5-yl)methyl)-1,2,3,4-tetrahydroisoquinoline-2-carbonyl)-1-methyl-cyclohexane-1-carboxylate (109 mg, 61%). LCMS (Method 2): 1.81 min, 764.4 [M+H]$^+$.

Step d. To a stirred solution of the above intermediate (109 mg, 0.14 mmol) in DCM (1.2 mL) was added triethylsilane (0.02 mL, 0.14 mmol), followed by TFA (0.01 mL, 0.14 mmol) and the resulting mixture was stirred at rt for 30 min. The reaction mixture was concentrated in vacuo and the residue purified by flash column chromatography on the Teledyne ISCO CombiFlash® Rf+ (12 g silica column Puriflash HC, 15 um, 0-5% MeOH in DCM). Fractions containing the desired product were combined and concentrated in vacuo. The residue was taken up in MeCN/water (1:1) and freeze dried to provide the title compound (65 mg, 71%). LCMS (Method 3): 4.45 min, 614.3 [M+H]$^+$. $^1$H NMR (400 MHz, DMSO-$d_6$) δ 11.87 (bs, 1H), 7.51 (d, 1H), 5.52 (dd, 1H), 5.27 (m, 1H), 5.10 (dd, 1H), 4.36-4.20 (m, 2H), 4.00-3.85 (m, 2H), 3.54 (m, 1H), 3.14 (d, 1H), 2.97 (m, 2H), 2.90-2.55 (m, 7H), 2.35-2.15 (m, 2H), 2.08 (d, 1H), 1.71-1.49 (m, 3H), 1.48-1.18 (m, 4H), 1.10 (s, 3H), 0.64-0.42 (m, 4H).

Example 147

(1S,2R)-2-((S)-5-chloro-8-((5-(difluoromethyl)-1-methyl-1H-1,2,3-triazol-4-yl)methoxy)-7-fluoro-1-((2-oxopyrrolidin-1-yl)methyl)-1,2,3,4-tetrahydroisoquinoline-2-carbonyl)-1-methylcyclohexane-1-carboxylic acid

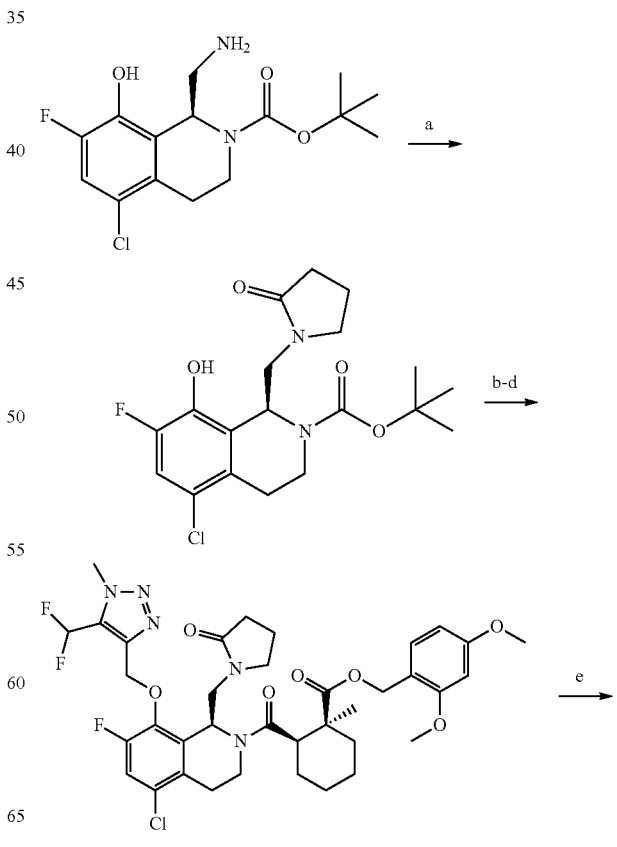

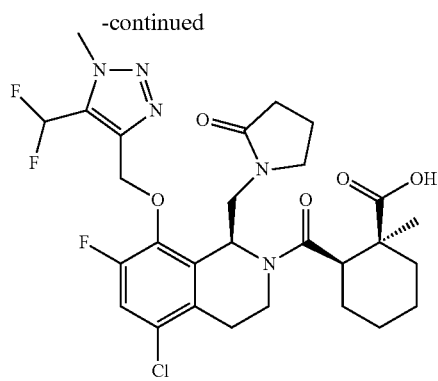

Step a. A solution of Intermediate 49 (240 mg, 0.73 mmol), methyl 4-bromobutanoate (0.11 mL, 0.80 mmol; CAS: 4897-84-1) and triethylamine (0.15 mL, 1.09 mmol) in toluene (3.4 mL) was heated under reflux for 24 h. The reaction mixture was allowed to cool to rt and concentrated in vacuo. The residue was diluted with brine and extracted with DCM. The combined organics were washed with brine, dried over $Na_2SO_4$ and concentrated in vacuo. The crude product was purified by flash column chromatography on the Teledyne ISCO CombiFlash® Rf+ (25 g silica column Puriflash HC, eluting 0 to 100% ethyl acetate in cyclohexane) to provide tert-butyl (S)-5-chloro-7-fluoro-8-hydroxy-14(2-oxopyrrolidin-1-yl)methyl)-3,4-dihydroisoquinoline-2(1H)-carboxylate (162 mg, 56%). LCMS (Method 2): 1.59 min, 421.1 [M+Na]⁺.

Step b. A mixture of the above intermediate (162 mg, 0.41 mmol), 4-(chloromethyl)-5-(difluoromethyl)-1-methyl-1H-1,2,3-triazole (96 mg, 0.53 mmol) and caesium carbonate (397 mg, 1.22 mmol) in DMF (1.2 mL) was stirred under nitrogen at rt for 18 h. The reaction mixture was diluted with water and extracted with EtOAc. The combined organics were washed with water, brine, dried over $Na_2SO_4$, filtered and concentrated in vacuo. Purification by flash column chromatography on the Teledyne ISCO CombiFlash® Rf+ (25 g silica column Puriflash HC, 0-100% EtOAc in cyclohexane) gave tert-butyl (S)-5-chloro-8-((5-(difluoromethyl)-1-methyl-1H-1,2,3-triazol-4-yl)methoxy)-7-fluoro-1-((2-oxopyrrolidin-1-yl)methyl)-3,4-dihydroisoquinoline-2(1H)-carboxylate (130 mg, 59%). LCMS (Method 2): 1.68 min, 566.2 [M+Na]⁺.

Step c. Hydrochloric acid (4M in dioxane; 1.19 mL, 4.78 mmol) was added to the above intermediate (130 mg, 0.24 mmol) and the resulting reaction mixture left to stir at rt for 1 h. The reaction mixture was concentrated in vacuo and azeotroped with toluene to give (S)-1-((5-chloro-8-((5-(difluoromethyl)-1-methyl-1H-1,2,3-triazol-4-yl)methoxy)-7-fluoro-1,2,3,4-tetrahydroisoquinolin-1-yl)methyl)pyrrolidin-2-one hydrochloride (128 mg, assumed quantitative). LCMS (Method 2): 1.00 min, 444.1 [M+H]⁺.

Step d. To a stirred solution of the above intermediate (115 mg, 0.24 mmol) and Intermediate 33 (163 mg, 0.36 mmol) in DMF (1 mL) was added DIPEA (0.08 mL, 0.48 mmol) and the resulting mixture was stirred at rt under argon for 5 days. The reaction mixture was diluted with EtOAc and saturated sodium bicarbonate solution and extracted with EtOAc. The combined organics were washed with water and brine, dried over $Na_2SO_4$, filtered and concentrated in vacuo. The crude product was purified by flash column chromatography on the Teledyne ISCO CombiFlash® Rf+ (12 g silica column Puriflash HC, 0-100% EtOAc in cyclohexane) to provide 2,4-dimethoxybenzyl (1S,2R)-2-((S)-5-chloro-8-((5-(difluoromethyl)-1-methyl-1H-1,2,3-triazol-4-yl)methoxy)-7-fluoro-1-((2-oxopyrrolidin-1-yl)methyl)-1,2,3,4-tetrahydroisoquinoline-2-carbonyl)-1-methylcyclohexane-1-carboxylate (90 mg, 49%). LCMS (Method 2): 1.82 min, 762.3 [M+H]⁺.

Step e. To a stirred solution of the above intermediate (90 mg, 0.12 mmol) in DCM (1.1 mL) was added triethylsilane (0.02 mL, 0.12 mmol), followed by TFA (0.01 mL, 0.12 mmol) and the resulting mixture was stirred at rt for 30 min. The reaction mixture was concentrated in vacuo and the residue purified by flash column chromatography on the Teledyne ISCO CombiFlash® Rf+ (12 g silica column Puriflash HC, 15 um, 0-5% MeOH in DCM). Fractions containing the desired product were combined and concentrated in vacuo. The residue was taken up in MeCN/water (1:1) and freeze dried to provide the title compound (53 mg, 71%). LCMS (Method 3): 4.51 min, 612.3 [M+H]⁺. ¹H NMR (400 MHz, DMSO-d₆) δ 11.90 (bs, 1H), 7.53 (d, 1H), 7.36 (t, 1H), 5.47 (dd, 1H), 5.41 (d, 1H), 5.24 (d, 1H), 4.14 (s, 3H), 3.97-3.78 (m, 2H), 3.54 (m, 1H), 3.42-3.20 (m, 1H), 3.06-2.86 (m, 3H), 2.78 (dd, 1H), 2.62 (m, 1H), 2.25-2.09 (m, 2H), 1.98 (m, 1H), 1.92-1.68 (m, 2H), 1.67-1.49 (m, 3H), 1.48-1.29 (m, 3H), 1.28-1.13 (m, 1H), 1.08 (s, 3H).

Example 151

1-(((S)-5-chloro-8-((5-(difluoromethyl)-1-methyl-1H-1,2,3-triazol-4-yl)methoxy)-2-((1R,2S)-2-methyl-2-(2H-tetrazol-5-yl)cyclohexane-1-carbonyl)-1,2,3,4-tetrahydroisoquinolin-1-yl)methyl)pyrrolidin-2-one

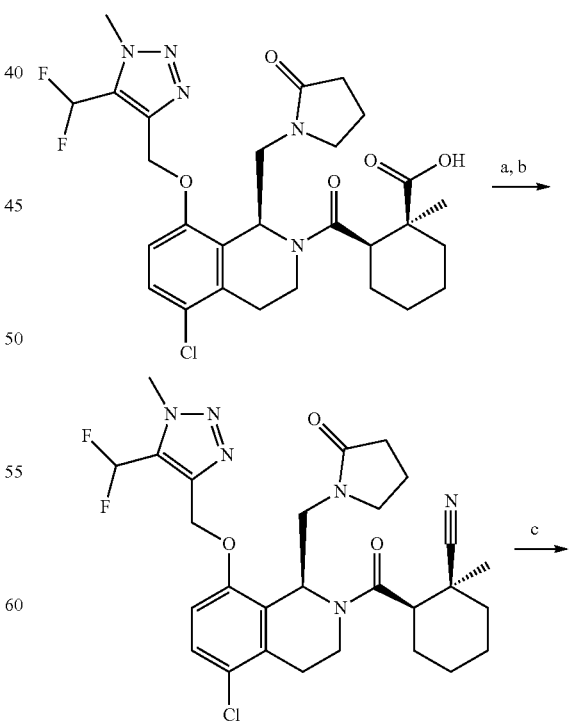

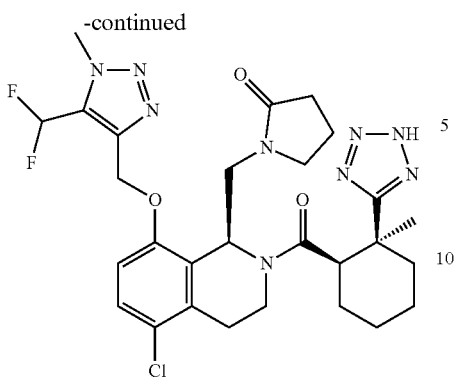

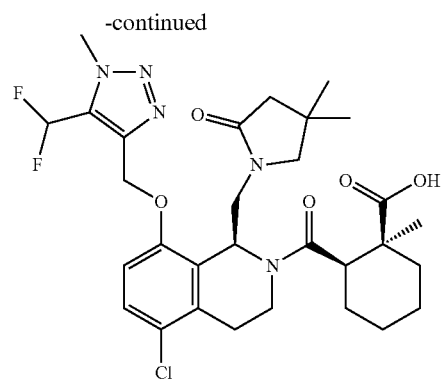

Step a. (1S,2R)-2-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxamide (60 mg, 0.10 mmol) was prepared from Example 91 (160 mg, 0.27 mmol) using a procedure similar to that described for Example 81, step a. LCMS (Method 10b): 0.74 min, 593.2 [M+H]⁺.

Step b. (1S,2R)-2-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carbonitrile (65 mg, assumed quantitative) was prepared from the above intermediate (60 mg, 0.10 mmol) using a procedure similar to that described for Example 81, step b. LCMS (Method 9): 0.92 min, 575.2 [M+H]⁺.

Step c. The title compound (2.2 mg, 0.004 mmol, 3.507% yield) was prepared from the above intermediate (58 mg, 0.10 mmol) using a procedure similar to that described for Example 81 step c. ¹H NMR (400 MHz, methanol-d₃) δ: 7.05-7.36 (m, 3H), 5.74 (d, J=9.2 Hz, 1H), 5.25 (d, J=12.4 Hz, 2H), 4.09-4.25 (m, 4H), 3.90-4.00 (dd, 1H), 3.66-3.77 (m, 1H), 3.48 (td, J=8.9, 5.0 Hz, 1H), 3.10 (dd, J=14.0, 2.5 Hz, 1H), 2.99 (q, J=8.1 Hz, 3H), 2.46-2.54 (m, 1H), 2.16-2.33 (m, 2H), 1.72-1.95 (m, 6H), 1.57-1.65 (m, 3H), 1.39 (s, 3H). LCMS (Method 14): 1.24 min, 618.1 [M+H]⁺.

Example 152

(1S,2R)-2-((S)-5-chloro-8-((5-(difluoromethyl)-1-methyl-1H-1,2,3-triazol-4-yl)methoxy)-1-((4,4-dimethyl-2-oxopyrrolidin-1-yl)methyl)-1,2,3,4-tetrahydroisoquinoline-2-carbonyl)-1-methylcyclohexane-1-carboxylic acid To a stirred solution of Example 123 (100 mg, 0.160 mmol) in acetic acid (10 mL) was added sodium acetate (40 mg, 0.48 mmol) and platinum(IV) oxide (13 mg, 0.05 mmol) and the mixture was stirred under a hydrogen atmosphere at rt under atmospheric pressure for 2 h. A further portion of platinum(IV) oxide (13 mg, 0.05 mmol, CAS: 1314-15-4) was added and after an additional 2 h stirring a further portion of platinum(IV) oxide (13 mg, 0.05 mmol) was added and the reaction stirred for a further 1 h. After standing for 18 h, further platinum(IV) oxide (13 mg, 0.05 mmol) was added and the reaction stirred under hydrogen for 3 h, after which further platinum(IV) oxide (25 mg, 0.10 mmol) was added and the reaction mixture stirred for 1 h. The mixture was filtered through Celite®, washed with EtOAc (50 mL). The organic layer was washed with water (50 mL) and the aqueous re-extracted with EtOAc (50 mL). The combined organics were washed with saturated Na₂CO₃ and brine, dried over MgSO₄ and concentrated in vacuo. Purification on the Biotage Isolera (30 g C18 SNAP, 5-95% MeCN in 0.1% aqueous formic acid) followed by MDAP (Method 5, 20% MeCN in 0.1% ammonium hydroxide) gave the title compound (4 mg, 4%). LCMS (Method 12): 1.34 min, 622.2 [M+H]⁺. ¹H NMR (300 MHz, CDCl₃) δ 7.30 (d, 1H), 6.98 (d, 1H), 6.95 (t, 1H), 5.91 (dd, 1H), 5.36-5.22 (m, 2H), 4.19 (s, 3H), 4.13-3.80 (m, 3H), 3.43 (d, 1H), 3.13-2.98 (m, 2H), 2.83-2.65 (m, 2H), 2.56 (m, 1H), 2.40 (m, 1H), 2.17-1.98 (m, 2H), 1.91-1.76 (m, 2H), 1.69-1.20 (m, 4H), 1.12 (s, 3H), 1.10 (s, 3H), 1.08 (s, 3H), 1.01 (m, 1H).

Example 156

(1S,2R)-2-((S)-5-chloro-8-((1,5-dimethyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid

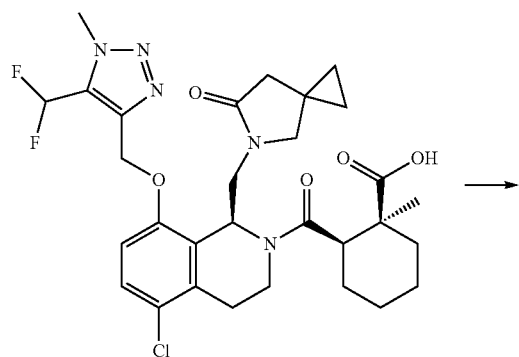

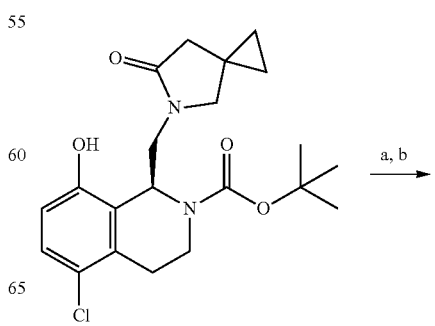

-continued

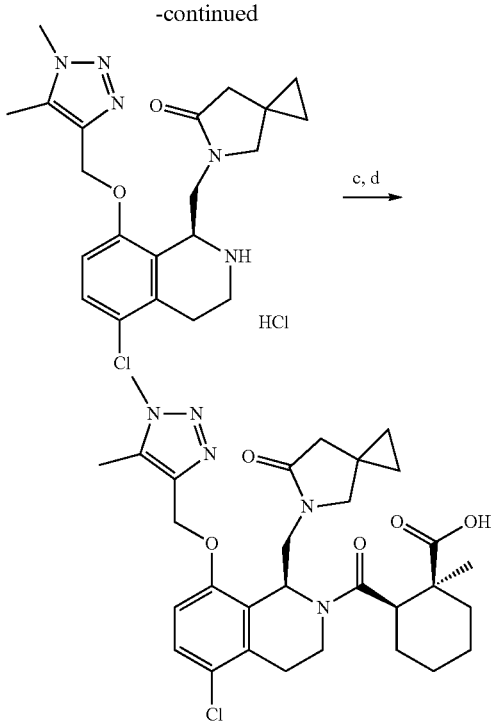

Step a. To a stirred solution of Intermediate 35 (500 mg, 1.23 mmol) and 4-(chloromethyl)-1,5-dimethyl-1H-1,2,3-triazole (268 mg, 1.47 mmol) in DMF (8 mL) was added caesium carbonate (1.44 g, 4.42 mmol) and the reaction mixture was stirred at 50° C. for 5 h, followed by stirring at for 16 h. The reaction mixture was cooled to rt and partitioned between water and EtOAc. The aqueous was extracted with EtOAc and the combined organics washed with water (×3), brine, dried over MgSO₄, filtered and concentrated in vacuo. The crude product was purified by flash silica chromatography (4% MeOH in DCM) to give tert-butyl (S)-5-chloro-8-((1,5-dimethyl-1H-1,2,3-triazol-4-yl)methoxy)-1-((6-oxo-5-azaspiro[2.4]heptan-5-yl)methyl)-3,4-dihydroisoquinoline-2(1H)-carboxylate (640 mg, 79%). LCMS (Method 9): 0.94 min, 516.2 [M+H]⁺. The above reaction was repeated with 5.0 g of Intermediate 35 and yielded 5.4 g (85%) of tert-butyl (S)-5-chloro-8-((1,5-dimethyl-1H-1,2,3-triazol-4-yl)methoxy)-1-((6-oxo-5-azaspiro[2.4]heptan-5-yl)methyl)-3,4-dihydroisoquinoline-2(1H)-carboxylate.

Step b. (S)-5-((5-chloro-8-((1,5-dimethyl-1H-1,2,3-triazol-4-yl)methoxy)-1,2,3,4-tetrahydroisoquinolin-1-yl)methyl)-5-azaspiro[2.4]heptan-6-one hydrochloride (560 mg, 86%) was prepared from the above intermediate (640 mg, 1.2 mmol) using the method described for Example 1, step d and used without further purification. LCMS (Method 9): 0.68 min, 416.2 [M+H]⁺. This reaction was repeated with the above intermediate (5.4 g, 10.5 mmol) and yielded 4.8 g (quantitative) of (S)-5-((5-chloro-8-((1,5-dimethyl-1H-1,2,3-triazol-4-yl)methoxy)-1,2,3,4-tetrahydroisoquinolin-1-yl)methyl)-5-azaspiro[2.4]heptan-6-one hydrochloride.

Step c. To a stirred solution of the above intermediate (560 mg, 1.24 mmol), Intermediate 29 (541 mg, 1.61 mmol) and DIPEA (1.29 mL, 7.43 mmol) in DMF (1.8 mL) was added HATU (706 mg, 1.86 mmol; CAS: 148893-10-1) and the reaction mixture was stirred at rt for 5 days. The mixture was partitioned between water and EtOAc and the aqueous further extracted with EtOAc. The combined organics were washed with water (×3), brine, dried over MgSO₄, filtered and concentrated in vacuo. The crude product was purified by flash silica chromatography (4% MeOH in DCM) to give the title compound (530 mg, 50%). LCMS (Method 9a): 1.66 min, 735.0 [M+H]⁺.

Step c method 2: To a stirred solution of the above intermediate (5.36 g, 11.84 mmol) in DMF (28 mL) was added Intermediate 33 (9.69 g, 21.32 mmol) and DIPEA (5.16 mL, 29.61 mmol), and the reaction mixture was stirred under nitrogen for 4 days. The mixture was diluted with water (120 mL) and extracted with EtOAc. The combined organics were concentrated in vacuo and the crude product was purified by flash column chromatography on the Teledyne ISCO CombiFlash® Rf+ (220 g silica column Puriflash HC, 0-4% MeOH in DCM) to give 2,4-dimethoxybenzyl (1S,2R)-2-((S)-5-chloro-8-((1,5-dimethyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylate (6.5 g, 75%). LCMS (Method 2): 1.74 min, 734.4 [M+H]⁺.

Step d. To a flask containing the above intermediate (530 mg, 0.72 mmol) at rt was added hydrogen chloride (4 M in dioxane; 3.0 mL, 12 mmol) and the reaction mixture stirred at rt for 5 mins. The mixture was concentrated in vacuo and the crude product was purified by reverse phase column chromatography on the Biotage Isolera (60 g C18 column, 5-40% MeCN in 0.1% aqueous ammonia). LCMS (Method 12, 2% B with 5% C and 93% A to 50% B with 5% C and 45% A in 3.00 mins, ramp to 95% B with 5% C to 4.50 mins. Hold at 95% B to 5.00 mins) 1.39 min, 584.2 [M+H]⁺. ¹H NMR (300 MHz, CDCl₃) δ 7.29 (d, 1H), 7.00 (d, 1H), 5.95 (dd, 1H), 5.28-5.02 (m, 2H), 4.11 (dd, 1H), 4.05-3.82 (m, 5H), 3.39 (d, 1H), 3.18 (dd, 1H), 3.12-2.94 (m, 2H), 2.73 (m, 1H), 2.59 (m, 1H), 2.49-2.26 (m, 5H), 2.12 (d, 1H), 1.92-1.74 (m, 2H), 1.73-1.45 (m, 3H), 1.44-1.21 (m, 1H), 1.12 (s, 3H), 1.02 (m, 1H), 0.71-0.43 (m, 4H).

Step d method 2. To a stirred solution of the above intermediate (6.5 g, 8.88 mmol) in DCM (40 mL) was added triethylsilane (1.42 mL, 8.88 mmol) followed by dropwise addition of 2,2,2-trifluoroacetic acid (0.82 mL, 10.7 mmol). The reaction mixture was stirred for 1 h and the precipitate removed by filtration through a PTFE frit. The filtrate was diluted with toluene and concentrated in vacuo. The crude product was purified by flash column chromatography on the Teledyne ISCO CombiFlash® Rf+ (220 g silica column Puriflash HC, 0-3% MeOH in DCM) followed by reverse phase flash column chromatography on the InterChim 4125 (320 g C18 InterChim HP, 20-80% CH₃CN in water with 0.1% HCOOH). The product containing fractions were combined, concentrated to half volume in vacuo and freeze dried. The product was further purified by flash column chromatography on the Teledyne ISCO CombiFlash® Rf+ (330 g silica column Puriflash HC, 5-90% methyl acetate in DCM) to provide the title compound (1.91 g, 37% yield). LCMS (Method 3) 4.15 min, 584.4 [M+H]⁺. ¹H NMR (400 MHz, CDCl₃) δ 15.33 (bs, 1H), 7.29 (d, 1H), 7.00 (d, 1H), 5.95 (dd, 1H), 5.19 (d, 1H), 5.11 (d, 1H), 4.11 (dd, 1H), 4.04-3.93 (m, 4H), 3.89 (m, 1H), 3.39 (d, 1H), 3.18 (dd, 1H), 3.07 (m, 1H), 3.01 (d, 1H), 2.74 (m, 1H), 2.59 (dd, 1H), 2.46-2.34 (m, 2H), 2.33 (s, 3H), 2.12 (d, 1H), 1.90-1.77 (m, 2H), 1.71-1.44 (m, 3H), 1.42-1.21 (m, 1H), 1.12 (s, 3H), 1.02 (m, 1H), 0.67-0.47 (m, 4H).

Example 170

(1S,2R)-2-((S)-5-chloro-1-((6-oxo-5-azaspiro[2.4]heptan-5-yl)methyl)-8-((4,5,6,7-tetrahydro-[1,2,3]triazolo[1,5-a]pyridin-3-yl)methoxy)-1,2,3,4-tetrahydroisoquinoline-2-carbonyl)-1-methylcyclohexane-1-carboxylic acid

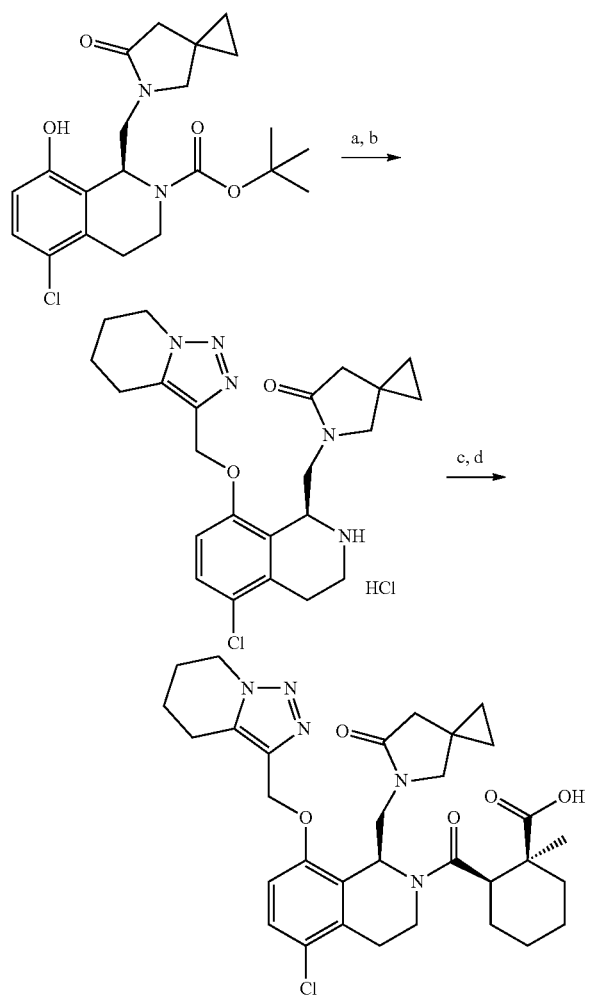

Step a. To a stirred suspension of Intermediate 35 (400 mg, 0.98 mmol) in DMF (4 mL) was added caesium carbonate (1.28 g, 3.93 mmol) and the mixture was stirred at rt for 3 min. To this was added a solution of 3-(chloromethyl)-4,5,6,7-tetrahydrotriazolo[1,5-a]pyridine (253 mg, 1.47 mmol) in DMF (4 mL). The reaction mixture was stirred at rt for 16 h. To this was added an additional portion of Intermediate 35 (253 mg, 1.47 mmol) and the reaction mixture was stirred at 45° C. for 26 h. The reaction mixture was diluted with water and extracted with DCM. The combined organics were dried over Na$_2$SO$_4$) and concentrated in vacuo. The crude product was purified by flash column chromatography on the Interchim Puriflash® 4100 (120 g silica column, 0-100% EtOAc in DCM and then 10% MeOH in DCM) then further purified by flash column chromatography on the Interchim Puriflash® 4100 (120 g silica column, 0-10% MeOH in DCM) followed by further purification by reverse phase column chromatography on the Interchim Puriflash® 4100 (80 g C18, 5-95% MeCN in water 0.1% NH$_4$O buffer) to give tert-butyl (S)-5-chloro-1-((6-oxo-5-azaspiro[2.4]heptan-5-yl)methyl)-8-((4,5,6,7-tetrahydro-[1,2,3]-triazolo[1,5-a]pyridin-3-yl)methoxy)-3,4-dihydroisoquinoline-2(1H)-carboxylate (250 mg, 47%). LCMS (Method 2): 1.46 min, 541.7 [M+H]$^+$.

Step b. (S)-5-((5-Chloro-8-((4,5,6,7-tetrahydro-[1,2,3]triazolo[1,5-a]pyridin-3-yl)methoxy)-1,2,3,4-tetrahydroisoquinolin-1-yl)methyl)-5-azaspiro[2.4]heptan-6-one hydrochloride (225 mg, assumed quantitative) was prepared from the above intermediate (250 mg, 0.46 mmol) using a procedure similar to that described for Example 1, step d and used without further purification. LCMS (Method 17): 1.49 min, 442.2 [M+H]$^+$.

Step c. To a stirred solution of Intermediate 29 (186 mg, 0.55 mmol) in DMF (1.5 mL) at rt was added HATU (262 mg, 0.69 mmol; CAS: 148893-10-1), the above intermediate (220 mg, 0.46 mmol) and DIPEA (0.4 mL, 2.3 mmol) and the reaction mixture was stirred at rt for 16 h. Additional Intermediate 29 (186 mg, 0.55 mmol), HATU (262 mg, 0.69 mmol) and DIPEA (0.4 mL, 2.3 mmol) were added and the reaction mixture stirred for a further 24 h. To this was added saturated aqueous NaHCO$_3$ and EtOAc. The aqueous layer was extracted further with EtOAc (×2). The combined organics were washed with water and brine, dried over Na$_2$SO$_4$, filtered and concentrated in vacuo. The crude product was purified by flash column chromatography on the Interchim Puriflash® 4100 (120 g silica column, 0-100% EtOAc in cyclohexane then 5% MeOH in DCM) then further purified by flash column chromatography on the Interchim Puriflash® 4100 (40 g silica column, 0-5% MeOH in DCM) to give 2,4-dimethoxybenzyl (1S,2R)-2-((S)-5-chloro-1-((6-oxo-5-azaspiro[2.4]heptan-5-yl)methyl)-8-((4,5,6,7-tetrahydro-[1,2,3]triazolo[1,5-a]pyridin-3-yl)methoxy)-1,2,3,4-tetrahydroisoquinoline-2-carbonyl)-1-methylcyclohexane-1-carboxylate (273 mg, 78%). LCMS (Method 2): 1.59 min, 759.7 [M+H]$^+$.

Step d. To a stirred solution of the above intermediate (283 mg, 0.37 mmol) in DCM (2.7 mL) was added triethylsilane (0.06 mL, 0.37 mmol), followed by TFA (0.03 mL, 0.37 mmol) and the reaction mixture was stirred at rt for 15 min. To this was added additional triethylsilane (0.01 mL, 0.07 mmol) and TFA (0.01 mL, 0.07 mmol) and the reaction mixture was stirred for 30 min, concentrated in vacuo and the residue azeotroped with toluene (×2) and concentrated in vacuo. The crude product was purified by flash column chromatography on the Interchim Puriflash® 4125 (40 g silica column, 0-5% MeOH in DCM) and further purified by flash column chromatography on the Interchim Puriflash® 4125 (40 g silica column, 0-10% MeOH in toluene) to give the title compound (28 mg, 12%). LCMS (Method 3): 4.37 min, 610.1 [M+H]$^+$. $^1$H NMR (400 MHz, CDCl$_3$) δ 15.32 (bs, 1H), 7.29 (d, 1H), 6.99 (d, 1H), 5.98 (dd, 1H), 5.20 (d, 1H), 5.12 (d, 1H), 4.35 (t, 2H), 4.12 (dd, 1H), 4.00 (m, 1H), 3.89 (m, 1H), 3.41 (d, 1H), 3.18 (dd, 1H), 3.07 (m, 1H), 3.02 (d, 1H), 2.93-2.67 (m, 3H), 2.59 (dd, 1H), 2.46-2.33 (m, 2H), 2.13 (d, 1H), 2.09-2.00 (m, 2H), 1.97-1.77 (m, 4H), 1.67-1.47 (m, 3H), 1.42-1.21 (m, 1H), 1.12 (s, 3H), 1.02 (m, 1H), 0.65-0.47 (m, 4H).

Example 174

(1S,2R)-1-Methyl-2-((S)-5-methyl-8-((1-methyl-5-(trifluoromethyl)-1H-1,2,3-triazol-4-yl)methoxy)-1-((2-oxopyrrolidin-1-yl)methyl)-1,2,3,4-tetrahydroisoquinoline-2-carbonyl)cyclohexane-1-carboxylic acid

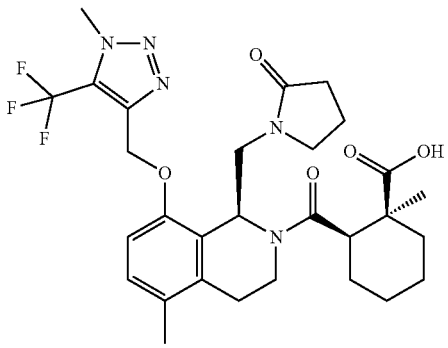 [SMILES: Cc1ccc(OCc2nnn(C)c2C(F)(F)F)c2c1CCN(C(=O)[C@@H]1CCCC[C@]1(C)C(=O)O)[C@@H]2CN1CCCC1=O]

To a stirred solution of Example 108 (44 mg, 0.072 mmol) in 1,4-dioxane (1 mL) and water (0.2 mL) was added XPhos Pd G2 (0.79 mg, 0.001 mmol, CAS: 1310584-14-5), XPhos (1.43 mg, 0.003 mmol, CAS: 564483-18-7), potassium carbonate (30 mg, 0.22 mmol) and trimethylboroxine (50% in THF, 0.02 mL, 0.072 mmol, CAS: 823-96-1) was added and the reaction was heated at 90° C. under microwave irradiation for 1 h. The reaction mixture was diluted with water and extracted with EtOAc. The combined organics were washed with water, brine, dried over MgSO$_4$, filtered and concentrated in vacuo. The crude product was purified by flash column chromatography on the Teledyne ISCO CombiFlash® Rf+ (12 g silica column Puriflash 15 μm, 0-8% MeOH in DCM) followed by flash column chromatography on the Teledyne ISCO CombiFlash® Rf+ (4 g silica column Puriflash 15 μm, 0-4% MeOH in DCM) to give the title compound (10 mg, 22%). LCMS (Method 3) 4.42 min, 592.3 [M+H]$^+$. $^1$H NMR (400 MHz, CDCl$_3$) δ 15.53 (bs, 1H), 7.09 (d, 1H), 6.95 (d, 1H), 5.97 (dd, 1H), 5.28 (m, 2H), 4.21 (m, 3H), 4.10-3.92 (m, 2H), 3.84 (m, 1H), 3.71 (m, 1H), 3.22-3.09 (m, 2H), 2.83 (m, 1H), 2.68 (m, 1H), 2.56 (dd, 1H), 2.40 (m, 1H), 2.28 (m, 1H), 2.20-2.10 (m, 4H), 1.98-1.77 (m, 4H), 1.68-1.44 (m, 3H), 1.41-1.17 (m, 1H), 1.12 (s, 3H), 1.00 (m, 1H).

Example 178

(1S,2R)-2-((S)-5-fluoro-8-((1-methyl-5-(trifluoromethyl)-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid

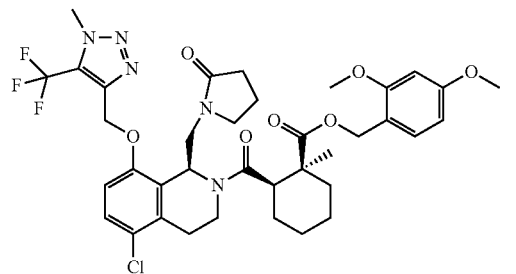

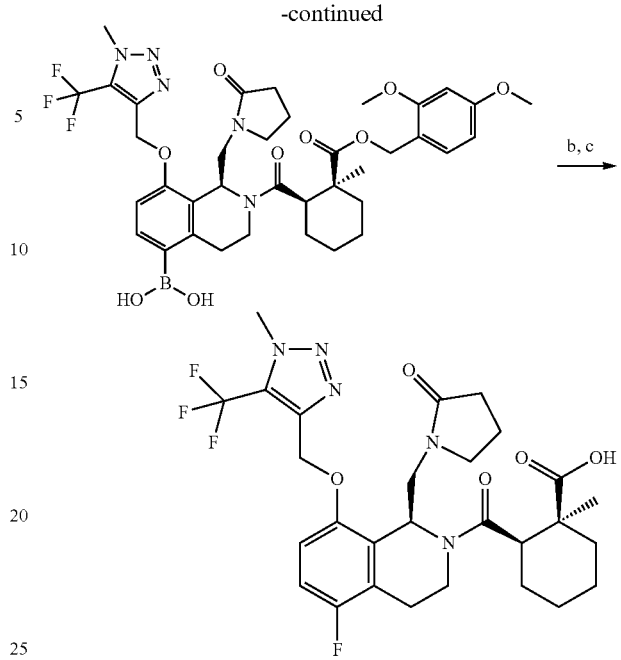

Step a. A stirred solution of 2,4-dimethoxybenzyl (1S,2R)-2-((S)-5-chloro-8-((1-methyl-5-(trifluoromethyl)-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylate (100 mg, 0.13 mmol, Example 108 step c), potassium acetate (39 mg, 0.39 mmol), XPhos Pd G2 (2 mg, 0.003 mmol, CAS: 1310584-14-5), XPhos (2.5 mg, 0.05 mmol, CAS: 564483-18-7) and tetrahydroxydiboron (35 mg, 0.39 mmol) in EtOH (1.3 mL) was degassed with argon for 10 min and then heated at 80° C. for 3 h. The reaction mixture was concentrated in vacuo, diluted with water and extracted with EtOAc. The combined organics were washed with water, brine, dried over Na$_2$SO$_4$, filtered and concentrated in vacuo to provide ((S)-2-(((1R,2S)-2-(((2,4-dimethoxybenzyl)oxy)carbonyl)-2-methylcyclohexane-1-carbonyl)-8-((1-methyl-5-(trifluoromethyl)-1H-1,2,3-triazol-4-yl)methoxy)-1-((2-oxopyrrolidin-1-yl)methyl)-1,2,3,4-tetrahydroisoquinolin-5-yl)boronic acid (105 mg, 52%). LCMS (Method 15): 1.49 min, 772.4 [M+H]$^+$.

Step b. To a stirred solution of the above intermediate (105. mg, 0.090 mmol) in MeOH (1 mL) under argon was added sodium hydroxide (3.7 mg, 0.09 mmol). The reaction mixture was stirred at rt for 15 min, cooled to 0° C. and to this was added silver trifluoromethanesulfonate (70 mg, 0.27 mmol, CAS: 2923-28-6). The reaction mixture was stirred for 0.5 h and concentrated in vacuo at 0° C. Acetone (1 mL) was added and the reaction mixture was again concentrated in vacuo at 0° C. (repeated twice). The residue was dissolved in acetone (0.5 mL) and to this was added powdered molecular sieves (3 Å; 50 mg), followed by 1-chloromethyl-4-fluoro-1,4-diazoniabicyclo[2.2.2]octane bis(tetrafluoroborate) (34 mg, 0.10 mmol, CAS: 140681-55-6) and the reaction mixture was stirred at rt for 3 h. The reaction mixture was filtered, diluted with water and extracted with DCM. The combined organics were washed with water, brine, dried over Na$_2$SO$_4$, filtered and concentrated in vacuo. The crude product was purified by flash column chromatography on the Interchim Puriflash® 4100 (40 g silica column InterChim HP, 0-100% EtOAc in cyclohexane) to provide 2,4-dimethoxybenzyl (1S,2R)-2-((S)-5-fluoro-8-((1-methyl-5-(trifluoromethyl)-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylate (25 mg, 24%). LCMS (Method 15): 1.68 min, 746.4 [M+H]⁺.

Step c. The title compound was prepared from the above intermediate (25 mg, 0.034 mmol) using a procedure similar to that described for Example 29 step b. The reaction mixture was concentrated in vacuo and the residue azeotroped with toluene (×2). The residue was purified by flash column chromatography on the Interchim Puriflash® 4125 (25 g 15 µm silica column Puriflash HP, 0-5% MeOH in DCM) followed by flash column chromatography on the Interchim Puriflash® 4125 (80 g 15 µm C18 Puriflash HP, 10-80% MeCN in 0.1% aqueous formic acid) to provide the title compound as a white solid (6.7 mg, 33%). LCMS (Method 3): 4.39 min, 596.0 [M+H]⁺. ¹H NMR (400 MHz, CDCl₃) δ 15.28 (bs, 1H), 7.03-6.91 (m, 2H), 5.94 (dd, 1H), 5.28 (m, 2H), 4.21 (m, 3H), 4.03 (dd, 1H), 3.94 (m, 1H), 3.84 (m, 1H), 3.70 (m, 1H), 3.24-3.11 (m, 2H), 3.00 (m, 1H), 2.72 (m, 1H), 2.55 (m, 1H), 2.40 (m, 1H), 2.29 (m, 1H), 2.16 (m, 1H), 1.99-1.87 (m, 2H), 1.87-1.77 (m, 2H), 1.68-1.44 (m, 3H), 1.35 (m, 1H), 1.12 (s, 3H), 1.01 (m, 1H).

Example 180

(1S,2R)-2-((S)-5-chloro-1-((6-oxo-5-azaspiro[2.4]heptan-5-yl)methyl)-8-((4,5,6,7-tetrahydro-[1,2,3]triazolo[1,5-a]pyridin-3-yl)methoxy)-1,2,3,4-tetrahydroisoquinoline-2-carbonyl)-1-methylcyclopentane-1-carboxylic acid

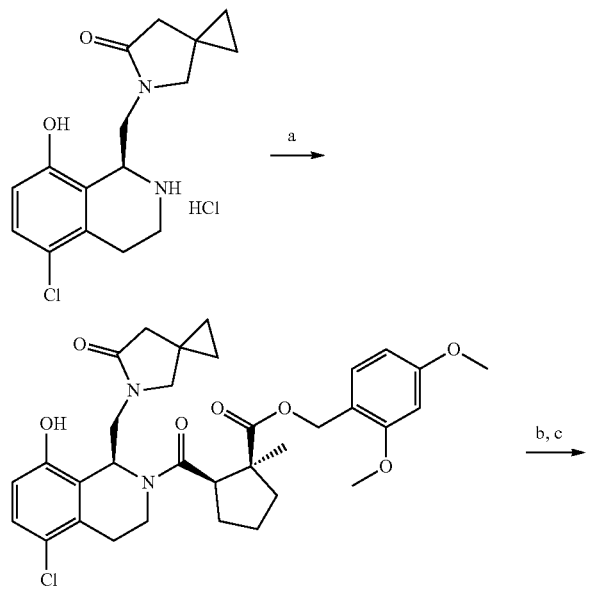

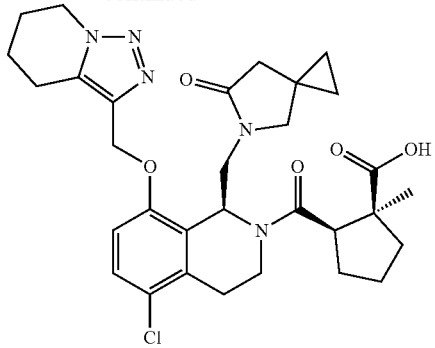

Step a. To a stirred solution of Intermediate 36 (299 mg, 0.87 mmol) and Intermediate 34 (767 mg, 1.74 mmol) in DMF (3 mL) was added DIPEA (0.3 mL, 1.74 mmol) and the reaction mixture was stirred at rt under argon for 18 h. The reaction mixture was diluted with EtOAc and the solid was removed by filtration. The filtrate was diluted with saturated sodium bicarbonate solution and the crude product extracted with EtOAc. The combined organics were dried over Na₂SO₄, filtered and concentrated in vacuo. The crude product was purified by flash column chromatography on the Teledyne ISCO CombiFlash® Rf+ (40 g silica column Puriflash HC, 0-100% EtOAc in cyclohexane) to provide 2,4-dimethoxybenzyl (1S,2R)-2-((S)-5-chloro-8-hydroxy-14(6-oxo-5-azaspiro[2.4]heptan-5-yl)methyl)-1,2,3,4-tetrahydroisoquinoline-2-carbonyl)-1-methyl-cyclopentane-1-carboxylate (190 mg, 36%). LCMS (Method 16): 1.46 min, 633.4 [M+Na]⁺.

Step b. 2,4-Dimethoxybenzyl (1S,2R)-2-((S)-5-chloro-1-((6-oxo-5-azaspiro[2.4]-heptan-5-yl)methyl)-8-((4,5,6,7-tetrahydro-[1,2,3]triazolo[1,5-a]pyridin-3-yl)methoxy)-1,2,3,4-tetrahydroisoquinoline-2-carbonyl)-1-methylcyclopentane-1-carboxylate (196 mg, 84%) was prepared from the above intermediate (190 mg, 0.31 mmol) and 3-(chloromethyl)-4,5,6,7-tetrahydrotriazolo[1,5-a]pyridine (71 mg, 1.3 mmol, Example 170) using a procedure similar to that described for Example 156 step b. The crude product was purified by flash column chromatography on the Teledyne ISCO CombiFlash® Rf+ (25 g silica column, 0-5% MeOH in DCM). LCMS (Method 16): 1.53 min, 746.6 [M+H]⁺.

Step c. The title compound (48 mg, 29%) was prepared from the above intermediate (196 mg, 0.26 mmol) using a procedure similar to that described for Example 29, step b. The crude product was purified by flash column chromatography on the Teledyne ISCO CombiFlash® Rf+ (12 g silica column, 0-2.5% MeOH in DCM) then by reverse phase preparative HPLC (X-Select CSH 5 um C18 19×250 mm, 10-98% MeCN in 0.1% aqueous formic acid. LCMS (LCMS Method 3): 4.02 min, 596.3 [M+H]⁺. ¹H NMR (400 MHz, DMSO-d₆) δ 11.44 (bs, 1H), 7.37 (d, 1H), 7.14 (d, 1H), 5.72 (dd, 1H), 5.21-5.09 (m, 2H), 4.30 (t, 2H), 4.02 (dd, 1H), 3.94 (dd, 1H), 3.57 (m, 1H), 3.42-3.28 (m, 1H), 3.06 (m, 1H), 2.95 (dd, 1H), 2.87-2.77 (m, 3H), 2.75-2.60 (m, 2H), 2.35 (m, 1H), 2.22-1.92 (m, 5H), 1.82 (m, 2H), 1.72-1.59 (m, 3H), 1.40 (m, 1H), 1.15 (s, 3H), 0.63-0.40 (m, 4H).

Example 190

(1S,2R)-1-methyl-2-((S)-8-((1-methyl-5-(trifluoromethyl)-1H-1,2,3-triazol-4-yl)methoxy)-1-((2-oxopyrrolidin-1-yl)methyl)-1,2,3,4-tetrahydroisoquinoline-2-carbonyl)cyclohexane-1-carboxylic acid

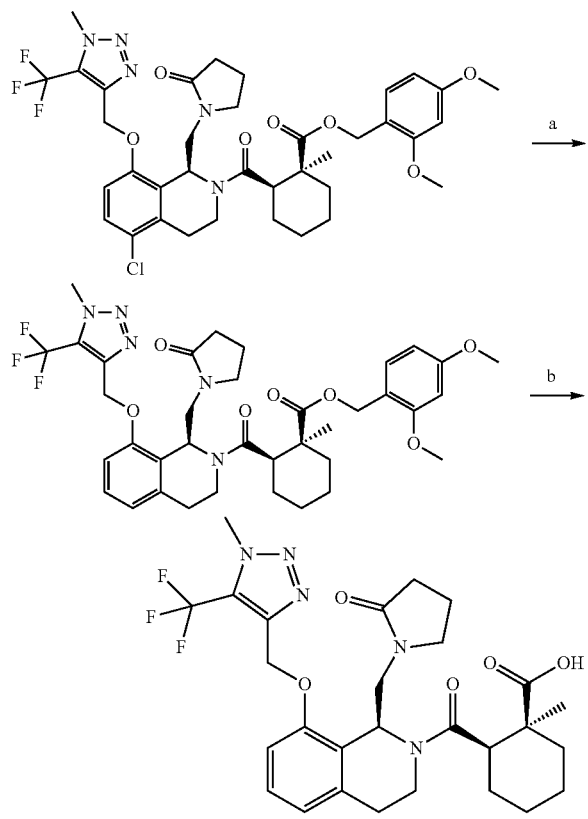

Step a. A suspension of potassium carbonate (82 mg, 0.59 mmol), XPhos Pd G3 (6.7 mg, 0.01 mmol, CAS: 1445085-55-1), XPhos (7.5 mg, 0.02 mmol, CAS: 564483-18-7) and 2,4-dimethoxybenzyl (1S,2R)-2-((S)-5-chloro-8-((1-methyl-5-(trifluoromethyl)-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylate (150 mg, 0.20 mmol, Example 108 step c) in EtOH (2 mL) under argon was stirred at 90° C. for 18 h. The reaction mixture was diluted with water and the crude product extracted into EtOAc. The combined organics were washed with water, brine, dried over Na$_2$SO$_4$, filtered and concentrated in vacuo. The crude product was combined with another batch (0.13 mmol and purified by flash column chromatography on the Interchim Puriflash® 4100 (40 g silica column, 0-5% MeOH in DCM) gave 2,4-dimethoxybenzyl (1S,2R)-1-methyl-2-((S)-8-((1-methyl-5-(trifluoromethyl)-1H-1,2,3-triazol-4-yl)methoxy)-1-((2-oxopyrrolidin-1-yl)methyl)-1,2,3,4-tetrahydroisoquinoline-2-carbonyl)cyclohexane-1-carboxylate (101 mg). LCMS (Method 2): 1.53 min, 728.5 [M+H]$^+$.

Step b. The title compound (62 mg, 77%) was prepared from the above intermediate using a procedure similar to that described for Example 29 step b. LCMS (Method 3): 4.22 min, 578.4 [M+H]$^+$. $^1$H NMR (400 MHz, CDCl$_3$) δ 15.49 (bs, 1H), 7.22 (t, 1H), 7.02 (d, 1H), 6.82 (d, 1H), 5.99 (dd, 1H), 5.30 (m, 2H), 4.22 (m, 3H), 4.03 (dd, 1H), 3.96 (m, 1H), 3.82-3.67 (m, 2H), 3.22-3.10 (m, 2H), 3.00-2.84 (m, 2H), 2.55 (dd, 1H), 2.40 (m, 1H), 2.28 (m, 1H), 2.16 (m, 1H), 1.99-1.77 (m, 4H), 1.67-1.45 (m, 3H), 1.34 (m, 1H), 1.11 (s, 3H), 1.00 (m, 1H).

Example 194

(1S,2R)-2-((S)-5-chloro-8-((5-(difluoromethyl)-1-methyl-1H-1,2,3-triazol-4-yl)methoxy)-1-(((R)-2-methyl-5-oxopyrrolidin-1-yl)methyl)-1,2,3,4-tetrahydroisoquinoline-2-carbonyl)-1-methylcyclohexane-1-carboxylic acid

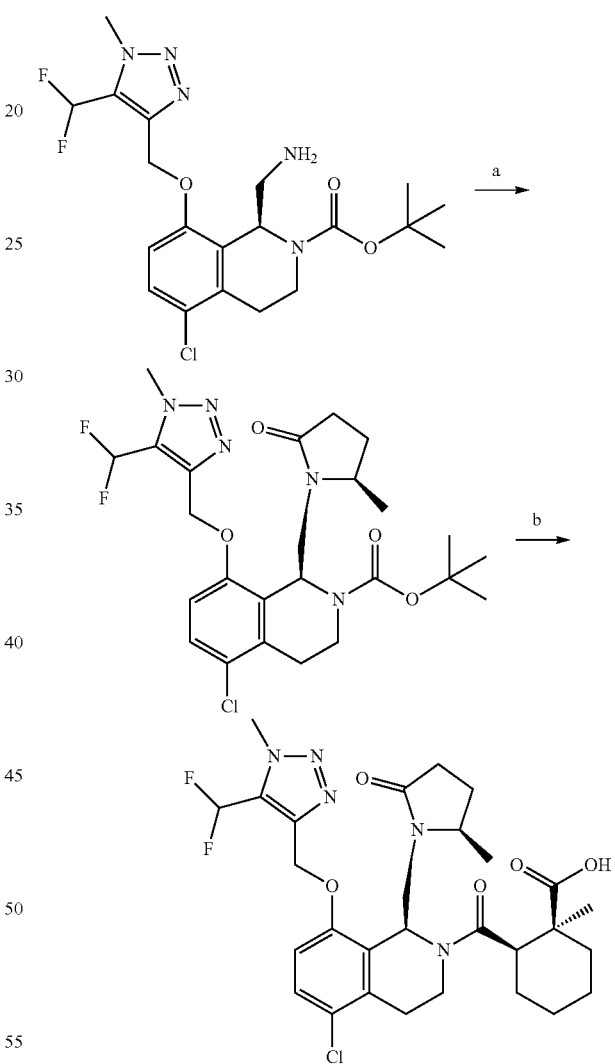

Step a. To a stirred solution of tert-butyl (S)-1-(aminomethyl)-5-chloro-8-((5-(difluoromethyl)-1-methyl-1H-1,2,3-triazol-4-yl)methoxy)-3,4-dihydroisoquinoline-2(1H)-carboxylate (50 mg, 0.11 mmol; Example 109 step c) and 4-oxopentanoic acid (13 mg, 0.11 mmol, CAS: 123-76-2) in DMSO (0.5 mL) was added formic acid (0.02 mL, 0.55 mmol) and triethylamine (0.02 mL, 0.11 mmol). The reaction mixture was degassed with argon for 5 min and heated at 100° C. for 16 h. The reaction mixture was cooled to rt, and NaOH (2M aqueous) was added and the mixture extracted with DCM (×3). The combined organics were washed with brine, dried over MgSO$_4$, filtered and concentrated in vacuo. Purification by flash column chromatography (100% EtOAc) gave tert-butyl (S)-5-chloro-8-((5-(difluoromethyl)-1-methyl-1H-1,2,3-triazol-4-yl)methoxy)-1-(((R)-2-methyl-5-oxopyrrolidin-1-yl)methyl)-3,4-dihydroisoquinoline-2(1H)-carboxylate (12 mg, 19%), LCMS (Method 9): 1.00 min, 540.6 [M+H]$^+$ and tert-butyl (S)-5-chloro-8-((5-(difluoromethyl)-1-methyl-1H-1,2,3-triazol-4-yl)methoxy)-1-(((S)-2-methyl-5-oxopyrrolidin-1-yl)methyl)-3,4-dihydroisoquinoline-2(1H)-carboxylate (10 mg, 7%), LCMS (Method 9): 0.98 min, 440.5 [M+H–CO$_2$$^t$Bu]$^+$.

Step b. The title compound (12 mg, 32%) was prepared from tert-butyl (S)-5-chloro-8-((5-(difluoromethyl)-1-methyl-1H-1,2,3-triazol-4-yl)methoxy)-1-(((R)-2-methyl-5-oxopyrrolidin-1-yl)methyl)-3,4-dihydroisoquinoline-2(1H)-carboxylate, and Intermediate 29 using a procedure similar to that described for Example 123. The crude product was purified by MDAP (Method 5, 40-55% MeCN in 0.1% aqueous formic acid) and further purified by flash column chromatography (2-4% MeOH in DCM). LCMS (Method 9b): 1.52 min, 608.3 [M+H]$^+$. $^1$H NMR (300 MHz, CDCl$_3$) δ 7.29 (d, 1H), 6.98 (d, 1H), 6.93 (t, 1H), 5.89 (dd, 1H), 5.36-5.22 (m, 2H), 4.26-4.10 (m, 4H), 3.92-3.77 (m, 2H), 3.45 (m, 1H), 3.21 (dd, 1H), 3.05 (m, 1H), 2.72 (m, 1H), 2.58 (m, 1H), 2.40 (m, 1H), 2.25-2.13 (m, 2H), 2.04 (m, 1H), 1.91-1.74 (m, 2H), 1.69-1.27 (m, 5H), 1.18-0.94 (m, 7H).

Example 195

(1S,2R)-2-((S)-5-chloro-8-((5-(difluoromethyl)-1-methyl-1H-1,2,3-triazol-4-yl)methoxy)-1-(((S)-2-methyl-5-oxopyrrolidin-1-yl)methyl)-1,2,3,4-tetrahydroisoquinoline-2-carbonyl)-1-methylcyclohexane-1-carboxylic acid The title compound (5 mg, 28%) was prepared from tert-butyl (S)-5-chloro-8-((5-(difluoromethyl)-1-methyl-1H-1,2,3-triazol-4-yl)methoxy)-1-(((S)-2-methyl-5-oxopyrrolidin-1-yl)methyl)-3,4-dihydroisoquinoline-2(1H)-carboxylate and Intermediate 29 using a procedure similar to that described for Example 123. The crude product was purified by MDAP (Method 5, 40-55% MeCN in 0.1% aqueous formic acid) and further purified by flash column chromatography (3% MeOH in DCM). LCMS (Method 9b): 1.53 min, 608.3 [M+H]$^+$. $^1$H NMR (300 MHz, CDCl$_3$) δ 7.30 (d, 1H), 6.98 (d, 1H), 6.92 (t, 1H), 5.88 (dd, 1H), 5.36 (d, 1H), 5.24 (d, 1H), 4.19 (s, 3H), 4.10-2.96 (m, 6H), 2.73 (m, 1H), 2.56 (m, 1H), 2.47-2.22 (m, 2H), 2.21-1.98 (m, 2H), 1.90-1.72 (m, 2H), 1.72-0.69 (m, 12H).

Example 196

(1S,2R)-2-((S)-5-chloro-1-((3-oxomorpholino)methyl)-8-((4,5,6,7-tetrahydro-[1,2,3]triazolo[1,5-a]pyridin-3-yl)methoxy)-1,2,3,4-tetrahydroisoquinoline-2-carbonyl-1-methylcyclohexane-1-carboxylic acid

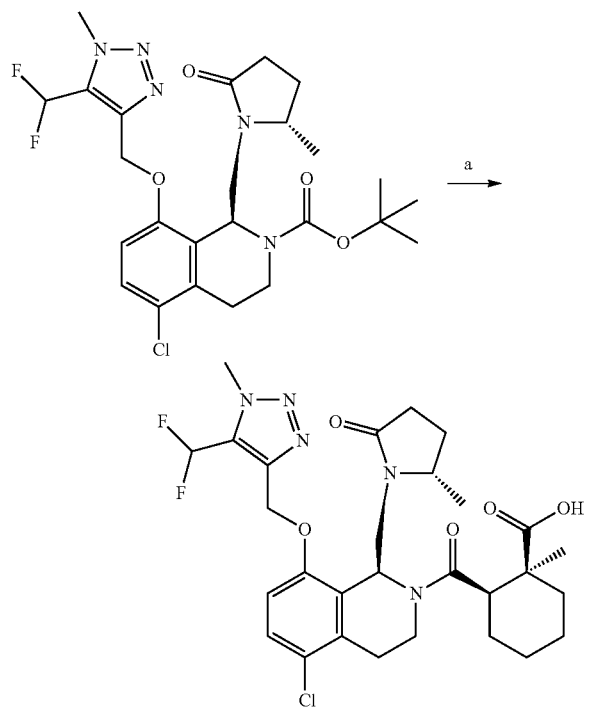
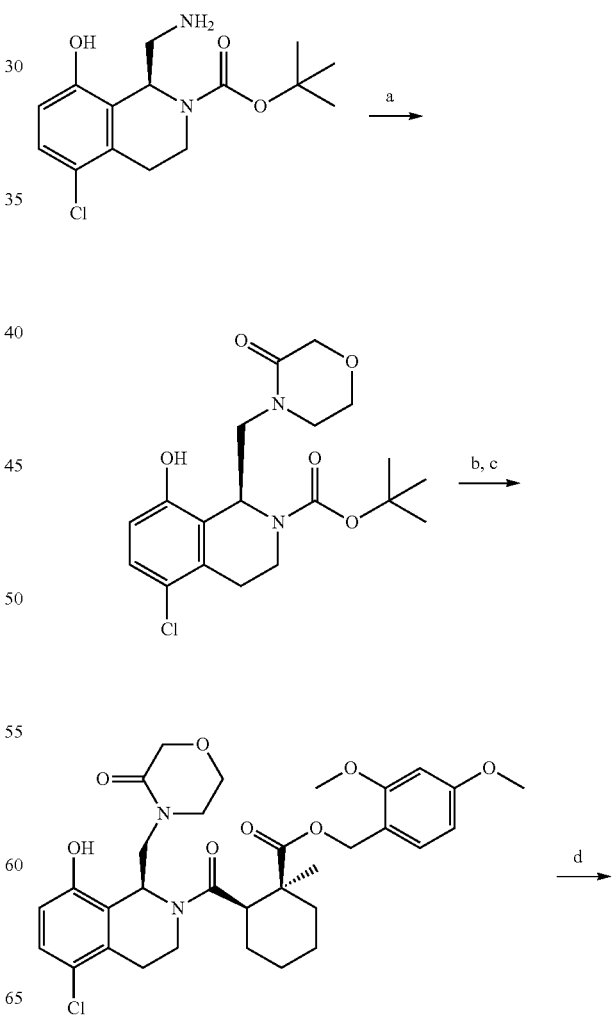

-continued

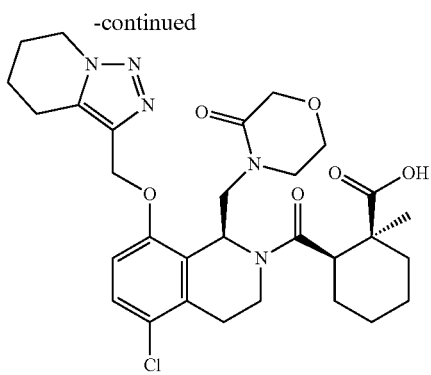

Step a. A solution of Intermediate 22 (500 mg, 1.6 mmol), methyl 2-(2-iodoethoxy)acetate (507.11 mg, 2.08 mmol, CAS: 84424-42-0) and triethylamine (0.33 mL, 2.4 mmol) in toluene (6 mL) was heated under reflux for 18 h. The reaction mixture was allowed to cool to rt and concentrated in vacuo. The residue was partitioned between DCM and 5% citric acid. The organic phase was separated and the aqueous was further extracted with DCM (×2). The combined organics were washed with brine, dried over $Na_2SO_4$ and concentrated in vacuo. Purification by flash column chromatography on the Teledyne ISCO CombiFlash® Rf+ (40 g silica column Puriflash HC, 0-100% EtOAc in cyclohexane) gave tert-butyl (S)-5-chloro-8-hydroxy-1-((3-oxomorpholino)methyl)-3,4-dihydroisoquinoline-2(1H)-carboxylate (503 mg, 79%). LCMS (Method 16): 1.28 min, 419.3 $[M+Na]^+$ Step b. (S)-4-((5-Chloro-8-hydroxy-1,2,3,4-tetrahydroisoquinolin-1-yl)methyl)-morpholin-3-one hydrochloride (422 mg, assumed quantitative) was prepared from the above intermediate (503 mg, 1.27 mmol) using a procedure similar to that described for Example 1, step d and used without further purification. LCMS (Method 16): 0.68 min, 297.1 $[M+H]^+$ Step c. To a stirred solution of the above intermediate (422 mg, 1.27 mmol) and Intermediate 33 (691 mg, 1.52 mmol) in DMF (5 mL) was added DIPEA (0.44 mL, 2.53 mmol) and the resulting mixture was stirred at rt under argon for 5 days. The reaction mixture was diluted with EtOAc, diluted with saturated sodium bicarbonate solution and the aqueous extracted with EtOAc. The combined organics were washed with water and brine, dried ($Na_2SO_4$), filtered and concentrated in vacuo. The crude product was purified by flash column chromatography on the Teledyne ISCO CombiFlash® Rf+ (40 g silica column Puriflash HC, 0-100% EtOAc in cyclohexane) to provide 2,4-dimethoxybenzyl (1S,2R)-2-((S)-5-chloro-8-hydroxy-1-((3-oxomorpholino)methyl)-1,2,3,4-tetrahydroisoquinoline-2-carbonyl)-1-methylcyclohexane-1-carboxylate (387 mg, 50%). LCMS (Method 16): 1.45 min, 637.3 $[M+Na]^+$.

Step d. 2,4-Dimethoxybenzyl (1S,2R)-2-((S)-5-chloro-1-((3-oxomorpholino)-methyl)-8-((4,5,6,7-tetrahydro-[1,2,3]triazolo[1,5-a]pyridin-3-yl)methoxy)-1,2,3,4-tetrahydroisoquinoline-2-carbonyl)-1-methylcyclohexane-1-carboxylate (252 mg, assumed quantitative) was prepared from the above intermediate (190 mg, 0.31 mmol) and 3-(chloromethyl)-4,5,6,7-tetrahydrotriazolo[1,5-a]pyridine (71 mg, 0.41 mmol) using a procedure similar to that described for Example 22 step c. The crude product was used without further purification. LCMS (Method 16): 1.49 min, 750.4 $[M+H]^+$.

Step e. The title compound (126 mg, 63%) was prepared from the above intermediate (232 mg, 0.31 mmol) using a procedure similar to that described for Example 156. The crude product was purified by flash column chromatography on the Teledyne ISCO CombiFlash® Rf+ (25 g silica column Puriflash HC, 0-5% MeOH in DCM). LCMS (Method 3): 4.21 min, 600.4 $[M+H]^+$. $^1$H NMR (400 MHz, DMSO-$d_6$) δ 11.78 (bs, 1H), 7.37 (d, 1H), 7.15 (d, 1H), 5.85 (dd, 1H), 5.22-5.13 (m, 2H), 4.39-4.26 (m, 3H), 4.04-3.89 (m, 2H), 3.85-3.55 (m, 4H), 3.43 (m, 1H), 2.98 (m, 1H), 2.93-2.77 (m, 5H), 2.69 (m, 1H), 2.26 (m, 1H), 2.02-1.92 (m, 2H), 1.87-1.77 (m, 2H), 1.70-1.47 (m, 3H), 1.44-1.20 (m, 4H), 1.10 (s, 3H).

Example 201

(1S,6R)-6-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohex-3-ene-1-carboxylic acid

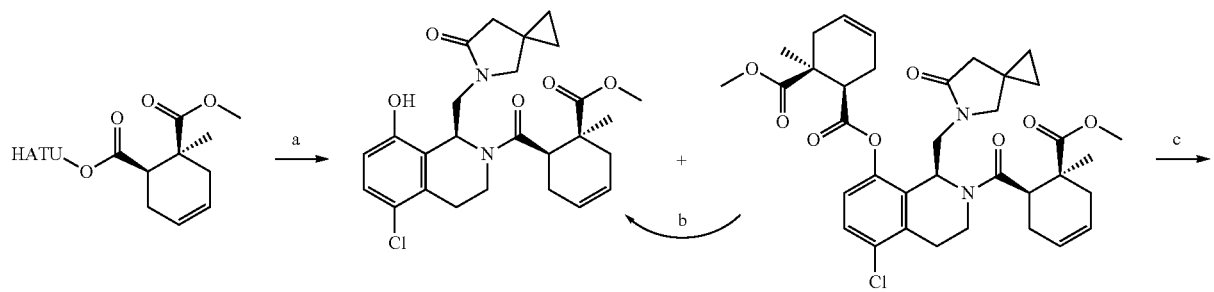

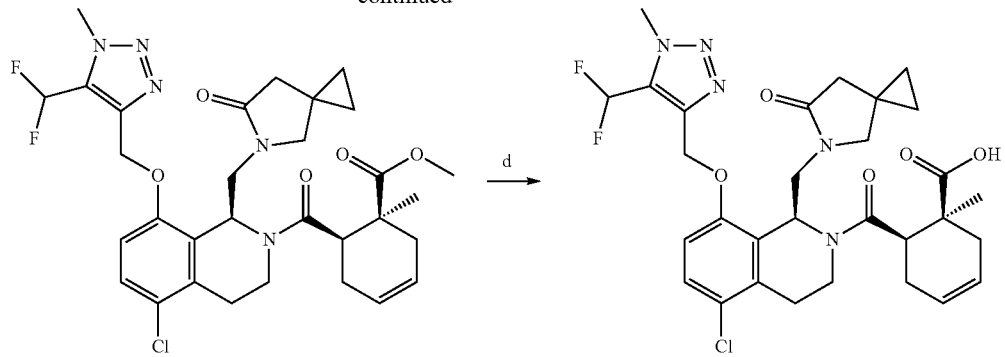

Step a. A mixture of Intermediate 36 (2.16 g, 6.29 mmol), Intermediate 40 (1.99 g, 6.29 mmol) and DIPEA (2.19 mL, 12.59 mmol), in DMF (39 mL) was stirred under nitrogen at rt for 28 h. The reaction mixture was diluted with ethyl acetate, washed with brine and the combined organics concentrated in vacuo. Purification by flash column chromatography on the Teledyne ISCO CombiFlash® Rf+ (80 g silica column Puriflash HC, 0-10% MeOH in DCM) gave methyl (1S,6R)-6-[(1S)-5-chloro-8-hydroxy-1-[(6-oxo-5-azaspiro[2.4]heptan-5-yl)methyl]-3,4-dihydro-1H-isoquinoline-2-carbonyl]-1-methyl-cyclohex-3-ene-1-carboxylate (1.64 g, 53%) and O2-[(1S)-5-chloro-2-[(1R,6S)-6-methoxycarbonyl-6-methyl-cyclohex-3-ene-1-carbonyl]-1-[(6-oxo-5-azaspiro[2.4]heptan-5-yl)methyl]-3,4-dihydro-1H-isoquinolin-8-yl] O1-methyl (1S,2R)-1-methylcyclohex-4-ene-1,2-dicarboxylate (1.22 g, 29%). Methyl (1S,6R)-6-[(1S)-5-chloro-8-hydroxy-1-[(6-oxo-5-azaspiro[2.4]heptan-5-yl)methyl]-3,4-dihydro-1H-isoquinoline-2-carbonyl]-1-methyl-cyclohex-3-ene-1-carboxylate: LCMS (Method 18): 1.43 min, 487.3 [M+H]+. O2-[(1S)-5-chloro-2-[(1R,6S)-6-methoxycarbonyl-6-methyl-cyclohex-3-ene-1-carbonyl]-1-[(6-oxo-5-azaspiro[2.4]heptan-5-yl)methyl]-3,4-dihydro-1H-isoquinolin-8-yl] O1-methyl (1S,2R)-1-methylcyclohex-4-ene-1,2-dicarboxylate: LCMS (Method 16): 1.66 min, 667.3 [M+H]+.

Step b. To a solution of lithium hydroxide monohydrate (305 mg, 7.26 mmol) in THF (20 mL) was added O2-[(1S)-5-chloro-2-[(1R,6S)-6-methoxycarbonylcyclohex-3-ene-1-carbonyl]-1-[(6-oxo-5-azaspiro[2.4]heptan-5-yl)methyl]-3,4-dihydro-1H-isoquinolin-8-yl] O1-methyl 1-methylcyclohex-4-ene-1,2-dicarboxylate (1.210 g, 0.92 mmol) in water (5 mL) and the reaction was stirred at rt for 3 days then concentrated in vacuo. The residue was diluted with citric acid (aq. 10%) and extracted with EtOAc. The combined organics were dried (MgSO4), filtered and concentrated in vacuo and the crude material was purified by flash column chromatography on the Teledyne ISCO CombiFlash® Rf+ (40 g silica column Puriflash HC/Biotage SNAP, 0-8% MeOH in DCM) to provide methyl (1S,6R)-6-[(1S)-5-chloro-8-hydroxy-1-[(6-oxo-5-azaspiro[2.4]heptan-5-yl)methyl]-3,4-dihydro-1H-isoquinoline-2-carbonyl]-1-methyl-cyclohex-3-ene-1-carboxylate (655 mg, 79%). LCMS (Method 16): 1.32 min, 487.2 [M+H]+.

Step c. Methyl (1S,6R)-6-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohex-3-ene-1-carboxylate (2.03 g, 95%) was prepared from the above intermediate (1.64 g, 3.37 mmol) using a procedure similar to that described for Example 22 step c. The crude product was purified by flash column chromatography on the Teledyne ISCO CombiFlash® (80 g silica column Puriflash HC, 0-4% MeOH in DCM). LCMS (Method 16): 1.42 min, 632.3 [M+H]+.

Step d. To a stirred solution of the above intermediate (503 mg, 0.800 mmol) in methanol (8 mL) was added a solution of sodium hydroxide (334 mg, 7.96 mmol) in water (2 mL) and the reaction vial sealed and heated under microwave irradiation at 100° C. for 4 h. The residue was diluted with citric acid (aq. 10%) and extracted with EtOAc. The combined organics were dried (MgSO4), filtered and concentrated in vacuo. The crude product was purified by flash column chromatography on the Teledyne ISCO CombiFlash® Rf+ (40 g silica column (15 µM) Puriflash HC/Biotage SNAP, 0-2% MeOH in DCM) and freeze dried to give the title compound (362 mg, 69%). LCMS (Method 3) 4.48 min, 618.3 [M+H]+. 1H NMR (400 MHz, CDCl3) δ 14.93 (bs, 1H), 7.30 (d, 1H), 6.99 (d, 1H), 6.93 (t, 1H), 5.98 (dd, 1H), 5.77-5.69 (m, 1H), 5.68-5.59 (m, 1H), 5.38-5.15 (m, 2H), 4.22-3.91 (m, 6H), 3.44 (d, 1H), 3.16 (dd, 1H), 3.11-2.99 (m, 3H), 2.93 (dd, 1H), 2.76 (m, 1H), 2.42 (d, 1H), 2.37-2.23 (m, 2H), 2.13 (d, 1H), 1.83 (m, 1H), 1.21 (s, 3H), 0.74-0.46 (m, 4H).

Example 203

(1S,2R)-2-((S)-5-chloro-8-((5-(difluoromethyl)-1-methyl-1H-1,2,3-triazol-4-yl)methoxy)-7-fluoro-1-((6-oxo-5-azaspiro[2.4]heptan-5-yl)methyl)-1,2,3,4-tetrahydroisoquinoline-2-carbonyl)-1-methylcyclohexane-1-carboxylic acid

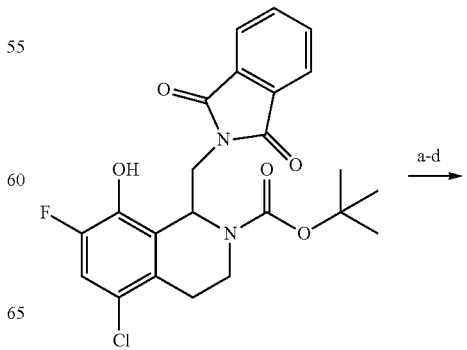

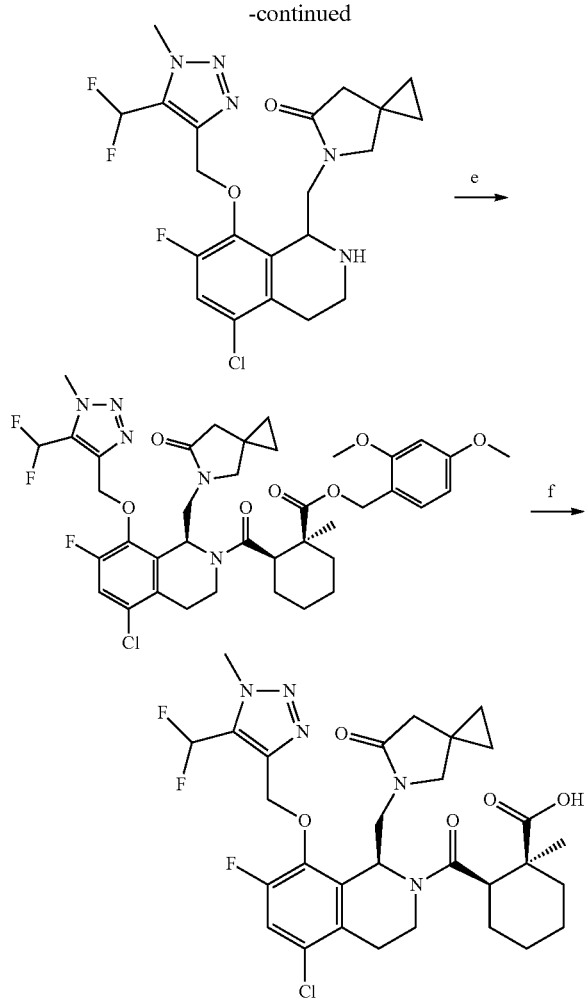

Step a. To a stirred solution of Intermediate 48 (racemic; 700 mg, 1.52 mmol) and caesium carbonate (1.78 g, 5.47 mmol) in DMF (25 mL) was added 4-(chloromethyl)-5-(difluoromethyl)-1-methyl-triazole hydrochloride (380 mg, 1.74 mmol). The reaction was left to stir at rt for 18 h overnight then heated at 50° C. for 24 h, then cooled to rt. The mixture was diluted with water, extracted with EtOAc and the combined organics washed with brine, dried over MgSO$_4$ and concentrated in vacuo. The crude product was purified by silica chromatography (Silicycle 25 g silica column, 0-2% MeOH in DCM) to give tert-butyl 5-chloro-8-((5-(difluoromethyl)-1-methyl-1H-1,2,3-triazol-4-yl) methoxy)-1-((1,3-dioxoisoindolin-2-yl)methyl)-7-fluoro-3,4-dihydroisoquinoline-2(1H)-carboxylate (0.91 g, 96%). LCMS (Method 9a): 2.99 min, 506.1 [M+H−CO$_2^t$Bu]$^+$.

Step b. To a stirred solution of the above intermediate (0.91 g, 1.5 mmol) in EtOH (25 mL) was added hydrazine hydrate (0.37 mL, 7.51 mmol; CAS: 10217-52-4) and the reaction mixture was stirred at 65° C. for 18 h, then cooled to rt. The reaction mixture was filtered, the filter cake with washed with EtOH and the filtrate was concentrated in vacuo. To this was added Et$_2$O and the precipitate removed by filtration, washing with Et$_2$O. The filtrate was concentrated in vacuo to give tert-butyl 1-(aminomethyl)-5-chloro-8-((5-(difluoromethyl)-1-methyl-1H-1,2,3-triazol-4-yl) methoxy)-7-fluoro-3,4-dihydroisoquinoline-2(1H)-carboxylate (581 mg, 71%). LCMS (Method 9a): 2.41 min, 476.2 [M+H]$^+$.

Step c. To a solution of the above intermediate (575 mg, 1.21 mmol) and methyl 2-(1-(bromomethyl)cyclopropyl) acetate (325 mg, 1.57 mmol CAS: 855473-50-6) in MeCN (42 mL) was added triethylamine (0.25 mL, 1.81 mmol) and the reaction mixture was heated at 90° C. for 48 h, then the temperature was increased to 95° C. for a further 7 h. The reaction mixture was diluted with water, extracted with EtOAC and washed with water, brine, dried (Mg$_2$SO$_4$) and concentrated in vacuo. The crude product was purified by silica chromatography (Biotage ZIP sphere 80 g, 0-3% methanol in dichloromethane) to give tert-butyl 5-chloro-8-((5-(difluoromethyl)-1-methyl-1H-1,2,3-triazol-4-yl) methoxy)-7-fluoro-1-((6-oxo-5-azaspiro[2.4]heptan-5-yl) methyl)-3,4-dihydroisoquinoline-2(1H)-carboxylate (541 mg, 77%). LCMS (Method 9a): 2.67 min, 470.2 [M−CO$_2^t$Bu+H]$^+$.

Step d. A solution of the above intermediate (540 mg, 0.950 mmol) in hydrogen chloride (4M in dioxane; 5.0 mL, 20 mmol) was stirred at rt for 1.5 h and concentrated in vacuo to give 54(5-chloro-8-((5-(difluoromethyl)-1-methyl-1H-1,2,3-triazol-4-yl)methoxy)-7-fluoro-1,2,3,4-tetrahydroisoquinolin-1-yl)methyl)-5-azaspiro[2.4]heptan-6-one (454 mg, 92%), used without further purification. LCMS (Method 9): 0.81 min, 470.2 [M+H]$^+$.

Step e. To a solution of the above intermediate (454 mg, 0.90 mmol), Intermediate 29 (392 mg, 1.17 mmol) and DIPEA (0.94 mL, 5.38 mmol) in DMF (3 mL) was added HATU (409 mg, 1.08 mmol; CAS: 148893-10-1) and the reaction mixture was stirred at rt for 6 days. The mixture was diluted with water, extracted with EtOAc and the combined organics dried over Na$_2$SO$_4$, filtered, and concentrated in vacuo. The crude product was purified by flash column chromatography on the Biotage Isolera One™ (200-400 nm diode array detector; 45 g silica column, 0-4% MeOH in DCM) followed by reverse phase column chromatography on the Biotage Isolera One™ (200-400 nm diode array detector, 60 g C18 column, 30-80% MeCN in 0.1% aqueous ammonia) to give two products. Mixed fractions were also collected, freeze dried, and purified again by reverse phase column chromatography on the Biotage Isolera One™ (200-400 nm diode array detector, 30 g C18 column, 30-80% MeCN in 0.1% ammonia solution). The clean fractions were combined with respective product from the first purification and each was freeze dried overnight giving two products: the first eluting isomer (isomer 1, 105 mg) and the second eluting isomer (isomer 2, 156 mg). Isomer 1: 2,4-dimethoxybenzyl (1S,2R)-2-((S)-5-chloro-8-((5-(difluoromethyl)-1-methyl-1H-1,2,3-triazol-4-yl)methoxy)-7-fluoro-1-((6-oxo-5-azaspiro[2.4]heptan-5-yl)methyl)-1,2,3,4-tetrahydroisoquinoline-2-carbonyl)-1-methylcyclohexane-1-carboxylate (105 mg, 13%), LCMS (Method 9a): 2.95 min, 788.3 [M+H]$^+$. Isomer 2: 2,4-dimethoxybenzyl (1S, 2R)-2-((R)-5-chloro-8-((5-(difluoromethyl)-1-methyl-1H-1,2,3-triazol-4-yl)methoxy)-7-fluoro-1-((6-oxo-5-azaspiro [2.4]heptan-5-yl)methyl)-1,2,3,4-tetrahydroisoquinoline-2-carbonyl)-1-methylcyclohexane-1-carboxylate (156 mg, 21%), LCMS (Method 9a): 3.02 min, 788.3 [M+H]$^+$. Absolute stereochemistry of diastereoisomers confirmed by small molecule X-ray crystallography of the carboxylic acid arising from isomer 2.

Step f. A mixture of the above intermediate (Isomer 1, 120 mg, 0.13 mmol) and hydrogen chloride (4M in dioxane; 15 mL, 60 mmol) was stirred at rt for 2 h. The reaction mixture was concentrated in vacuo and the crude product purified by reverse phase chromatography (Biotage C18 SNAP 60 g, 5-50% MeCN in 0.1% aqueous ammonia) to give the title compound (29 mg, 33%). LCMS (Method 14—specific gradient: MeCN with 5% D2 and 93% Water to 50% MeCN with 5% D2 and 45% Water in 3.00 mins. Ramp to 95% MeCN with 5% D2 to 4.50 mins): 1.76 min, 638.22 [M+H]⁺.
¹H NMR (400 MHz, CDCl₃) δ 7.20 (d, 1H), 6.82 (t, 1H), 5.48 (dd, 1H), 5.40 (d, 1H), 5.23 (d, 1H), 4.16 (s, 3H), 4.06 (dd, 1H), 4.00-3.89 (m, 1H), 3.83 (m, 1H), 3.24 (d, 1H), 3.13 (d, 1H), 3.08 (dd, 1H), 2.99 (m, 1H), 2.67 (m, 1H), 2.57 (dd, 1H), 2.47-2.36 (m, 2H), 2.07 (d, 1H), 1.85-1.72 (m, 2H), 1.70-1.43 (m, 3H), 1.41-1.23 (m, 1H), 1.12 (s, 3H), 1.03 (m, 1H), 0.69-0.50 (m, 4H).

Example 207

(1R,3S,4R,6S)-4-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-3-methylbicyclo[4.1.0]heptane-3-carboxylic acid

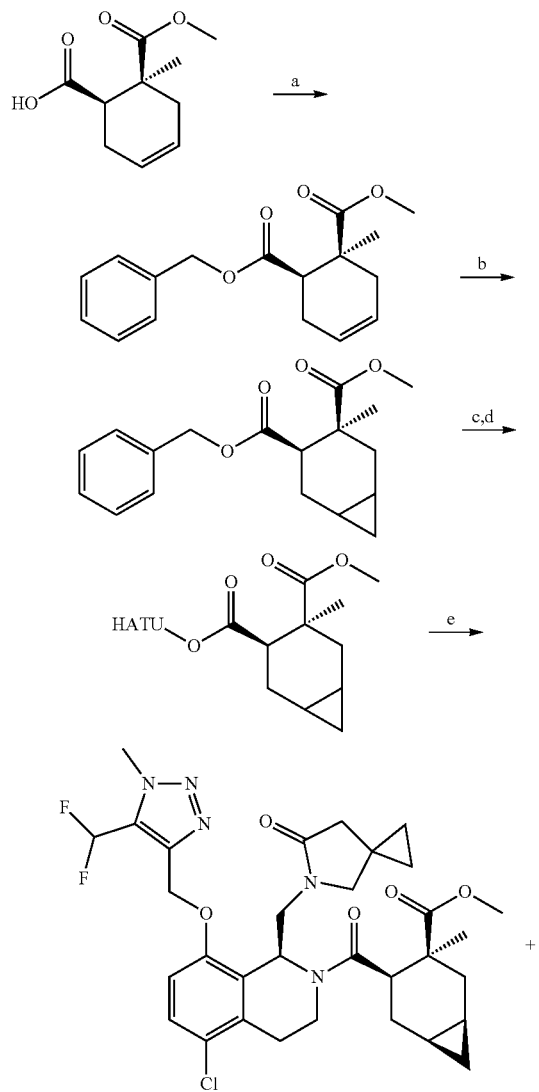

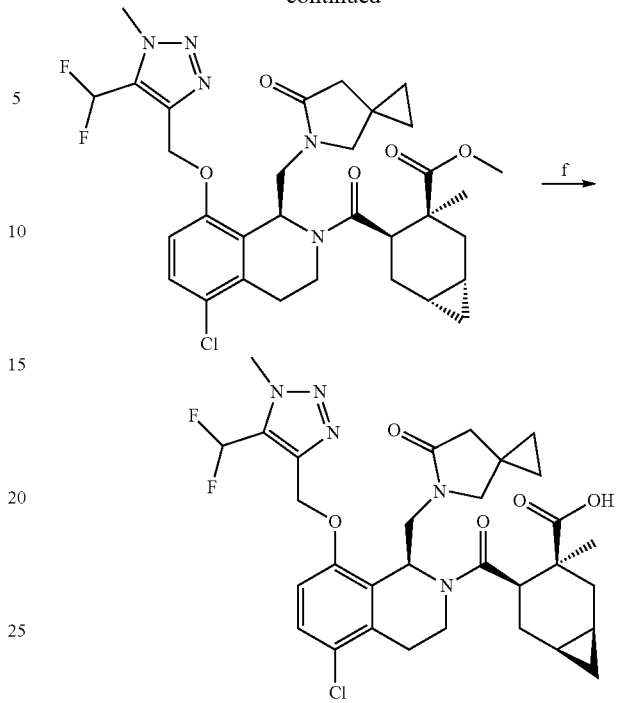

Step a. Intermediate 39 (1.5 g, 7.57 mmol) was dissolved in DMF (15 mL) and potassium carbonate (1.57 g, 11.4 mmol), bromomethylbenzene (1.35 mL, 11.35 mmol; CAS: 100-39-0) and potassium iodide (37 mg, 1.51 mmol) was added. The solution was stirred at rt for 2 h. The reaction was partitioned between EtOAc and brine, the organic layer was separated, dried (MgSO₄) and concentrated in vacuo. The crude product was purified by flash column chromatography on the Teledyne ISCO CombiFlash® Rf+ (120 g silica column Puriflash HC, 0-2% MeOH in DCM) to provide 2-benzyl 1-methyl (1S,2R)-1-methylcyclohex-4-ene-1,2-dicarboxylate (1.7 g, 74% yield). ¹H NMR (400 MHz, CDCl₃) δ 7.36-7.29 (m, 5H), 5.67-5.58 (m, 2H), 5.10-5.04 (m, 2H), 3.58-3.57 (m, 3H), 3.03 (dd, 1H), 2.81-2.73 (m, 1H), 2.62-2.55 (m, 1H), 2.43-2.34 (m, 1H), 2.08-2.02 (m, 1H), 1.24 (s, 3H).

Step b. To a solution of diethylzinc (13.87 mL, 13.87 mmol) in DCM (30 mL) at −5° C. under argon was added TFA (0.85 mL, 11.1 mmol) dropwise over 10 mins, followed by diiodomethane (1.12 mL, 13.87 mmol) dropwise over 15 mins. The solution was then stirred at −5° C. for 15 mins. To this was added a solution of the above intermediate (800 mg, 2.77 mmol) in DCM (3 mL) dropwise at −15° C. over 15 mins and the solution was slowly warmed to rt and stirred for 16 h. The reaction mixture was diluted with water and extracted with DCM. The combined organics were dried (Na₂SO₄) and concentrated in vacuo. The crude residue was then purified by flash column chromatography on the Teledyne ISCO CombiFlash® Rf+ (120 g silica column Puriflash HC/Biotage SNAP, dry loading, 0-20% THF in cyclohexane) to provide a colourless oil (725 mg). The mixture was diluted in DCM and treated with 3-chloroperbenzoic acid (430 mg, 1.92 mmol) and the resulting solution was stirred at rt for 16 h. The reaction mixture was diluted with DCM, washed with water, saturated NaHCO₃ and brine. The combined organics were dried over Na₂SO₄, filtered, and concentrated in vacuo. The crude product was purified by flash column chromatography on the Interchim Puriflash®

4125 (120 g silica column Puriflash InterChim, 0-30% THF in cyclohexane) to provide 4-benzyl 3-methyl (3S,4R)-3-methylbicyclo[4.1.0]heptane-3,4-dicarboxylate (310 mg, 70%) as a mixture of diastereoisomers. LCMS (Method 2): 1.33 min, no mass ion observed.

Step c. To a solution of the above intermediate (242 mg, 0.80 mmol) in EtOH (4 mL) was added Pd/C (10%; 26 mg, 0.24 mmol) and the resulting mixture stirred under a hydrogen atmosphere at ambient pressure for 16 h. The reaction mixture was diluted with IMS and filtered through Celite®. The filtrate was concentrated in vacuo to provide (3R,4S)-4-(methoxycarbonyl)-4-methylbicyclo[4.1.0]heptane-3-carboxylic acid (263 mg, assumed quantitative) as a mixture of diastereoisomers. LCMS (Method 2): 1.23 min, 213.1 [M+H]⁺.

Step d. To a stirred solution of the above intermediate (262 mg, 1.23 mmol) in DMF (3 mL) was added HATU (516 mg, 1.36 mmol; CAS: 148893-10-1) and the resulting mixture was stirred at rt under argon for 5 min. DIPEA (0.24 mL, 1.36 mmol) was added and the resulting mixture was stirred for 2 h, diluted with water and the extracted with EtOAc. The combined organics were washed with water, brine, dried (Na₂SO₄), filtered and concentrated in vacuo. The crude product was purified by flash column chromatography on the Teledyne ISCO CombiFlash® Rf+ (40 g silica column Puriflash HP, 0-50% EtOAc in cyclohexane) to provide 4-(3H-[1,2,3]triazolo[4,5-b]pyridin-3-yl) 3-methyl (3S,4R)-3-methylbicyclo[4.1.0]heptane-3,4-dicarboxylate (353 mg, 87%) as a mixture of diastereomers. LCMS (Method 2): 1.51& 1.52 min, 331.0 [M+H]⁺.

Step e. To a solution of (S)-5-((5-chloro-8-((5-(difluoromethyl)-1-methyl-1H-1,2,3-triazol-4-yl)methoxy)-1,2,3,4-tetrahydroisoquinolin-1-yl)methyl)-5-azaspiro[2.4]heptan-6-one hydrochloride (200 mg, 0.41 mmol, Example 110 step b) and the above intermediate (162 mg, 0.49 mmol) in DMF (1.6 mL) was added DIPEA (0.14 mL, 0.820 mmol) and the resulting mixture was stirred at rt under argon for 18 h. Additional 4-(3H-[1,2,3]triazolo[4,5-b]pyridin-3-yl) 3-methyl (3S,4R)-3-methylbicyclo[4.1.0]heptane-3,4-dicarboxylate (80 mg, 0.24 mmol) and DIPEA (0.08 mL, 0.47 mmol) were added and the reaction mixture was further stirred for 24 h. The reaction mixture was diluted with saturated sodium bicarbonate solution and extracted with EtOAc. The combined organics were washed with water and brine, dried over Na₂SO₄, filtered and concentrated in vacuo. The crude product was purified by flash column chromatography on the Teledyne ISCO CombiFlash® Rf+ (80 g silica column Puriflash HC, 0-100% EtOAc in cyclohexane) to provide methyl (1R,3S,4R,6S)-4-((S)-5-chloro-8-((5-(difluoromethyl)-1-methyl-1H-1,2,3-triazol-4-yl) methoxy)-1-((6-oxo-5-azaspiro[2.4]heptan-5-yl)methyl)-1,2,3,4-tetrahydroisoquinoline-2-carbonyl)-3-methylbicyclo[4.1.0]heptane-3-carboxylate (173 mg, 65%) and methyl (1S,3S,4R,6R)-4-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-3-methylbicyclo[4.1.0]heptane-3-carboxylate (43 mg, 16%). Methyl (1R,3S,4R,6S)-4-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-3-methylbicyclo[4.1.0]heptane-3-carboxylate: LCMS (Method 15): 1.62 min, 646.4 [M+H]⁺. Methyl (1S,3S,4R,6R)-4-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-3-methylbicyclo[4.1.0]heptane-3-carboxylate: LCMS (Method 15): 1.61 min, 646.4 [M+H]⁺.

Step f. To stirred a solution of methyl (1R,3S,4R,6S)-4-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-3-methylbicyclo[4.1.0]heptane-3-carboxylate (173 mg, 0.27 mmol) in MeOH (3 mL) was added a solution of sodium hydroxide (3 M; 0.89 mL, 2.68 mmol) and the resulting mixture was heated at 100° C. under microwave irradiation for 3 h. The reaction mixture was concentrated in vacuo and the residue was diluted with water, acidified to pH 4 using 5% citric acid solution and the aqueous extracted with EtOAc. The combined organics were washed with water, brine, dried (Na₂SO₄) and concentrated in vacuo. The crude product was purified by reverse phase flash column chromatography on the InterChim 4125 (80 g C18 InterChim HP, 5-70% MeCN in water with 0.1% HCOOH buffer). Fractions containing the desired product were combined and freeze dried to provide the title compound (116 mg, 66%). LCMS (Method 11): 4.72 min, 632.3 [M+H]⁺. ¹H NMR (400 MHz, CDCl₃) δ 15.03 (bs, 1H), 7.30 (d, 1H), 6.98 (d, 1H), 6.91 (t, 1H), 5.93 (dd, 1H), 5.43-5.13 (m, 2H), 4.20-3.98 (m, 6H), 3.43 (d, 1H), 3.19-3.01 (m, 3H), 2.90 (d, 1H), 2.75 (m, 1H), 2.62 (dd, 1H), 2.42 (d, 1H), 2.25 (m, 1H), 2.17 (d, 1H), 1.67-1.42 (m, 2H), 1.08 (s, 3H), 1.03 (m, 1H), 0.86 (m, 1H), 0.70-0.49 (m, 5H), 0.26 (dd, 1H).

Example 208

(1S,3S,4R,6R)-4-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-3-methylbicyclo[4.1.0]heptane-3-carboxylic acid

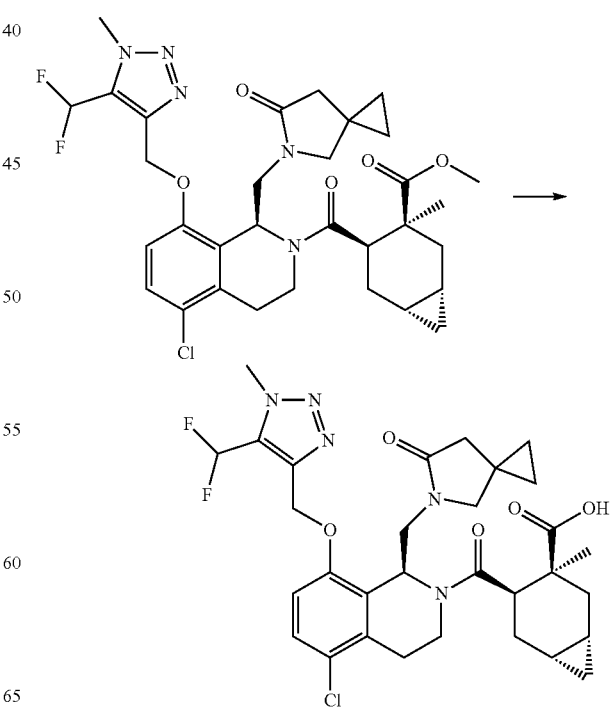

To stirred a solution of methyl (1S,3S,4R,6R)-4-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-3-methylbicyclo[4.1.0]heptane-3-carboxylate (43 mg, 0.03 mmol; Example 207 step e) in MeOH (0.8 mL) was added a solution of sodium hydroxide (3 M; 0.22 mL, 0.33 mmol) and the resulting mixture was heated at 100° C. under microwave irradiation for 15 h. The reaction mixture was concentrated in vacuo and the residue was diluted with water, acidified to pH 4 using 5% citric acid solution and the aqueous extracted with EtOAc. The combined organics were washed with water, brine, dried (Na$_2$SO$_4$) and concentrated in vacuo. The crude product was purified by reverse phase flash column chromatography on the InterChim 4125 (40 g C18 InterChim HP, 5-70% MeCN in water with 0.1% HCOOH buffer). Fractions containing the desired product were combined and freeze dried to provide the title compound (7 mg, 33%). LCMS (Method 11): 4.92 min, 632.3 [M+H]$^+$. $^1$H NMR (400 MHz, CDCl$_3$) δ 7.18 (m, 1H), 6.91 (t, 1H), 6.86 (d, 1H), 5.85 (m, 1H), 5.23 (d, 1H), 5.17 (d, 1H), 4.31 (bm, 1H), 4.16 (m, 3H), 4.04 (m, 1H), 3.71-3.50 (m, 2H), 2.97 (m, 1H), 2.92-2.70 (m, 3H), 2.69-2.50 (m, 2H), 2.20 (d, 1H), 2.08 (m, 1H), 1.93 (m, 1H), 1.82-1.51 (m, 2H), 1.39 (s, 3H), 1.06-0.95 (m, 1H), 0.94-0.77 (m, 1H), 0.73-0.63 (m, 2H), 0.62-0.47 (m, 2H), 0.47-0.37 (m, 1H), 0.03-0.04 (m, 1H).

To a stirred solution of Example 201 (300 mg, 0.49 mmol) in MeOH (10 mL) was added Pd/C (10%; 5.2 mg, 0.05 mmol). Deuterium gas was bubbled through the reaction mixture via balloon and the reaction stirred at rt for 16 h. Over this duration two additional portions of Pd/C (5.2 mg) and were deuterium gas was continuously bubbled through the mixture. After this time the reaction mixture was filtered through Celite® and concentrated in vacuo. The residue was taken up in MeOH (10 mL) and an additional portion of Pd/C (10%; 5.17 mg, 0.050 mmol) was added and deuterium gas was bubbled through the reaction mixture via balloon and the reaction mixture stirred at rt for 6 h. The reaction was filtered Celite® and concentrated in vacuo, then purified by flash column chromatography on the Teledyne ISCO CombiFlash® Rf+ (12 g silica column Puriflash HC/Biotage SNAP, 0-1.5% MeOH in DCM) followed by flash column chromatography on the Interchim Puriflash® 4100 (80 g C18 Puriflash HP, 5-70% MeCN in water with 0.1% formic acid) to provide the title compound (82 mg, 26%). LCMS (Method 3): 4.57 min, 622.4 [M+H]$^+$. $^1$H NMR (400 MHz, CDCl$_3$) δ 15.27 (bs, 1H), 7.30 (d, 1H), 6.98 (d, 1H), 6.92 (t, 1H), 5.95 (dd, 1H), 5.50-5.13 (m, 2H), 4.18 (m, 3H), 4.11 (dd, 1H), 4.00 (m, 1H), 3.88 (m, 1H), 3.44 (d, 1H), 3.21-3.02 (m, 3H), 2.76 (m, 1H), 2.59 (m, 1H), 2.46-2.35 (m, 2H), 2.12 (d, 1H), 1.88-1.74 (m, 2H), 1.64-1.47 (m, 2H), 1.13 (s, 3H), 1.01 (t, 1H), 0.74-0.47 (m, 4H).

Example 210

(1S,2R,4S,5R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic-4,5-d$_2$ acid Example 212

(1S,2R)-2-((1S)-5-chloro-8-((5-(difluoromethyl)-1-methyl-1H-1,2,3-triazol-4-yl)methoxy)-1-((2-oxo-4-(trifluoromethyl)pyrrolidin-1-yl)methyl)-1,2,3,4-tetrahydroisoquinoline-2-carbonyl)-1-methylcyclohexane-1-carboxylic acid (Isomer 1)

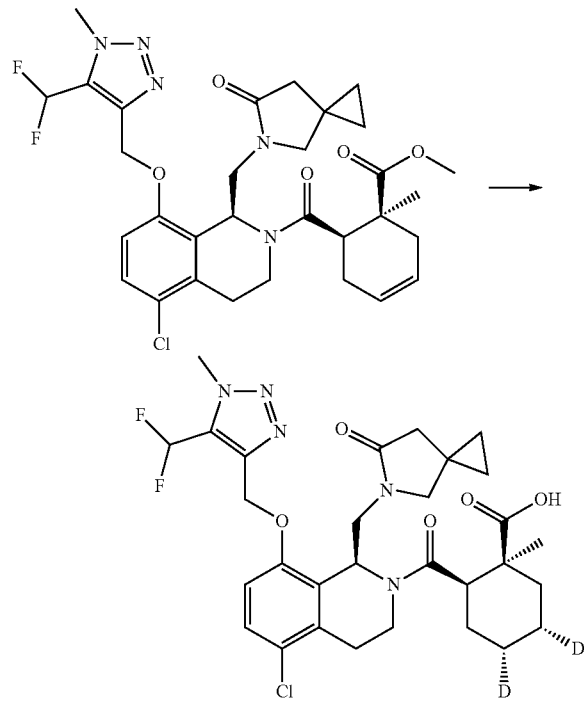

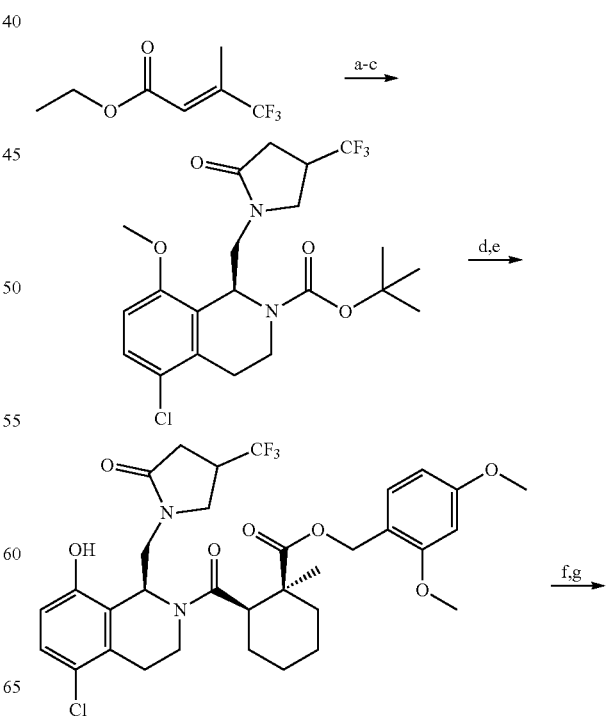

-continued

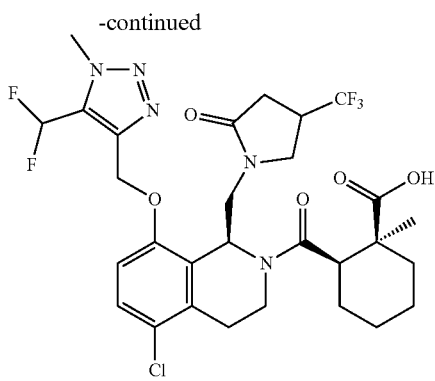

Step a. A mixture of ethyl (E)-4,4,4-trifluoro-3-methyl-but-2-enoate (2.0 g, 11.0 mmol; CAS: 24490-03-7), NBS (2.15 g, 12.08 mmol) and AIBN (0.09 g, 0.50 mmol) in carbon tetrachloride (16 mL) was heated at reflux with a halogen lamp for 4 h, then without a halogen lamp for 16 h. To the mixture was added saturated aqueous sodium bicarbonate solution and mixture extracted with Et$_2$O. The combined organics were dried (MgSO$_4$), filtered and concentrated in vacuo to give ethyl (Z)-3-(bromomethyl)-4,4,4-trifluoro-but-2-enoate (2.58 g, 81%). $^1$H NMR (301 MHz, CDCl$_3$) δ 6.45 (d, 1H), 4.52 (s, 2H), 4.33-4.22 (m, 2H), 1.36-1.29 (m, 3H).

Step b. To a stirred solution of Intermediate 58 (1.88 g, 5.75 mmol) in MeCN (35 mL) was added the above intermediate (1.58 g, 6.04 mmol) and triethylamine (0.96 mL, 6.9 mmol) and the mixture was heated at 80° C. for 25 min. The mixture was concentrated in vacuo and the crude product was purified by automated reverse phase column chromatography on the Biotage Isolera One™ (200-400 nm diode array detector, 10 g C18 column, 20-65% MeCN in water, 0.1% ammonia throughout) to provide tert-butyl (S)-5-chloro-8-methoxy-1-((2-oxo-4-(trifluoromethyl)-2,5-dihydro-1H-pyrrol-1-yl)methyl)-3,4-dihydroisoquinoline-2(1H)-carboxylate (940 mg, 30%). LCMS (Method 9a): 2.96 min, 361.1 [M+H−CO$_2^t$Bu]$^+$.

Step c. To a solution of the above intermediate (940 mg, 2.04 mmol) in IPA (70 mL) was added Pd/C (10%; 98 mg, 0.92 mmol). The mixture was stirred under a hydrogen atmosphere at ambient pressure for 7 h. The mixture was filtered through Celite® and the filter cake washed with IPA. The filtrate was concentrated in vacuo and the crude product was purified by automated column chromatography on the Biotage Isolera One (200-400 nm diode array detector, 45 g Zip sphere column, 0-40% EtOAc in heptanes) to provide tert-butyl (1S)-5-chloro-8-methoxy-1-((2-oxo-4-(trifluoromethyl)pyrrolidin-1-yl)methyl)-3,4-dihydroisoquinoline-2(1H)-carboxylate as two separate diastereoisomers. Diastereoisomer 1 (256 mg, 26%), LCMS (Method 9a): 2.86 min, 363.1 [M+H−CO$_2^t$Bu]$^+$. Diastereoisomer 2 (348 mg, 35%), LCMS (Method 9a): 2.82 min, 363.1 [M+H−CO$_2^t$Bu]$^+$.

Step d. To a solution of the above intermediate (diastereoisomer 1; 256 mg, 0.55 mmol) in DCM (34 mL) was added boron tribromide (1M in DCM; 11.1 mL, 11.1 mmol). The reaction mixture was stirred at rt for 16 h, cooled with an ice bath (0-5° C.) and MeOH (~10 mL) added slowly. The mixture was concentrated in vacuo, additional MeOH was added and the mixture again concentrated in vacuo to give 1-(((S)-5-chloro-8-hydroxy-1,2,3,4-tetrahydroisoquinolin-1-yl)methyl)-4-(trifluoromethyl)pyrrolidin-2-one hydrobromide (isomer 1; 237 mg, 82%) used without further purification. LCMS (Method 9): 0.65 min, 349.1 [M+H]$^+$.

Step e. To a stirred solution of the above intermediate (isomer 1; 217 mg, 0.51 mmol) in DMF (2.5 mL) was added Intermediate 33 (230 mg, 0.51 mmol) and DIPEA (0.18 mL, 1.01 mmol) and the reaction mixture stirred at rt for 96 h. The mixture was combined with a smaller scale trial (same conditions from 20 mg of the above intermediate), diluted with water and extracted with EtOAc. The combined organics were washed with water, dried (MgSO$_4$), filtered and concentrated in vacuo. The crude product was purified by automated reverse phase column chromatography on the Biotage Isolera One™ (200-400 nm diode array detector, 30 g C18 column, 20-80% MeCN in water, 0.1% ammonia throughout) to give 2,4-dimethoxybenzyl (1S,2R)-2-((1S)-5-chloro-8-hydroxy-1-((2-oxo-4-(trifluoromethyl)pyrrolidin-1-yl)methyl)-1,2,3,4-tetrahydroisoquinoline-2-carbonyl)-1-methylcyclohexane-1-carboxylate (isomer 2; 120 mg, 26%). LCMS (Method 9): 1.02 min, 665.2 [M−H]$^-$.

Step f. The title compound (22 mg, 44%) was prepared from the above intermediate (22 mg, 0.027 mmol) using a procedure similar to that described for Example 1 step d. LCMS (Method 4a): 1.29 min, 662.6 [M+H]$^+$. $^1$H NMR (400 MHz, CDCl$_3$) δ 7.32 (d, 1H), 6.98 (d, 1H), 6.95 (t, 1H), 5.92 (dd, 1H), 5.33-5.22 (m, 2H), 4.18 (s, 3H), 4.05 (dd, 1H), 3.96-3.76 (m, 3H), 3.15 (dd, 1H), 3.11-3.02 (m, 2H), 2.96 (m, 1H), 2.75 (m, 1H), 2.56 (dd, 1H), 2.51-2.32 (m, 3H), 1.88-1.75 (m, 2H), 1.73-1.42 (m, 3H), 1.35 (m, 1H), 1.12 (s, 3H), 1.03 (m, 1H).

Example 213

(1S,2R)-2-((1S)-5-chloro-8-((5-(difluoromethyl)-1-methyl-1H-1,2,3-triazol-4-yl)methoxy)-1-((2-oxo-4-(trifluoromethyl)pyrrolidin-1-yl)methyl)-1,2,3,4-tetrahydroisoquinoline-2-carbonyl)-1-methylcyclohexane-1-carboxylic acid (Isomer 2)

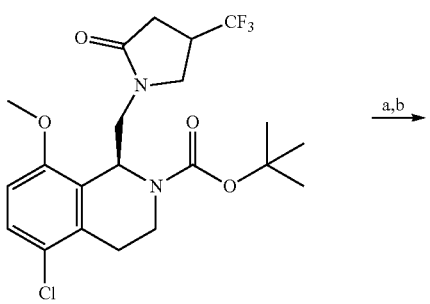

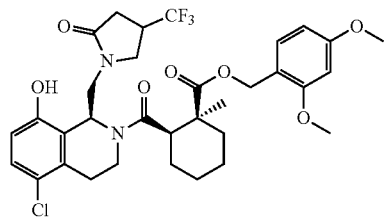
+
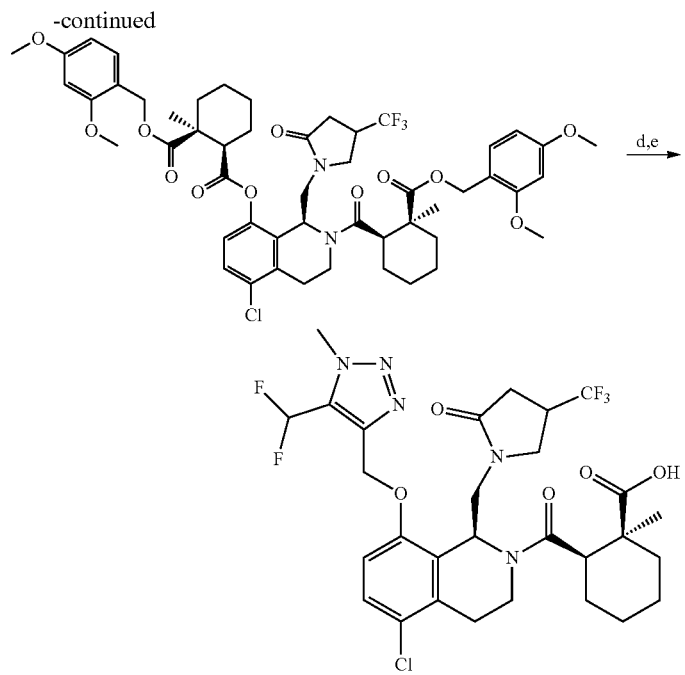

Step a. To a solution of tert-butyl (1S)-5-chloro-8-methoxy-1-((2-oxo-4-(trifluoromethyl)pyrrolidin-1-yl)methyl)-3,4-dihydroisoquinoline-2(1H)-carboxylate (Example 212 step c, diastereoisomer 2; 333 mg, 0.72 mmol) in DCM (44 mL) was added boron tribromide (1M in DCM; 14.4 mL, 14.4 mmol). The reaction mixture was stirred at rt for 16 h, cooled with an ice bath (0-5° C.) and MeOH (~3 mL) added slowly. The mixture was concentrated in vacuo, additional MeOH was added and the mixture again concentrated in vacuo. The crude product was dissolved in DMSO and 33% aqueous ammonia solution (0.1 mL) was added. The mixture was allowed to stand for 5 min then filtered through a filter pad. The crude residue was purified by automated reverse phase column chromatography on the Biotage Isolera one (200-400 nm diode array detector, 30 g C18 column, 10-40% MeCN in water containing 0.1% ammonia throughout) to give 1-(((S)-5-chloro-8-hydroxy-1,2,3,4-tetrahydroisoquinolin-1-yl)methyl)-4-(trifluoromethyl)pyrrolidin-2-one (isomer 2; 250 mg, quantitative).

Step b. To a stirred solution of the above intermediate (isomer 2; 250 mg, 0.72 mmol) in DMF (2.5 mL) was added Intermediate 33 (326 mg, 0.72 mmol) and DIPEA (0.25 mL, 1.43 mmol) and the reaction mixture stirred at rt for 96 h. The reaction mixture was diluted with water and extracted with EtOAc. The combined organics were washed with water, dried (MgSO₄), filtered and concentrated in vacuo. The crude product was purified by automated reverse phase column chromatography on the Biotage Isolera One™ (200-400 nm diode array detector, 30 g C18 column, 20-80% MeCN in water; 0.1% ammonia throughout) to give two products. 2,4-Dimethoxybenzyl (1S,2R)-2-((1S)-5-chloro-8-hydroxy-1-((2-oxo-4-(trifluoromethyl)pyrrolidin-1-yl)methyl)-1,2,3,4-tetrahydroisoquinoline-2-carbonyl)-1-methylcyclohexane-1-carboxylate (isomer 2; 51 mg, 9% yield), LCMS (Method 9): 1.17, 667.3 [M+H]+. 2-((1S)-5-Chloro-2-(((1R,2S)-2-(((2,4-dimethoxybenzyl)oxy)carbonyl)-2-methylcyclohexane-1-carbonyl)-1-((2-oxo-4-(trifluoromethyl)pyrrolidin-1-yl)methyl)-1,2,3,4-tetrahydroisoquinolin-8-yl) 1-(2,4-dimethoxybenzyl) (1S, 2R)-1-methylcyclohexane-1,2-dicarboxylate (63 mg, 7% yield), LCMS (Method 9): 1.36 min, 986.5 [M+H]⁺.

Step c. To a stirred solution of 2-((1S)-5-chloro-2-((1R,2S)-2-(((2,4-dimethoxybenzyl)oxy)carbonyl)-2-methylcyclohexane-1-carbonyl)-1-((2-oxo-4-(trifluoromethyl)pyrrolidin-1-yl)methyl)-1,2,3,4-tetrahydroisoquinolin-8-yl) 1-(2,4-dimethoxybenzyl) (1S,2R)-1-methylcyclohexane-1,2-dicarboxylate (63 mg, 0.064 mmol) in THF (2 mL) was added a solution of lithium hydroxide (15 mg, 0.64 mmol) in water (0.5 mL) and the reaction mixture stirred at rt for 16 h. The reaction mixture was extracted with EtOAc and the combined organics were dried (MgSO₄), filtered and concentrated in vacuo. The residue was purified by automated reverse phase column chromatography on the Biotage Isolera one (200-400 nm diode array detector, 12 g C18 column, 20-70% MeCN in water; 0.1% ammonia throughout) to give 2,4-dimethoxybenzyl (1S,2R)-2-((1S)-5-chloro-8-hydroxy-1-((2-oxo-4-(trifluoromethyl)pyrrolidin-1-yl)methyl)-1,2,3,4-tetrahydroisoquinoline-2-carbonyl)-1-methylcyclohexane-1-carboxylate (isomer 2; 25 mg, 52%) LCMS (Method 9a): 2.67 min, 665.2 [M−H]−.

Step d. 2,4-Dimethoxybenzyl (1S,2R)-2-((1S)-5-chloro-8-((5-(difluoromethyl)-1-methyl-1H-1,2,3-triazol-4-yl)methoxy)-1-((2-oxo-4-(trifluoromethyl)pyrrolidin-1-yl)methyl)-1,2,3,4-tetrahydroisoquinoline-2-carbonyl)-1-methylcyclohexane-1-carboxylate (isomer 2, 22 mg, 64%) was prepared from the above intermediate (isomer 2; 25 mg, 0.037 mmol)) using a procedure similar to that described for Example 143, step c. (LCMS (Method 9a): 2.96 min, 812.3 [M+H]⁺.

Step e. The title compound (8 mg, 44%) was prepared from the above intermediate (22 mg, 0.027 mmol) using a procedure similar to that described for Example 1 step d. LCMS (Method 4a): 1.28 min, 662.56 [M+H]⁺. ¹H NMR (400 MHz, CDCl₃) δ 7.32 (d, 1H), 7.10-6.81 (m, 2H), 5.93 (dd, 1H), 5.30 (m, 1H), 5.23 (m, 1H), 4.18 (s, 3H), 4.08 (dd, 1H), 3.95-3.83 (m, 2H), 3.76 (dd, 1H), 3.22-3.11 (m, 2H), 3.10-2.95 (m, 2H), 2.83-2.68 (m, 1H), 2.55 (dd, 1H), 2.49

(dd, 1H), 2.41 (dt, 1H), 2.34 (dd, 1H), 1.88-1.75 (m, 2H), 1.71-1.40 (m, 3H), 1.33 (m, 1H), 1.11 (s, 3H), 1.01 (m, 1H).

Example 217

(1S,2R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-4,4-difluoro-1-methylcyclohexane-1-carboxylic acid

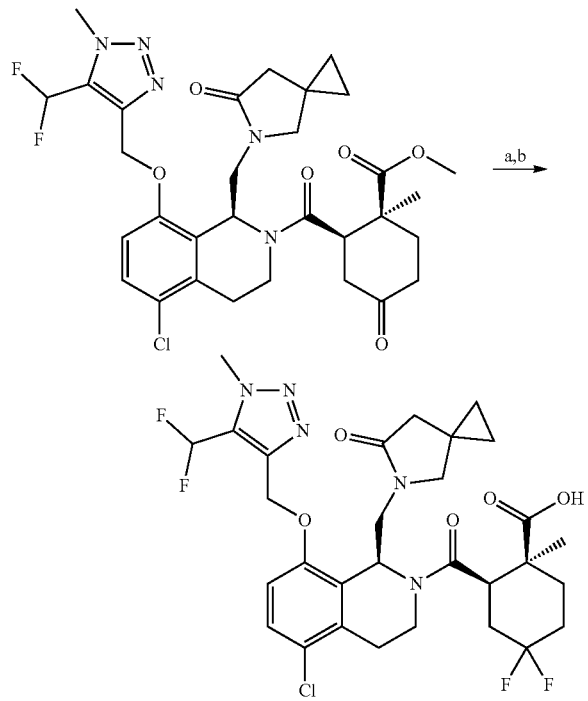

Step a. A solution of methyl (1S,2R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methyl-4-oxocyclohexane-1-carboxylate (Example 219 step j; 199 mg, 0.31 mmol) in DCM (4 mL) was added dropwise to a stirred solution of DAST (0.11 mL, 0.80 mmol; CAS: 38078-09-0) in DCM (4 mL) at 0° C. under argon and the reaction mixture was stirred at rt for 24 h. The reaction mixture was cooled in an ice bath and quenched by dropwise addition of water (4 mL), warmed to rt and extracted with DCM. The combined organics were washed with brine, dried over Na$_2$SO$_4$, filtered and concentrated in vacuo. The crude product was purified by flash column chromatography on the Teledyne ISCO CombiFlash® Rf+ (25 g silica column Puriflash HC, 0-100% EtOAc in cyclohexane) to provide methyl (1S,2R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-4,4-difluoro-1-methylcyclohexane-1-carboxylate (132 mg, 64%). LCMS (Method 2): 1.76 min, 670.3 [M+H]$^+$.

Step b. To a solution of the above intermediate (132 mg, 0.20 mmol) in MeOH (2 mL) was added a solution of sodium hydroxide (79 mg, 1.97 mmol) in water (0.50 mL) and the resulting mixture was heated at 100° C. under microwave irradiation for 12 h. The reaction mixture was concentrated in vacuo and the residue diluted with water and acidified to pH 4 using 10% aqueous citric acid solution. The resulting precipitate was collected by filtration and purified by flash column chromatography on the Teledyne ISCO CombiFlash® Rf+ (25 g silica column Puriflash HC, 15 um, 0-5% MeOH in DCM). Fractions containing the desired product were combined and concentrated in vacuo. The residue was dissolved in 1:1 MeCN/water and freeze dried overnight to provide the title compound (70 mg, 53%). LCMS (Method 3): 4.56 min, 656.3 [M+H]$^+$. $^1$H NMR (400 MHz, DMSO-d$_6$) δ 12.10 (bs, 1H), 7.57 (t, 1H), 7.40 (d, 1H), 7.16 (d, 1H), 5.74 (dd, 1H), 5.37-5.22 (m, 2H), 4.15 (s, 3H), 4.03-3.85 (m, 2H), 3.69 (m, 1H), 3.45-3.20 (m, 1H), 3.11 (dd, 1H), 2.94 (dd, 1H), 2.87 (dd, 1H), 2.70 (m, 1H), 2.58-2.29 (m, 2H), 2.26-1.81 (m, 6H), 1.60 (m, 1H), 1.05 (s, 3H), 0.66-0.31 (m, 4H).

Example 218

(1S,2R,4S)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-4-fluoro-1-methylcyclohexane-1-carboxylic acid

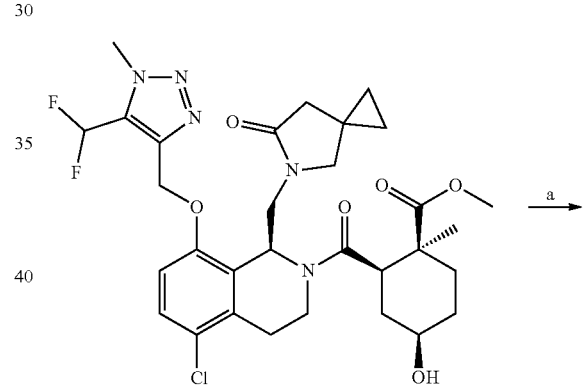

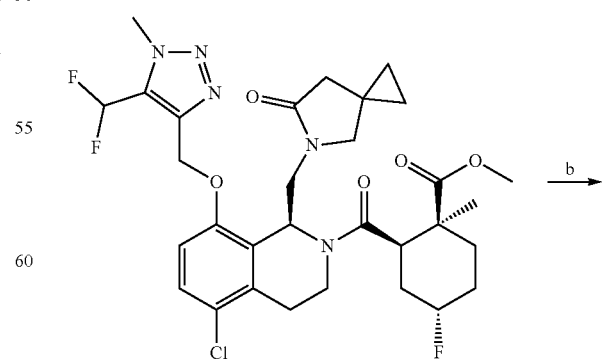

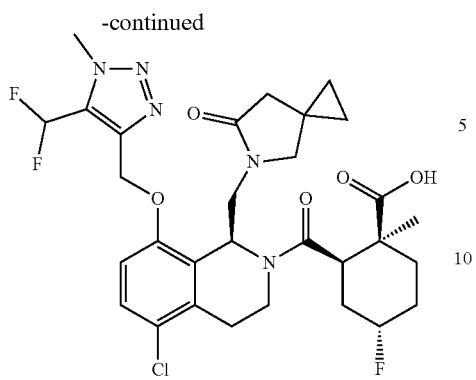

Step a. To a stirred solution of methyl (1S,2R,4R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-4-hydroxy-1-methylcyclohexane-1-carboxylate (Example 219 step i; 250 mg, 0.38 mmol) in DCM (7 mL) was added dropwise a solution of Deoxo-Fluor® (50% in THF; 0.37 mL, 1 mmol) at 0° C. under argon, and the reaction mixture stirred at rt for 20 h. The reaction mixture was cooled in an ice bath and quenched by dropwise addition of water, warmed to rt and extracted with DCM. The combined organics were washed with brine, dried over $Na_2SO_4$, filtered and concentrated in vacuo. The crude product was purified by flash column chromatography on the InterChim 4125 (40 g 15 µM silica column Puriflash HP, 0-5% MeOH in DCM) to provide the title compound (132 mg, 53%). LCMS (Method 2): 1.42 min, 674.3 [M+Na]+.

Step b. To a stirred solution of the above intermediate (22 mg, 0.03 mmol) in MeCN (0.400 mL) under argon was added sodium iodide (13 mg, 0.08 mmol) followed by chlorotrimethylsilane (11 mg, 0.10 mmol; CAS: 75-77-4) dropwise. The reaction mixture was heated at 60° C. in a sealed tube for 3 h, diluted with water and extracted with EtOAc. The combined organics were dried ($Na_2SO_4$), filtered and concentrated in vacuo. The crude product was purified by flash column chromatography on the InterChim 4125 (40 g C18 InterChim HP, 5-75% MeCN in water with 0.1% formic acid buffer) then freeze dried to give the title compound (5.5 mg). LCMS (Method 3) 4.56 min, 638.4 [M+H]+. 1H NMR (400 MHz, $CDCl_3$) δ 15.28 (bs, 1H), 7.31 (d, 1H), 6.98 (d, 1H), 6.92 (t, 1H), 5.94 (dd, 1H), 5.35-5.21 (m, 2H), 4.95 (m, 1H), 4.18 (m, 3H), 4.11 (dd, 1H), 4.07-3.88 (m, 2H), 3.43 (d, 1H), 3.20-3.04 (m, 3H), 3.01 (d, 1H), 2.77 (m, 1H), 2.39 (d, 1H), 2.33-2.17 (m, 2H), 2.10 (d, 1H), 2.01-1.63 (m, 3H), 1.44 (m, 1H), 1.19 (s, 3H), 0.73-0.45 (m, 4H).

Example 219

(1S,2R,4R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic-4-d acid

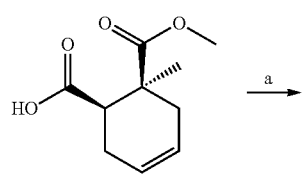

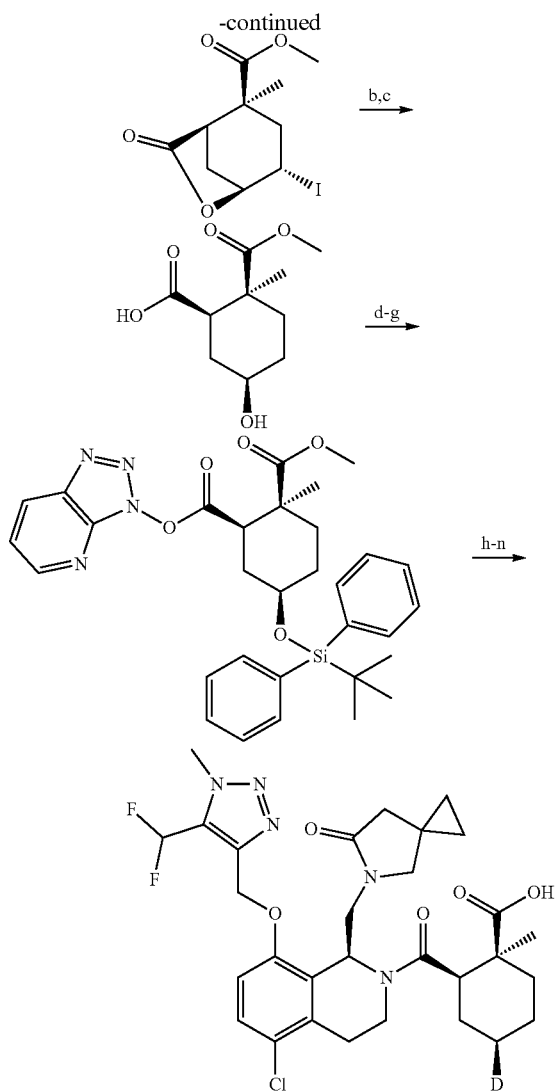

Step a. To a solution of Intermediate 39 (250 mg, 1.26 mmol) in DCM (5 mL) was added N-iodosuccinimide (295 mg, 1.31 mmol; CAS: 516-12-1) portionwise and the resulting mixture was stirred at rt under argon for 3 h. The reaction mixture was diluted with DCM, washed with saturated sodium thiosulfate and saturated sodium bicarbonate solutions. The organic layer was dried over sodium sulfate and concentrated in vacuo. The crude product was purified by flash column chromatography on the Teledyne ISCO CombiFlash® Rf+ (25 g silica column Puriflash HC, 0-50% EtOAc in cyclohexane) to provide methyl (1R,2S,4S,5S)-4-iodo-2-methyl-7-oxo-6-oxabicyclo[3.2.1]octane-2-carboxylate (131 mg, 32%). 1H NMR (400 MHz, $CDCl_3$) δ 4.87-4.84 (m, 1H), 4.51-4.47 (m, 1H), 3.75 (s, 3H), 3.01-2.90 (m, 3H), 2.43-2.34 (m, 1H), 2.18 (d, 1H), 1.65 (s, 3H). LCMS (Method 16): 1.16 min, 324.9 [M+H]+.

Step b. A stirred solution of the above intermediate (1.91 g, 5.89 mmol) in toluene (17.5 mL) was degassed with argon for 5 minutes. To this was added a solution of tris(trimethylsilyl)silane (1.82 mL, 5.89 mmol; CAS: 1873-77-4) and AIBN (97 mg, 0.59 mmol; CAS: 78-67-1) in degassed toluene (2.9 mL) and the reaction mixture heated at 60° C. for 2 h. The reaction mixture was cooled to rt, diluted with 5% aqueous citric acid and extracted with EtOAc. The combined organics were washed with water, saturated aq. sodium bicarbonate and brine, dried over $Na_2SO_4$, filtered and concentrated in vacuo. The crude product was purified by flash column chromatography on the Teledyne ISCO CombiFlash® Rf+ (80 g silica column Puriflash HC, 0-100% EtOAc in cyclohexane) to provide methyl (1R,2S,5R)-2-methyl-7-oxo-6-oxabicyclo[3.2.1]octane-2-carboxylate (787 mg, 67%). $^1$H NMR (400 MHz, CDCl$_3$) δ 4.77 (t, 1H), 3.75 (s, 3H), 2.96 (d, 1H), 2.32-2.16 (m, 2H), 2.08 (d, 1H), 2.06-1.99 (m, 1H), 1.74-1.62 (m, 2H), 1.36 (s, 3H).

Step c. To a solution of the above intermediate (390 mg, 1.97 mmol) in THF (8 mL) and water (8 mL) cooled in an ice bath was added lithium hydroxide monohydrate (91 mg, 2.16 mmol) and the resulting mixture was stirred for 1 h. The reaction mixture was acidified to pH 3 using 5% citric acid and extracted with EtOAc. The combined organics were washed with water and brine, dried over $Na_2SO_4$, filtered and concentrated in vacuo to provide (1R,2S,5R)-5-hydroxy-2-(methoxycarbonyl)-2-methylcyclohexane-1-carboxylic acid (241 mg, 57%). The aqueous layers from the extraction were combined and further extracted with EtOAc, washed with water and brine, dried over $Na_2SO_4$, filtered and concentrated in vacuo. The residue was purified by flash column chromatography on the Teledyne ISCO CombiFlash® Rf+ (25 g silica column Puriflash HC, 0-100% EtOAc in cyclohexane) to provide a second batch of (1R,2S,5R)-5-hydroxy-2-(methoxycarbonyl)-2-methylcyclohexane-1-carboxylic acid (153 mg, 36%). Combined product (394 mg, 93%). $^1$H NMR (400 MHz, DMSO-d$_6$) δ 12.07 (s, 1H), 4.59 (s, 1H), 3.56 (s, 3H), 3.51-3.43 (m, 1H), 2.33 (dd, 1H), 2.00-1.74 (m, 3H), 1.63-1.57 (m, 1H), 1.38-1.26 (m, 2H), 1.25 (s, 3H).

Step d. Benzyl bromide (0.16 mL, 1.35 mmol; CAS: 100-39-0) was added to a mixture of the above intermediate (265 mg, 1.23 mmol) and potassium carbonate (186 mg, 1.35 mmol) in DMF (3 mL) under argon and the resulting mixture was stirred at rt for 2 h. The reaction mixture was diluted with water, extracted with EtOAc ethyl acetate and the combined organics were washed with water, brine, dried over $Na_2SO_4$, filtered and concentrated in vacuo. The crude product was purified by flash column chromatography on the Teledyne ISCO CombiFlash® Rf+ (25 g silica column Puriflash HC, 0-100% EtOAc in cyclohexane) to provide 2-benzyl 1-methyl (1S,2R,4R)-4-hydroxy-1-methylcyclohexane-1,2-dicarboxylate (339 mg, 90%). 1H NMR (400 MHz, CDCl$_3$) δ: 7.36-7.30 (m, 5H), 5.13 (s, 2H), 3.77-3.68 (m, 1H), 3.58 (s, 3H), 2.51 (dd, 1H), 2.25-2.15 (m, 2H), 2.10-2.01 (m, 1H), 1.84-1.75 (m, 1H), 1.59-1.56 (m, 1H), 1.46-1.39 (m, 1H), 1.35 (s, 3H).

Step e. To a solution of the above intermediate (339 mg, 1.11 mmol) in DMF (4.8 mL) under argon was added imidazole (226 mg, 3.32 mmol) and tert-butyl(chloro)diphenylsilane (0.63 mL, 2.43 mmol; CAS: 58479-61-1) and the reaction mixture was stirred at rt under argon for 2 h. The reaction mixture was diluted with water, extracted with EtOAc and the combined organics washed with water, brine, dried over $Na_2SO_4$, filtered and concentrated in vacuo. The crude product was purified by flash column chromatography on the Teledyne ISCO CombiFlash® Rf+ (40 g silica column Puriflash HC, 0-10% EtOAc in cyclohexane) to provide 2-benzyl 1-methyl (1S,2R,4R)-4-((tert-butyldiphenylsilyl)oxy)-1-methylcyclohexane-1,2-dicarboxylate (1.03 g, assumed quantitative). LCMS (Method 2): 2.01 min, 545.3 [M+H]$^+$.

Step f. To a solution of the above intermediate (602 mg, 1.11 mmol) in EtOH (10 mL) was added Pd/C (10%; 100 mg, 0.94 mmol) and the reaction mixture was stirred under a hydrogen atmosphere at ambient pressure for 18 h. An additional portion of Pd/C (10%; 100 mg, 0.94 mmol) was added and the resulting mixture was heated at 40° C. for 4 h under a hydrogen atmosphere. The reaction mixture was cooled to rt, diluted with IMS and filtered through Celite®. The filtrate was concentrated in vacuo and purified by flash column chromatography on the Teledyne ISCO CombiFlash® Rf+ (40 g silica column Puriflash HC, 0-50% EtOAc in cyclohexane) to provide (1R,2S,5R)-5-((tert-butyldiphenylsilyl)oxy)-2-(methoxycarbonyl)-2-methylcyclohexane-1-carboxylic acid (412 mg, 82%). $^1$H NMR (400 MHz, CDCl$_3$) δ 7.67-7.63 (m, 4H), 7.44-7.34 (m, 6H), 3.73 (s, 3H), 3.71-3.66 (m, 1H), 2.39-2.36 (m, 1H), 2.22-2.01 (m, 2H), 1.60-1.53 (m, 1H), 1.44-1.34 (m, 1H), 1.26-1.23 (m, 4H), 1.22-1.17 (m, 1H), 1.03 (s, 9H). LCMS (Method 2): 1.77 min, 477.2 [M+Na]$^+$.

Step g. To a stirred solution of the above intermediate (412 mg, 0.91 mmol) in DMF (2 ML) was added HATU (379 mg, 1.0 mmol) and the reaction mixture was stirred at rt under argon for 5 min. To this was added DIPEA (0.17 mL, 1 mmol) and the mixture stirred for 2 h. The reaction mixture was diluted with water, extracted with EtOAc and the combined organics washed with water, brine, dried over $Na_2SO_4$, filtered and concentrated in vacuo. The crude product was purified by flash column chromatography on the Teledyne ISCO CombiFlash® Rf+ (40 g silica column Puriflash HC, 0-50% EtOAc in cyclohexane) to provide 2-(3H-[1,2,3]triazolo[4,5-b]pyridin-3-yl) 1-methyl (1S,2R,4R)-4-((tert-butyldiphenylsilyl)oxy)-1-methylcyclohexane-1,2-dicarboxylate (471 mg, 91%). LCMS (Method 2): 1.88 min, 595.2 [M+Na]$^+$.

Step h. To a stirred solution of (S)-5-((5-chloro-8-((5-(difluoromethyl)-1-methyl-1H-1,2,3-triazol-4-yl)methoxy)-1,2,3,4-tetrahydroisoquinolin-1-yl)methyl)-5-azaspiro[2.4]heptan-6-one hydrochloride (Example 110 step b; 525 mg, 1.08 mmol) and the above intermediate (739 mg, 1.29 mmol) in DMF (4.4 mL) was added DIPEA (0.37 mL, 2.15 mmol) and the reaction mixture was stirred at rt under argon for 4 days. The reaction mixture was diluted with saturated sodium bicarbonate solution, extracted with EtOAc and the combined organics washed with water and brine, dried over $Na_2SO_4$, filtered and concentrated in vacuo. The crude product was purified by flash column chromatography on the Teledyne ISCO CombiFlash® Rf+ (40 g silica column Puriflash HC, 0-100% EtOAc in cyclohexane) to provide methyl (1S,2R,4R)-4-((tert-butyldiphenylsilyl)oxy)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methyl-cyclohexane-1-carboxylate (669 mg, 70%). LCMS (Method 2): 1.96 min, 910.3 [M+Na]$^+$.

Step i. To a stirred solution of the above intermediate (669 mg, 0.75 mmol) in THF (12.8 mL) was added tetrabutylammonium fluoride solution (1M in THF; 6.5 mL, 6.5 mmol; CAS: 429-41-4) and the reaction mixture was heated at 60° C. for 3 h. The reaction mixture was allowed to cool to rt, diluted with water, extracted into EtOAc and the combined organics were washed with brine, dried over $Na_2SO_4$, filtered and concentrated in vacuo. The crude product was purified by flash column chromatography on the Teledyne ISCO CombiFlash® Rf+ (40 g silica column Puriflash HC, 0-5% MeOH in DCM) to provide methyl (1S,2R,4R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-4-hydroxy-1-methylcyclohexane-1-carboxylate (406 mg, 83%). LCMS (Method 2): 1.25 min, 650.3 [M+H]$^+$.

Step j. To a solution of the above intermediate (400 mg, 0.62 mmol) in DCM (6 mL) was added Dess-Martin periodinane (339 mg, 0.800 mmol; CAS: 87413-09-0) and the reaction mixture was stirred at rt under argon for 1 h. The reaction mixture was diluted with sodium thiosulfate solution, extracted with EtOAc and the combined organics washed with water and brine, dried over $Na_2SO_4$, filtered and concentrated in vacuo. The crude product was purified by flash column chromatography on the Teledyne ISCO CombiFlash® Rf+ (25 g silica column Puriflash HC, 0-100% EtOAc in cyclohexane) to provide methyl (1S,2R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methyl-4-oxocyclohexane-1-carboxylate (365 mg, 92%). LCMS (Method 2): 1.30 min, 648.3 [M+H]$^+$.

Step k. To a solution of the above intermediate (150 mg, 0.23 mmol) in methanol-c/a (3.0 mL) at 0° C. was added sodium borodeuteride (12 mg, 0.28 mmol; CAS: 15681-89-7) and the reaction mixture was stirred under argon for 0.5 h. The reaction mixture was diluted with water, extracted with EtOAc and the combined organics dried over $Na_2SO_4$, filtered and concentrated in vacuo. The crude product was purified by flash column chromatography on the Teledyne ISCO CombiFlash® Rf+ (12 g silica column Puriflash HC, 0-5% MeOH in DCM) to provide methyl (1S,2R,4R)-2-((S)-5-chloro-8-((5-(difluoro-methyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-4-hydroxy-1-methylcyclohexane-1-carboxylate-4-d (131 mg, 87%). LCMS (Method 2): 1.27 min, 651.3 [M+H]$^+$.

Step l. To a solution of the above intermediate (80 mg, 0.12 mmol) in THF (4 mL) at 0° C. under argon was added carbon disulfide solution (5 M in THF; 0.06 mL, 0.310 mmol; CAS: 75-15-0) followed by sodium hydride (60% dispersion in mineral oil; 12 mg, 0.31 mmol; CAS: 75-15-0) and the reaction mixture was stirred for 0.5 h, allowed to warm to rt and stirred for a further 0.5 h. The reaction mixture was cooled to 0° C., treated with iodomethane (0.02 mL, 0.310 mmol), allowed to warm to rt and stirred for 1 h. The reaction was diluted with saturated ammonium chloride solution, extracted with EtOAc and the combined organics washed with water, brine, dried over $Na_2SO_4$, filtered and concentrated in vacuo. The crude product was purified by flash column chromatography on the Teledyne ISCO CombiFlash® Rf+ (25 g silica column Puriflash HC, 0-100% EtOAc in cyclohexane) to provide methyl (1S,2R,4R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methyl-4-(((methylthio)carbonothioyl)oxy)cyclohexane-1-carboxylate-4-d (77 mg, 85%). LCMS (Method 2): 1.60 min, 741.3 [M+H]$^+$.

Step m. To a solution of the above intermediate (175 mg, 0.24 mmol) and AIBN (7.74 mg, 0.050 mmol; CAS: 78-67-1) in toluene (5 mL) under argon was added tris(trimethylsilyl)silane (0.09 mL, 0.280 mmol; CAS: 1873-77-4) and the reaction mixture heated at 100° C. in a sealed vial for 2 h. The reaction mixture was allowed to cool to rt, diluted with 5% aqueous citric acid, extracted with EtOAc and the combined organics washed with water, saturated aq. sodium bicarbonate and brine, dried over $Na_2SO_4$, filtered and concentrated in vacuo. The crude product was purified by flash column chromatography on the Teledyne ISCO CombiFlash® Rf+ (25 g silica column Puriflash HC, 0-100% EtOAc in cyclohexane) to provide methyl (1S,2R,4S)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylate-4-d (122 mg, 81%). LCMS (Method 2): 1.46 min, 635.3 [M+H]$^+$.

Step n. To a solution of the above intermediate (122 mg, 0.190 mmol) in MeOH (2 mL) was added a solution of sodium hydroxide (77 mg, 1.92 mmol) in water (0.5 mL) and the reaction mixture was heated at 100° C. under microwave irradiation for 30 h. The reaction mixture was concentrated in vacuo and the residue diluted with water and acidified to pH 4 using 10% aqueous citric acid solution. The mixture was extracted with EtOAc and the combined organics washed with water, brine, dried over $Na_2SO_4$, filtered and concentrated in vacuo. The residue was purified by flash column chromatography on the Teledyne ISCO CombiFlash® Rf+ (25 g silica column Puriflash HC, 15 um, 0-100% EtOAc in cyclohexane). Fractions containing the desired product were combined and concentrated in vacuo. The residue was dissolved in 1:1 MeCN/water and freeze dried overnight to provide the title compound (55 mg, 45%). LCMS (Method 3): 4.56 min, 621.4 [M+H]$^+$. $^1$H NMR (400 MHz, $CDCl_3$) δ 15.26 (bs, 1H), 7.30 (d, 1H), 6.98 (d, 1H), 6.92 (t, 1H), 5.95 (dd, 1H), 5.37-5.21 (m, 2H), 4.18 (m, 3H), 4.11 (dd, 1H), 4.00 (m, 1H), 3.88 (m, 1H), 3.44 (d, 1H), 3.20-3.02 (m, 3H), 2.76 (m, 1H), 2.59 (dd, 1H), 2.47-2.35 (m, 2H), 2.12 (d, 1H), 1.83 (m, 1H), 1.69-1.47 (m, 3H), 1.39-1.21 (m, 1H), 1.13 (s, 3H), 1.02 (m, 1H), 0.72-0.48 (m, 4H).

Example 220

(1S,2R,4S)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-4-hydroxy-1-methylcyclohexane-1-carboxylic acid

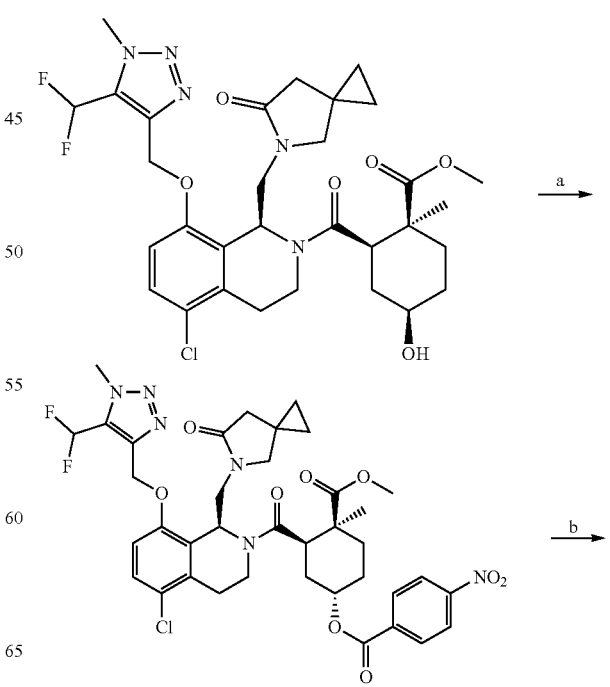

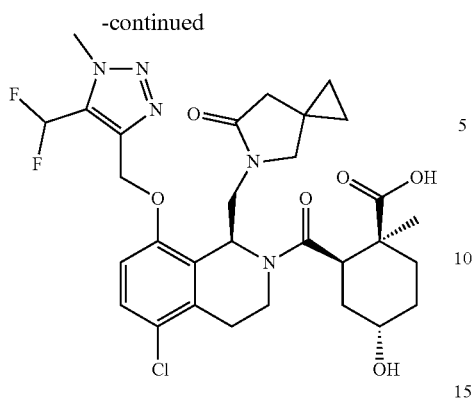

Step a. To a solution of methyl (1S,2R,4R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-4-hydroxy-1-methylcyclohexane-1-carboxylate (Example 219 step i, 100 mg, 0.15 mmol), 4-nitrobenzoic acid (51 mg, 0.31 mmol) and triphenylphosphine (80.79 mg, 0.31 mmol) in THF (2 mL) under argon was added DIAD (0.06 mL, 0.310 mmol; CAS: 2446-83-5) dropwise and the reaction mixture was stirred at rt for 2 h. The reaction mixture was diluted with water, extracted with EtOAc and the combined organics dried over Na$_2$SO$_4$, filtered and concentrated in vacuo. The crude product was purified by flash column chromatography on the Teledyne ISCO CombiFlash® Rf+ (40 g silica column Puriflash HC, 0-100% EtOAc/IMS (3:1) in cyclohexane). The crude product was further purified by flash column chromatography on the Teledyne ISCO CombiFlash® Rf+ (12 g silica column Puriflash HC, 0-100% EtOAc cyclohexane) to provide (1S,3R,4S)-3-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-4-(methoxycarbonyl)-4-methylcyclohexyl-4-nitrobenzoate (95 mg, 77%). LCMS (Method 2): 1.58 min, 799.3 [M+H]$^+$.

Step b. To a solution of the above intermediate (95 mg, 0.12 mmol) in MeOH (1.6 mL) was added a solution of sodium hydroxide (48 mg, 1.19 mmol) in water (0.40 mL) and the reaction mixture was heated at 100° C. under microwave irradiation for 18 h. The reaction mixture was concentrated in vacuo and the residue diluted with water, acidified to pH 4 using 10% aqueous citric acid solution and extracted with DCM. The combined organics were dried over Na$_2$SO$_4$, filtered and concentrated in vacuo. The crude product was purified by flash column chromatography on the Teledyne ISCO CombiFlash® Rf+ (12 g silica column Puriflash HC, 15 um, 0-5% MeOH in DCM). Fractions containing the desired product were combined and concentrated in vacuo. The residue was dissolved in 1:1 MeCN/water and freeze dried overnight to provide the title compound (47 mg, 59%). LCMS (Method 3): 3.96 min, 636.5 [M+H]$^+$. $^1$H NMR (400 MHz, DMSO-d$_6$) δ 11.92 (bs, 1H), 7.57 (t, 1H), 7.38 (d, 1H), 7.14 (d, 1H), 5.76 (dd, 1H), 5.39-5.22 (m, 2H), 4.35 (d, 1H), 4.16 (s, 3H), 4.02-3.88 (m, 2H), 3.62 (m, 1H), 3.50 (m, 1H), 3.42-3.25 (m, 1H), 3.16 (m, 1H), 2.99 (dd, 1H), 2.83 (dd, 1H), 2.78-2.63 (m, 2H), 2.43-2.19 (m, 2H), 2.14 (d, 1H), 1.78-1.63 (m, 2H), 1.62-1.44 (m, 2H), 1.30 (m, 1H), 1.12 (s, 3H), 0.66-0.35 (m, 4H).

Example 221

(1R,2R,6S)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-6-hydroxy-1-methylcyclohexane-1-carboxylic acid

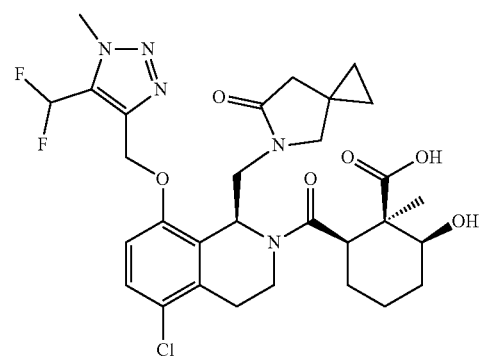 [SMILES: Cn1nnc(COc2ccc(Cl)c3c2[C@@H](CN2CC4(CC4)CC2=O)N(C(=O)[C@@H]2CCC[C@H](O)[C@]2(C)C(=O)O)CC3)c1C(F)F]

Example 222

(1R,2R,6R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-6-hydroxy-1-methylcyclohexane-1-carboxylic acid

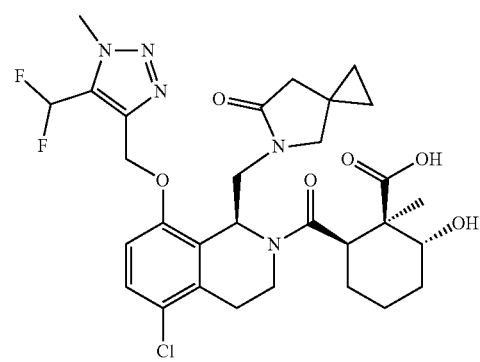 [SMILES: Cn1nnc(COc2ccc(Cl)c3c2[C@@H](CN2CC4(CC4)CC2=O)N(C(=O)[C@@H]2CCC[C@@H](O)[C@]2(C)C(=O)O)CC3)c1C(F)F]

Example 223

(1S,2R,5S)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-5-hydroxy-1-methylcyclohexane-1-carboxylic acid

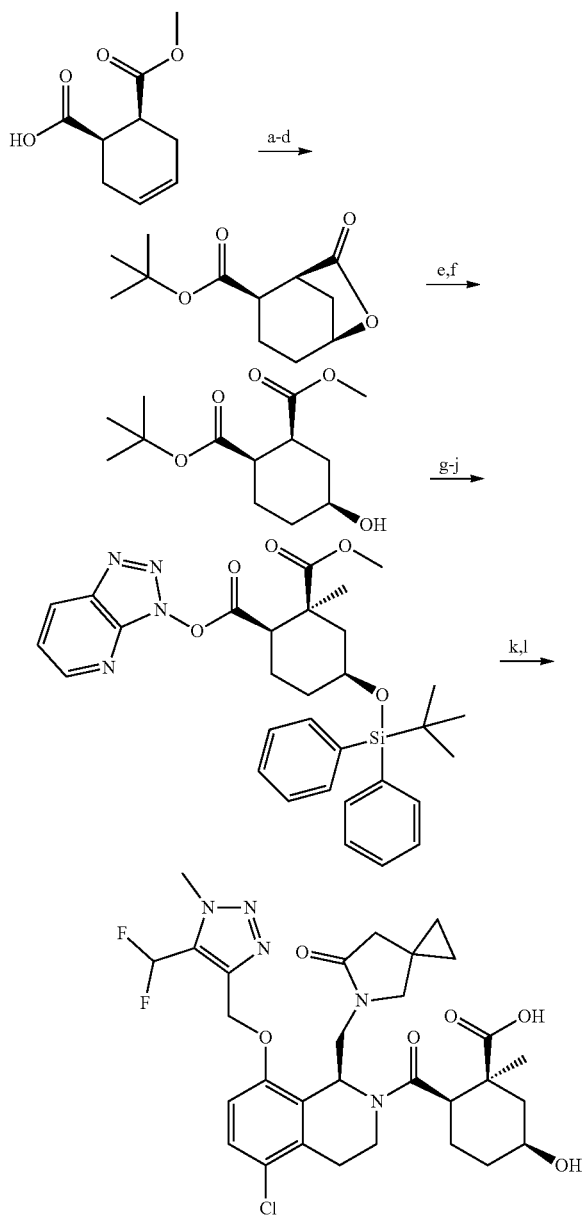

Step a. To a stirred solution of (1R,6S)-6-methoxycarbonylcyclohex-3-ene-1-carboxylic acid (5.00 g, 27.2 mmol; CAS: 88335-93-7) in toluene (70 mL) under argon heated to 110° C. was added 1,1-di-tert-butoxy-N,N-dimethylmethylamine (5.52 g, 27.2 mmol; CAS: 36805-97-7) dropwise and the resulting mixture was stirred at 110° C. under argon for 4 h. The reaction mixture was cooled to rt, and washed sequentially with water, sat NaHCO$_3$ and brine. The organic layer was dried over Na$_2$SO$_4$ and concentrated in vacuo to give 1-(tert-butyl) 2-methyl (1R,2S)-cyclohex-4-ene-1,2-dicarboxylate (4.17 g, 63%). $^1$H NMR (400 MHz, CDCl$_3$) δ 5.67 (d, 2H), 3.69 (s, 3H), 3.03-2.93 (m, 2H), 2.55-2.45 (m, 2H), 2.36-2.24 (m, 2H), 1.43 (s, 9H).

Step b. To a solution of the above intermediate (4.17 g, 17.4 mmol) in THF (82 mL) was added lithium hydroxide monohydrate solution (728 mg, 17.4 mmol) in water (82 mL) and the resulting mixture was stirred at rt under argon for 16 h. The reaction mixture was acidified to ~pH 3 using 10% aqueous citric acid extracted with EtOAc. The combined organics were dried over Na$_2$SO$_4$, filtered and concentrated in vacuo to (1S,6R)-6-(tert-butoxycarbonyl)cyclohex-3-ene-1-carboxylic acid (3.16 g, 76%). $^1$H NMR (400 MHz, CDCl$_3$) δ 11.11 (br. s, 1H), 5.70-5.67 (m, 2H), 3.05-2.97 (m, 2H), 2.59-2.47 (m, 2H), 2.38-2.28 (m, 2H), 1.43 (s, 9H).

Step c. To a solution of the above intermediate (3.9 g, 17.2 mmol) in DCM (45 mL) was added N-iodosuccinimide (4.03 g, 17.9 mmol) portionwise and the resulting mixture was stirred at rt under argon for 4 h. The reaction mixture was diluted with DCM, washed with saturated aqueous sodium thiosulfate and saturated aqueous sodium bicarbonate solution. The organic layer was dried over Na$_2$SO$_4$ and concentrated in vacuo to provide tert-butyl (1S,2R,4R,5R)-4-iodo-7-oxo-6-oxabicyclo[3.2.1]octane-2-carboxylate (4.43 g, 69%). LCMS (Method 2): 1.38 min, 374.9 [M+Na]$^+$.

Step d. To a stirred solution of the above intermediate (4.43 g, 12.6 mmol) in toluene (128 mL) degassed with argon (for 5 mins) was added a solution of tris(trimethylsilyl)silane (3.88 mL, 12.6 mmol; CAS: 1873-77-4) and AIBN (206 mg, 1.26 mmol; CAS: 78-67-1) in degassed toluene (8 mL). The reaction mixture was heated at 60° C. for 4 h, cooled to rt, diluted with 5% aqueous citric acid and extracted with EtOAc. The combined organics were separated, washed with water, saturated aqueous sodium bicarbonate and brine, dried over Na$_2$SO$_4$, filtered and concentrated in vacuo. The crude product was purified by flash column chromatography on the InterChim 4125 (120 g silica column Puriflash HP, 0-100% EtOAc in cyclohexane) to provide tert-butyl (1S,2R,5S)-7-oxo-6-oxabicyclo[3.2.1]octane-2-carboxylate (2.2 g, 76%). $^1$H NMR (400 MHz, CDCl$_3$) δ 4.80 (t, 1H), 3.04 (d, 1H), 2.58-2.46 (m, 2H), 2.14-1.87 (m, 3H), 1.77 (d, 1H), 1.56-1.55 (m, 1H), 1.47 (s, 9H).

Step e. To a solution of the above intermediate (1.48 g, 6.54 mmol) in THF (26 mL) and water (26 mL) cooled in an ice bath was added lithium hydroxide monohydrate (302 mg, 7.19 mmol) and the resulting mixture was stirred for 1 h. The reaction mixture was acidified to pH 3 using 5% aqueous citric acid, extracted with EtOAc and the combined organics were washed with water and brine, dried over Na$_2$SO$_4$, filtered and concentrated in vacuo to provide (1S,2R,5S)-2-(tert-butoxycarbonyl)-5-hydroxycyclohexane-1-carboxylic acid (1.74 g, 98%). LCMS (Method 2): 0.88 min, 243.1 [M–H]$^-$.

Step f. To a stirred solution of the above intermediate (1.0 g, 4.09 mmol) in DMF (10 mL) under argon was added iodomethane (0.28 mL, 4.5 mmol) and potassium carbonate (622 mg, 4.5 mmol) and the reaction mixture was stirred at rt for 2 h. Additional potassium carbonate (622 mg, 4.5 mmol) and iodomethane (0.28 mL, 4.5 mmol) were added and the reaction mixture stirred for 2 h. Additional potassium carbonate (622 mg, 4.5 mmol) and iodomethane (0.28 mL, 4.5 mmol) were added and the reaction mixture stirred for another 2 h. Additional potassium carbonate (622 mg, 4.5 mmol) and iodomethane (0.28 mL, 4.5 mmol) were added and the reaction mixture stirred for a further 14 h. The reaction mixture was diluted with water, extracted with EtOAc and the combined organics were washed with water, brine, dried over $Na_2SO_4$, filtered and concentrated in vacuo. The crude product was purified by flash column chromatography on the Teledyne ISCO CombiFlash® Rf+ (80 g silica column Puriflash HC, 0-100% EtOAc in cyclohexane) to provide 1-(tert-butyl) 2-methyl (1R,2S,4S)-4-hydroxycyclohexane-1,2-dicarboxylate (860 mg, 77%). $^1$H NMR (400 MHz, DMSO-d$_6$) δ 4.62 (d, 1H), 3.57-3.57 (m, 3H), 3.46-3.36 (m, 1H), 2.87 (q, 1H), 2.58 (d, 1H), 1.99-1.98 (m, 2H), 1.65-1.45 (m, 3H), 1.36 (s, 9H), 1.09 (td, 1H).

Step g. To a solution of the above intermediate (850 mg, 3.29 mmol) in DMF (11 mL) under argon was added imidazole (717 mg, 10.5 mmol) and tert-butyl(chloro)diphenylsilane (1.37 mL, 5.26 mmol; CAS: 58479-61-1) and the reaction mixture was stirred at rt under argon for 2 h. The reaction mixture was diluted with water, extracted with EtOAc and the combined organics washed with water, brine, dried over $Na_2SO_4$, filtered and concentrated in vacuo. The crude product was purified by flash column chromatography on the InterChim 4125 (80 g silica column InterChim HP, 0-10% EtOAc in cyclohexane) to provide 1-(tert-butyl) 2-methyl (1R,2S,4S)-4-((tert-butyldiphenylsilyl)oxy)cyclohexane-1,2-dicarboxylate (950 mg, 56%). LCMS (Method 2): 1.99 min, 519.3 [M+Na]$^+$.

Step h. To a stirred solution of the above intermediate (810 mg, 1.63 mmol) in DCM (60.353 mL) under argon at 0° C. was added 2,6-lutidine (3.61 mL, 31.0 mmol; CAS: 108-48-5) followed by trimethylsilyl trifluoromethanesulfonate (2.8 mL, 15.49 mmol; CAS: 27607-77-8) dropwise and the reaction mixture was stirred from 0° C. to rt under argon for 2 h. The reaction mixture was cooled to 0° C., diluted with saturated $NaHCO_3$, and extracted with EtOAc. The combined organics were washed with 10% citric acid solution, water, brine, dried over $Na_2SO_4$, filtered and concentrated in vacuo to provide (1R,2S,4S)-4-((tert-butyldiphenylsilyl)oxy)-2-(methoxycarbonyl)cyclohexane-1-carboxylic acid (695 mg, 92%). $^1$H NMR (400 MHz, CDCl$_3$) δ 11.44-9.47 (br. s, 1H), 7.68-7.64 (m, 4H), 7.44-7.34 (m, 6H), 3.76-3.66 (m, 1H), 3.63 (s, 3H), 2.86 (s, 1H), 2.60 (s, 1H), 2.29-2.10 (m, 2H), 2.05-2.04 (m, 2H), 1.59-1.41 (m, 2H), 1.06-1.05 (m, 9H).

Step i. To a stirred solution of the above intermediate (690 mg, 1.57 mmol) in anhydrous THF (6 mL), cooled to −25° C. under argon, was added dropwise lithium diisopropylamide solution (1.0 M in THF/hexanes; 3.92 mL, 3.92 mmol; CAS: 4111-54-0) and the reaction mixture was stirred at −25° C. for 30 min. To this was added dropwise iodomethane (0.29 mL, 4.7 mmol) and the solution was allowed to slowly warm to 15° C. over 3 h. The reaction mixture was diluted with saturated $NH_4Cl$, extracted with EtOAc and the combined organics washed with 10% aqueous citric acid, brine, dried over $Na_2SO_4$, filtered, and concentrated in vacuo to give (1R,2S,4S)-4-((tert-butyldiphenylsilyl)oxy)-2-(methoxycarbonyl)-2-methylcyclohexane-1-carboxylic acid (720 mg, 99%). $^1$H NMR (400 MHz, CDCl$_3$) δ 10.66 (br. s, 1H), 7.69-7.65 (m, 4H), 7.44-7.35 (m, 6H), 3.83-3.75 (m, 1H), 3.61 (s, 3H), 2.63 (t, 1H), 2.28-2.13 (m, 2H), 1.78-1.56 (m, 3H), 1.49-1.32 (m, 2H), 1.06 (s, 11H).

Step j. To a stirred solution of the above intermediate (709 mg, 1.56 mmol) in DMF (3 mL) at rt under argon was added HATU (652 mg, 1.72 mmol) and the reaction mixture was stirred for 5 min. To this was added DIPEA (0.3 mL, 1.72 mmol) and the mixture stirred for 16 h. The reaction mixture was diluted with water, extracted with EtOAc, and the combined organics washed with water, brine, dried over $Na_2SO_4$, filtered and concentrated in vacuo. The crude product was purified by flash column chromatography on the InterChim 4125 (80 g silica column Puriflash HP, 0-50% EtOAc in cyclohexane) to provide 2-(3H-[1,2,3]triazolo[4,5-b]pyridin-3-yl) 1-methyl (1S,2R,5S)-5-((tert-butyldiphenylsilyl)oxy)-1-methylcyclohexane-1,2-dicarboxylate (630 mg, 67%). $^1$H NMR (400 MHz, CDCl$_3$) δ 8.72 (dd, 1H), 8.41 (dd, 1H), 7.70-7.66 (m, 4H), 7.45-7.35 (m, 7H), 3.87-3.81 (m, 1H), 3.73 (s, 3H), 3.13 (dd, 1H), 2.46-2.39 (m, 1H), 2.25 (dd, 1H), 1.96-1.82 (m, 1H), 1.76-1.70 (m, 1H), 1.66-1.56 (m, 2H), 1.18 (s, 3H), 1.05 (s, 9H).

Step k. To a stirred solution of (S)-5-((5-chloro-8-((5-(difluoromethyl)-1-methyl-1H-1,2,3-triazol-4-yl)methoxy)-1,2,3,4-tetrahydroisoquinolin-1-yl)methyl)-5-azaspiro[2.4]heptan-6-one hydrochloride (Example 110, step b; 310 mg, 0.63 mmol) in DMF (13 mL) was added the above intermediate (436 mg, 0.76 mmol) and DIPEA (0.27 mL, 1.52 mmol) and the reaction mixture stirred at rt under argon for 3.5 days. The reaction mixture was diluted with saturated sodium bicarbonate solution, extracted with EtOAc and the combined organics washed with water, brine, dried over $Na_2SO_4$, filtered and concentrated in vacuo. The crude product was purified by flash column chromatography on the InterChim 4125 (80 g silica column Puriflash HP, 0-100% EtOAc in cyclohexane) to provide methyl (1S,2R,5S)-5-((tert-butyldiphenylsilyl)oxy)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylate (880 mg, assumed quantitative). $^1$H NMR (400 MHz, CDCl$_3$) δ 7.70-7.65 (m, 4H), 7.44-7.33 (m, 6H), 7.24 (d, 1H), 6.98-6.92 (m, 2H), 5.84 (dd, 1H), 5.27 (dd, 2H), 4.19 (s, 3H), 4.07 (dd, 1H), 3.82-3.78 (m, 2H), 3.72-3.63 (m, 1H), 3.48 (d, 1H), 3.27 (s, 3H), 3.11-3.04 (m, 2H), 2.92-2.72 (m, 3H), 2.56 (t, 1H), 2.41 (d, 1H), 2.22 (d, 1H), 1.83 (dd, 1H), 1.69-1.52 (m, 2H), 1.46-1.37 (m, 2H), 1.09 (s, 9H), 0.92 (s, 3H), 0.79-0.70 (m, 2H), 0.66-0.55 (m, 2H).

Step l. To a stirred solution of the above intermediate (60 mg, 0.07 mmol) in MeOH (4.2 mL) was added a solution of sodium hydroxide (32 mg, 0.81 mmol) in water (0.48 mL) and the reaction mixture was heated at 100° C. under microwave irradiation for 15 h then concentrated in vacuo. The residue was diluted with water, acidified to pH 4 using 5% aqueous citric acid solution and the resulting precipitate was collected by filtration. The crude product was purified by reverse phase flash column chromatography on the InterChim 4125 (40 g C18 InterChim HP, 5-70% MeCN in water 0.1% HCOOH buffer). Fractions containing the desired product were combined and freeze dried overnight to provide the title compound (16 mg, 36%). LCMS (Method 3): 3.70 min, 636.4 [M+H]$^+$. $^1$H NMR (400 MHz, CDCl$_3$) δ 7.30 (d, 1H), 6.99 (d, 1H), 6.93 (t, 1H), 5.96 (dd, 1H), 5.37-5.17 (m, 2H), 4.18 (m, 3H), 4.16-3.96 (m, 3H), 3.85 (m, 1H), 3.42 (d, 1H), 3.16 (dd, 1H), 3.12-3.02 (m, 2H), 2.86-2.67 (m, 2H), 2.60 (m, 1H), 2.41 (d, 1H), 2.14 (d, 1H), 2.06-1.90 (m, 2H), 1.87-1.22 (m, 3H), 1.17 (s, 3H), 0.73-0.49 (m, 4H).

Example 224

(1S,2R,5R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-5-hydroxy-1-methylcyclohexane-1-carboxylic acid

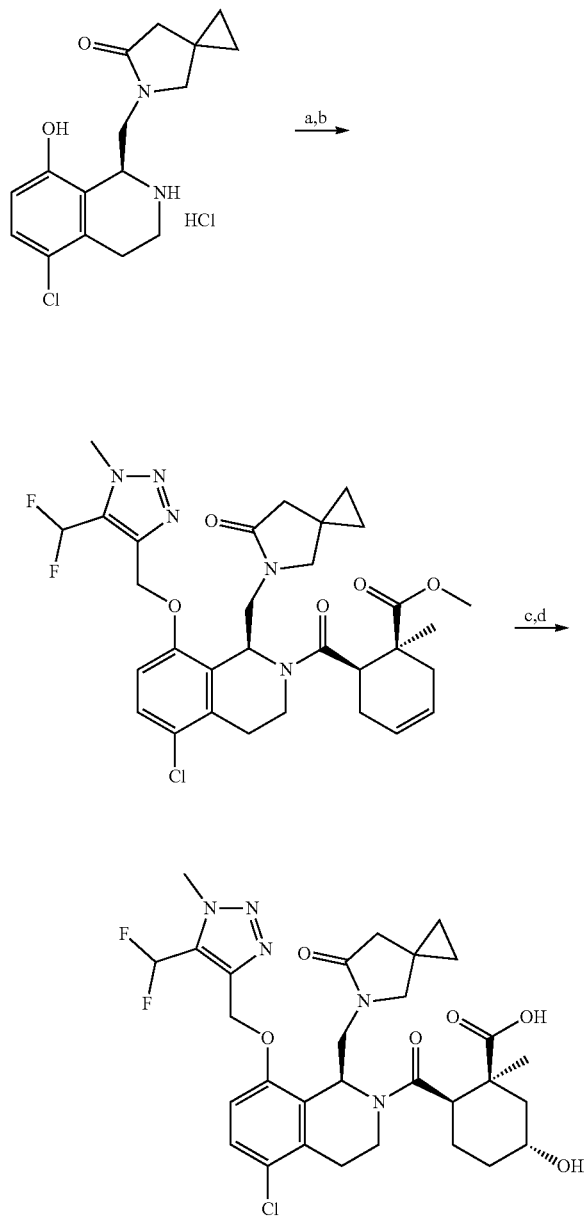

Step a. To a stirred solution of mixture of Intermediate 36 (2.16 g, 6.29 mmol) in DMF (39 mL) was added Intermediate 40 (1.99 g, 6.29 mmol), DIPEA (2.19 mL, 12.6 mmol) and the reaction mixture was stirred at rt stirred under nitrogen for 28 h. The reaction was diluted with brine, extracted with EtOAc and concentrated in vacuo. Purification by flash column chromatography on the Teledyne ISCO CombiFlash® Rf+ (80 g silica column Puriflash HC, 0-10% MeOH in DCM) gave methyl (1S,6R)-6-((S)-5-chloro-8-hydroxy-1-((6-oxo-5-azaspiro[2.4]heptan-5-yl)methyl)-1,2, 3,4-tetrahydroisoquinoline-2-carbonyl)-1-methylcyclohex-3-ene-1-carboxylate (1.64 g, 53%). LCMS (Method 18): 1.43 min, 487.3 [M+H]$^+$.

Step b. Methyl (1S,6R)-6-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohex-3-ene-1-carboxylate (2.03 g, 95%) was prepared from the above intermediate (1.64 g, 3.37 mmol) using a procedure similar to that described for Example 11 step b. LCMS (Method 16): 1.42 min, 632.3 [M+H]$^+$.

Step c. To a stirred solution of methyl (1S,6R)-6-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohex-3-ene-1-carboxylate (Example 201 step c; 304 mg, 0.48 mmol) in THF (2 mL) at 0° C. was added borane dimethyl sulfide complex (0.09 mL, 0.96 mmol; CAS: 13292-87-0) dropwise and the mixture stirred for 1 h at 0° C. To this was added sodium hydroxide (0.8 mL, 2.4 mmol) dropwise followed by hydrogen peroxide solution (30 wt. % in water; 0.24 mL, 2.4 mmol; CAS: 7722-84-1) dropwise. The mixture was stirred for 4 h then diluted with water, extracted with EtOAc and the combined organics washed with sodium bisulphite, brine, dried (MgSO$_4$) and evaporated. The crude product was purified by flash column chromatography on the Teledyne ISCO CombiFlash® Rf+ (12 g silica column Puriflash HC, 0-2% MeOH in DCM) to give methyl (1S,2R,5R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-5-hydroxy-1-methylcyclohexane-1-carboxylate (50 mg, 12%). $^1$H NMR (400 MHz, CDCl$_3$) δ 7.26 (d, 1H), 6.99 (t, 1H), 6.95 (d, 1H), 5.89 (dd, 1H), 5.25 (q, 2H), 4.18 (s, 3H), 4.26-4.19 (m, 1H), 4.12-4.04 (m, 1H), 3.90-3.83 (m, 2H), 3.55 (s, 2H), 3.49 (d, 1H), 3.14-3.07 (m, 1H), 3.03-2.89 (m, 2H), 2.81-2.68 (m, 1H), 2.66-2.59 (m, 1H), 2.37 (d, 1H), 2.30-2.22 (m, 1H), 2.23 (d, 1H), 2.09-1.91 (m, 3H), 1.44-1.31 (m, 2H), 1.29-1.24 (m, 1H), 1.21 (s, 3H), 0.67-0.52 (m, 4H).

Step d. To a solution of the above intermediate (45 mg, 0.070 mmol) in MeOH (0.80 mL) was added a solution of sodium hydroxide (28 mg, 0.69 mmol) in water (0.20 mL) and the reaction mixture was heated at 100° C. under microwave irradiation for 15 h. The mixture was concentrated in vacuo, diluted with water, acidified to pH 4 using 5% aqueous citric acid solution and extracted with EtOAc. The combined organics were washed with water, brine, dried (Na$_2$SO$_4$) and concentrated in vacuo. The crude product was purified by reverse phase flash column chromatography on the InterChim 4125 (40 g C18 InterChim HP, 5-70% MeCN in water 0.1% HCOOH buffer). Fractions containing the desired product were combined and freeze dried overnight to provide the title compound (15 mg, 33%). LCMS (Method 3): 3.91 min, 636.4 [M+H]$^+$. $^1$H NMR (400 MHz, CDCl$_3$) δ 15.36 (bs, 1H), 7.31 (d, 1H), 6.98 (d, 1H), 6.92 (t, 1H), 5.95 (dd, 1H), 5.39-5.21 (m, 2H), 4.17 (m, 3H), 4.11 (dd, 1H), 4.07-3.81 (m, 3H), 3.42 (d, 1H), 3.16 (dd, 1H), 3.13-3.02 (m, 2H), 2.76 (m, 1H), 2.64 (m, 1H), 2.56 (dd, 1H), 2.41 (d, 1H), 2.17-2.04 (m, 2H), 1.94 (m, 1H), 1.78-1.44 (m, 1H), 1.33 (m, 1H), 1.18 (s, 3H), 1.05 (dd, 1H), 0.75-0.47 (m, 4H).

Example 225

(1S,2R,4R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-4-hydroxy-1-methylcyclohexane-1-carboxylic acid

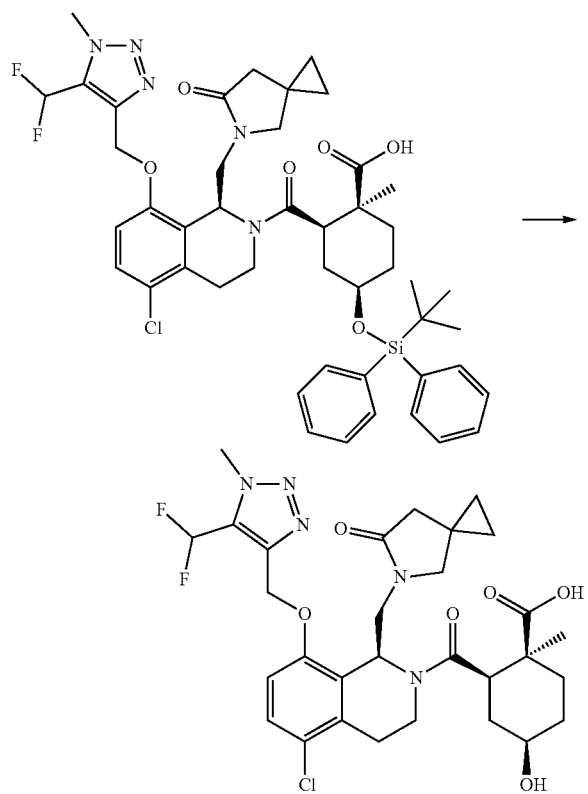

To a stirred solution of methyl (1S,2R,4R)-4-(((tert-butyldiphenylsilyl)oxy)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylate (Example 219 step h; 50 mg, 0.06 mmol) in MeOH (3.5 mL) was added a solution of sodium hydroxide (23 mg, 0.56 mmol) in water (0.50 mL) and the reaction mixture was heated at 100° C. under microwave irradiation for 17 h. The reaction mixture was concentrated in vacuo, diluted with water, acidified to pH 4 using 5% aqueous citric acid solution and the resulting precipitate was collected by filtration. The precipitate was purified by flash column chromatography on the Teledyne ISCO CombiFlash® Rf+ (12 g silica column Puriflash HC, 15 um, 0-5% MeOH in DCM). Fractions containing the desired product were combined and concentrated in vacuo. The residue was dissolved in 1:1 MeCN/water and freeze dried overnight to provide the title compound (14 mg, 38%). LCMS (Method 3): 4.08 min, 636.4 [M+H]$^+$. $^1$H NMR (400 MHz, DMSO-d$_6$) δ 12.91 (bs, 1H), 7.57 (t, 1H), 7.40 (d, 1H), 7.17 (d, 1H), 5.78 (dd, 1H), 5.41-5.23 (m, 2H), 4.62 (d, 1H), 4.15 (s, 3H), 4.05 (dd, 1H), 3.97 (dd, 1H), 3.68 (m, 1H), 3.56 (m, 1H), 3.44-3.19 (m, 1H), 3.05-2.78 (m, 3H), 2.77-2.57 (m, 2H), 2.22-2.09 (m, 2H), 1.93-1.44 (m, 5H), 1.33 (m, 1H), 0.94 (s, 3H), 0.67-0.35 (m, 4H).

Example 226

(2S,3R)-3-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)tetrahydro-2H-pyran-2-carboxylic acid

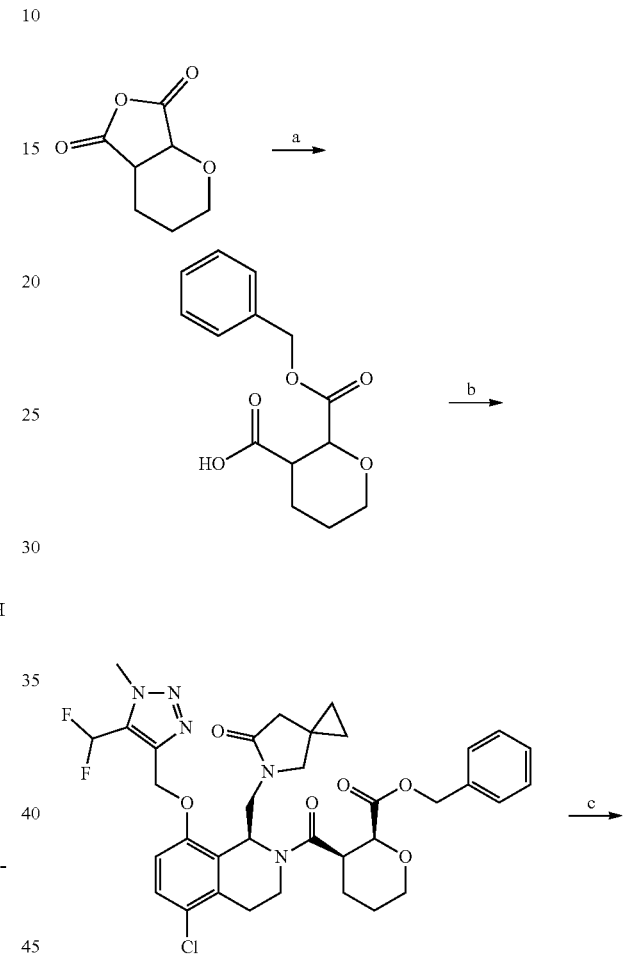

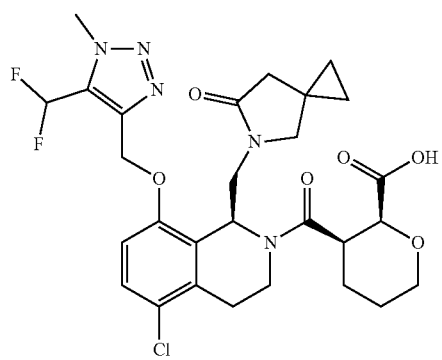

Step a. Benzyl alcohol (0.17 mL, 1.67 mmol) was added to a solution of tetrahydro-2H-furo[3,4-b]pyran-5,7-dione (Intermediate for Example 140 & 226; 260 mg, 1.67 mmol) in toluene (6.5 mL). The reaction mixture was stirred at 100° C. for 18 h, cooled to rt and concentrated in vacuo. The crude material was purified on Isolera (Biotage Silica ZIP-Sphere 10 g, 0-80% EtOAc in heptane) to give 2-((benzyloxy)carbonyl)tetrahydro-2H-pyran-3-carboxylic acid (340 mg, 70%). $^1$H NMR (300 MHz, CDCl$_3$) δ 7.37-7.32 (m, 5H), 5.29-5.18 (q, 2H), 4.25 (d, 1H), 4.14-4.05 (m, 1H), 3.62-3.55 (m, 1H), 3.17 (m, 1H), 2.34-2.28 (m, 1H), 1.92-1.72 (m, 2H), 1.56-1.50 (m, 1H).

Step b. To a stirred solution of HATU (110 mg, 0.29 mmol) and DIPEA (0.24 mL, 1.36 mmol) in DMF (3 mL) was added (S)-5-((5-chloro-8-((5-(difluoromethyl)-1-methyl-1H-1,2,3-triazol-4-yl)methoxy)-1,2,3,4-tetrahydroisoquinolin-1-yl)methyl)-5-azaspiro[2.4]-heptan-6-one hydrochloride (Example 110 step b; 123 mg, 0.23 mmol) and the above intermediate (60 mg, 0.230 mmol). The reaction mixture was stirred at rt for 5 days, diluted with water and extracted with EtOAc. The combined organics were washed with water, brine, dried over MgSO$_4$, filtered and concentrated in vacuo. The crude product was purified by prep-HPLC (Method 6; 0.1% NH$_4$OH 63% to 44% in MeCN over 12 minutes) to give benzyl 3-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)tetrahydro-2H-pyran-2-carboxylate as two isomers. Isomer 1 (34 mg, 21% yield): LCMS (Method 9a): 2.32 min, 698.31 [M+H]$^+$. Isomer 2 (56 mg, 35% yield): LCMS (Method 9a): 2.41 min, 698.32 [M+H]$^+$.

Step c. TJM-003-096 To a stirred solution of the above intermediate (isomer 1) (34 mg, 0.05 mmol) in EtOH (2 mL) was added Pd/C (10%; 3 mg, 0.02 mmol) and the reaction mixture was stirred under a hydrogen atmosphere at atmospheric pressure for 40 minutes. The reaction mixture was filtered through Celite® and the filter cake washed further with IMS. The combined organics were concentrated under reduced pressure and the crude product purified by preparative HPLC (Method 6) to give the title compound (1.4 mg, 5%). UPLC (Method 13): 1.94 min, 608.2 [M+H]$^+$. $^1$H NMR (300 MHz, CDCl$_3$) δ 7.27-7.20 (m, 1H), 6.94 (t, 1H), 6.91 (d, 1H), 5.88 (dd, 1H), 5.40-5.16 (m, 2H), 4.23-3.70 (m, 8H), 3.66-3.41 (m, 2H), 3.30 (m, 1H), 3.08 (dd, 1H), 2.96 (m, 1H), 2.88 (m, 1H), 2.78 (m, 1H), 2.27 (m, 2H), 2.11-1.14 (m, 4H), 0.78-0.43 (m, 4H).

Example 227

(1S,2S,3R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-3-hydroxy-1-methylcyclohexane-1-carboxylic acid

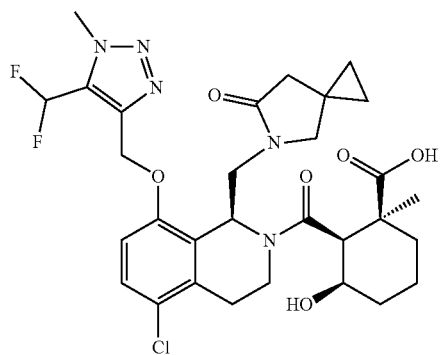 [SMILES: Cn1nnc(COc2ccc(Cl)c3c2[C@@H](CN2CC4(CC4)CC2=O)N(C(=O)[C@@H]2[C@H](O)CCC[C@]2(C)C(=O)O)CC3)c1C(F)F]

Example 228

(1S,2S,3S)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-3-hydroxy-1-methylcyclohexane-1-carboxylic acid

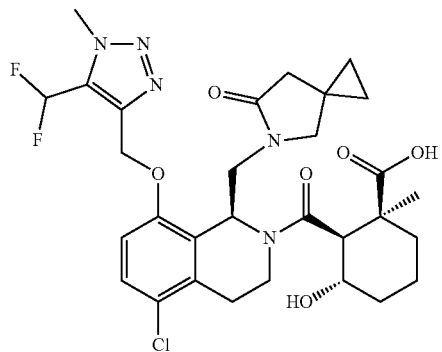 [SMILES: Cn1nnc(COc2ccc(Cl)c3c2[C@@H](CN2CC4(CC4)CC2=O)N(C(=O)[C@@H]2[C@@H](O)CCC[C@]2(C)C(=O)O)CC3)c1C(F)F]

Compounds in Table 3 were synthesised by methods analogous to the above Examples.

TABLE 3

| Ex. | Structure | Name | Analogous Example | 1H NMR δ ppm | LCMS |
|---|---|---|---|---|---|
| 65 | 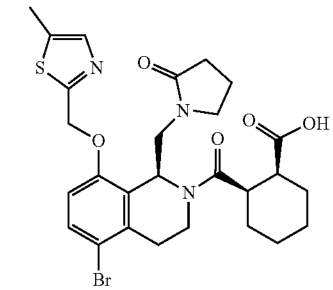 [SMILES: Cc1cnc(COc2ccc(Br)c3c2[C@@H](CN2CCCC2=O)N(C(=O)[C@@H]2CCCC[C@@H]2C(=O)O)CC3)s1] | (1S,2R)-2-((S)-5-bromo-8-((5-methylthiazol-2-yl)methoxy)-1-((2-oxopyrrolidin-1-yl)methyl)-1,2,3,4-tetrahydroisoquinoline-2-carbonyl)cyclohexane-1-carboxylic acid | 64 | (400 MHz, DMSO-d$_6$) δ 11.64 (bs, 1H), 7.54 (m, 1H), 7.52 (d, 1H), 7.02 (d, 1H), 5.93 (dd, 1H), 5.44 (d, 1H), 5.36 (d, 1H), 4.01-3.85 (m, 2H), 3.65 (m, 1H), 3.56 (m, 1H), 3.38-3.22 (m, 1H), 3.17-3.03 (m, 2H), 2.78 (dd, 1H), 2.67 (m, 1H), 2.48 (d, 3H), 2.36 (m, 1H), 2.26-1.98 (m, 3H), 1.97-1.63 (m, 5H), 1.58-1.38 (m, 2H), 1.29-1.09 (m, 2H). | Method 3: 4.20 min, 590.0 [M + H]$^+$ |
| 66 | 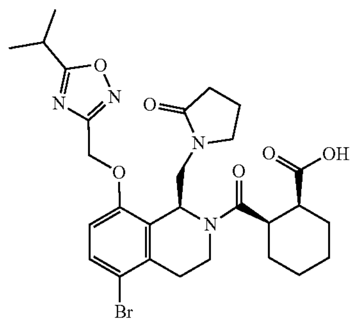 [SMILES: CC(C)c1nc(COc2ccc(Br)c3c2[C@@H](CN2CCCC2=O)N(C(=O)[C@@H]2CCCC[C@@H]2C(=O)O)CC3)no1] | (1S,2R)-2-((S)-5-bromo-8-((5-isopropyl-1,2,4-oxadiazol-3-yl)methoxy)-1-((2-oxopyrrolidin-1-yl)methyl)-1,2,3,4-tetrahydroisoquinoline-2-carbonyl)cyclohexane-1-carboxylic acid | 64 | (400 MHz, DMSO-d$_6$) δ 11.70 (bs, 1H), 7.54 (d, 1H), 7.04 (d, 1H), 5.88 (dd, 1H), 5.36 (d, 1H), 5.29 (d, 1H), 4.02-3.84 (m, 2H), 3.69-3.51 (m, 2H), 3.41-3.26 (m, 2H), 3.17 (m, 1H), 3.10 (dd, 1H), 2.77 (dd, 1H), 2.67 (m, 1H), 2.35 1H), 2.25-1.96 (m, 3H), 1.95-1.77 (m, 2H), 1.77-1.64 (m, 3H), 1.57-1.38 (m, 2H), 1.36-1.32 (m, 6H), 1.27-1.07 (m, 2H). | Method 3: 4.48 min, 603.0 [M + H]$^+$ |
| 67 | 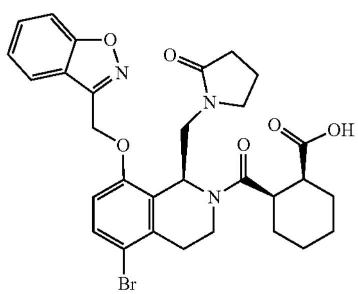 [SMILES: O=C(O)[C@H]1CCCC[C@H]1C(=O)N1CCc2c(Br)ccc(OCc3noc4ccccc34)c2[C@H]1CN1CCCC1=O] | (1S,2R)-2-((S)-8-(benzo[d]isoxazol-3-yl)methoxy)-5-bromo-1-((2-oxopyrrolidin-1-yl)methyl)-1,2,3,4-tetrahydroisoquinoline-2-carbonyl)cyclohexane-1-carboxylic acid | 64 | (400 MHz, DMSO-d$_6$) δ 11.65 (bs, 1H), 8.05 (m, 1H), 7.83 (m, 1H), 7.72 (m, 1H), 7.57 (d, 1H), 7.48 (m, 1H), 7.14 (d, 1H), 5.87 (dd, 1H), 5.71 (d, 1H), 5.62 (d, 1H), 3.95 (dd, 1H), 3.87 (d, 1H), 3.62 (m, 1H), 3.43-3.15 (m, 2H), 2.99 (dd, 1H), 2.80 (dd, 1H), 2.69 (m, 1H), 2.59 (m, 1H), 2.34 (m, 1H), 2.20-2.02 (m, 2H), 1.95 (m, 1H), 1.82-1.57 (m, 5H), 1.49 (m, 1H), 1.40 (m, 1H), 1.30-1.01 (m, 2H). | Method 1: 4.57 min, 610.0 [M + H]$^+$ |
| 69 | 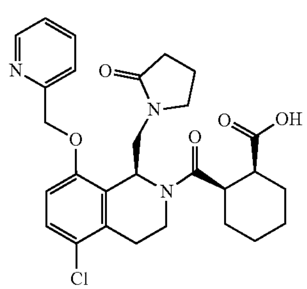 [SMILES: O=C(O)[C@H]1CCCC[C@H]1C(=O)N1CCc2c(Cl)ccc(OCc3ccccn3)c2[C@H]1CN1CCCC1=O] | (1S,2R)-2-((S)-5-chloro-1-((2-oxopyrrolidin-1-yl)methyl)-8-(pyridin-2-ylmethoxy)-1,2,3,4-tetrahydroisoquinoline-2-carbonyl)cyclohexane-1-carboxylic acid | 64 | (400 MHz, DMSO-d$_6$) δ 11.72 (bs, 1H), 8.61 (m, 1H), 7.92 (td, 1H), 7.63 (m, 1H), 7.39 (m, 1H), 7.35 (d, 1H), 7.04 (d, 1H), 5.94 (dd, 1H), 5.26-5.17 (m, 2H), 3.97 (dd, 1H), 3.90 (dd, 1H), 3.65 (m, 1H), 3.49 (m, 1H), 3.41-3.20 (m, 1H), 3.15 (m, 1H), 3.02 (m, 1H), 2.84 (dd, 1H), 2.71 (m, 1H), 2.36 (m, 1H), 2.26-1.96 (m, 3H), 1.94-1.62 (m, 5H), 1.52 (m, 1H), 1.42 (m, 1H), 1.28-1.08 (m, 2H). | Method 3: 3.62 min, 526.1 [M + H]$^+$ |

TABLE 3-continued

| Ex. | Structure | Name | Analogous Example | 1H NMR δ ppm | LCMS |
|---|---|---|---|---|---|
| 70 | 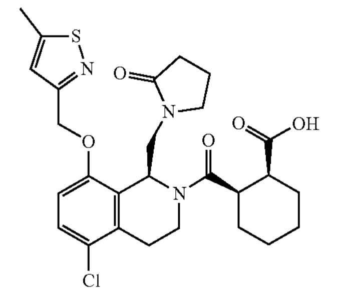 [SMILES: Cc1cc(COc2ccc(Cl)c3c2[C@@H](CN2CCCC2=O)N(C(=O)[C@@H]2CCCC[C@@H]2C(=O)O)CC3)ns1] | (1S,2R)-2-((S)-5-Chloro-8-((5-methylisothiazol-3-yl)methoxy)-1-((2-oxopyrrolidin-1-yl)methyl)-1,2,3,4-tetrahydroisoquinoline-2-carbonyl)cyclohexane-1-carboxylic acid | 64 | (400 MHz, DMSO-d$_6$) δ 11.71 (bs, 1H), 7.35 (d, 1H), 7.30 (m, 1H), 7.02 (d, 1H), 5.89 (dd, 1H), 5.23 (d, 1H), 5.17 (d, 1H), 3.96 (dd, 1H), 3.88 (dd, 1H), 3.63 (m, 1H), 3.50 (m, 1H), 3.44-3.20 (m, 1H), 3.15-3.01 (m, 2H), 2.83 (dd, 1H), 2.70 (m, 1H), 2.59 (d, 3H), 2.35 (m, 1H), 2.27-2.08 (m, 2H), 2.03 (m, 1H), 1.96-1.62 (m, 5H), 1.51 (m, 1H), 1.42 (m, 1H), 1.29-1.08 (m, 2H). | Method 3: 4.34 min, 546.1 [M + H]$^+$ |
| 71 | 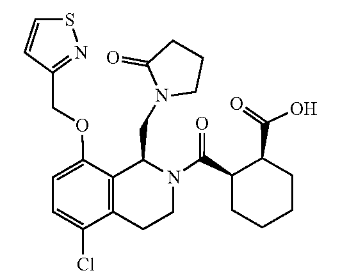 [SMILES: O=C(O)[C@H]1CCCC[C@H]1C(=O)N1CCc2c(Cl)ccc(OCc3ccsn3)c2[C@H]1CN1CCCC1=O] | (1S,2R)-2-((S)-5-Chloro-8-isothiazol-3-ylmethoxy)-1-((2-oxopyrrolidin-1-ylmethyl)-1,2,3,4-tetrahydroisoquinoline-2-carbonyl)cyclohexane-1-carboxylic acid | 64 | (400 MHz, DMSO-d$_6$) δ 11.71 (bs, 1H), 9.16 (d, 1H), 7.56 (d, 1H), 7.36 (d, 1H), 7.05 (d, 1H), 5.89 (dd, 1H), 5.33 (d, 1H), 5.26 (d, 1H), 3.96 (dd, 1H), 3.88 (dd, 1H), 3.63 (m, 1H), 3.46 (m, 1H), 3.40-3.25 (m, 1H), 3.09 (dd, 1H), 3.00 (m, 1H), 2.84 (dd, 1H), 2.70 (m, 1H), 2.35 (m, 1H), 2.24-2.08 (m, 2H), 2.02 (m, 1H), 1.95-1.62 (m, 5H), 1.52 (m, 1H), 1.43 (m, 1H), 1.28-1.07 (m, 2H). | Method 3: 4.12 min, 532.1 [M + H]$^+$ |
| 72 | 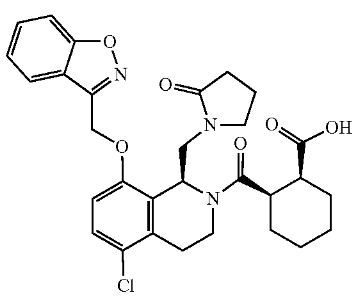 [SMILES: O=C(O)[C@H]1CCCC[C@H]1C(=O)N1CCc2c(Cl)ccc(OCc3noc4ccccc34)c2[C@H]1CN1CCCC1=O] | (1S,2R)-2-((S)-8-(Benzo[d]isoxazol-3-ylmethoxy)-5-chloro-1-((2-oxopyrrolidin-1-yl)methyl)-1,2,3,4-tetrahydroisoquinoline-2-carbonyl)cyclohexane-1-carboxylic acid | 64 | (400 MHz, DMSO-d$_6$) δ 11.71 (bs, 1H), 8.05 (m, 1H), 7.83 (m, 1H), 7.72 (m, 1H), 7.48 (m, 1H), 7.42 (d, 1H), 7.19 (d, 1H), 5.87 (dd, 1H), 5.71 (d, 1H), 5.62 (d, 1H), 3.95 (dd, 1H), 3.87 (dd, 1H), 3.62 (m, 1H), 3.39-3.27 (m, 1H), 3.23 (m, 1H), 2.99 (dd, 1H), 2.84 (dd, 1H), 2.78-2.64 (m, 1H), 2.60 (m, 1H), 2.35 (m, 1H), 2.19-2.03 (m, 2H), 1.95 (m, 1H), 1.82-1.57 (m, 5H), 1.50 (m, 1H), 1.40 (m, 1H), 1.28-1.01 (m, 2H). | Method 1: 4.50 min, 566 [M + H]$^+$ |
| 75 | 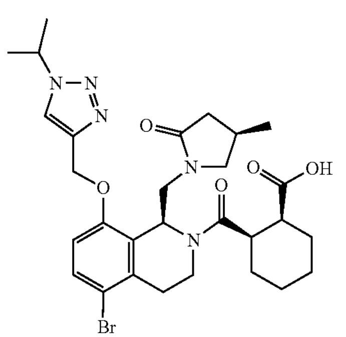 [SMILES: CC(C)n1cc(COc2ccc(Br)c3c2[C@@H](CN2C[C@H](C)CC2=O)N(C(=O)[C@@H]2CCCC[C@@H]2C(=O)O)CC3)nn1] | (1S,2R)-2-((S)-5-Bromo-8-((1-isopropyl-1H-1,2,3-triazol-4-yl)methoxy)-1-(((R)-4-methyl-2-oxopyrrolidin-1-yl)methyl)-1,2,3,4-tetrahydroisoquinoline-2-carbonyl)cyclohexane-1-carboxylic acid | 64 | (400 MHz, DMSO-d$_6$) δ 11.70 (bs, 1H), 8.43 (s, 1H), 7.52 (d, 1H), 7.07 (d, 1H), 5.76 (dd, 1H), 5.25-5.10 (m, 2H), 4.87 (m, 1H), 3.95 (dd, 1H), 3.86 (dd, 1H), 3.61 (m, 1H), 3.39-3.24 (m, 1H), 3.02-2.87 (m, 3H), 2.82-2.61 (m, 2H), 2.40-2.18 (m, 3H), 2.10 (m, 1H), 1.81-1.61 (m, 4H), 1.57-1.32 (m, 8H), 1.31-1.10 (m, 2H), 0.96 (d, 3H). | Method 3: 4.14 min, 616 [M + H]$^+$ |

TABLE 3-continued

| Ex. | Structure | Name | Analogous Example | 1H NMR δ ppm | LCMS |
|---|---|---|---|---|---|
| 76 | 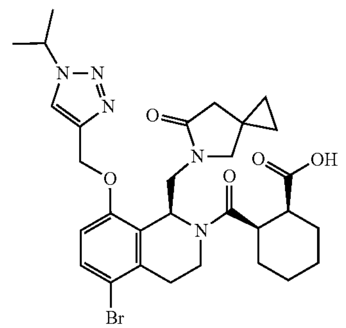 [SMILES: CC(C)n1cc(COc2ccc(Br)c3c2[C@@H](CN2CC4(CC4)CC2=O)N(C(=O)[C@@H]2CCCC[C@@H]2C(=O)O)CC3)nn1] | (1S,2R)-2-((S)-5-bromo-8-((1-isopropyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)cyclohexane-1-carboxylic acid | 135 | (400 MHz, DMSO-$d_6$) δ 11.71 (bs, 1H), 8.39 (s, 1H), 7.52 (d, 1H), 7.07 (d, 1H), 5.79 (dd, 1H), 5.23-5.10 (m, 2H), 4.84 (m, 1H), 4.04-3.87 (m, 2H), 3.62 (m, 1H), 3.41-3.24 (m, 2H), 3.04 (dd, 1H), 2.84-2.73 (m, 2H), 2.66 (m, 1H), 2.33 (m, 1H), 2.27-2.04 (m, 3H), 1.81-1.62 (m, 3H), 1.58-1.31 (m, 8H), 1.30-1.10 (m, 2H), 0.59 (m, 1H), 0.55-0.47 (m, 2H), 0.44 (m, 1H). | Method 3: 4.21 min, 628 [M + H]+ |
| 77 | 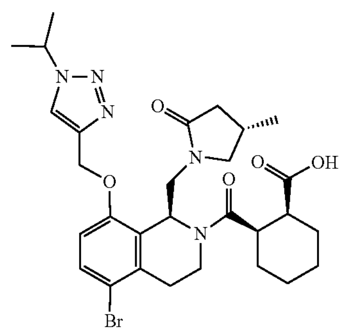 [SMILES: CC(C)n1cc(COc2ccc(Br)c3c2[C@@H](CN2C[C@@H](C)CC2=O)N(C(=O)[C@@H]2CCCC[C@@H]2C(=O)O)CC3)nn1] | (1S,2R)-2-((S)-5-Bromo-8-((1-isopropyl-1H-1,2,3-triazol-4-yl)methoxy)-1-(((S)-4-methyl-2-oxopyrrolidin-1-yl)methyl)-1,2,3,4-tetrahydroisoquinoline-2-carbonyl)cyclohexane-1-carboxylic acid | 64 separated in last step from Example 75 | (400 MHz, DMSO-$d_6$) δ 11.14 (bs, 1H), 8.41 (s, 1H), 7.52 (d, 1H), 7.08 (d, 1H), 5.77 (dd, 1H), 5.24-5.10 (m, 2H), 4.87 (m, 1H), 3.95 (dd, 1H), 3.83 (dd, 1H), 3.58 (m, 1H), 3.44 (m, 1H), 3.40-3.20 (m, 1H), 2.96 (dd, 1H), 2.82-2.56 (m, 2H), 2.55-2.42 (m, 1H), 2.33 (m, 1H), 2.24-2.02 (m, 3H), 1.82 (m, 1H), 1.76-1.62 (m, 3H), 1.56-1.33 (m, 8H), 1.15 (m, 2H), 0.96 (d, 3H). | Method 3: 4.12 min, 616 [M + H]+. |
| 78 | 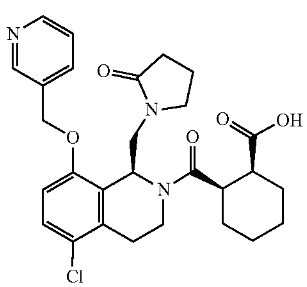 [SMILES: O=C(O)[C@H]1CCCC[C@H]1C(=O)N1CCc2c(Cl)ccc(OCc3cccnc3)c2[C@H]1CN1CCCC1=O] | (1S,2R)-2-((S)-5-Chloro-1-((2-oxopyrrolidin-1-yl)methyl)-8-(pyridin-3-ylmethoxy)-1,2,3,4-tetrahydroisoquinoline-2-carbonyl)cyclohexane-1-carboxylic acid | 68 | (400 MHz, DMSO-$d_6$) δ 11.67 (bs, 1H), 8.76 (d, 1H), 8.60 (dd, 1H), 7.97 (dt, 1H), 7.49 (m, 1H), 7.39 (d, 1H), 7.08 (d, 1H), 5.87 (dd, 1H), 5.23 (d, 1H), 5.14 (d, 1H), 3.96 (dd, 1H), 3.88 (dd, 1H), 3.63 (m, 1H), 3.43-3.27 (m, 2H), 3.02 (dd, 1H), 2.89-2.79 (m, 2H), 2.70 (m, 1H), 2.34 (m, 1H), 2.26-2.04 (m, 2H), 2.00 (m, 1H), 1.91-1.62 (m, 5H), 1.50 (m, 1H), 1.42 (m, 1H), 1.27-1.05 (m, 2H). | Method 3: 3.17 min, 526.2 [M + H]+ |
| 82 | 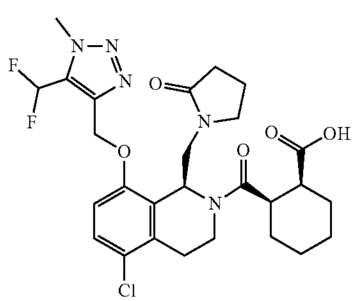 [SMILES: Cn1nnc(COc2ccc(Cl)c3c2[C@@H](CN2CCCC2=O)N(C(=O)[C@@H]2CCCC[C@@H]2C(=O)O)CC3)c1C(F)F] | (1S,2R)-2-((S)-5-Chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)cyclohexane-1-carboxylic acid | 68 | (400 MHz, DMSO-$d_6$) δ 7.58 (t, 1H), 7.39 (d, 1H), 7.16 (d, 1H), 5.75 (dd, 1H), 5.29 (s, 2H), 4.18 (s, 3H), 3.93 (dd, 1H), 3.82 (dd, 1H), 3.56 (m, 1H), 3.48-3.27 (m, 2H), 2.95 (dd, 1H), 2.90-2.65 (m, 3H), 2.23-2.08 (m, 3H), 1.99 (m, 1H), 1.90-1.62 (m, 5H), 1.52-1.31 (m, 2H), 1.29-1.10 (m, 2H). | Method 3: 3.93 min, 580.2 [M + H]+ |

TABLE 3-continued

| Ex. | Structure | Name | Analogous Example | 1H NMR δ ppm | LCMS |
|---|---|---|---|---|---|
| 83 | 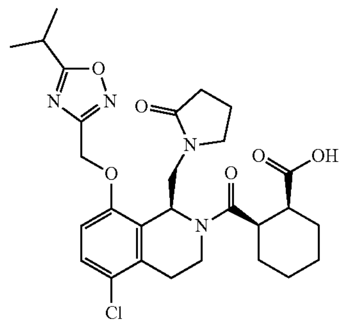 [SMILES: CC(C)c1nc(COc2ccc(Cl)c3c2[C@@H](CN2CCCC2=O)N(C(=O)[C@@H]2CCCC[C@@H]2C(=O)O)CC3)no1] | (1S,2R)-2-((S)-5-Chloro-8-((5-isopropyl-1,2,4-oxadiazol-3-yl)methoxy)-1-((2-oxopyrrolidin-1-yl)methyl)-1,2,3,4-tetrahydroisoquinoline-2-carbonyl)cyclohexane-1-carboxylic acid | 68 | (400 MHz, DMSO-$d_6$) δ 11.71 (bs, 1H), 7.38 (d, 1H), 7.09 (d, 1H), 5.88 (dd, 1H), 5.37 (d, 1H), 5.29 (d, 1H), 4.02-3.85 (m, 2H), 3.68-3.52 (m, 2H), 3.43-3.24 (m, 2H), 3.17 (m, 1H), 3.10 (dd, 1H), 2.83 (dd, 1H), 2.76-2.63 (m, 1H), 2.34 (m, 1H), 2.25-2.08 (m, 2H), 2.02 (m, 1H), 1.95-1.77 (m, 2H), 1.77-1.64 (m, 3H), 1.51 (m, 1H), 1.42 (m, 1H), 1.34 (m, 6H), 1.25-1.10 (m, 2H). | Method 3: 4.39 min, 559.3 [M + H]$^+$ |
| 85 | 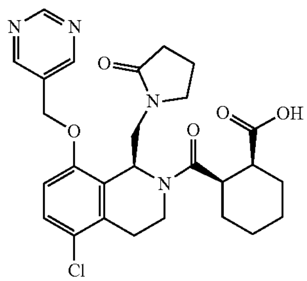 [SMILES: O=C(O)[C@H]1CCCC[C@H]1C(=O)N1CCc2c(Cl)ccc(OCc3cncnc3)c2[C@H]1CN1CCCC1=O] | (1S,2R)-2-((S)-5-chloro-1-((2-oxopyrrolidin-1-yl)methyl)-8-(pyrimidin-5-yl)methoxy)-1,2,3,4-tetrahydroisoquinoline-2-carbonyl)cyclohexane-1-carboxylic acid | 11 | (400 MHz, DMSO-$d_6$) δ 11.65 (bs, 1H), 9.23 (s, 1H), 9.02 (s, 2H), 7.41 (d, 1H), 7.09 (d, 1H), 5.86 (dd, 1H), 5.26 (d, 1H), 5.17 (d, 1H), 3.97 (dd, 1H), 3.87 (dd, 1H), 3.63 (m, 1H), 3.48-3.12 (m, 2H), 3.03 (dd, 1H), 2.91-2.78 (m, 2H), 2.71 (m, 1H), 2.33 (m, 1H), 2.23-2.05 (m, 2H), 1.99 (m, 1H), 1.91-1.63 (m, 5H), 1.51 (m, 1H), 1.41 (m, 1H), 1.27-1.06 (m, 2H). | Method 3: 3.62 min, 527.2 [M + H]$^+$ |
| 88 | 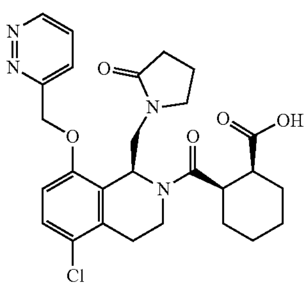 [SMILES: O=C(O)[C@H]1CCCC[C@H]1C(=O)N1CCc2c(Cl)ccc(OCc3cccnn3)c2[C@H]1CN1CCCC1=O] | (1S,2R)-2-((S)-5-Chloro-1-((2-oxopyrrolidin-1-yl)methyl)-8-(pyridazin-3-ylmethoxy)-1,2,3,4-tetrahydroisoquinoline-2-carbonyl)cyclohexane-1-carboxylic acid | 11 | (400 MHz, DMSO-$d_6$) δ 11.66 (bs, 1H), 9.26 (dd, 1H), 7.94 (dd, 1H), 7.84 (dd, 1H), 7.38 (d, 1H), 7.11 (d, 1H), 5.91 (dd, 1H), 5.48 (d, 1H), 5.42 (d, 1H), 3.97 (dd, 1H), 3.88 (dd, 1H), 3.64 (m, 1H), 3.43 (m, 1H), 3.39-3.24 (m, 1H), 3.12 (dd, 1H), 2.97 (m, 1H), 2.85 (dd, 1H), 2.71 (m, 1H), 2.35 (m, 1H), 2.25-2.07 (m, 2H), 2.01 (m, 1H), 1.93-1.62 (m, 5H), 1.52 (m, 1H), 1.42 (m, 1H), 1.27-1.08 (m, 2H). | Method 3: 3.57 min, 527.2 [M + H]$^+$ |
| 89 | 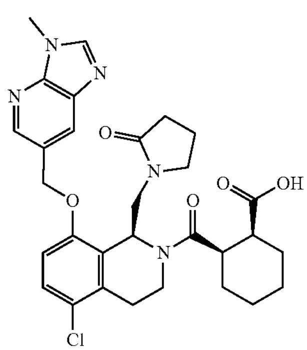 [SMILES: Cn1cnc2cc(COc3ccc(Cl)c4c3[C@@H](CN3CCCC3=O)N(C(=O)[C@@H]3CCCC[C@@H]3C(=O)O)CC4)cnc21] | (1S,2R)-2-((S)-5-Chloro-8-((3-methyl-3H-imidazo[4,5-b]pyridin-6-yl)methoxy)-1-((2-oxopyrrolidin-1-yl)methyl)-1,2,3,4-tetrahydroisoquinoline-2-carbonyl)cyclohexane-1-carboxylic acid | 11 | (400 MHz, DMSO-$d_6$) δ 11.76 (bs, 1H), 8.57 (d, 1H), 8.47 (s, 1H), 8.28 (d, 1H), 7.38 (d, 1H), 7.13 (d, 1H), 5.86 (dd, 1H), 5.34 (d, 1H), 5.26 (d, 1H), 3.95 (dd, 1H), 3.91-3.81 (m, 4H), 3.62 (m, 1H), 3.48-3.16 (m, 2H), 3.03 (dd, 1H), 2.84 (dd, 1H), 2.79-2.63 (m, 2H), 2.32 (m, 1H), 2.20-2.03 (m, 2H), 1.96 (m, 1H), 1.77-1.60 (m, 5H), 1.49 (m, 1H), 1.40 (m, 1H), 1.26-1.05 (m, 2H). | Method 3: 3.55 min, 580.3 [M + H]$^+$ |

TABLE 3-continued

| Ex. | Structure | Name | Analogous Example | 1H NMR δ ppm | LCMS |
|---|---|---|---|---|---|
| 90 | 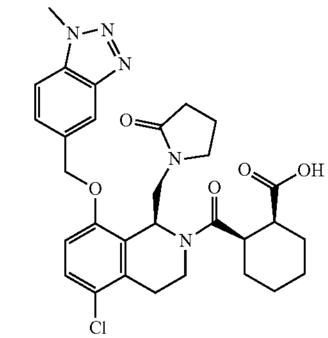 [SMILES: Cn1nnc2cc(COc3ccc(Cl)c4c3[C@@H](CN3CCCC3=O)N(C(=O)[C@@H]3CCCC[C@@H]3C(=O)O)CC4)ccc21] | (1S,2R)-2-((S)-5-Chloro-8-((1-methyl-1H-benzo[d][1,2,3]triazol-5-yl)methoxy)-1-((2-oxopyrrolidin-1-yl)methyl)-1,2,3,4-tetrahydroisoquinoline-2-carbonyl)cyclohexane-1-carboxylic acid | 11 | (400 MHz, DMSO-$d_6$) δ 11.70 (bs, 1H), 8.20 (s, 1H), 7.93 (dd, 1H), 7.73 (dd, 1H), 7.38 (d, 1H), 7.10 (d, 1H), 5.92 (dd, 1H), 5.35 (d, 1H), 5.27 (d, 1H), 4.33 (s, 3H), 3.96 (dd, 1H), 3.89 (dd, 1H), 3.63 (m, 1H), 3.48-3.18 (m, 2H), 3.08 (dd, 1H), 2.93-2.79 (m, 2H), 2.78-2.64 (m, 1H), 2.31 (m, 1H), 2.20-2.06 (m, 2H), 1.98 (m, 1H), 1.80-1.63 (m, 5H), 1.49 (m, 1H), 1.41 (m, 1H), 1.24-1.09 (m, 2H). | Method 11: 1.25 min, 578.0 [M − H]− |
| 92 | 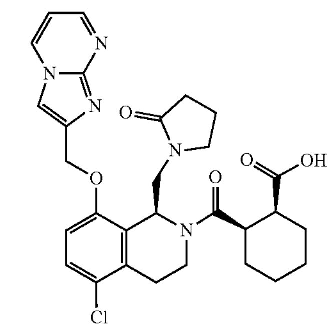 [SMILES: O=C(O)[C@H]1CCCC[C@H]1C(=O)N1CCc2c(Cl)ccc(OCc3cn4cccnc4n3)c2[C@H]1CN1CCCC1=O] | (1S,2R)-2-((S)-5-Chloro-8-(imidazo[1,2-a]pyrimidin-2-ylmethoxy)-1-((2-oxopyrrolidin-1-yl)methyl)-1,2,3,4-tetrahydroisoquinoline-2-carbonyl)cyclohexane-1-carboxylic acid | 11 | (400 MHz, DMSO-$d_6$) δ 11.72 (bs, 1H), 9.02 (dd, 1H), 8.55 (dd, 1H), 8.03 (s, 1H), 7.35 (d, 1H), 7.13 (d, 1H), 7.07 (dd, 1H), 5.92 (dd, 1H), 5.33 (s, 2H), 3.96 (dd, 1H), 3.87 (dd, 1H), 3.62 (m, 1H), 3.49 (m, 1H), 3.44-3.24 (m, 1H), 3.21 (dd, 1H), 3.07 (m, 1H), 2.83 (m, 1H), 2.74 (m, 1H), 2.31 (m, 1H), 2.23-2.07 (m, 2H), 2.01 (m, 1H), 1.87-1.65 (m, 5H), 1.50 (m, 1H), 1.42 (m, 1H), 1.24-1.10 (m, 2H). | Method 3: 3.26 min, 566.2 [M + H]+ |
| 93 | 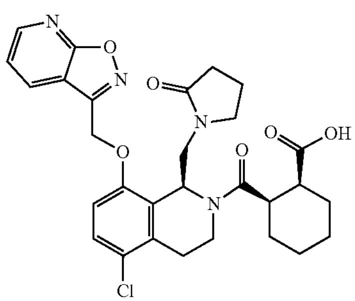 [SMILES: O=C(O)[C@H]1CCCC[C@H]1C(=O)N1CCc2c(Cl)ccc(OCc3noc4ncccc34)c2[C@H]1CN1CCCC1=O] | (1S,2R)-2-((S)-5-Chloro-8-(isoxazolo[5,4-b]pyridin-3-ylmethoxy)-1-((2-oxopyrrolidin-1-yl)methyl)-1,2,3,4-tetrahydroisoquinoline-2-carbonyl)cyclohexane-1-carboxylic acid | 11 | (400 MHz, DMSO-$d_6$) δ 11.73 (bs, 1H), 8.74 (dd, 1H), 8.57 (dd, 1H), 7.60 (dd, 1H), 7.41 (d, 1H), 7.17 (d, 1H), 5.89 (dd, 1H), 5.71 (d, 1H), 5.63 (d, 1H), 3.96 (dd, 1H), 3.87 (dd, 1H), 3.63 (m, 1H), 3.45-3.19 (m, 2H), 3.01 (dd, 1H), 2.84 (dd, 1H), 2.78-2.64 (m, 2H), 2.33 (m, 1H), 2.22-2.05 (m, 2H), 1.96 (m, 1H), 1.79-1.61 (m, 5H), 1.50 (m, 1H), 1.41 (m, 1H), 1.26-1.06 (m, 2H). | Method 11: 3.18 min, 567.3 [M + H]+ |
| 94 | 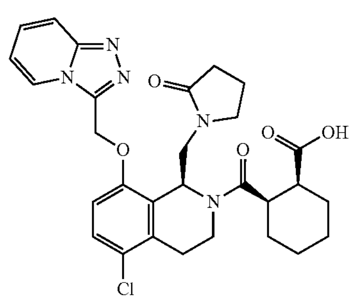 [SMILES: O=C(O)[C@H]1CCCC[C@H]1C(=O)N1CCc2c(Cl)ccc(OCc3nnc4ccccn34)c2[C@H]1CN1CCCC1=O] | (1S,2R)-2-((S)-8-([1,2,4]Triazolo[4,3-a]pyridin-3-ylmethoxy)-5-chloro-1-((2-oxopyrrolidin-1-yl)methyl)-1,2,3,4-tetrahydroisoquinoline-2-carbonyl)cyclohexane-1-carboxylic acid | 11 | (400 MHz, DMSO-$d_6$) δ 11.69 (bs, 1H), 8.72 (dt, 1H), 7.86 (dt, 1H), 7.48 (m, 1H), 7.42 (d, 1H), 7.25 (d, 1H), 7.12 (td, 1H), 5.81-5.68 (m, 3H), 3.95 (dd, 1H), 3.80 (dd, 1H), 3.57 (m, 1H), 3.50-3.18 (m, 1H), 3.06 (m, 1H), 2.87-2.77 (m, 2H), 2.69 (m, 1H), 2.41-2.25 (m, 2H), 2.15-2.02 (m, 2H), 1.92 (m, 1H), 1.76-1.56 (m, 5H), 1.47 (m, 1H), 1.37 (m, 1H), 1.25-0.99 (m, 2H). | Method 3: 2.87 min, 566.3 [M + H]+ |

TABLE 3-continued

| Ex. | Structure | Name | Analogous Example | 1H NMR δ ppm | LCMS |
|---|---|---|---|---|---|
| 95 | 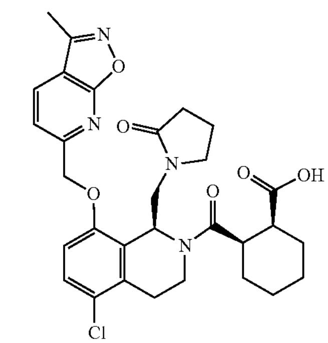 [SMILES: Cc1noc2nc(COc3ccc(Cl)c4c3[C@@H](CN3CCCC3=O)N(C(=O)[C@@H]3CCCC[C@@H]3C(=O)O)CC4)ccc12] | (1S,2R)-2-((S)-5-Chloro-8-((3-methylisoxazolo[5,4-b]pyridin-6-yl)methoxy)-1-((2-oxopyrrolidin-1-yl)methyl)-1,2,3,4-tetrahydroisoquinoline-2-carbonyl)cyclohexane-1-carboxylic acid | 11 | (400 MHz, DMSO-d₆) δ 11.75 (bs, 1H), 8.53 (d, 1H), 7.72 (d, 1H), 7.36 (d, 1H), 7.04 (d, 1H), 6.00 (dd, 1H), 5.48-5.33 (m, 2H), 4.04-3.82 (m, 2H), 3.66 (m, 1H), 3.57 (m, 1H), 3.46-3.27 (m, 1H), 3.24 (dd, 1H), 3.15 (m, 1H), 2.90-2.68 (m, 2H), 2.60 (s, 3H), 2.31 (m, 1H), 2.27-1.96 (m, 3H), 1.96-1.62 (m, 5H), 1.52 (m, 1H), 1.43 (m, 1H), 1.28-1.08 (m, 2H). | Method 11: 3.26 min, 581.3 [M + H]⁺ |
| 97 | 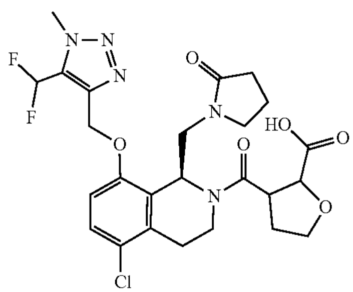 [SMILES: Cn1nnc(COc2ccc(Cl)c3c2[C@@H](CN2CCCC2=O)N(C(=O)C2CCOC2C(=O)O)CC3)c1C(F)F] | 3-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)tetrahydrofuran-2-carboxylic acid | 226 | — | Method 3: 3.43 min, 566.2 [M − H]⁻ |
| 98 | 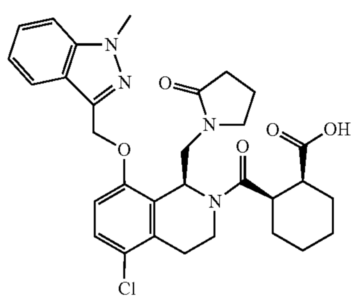 [SMILES: Cn1nc(COc2ccc(Cl)c3c2[C@@H](CN2CCCC2=O)N(C(=O)[C@@H]2CCCC[C@@H]2C(=O)O)CC3)c2ccccc21] | (1S,2R)-2-((S)-5-Chloro-8-((1-methyl-1H-indazol-3-yl)methoxy)-1-((2-oxopyrrolidin-1-yl)methyl)-1,2,3,4-tetrahydroisoquinoline-2-carbonyl)cyclohexane-1-carboxylic acid | 11 | (400 MHz, DMSO-d₆) δ 11.72 (bs, 1H), 7.91 (m, 1H), 7.67 (m, 1H), 7.44 (m, 1H), 7.38 (d, 1H), 7.28-7.17 (m, 2H), 5.78 (dd, 1H), 5.50 (d, 1H), 5.44 (d, 1H), 4.07 (s, 3H), 3.93 (dd, 1H), 3.82 (dd, 1H), 3.59 (m, 1H), 3.45-3.20 (m, 1H), 3.13 (m, 1H), 2.95 (dd, 1H), 2.82 (dd, 1H), 2.76-2.62 (m, 1H), 2.44 (m, 1H), 2.31 (m, 1H), 2.16-2.01 (m, 2H), 1.99-1.86 (m, 1H), 1.77-1.55 (m, 5H), 1.47 (m, 1H), 1.38 (m, 1H), 1.13 (m, 2H). | Method 3: 4.62 min, 577.2 [M − H]⁻ |
| 99 | 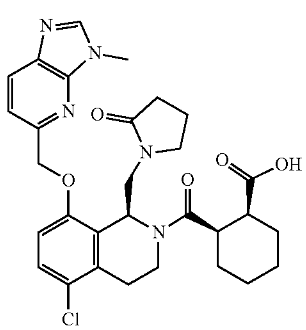 [SMILES: Cn1cnc2ccc(COc3ccc(Cl)c4c3[C@@H](CN3CCCC3=O)N(C(=O)[C@@H]3CCCC[C@@H]3C(=O)O)CC4)nc21] | (1S,2R)-2-((S)-5-chloro-8-((3-methyl-3H-imidazo[4,5-b]pyridin-5-yl)methoxy)-1-((2-oxopyrrolidin-1-yl)methyl)-1,2,3,4-tetrahydroisoquinoline-2-carbonyl)cyclohexane-1-carboxylic acid | 29 | (400 MHz, DMSO-d₆) δ 11.67 (bs, 1H), 8.45 (s, 1H), 8.18 (d, 1H), 7.54 (d, 1H), 7.35 (d, 1H), 7.09 (d, 1H), 5.96 (dd, 1H), 5.37 (d, 1H), 5.31 (d, 1H), 3.97 (dd, 1H), 3.91 (dd, 1H), 3.85 (s, 3H), 3.64 (m, 1H), 3.45 (m, 1H), 3.41-3.23 (m, 1H), 3.19 (dd, 1H), 2.92 (m, 1H), 2.84 (dd, 1H), 2.79-2.65 (m, 1H), 2.32 (bm, 1H), 2.22-2.05 (m, 2H), 2.00 (m, 1H), 1.86-1.63 (m, 5H), 1.51 (bm, 1H), 1.42 (bm, 1H), 1.18 (bm, 2H). | Method 3: 3.52 min, 578.3 [M − H]⁻ |

TABLE 3-continued

| Ex. | Structure | Name | Analogous Example | 1H NMR δ ppm | LCMS |
|---|---|---|---|---|---|
| 100 | 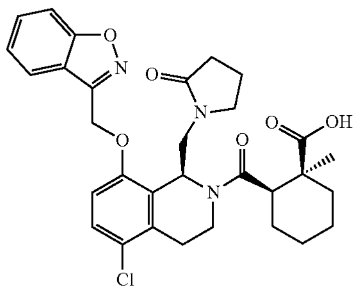 [SMILES: C[C@]1(C(=O)O)CCCC[C@H]1C(=O)N1CCc2c(Cl)ccc(OCc3noc4ccccc34)c2[C@H]1CN1CCCC1=O] | (1S,2R)-2-((S)-8-(benzo[d]isoxazol-3-ylmethoxy)-5-chloro-1-((2-oxopyrrolidin-1-yl)methyl)-1,2,3,4-tetrahydroisoquinoline-2-carbonyl)-1-methylcyclohexane-1-carboxylic acid | 91 | (400 MHz, DMSO-$d_6$) δ 11.84 (bs, 1H), 8.04 (dt, 1H), 7.83 (dt, 1H), 7.72 (m, 1H), 7.48 (m, 1H), 7.41 (d, 1H), 7.18 (d, 1H), 5.88 (dd, 1H), 5.71 (d, 1H), 5.63 (d, 1H), 3.95 (dd, 1H), 3.87 (dd, 1H), 3.61 (m, 1H), 3.24 (m, 1H), 3.04-2.95 (m, 2H), 2.84 (dd, 1H), 2.79-2.65 (m, 1H), 2.61 (m, 1H), 2.24 (m, 1H), 2.10 (m, 1H), 1.95 (m, 1H), 1.73-1.60 (m, 3H), 1.60-1.45 (m, 2H), 1.45-1.27 (m, 3H), 1.26-1.12 (m, 1H), 1.09 (s, 3H). | Method 3: 4.90 min, 580.2 [M + H]$^+$ |
| 103 | 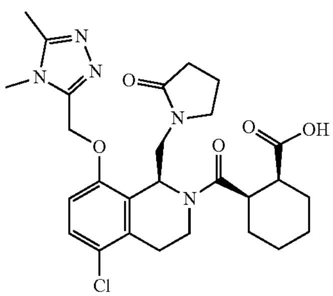 [SMILES: Cc1nnc(COc2ccc(Cl)c3c2[C@@H](CN2CCCC2=O)N(C(=O)[C@@H]2CCCC[C@@H]2C(=O)O)CC3)n1C] | (1S,2R)-2-((S)-5-chloro-8-((4,5-dimethyl-4H-1,2,4-triazol-3-yl)methoxy)-1-((2-oxopyrrolidin-1-yl)methyl)-1,2,3,4-tetrahydroisoquinoline-2-carbonyl)cyclohexane-1-carboxylic acid | 29 | (400 MHz, DMSO-$d_6$) δ 11.73 (bs, 1H), 7.38 (d, 1H), 7.19 (d, 1H), 5.82 (m, 1H), 5.40-5.25 (m, 2H), 3.96 (dd, 1H), 3.85 (dd, 1H), 3.70-3.53 (m, 4H), 3.53-3.06 (m, 2H), 3.00-2.87 (m, 2H), 2.82 (m, 1H), 2.71 (m, 1H), 2.40-2.26 (m, 4H), 2.23-1.94 (m, 3H), 1.93-1.60 (m, 5H), 1.51 (m, 1H), 1.42 (m, 1H), 1.27-1.06 (m, 2H). | Method 1: 3.14 min, 545.1 [M + H]$^+$ |
| 106 | 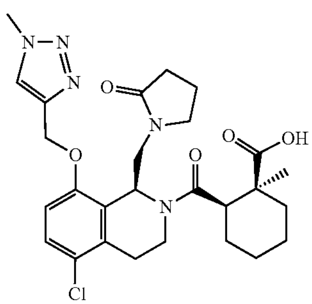 [SMILES: Cn1cc(COc2ccc(Cl)c3c2[C@@H](CN2CCCC2=O)N(C(=O)[C@@H]2CCCC[C@]2(C)C(=O)O)CC3)nn1] | (1S,2R)-2-((S)-5-chloro-8-((1-methyl-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid | 91 | (400 MHz, DMSO-$d_6$) δ 11.76 (bs, 1H), 8.24 (s, 1H), 7.35 (d, 1H), 7.13 (d, 1H), 5.81 (dd, 1H), 5.26-5.16 (m, 2H), 4.07 (s, 3H), 3.95 (dd, 1H), 3.83 (dd, 1H), 3.59 (m, 1H), 3.42 (m, 1H), 3.08-2.92 (m, 3H), 2.82 (dd, 1H), 2.69 (m, 1H), 2.30-2.09 (m, 2H), 2.01 (m, 1H), 1.94-1.71 (m, 2H), 1.71-1.47 (m, 3H), 1.46-1.28 (m, 3H), 1.28-1.13 (m, 1H), 1.10 (s, 3H). | Method 3: 3.93 min, 544.3 [M + H]$^+$ |
| 107 | 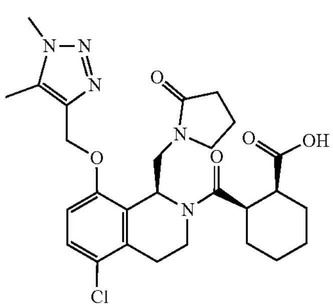 | (1S,2R)-2-((S)-5-Chloro-8-((1,5-dimethyl-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid | 105 | (300 MHz, CDCl$_3$) δ 7.29 (d, 1H), 7.00 (d, 1H), 5.95 (m, 1H), 5.20 (d, 1H), 5.11 (d, 1H), 4.11-3.53 (m, 7H), 3.24-2.98 (m, 3H), 2.74 (m, 1H), 2.57 (m, 1H), 2.47-2.06 (m, 6H), 1.98-0.89 (m, 12H). | Method 8: 1.10 min, 558.4 [M + H]+ |

TABLE 3-continued

| Ex. | Structure | Name | Analogous Example | 1H NMR δ ppm | LCMS |
|---|---|---|---|---|---|
| 113 | 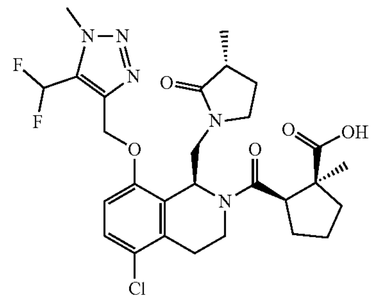 [SMILES: C[C@@H]1CCN(C[C@@H]2c3c(OCc4nnn(C)c4C(F)F)ccc(Cl)c3CCN2C(=O)[C@@H]2CCC[C@]2(C)C(=O)O)C1=O] | (1S,2R)-2-((1S)-5-Chloro-8-((5-(difluoromethyl)-1-methyl-1H-1,2,3-triazol-4-yl)methoxy)-1-(((R)-3-methyl-2-oxopyrrolidin-1-yl)methyl)-1,2,3,4-tetrahydroisoquinoline-2-carbonyl)-1-methylcyclopentane-1-carboxylic acid | 112 | (400 MHz, CDCl$_3$) δ 7.31-7.21 (m, 1H), 7.13-6.81 (m, 2H), 5.89 (m, 1H), 5.33-5.20 (m, 2H), 4.19 (s, 3H), 4.01 (m, 1H), 3.89 (m, 2H), 3.55 (m, 1H), 3.12 (m, 1H), 2.99 (m, 2H), 2.79 (m, 2H), 2.53 (m, 1H), 2.24 (m, 1H), 2.13 (m, 2H), 1.74 (m, 1H), 1.52 (m, 1H), 1.41 (m, 1H), 1.31-1.22 (m, 4H), 1.18-1.06 (m, 4H). | Method 10: 2.28 min, 594.5 [M + H]$^+$ |
| 114 | 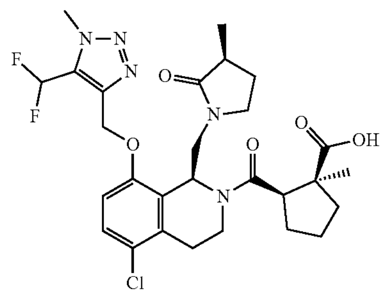 [SMILES: C[C@H]1CCN(C[C@@H]2c3c(OCc4nnn(C)c4C(F)F)ccc(Cl)c3CCN2C(=O)[C@@H]2CCC[C@]2(C)C(=O)O)C1=O] | (1S,2R)-2-((1S)-5-Chloro-8-((5-(difluoromethyl)-1-methyl-1H-1,2,3-triazol-4-yl)methoxy)-1-(((S)-3-methyl-2-oxopyrrolidin-1-yl)methyl)-1,2,3,4-tetrahydroisoquinoline-2-carbonyl)-1-methylcyclopentane-1-carboxylic acid | 112 | (400 MHz, CDCl$_3$) δ 7.27 (d, 1H), 6.97 (t, 1H), 6.95 (d, 1H), 5.91 (dd, 1H), 5.32-5.21 (m, 2H), 4.19 (s, 3H), 3.99 (dd, 1H), 3.90 (m, 2H), 3.50 (td, 1H), 3.08 (dd, 1H), 3.04-2.95 (m, 2H), 2.84-2.70 (m, 2H), 2.54 (m, 1H), 2.34 (m, 1H), 2.13 (m, 2H), 1.92-1.33 (m, 3H), 1.31-1.21 (m, 4H), 1.15-1.06 (m, 4H). | Method 10: 2.26 min, 594.2 [M + H]$^+$ |
| 115 | 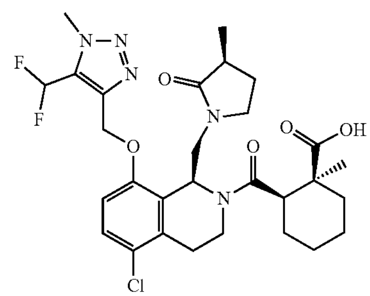 [SMILES: C[C@H]1CCN(C[C@@H]2c3c(OCc4nnn(C)c4C(F)F)ccc(Cl)c3CCN2C(=O)[C@@H]2CCCC[C@]2(C)C(=O)O)C1=O] | (1S,2R)-2-((1S)-5-Chloro-8-((5-(difluoromethyl)-1-methyl-1H-1,2,3-triazol-4-yl)methoxy)-1-(((S)-3-methyl-2-oxopyrrolidin-1-yl)methyl)-1,2,3,4-tetrahydroisoquinoline-2-carbonyl)-1-methylcyclohexane-1-carboxylic acid | 112 | (400 MHz, CDCl$_3$) δ 7.30 (d, 1H), 6.98 (d, 1H), 6.95 (t, 1H), 5.95 (dd, 1H), 5.35-5.22 (m, 2H), 4.20 (s, 3H), 4.07-3.94 (m, 2H), 3.86 (m, 1H), 3.52 (td, 1H), 3.16-2.96 (m, 3H), 2.75 (m, 1H), 2.54 (m, 1H), 2.44-2.29 (m, 2H), 2.20-2.11 (m, 1H), 1.86-1.73 (m, 2H), 1.70-1.15 (m, 5H), 1.12 (s, 3H), 1.08 (d, 3H), 1.01 (m, 1H). | Method 10: 2.50 min, 608.5 [M + H]$^+$ |
| 116 | 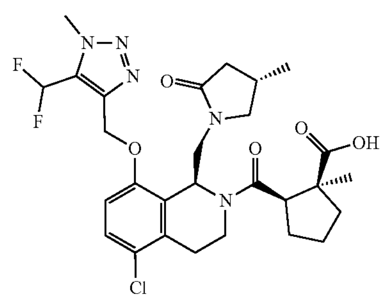 [SMILES: C[C@H]1CC(=O)N(C[C@@H]2c3c(OCc4nnn(C)c4C(F)F)ccc(Cl)c3CCN2C(=O)[C@@H]2CCC[C@]2(C)C(=O)O)C1] | (1S,2R)-2-((S)-5-chloro-8-((5-(difluoromethyl)-1-methyl-1H-1,2,3-triazol-4-yl)methoxy)-1-(((S)-4-methyl-2-oxopyrrolidin-1-yl)methyl)-1,2,3,4-tetrahydroisoquinoline-2-carbonyl)-1-methylcyclopentane-1-carboxylic acid | 111 | (300 MHz, DMSO-d$_6$) δ 7.60 (t, 1H), 7.39 (d, 1H), 7.16 (d, 1H), 5.84 (m, 1H), 5.31 (s, 2H), 4.18 (s, 3H), 3.83 (m, 1H), 3.48 (m, 2H), 3.38-1.33 (m, 15H), 0.99-0.95 (m, 6H). | Method 10: 2.28 min, 594.2 [M + H]$^+$ |
| 118 | 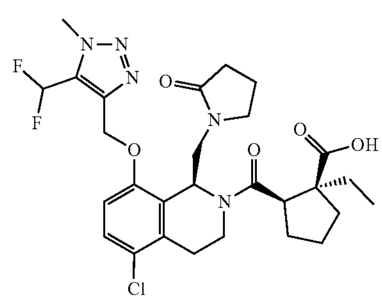 [SMILES: CC[C@]1(C(=O)O)CCC[C@H]1C(=O)N1CCc2c(Cl)ccc(OCc3nnn(C)c3C(F)F)c2[C@H]1CN1CCCC1=O] | (1S,2R)-2-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)-1-ethylcyclopentane-1-carboxylic acid | 117 | (400 MHz, DMSO-d$_6$) δ 11.43 (bs, 1H), 7.59 (t, 1H), 7.39 (d, 1H), 7.15 (d, 1H), 5.72 (dd, 1H), 5.29 (s, 2H), 4.18 (s, 3H), 4.01 (dd, 1H), 3.85 (dd, 1H), 3.66-3.51 (m, 1H), 3.40 (m, 1H), 3.07 (m, 1H), 2.96-2.89 (dd, 1H), 2.89-2.78 (m, 2H), 2.75-2.60 (m, 1H), 2.25-2.10 (m, 2H), 2.02-1.89 (m, 2H), 1.89-1.66 (m, 2H), 1.63-1.38 (m, 6H), 0.75 (t, 3H). | Method 3: 4.23 min, 592.5 [M + H]$^+$ |

TABLE 3-continued

| Ex. | Structure | Name | Analogous Example | 1H NMR δ ppm | LCMS |
|---|---|---|---|---|---|
| 119 | 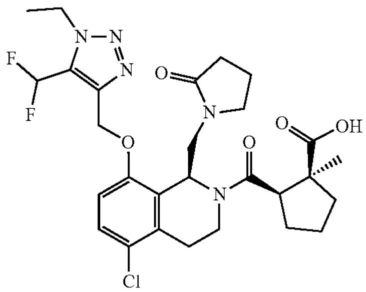 [SMILES: CCn1nnc(COc2ccc(Cl)c3c2[C@@H](CN2CCCC2=O)N(C(=O)[C@@H]2CCC[C@]2(C)C(=O)O)CC3)c1C(F)F] | (1S,2R)-2-((S)-5-chloro-8-((5-(difluoromethyl)-1-ethyl-1H-1,2,3-triazol-4-yl)methoxy)-1-((2-oxopyrrolidin-1-yl)methyl)-1,2,3,4-tetrahydroisoquinoline-2-carbonyl)-1-methylcyclopentane-1-carboxylic acid | 102 | (400 MHz, DMSO-$d_6$) δ 11.44 (bs, 1H), 7.63 (t, 1H), 7.40 (d, 1H), 7.15 (d, 1H), 5.70 (dd, 1H), 5.28 (s, 2H), 4.55 (m, 2H), 3.99 (dd, 1H), 3.85 (dd, 1H), 3.56 (m, 1H), 3.47-3.20 (m, 1H), 3.03 (m, 1H), 2.90 (dd, 1H), 2.84 (dd, 1H), 2.76-2.60 (m, 2H), 2.36-2.23 (m, 1H), 2.23-1.51 (m, 8H), 1.50-1.34 (m, 4H), 1.14 (s, 3H). | Method 3a: 2.75 min, 592.4 [M − H]$^-$ |
| 120 | 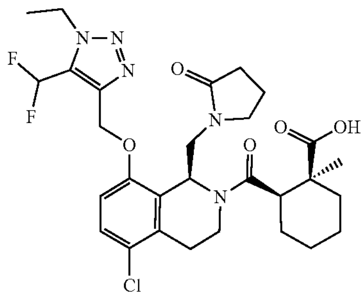 [SMILES: CCn1nnc(COc2ccc(Cl)c3c2[C@@H](CN2CCCC2=O)N(C(=O)[C@@H]2CCCC[C@]2(C)C(=O)O)CC3)c1C(F)F] | (1S,2R)-2-((S)-5-chloro-8-((5-(difluoromethyl)-1-ethyl-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid | 91 | (400 MHz; DMSO-$d_6$) δ: 11.81 (bs, 1H), 7.62 (t, 1H), 7.41 (d, 0.07 H), 7.38 (d, 0.93 H), 7.19 (d, 0.07 H), 7.14 (d, 0.93H), 5.76 (dd, 0.75 H), 5.01 (dd, 0.25 H), 5.29 (s, 2 H), 4.56 (q, 2 H), 3.95 (dd, 1 H), 3.83 (dd, 1H), 3.65-3.51 (m, 1 H), 2.98-2.91 (m, 2 H), 2.80-2.66 (m, 3 H), 2.26-2.11 (m, 3H), 2.02-1.94 (m, 1H), 1.85-1.71 (m, 2 H), 1.64-1.49 (m, 3H), 1.46 (t, 3H), 1.42-1.32 (m, 3H), 1.21-1.14 (m, 1H), 1.09 (s, 3H). | Method 3a: 3.00 min, 608.5 [M + H]$^+$ |
| 121 | 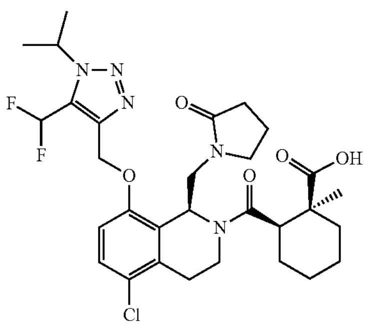 [SMILES: CC(C)n1nnc(COc2ccc(Cl)c3c2[C@@H](CN2CCCC2=O)N(C(=O)[C@@H]2CCCC[C@]2(C)C(=O)O)CC3)c1C(F)F] | (1S,2R)-2-((S)-5-chloro-8-((5-(difluoromethyl)-1-isopropyl-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid | 91 | (400 MHz, DMSO-$d_6$) δ 11.81 (bs, 1H), 7.64 (t, 1H), 7.39 (d, 1H), 7.14 (d, 1H), 5.75 (dd, 1H), 5.32-5.24 (m, 2H), 4.92 (m, 1H), 3.95 (dd, 1H), 3.84 (m, 1H), 3.57 (m, 1H), 3.41-3.17 (m, 1H), 2.97 (m, 1H), 2.90 (dd, 1H), 2.82 (dd, 1H), 2.76-2.63 (m, 2H), 2.30-2.08 (m, 2H), 1.97 (m, 1H), 1.84-1.67 (m, 2H), 1.66-1.45 (m, 9H), 1.44-1.26 (m, 3H), 1.24-1.00 (m, 4H). | Method 3: 4.79 min, 622.0 [M + H]$^+$ |
| 122 | 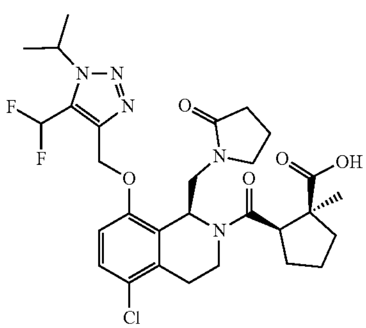 [SMILES: CC(C)n1nnc(COc2ccc(Cl)c3c2[C@@H](CN2CCCC2=O)N(C(=O)[C@@H]2CCC[C@]2(C)C(=O)O)CC3)c1C(F)F] | (1S,2R)-2-((S)-5-chloro-8-((5-(difluoromethyl)-1-isopropyl-1H-1,2,3-triazol-4-yl)methoxy)-1-((2-oxopyrrolidin-1-yl)methyl)-1,2,3,4-tetrahydroisoquinoline-2-carbonyl)-1-methylcyclopentane-1-carboxylic acid | 102 | (400 MHz, DMSO-$d_6$) δ 11.45 (bs, 1H), 7.64 (t, 1H), 7.40 (d, 1H), 7.14 (d, 1H), 5.68 (dd, 1H), 5.40-5.22 (m, 2H), 4.92 (m, 1H), 3.99 (dd, 1H), 3.86 (dd, 1H), 3.55 (m, 1H), 3.47-3.20 (m, 1H), 3.03 (m, 1H), 2.91-2.76 (m, 2H), 2.72-2.58 (m, 2H), 2.35-2.24 (m, 1H), 2.21-1.83 (m, 3H), 1.80-1.50 (m, 11H), 1.44-1.34 (m, 1H), 1.14 (s, 3H). | Method 3a: 2.64 min, 608.5 [M + H]$^+$ |
| 124 | 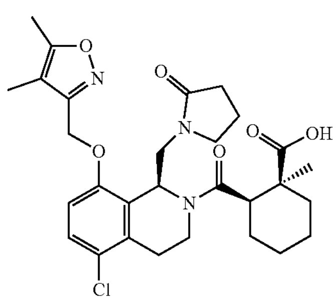 [SMILES: Cc1onc(COc2ccc(Cl)c3c2[C@@H](CN2CCCC2=O)N(C(=O)[C@@H]2CCCC[C@]2(C)C(=O)O)CC3)c1C] | (1S,2R)-2-((S)-5-chloro-8-((4,5-dimethylisoxazol-3-yl)methoxy)-1-((2-oxopyrrolidin-1-yl)methyl)-1,2,3,4-tetrahydroisoquinoline-2-carbonyl)-1-methylcyclohexane-1-carboxylic acid | 91 | (400 MHz, DMSO-$d_6$) δ 11.82 (bs, 1H), 7.37 (d, 1H), 7.09 (d, 1H), 5.86 (dd, 1H), 5.24 (d, 1H), 5.18 (d, 1H), 3.96 (dd, 1H), 3.88 (dd, 1H), 3.61 (m, 1H), 3.48 (m, 1H), 3.06-2.93 (m, 3H), 2.83 (dd, 1H), 2.78-2.64 (m, 1H), 2.35 (s, 3H), 2.30-2.10 (m, 2H), 2.06-1.94 (m, 4H), 1.94-1.72 (m, 2H), 1.71-1.47 (m, 3H), 1.45-1.28 (m, 3H), 1.27-1.14 (m, 1H), 1.10 (s, 3H). | Method 2: 4.69 min, 556.4 [M − H]$^-$ |

TABLE 3-continued

| Ex. | Structure | Name | Analogous Example | 1H NMR δ ppm | LCMS |
|---|---|---|---|---|---|
| 125 | 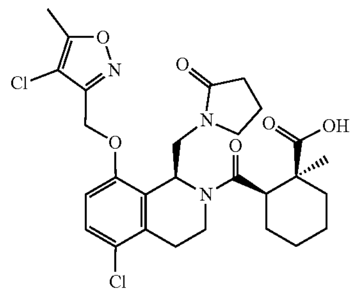 [SMILES: Cc1onc(COc2ccc(Cl)c3c2[C@@H](CN2CCCC2=O)N(C(=O)[C@@H]2CCCC[C@]2(C)C(=O)O)CC3)c1Cl] | (1S,2R)-2-((S)-5-chloro-8-((4-chloro-5-methylisoxazol-3-yl)methoxy)-1-((2-oxopyrrolidin-1-yl)methyl)-1,2,3,4-tetrahydroisoquinoline-2-carbonyl)-1-methylcyclohexane-1-carboxylic acid | 91 | (400 MHz, DMSO-$d_6$) δ 11.84 (bs, 1H), 7.38 (d, 1H), 7.10 (d, 1H), 5.87 (dd, 1H), 5.32 (d, 1H), 5.23 (d, 1H), 3.95 (dd, 1H), 3.88 (dd, 1H), 3.60 (m, 1H), 3.51 (m, 1H), 3.10-2.92 (m, 3H), 2.87-2.65 (m, 2H), 2.47 (s, 3H), 2.30-2.11 (m, 2H), 2.00 (m, 1H), 1.94-1.73 (m, 2H), 1.71-1.47 (m, 3H), 1.46-1.13 (m, 4H), 1.08 (s, 3H). | Method 1: 4.87 min, 578.4 [M + H]$^-$ |
| 126 | 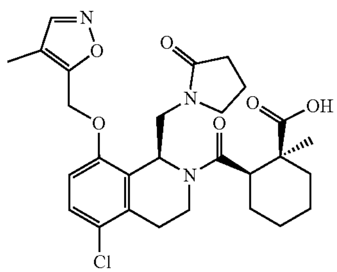 [SMILES: Cc1cnoc1COc1ccc(Cl)c2c1[C@@H](CN1CCCC1=O)N(C(=O)[C@@H]1CCCC[C@]1(C)C(=O)O)CC2] | (1S,2R)-2-((S)-5-chloro-8-((4-methylisoxazol-5-yl)methoxy)-1-((2-oxopyrrolidin-1-yl)methyl)-1,2,3,4-tetrahydroisoquinoline-2-carbonyl)-1-methylcyclohexane-1-carboxylic acid | 91 | (400 MHz, DMSO-$d_6$) δ 11.80 (bs, 1H), 8.52 (s, 1H), 7.40 (d, 1H), 7.09 (d, 1H), 5.82 (dd, 1H), 5.35-5.26 (m, 2H), 3.96 (dd, 1H), 3.89 (dd, 1H), 3.60 (m, 1H), 3.44 (m, 1H), 3.03-2.90 (m, 3H), 2.83 (dd, 1H), 2.78-2.65 (m, 1H), 2.31-2.12 (m, 2H), 2.09 (s, 3H), 2.00 (m, 1H), 1.94-1.72 (m, 2H), 1.71-1.47 (m, 3H), 1.46-1.27 (m, 3H), 1.27-1.13 (m, 1H), 1.10 (s, 3H). | Method 2: 4.43 min, 544.4 [M + H]$^+$ |
| 127 | 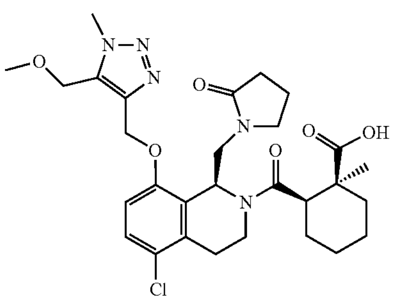 [SMILES: COCc1c(COc2ccc(Cl)c3c2[C@@H](CN2CCCC2=O)N(C(=O)[C@@H]2CCCC[C@]2(C)C(=O)O)CC3)nnn1C] | (1S,2R)-2-((S)-5-chloro-8-((5-(methoxymethyl)-1-methyl-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid | 123 | (300 MHz, CDCl$_3$) δ 7.30 (d, 1H), 6.98 (d, 1H), 5.94 (m, 1H), 5.24 (d, 1H), 5.14 (d, 1H), 4.61-4.48 (m, 2H), 4.07 (s, 3H), 4.05-3.80 (m, 3H), 3.59 (m, 1H), 3.37 (s, 3H), 3.17 (dd, 1H), 3.11-2.99 (m, 2H), 2.73 (m, 1H), 2.57 (m, 1H), 2.40 (m, 1H), 2.35-2.04 (m, 2H), 2.00-1.73 (m, 4H), 1.71-1.43 (m, 3H), 1.42-1.22 (m, 1H), 1.11 (s, 3H), 1.01 (m, 1H). | Method 10: 1.96 min, 588.3 [M + H]$^+$ |
| 128 | 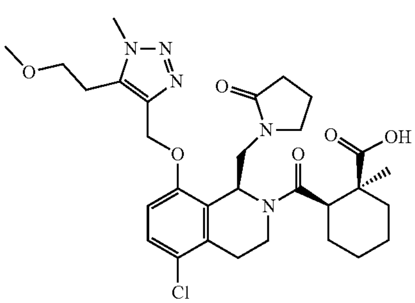 [SMILES: COCCc1c(COc2ccc(Cl)c3c2[C@@H](CN2CCCC2=O)N(C(=O)[C@@H]2CCCC[C@]2(C)C(=O)O)CC3)nnn1C] | (1S,2R)-2-((i)-5-chloro-8-((5-(2-methoxyethyl)-1-methyl-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid | 123 | (300 MHz, CDCl$_3$) δ 7.30 (d, 1H), 7.00 (d, 1H), 5.95 (dd, 1H), 5.20 (d, 1H), 5.10 (d, 1H), 4.09-3.82 (m, 6H), 3.62-3.45 (m, 3H), 3.27 (s, 3H), 3.17 (dd, 1H), 3.11-2.90 (m, 4H), 2.74 (m, 1H), 2.58 (dd, 1H), 2.40 (m, 1H), 2.33-2.20 (m, 1H), 2.19-2.08 (m, 1H), 1.97-1.76 (m, 4H), 1.69-1.42 (m, 3H), 1.41-1.25 (m, 1H), 1.11 (s, 3H), 1.01 (m, 1H). | Method 10: 2.00 min, 602.4 [M + H]$^+$ |
| 129 | 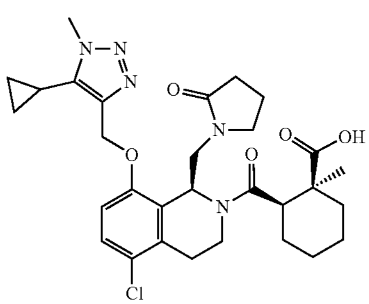 [SMILES: Cn1nnc(COc2ccc(Cl)c3c2[C@@H](CN2CCCC2=O)N(C(=O)[C@@H]2CCCC[C@]2(C)C(=O)O)CC3)c1C1CC1] | (1S,2R)-2-((S)-5-chloro-8-((5-cyclopropyl-1-methyl-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid | 123 | (300 MHz, CDCl$_3$) δ 7.29 (d, 1H), 7.06 (d, 1H), 5.97 (dd, 1H), 5.22-5.12 (m, 2H), 4.09-3.92 (m, 5H), 3.86 (m, 1H), 3.62 (m, 1H), 3.19 (dd, 1H), 3.14-3.01 (m, 2H), 2.74 (m, 1H), 2.57 (m, 1H), 2.40 (m, 1H), 2.34-2.21 (m, 1H), 2.20-2.10 (m, 1H), 1.99-1.77 (m, 4H), 1.71 (m, 1H), 1.67-1.43 (m, 3H), 1.41-1.22 (m, 1H), 1.14-1.06 (m, 5H), 1.01 (m, 1H), 0.85-0.73 (m, 2H). | Method 10: 2.09 min, 584.3 [M + H]$^+$ |

TABLE 3-continued

| Ex. | Structure | Name | Analogous Example | 1H NMR δ ppm | LCMS |
|---|---|---|---|---|---|
| 130 | 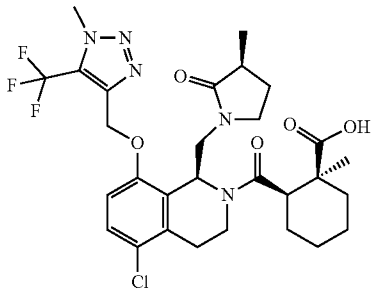 [SMILES: C[C@H]1CCN(C[C@@H]2c3c(OCc4nnn(C)c4C(F)(F)F)ccc(Cl)c3CCN2C(=O)[C@@H]2CCCC[C@]2(C)C(=O)O)C1=O] | (1S,2R)-2-((S)-5-chloro-1-(((S)-3-methyl-2-oxopyrrolidin-1-yl)methyl)-8-((1-methyl-5-(trifluoromethyl)-1H-1,2,3-triazol-4-yl)methoxy)-1,2,3,4-tetrahydroisoquinoline-2-carbonyl)-1-methylcyclohexane-1-carboxylic acid | 112 | (400 MHz, DMSO-$d_6$) δ 12.02 (bs, 1H), 7.38 (d, 1H), 7.16 (d, 1H), 5.80 (dd, 1H), 5.41-5.25 (m, 2H), 4.24 (m, 3H), 3.96 (dd, 1H), 3.84 (dd, 1H), 3.59 (m, 1H), 2.99-2.88 (m, 2H), 2.87-2.68 (m, 3H), 2.27 (m, 1H), 2.21-2.03 (m, 2H), 1.71-1.45 (m, 3H), 1.43-1.19 (m, 6H), 1.07 (s, 3H), 0.96 (d, 3H). | Method 13: 2.69 min, 626.5 [M + H]+ |
| 131 | 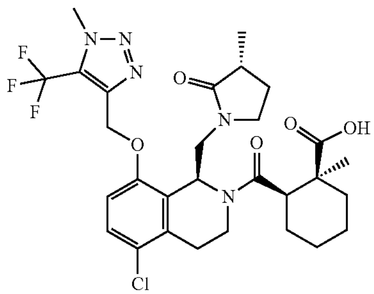 [SMILES: C[C@@H]1CCN(C[C@@H]2c3c(OCc4nnn(C)c4C(F)(F)F)ccc(Cl)c3CCN2C(=O)[C@@H]2CCCC[C@]2(C)C(=O)O)C1=O] | (1S,2R)-2-((S)-5-chloro-1-(((R)-3-methyl-2-oxopyrrolidin-1-yl)methyl)-8-((1-methyl-5-(trifluoromethyl)-1H-1,2,3-triazol-4-yl)methoxy)-1,2,3,4-tetrahydroisoquinoline-2-carbonyl)-1-methylcyclohexane-1-carboxylic acid | 112 | (300 MHz, DMSO-$d_6$) δ 11.83 (bs, 1H), 7.38 (d, 1H), 7.16 (d, 1H), 5.77 (dd, 1H), 5.45-5.24 (m, 2H), 4.24 (m, 3H), 4.03-3.79 (m, 2H), 3.58 (m, 1H), 3.04-2.89 (m, 2H), 2.89-2.63 (m, 3H), 2.31-1.99 (m, 3H), 1.73-1.12 (m, 9H), 1.08 (s, 3H), 0.99 (d, 3H). | Method 13: 2.70 min, 626.3 [M + H]+ |
| 132 | 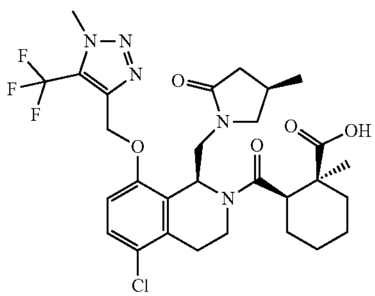 [SMILES: C[C@@H]1CC(=O)N(C[C@@H]2c3c(OCc4nnn(C)c4C(F)(F)F)ccc(Cl)c3CCN2C(=O)[C@@H]2CCCC[C@]2(C)C(=O)O)C1] | (1S,2R)-2-((S)-5-chloro-1-(((R)-4-methyl-2-oxopyrrolidin-1-yl)methyl)-8-((1-methyl-5-(trifluoromethyl)-1H-1,2,3-triazol-4-yl)methoxy)-1,2,3,4-tetrahydroisoquinoline-2-carbonyl)-1-methylcyclohexane-1-carboxylic acid | 109 | (300 MHz, DMSO-$d_6$) δ 7.38 (d, 1H), 7.16 (d, 1H), 5.76 (m, 1H), 5.41-5.24 (m, 2H), 4.25 (m, 3H), 4.02-3.81 (m, 2H), 3.61 (m, 1H), 3.08-2.70 (m, 6H), 2.36-2.13 (m, 3H), 1.77-1.18 (m, 8H), 1.08 (s, 3H), 0.98 (d, 3H). | Method 13: 2.67 min, 626.2 [M + H]+ |
| 133 | 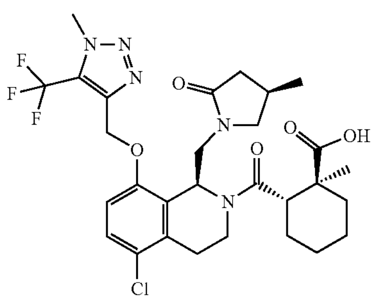 [SMILES: C[C@@H]1CC(=O)N(C[C@@H]2c3c(OCc4nnn(C)c4C(F)(F)F)ccc(Cl)c3CCN2C(=O)[C@H]2CCCC[C@]2(C)C(=O)O)C1] | (1S,2S)-2-((S)-5-chloro-1-(((R)-4-methyl-2-oxopyrrolidin-1-yl)methyl)-8-((1-methyl-5-(trifluoromethyl)-1H-1,2,3-triazol-4-yl)methoxy)-1,2,3,4-tetrahydroisoquinoline-2-carbonyl)-1-methylcyclohexane-1-carboxylic acid | isolated from 132 | (300 MHz, CDCl$_3$) δ 7.31-7.18 (m, 1H), 6.95 (d, 1H), 5.94 (dd, 1H), 5.34-5.16 (m, 2H), 4.20 (m, 3H), 4.09-3.88 (m, 2H), 3.87-3.72 (m, 1H), 3.33 (dd, 1H), 3.19 (m, 1H), 3.13-3.00 (m, 2H), 2.98-2.72 (m, 2H), 2.51-2.26 (m, 2H), 1.96-1.19 (m, 12H), 1.07 (d, 3H). | Method 13: 2.63 min, 626.2 [M + H]+ |
| 134 | 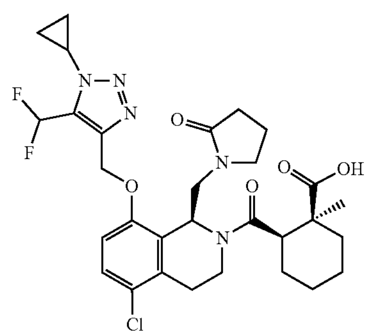 [SMILES: C[C@]1(C(=O)O)CCCC[C@H]1C(=O)N1CCc2c(Cl)ccc(OCc3nnn(C4CC4)c3C(F)F)c2[C@H]1CN1CCCC1=O] | (1S,2R)-2-((S)-5-chloro-8-((1-cyclopropyl-5-(difluoromethyl)-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid | 91 | (400 MHz, CDCl$_3$) δ 15.08 (bs, 1H), 7.29 (d, 1H), 7.05 (t, 1H), 7.00 (d, 1H), 5.97 (dd, 1H), 5.28 (s, 2H), 4.09-3.91 (m, 2H), 3.86 (m, 1H), 3.74-3.60 (m, 2H), 3.18 (dd, 1H), 3.13-3.00 (m, 2H), 2.74 (m, 1H), 2.56 (dd, 1H), 2.40 (m, 1H), 2.28 (m, 1H), 2.15 (m, 1H), 1.98-1.76 (m, 4H), 1.69-1.45 (m, 3H), 1.44-1.18 (m, 5H), 1.12 (s, 3H), 1.01 (m, 1H). | Method 3: 4.57 min, 620.0 [M + H]+ |

TABLE 3-continued

| Ex. | Structure | Name | Analogous Example | 1H NMR δ ppm | LCMS |
|---|---|---|---|---|---|
| 136 | 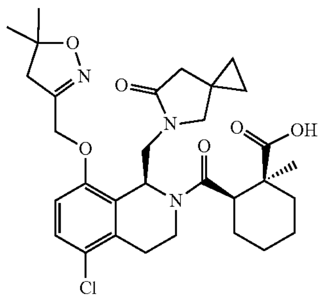 [SMILES: CC1(C)CC(COc2ccc(Cl)c3c2[C@@H](CN2CC4(CC4)CC2=O)N(C(=O)[C@@H]2CCCC[C@]2(C)C(=O)O)CC3)=NO1] | (1S,2R)-2-((S)-5-chloro-8-((5,5-dimethyl-4,5-dihydroisoxazol-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid | 170 | (300 MHz, methanol-$d_3$) δ 7.32 (m, 1H), 6.97 (m, 1H), 6.05 (m, 1H), 5.02-4.67 (m, 2H), 4.22-3.96 (m, 2H), 3.91-3.53 (m, 2H), 3.47-3.18 (m, 1H), 3.16-2.17 (m, 9H), 1.90-1.06 (m, 16H), 0.83-0.51 (m, 4H). | Method 14 (to 50% A 3 mins): 1.77 min, 586.1 [M + H]$^+$ |
| 137 | 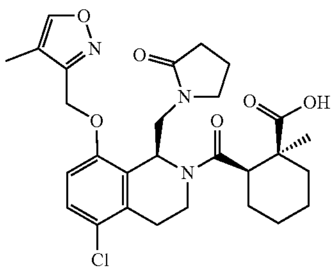 [SMILES: Cc1conc1COc1ccc(Cl)c2c1[C@@H](CN1CCCC1=O)N(C(=O)[C@@H]1CCCC[C@]1(C)C(=O)O)CC2] | (1S,2R)-2-((S)-5-chloro-8-((4-methylisoxazol-3-yl)methoxy)-1-((2-oxopyrrolidin-1-yl)methyl)-1,2,3,4-tetrahydroisoquinoline-2-carbonyl)-1-methylcyclohexane-1-carboxylic acid | 91 | (400 MHz, CDCl$_3$) δ 15.21 (bs, 1H), 8.24 (m, 1H), 7.31 (d, 1H), 6.92 (d, 1H), 6.03 (dd, 1H), 5.22 (d, 1H), 5.13 (d, 1H), 4.06 (dd, 1H), 3.98 (m, 1H), 3.88 (m, 1H), 3.69 (m, 1H), 3.17-3.01 (m, 3H), 2.76 (m, 1H), 2.57 (dd, 1H), 2.41 (m, 1H), 2.28 (m, 1H), 2.21-2.09 (m, 4H), 1.98-1.77 (m, 4H), 1.68-1.44 (m, 3H), 1.34 (m, 1H), 1.13 (s, 3H), 1.02 (m, 1H). | Method 3: 4.48 min, 544.1 [M + H]$^+$ |
| 138 | 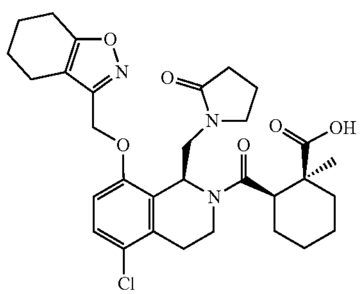 [SMILES: C[C@]1(C(=O)O)CCCC[C@H]1C(=O)N1CCc2c(Cl)ccc(OCc3noc4c3CCCC4)c2[C@H]1CN1CCCC1=O] | (1S,2R)-2-((S)-5-chloro-1-((2-oxopyrrolidin-1-yl)methyl)-8-((4,5,6,7-tetrahydrobenzo[d]isoxazol-3-yl)methoxy)-1,2,3,4-tetrahydroisoquinoline-2-carbonyl)-1-methylcyclohexane-1-carboxylic acid | 91 | (400 MHz, DMSO-$d_6$) δ 11.84 (bs, 1H), 7.37 (d, 1H), 7.08 (d, 1H), 5.86 (dd, 1H), 5.26 (d, 1H), 5.19 (d, 1H), 4.02-3.82 (m, 2H), 3.61 (m, 1H), 3.50 (m, 1H), 3.08-2.93 (m, 3H), 2.88-2.64 (m, 4H), 2.56-2.41 (m, 2H), 2.30-2.11 (m, 2H), 2.01 (m, 1H), 1.94-1.48 (m, 9H), 1.47-1.28 (m, 3H), 1.21 (m, 1H), 1.10 (s, 3H). | Method 3: 4.89 min, 584.1 [M + H]$^+$ |
| 139 | 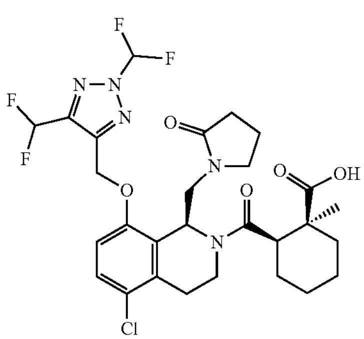 | (1S,2R)-2-((S)-8-((2,5-bis(difluoromethyl)-2H-1,2,3-triazol-4-yl)methoxy)-5-chloro-1((2-oxopyrrolidin-1-yl)methyl)-1,2,3,4-tetrahydroisoquinoline-2-carbonyl)-1-methylcyclohexane-1-carboxylic acid | 193 | (300 MHz, CDCl$_3$) δ 7.33 (t, 1H), 7.32 (d, 1H), 6.90 (t, 1H), 6.90 (d, 1H), 6.07 (dd, 1H), 5.39-5.23 (m, 2H), 4.14 (dd, 1H), 4.02 (m, 1H), 3.90 (m, 1H), 3.54 (d, 1H), 3.23 (dd, 1H), 3.16-3.02 (m, 2H), 2.76 (m, 1H), 2.59 (m, 1H), 2.47-2.34 (m, 2H), 2.13 (d, 1H), 1.92-1.76 (m, 2H), 1.74-1.21 (m, 4H), 1.13 (s, 3H), 1.09-0.95 (m, 1H), 0.73-0.45 (m, 4H). | Method 9b: 1.80 min, 656.3 [M + H]$^+$ |

TABLE 3-continued

| Ex. | Structure | Name | Analogous Example | 1H NMR δ ppm | LCMS |
|---|---|---|---|---|---|
| 145 | 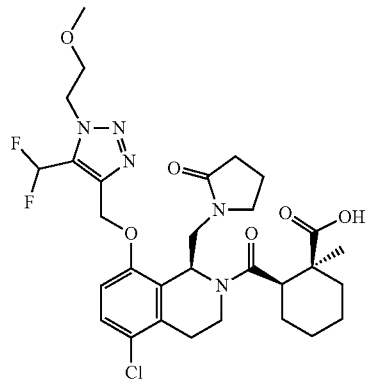 [SMILES: COCCn1nnc(COc2ccc(Cl)c3c2[C@@H](CN2CCCC2=O)N(C(=O)[C@@H]2CCCC[C@]2(C)C(=O)O)CC3)c1C(F)F] | (1S,2R)-2-((S)-5-chloro-8-((5-(difluoromethyl)-1-(2-methoxyethyl)-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid | 91 | (400 MHz, CDCl$_3$) δ 15.31 (bs, 1H), 7.30 (d, 1H), 7.12 (t, 1H), 7.01 (d, 1H), 5.98 (dd, 1H), 5.30 (s, 2H), 4.62 (m, 2H), 4.08-3.91 (m, 2H), 3.86 (m, 1H), 3.77 (t, 2H), 3.67 (m, 1H), 3.31 (s, 3H), 3.22 (dd, 1H), 3.16-3.01 (m, 2H), 2.74 (m, 1H), 2.56 (dd, 1H), 2.40 (m, 1H), 2.27 (m, 1H), 2.15 (m, 1H), 1.99-1.76 (m, 4H), 1.68-1.44 (m, 3H), 1.34 (m, 1H), 1.12 (s, 3H), 1.01 (m, 1H). | Method 3: 4.45 min, 638.1 [M + H]$^+$ |
| 148 | 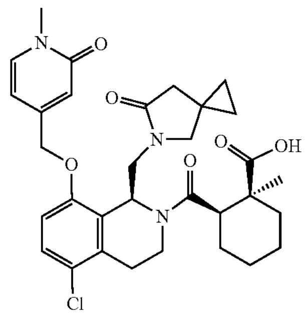 [SMILES: Cn1ccc(COc2ccc(Cl)c3c2[C@@H](CN2CC4(CC4)CC2=O)N(C(=O)[C@@H]2CCCC[C@]2(C)C(=O)O)CC3)cc1=O] | (1S,2R)-2-((S)-5-chloro-8-((1-methyl-2-oxo-1,2-dihydropyridin-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid | 135 | (400 MHz, CDCl$_3$) δ 7.35-7.21 (m, 2H), 6.70 (d, 1H), 6.58 (s, 1H), 6.19-6.08 (m, 2H), 4.99-4.86 (m, 2H), 4.19 (dd, 1H), 4.03 (m, 1H), 3.91 (dd, 1H), 3.64 (d, 1H), 3.53 (s, 3H), 3.26 (d, 1H), 3.20 (dd, 1H), 3.09 (dd, 1H), 2.78 (m, 1H), 2.63 (m, 1H), 2.51-2.36 (m, 2H), 2.15 (d, 1H), 1.89-1.76 (m, 2H), 1.73-1.45 (m, 3H), 1.44-1.27 (m, 1H), 1.15 (s, 3H), 1.11-0.99 (m, 1H), 0.78-0.53 (m, 4H). | Method 9b: 1.39 min, 596.3 [M + H]$^+$ |
| 149 | 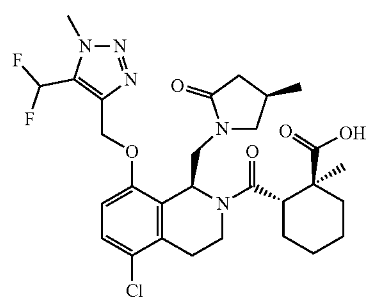 [SMILES: C[C@@H]1CC(=O)N(C[C@@H]2c3c(OCc4nnn(C)c4C(F)F)ccc(Cl)c3CCN2C(=O)[C@H]2CCCC[C@]2(C)C(=O)O)C1] | (1S,2S)-2-((S)-5-chloro-8-((5-(difluoromethyl)-1-methyl-1H-1,2,3-triazol-4-yl)methoxy)-1-(((R)-4-methyl-2-oxopyrrolidin-1-yl)methyl)-1,2,3,4-tetrahydroisoquinoline-2-carbonyl)-1-methylcyclohexane-1-carboxylic acid | isolated from synthesis of example 111 | (400 MHz, DMSO-d$_6$) δ 7.59 (t, 1H), 7.37 (d, 1H), 7.14 (d, 1H), 5.78 (m, 1H), 5.45-5.17 (m, 2H), 4.18 (s, 3H), 4.01 (m, 1H), 3.85 (dd, 1H), 3.60 (m, 1H), 3.14-2.63 (m, 6H), 2.38-2.17 (m, 2H), 1.80-0.71 (m, 15H) | Method 9a: 0.97 min, 608.3 [M + H]$^+$ |
| 150 | 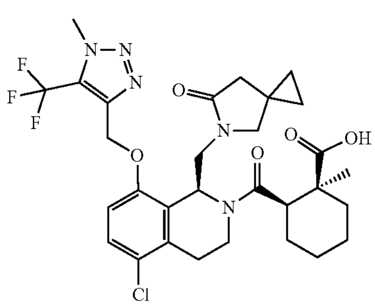 [SMILES: Cn1nnc(COc2ccc(Cl)c3c2[C@@H](CN2CC4(CC4)CC2=O)N(C(=O)[C@@H]2CCCC[C@]2(C)C(=O)O)CC3)c1C(F)(F)F] | (1S,2R)-2-((S)-5-chloro-8-((1-methyl-5-(trifluoromethyl)-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid | 112 | (300 MHz, CDCl$_3$) δ: $^1$H NMR (300 MHz, CDCl3) δ 7.29 (d, 1H), 7.01 (d, 1H), 5.95 (dd, 1H), 5.36-5.24 (m, 2H), 4.20 (m, 3H), 4.11 (dd, 1H), 4.05-3.79 (m, 2H), 3.48 (d, 1H), 3.17 (dd, 1H), 3.13-2.99 (m, 2H), 2.74 (m, 1H), 2.58 (m, 1H), 2.48-2.34 (m, 2H), 2.12 (d, 1H), 1.92-1.75 (m, 2H), 1.74-1.45 (m, 3H), 1.35 (m, 1H), 1.12 (s, 3H), 1.01 (m, 1H), 0.76-0.45 (m, 4H). | Method 13* 2.41 min, 638.2 [M + H]$^+$. Specifc gradient: 20% B with 80% C to 70% B with 30% C over 3 min, to 95% B with 5% C to 4.5 min) |

TABLE 3-continued

| Ex. | Structure | Name | Analogous Example | 1H NMR δ ppm | LCMS |
|---|---|---|---|---|---|
| 153 | 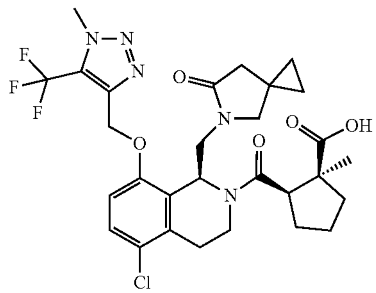 [SMILES: Cn1nnc(COc2ccc(Cl)c3c2[C@@H](CN2CC4(CC4)CC2=O)N(C(=O)[C@@H]2CCC[C@]2(C)C(=O)O)CC3)c1C(F)(F)F] | (1S,2R)-2-((S)-5-chloro-8-((1-methyl-5-(trifluoromethyl)-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclopentane-1-carboxylic acid | 112 | (300 MHz, CDCl$_3$) δ 7.26 (d, 1H), 6.99 (d, 1H), 5.93 (dd, 1H), 5.35-5.17 (m, 2H), 4.19 (s, 3H), 4.09 (dd, 1H), 3.91 (m, 2H), 3.63-3.40 (m, 1H), 3.23-2.89 (m, 3H), 2.88-2.65 (m, 2H), 2.57 (m, 1H), 2.37 (d, 1H), 2.27-2.03 (m, 2H), 1.93-1.60 (m, 3H), 1.50-1.32 (m, 1H), 1.28 (s, 3H), 0.73-0.42 (m, 4H). | Method 13: 2.53 min, 624.2 [M + H]$^+$. |
| 154 | 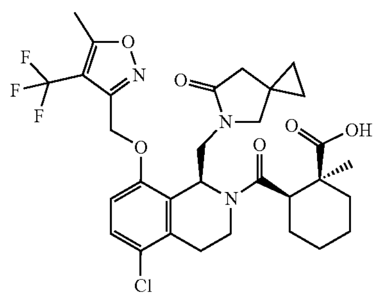 [SMILES: Cc1onc(COc2ccc(Cl)c3c2[C@@H](CN2CC4(CC4)CC2=O)N(C(=O)[C@@H]2CCCC[C@]2(C)C(=O)O)CC3)c1C(F)(F)F] | (1S,2R)-2-((S)-5-chloro-8-((5-methyl-4-(trifluoromethyl)isoxazol-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid | 135 | (300 MHz, CDCl$_3$) δ 7.29 (d, 1H), 6.91 (d, 1H), 6.05 (dd, 1H), 5.27-5.12 (m, 2H), 4.13 (dd, 1H), 4.08-3.81 (m, 2H), 3.57 (d, 1H), 3.27-3.14 (m, 2H), 3.08 (m, 1H), 2.76 (m, 1H), 2.64-2.52 (m, 4H), 2.49-2.34 (m, 2H), 2.13 (d, 1H), 1.92-1.75 (m, 2H), 1.71-1.18 (m, 4H), 1.13 (s, 3H), 1.02 (m, 1H), 0.76-0.50 (m, 4H). | Method 14: 3.04 min, 638.2 [M + H]$^+$. |
| 155 | 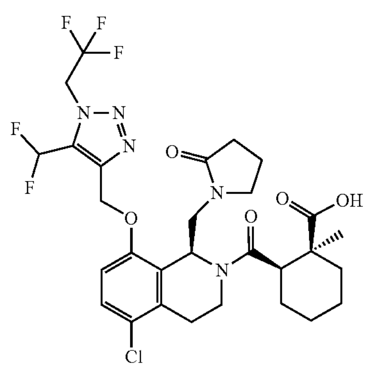 [SMILES: C[C@]1(C(=O)O)CCCC[C@H]1C(=O)N1CCc2c(Cl)ccc(OCc3nnn(CC(F)(F)F)c3C(F)F)c2[C@H]1CN1CCCC1=O] | (1S,2R)-2-((S)-5-chloro-8-((5-(difluoromethyl)-1-(2,2,2-trifluoroethyl)-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid | 127 | (300 MHz, CD$_3$OH) δ 7.38 (t, 1H), 7.35 (d, 1H), 7.11 (d, 1H), 5.89 (m, 1H), 5.56-5.43 (m, 2H), 5.42-5.26 (m, 2H), 4.13-3.66 (m, 3H), 3.61-3.48 (m, 1H), 3.18 (dd, 1H), 3.10-2.74 (m, 4H), 2.45-2.09 (m, 3H), 2.03-1.26 (m, 9H), 1.21 (s, 3H). | Method 10: 2.41 min, 662.3 [M + H]$^+$ |
| 157 | 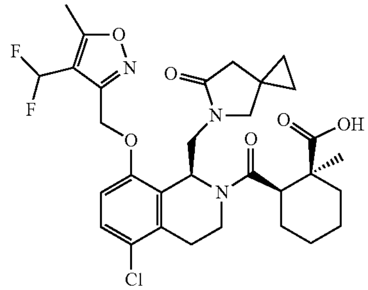 [SMILES: Cc1onc(COc2ccc(Cl)c3c2[C@@H](CN2CC4(CC4)CC2=O)N(C(=O)[C@@H]2CCCC[C@]2(C)C(=O)O)CC3)c1C(F)F] | (1S,2R)-2-((S)-5-chloro-8-((4-(difluoromethyl)-5-methylisoxazol-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid | 156 | (300 MHz, CDCl$_3$) δ 7.28 (d, 1H), 6.90 (d, 1H), 6.68 (t, 1H), 6.05 (dd, 1H), 5.29-5.16 (m, 2H), 4.12 (dd, 1H), 4.07-3.77 (m, 2H), 3.56 (d, 1H), 3.27-3.13 (m, 2H), 3.07 (m, 1H), 2.76 (m, 1H), 2.59 (dd, 1H), 2.52 (t, 3H), 2.47-2.35 (m, 2H), 2.13 (d, 1H), 1.95-1.45 (m, 5H), 1.35 (m, 1H), 1.13 (s, 3H), 1.02 (m, 1H), 0.74-0.48 (m, 4H). | Method 9b: 1.76 min, 620.2 [M + H]$^+$ |

TABLE 3-continued

| Ex. | Structure | Name | Analogous Example | 1H NMR δ ppm | LCMS |
|---|---|---|---|---|---|
| 158 | 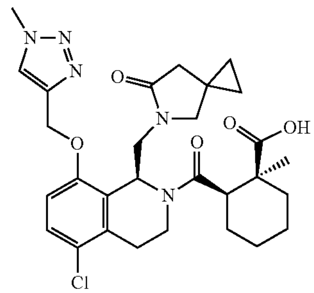 [SMILES: Cn1cc(COc2ccc(Cl)c3c2[C@@H](CN2CC4(CC4)CC2=O)N(C(=O)[C@@H]2CCCC[C@]2(C)C(=O)O)CC3)nn1] | (1S,2R)-2-((S)-5-chloro-8-((1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid | 156 | (300 MHz, CDCl$_3$) δ 7.61 (s, 1H), 7.28 (d, 1H), 6.91 (d, 1H), 5.99 (dd, 1H), 5.24 (d, 1H), 5.18 (d, 1H), 4.18-4.06 (m, 4H), 4.05-3.83 (m, 2H), 3.44 (d, 1H), 3.20 (m, 1H), 3.12-3.00 (m, 2H), 2.73 (m, 1H), 2.60 (dd, 1H), 2.48-2.32 (m, 2H), 2.12 (d, 1H), 1.92-1.74 (m, 2H), 1.72-1.46 (m, 3H), 1.35 (m, 1H), 1.13 (s, 3H), 1.02 (m, 1H), 0.72-0.47 (m, 4H). | Method 9b: 1.44 min, 570.2 [M + H]$^+$ |
| 159 | 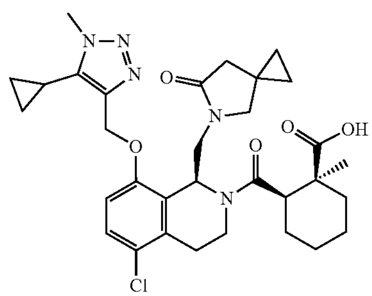 [SMILES: Cn1nnc(COc2ccc(Cl)c3c2[C@@H](CN2CC4(CC4)CC2=O)N(C(=O)[C@@H]2CCCC[C@]2(C)C(=O)O)CC3)c1C1CC1] | (1S,2R)-2-((S)-5-chloro-8-((5-cyclopropyl-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid | 156 | (300 MHz, CDCl$_3$) δ 7.29 (d, 1H), 7.04 (d, 1H), 5.96 (dd, 1H), 5.23-5.10 (m, 2H), 4.17-3.82 (m, 6H), 3.39 (d, 1H), 3.17 (dd, 1H) 3.06 (m, 1H), 2.99 (d, 1H), 2.74 (m, 1H), 2.58 (m, 1H), 2.46-2.30 (m, 2H), 2.12 (d, 1H), 1.91-1.75 (m, 2H), 1.74-1.46 (m, 4H), 1.33 (m, 1H), 1.17-0.93 (m, 6H), 0.88-0.68 (m, 2H), 0.66-0.46 (m, 4H). | Method 9b: 1.64 min, 610.3 [M + H]$^+$. |
| 160 | 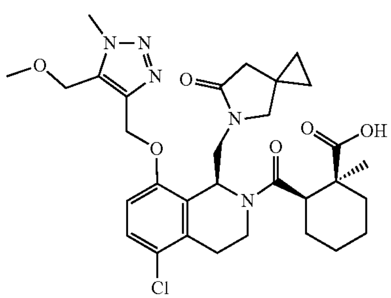 [SMILES: COCc1c(COc2ccc(Cl)c3c2[C@@H](CN2CC4(CC4)CC2=O)N(C(=O)[C@@H]2CCCC[C@]2(C)C(=O)O)CC3)nnn1C] | (1S,2R)-2-((S)-5-chloro-8-((5-(methoxymethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid | 156 | (400 MHz, CDCl$_3$) δ 7.30 (d, 1H), 6.98 (d, 1H), 5.94 (dd, 1H), 5.24 (d, 1H), 5.13 (d, 1H), 4.53 (d, 1H), 4.49 (d, 1H), 4.10 (dd, 1H), 4.05 (s, 3H), 4.04-3.85 (m, 2H), 3.38 (d, 1H), 3.36 (s, 3H), 3.16 (dd, 1H), 3.07 (m, 1H), 2.95 (d, 1H), 2.74 (m, 1H), 2.59 (dd, 1H), 2.46-2.31 (m, 2H), 2.12 (d, 1H), 1.90-1.76 (m, 2H), 1.70-1.49 (m, 3H), 1.45-1.19 (m, 1H), 1.12 (s, 3H), 1.02 (m, 1H), 0.69-0.46 (m, 4H). | Method 12: 1.43 min, 614.8 [M + H]$^+$ |
| 161 | 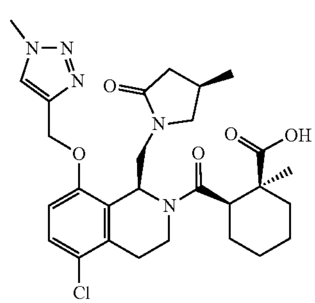 [SMILES: C[C@@H]1CC(=O)N(C[C@@H]2c3c(OCc4cn(C)nn4)ccc(Cl)c3CCN2C(=O)[C@@H]2CCCC[C@]2(C)C(=O)O)C1] | (1S,2R)-2-((S)-5-chloro-8-((1-methyl-1H-1,2,3-triazol-4-yl)methoxy)-(((R)-4-methyl-2-oxopyrrolidin-1-yl)methyl)-1,2,3,4-tetrahydroisoquinoline-2-carbonyl)-1-methylcyclohexane-1-carboxylic acid | 109 | (300 MHz, CDCl$_3$) δ 7.66 (s, 1H), 7.27 (d, 1H), 6.91 (d, 1H), 5.96 (dd, 1H), 5.25 (d, 1H), 5.16 (d, 1H), 4.12 (s, 3H), 4.10-3.80 (m, 3H), 3.25 (dd, 1H), 3.20-3.09 (m, 2H), 3.04 (m, 1H), 2.72 (m, 1H), 2.56 (m, 1H), 2.48-2.23 (m, 3H), 1.94-1.70 (m, 3H), 1.68-1.44 (m, 3H), 1.42-1.20 (m, 1H), 1.17-0.92 (m, 7H). | Method 9b: 1.25 min, 558.2 [M + H]$^+$ |

TABLE 3-continued

| Ex. | Structure | Name | Analogous Example | 1H NMR δ ppm | LCMS |
|---|---|---|---|---|---|
| 162 | 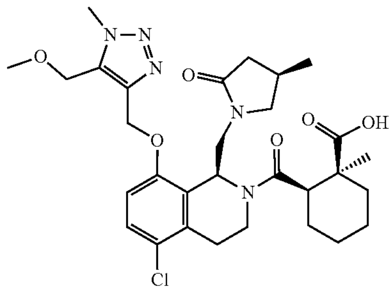 | (1S,2R)-2-((S)-5-chloro-8-((5-(methoxymethyl)-1-methyl-1H-1,2,3-triazol-4-yl)methoxy)-1-(((R)-4-methyl-2-oxopyrrolidin-1-yl)methyl)-1,2,3,4-tetrahydroisoquinoline-2-carbonyl)-1-methylcyclohexane-1-carboxylic acid | 109 | (300 MHz, CDCl$_3$) δ 7.30 (d, 1H), 6.98 (d, 1H), 5.93 (m, 1H), 5.26 (d, 1H), 5.14 (d, 1H), 4.61-4.48 (m, 2H), 4.13-3.80 (m, 6H), 3.38 (s, 3H), 3.21 (dd, 1H), 3.16-3.00 (m, 3H), 2.73 (m, 1H), 2.56 (m, 1H), 2.49-2.24 (m, 3H), 1.95-1.73 (m, 3H), 1.71-1.19 (m, 4H), 1.11 (s, 3H), 1.08-0.94 (m, 4H). | Method 9b: 1.53 min, 602.3 [M + H]$^+$ |
| 163 | 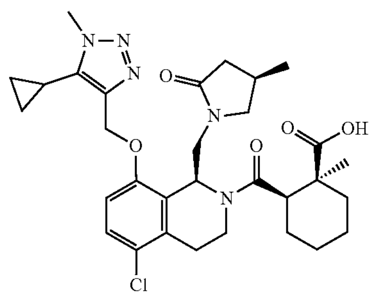 [SMILES: C[C@@H]1CC(=O)N(C[C@@H]2c3c(OCc4nnn(C)c4C4CC4)ccc(Cl)c3CCN2C(=O)[C@@H]2CCCC[C@]2(C)C(=O)O)C1] | (1S,2R)-2-((S)-5-chloro-8-((5-cyclopropyl-1-methyl-1H-1,2,3-triazol-4-yl)methoxy)-1-(((R)-4-methyl-2-oxopyrrolidin-1-yl)methyl)-1,2,3,4-tetrahydroisoquinoline-2-carbonyl)-1-methylcyclohexane-1-carboxylic acid | 109 | (300 MHz, CDCl$_3$) δ 7.29 (d, 1H), 7.03 (d, 1H), 5.94 (m, 1H), 5.24-5.10 (m, 2H), 4.19-3.79 (m, 6H), 3.29-2.97 (m, 4H), 2.72 (m, 1H), 2.55 (d, 1H), 2.48-2.24 (m, 3H), 1.98-0.92 (m, 17H), 0.89-0.70 (m, 2H). | Method 10a: 2.44 min, 598.3 [M + H]$^+$ |
| 164 | 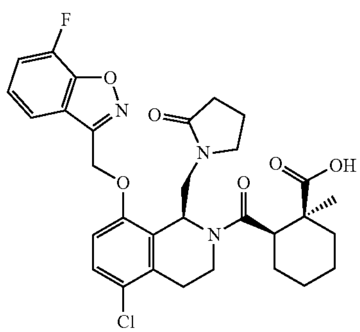 [SMILES: C[C@]1(C(=O)O)CCCC[C@H]1C(=O)N1CCc2c(Cl)ccc(OCc3noc4c(F)cccc34)c2[C@H]1CN1CCCC1=O] | (1S,2R)-2-((S)-5-chloro-8-((7-fluorobenzo[d]isoxazol-3-yl)methoxy)-1-((2-oxopyrrolidin-1-yl)methyl)-1,2,3,4-tetrahydroisoquinoline-2-carbonyl)-1-methylcyclohexane-1-carboxylic acid | 109 | (400 MHz, DMSO-d$_6$) δ 11.82 (bs, 1H), 7.87 (dd, 1H), 7.66 (m, 1H), 7.48 (td, 1H), 7.42 (d, 1H), 7.18 (d, 1H), 5.89 (dd, 1H), 5.75 (d, 1H), 5.67 (d, 1H), 3.95 (dd, 1H), 3.88 (dd, 1H), 3.62 (m, 1H), 3.36-3.22 (m, 1H), 3.06-2.94 (m, 2H), 2.84 (dd, 1H), 2.78-2.64 (m, 2H), 2.24 (m, 1H), 2.12 (m, 1H), 1.96 (m, 1H), 1.85-1.46 (m, 5H), 1.45-1.28 (m, 3H), 1.19 (m, 1H), 1.10 (s, 3H). | Method 3: 4.97 min, 598.1 [M + H]$^+$ |
| 165 | 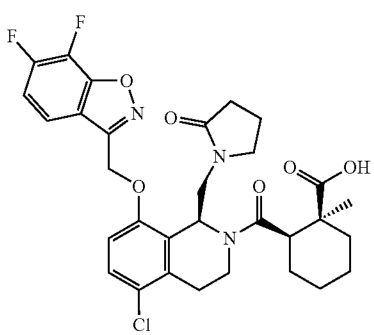 [SMILES: C[C@]1(C(=O)O)CCCC[C@H]1C(=O)N1CCc2c(Cl)ccc(OCc3noc4c(F)c(F)ccc34)c2[C@H]1CN1CCCC1=O] | (1S,2R)-2-((S)-5-chloro-8-((6,7-difluorobenzo[d]isoxazol-3-yl)methoxy)-1-((2-oxopyrrolidin-1-yl)methyl)-1,2,3,4-tetrahydroisoquinoline-2-carbonyl)-1-methylcyclohexane-1-carboxylic acid | 109 | (400 MHz, CDCl$_3$) δ 15.04 (bs, 1H), 7.54 (m, 1H), 7.33 (d, 1H), 7.31-7.22 (m, 1H), 6.94 (d, 1H), 6.10 (dd, 1H), 5.55 (d, 1H), 5.45 (d, 1H), 4.12-3.94 (m, 2H), 3.88 (m, 1H), 3.50 (m, 1H), 3.14-3.02 (m, 2H), 2.88 (m, 1H), 2.77 (m, 1H), 2.59 (m, 1H), 2.41 (m, 1H), 2.26 (m, 1H), 2.14 (m, 1H), 1.92-1.77 (m, 3H), 1.70-1.43 (m, 4H), 1.34 (m, 1H), 1.13 (s, 3H), 1.02 (m, 1H). | Method 3: 5.07 min, 616.0 [M + H]$^+$ |
| 166 | 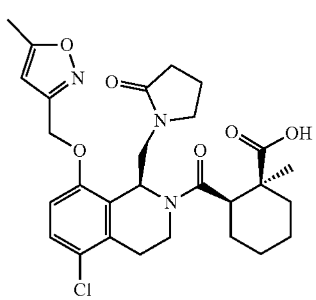 [SMILES: Cc1cc(COc2ccc(Cl)c3c2[C@@H](CN2CCCC2=O)N(C(=O)[C@@H]2CCCC[C@]2(C)C(=O)O)CC3)no1] | (1S,2R)-2-((S)-5-chloro-8-((5-methylisoxazol-3-yl)methoxy)-1-((2-oxopyrrolidin-1-yl)methyl)-1,2,3,4-tetrahydroisoquinoline-2-carbonyl)-1-methylcyclohexane-1-carboxylic acid | 109 | (400 MHz, CDCl$_3$) δ 15.18 (bs, 1H), 7.29 (d, 1H), 6.84 (d, 1H), 6.10 (m, 1H), 6.06 (dd, 1H), 5.18 (d, 1H), 5.10 (d, 1H), 4.07 (dd, 1H), 3.98 (m, 1H), 3.89 (m, 1H), 3.77 (m, 1H), 3.22-3.12 (m, 2H), 3.07 (m, 1H), 2.75 (m, 1H), 2.58 (dd, 1H), 2.45 (d, 3H), 2.41 (m, 1H), 2.29 (m, 1H), 2.18 (m, 1H), 2.00-1.89 (m, 2H), 1.89-1.77 (m, | Method 3: 4.50 min, 544.1 [M + H]$^+$ |

TABLE 3-continued

| Ex. | Structure | Name | Analogous Example | 1H NMR δ ppm | LCMS |
|---|---|---|---|---|---|
| | | | | 2H), 1.69-1.46 (m, 3H), 1.35 (m, 1H), 1.14 (s, 3H), 1.02 (m, 1H). | |
| 167 | 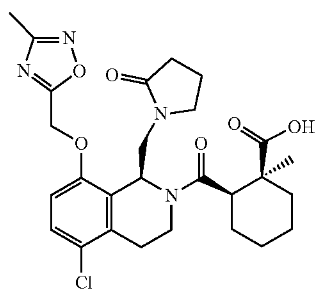 [SMILES: Cc1noc(COc2ccc(Cl)c3c2[C@@H](CN2CCCC2=O)N(C(=O)[C@@H]2CCCC[C@]2(C)C(=O)O)CC3)n1] | (1S,2R)-2-((S)-5-chloro-8-((3-methyl-1,2,4-oxadiazol-5-yl)methoxy)-1-((2-oxopyrrolidin-1-yl)methyl)-1,2,3,4-tetrahydroisoquinoline-2-carbonyl)-1-methylcyclohexane-1-carboxylic acid | 109 | (400 MHz, DMSO-$d_6$) δ 11.80 (bs, 1H), 7.38 (d, 1H), 7.03 (d, 1H), 5.94 (dd, 1H), 5.59 (d, 1H), 5.53 (d, 1H), 4.02-3.86 (m, 2H), 3.72-3.54 (m, 2H), 3.24 (m, 1H), 3.14 (dd, 1H) 3.00 (t, 1H), 2.85 (dd, 1H), 2.72 (m, 1H), 2.39 (s, 3H), 2.30-2.12 (m, 2H), 2.03 (m, 1H), 1.97-1.75 (m, 2H), 1.72-1.48 (m, 3H), 1.48-1.29 (m, 3H), 1.22 (m, 1H), 1.11 (s, 3H). | Method 3: 4.24 min, 545.0 [M + H]$^+$ |
| 168 | 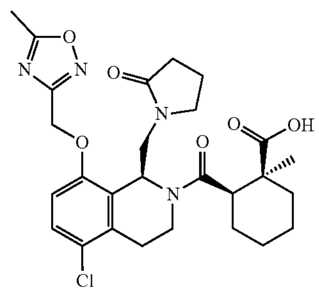 [SMILES: Cc1nc(COc2ccc(Cl)c3c2[C@@H](CN2CCCC2=O)N(C(=O)[C@@H]2CCCC[C@]2(C)C(=O)O)CC3)no1] | (1S,2R)-2-((S)-5-chloro-8-((5-methyl-1,2,4-oxadiazol-3-yl)methoxy)-1-((2-oxopyrrolidin-1-yl)methyl)-1,2,3,4-tetrahydroisoquinoline-2-carbonyl)-1-methylcyclohexane-1-carboxylic acid | 109 | (400 MHz, DMSO-$d_6$) δ 11.81 (s, 1H), 7.37 (d, 1H), 7.08 (d, 1H), 5.89 (dd, 1H), 5.36 (d, 1H), 5.30 (d, 1H), 4.01-3.83 (dd, 2H), 3.68-3.52 (m, 2H), 3.20 (m, 1H), 3.14 (dd, 1H), 2.98 (m, 1H), 2.84 (dd, 1H), 2.77-2.60 (m, 4H), 2.30-2.11 (m, 2H), 2.02 (m, 1H), 1.97-1.74 (m, 2H), 1.72-1.48 (m, 3H), 1.47-1.29 (m, 3H), 1.28-1.14 (m, 1H), 1.10 (s, 3H). | Method 3: 4.24 min, 545.2 [M + H]$^+$ |
| 169 | 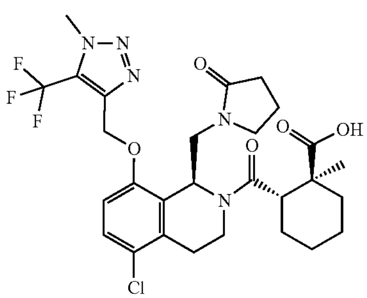 [SMILES: Cn1nnc(COc2ccc(Cl)c3c2[C@@H](CN2CCCC2=O)N(C(=O)[C@H]2CCCC[C@]2(C)C(=O)O)CC3)c1C(F)(F)F] | (1S,2S)-2-((S)-5-chloro-8-((1-methyl-5-(trifluoromethyl)-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid | isolated from synthesis of example 108 | (400 MHz, CDCl$_3$) δ 7.25-7.20 (d, 1H), 6.94 (d, 1H), 5.97 (dd, 1H), 5.24 (m, 2H), 4.19 (m, 3H), 4.06-3.91 (m, 2H), 3.85-3.64 (m, 2H), 3.19-2.99 (m, 3H), 2.91 (dd, 1H), 2.80 (m, 1H), 2.36-2.10 (m, 2H), 1.95-1.84 (m, 2H), 1.80 (m, 1H), 1.73-1.43 (m, 6H), 1.41-1.28 (m, 4H). | Method 3: 4.39 min, 612.0 [M + H]$^+$ |
| 171 | 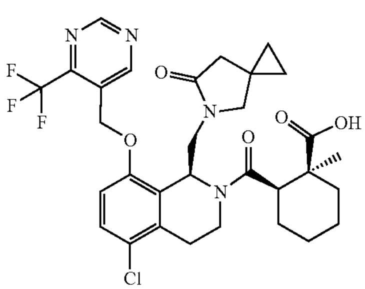 [SMILES: C[C@]1(C(=O)O)CCCC[C@H]1C(=O)N1CCc2c(Cl)ccc(OCc3cncnc3C(F)(F)F)c2[C@H]1CN1CC2(CC2)CC1=O] | (1S,2R)-2-((S)-5-chloro-1-((6-oxo-5-azaspiro[2.4]heptan-5-yl)methyl)-8-((4-(trifluoromethyl)pyrimidin-5-yl)methoxy)-1,2,3,4-tetrahydroisoquinoline-2-carbonyl)-1-methylcyclohexane-1-carboxylic acid | 156 | (400 MHz, CDCl$_3$) δ 14.91 (bs, 1H), 9.37 (s, 1H), 9.17 (s, 1H), 7.34 (d, 1H), 6.80 (d, 1H), 6.10 (dd, 1H), 5.38 (d, 1H), 5.27 (d, 1H), 4.21 (dd, 1H), 4.04 (m, 1H), 3.92 (m, 1H), 3.49 (d, 1H), 3.16-3.06 (m, 2H), 3.03 (d, 1H), 2.80 (m, 1H), 2.62 (m, 1H), 2.47-2.38 (m, 2H), 2.13 (m, 1H), 1.87-1.77 (m, 2H), 1.69-1.46 (m, 3H), 1.43-1.28 (m, 1H), 1.15 (s, 3H), 1.04 (m, 1H), 0.73-0.48 (m, 4H). | Method 3: 4.86 min, 635.0 [M + H]$^+$ |

TABLE 3-continued

| Ex. | Structure | Name | Analogous Example | 1H NMR δ ppm | LCMS |
|---|---|---|---|---|---|
| 172 | 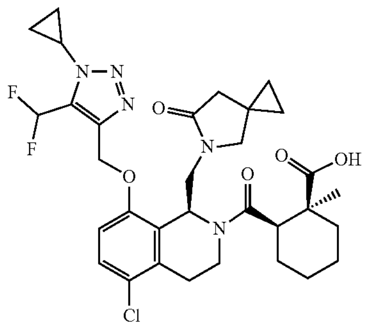 [SMILES: C[C@]1(C(=O)O)CCCC[C@H]1C(=O)N1CCc2c(Cl)ccc(OCc3nnn(C4CC4)c3C(F)F)c2[C@H]1CN1CC2(CC2)CC1=O] | (1S,2R)-2-((S)-5-chloro-8-((1-cyclopropyl-5-(difluoromethyl)-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid | 156 | (400 MHz, CDCl$_3$) δ 15.34 (bs, 1H), 7.29 (d, 1H), 7.04 (t, 1H), 7.00 (d, 1H), 5.97 (dd, 1H), 5.36-5.20 (m, 2H), 4.10 (dd, 1H), 3.99 (m, 1H), 3.88 (m, 1H), 3.67 (m, 1H), 3.45 (d, 1H), 3.18 (dd, 1H), 3.11-3.01 (m, 2H), 2.75 (m, 1H), 2.58 (dd, 1H), 2.48-2.34 (m, 2H), 2.12 (d, 1H), 1.91-1.76 (m, 2H), 1.68-1.50 (m, 3H), 1.47-1.21 (m, 5H), 1.13 (s, 3H), 1.02 (m, 1H), 0.71-0.47 (m, 4H). | Method 3: 4.80 min, 646.0 [M + H]$^+$ |
| 173 | 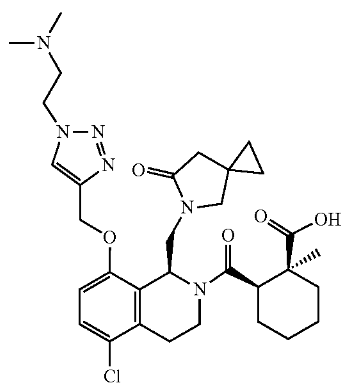 [SMILES: CN(C)CCn1cc(COc2ccc(Cl)c3c2[C@@H](CN2CC4(CC4)CC2=O)N(C(=O)[C@@H]2CCCC[C@]2(C)C(=O)O)CC3)nn1] | (1S,2R)-2-((S)-5-chloro-8-((1-(2-(dimethylamino)ethyl)-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid | 156 | (400 MHz, DMSO-d$_6$) δ 11.93 (bs, 1H), 8.27 (s, 1H), 7.35 (d, 1H), 7.11 (d, 1H), 5.81 (dd, 1H), 5.26-5.12 (m, 2H), 4.46 (t, 2H), 4.03-3.83 (m, 2H), 3.58 (m, 1H), 3.45-3.24 (m, 1H), 3.08-2.95 (m, 2H), 2.86-2.72 (m, 3H), 2.67 (t, 2H), 2.36-2.24 (m, 1H), 2.22-2.04 (m, 8H), 1.73-1.45 (m, 3H), 1.44-1.17 (m, 4H), 1.08 (s, 3H), 0.67-0.39 (m, 4H). | Method 3: 3.10 min, 627.4 [M + H]$^+$ |
| 175 | 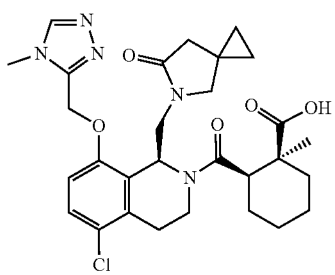 [SMILES: Cn1cnnc1COc1ccc(Cl)c2c1[C@@H](CN1CC3(CC3)CC1=O)N(C(=O)[C@@H]1CCCC[C@]1(C)C(=O)O)CC2] | (1S,2R)-2-((S)-5-chloro-8-((4-methyl-4H-1,2,4-triazol-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid | 156 | (400 MHz, DMSO-d$_6$) δ 11.82 (bs, 1H), 8.55 (s, 1H), 7.39 (d, 1H), 7.16 (d, 1H), 5.82 (dd, 1H), 5.39 (d, 1H), 5.34 (d, 1H), 4.04-3.90 (m, 2H), 3.74 (s, 3H), 3.61 (m, 1H), 3.38-3.29 (m, 1H), 3.02 (m, 1H), 2.96 (dd, 1H), 2.84 (dd, 1H), 2.77-2.62 (m, 2H), 2.30 (m, 1H), 2.23-2.06 (m, 2H), 1.73-1.47 (m, 3H), 1.45-1.18 (m, 4H), 1.11 (s, 3H), 0.62-0.41 (m, 4H). | Method 3: 3.68 min, 569.9 [M + H]$^+$ |
| 176 | 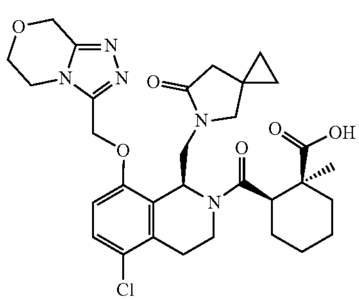 [SMILES: C[C@]1(C(=O)O)CCCC[C@H]1C(=O)N1CCc2c(Cl)ccc(OCc3nnc4n3CCOC4)c2[C@H]1CN1CC2(CC2)CC1=O] | (1S,2R)-2-((S)-5-chloro-8-((5,6-dihydro-8H-[1,2,4]triazolo[3,4-c][1,4]oxazin-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid | 156 | (400 MHz, CDCl$_3$) δ 14.96 (bs, 1H), 7.31 (d, 1H), 7.02 (d, 1H), 6.02 (dd, 1H), 5.37 (d, 1H), 5.27 (d, 1H), 4.94 (s, 2H), 4.27-3.96 (m, 6H), 3.91 (m, 1H), 3.40 (d, 1H), 3.14-3.01 (m, 2H), 2.99 (d, 1H), 2.78 (m, 1H), 2.62 (dd, 1H), 2.47-2.33 (2H), 2.15 (d, 1H), 1.88-1.75 (m, 2H), 1.67-1.49 (m, 3H), 1.37 (m, 1H), 1.25 (s, 3H), 1.13 (m, 1H), 0.72-0.48 (m, 4H). | Method 3: 3.71 min, 612.3 [M + H]$^+$ |

TABLE 3-continued

| Ex. | Structure | Name | Analogous Example | 1H NMR δ ppm | LCMS |
|---|---|---|---|---|---|
| 177 | 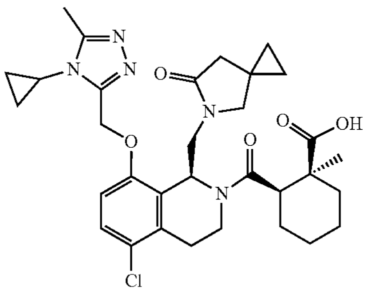 [SMILES: Cc1nnc(COc2ccc(Cl)c3c2[C@@H](CN2CC4(CC4)CC2=O)N(C(=O)[C@@H]2CCCC[C@]2(C)C(=O)O)CC3)n1C1CC1] | (1S,2R)-2-((S)-5-chloro-8-((4-cyclopropyl-5-methyl-4H-1,2,4-triazol-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid | 156 | (400 MHz, CDCl$_3$) δ 14.98 (bs, 1H), 7.31 (d, 1H), 7.07 (d, 1H), 6.03 (dd, 1H), 5.32 (s, 2H), 4.14 (dd, 1H), 4.03 (m, 1H), 3.90 (m, 1H), 3.38 (d, 1H), 3.15-3.05 (m, 3H), 3.02 (d, 1H), 2.77 (m, 1H), 2.60 (m, 1H), 2.50 (s, 3H), 2.45-2.34 (m, 2H), 2.14 (d, 1H), 1.89-1.77 (m, 2H), 1.71-1.48 (m, 3H), 1.43-0.93 (m, 9H), 0.68-0.49 (m, 4H). | Method 3: 3.84 min, 610.4 [M + H]$^+$ |
| 179 | 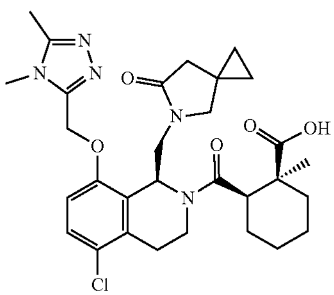 [SMILES: Cc1nnc(COc2ccc(Cl)c3c2[C@@H](CN2CC4(CC4)CC2=O)N(C(=O)[C@@H]2CCCC[C@]2(C)C(=O)O)CC3)n1C] | (1S,2R)-2-((S)-5-chloro-8-((4,5-dimethyl-4H-1,2,4-triazol-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid | 156 | (400 MHz, CDCl$_3$) δ 15.13 (bs, 1H), 7.31 (d, 1H), 7.06 (d, 1H), 6.00 (dd, 1H), 5.32 (d, 1H), 5.24 (d, 1H), 4.14 (dd, 1H), 4.00 (m, 1H), 3.91 (m, 1H), 3.64 (s, 3H), 3.39 (d, 1H), 3.14-3.02 (m, 2H), 2.97 (d, 1H), 2.76 (m, 1H), 2.60 (m, 1H), 2.47-2.34 (m, 5H), 2.14 (d, 1H), 1.90-1.77 (m, 2H), 1.70-1.48 (m, 3H), 1.43-1.21 (m, 1H), 1.13 (s, 3H), 1.03 (m, 1H), 0.68-0.49 (m, 4H). | Method 3: 3.58 min, 584.3 [M + H]$^+$ |
| 181 | 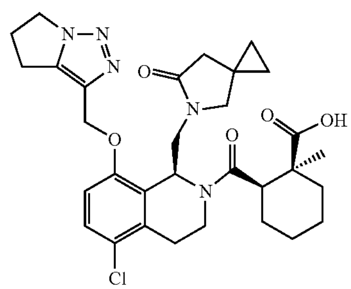 [SMILES: C[C@]1(C(=O)O)CCCC[C@H]1C(=O)N1CCc2c(Cl)ccc(OCc3nnn4c3CCC4)c2[C@H]1CN1CC2(CC2)CC1=O] | (1S,2R)-2-((S)-5-chloro-8-((5,6-dihydro-4H-pyrrolo[1,2-c][1,2,3]triazol-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid | 135 | (400 MHz, DMSO-d$_6$) δ 11.84 (bs, 1H), 7.35 (d, 1H), 7.10 (d, 1H), 5.81 (dd, 1H), 5.18 (s, 2H), 4.29 (m, 2H), 4.02-3.87 (m, 2H), 3.61 (m, 1H), 3.39 (d, 1H), 3.07-2.97 (m, 2H), 2.91-2.78 (m, 4H), 2.75-2.63 (m, 3H), 2.34-2.24 (m, 1H), 2.21 (d, 1H), 2.12 (d, 1H), 1.74-1.46 (m, 3H), 1.46-1.19 (m, 4H), 1.11 (s, 3H), 0.64-0.46 (m, 4H). | Method 3: 4.17 min, 596.3 [M + H]$^+$ |
| 182 | 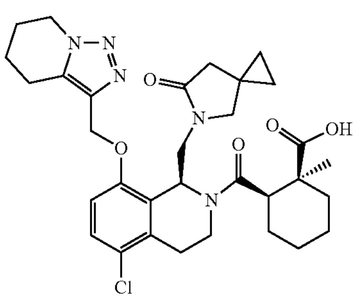 | (1S,2R)-2-((S)-5-fluoro-1-((6-oxo-5-azaspiro[2.4]heptan-5-yl)methyl)-8-((4,5,6,7-tetrahydro-[1,2,3]triazolo[1,5-a]pyridin-3-yl)methoxy)-1,2,3,4-tetrahydroisoquinoline-2-carbonyl)-1-methylcyclohexane-1-carboxylic acid | 178 | (400 MHz, CDCl$_3$) δ 15.33 (bs, 1H), 7.05-6.90 (m, 2H), 5.97 (dd, 1H), 5.18 (d, 1H), 5.10 (d, 1H), 4.36 (t, 2H), 4.11 (m, 1H), 4.02-3.82 (m, 2H), 3.42 (d, 1H), 3.20 (dd, 1H), 3.08-2.96 (m, 2H), 2.93-2.65 (m, 3H), 2.59 (m, 1H), 2.47-2.33(m, 2H), 2.13 (d, 1H), 2.10-2.00 (m, 2H), 1.93 (m, 2H), 1.83 (m, 2H), 1.69-1.46 (m, 3H), 1.36 (m, 1H), 1.12 (s, 3H), 1.02 (m, 1H), 0.69-0.47 (m, 4H). | Method 3: 4.18 min, 594.5 [M + H]$^+$ |

TABLE 3-continued

| Ex. | Structure | Name | Analogous Example | 1H NMR δ ppm | LCMS |
|---|---|---|---|---|---|
| 183 | 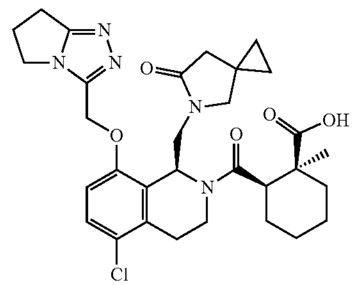 [SMILES: C[C@]1(C(=O)O)CCCC[C@H]1C(=O)N1CCc2c(Cl)ccc(OCc3nnc4n3CCC4)c2[C@H]1CN1CC2(CC2)CC1=O] | (1S,2R)-2-((S)-5-chloro-8-((6,7-dihydro-5H-pyrrolo[2,1-c][1,2,4]triazol-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid | 156 | (400 MHz, CDCl$_3$) δ 15.15 (bs, 1H), 7.29 (d, 1H), 6.99 (d, 1H), 6.05 (dd, 1H), 5.33-5.22 (m, 2H), 4.15 (dd, 1H), 4.10-3.86 (m, 4H), 3.45 (d, 1H), 3.15-3.05 (m, 3H), 2.99-2.92 (m, 2H), 2.84-2.71 (m, 3H), 2.62 (m, 1H), 2.46-2.36 (m, 2H), 2.15 (d, 1H), 1.89-1.78 (m, 2H), 1.70-1.50 (m, 3H), 1.43-1.26 (m, 1H), 1.13 (s, 3H), 1.04 (m, 1H), 0.68-0.52 (m, 4H). | Method 3: 3.76 min, 596.4 [M + H]$^+$ |
| 184 | 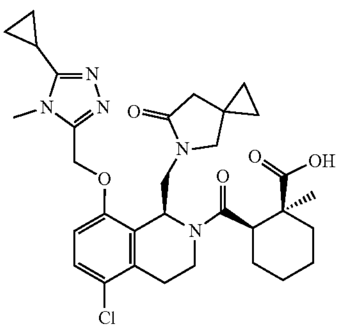 [SMILES: Cn1c(COc2ccc(Cl)c3c2[C@@H](CN2CC4(CC4)CC2=O)N(C(=O)[C@@H]2CCCC[C@]2(C)C(=O)O)CC3)nnc1C1CC1] | (1S,2R)-2-((S)-5-chloro-8-((5-cyclopropyl-4-methyl-4H-1,2,4-triazol-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid | 176 | (400 MHz, CDCl$_3$) δ 15.18 (bs, 1H), 7.31 (d, 1H), 7.03 (d, 1H), 6.00 (dd, 1H), 5.32 (d, 1H), 5.20 (d, 1H), 4.13 (dd, 1H), 4.06-3.86 (m, 2H), 3.74 (s, 3H), 3.38 (d, 1H), 3.14-3.00 (m, 2H), 2.93 (d, 1H), 2.76 (m, 1H), 2.61 (m, 1H), 2.42 (m, 1H), 2.37 (d, 1H), 2.14 (d, 1H), 1.90-1.78 (m, 2H), 1.73 (m, 1H), 1.69-1.49 (m, 3H), 1.42-1.25 (m, 1H), 1.17-0.96 (m, 8H), 0.67-0.49 (m, 4H). | Method 3: 3.87 min, 610.4 [M + H]$^+$ |
| 185 | 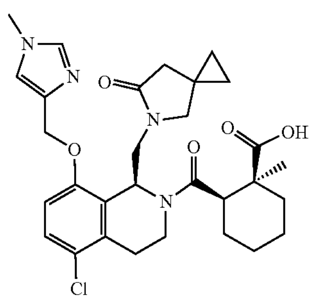 [SMILES: Cn1cnc(COc2ccc(Cl)c3c2[C@@H](CN2CC4(CC4)CC2=O)N(C(=O)[C@@H]2CCCC[C@]2(C)C(=O)O)CC3)c1] | (1S,2R)-2-((S)-5-chloro-8-((1-methyl-1H-imidazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid | 176 | (400 MHz, DMSO-d$_6$) δ 11.78 (bs, 1H), 8.76 (s, 1H), 7.72 (s, 1H), 7.38 (d, 1H), 7.09 (d, 1H), 5.81 (dd, 1H), 5.16 (d, 1H), 5.11 (d, 1H), 3.99 (dd, 1H), 3.91 (dd, 1H), 3.82 (s, 3H), 3.61 (m, 1H), 3.52-3.22 (m, 1H), 3.08 (dd, 1H), 3.01 (m, 1H), 2.89-2.75 (m, 2H), 2.69 (m, 1H), 2.35-2.18 (m, 2H), 2.12 (d, 1H), 1.73-1.47 (m, 3H), 1.46-1.18 (m, 4H), 1.11 (s, 3H), 0.65-0.45 (m, 4H). | Method 3: 3.32 min, 569.4 [M + H]$^+$ |
| 186 | 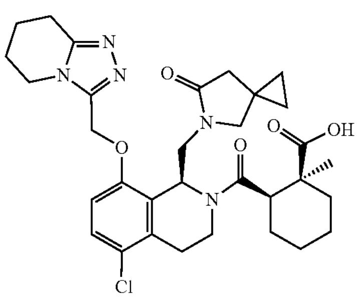 [SMILES: C[C@]1(C(=O)O)CCCC[C@H]1C(=O)N1CCc2c(Cl)ccc(OCc3nnc4n3CCCC4)c2[C@H]1CN1CC2(CC2)CC1=O] | (1S,2R)-2-((S)-5-chloro-1-((6-oxo-5-azaspiro[2.4]heptan-5-yl)methyl)-8-((5,6,7,8-tetrahydro-[1,2,4]triazolo[4,3-a]pyridin-3-yl)methoxy)-1,2,3,4-tetrahydroisoquinoline-2-carbonyl)-1-methylcyclohexane-1-carboxylic acid | 176 | (400 MHz, CDCl$_3$) δ 15.19 (bs, 1H), 7.31 (d, 1H), 7.04 (d, 1H), 6.02 (dd, 1H), 5.32 (d, 1H), 5.22 (d, 1H), 4.20-3.85 (m, 5H), 3.38 (d, 1H), 3.14-2.91 (m, 5H), 2.77 (m, 1H), 2.61 (m, 1H), 2.46-2.33 (m, 2H), 2.14 (d, 1H), 2.08-1.98 (m, 2H), 1.97-1.87 (m, 2H), 1.87-1.77 (m, 2H), 1.70-1.48 (m, 3H), 1.35 (m, 1H), 1.12 (s, 3H), 1.03 (m, 1H), 0.66-0.49 (m, 4H). | Method 3: 3.78 min, 610.4 [M + H]$^+$ |

TABLE 3-continued

| Ex. | Structure | Name | Analogous Example | 1H NMR δ ppm | LCMS |
|---|---|---|---|---|---|
| 187 | 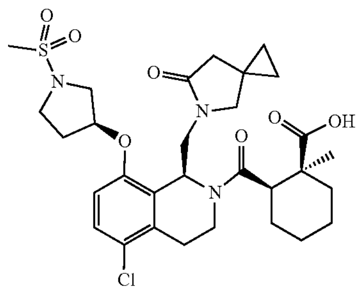 [SMILES: C[C@]1(C(=O)O)CCCC[C@H]1C(=O)N1CCc2c(Cl)ccc(O[C@H]3CCN(S(C)(=O)=O)C3)c2[C@H]1CN1CC2(CC2)CC1=O] | (1S,2R)-2-((S)-5-chloro-8-(((S)-1-(methylsulfonyl)pyrrolidin-3-yl)oxy)-1-((6-oxo-5-azaspiro[2.4]heptan-5-yl)methyl)-1,2,3,4-tetrahydroisoquinoline-2-carbonyl)-1-methylcyclohexane-1-carboxylic acid | 176 & 11 | (400 MHz, CDCl$_3$) δ 14.96 (bs, 1H), 7.29 (d, 1H), 6.64 (d, 1H), 6.02 (m, 1H), 5.00 (m, 1H), 4.17 (m, 1H), 4.09-3.86 (m, 2H), 3.69-3.44 (m, 5H), 3.34 (d, 1H), 3.19-3.01 (m, 2H), 2.86-2.69 (m, 4H), 2.61 (d, 1H), 2.48-2.37 (m, 2H), 2.36-2.25 (m, 2H), 2.17 (d, 1H), 1.83 (m, 2H), 1.71-1.47 (m, 3H), 1.43-1.21 (m, 1H), 1.12 (s, 3H), 1.03 (m, 1H), 0.79-0.57 (m, 4H). | Method 3: 4.37 min, 622.4 [M + H]$^+$ |
| 188 | 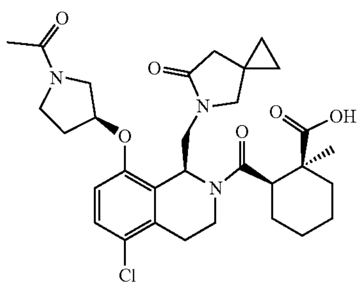 [SMILES: CC(=O)N1CC[C@H](Oc2ccc(Cl)c3c2[C@@H](CN2CC4(CC4)CC2=O)N(C(=O)[C@@H]2CCCC[C@]2(C)C(=O)O)CC3)C1] | (1S,2R)-2-((S)-8-(((S)-1-acetylpyrrolidin-3-yl)oxy)-5-chloro-1-((6-oxo-5-azaspiro[2.4]heptan-5-yl)methyl)-1,2,3,4-tetrahydroisoquinoline-2-carbonyl)-1-methylcyclohexane-1-carboxylic acid | 176 & 11 | (400 MHz, CDCl$_3$; rotamers observed, both reported) δ 15.08 (bs, 1H), 7.29 (d, 0.4H), 7.27 (d, 0.6H), 6.71 (d, 0.4H), 6.67 (d, 0.6H), 5.99 (dd, 0.4H), 5.95 (dd, 0.6H), 5.00 (m, 0.4H), 4.96 (m, 0.6H), 4.15 (m, 1H), 4.05-3.85 (m, 2H), 3.84-3.46 (m, 5H), 3.16 (m, 1H), 3.12-2.97 (m, 2H), 2.82-2.69 (m, 1H), 2.65-2.56 (m, 1H), 2.47-2.01 (m, 8H), 1.90-1.76 (m, 2H), 1.69-1.50 (m, 3H), 1.42-1.26 (m, 1H), 1.16 (s, 1.8H), 1.13 (s, 1.2H), 1.08-0.98 (m, 1H), 0.78-0.55 (m, 4H). | Method 3: 4.04 min, 586.4 [M + H]$^+$ |
| 189 | 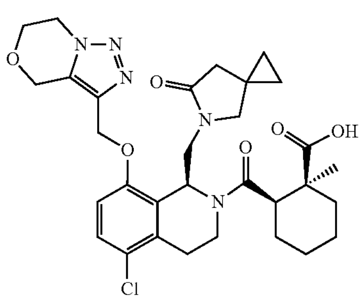 [SMILES: C[C@]1(C(=O)O)CCCC[C@H]1C(=O)N1CCc2c(Cl)ccc(OCc3nnn4c3COCC4)c2[C@H]1CN1CC2(CC2)CC1=O] | (1S,2R)-2-((S)-5-chloro-8-((6,7-dihydro-4H-[1,2,3]triazolo[5,1-c][1,4]oxazin-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid | 176 | (400 MHz, CDCl$_3$) δ 15.18 (bs, 1H), 7.29 (d, 1H), 6.93 (d, 1H), 5.96 (dd, 1H), 5.22 (d, 1H), 5.14 (d, 1H), 4.93 (d, 1H), 4.84 (d, 1H), 4.42 (t, 2H), 4.17-3.94 (m, 4H), 3.94 (m, 1H), 3.45 (d, 1H), 3.14 (dd, 1H), 3.11-3.02 (m, 2H), 2.76 (m, 1H), 2.60 (m, 1H), 2.45-2.35 (m, 2H), 2.13 (d, 1H), 1.88-1.75 (m, 2H), 1.70-1.50 (m, 3H), 1.35 (m, 1H), 1.13 (s, 3H), 1.03 (m, 1H), 0.70-0.48 (m, 4H). | Method 3: 4.20 min, 612.3 [M + H]+ |
| 191 | 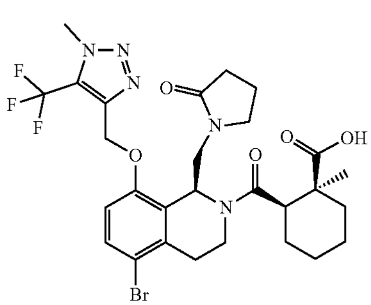 [SMILES: Cn1nnc(COc2ccc(Br)c3c2[C@@H](CN2CCCC2=O)N(C(=O)[C@@H]2CCCC[C@]2(C)C(=O)O)CC3)c1C(F)(F)F] | (1S,2R)-2-((S)-5-bromo-8-((1-methyl-5-(trifluoromethyl)-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid | 63 from Example 190 | (400 MHz, CDCl$_3$) δ 15.21 (bs, 1H), 7.48 (d, 1H), 6.97 (d, 1H), 5.97 (dd, 1H), 5.30 (s, 2H), 4.22 (m, 3H), 4.08-3.92 (m, 2H), 3.84 (m, 1H), 3.70 (m, 1H), 3.21-3.10 (m, 2H), 3.03 (m, 1H), 2.73 (m, 1H), 2.56 (m, 1H), 2.40 (m, 1H), 2.28 (m, 1H), 2.16 (m, 1H), 1.98-1.87 (m, 2H), 1.83 (m, 2H), 1.68-1.45 (m, 3H), 1.42-1.25 (m, 1H), 1.12 (s, 3H), 1.01 (m, 1H). | Method 3: 4.72 min, 656.3 [M + H]$^+$ |

TABLE 3-continued

| Ex. | Structure | Name | Analogous Example | 1H NMR δ ppm | LCMS |
|---|---|---|---|---|---|
| 192 | 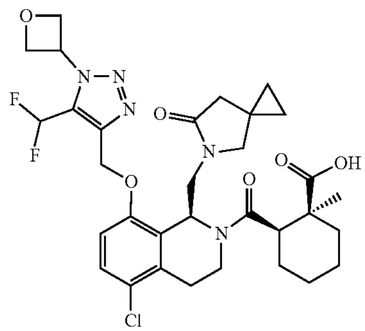 [SMILES: C[C@]1(C(=O)O)CCCC[C@H]1C(=O)N1CCc2c(Cl)ccc(OCc3nnn(C4COC4)c3C(F)F)c2[C@H]1CN1CC2(CC2)CC1=O] | (1S,2R)-2-((S)-5-chloro-8-((5-(difluoromethyl)-1-(oxetan-3-yl)-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid | 176 | (300 MHz, CDCl$_3$) δ 15.15 (bs, 1H), 7.30 (d, 1H), 6.97 (d, 1H), 6.94 (t, 1H), 5.96 (dd, 1H), 5.72 (m, 1H), 5.38-5.19 (m, 4H), 5.08 (m, 2H), 4.17-3.81 (m, 3H), 3.42 (d, 1H), 3.19-3.00 (m, 3H), 2.76 (m, 1H), 2.59 (d, 1H), 2.47-2.30 (m, 2H), 2.11 (d, 1H), 1.89-1.73 (m, 2H), 1.71-1.48 (m, 3H), 1.44-1.20 (m, 1H), 1.12 (s, 3H), 1.02 (m, 1H), 0.70-0.43 (m, 4H). | Method 3: 4.72 min, 662.4 [M + H]$^+$ |
| 193 | 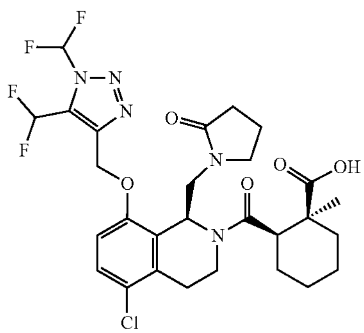 | (1S,2R)-2-((S)-8-((1,5-bis(difluoromethyl)-1H-1,2,3-triazol-4-yl)methoxy)-5-chloro-1-((2-oxopyrrolidin-1-yl)methyl)-1,2,3,4-tetrahydroisoquinoline-2-carbonyl)-1-methylcyclohexane-1-carboxylic acid | 176 | (300 MHz, CDCl$_3$) δ 7.67 (t, 1H), 7.32 (d, 1H), 7.12 (t, 1H), 6.97 (d, 1H), 5.97 (dd, 1H), 5.41-5.27 (m, 2H), 4.12 (dd, 1H), 4.06-3.76 (m, 2H), 3.46 (d, 1H), 3.19 (dd, 1H), 3.13-3.00 (m, 2H), 2.75 (m, 1H), 2.58 (m, 1H), 2.47-2.33 (m, 2H), 2.11 (d, 1H), 1.90-1.75 (m, 2H), 1.72-1.21 (m, 4H), 1.13 (s, 3H), 1.02 (m, 1H), 0.71-0.45 (m, 4H). | Method 10: 2.47 min, 656.3 [M + H]$^+$ |
| 197 | 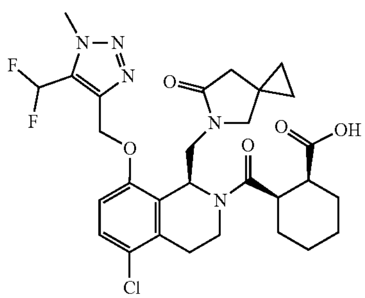 [SMILES: Cn1nnc(COc2ccc(Cl)c3c2[C@@H](CN2CC4(CC4)CC2=O)N(C(=O)[C@@H]2CCCC[C@@H]2C(=O)O)CC3)c1C(F)F] | (1S,2R)-2-((S)-5-Chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)cyclohexane-1-carboxylic acid | 123 | (300 MHz, DMSO-d$_6$) δ 11.69 (bs, 1H), 7.80-7.31 (m, 2H), 7.14 (d, 1H), 5.77 (m, 1H), 5.28 (s, 3H), 4.16 (s, 3H), 4.06-3.82 (m, 2H), 3.60 (m, 1H), 3.42-3.21 (m, 2H), 2.96 (m, 1H), 2.84 (m, 1H), 2.76-2.56 (m, 2H), 2.34 (m, 1H), 2.26-2.01 (m, 3H), 1.83-1.60 (m, 3H), 1.59-1.32 (m, 2H), 1.31-1.04 (m, 2H), 0.64-0.34 (m, 4H). | Method 13: 2.43 min, 606.3 [M + H]$^+$ |
| 198 | 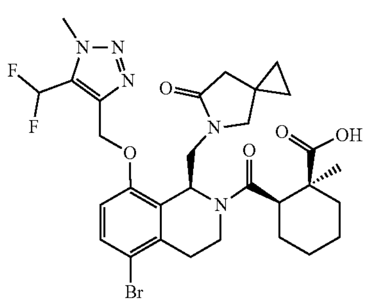 [SMILES: Cn1nnc(COc2ccc(Br)c3c2[C@@H](CN2CC4(CC4)CC2=O)N(C(=O)[C@@H]2CCCC[C@]2(C)C(=O)O)CC3)c1C(F)F] | (1S,2R)-2-((S)-5-bromo-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid | 190 & 63 from Example 123 | (400 MHz, DMSO-d$_6$) δ 15.27 (bs, 1H), 7.48 (d, 1H), 7.07-6.76 (m, 2H), 5.96 (dd, 1H), 5.30 (d, 1H), 5.25 (d, 1H), 4.18 (s, 3H), 4.11 (dd, 1H), 4.00 (m, 1H), 3.87 (m, 1H), 3.44 (d, 1H), 3.15 (dd, 1H), 3.09-2.98 (m, 2H), 2.74 (m, 1H), 2.58 (m, 1H), 2.45-2.35 (m, 2H), 2.12 (d, 1H), 1.89-1.77 (m, 2H), 1.68-1.47 (m, 3H), 1.42-1.25 (m, 1H), 1.13 (s, 3H), 1.02 (m, 1H), 0.72-0.42 (m, 4H). | Method 3: 4.64 min, 664.3 [M + H]$^+$ |

TABLE 3-continued

| Ex. | Structure | Name | Analogous Example | 1H NMR δ ppm | LCMS |
|---|---|---|---|---|---|
| 199 | 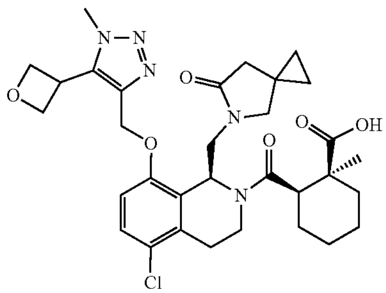 [SMILES: Cn1nnc(COc2ccc(Cl)c3c2[C@@H](CN2CC4(CC4)CC2=O)N(C(=O)[C@@H]2CCCC[C@]2(C)C(=O)O)CC3)c1C1COC1] | (1S,2R)-2-((S)-5-chloro-8-((1-methyl-5-(oxetan-3-yl)-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid | 176 | (400 MHz, CDCl$_3$) δ 15.22 (bs, 1H), 7.31 (d, 1H), 7.10 (d, 1H), 5.94 (dd, 1H), 5.39 (d, 1H), 5.33 (d, 1H), 5.14 (dd, 1H), 5.08 (dd, 1H), 4.83 (t, 1H), 4.76 (t, 1H), 4.40 (m, 1H), 4.12 (dd, 1H), 4.06-3.95 (m, 4H), 3.88 (m, 1H), 3.36 (d, 1H), 3.20 (dd, 1H), 3.08 (m, 1H), 3.03 (d, 1H), 2.75 (m, 1H), 2.60 (dd, 1H), 2.45-2.34 (m, 2H), 2.12 (d, 1H), 1.89-1.75 (m, 2H), 1.67-1.47 (m, 3H), 1.42-1.26 (m, 1H), 1.13 (s, 3H), 1.03 (m, 1H), 0.66-0.45 (m, 4H). | Method 3: 4.10 min, 626.4 [M + H]$^+$ |
| 200 | 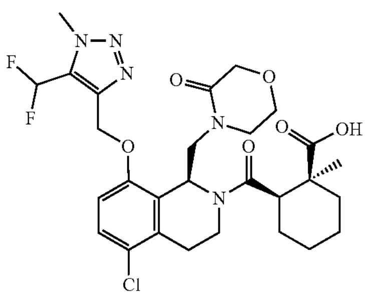 [SMILES: Cn1nnc(COc2ccc(Cl)c3c2[C@@H](CN2CCOCC2=O)N(C(=O)[C@@H]2CCCC[C@]2(C)C(=O)O)CC3)c1C(F)F] | (1S,2R)-2-((S)-5-chloro-8-((5-(difluoromethyl)-1-methyl-1H-1,2,3-triazol-4-yl)methoxy)-1-((3-oxomorpholino)methyl)-1,2,3,4-tetrahydroisoquinoline-2-carbonyl)-1-methylcyclohexane-1-carboxylic acid | 196 | (400 MHz, DMSO-d$_6$) δ 11.77 (bs, 1H), 7.58 (t, 1H), 7.39 (d, 1H), 7.15 (d, 1H), 5.84 (dd, 1H), 5.42-5.23 (m, 2H), 4.33 (dd, 1H), 4.17 (s, 3H), 4.03-3.88 (m, 2H), 3.85-3.55 (m, 4H), 3.39 (m, 1H), 2.97 (m, 1H), 2.90-2.76 (m, 3H), 2.70 (m, 1H), 2.25 (m, 1H), 1.71-1.46 (m, 3H), 1.45-1.17 (m, 4H), 1.10 (s, 3H) | Method 3: 4.37 min, 610.4 [M + H]$^+$ |
| 202 | 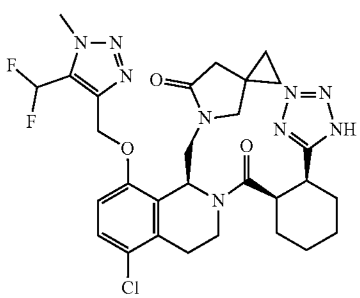 [SMILES: Cn1nnc(COc2ccc(Cl)c3c2[C@@H](CN2CC4(CC4)CC2=O)N(C(=O)[C@@H]2CCCC[C@@H]2c2nnn[nH]2)CC3)c1C(F)F] | 5-(((S)-2-((1R,2S)-2-(1H-tetrazol-5-yl)cyclohexane-1-carbonyl)-5-chloro-8-((5-(difluoromethyl)-1-methyl-1H-1,2,3-triazol-4-yl)methoxy)-1,2,3,4-tetrahydroisoquinolin-1-yl)methyl)-5-azaspiro[2.4]heptan-6-one | 81 | (400 MHz, CDCl$_3$) δ 7.29-7.22 (m, 1H), 6.96 (t, 1H), 6.93 (d, 1H), 6.04 (m, 1H), 5.34-5.23 (m, 2H), 4.19 (s, 3H), 4.09 (dd, 1H), 4.03-3.81 (m, 2H), 3.52 (d, 1H), 3.41 (m, 1H), 3.19-2.86 (m, 4H), 2.81-2.59 (m, 2H), 2.38 (d, 1H), 2.16 (d, 1H), 1.83-1.33 (m, 7H), 0.74-0.48 (m, 4H). | Method 9b: 1.55 min, 630.2 [M + H]$^+$ |
| 204 | 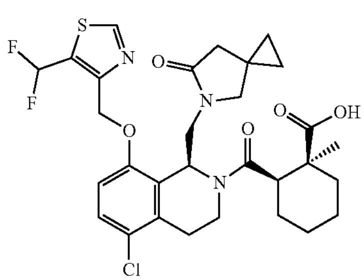 [SMILES: C[C@]1(C(=O)O)CCCC[C@H]1C(=O)N1CCc2c(Cl)ccc(OCc3ncsc3C(F)F)c2[C@H]1CN1CC2(CC2)CC1=O] | (1S,2R)-2-((S)-5-chloro-8-((5-(difluoromethyl)thiazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid | 135 | (400 MHz, CDCl$_3$) δ 8.88 (s, 1H), 7.30 (d, 1H), 7.03 (t, 1H), 6.92 (d, 1H), 5.99 (m, 1H), 5.39-5.22 (m, 2H), 4.12 (m, 1H), 4.05-3.83 (m, 2H), 3.45 (m, 1H), 3.18 (m, 1H), 3.07 (m, 1H), 2.97 (m, 1H), 2.76 (m, 1H), 2.58 (d, 1H), 2.48-2.26 (m, 2H), 2.12 (m, 1H), 1.92-1.75 (m, 2H), 1.73-1.44 (m, 3H), 1.43-1.19 (m, 1H), 1.13 (s, 3H), 1.02 (m, 1H), 0.73-0.41 (m, 4H). | Method 9b: 1.61 min, 622.2 [M + H]$^+$ |

TABLE 3-continued

| Ex. | Structure | Name | Analogous Example | 1H NMR δ ppm | LCMS |
|---|---|---|---|---|---|
| 205 | 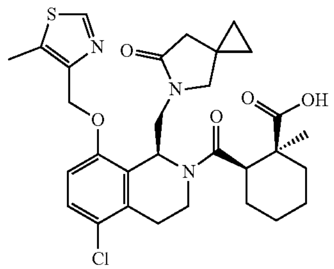 [SMILES: Cc1scnc1COc1ccc(Cl)c2c1[C@@H](CN1CC3(CC3)CC1=O)N(C(=O)[C@@H]1CCCC[C@]1(C)C(=O)O)CC2] | (1S,2R)-2-((S)-5-chloro-8-((5-methylthiazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid | 204 | (300 MHz, CDCl$_3$) δ 8.58 (s, 1H), 7.30 (d, 1H), 6.94 (d, 1H), 5.97 (dd, 1H), 5.18 (d, 1H), 5.12 (d, 1H), 4.11 (dd, 1H), 4.03-3.76 (m, 2H), 3.39 (d, 1H), 3.18 (dd, 1H), 3.06 (m, 1H), 2.83 (d, 1H), 2.73 (m, 1H), 2.58 (dd, 1H), 2.52 (s, 3H), 2.41 (m, 1H), 2.35 (d, 1H), 2.12 (d, 1H), 1.92-1.74 (m, 2H), 1.73-1.19 (m, 4H), 1.13 (s, 3H), 1.01 (m, 1H), 0.67-0.40 (m, 4H). | Method 14 (to 50% A): 1.59 min, 586.4 [M + H]$^+$ |
| 206 | 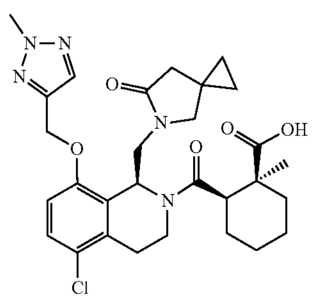 [SMILES: Cn1ncc(COc2ccc(Cl)c3c2[C@@H](CN2CC4(CC4)CC2=O)N(C(=O)[C@@H]2CCCC[C@]2(C)C(=O)O)CC3)n1] | (1S,2R)-2-((S)-5-chloro-8-((2-methyl-2H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid | 204 | (300 MHz, CDCl$_3$) δ 7.59 (s, 1H), 7.30 (d, 1H), 6.87 (d, 1H), 6.00 (dd, 1H), 5.18 (d, 1H), 5.11 (d, 1H), 4.22-4.07 (m, 4H), 4.05-3.77 (m, 2H), 3.52 (d, 1H), 3.16 (dd, 1H), 3.12-2.98 (m, 2H), 2.74 (m, 1H), 2.59 (m, 1H), 2.48-2.34 (m, 2H), 2.13 (d, 1H), 1.92-1.75 (m, 2H), 1.74-1.20 (m, 4H), 1.14 (s, 3H), 1.02 (m, 1H), 0.74-0.45 (m, 4H). | Method 14 (to 50% A): 1.48 min, 570.5 [M + H]$^+$ |
| 209 | 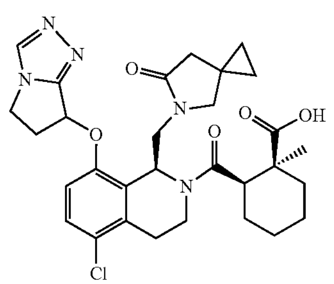 [SMILES: C[C@]1(C(=O)O)CCCC[C@H]1C(=O)N1CCc2c(Cl)ccc(OC3CCn4cnnc43)c2[C@H]1CN1CC2(CC2)CC1=O] | (1S,2R)-2-((1S)-5-chloro-8-((6,7-dihydro-5H-pyrrolo[2,1-c][1,2,4]triazol-7-yl)oxy)-1-((6-oxo-5-azaspiro[2.4]heptan-5-yl)methyl)-1,2,3,4-tetrahydroisoquinoline-2-carbonyl)-1-methylcyclohexane-1-carboxylic acid | 135 | (400 MHz, MeOD) δ 8.54 (s, 1H), 7.38 (m, 1H), 7.20 (m, 1H), 5.92 (m, 1H), 5.87 (m, 1H), 4.39 (m, 1H), 4.29-4.19 (m, 1H), 4.15-3.99 (m, 2H), 3.78 (m, 1H), 3.40 (m, 1H), 3.35-3.23 (m, 1H), 3.17 (dd, 1H), 3.13-3.03 (m, 2H), 2.99 (m, 1H), 2.94-2.80 (m, 2H), 2.46-2.33 (m, 2H), 2.22 (m, 1H), 1.88-1.16 (m, 9H), 0.99-0.87 (m, 1H), 0.69-0.51 (m, 4H). | Method 9b: 1.24 min, 582.3 [M + H]$^+$ |
| 211 | 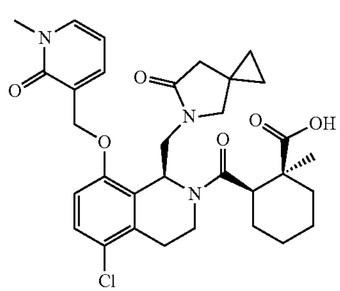 [SMILES: Cn1cccc(COc2ccc(Cl)c3c2[C@@H](CN2CC4(CC4)CC2=O)N(C(=O)[C@@H]2CCCC[C@]2(C)C(=O)O)CC3)c1=O] | (1S,2R)-2-((S)-5-chloro-8-((1-methyl-2-oxo-1,2-dihydropyridin-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid | 135 | (400 MHz, CDCl$_3$) δ 7.43 (m, 1H), 7.32 (dd, 1H), 7.28 (d, 1H), 6.86 (d, 1H), 6.16 (t, 1H), 6.07 (dd, 1H), 5.12 (d, 1H), 4.94 (d, 1H), 4.16 (dd, 1H), 4.01 (m, 1H), 3.90 (dd, 1H), 3.61 (d, 1H), 3.58 (s, 3H), 3.28 (dd, 1H), 3.16 (d, 1H), 3.08 (dd, 1H), 2.75 (m, 1H), 2.61 (d, 1H), 2.48-2.34 (m, 2H), 2.14 (d, 1H), 1.91-1.77 (m, 2H), 1.76-1.20 (m, 4H), 1.14 (s, 3H), 1.03 (m, 1H), 0.89-0.44 (m, 4H). | Method 9b: 1.53 min, 596.3 [M + H]$^+$ |

TABLE 3-continued

| Ex. | Structure | Name | Analogous Example | 1H NMR δ ppm | LCMS |
|---|---|---|---|---|---|
| 214 | 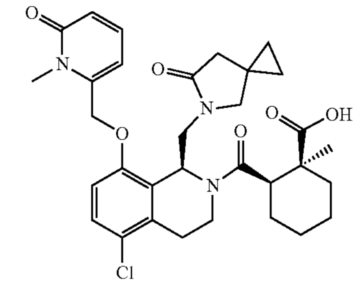 [SMILES: Cn1c(COc2ccc(Cl)c3c2[C@@H](CN2CC4(CC4)CC2=O)N(C(=O)[C@@H]2CCCC[C@]2(C)C(=O)O)CC3)cccc1=O] | (1S,2R)-2-((S)-5-chloro-8-((1-methyl-6-oxo-1,6-dihydropyridin-2-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid | 135 | (300 MHz, CDCl$_3$) δ 7.38-7.26 (m, 2H), 6.80 (d, 1H), 6.68-6.60 (m, 1H), 6.32-6.25 (m, 1H), 6.04 (dd, 1H), 5.04-4.87 (m, 2H), 4.19 (dd, 1H), 4.06-3.76 (m, 2H), 3.60 (s, 3H), 3.43 (d, 1H), 3.16-2.95 (m, 2H), 2.89 (d, 1H), 2.77 (m, 1H), 2.60 (dd, 1H), 2.48-2.30 (m, 2H), 2.13 (d, 1H), 1.90-1.75 (m, 2H), 1.72-1.22 (m, 4H), 1.14 (s, 3H), 1.04 (m, 1H), 0.72-0.43 (m, 4H). | Method 13: 2.19 min, 596.3 [M + H]$^+$ |
| 215 | 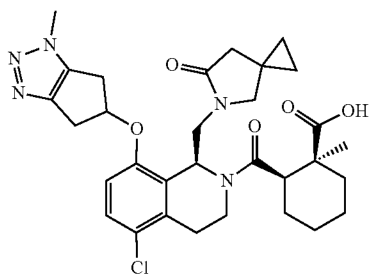 [SMILES: Cn1nnc2c1CC(Oc1ccc(Cl)c3c1[C@@H](CN1CC4(CC4)CC1=O)N(C(=O)[C@@H]1CCCC[C@]1(C)C(=O)O)CC3)C2] | (1S,2R)-2-((1S)-5-chloro-8-((1-methyl-1,4,5,6-tetrahydrocyclopenta[d][1,2,3]triazol-5-yl)oxy)-1-((6-oxo-5-azaspiro[2.4]heptan-5-yl)methyl)-1,2,3,4-tetrahydroisoquinoline-2-carbonyl)-1-methylcyclohexane-1-carboxylic acid (isomer 1) | 135 | (300 MHz, CDCl$_3$) δ 7.35 (d, 1H), 6.88 (d, 1H), 5.92 (dd, 1H), 5.78 (m, 1H), 4.11 (dd, 1H), 4.04-3.83 (m, 5H), 3.38 (d, 1H), 3.17-2.98 (m, 3H), 2.95-2.54 (m, 6H), 2.47-2.35 (m, 2H), 2.09 (d, 1H), 1.88-1.75 (m, 2H), 1.71-1.21 (m, 4H), 1.14 (s, 3H), 1.02 (m, 1H), 0.72-0.51 (m, 4H) | Method 9d: 3.11 min, 595.9 [M + H]$^+$ |
| 216 | 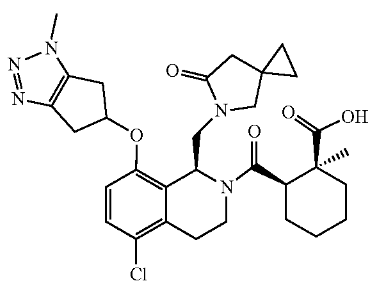 [SMILES: Cn1nnc2c1CC(Oc1ccc(Cl)c3c1[C@@H](CN1CC4(CC4)CC1=O)N(C(=O)[C@@H]1CCCC[C@]1(C)C(=O)O)CC3)C2] | (1S,2R)-2-((1S)-5-chloro-8-((1-methyl-1,4,5,6-tetrahydrocyclopenta[d][1,2,3]triazol-5-yl)oxy)-1-((6-oxo-5-azaspiro[2.4]heptan-5-yl)methyl)-1,2,3,4-tetrahydroisoquinoline-2-carbonyl)-1-methylcyclohexane-1-carboxylic acid (isomer 2) | 135 | (300 MHz, CDCl$_3$) δ 7.34 (d, 1H), 6.78 (d, 1H), 5.93 (dd, 1H), 5.67 (dd, 1H), 4.13 (dd, 1H), 4.05 (s, 3H), 4.01-3.88 (m, 2H), 3.30-2.64 (m, 9H), 2.60 (m, 1H), 2.42 (m, 1H), 2.33 (d, 1H), 2.12 (d, 1H), 1.89-1.76 (m, 2H), 1.73-1.21 (m, 4H), 1.14 (s, 3H), 1.02 (m, 1H), 0.68-0.47 (m, 4H). | Method 9d: 3.12 min, 595.9 [M + H]$^+$ |

Biological Assays

KEAP1 Kelch Fluorescence Polarization (FP) Assay Method

Inhibition of the Kelch domain-NRF2 interaction was determined using a fluorescence polarization-based competition assay in a black 384-well microplate. Compounds were tested at a starting concentration of 10 μM serially diluted 1:3 to generate a 12-point dose response curve on the Biomek FX robot. Each well contained 2 nM FITC-labelled NRF2 peptide (FITC-LDEETGEFL-NH2) and 25 nM human KEAP1 (N-term, residues 321-609) enzyme in a final volume of 20 μL of assay buffer (50 mM Tris-HCl pH 8.0, 100 mM NaCl, 5 mM MgCl$_2$, 0.005% Tween-20, 0.005% BSA, 0.5% DMSO) in the presence of varying concentrations of test compound. Unlabelled peptide (LDEETGEFL-NH2) at 50 μM (negative control) and 0.5% DMSO (positive control) was used to determine the assay window.

After 1 h at room temperature, fluorescence polarization (excitation 470 nm/emission 530 nm) was measured using an Envision plate reader. IC$_{50}$ values were determined by fitting the data to a four parameter logistic fit using XLfit or XE Runner within ActivityBase. The assay limit is such that compounds below 10 nM cannot be differentiated. IC$_{50}$ values for the Example compounds are shown in Table 4.

TABLE 4

| Example No. | IC$_{50}$ (nM) |
|---|---|
| 1 | 12 |
| 2 | 12 |
| 3 | 5.6 |
| 4 | 9.0 |
| 5 | 6.1 |
| 6 | 5.6 |
| 7 | 6.2 |
| 8 | 8.2 |
| 9 | 7.7 |
| 10 | 15 |
| 11 | 5.1 |
| 12 | 5.8 |
| 13 | 8.5 |
| 14 | 3.7 |
| 15 | 5.1 |
| 16 | 8.1 |
| 17 | 9.7 |
| 18 | 10 |
| 19 | 9.7 |
| 20 | 5.4 |
| 21 | 4.7 |
| 22 | 4.7 |
| 23 | 10 |
| 24 | 9.1 |
| 25 | 15 |
| 26 | 14 |

TABLE 4-continued

| Example No. | IC$_{50}$ (nM) |
|---|---|
| 27 | 8.3 |
| 28 | 14 |
| 29 | 16 |
| 30 | 9.2 |
| 31 | 4.5 |
| 32 | 6.0 |
| 33 | 5.1 |
| 34 | 5.0 |
| 35 | 9.9 |
| 36 | 11 |
| 37 | 13 |
| 38 | 9.3 |
| 39 | 8.3 |
| 40 | 9.0 |
| 41 | 5.2 |
| 42 | 7.9 |
| 43 | 10 |
| 44 | 4.2 |
| 45 | 4.9 |
| 46 | 37 |
| 47 | 68 |
| 48 | 8.0 |
| 49 | 11 |
| 50 | 7.7 |
| 51 | 10 |
| 52 | 13 |
| 53 | 6.2 |
| 54 | 3.6 |
| 55 | 5.6 |
| 56 | 4.2 |
| 57 | 6.6 |
| 58 | 8.0 |
| 59 | 11 |
| 60 | 96 |
| 61 | 5.6 |
| 62 | 14 |
| 63 | 9.1 |
| 64 | 6.3 |
| 65 | 11 |
| 66 | 5.7 |
| 67 | 8.5 |
| 68 | 8.4 |
| 69 | 6.9 |
| 70 | 5.9 |
| 71 | 6.5 |
| 72 | 4.8 |
| 73 | 16 |
| 74 | 6.8 |
| 75 | 6.5 |
| 76 | 6.7 |
| 77 | 7.8 |
| 78 | 7.8 |
| 79 | 6.7 |
| 80 | 4.8 |
| 81 | 14 |
| 82 | 7.7 |
| 83 | 7.8 |
| 84 | 6.1 |
| 85 | 9.9 |
| 86 | 5.0 |
| 87 | 150 |
| 88 | 11 |
| 89 | 8.2 |
| 90 | 9.1 |
| 91 | 6.1 |
| 92 | 15 |
| 93 | 7.2 |
| 94 | 7.7 |
| 95 | 8.0 |
| 96 | 18 |
| 97 | 17 |
| 98 | 10 |
| 99 | 9.7 |
| 100 | 5.1 |
| 101 | 1900 |
| 102 | 4.8 |
| 103 | 6.7 |
| 104 | 5.5 |
| 105 | 7.1 |
| 106 | 5.1 |
| 107 | 6.6 |
| 108 | 5.9 |
| 109 | 9.7 |
| 110 | 6.3 |
| 111 | 6.1 |
| 112 | 9.4 |
| 113 | 10 |
| 114 | 7.4 |
| 115 | 9.7 |
| 116 | 73 |
| 117 | 8.2 |
| 118 | 8.4 |
| 119 | 8.1 |
| 120 | 6.2 |
| 121 | 6.3 |
| 122 | 9.7 |
| 123 | 5.8 |
| 124 | 8.4 |
| 125 | 9.2 |
| 126 | 5.6 |
| 127 | 7.0 |
| 128 | 8.7 |
| 129 | 5.5 |
| 130 | 6.7 |
| 131 | 12 |
| 132 | 5.1 |
| 133 | ND |
| 134 | 8.2 |
| 135 | 5.3 |
| 136 | 22 |
| 137 | 6.3 |
| 138 | 7.9 |
| 139 | 5.7 |
| 140 | 4.5 |
| 141 | 7.0 |
| 142 | 5.0 |
| 143 | 5.2 |
| 144 | 3.6 |
| 145 | 6.4 |
| 146 | 5.7 |
| 147 | 5.1 |
| 148 | 6.6 |
| 149 | 28 |
| 150 | 5.0 |
| 151 | ND |
| 152 | 7.2 |
| 153 | 9.0 |
| 154 | 9.3 |
| 155 | 16 |
| 156 | 5.1 |
| 157 | 5.9 |
| 158 | 6.3 |
| 159 | 6.7 |
| 160 | 5.0 |
| 161 | 7.9 |
| 162 | 6.3 |
| 163 | 5.3 |
| 164 | 6.0 |
| 165 | 8.4 |
| 166 | 7.5 |
| 167 | 16 |
| 168 | 8.5 |
| 169 | 62 |
| 170 | 6.6 |
| 171 | 6.4 |
| 172 | 6.0 |
| 173 | 6.5 |
| 174 | 11 |
| 175 | 14 |
| 176 | 6.2 |
| 177 | 5.3 |
| 178 | 6.4 |
| 179 | 5.3 |
| 180 | 7.6 |
| 181 | 5.1 |
| 182 | 5.1 |

TABLE 4-continued

| Example No. | IC$_{50}$ (nM) |
|---|---|
| 183 | 5.4 |
| 184 | 2.9 |
| 185 | 6.2 |
| 186 | 5.6 |
| 187 | 6.0 |
| 188 | 4.9 |
| 189 | 5.0 |
| 190 | 5.6 |
| 191 | 5.2 |
| 192 | 8.5 |
| 193 | 7.7 |
| 194 | 7.9 |
| 195 | 13 |
| 196 | 5.6 |
| 197 | 5.1 |
| 198 | 5.2 |
| 199 | 5.3 |
| 200 | 5.1 |
| 201 | 3.3 |
| 202 | 9.8 |
| 203 | 6.2 |
| 204 | 6.9 |
| 205 | 5.5 |
| 206 | 6.6 |
| 207 | 5.1 |
| 208 | 580 |
| 209 | 8.4 |
| 210 | 5.9 |
| 211 | 6.8 |
| 212 | 5.7 |
| 213 | 5.2 |
| 214 | 5.2 |
| 215 | 71 |
| 216 | 6.4 |
| 217 | 9.8 |
| 218 | 6.8 |
| 219 | 5.3 |
| 220 | 7.0 |
| 223 | 5.0 |
| 224 | 5.8 |
| 225 | 6.5 |
| 226 | 5.0 |

ND = not determined

Beas2B NQO1 mRNA Cell Based Assay

The up regulation of the NRF2 mediated gene NAD(P)H:quinone acceptor oxidoreductase 1 (NQO1) was measured using the following assay method: BEAS-2B cells (ATCC CRL-9609) were plated in 96-well clear plates at 20,000 cells/well in 75 µL of cell culture media and incubated overnight (37° C., 5% CO$_2$). On day 2, 25 µL of compound or controls were added to the cells for 24 h. On day 3, the medium was aspirated from the plate and the Cells-to-CT™ 1-Step TaqMan® Kit (Ambion A25603) was used to perform expression analysis directly from cultured cells without RNA purification according to the manufacturer's instructions.

Briefly, cells were washed with ice cold PBS and 22.5 µL of room-temperature DNase/Lysis solution was added to the cells and incubated at room temperature for 5 minutes. To stop the reaction, 2.25 µL of stop solution was added to the cell lysate. The samples were diluted 1:5 using nuclease free water and 2.5 µL transferred into the PCR plate. Real-time PCR was performed using the C-1000 Thermal Cycler (Bio-Rad) using human beta actin as the internal control. The cDNA was amplified with a specific primer for NQO1 using the 1-step RT-PCR master mix (Ambion Cells-to-CT™ 1-Step TaqMan® Kit A25603). The primers/probes sets that were used for amplification of cDNA were obtained from TaqMan Gene Expression Assays (Applied Biosystems). The comparative CT (ΔΔCT) relative quantification method was used to calculate the relative mRNA level of the target gene NQO1 as described in the Applied Biosystems Chemistry Guide. The data are expressed as an increase in target gene mRNA compared to vehicle (0.1% DMSO) control and the EC$_{50}$ values were determined by fitting the data to a four parameter logistic fit using XLfit or XE Runner within ActivityBase. EC$_{50}$ values for the Example compounds are shown in Table 5.

TABLE 5

| Example No. | EC$_{50}$ (nM) |
|---|---|
| 1 | 850 |
| 2 | 150 |
| 3 | 120 |
| 4 | 13 |
| 5 | 2.5 |
| 6 | 78 |
| 7 | 48 |
| 8 | 48 |
| 9 | 24 |
| 10 | 140* |
| 11 | 3.5 |
| 12 | 8.6 |
| 13 | 530 |
| 14 | 2.9 |
| 15 | 850 |
| 16 | 2.0 |
| 17 | 110 |
| 18 | 73 |
| 19 | 130 |
| 20 | 20 |
| 21 | 7.9 |
| 22 | 15 |
| 23 | 33 |
| 24 | 41 |
| 25 | 150 |
| 26 | 58 |
| 27 | 18 |
| 28 | 93 |
| 29 | 100 |
| 30 | 17 |
| 31 | 8.5 |
| 32 | 75 |
| 33 | 22 |
| 34 | 3.3 |
| 35 | 7.5 |
| 36 | 130 |
| 37 | 44 |
| 38 | 17 |
| 39 | 45 |
| 40 | 94 |
| 41 | 1.5 |
| 42 | 18 |
| 43 | 18 |
| 44 | 10 |
| 45 | 110 |
| 46 | 60 |
| 47 | 76 |
| 48 | 4.4 |
| 49 | 19 |
| 50 | 2.0 |
| 51 | 110.0 |
| 52 | 140.0 |
| 53 | 1.4 |
| 54 | 7.2 |
| 55 | 73 |
| 56 | 4.8 |
| 57 | 2.7 |
| 58 | 68 |
| 59 | 21 |
| 60 | 2.8 |
| 61 | 63 |
| 62 | 120 |
| 63 | 84 |
| 64 | 23 |
| 65 | 97 |
| 66 | 27 |
| 67 | 4.8 |

TABLE 5-continued

| Example No. | EC$_{50}$ (nM) |
|---|---|
| 68 | 32 |
| 69 | 140 |
| 70 | 55 |
| 71 | 78 |
| 72 | 2.8 |
| 73 | 130 |
| 74 | 22 |
| 75 | 8.3 |
| 76 | 2.5 |
| 77 | 6.7 |
| 78 | 57 |
| 79 | 1.2 |
| 80 | 110 |
| 81 | 260 |
| 82 | 1.3 |
| 83 | 35 |
| 84 | 36 |
| 85 | 34 |
| 86 | 8.3 |
| 87 | 300 |
| 88 | 78 |
| 89 | 5.1 |
| 90 | 8.1 |
| 91 | 0.21 |
| 92 | 180 |
| 93 | 15 |
| 94 | 7.8 |
| 95 | 3.7 |
| 96 | 210 |
| 97 | 750 |
| 98 | 330 |
| 99 | 520 |
| 100 | 3.4 |
| 101 | 710 |
| 102 | 1.0 |
| 103 | 67 |
| 104 | 27 |
| 105 | 24 |
| 106 | 2.9 |
| 107 | 0.35 |
| 108 | 1.5 |
| 109 | 7.4 |
| 110 | 1.3 |
| 111 | 2.5 |
| 112 | 280 |
| 113 | 240 |
| 114 | 16 |
| 115 | 4.2 |
| 116 | 1900 |
| 117 | 37 |
| 118 | 59 |
| 119 | 18 |
| 120 | 1.2 |
| 121 | 11 |
| 122 | 86 |
| 123 | 0.26 |
| 124 | 6.8 |
| 125 | 30 |
| 126 | 32 |
| 127 | 2.6 |
| 128 | 1.9 |
| 129 | 0.95 |
| 130 | 21 |
| 131 | 200 |
| 132 | 5.7 |
| 133 | 20 |
| 134 | 2.2 |
| 135 | 0.91 |
| 136 | 1700 |
| 137 | 6.7 |
| 138 | 0.8 |
| 139 | 140 |
| 140 | 150 |
| 141 | 35 |
| 142 | 0.21 |
| 143 | 0.05 |
| 144 | 0.022 |
| 145 | 4.9 |

TABLE 5-continued

| Example No. | EC$_{50}$ (nM) |
|---|---|
| 146 | 0.23 |
| 147 | 0.29 |
| 148 | 22 |
| 149 | 73 |
| 150 | 0.97 |
| 151 | 16 |
| 152 | 10 |
| 153 | 7.0 |
| 154 | 18 |
| 155 | 4.8 |
| 156 | 0.29 |
| 157 | 4.9 |
| 158 | 1.2 |
| 159 | 0.22 |
| 160 | 0.72 |
| 161 | 11 |
| 162 | 2.4 |
| 163 | 0.78 |
| 164 | 2.6 |
| 165 | 11 |
| 166 | 40 |
| 167 | 280 |
| 168 | 85 |
| 169 | 140 |
| 170 | 0.11 |
| 171 | 19 |
| 172 | 1.1 |
| 173 | 35 |
| 174 | 6.6 |
| 175 | 35 |
| 176 | 2.8 |
| 177 | 2.2 |
| 178 | 13 |
| 179 | 4.1 |
| 180 | 1.1 |
| 181 | 0.69 |
| 182 | 0.83 |
| 183 | 5.8 |
| 184 | 5.6 |
| 185 | 56 |
| 186 | 4.7 |
| 187 | 43 |
| 188 | 7.9 |
| 189 | 0.27 |
| 190 | 8.6 |
| 191 | 2.1 |
| 192 | 3.8 |
| 193 | 1.8 |
| 194 | 12 |
| 195 | 6.8 |
| 196 | 0.97 |
| 197 | 0.51 |
| 198 | 0.24 |
| 199 | 0.34 |
| 200 | 1.2 |
| 201 | 0.33 |
| 202 | 79 |
| 203 | 0.4 |
| 204 | 13 |
| 205 | 19 |
| 206 | 34 |
| 207 | 0.89 |
| 208 | 3300 |
| 209 | 290 |
| 210 | 0.24 |
| 211 | 43 |
| 212 | 1.9 |
| 213 | 2.2 |
| 214 | 41 |
| 215 | 550 |
| 216 | 110 |
| 217 | 43 |
| 218 | 0.98 |

TABLE 5-continued

| Example No. | EC$_{50}$ (nM) |
|---|---|
| 219 | 0.18 |
| 220 | 15 |
| 223 | 15 |
| 224 | 42 |
| 225 | 110 |
| 226 | 14 |

*on one test occasion >500 nM

PK/PD Method

Male Wistar Han rats (Charles River labs) were administered the test item orally or intravenously at the designated dose concentration. The intravenous dose was administered as a slow bolus via the tail vein. The oral formulation was administered by gastric gavage into the stomach. Actual dose times were recorded.

At the designated time points, 2×0.25 mL blood samples were collected into KEDTA blood tubes via the tail vein. The collected blood samples were then either centrifuged for plasma or decanted into the 1.5 mL PCR RNAlater tubes containing 650 µL of RNAlater.

Immediately following collection, blood samples were placed on wet ice. As soon as practically possible the 0.25 mL blood samples in K$_2$EDTA were centrifuged (+4° C., 1500 g, 10 min) and the resulting plasma stored in appropriately labelled polypropylene tubes in a freezer set to maintain a temperature of −80° C. until determination of plasma pharmacokinetics. The additional 0.25 mL blood samples in the 1.5 mL PCR RNAlater tubes containing 650 µL of RNAlater were stored in a refrigerator at 4° C. until determination of blood pharmacodynamics.

Following the last sample collection each animal was sacrificed by anesthetic overdose by IP injection of Pentobarbitone Na as soon as practically possible and death was confirmed by cervical dislocation.

The lungs from each animal were removed and divided into 4 equal pieces immediately after extraction. The first two sections of lung (labelled left and right) were placed in 5 mL RNAlater tissue protect tube containing 5 mL RNAlater stabilisation reagent and stored at 4° C. to allow RNA stabilization (PD analysis). The remaining two sections (labelled left and right) were weighed and snap frozen by immersion in liquid nitrogen in polypropylene tubes (PK analysis).

The liver was also collected from each animal. Six representative pieces (of a similar size to the lung pieces) from different areas (no more than 0.5 cm thickness) were collected. Four pieces (no more than 0.5 cm thickness) were placed in two separate (two pieces per tube) 5 mL RNAlater tissue protect tubes containing 5 mL RNAlater stabilisation reagent (tissue sections were completely submerged into the RNA later solution) and stored at 4° C. (PD analysis). The remaining two pieces were weighed and snap frozen by immersion in liquid nitrogen in separate polypropylene tubes (a maximum of 0.5 g per tube, PK analysis).

In some studies, the heart, spleen and brain were also collected from each animal. These tissues were sectioned into four equal sized pieces and two pieces placed in a single 5 mL RNA later tissue protect tube containing 5 mL RNAlater stabilisation reagent and stored at 4° C. The remaining two pieces were weighed and placed individually into polypropylene tubes and snap frozen by immersion in liquid nitrogen.

Study sample tubes containing RNAlater RNA Stabilisation Reagent were stored at ca +4° C. to allow RNA stabilisation reagent to perfuse the tissue. Sections snap frozen were stored in a freezer set to maintain a temperature of −80° C.

PK study samples were quantified using a method based on protein precipitation and LC-MS/MS analysis. Prior to analysis defrosted tissue samples were weighed and homogenised following the addition of HPLC grade water using an Omni-Prep Bead Ruptor (Omni Inc., Kennesaw, GA) at 4° C. Plasma and tissue homogenate samples were extracted using protein precipitation with acetonitrile acidified with 0.1% formic acid containing internal standard(s). Samples were mixed and centrifuged at 4000 rpm at 4° C. for 30 minutes to remove precipitated proteins, and the supernatant diluted appropriately with HPLC grade water in a 96-well plate. Representative aliquots of plasma and tissue homogenates were assayed for test item by LC-MS/MS using a Waters Xevo TQ-S (Waters, Elstree, UK) against matrix matched calibration curves and quality control standards. The standards were prepared by spiking aliquots of control plasma and tissue homogenate with the test item and extracted as described for the experimental samples.

RNA extraction and real-time PCR analysis for NQO1 gene expression in in-vivo PD studies was performed as detailed below.

Total RNA was isolated using RNeasy plus mini RNA isolation kit (Qiagen) or Mouse RiboPure™-Blood RNA Isolation Kit (ThermoFisher Scientific) according to the manufacturer's instructions and quantified using an Agilent RNA 6000 Nano instrument. Real-time PCR was performed using the C-1000 Thermal Cycler (Bio-Rad) using rat beta actin as the internal control. The cDNA was amplified with specific primer for NQO1/Nqo1 using universal master mix (Applied Biosystems). The primers/probes sets used for amplification of cDNA were obtained from TaqMan Gene Expression Assays (Applied Biosystems). The comparative CT (ΔΔCT) relative quantification method is used to calculate the relative mRNA level of the target gene NQO1 as described in the Applied Biosystems Chemistry Guide. The data is expressed as an increase in target gene mRNA compared to vehicle control treated for each tissue type.

The invention claimed is:

1. A compound of Formula I

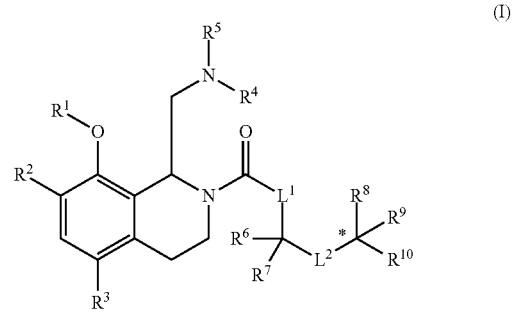

wherein:
R$^1$ is selected from C$_{1-4}$alkylene-R$^{11}$, heterocyclyl and 8-10 membered bicyclic heteroaryl; wherein said heterocyclyl is optionally substituted with one or more substituents independently selected from C$_{1-4}$alkyl, —C(O)—R$^{12}$, SO$_2$—R$^{13}$, C$_{1-3}$alkylene-OR$^{14}$ and heteroaryl which is optionally substituted with one or more substituents independently selected from C$_{1-4}$alkyl, C$_{3-7}$cycloalkyl, halo, OH, C$_{1-3}$alkoxy and cyano;

and wherein said 8-10 membered bicyclic heteroaryl is optionally substituted with one or more substituents independently selected from $C_{1-4}$alkyl, $C_{3-7}$cycloalkyl, halo, OH and $C_{1-3}$alkoxy;

$R^2$ is selected from hydrogen, fluoro, chloro and $C_{1-3}$alkyl;

$R^3$ is selected from hydrogen, fluoro, chloro, bromo, $C_{1-3}$alkoxy, $C_{1-3}$alkyl, $C_{1-3}$haloalkyl and cyano;

$R^4$ is hydrogen or $C_{1-4}$alkyl; and $R^5$ is —C(O)—$C_{1-4}$alkyl, —C(O)-heteroaryl or —C(O)-aryl, wherein said heteroaryl and aryl are optionally substituted with one or more substituents selected from $C_{1-4}$alkyl, halo, hydroxy, $C_{1-3}$alkoxy, $CO_2R^{15}$ and cyano; or $R^4$ and $R^5$, taken together with the nitrogen atom to which they are attached, form a 4-, 5-, or 6-membered heteroaryl or heterocyclyl ring, wherein:
  said heterocyclyl ring comprises one or more-C(O)-moieties attached to the nitrogen atom and is optionally fused to an aryl or heteroaryl ring, or optionally spiro-attached to a $C_{3-7}$cycloalkyl group; and
  said heteroaryl and heterocyclyl rings are optionally substituted with one or more substituents independently selected from $C_{1-4}$alkyl, halo, OH, $C_{1-3}$alkoxy, $C_{1-3}$haloalkyl, cyano, $NR^{16}R^{17}$, C(O)$R^{18}$, S(O)$R^{19}$ and $SO_2R^{20}$, $L^1$ and $L^2$ are independently selected from a bond and —$CR^{21}R^{22}$—;

$R^6$ and $R^7$ are independently selected from hydrogen, $C_{1-4}$alkyl, and $C_{3-7}$cycloalkyl; or $R^6$ and $R^7$, taken together with the carbon atom to which they are attached, form a 3-, 4-, 5-, or 6-membered cycloalkyl ring;

$R^8$ is selected from $CO_2R^{23}$, $C(O)NHSO_2C_{1-3}$alkyl, tetrazolyl, 3-trifluoromethyl-1,2,4-triazol-5-yl and a carboxylic acid mimetic group selected from hydroxamic acids, hydroxamic esters, phosphonic acids, phosphinic acids, sulfonic acids, sulfinic acids, sulphonamides, sulfonyl ureas, acyl ureas, thiazolidine dione, oxazolidine dione, oxadiazol-5(4H)-one, thiadiazol-5(4H)-one, oxathiadiazole-2-oxide, oxadiazol-5(4H)-thione, isoxazole, tetramic acid, cyclopentane-1,3-diones and cyclopentane-1,2-diones;

$R^9$ is selected from hydrogen, $C_{1-4}$alkyl, hydroxy, $C_{1-3}$alkoxy and halo; and $R^{10}$ is selected from hydrogen and $C_{1-4}$alkyl; or $R^9$ and $R^{10}$, taken together with the carbon atom to which they are attached, form a 3-, 4-, 5-, or 6-membered cycloalkyl ring; or $L^2$ is a bond and $R^7$ and $R^{10}$, taken together with the atoms to which they are attached, form a 4-, 5-, 6- or 7-membered cycloalkyl or heterocyclyl ring, wherein:
  said heterocyclyl ring contains 1 or 2 heteroatoms independently selected from nitrogen, oxygen and sulfur;
  said cycloalkyl ring optionally comprises 1 or 2 carbon-carbon double bonds and is optionally bridged by a $C_{1-3}$alkylene group connecting two carbon atoms of the ring, or $R^9$ is optionally a $C_{1-3}$alkylene group connecting C* to a carbon atom of the ring; and
  said cycloalkyl and heterocyclyl rings are optionally substituted with one or more substituents independently selected from $C_{1-4}$alkyl, halo, OH, $C_{1-3}$alkoxy, $C_{1-3}$haloalkyl and deuterium;

$R^{11}$ is selected from —C(O)—$R^{24}$, —$SO_2$—$R^{25}$, —$NR^{26}C(O)$—$R^{27}$, —$NR^{28}SO_2$—$R^{29}$, heterocyclyl, aryl and heteroaryl; wherein said aryl and heteroaryl groups are optionally substituted with one or more substituents independently selected from $C_{1-4}$alkyl, $C_{1-3}$haloalkyl, $C_{3-7}$cycloalkyl, $C_{1-4}$alkylene-$R^{30}$, halo, OH, $C_{1-3}$alkoxy, heterocyclyl and cyano; and said heterocyclyl group is optionally substituted with one or more substituents independently selected from $C_{1-4}$alkyl, $C_{1-3}$haloalkyl, $C_{3-7}$cycloalkyl, $C_{1-4}$alkylene-$R^{30}$, halo, OH, $C_{1-3}$alkoxy, oxo and cyano;

$R^{12}$ is selected from $C_{1-4}$alkyl, $C_{3-7}$cycloalkyl, $OR^{31}$, $NR^{32}R^{33}$, aryl and heteroaryl, wherein said aryl and heteroaryl are optionally substituted with one or more substituents independently selected from $C_{1-4}$alkyl, halo, OH, $C_{1-3}$alkoxy and cyano;

$R^{13}$ is selected from $C_{1-4}$alkyl, $C_{3-7}$cycloalkyl, heteroaryl, heterocyclyl and $NR^{34}R^{35}$, wherein said heteroaryl and heterocyclyl are optionally substituted with one or more substituents independently selected from $C_{1-4}$alkyl, halo, OH, $C_{1-3}$alkoxy and cyano;

$R^{17}$ is selected from hydrogen, $C_{1-4}$alkyl, $C(O)C_{1-3}$alkyl and $C(O)NR^{36}R^{37}$;

$R^{18}$, $R^{19}$ and $R^{20}$ are independently selected from $C_{1-4}$alkyl, OH, $C_{1-3}$alkoxy and $NR^{38}R^{39}$;

$R^{24}$ is selected from $C_{1-4}$alkyl, $NR^{40}R^{41}$ and $OR^{42}$;

$R^{25}$ is selected from $C_{1-4}$alkyl and $NR^{43}R^{44}$, $R^{27}$ is selected from $C_{1-4}$alkyl, $C_{3-7}$cycloalkyl, $C_{1-3}$haloalkyl, heterocyclyl, aryl and heteroaryl, wherein said aryl and heteroaryl are optionally substituted with one or more substituents independently selected from $C_{1-4}$alkyl, $C_{1-3}$haloalkyl, $C_{3-7}$cycloalkyl, $C_{1-4}$alkylene-$R^{45}$, halo, OH, $C_{1-3}$alkoxy and cyano;

$R^{29}$ is selected from $C_{1-4}$alkyl, $C_{3-7}$cycloalkyl, $C_{1-3}$haloalkyl, aryl and heteroaryl, wherein said aryl and heteroaryl are optionally substituted with one or more substituents independently selected from $C_{1-4}$alkyl, $C_{1-3}$haloalkyl, $C_{3-7}$cycloalkyl, $C_{1-4}$alkylene-$R^{46}$, halo, OH, $C_{1-3}$alkoxy and cyano;

$R^{30}$ is selected from hydroxy, $C_{1-3}$alkoxy, $C_{3-7}$cycloalkyl, cyano and $NR^{47}R^{48}$, $R^{40}$ is selected from hydrogen and $C_{1-4}$alkyl;

$R^{41}$ is selected from hydrogen, $C_{1-4}$alkyl, $C_{3-7}$cycloalkyl, $C_{1-3}$alkoxy, aryl and heteroaryl; or $R^{40}$ and $R^{41}$, taken together with the nitrogen atom to which they are attached, form a 4-, 5-, or 6-membered heteroaryl or heterocyclyl ring, wherein said heteroaryl and heterocyclyl rings are optionally substituted with one or more substituents independently selected from $C_{1-4}$alkyl, halo, OH, $C_{1-3}$alkoxy, $C_{3-7}$cycloalkyl and cyano;

$R^{45}$ and $R^{46}$ are independently selected from hydroxy, $C_{1-3}$alkoxy and $C_{3-7}$cycloalkyl; and $R^{14}$, $R^{15}$, $R^{16}$, $R^{21}$, $R^{22}$, $R^{23}$, $R^{26}$, $R^{28}$, $R^{31}$, $R^{32}$, $R^{33}$, $R^{34}$, $R^{35}$, $R^{36}$, $R^{37}$, $R^{38}$, $R^{39}$, $R^{42}$, $R^{43}$, $R^{44}$, $R^{47}$ and $R^{48}$ are independently selected from hydrogen, $C_{1-4}$alkyl and $C_{3-7}$cycloalkyl;

or a pharmaceutically acceptable salt thereof.

2. A compound according to claim 1, wherein said compound has the structural formula IA shown below

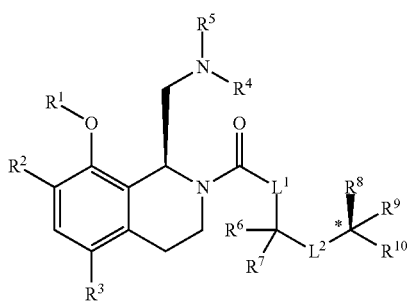

(IA)

wherein $L^1$ and $L^2$ and $R^1$ to $R^{10}$ are as defined in claim 1.

3. A compound according to claim 1, wherein $L^2$ is a bond and $R^7$ and $R^{10}$, taken together with the atoms to which they are attached, form a 4-, 5- or 6-membered cycloalkyl ring.

4. A compound according to claim 1, wherein said compound has the structural formula IB shown below

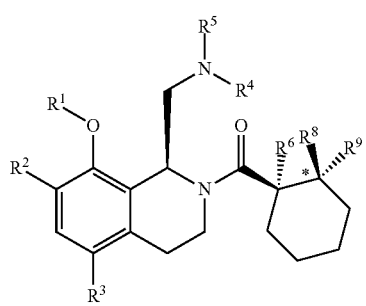

(IB)

wherein $R^1$ to $R^6$, $R^8$ and $R^9$ are as defined in claim 1 and the cyclohexyl ring is optionally substituted with one or more substituents independently selected from $C_{1-4}$alkyl, halo, OH, $C_{1-3}$alkoxy and deuterium and the cyclohexyl ring is optionally bridged by a $C_{1-3}$alkylene group connecting two carbon atoms of the ring, or $R^9$ is optionally a $C_{1-3}$alkylene group connecting C* to a carbon atom of the ring.

5. A compound according to claim 1, wherein $R^8$ is $CO_2R^{23}$ and $R^{23}$ is hydrogen.

6. A compound according to claim 1, wherein $R^9$ is hydrogen or $C_{1-4}$alkyl.

7. A compound according to claim 1, wherein $R^1$ is $C_{1-4}$alkylene-$R^{11}$.

8. A compound according to claim 1, wherein $R^{11}$ is:

(A) selected from —C(O)—$R^{24}$, —NR$^{26}$C(O)—$R^{27}$, heterocyclyl, aryl and heteroaryl, wherein said aryl and heteroaryl groups are optionally substituted with one or more substituents independently selected from $C_{1-4}$alkyl, $C_{1-3}$haloalkyl, $C_{3-7}$cycloalkyl, $C_{1-4}$alkylene-$R^{30}$, halo, OH, $C_{1-3}$alkoxy, heterocyclyl and cyano; and said heterocyclyl group is optionally substituted with one or more substituents independently selected from $C_{1-4}$alkyl, $C_{1-3}$haloalkyl, $C_{3-7}$cycloalkyl, $C_{1-4}$alkylene-$R^{30}$, halo, OH, $C_{1-3}$alkoxy, oxo and cyano;

(B) heteroaryl optionally substituted with one or more substituents independently selected from $C_{1-4}$alkyl, $C_{1-3}$haloalkyl, $C_{3-7}$cycloalkyl, $C_{1-4}$alkylene-$R^{30}$, halo, OH, $C_{1-3}$alkoxy, heterocyclyl and cyano;

(C) heteroaryl optionally substituted with one or more substituents independently selected from methyl, ethyl, isopropyl, difluoromethyl, trifluoromethyl, chloro, fluoro, cyclopropyl, methoxy, cyano, oxetanyl, $CH_2$—$R^{30}$ and $C_2H_4$—$R^{30}$;

(D) pyridyl, pyrimidinyl, pyridazinyl, oxazolyl, isoxazolyl, 1,2,3-triazolyl, 1,2,4-oxadiazolyl, benzotriazolyl, benzisoxazolyl, isoxazolopyridinyl, imidazopyridinyl or triazolopyridinyl, each optionally substituted with one or more substituents independently selected from $C_{1-4}$alkyl, $C_{1-3}$haloalkyl, $C_{3-7}$cycloalkyl, $C_{1-4}$alkylene-$R^{30}$, halo, OH, $C_{1-3}$alkoxy, heterocyclyl and cyano; or (E) heteroaryl selected from:

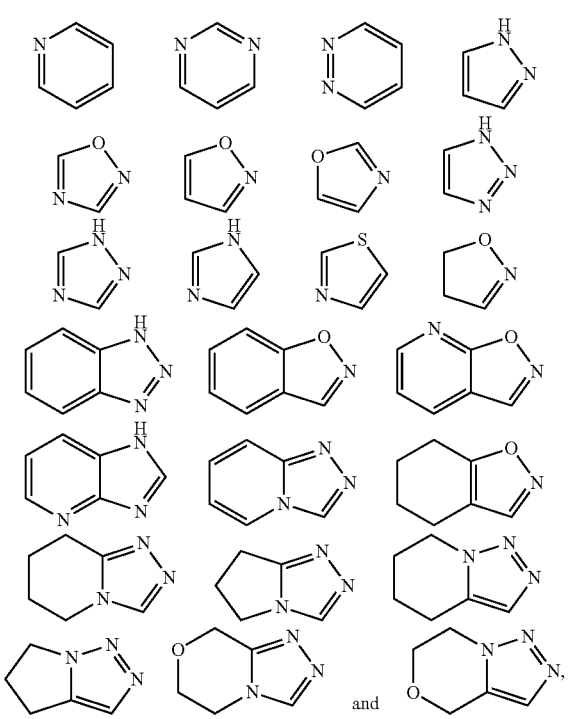

and each heteroaryl being optionally substituted with one or more substituents independently selected from $C_{1-4}$alkyl, $C_{1-3}$haloalkyl, $C_{3-7}$cycloalkyl, $C_{1-4}$alkylene-$R^{30}$, halo, OH, $C_{1-3}$alkoxy, heterocyclyl and cyano.

9. A compound according to claim 1, wherein $R^1$ is selected from one of the following groups:

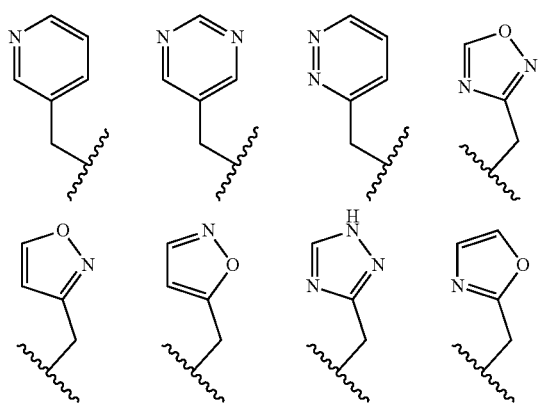

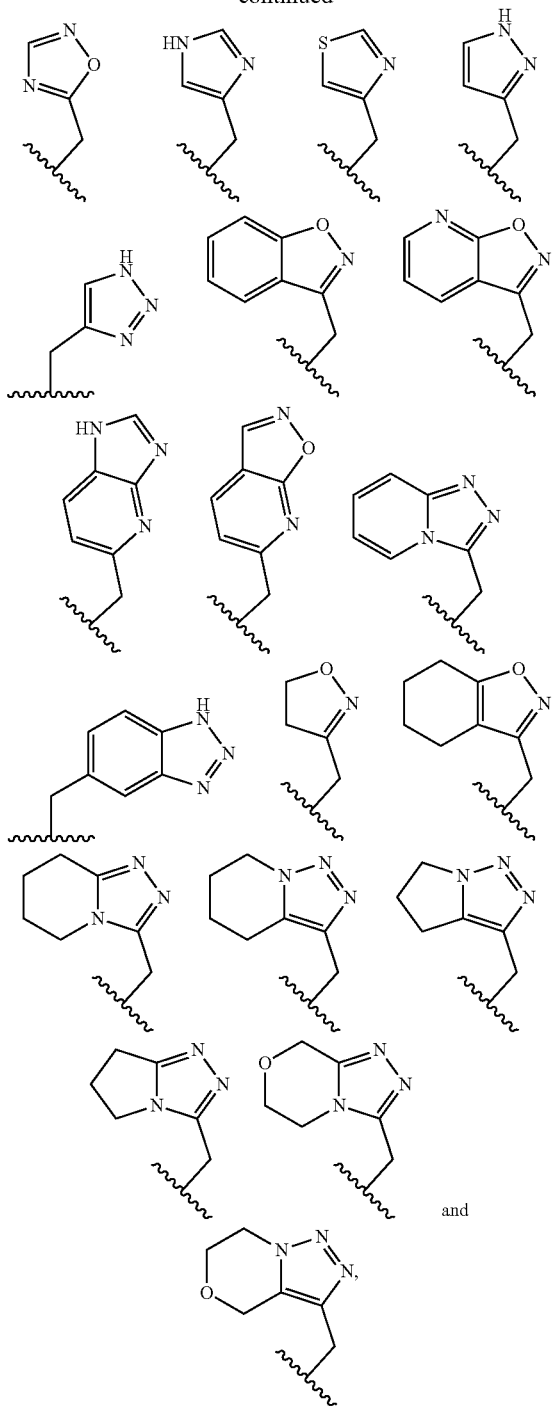

wherein ∿ represents the point of attachment of the group to the oxygen atom of the rest of the compound and wherein each group is optionally substituted with one or more substituents independently selected from $C_{1-4}$alkyl, $C_{1-3}$haloalkyl, $C_{3-7}$cycloalkyl, $C_{1-4}$alkylene-$R^{30}$, halo, OH, $C_{1-3}$alkoxy, heterocyclyl and cyano.

10. A compound according to claim 1, wherein $R^1$ is:
(A) heterocyclyl optionally substituted with one or more substituents independently selected from —C(O)—$R^{12}$, $SO_2$—$R^{13}$, heteroaryl and $C_{1-3}$alkylene-$OR^{14}$, wherein said heteroaryl is optionally substituted with one or more substituents independently selected from $C_{1-4}$alkyl, $C_{3-7}$cycloalkyl, halo, OH, $C_{1-3}$alkoxy and cyano;

(B) piperidinyl or pyrrolidinyl, each optionally substituted with one or more substituents independently selected from —C(O)—$R^{12}$, $SO_2$—$R^{13}$, heteroaryl and $C_{1-3}$alkylene-$OR^{14}$, wherein said heteroaryl is optionally substituted with one or more substituents independently selected from $C_{1-4}$alkyl, $C_{3-7}$cycloalkyl, halo, OH, $C_{1-3}$alkoxy and cyano;

(C) pyrrolidinyl optionally substituted with one or more substituents independently selected from —C(O)—$R^{12}$, $SO_2$—$R^{13}$, heteroaryl and $C_{1-3}$alkylene-$OR^{14}$, wherein said heteroaryl is optionally substituted with $C_{1-4}$alkyl or $C_{3-7}$cycloalkyl; or (D) selected from one of the following groups:

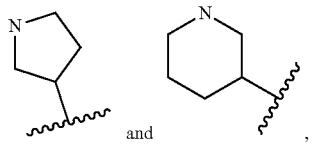

and wherein ∿ represents the point of attachment of the group to the oxygen atom of the rest of the compound and wherein each group is optionally substituted with one or more substituents independently selected from —C(O)—$R^{12}$, $SO_2$—$R^{13}$, heteroaryl and $C_{1-3}$alkylene-$OR^{14}$, wherein said heteroaryl is optionally substituted with $C_{1-4}$alkyl or $C_{3-7}$cycloalkyl.

11. A compound according to claim 1, wherein $R^2$ is hydrogen or fluoro.

12. A compound according to claim 1, wherein $R^3$ is hydrogen or chloro.

13. A compound according to claim 1, wherein $R^4$ is hydrogen and $R^5$ is —C(O)—$C_{1-4}$alkyl or —C(O)-aryl, wherein said aryl is optionally substituted with one or more substituents selected from $C_{1-4}$alkyl, halo, hydroxy, $C_{1-3}$alkoxy, $CO_2R^{15}$ and cyano.

14. A compound according to claim 1, wherein $R^4$ and $R^5$, taken together with the nitrogen atom to which they are attached, form a 5-membered heteroaryl or heterocyclyl ring, wherein said heterocyclyl comprises a —C(O)— moiety attached to the nitrogen atom and is optionally fused to an aryl or heteroaryl ring, or optionally spiro-attached to a $C_{3-7}$cycloalkyl group, and wherein said heteroaryl and heterocyclyl are optionally substituted with one or more substituents independently selected from $C_{1-4}$alkyl, halo, OH, $C_{1-3}$alkoxy and cyano.

15. A compound according to claim 14, wherein $R^4$ and $R^5$, taken together with the nitrogen atom to which they are attached, form a 5-membered heteroaryl ring optionally substituted with one or more substituents independently selected from $C_{1-4}$alkyl, halo and OH.

16. A compound according to claim 1, wherein $R^4$ and $R^5$, taken together with the nitrogen atom to which they are attached, form:
(A) a 5- or 6-membered heterocyclyl ring, wherein said heterocyclyl comprises a —C(O)— moiety attached to the nitrogen atom and is optionally fused to an aryl ring, or optionally spiro-attached to a $C_{3-7}$cycloalkyl group, and wherein said heterocyclyl is optionally substituted with one or more substituents independently selected from $C_{1-4}$alkyl, halo and OH; or (B) a heterocyclic moiety selected from one of the following:

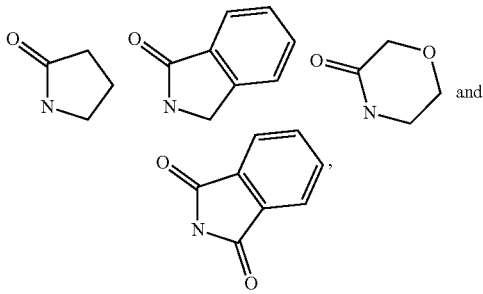

wherein the saturated ring of the heterocyclic moiety is optionally spiro-attached to a $C_{3-7}$cycloalkyl group, and wherein said heterocyclic moiety is optionally substituted with one or more substituents independently selected from $C_{1-4}$alkyl, halo and OH.

17. A compound according to claim 1, which is selected from any one of the following:

(1S,2R)-2-((S)-1-((1,3-dioxoisoindolin-2-yl)methyl)-8-(2-(5-methylisoxazole-3-carboxamido)ethoxy)-1,2,3,4-tetrahydroisoquinoline-2-carbonyl)cyclohexane-1-carboxylic acid;

(1S,2R)-2-((S)-8-(2-(Benzo[d]oxazole-2-carboxamido)ethoxy)-1-((1,3-dioxoisoindolin-2-yl)methyl)-1,2,3,4-tetrahydroisoquinoline-2-carbonyl)cyclohexane-1-carboxylic acid;

(1S,2R)-2-((S)-8-(((S)-1-Acetylpyrrolidin-3-yl)oxy)-1-((1,3-dioxoisoindolin-2-yl)methyl)-1,2,3,4-tetrahydroisoquinoline-2-carbonyl)cyclohexane-1-carboxylic acid;

(1S,2R)-2-((S)-1-((1,3-dioxoisoindolin-2-yl)methyl)-8-(((S)-1-(5-methylisoxazole-3-carbonyl)pyrrolidin-3-yl)oxy)-1,2,3,4-tetrahydroisoquinoline-2-carbonyl)cyclohexane-1-carboxylic acid;

(1S,2R)-2-((S)-5-bromo-1-((1,3-dioxoisoindolin-2-yl)methyl)-8-(((S)-1-(thiazole-5-carbonyl)pyrrolidin-3-yl)oxy)-1,2,3,4-tetrahydroisoquinoline-2-carbonyl)cyclohexane-1-carboxylic acid;

(1S,2R)-2-((S)-1-((1,3-dioxoisoindolin-2-yl)methyl)-8-(((S)-1-(thiazole-5-carbonyl)pyrrolidin-3-yl)oxy)-1,2,3,4-tetrahydroisoquinoline-2-carbonyl)cyclohexane-1-carboxylic acid;

(1S,2R)-2-((S)-1-((1,3-dioxoisoindolin-2-yl)methyl)-8-(((S)-1-(2-methylthiazole-5-carbonyl)pyrrolidin-3-yl)oxy)-1,2,3,4-tetrahydroisoquinoline-2-carbonyl)cyclohexane-1-carboxylic acid;

(1S,2R)-2-((S)-1-((1,3-dioxoisoindolin-2-yl)methyl)-8-((1-methyl-1H-benzo[d][1,2,3]triazol-5-yl)methoxy)-1,2,3,4-tetrahydroisoquinoline-2-carbonyl)cyclohexane-1-carboxylic acid;

(1S,2R)-2-((S)-1-((1,3-dioxoisoindolin-2-yl)methyl)-8-((1-methyl-1H-1,2,3-triazol-4-yl)methoxy)-1,2,3,4-tetrahydroisoquinoline-2-carbonyl)cyclohexane-1-carboxylic acid;

(1S,2R)-2-((S)-1-((1,3-dioxoisoindolin-2-yl)methyl)-8-((1-methyl-1H-benzo[d]imidazol-5-yl)methoxy)-1,2,3,4-tetrahydroisoquinoline-2-carbonyl)cyclohexane-1-carboxylic acid;

(1S,2R)-2-((S)-8-(((S)-1-acetylpyrrolidin-3-yl)oxy)-5-bromo-1-((1,3-dioxoisoindolin-2-yl)methyl)-1,2,3,4-tetrahydroisoquinoline-2-carbonyl)cyclohexane-1-carboxylic acid;

(1S,2R)-2-((S)-8-(((S)-1-acetylpyrrolidin-3-yl)oxy)-5-chloro-1-((1,3-dioxoisoindolin-2-yl)methyl)-1,2,3,4-tetrahydroisoquinoline-2-carbonyl)cyclohexane-1-carboxylic acid;

(1S,2R)-2-((S)-8-(((S)-1-acetylpyrrolidin-3-yl)oxy)-5,7-dichloro-1-((1,3-dioxoisoindolin-2-yl)methyl)-1,2,3,4-tetrahydroisoquinoline-2-carbonyl)cyclohexane-1-carboxylic acid;

(1S,2R)-2-((S)-5-chloro-1-((1,3-dioxoisoindolin-2-yl)methyl)-8-(((S)-1-(thiazole-5-carbonyl)pyrrolidin-3-yl)oxy)-1,2,3,4-tetrahydroisoquinoline-2-carbonyl)cyclohexane-1-carboxylic acid;

(1S,2R)-2-((S)-1-((1-oxoisoindolin-2-yl)methyl)-8-(((S)-1-(thiazole-5-carbonyl)pyrrolidin-3-yl)oxy)-1,2,3,4-tetrahydroisoquinoline-2-carbonyl)cyclohexane-1-carboxylic acid;

(1S,2R)-2-((S)-8-([1,2,4]triazolo[4,3-a]pyridin-3-ylmethoxy)-5-bromo-1-((1-oxoisoindolin-2-yl)methyl)-1,2,3,4-tetrahydroisoquinoline-2-carbonyl)cyclohexane-1-carboxylic acid;

(1S,2R)-2-((S)-8-((1-isopropyl-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-8-((1-methyl-1H-benzo[d][1,2,3]triazol-5-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-8-(((S)-1-acetylpyrrolidin-3-yl)oxy)-5-bromo-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-(((S)-1-(2-methylthiazole-5-carbonyl)pyrrolidin-3-yl)oxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-(((S)-1-(5-methylthiazol-2-yl)pyrrolidin-3-yl)oxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-(((S)-1-(5-methylpyridazin-3-yl)pyrrolidin-3-yl)oxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-((4-methyl-4H-1,2,4-triazol-3-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-((5-methyl-1,2,4-oxadiazol-3-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-Bromo-8-((1-methyl-1H-imidazol-4-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-((5-methylisoxazol-3-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-((2-ethyl-2H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((1S)-5-bromo-8-((5-methylthiazol-2-yl)methoxy)-1-((1-oxo-1,3,3a,4,5,6-hexahydro-2H-isoindol-2-yl)methyl)-1,2,3,4-tetrahydroisoquinoline-2-carbonyl)cyclohexane-1-carboxylic acid;

(1S,2R)-2-((S)-5-bromo-8-((1-methyl-1H-1,2,4-triazol-5-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-1-((1-oxoisoindolin-2-yl)methyl)-8-(pyridazin-3-ylmethoxy)-1,2,3,4-tetrahydroisoquinoline-2-carbonyl)cyclohexane-1-carboxylic acid;

(1S,2R)-2-((S)-5-bromo-8-((1-(cyclopropylmethyl)-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-(imidazo[1,2-a]pyridin-7-ylmethoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-((1-methyl-1H-benzo[d]imidazol-5-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-((1-methyl-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-((1-isopropyl-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-((5-methyl-1,3,4-oxadiazol-2-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-((7-methoxy-1-methyl-1H-benzo[d][1,2,3]triazol-5-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-((1-methyl-1H-benzo[d][1,2,3]triazol-5-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-((1-methyl-1H-1,2,4-triazol-3-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-((1-isopropyl-1H-imidazol-2-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-((5-(difluoromethyl)-1-methyl-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-((4-ethyl-4H-1,2,4-triazol-3-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-8-((5-cyano-1-ethyl-1H-imidazol-4-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-bromo-1-((1-oxoisoindolin-2-yl)methyl)-8-((5,6,7,8-tetrahydro-[1,2,4]triazolo[4,3-a]pyridin-3-yl)methoxy)-1,2,3,4-tetrahydroisoquinoline-2-carbonyl)cyclohexane-1-carboxylic acid;

(1S,2R)-2-((1S)-5-bromo-8-(1-(1-methyl-1H-1,2,3-triazol-4-yl)ethoxy)-1-((1-oxoisoindolin-2-yl)methyl)-1,2,3,4-tetrahydroisoquinoline-2-carbonyl)cyclohexane-1-carboxylic acid;

(1S,2R)-2-((1S)-5-bromo-8-(1-(1-isopropyl-1H-1,2,3-triazol-4-yl)ethoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-chloro-8-((1-methyl-1H-benzo[d][1,2,3]triazol-5-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-chloro-8-((5-methylisoxazol-3-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-8-([1,2,4]triazolo[4,3-a]pyridin-3-ylmethoxy)-5-chloro-1-((1-oxoisoindolin-2-yl)methyl)-1,2,3,4-tetrahydroisoquinoline-2-carbonyl)cyclohexane-1-carboxylic acid;

(1S,2R)-2-((S)-5-chloro-1-((1-oxoisoindolin-2-yl)methyl)-8-((1-(2,2,2-trifluoroethyl)-1H-imidazol-2-yl)methoxy)-1,2,3,4-tetrahydroisoquinoline-2-carbonyl)cyclohexane-1-carboxylic acid;

(1S,2R)-2-((S)-5-chloro-8-((1-(2,2-difluoroethyl)-1H-imidazol-2-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-chloro-8-((5-(difluoromethyl)-1-methyl-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-chloro-8-((1-methyl-5-(trifluoromethyl)-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-chloro-8-((1-ethyl-1H-pyrazol-3-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-chloro-8-((5-(difluoromethyl)-1-methyl-1H-imidazol-4-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-chloro-8-((1-isopropyl-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-5-fluoro-8-((1-isopropyl-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-8-((1-isopropyl-1H-1,2,3-triazol-4-yl)methoxy)-5-methyl-1-((1-oxoisoindolin-2-yl)methyl)-1,2,3,4-tetrahydroisoquinoline-2-carbonyl)cyclohexane-1-carboxylic acid;

(1S,2R)-2-((S)-5-cyano-8-((1-isopropyl-1H-1,2,3-triazol-4-yl)methoxy)-1-((1-oxoisoindolin-2-yl)methyl)-1,2,3,4-tetrahydroisoquinoline-2-carbonyl)cyclohexane-1-carboxylic acid;

(1S,2R)-2-((S)-8-((1-isopropyl-1H-1,2,3-triazol-4-yl)methoxy)-5-methoxy-1-((1-oxoisoindolin-2-yl)methyl)-1,2,3,4-tetrahydroisoquinoline-2-carbonyl)cyclohexane-1-carboxylic acid;

(1S,2R)-2-((S)-8-((1-isopropyl-1H-1,2,3-triazol-4-yl)methoxy)-1-((1-oxoisoindolin-2-yl)methyl)-5-(trifluoromethyl)-1,2,3,4-tetrahydroisoquinoline-2-carbonyl)cyclohexane-1-carboxylic acid;

(1S,2R)-2-((S)-5-bromo-1-((2-oxopyrrolidin-1-yl)methyl)-8-(((S)-1-(thiazole-5-carbonyl)pyrrolidin-3-yl)oxy)-1,2,3,4-tetrahydroisoquinoline-2-carbonyl)cyclohexane-1-carboxylic acid;

(1S,2R)-2-((S)-8-([1,2,4]triazolo[4,3-a]pyridin-3-ylmethoxy)-5-bromo-1-((2-oxopyrrolidin-1-yl)methyl)-1,2,3,4-tetrahydroisoquinoline-2-carbonyl)cyclohexane-1-carboxylic acid;

(1S,2R)-2-((S)-5-bromo-8-((5-methylthiazol-2-yl)methoxy)-1-((2-oxopyrrolidin-1-yl)methyl)-1,2,3,4-tetrahydroisoquinoline-2-carbonyl)cyclohexane-1-carboxylic acid;

(1S,2R)-2-((S)-5-bromo-8-((5-isopropyl-1,2,4-oxadiazol-3-yl)methoxy)-1-((2-oxopyrrolidin-1-yl)methyl)-1,2,3,4-tetrahydroisoquinoline-2-carbonyl)cyclohexane-1-carboxylic acid;

(1S,2R)-2-((S)-8-(benzo[d]isoxazol-3-ylmethoxy)-5-bromo-1-((2-oxopyrrolidin-1-yl)methyl)-1,2,3,4-tetrahydroisoquinoline-2-carbonyl)cyclohexane-1-carboxylic acid;

(1S,2R)-2-((S)-8-(benzo[d]isothiazol-3-ylmethoxy)-5-chloro-1-((2-oxopyrrolidin-1-yl)methyl)-1,2,3,4-tetrahydroisoquinoline-2-carbonyl)cyclohexane-1-carboxylic acid;

(1S,2R)-2-((S)-5-chloro-1-((2-oxopyrrolidin-1-yl)methyl)-8-(pyridin-2-ylmethoxy)-1,2,3,4-tetrahydroisoquinoline-2-carbonyl)cyclohexane-1-carboxylic acid;

(1S,2R)-2-((S)-5-chloro-8-((5-methylisothiazol-3-yl)methoxy)-1-((2-oxopyrrolidin-1-yl)methyl)-1,2,3,4-tetrahydroisoquinoline-2-carbonyl)cyclohexane-1-carboxylic acid;

(1S,2R)-2-((S)-5-chloro-8-(isothiazol-3-ylmethoxy)-1-((2-oxopyrrolidin-1-yl)methyl)-1,2,3,4-tetrahydroisoquinoline-2-carbonyl)cyclohexane-1-carboxylic acid;

(1S,2R)-2-((S)-8-(benzo[d]isoxazol-3-ylmethoxy)-5-chloro-1-((2-oxopyrrolidin-1-yl)methyl)-1,2,3,4-tetrahydroisoquinoline-2-carbonyl)cyclohexane-1-carboxylic acid;

(1S,2R)-2-((1S)-5-bromo-8-((1-isopropyl-1H-1,2,3-triazol-4-yl)methoxy)-1-((3-methyl-2-oxopyrrolidin-1-yl)methyl)-1,2,3,4-tetrahydroisoquinoline-2-carbonyl)cyclohexane-1-carboxylic acid;

(1S,2R)-2-((S)-5-bromo-8-((1-isopropyl-1H-1,2,3-triazol-4-yl)methoxy)-1-(((R)-4-methyl-2-oxopyrrolidin-1-yl)methyl)-1,2,3,4-tetrahydroisoquinoline-2-carbonyl)cyclohexane-1-carboxylic acid;

(1S,2R)-2-((S)-5-bromo-8-((1-isopropyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)cyclohexane-1-carboxylic acid;

(1S,2R)-2-((S)-5-bromo-8-((1-isopropyl-1H-1,2,3-triazol-4-yl)methoxy)-1-(((S)-4-methyl-2-oxopyrrolidin-1-yl)methyl)-1,2,3,4-tetrahydroisoquinoline-2-carbonyl)cyclohexane-1-carboxylic acid;

(1S,2R)-2-((S)-5-chloro-1-((2-oxopyrrolidin-1-yl)methyl)-8-(pyridin-3-ylmethoxy)-1,2,3,4-tetrahydroisoquinoline-2-carbonyl)cyclohexane-1-carboxylic acid;

(1S,2R)-2-((S)-5-chloro-8-((5-(difluoromethyl)-1-ethyl-1H-1,2,3-triazol-4-yl)methoxy)-1-((2-oxopyrrolidin-1-yl)methyl)-1,2,3,4-tetrahydroisoquinoline-2-carbonyl)cyclohexane-1-carboxylic acid;

(R)-4-((S)-8-(benzo[d]isoxazol-3-ylmethoxy)-5-chloro-1-((2-oxopyrrolidin-1-yl)methyl)-3,4-dihydroisoquinolin-2(1H)-yl)-3-methyl-4-oxobutanoic acid;

1-(((S)-2-((1R,2S)-2-(2H-tetrazol-5-yl)cyclohexane-1-carbonyl)-8-(benzo[d]isoxazol-3-ylmethoxy)-5-chloro-1,2,3,4-tetrahydroisoquinolin-1-yl)methyl)pyrrolidin-2-one;

(1S,2R)-2-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)cyclohexane-1-carboxylic acid;

(1S,2R)-2-((S)-5-chloro-8-((5-isopropyl-1,2,4-oxadiazol-3-yl)methoxy)-1-((2-oxopyrrolidin-1-yl)methyl)-1,2,3,4-tetrahydroisoquinoline-2-carbonyl)cyclohexane-1-carboxylic acid;

(1S,2R)-2-((S)-5-chloro-8-((5-(difluoromethyl)-1-methyl-1H-1,2,3-triazol-4-yl)methoxy)-1-((4-methyl-1H-pyrazol-1-yl)methyl)-1,2,3,4-tetrahydroisoquinoline-2-carbonyl)cyclohexane-1-carboxylic acid;

(1S,2R)-2-((S)-5-chloro-1-((2-oxopyrrolidin-1-yl)methyl)-8-(pyrimidin-5-ylmethoxy)-1,2,3,4-tetrahydroisoquinoline-2-carbonyl)cyclohexane-1-carboxylic acid;

(1S,2R)-2-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)cyclopentane-1-carboxylic acid;

(1R,2S)-2-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)cyclopentane-1-carboxylic acid;

(1S,2R)-2-((S)-5-chloro-1-((2-oxopyrrolidin-1-yl)methyl)-8-(pyridazin-3-ylmethoxy)-1,2,3,4-tetrahydroisoquinoline-2-carbonyl)cyclohexane-1-carboxylic acid;

(1S,2R)-2-((S)-5-chloro-8-((3-methyl-3H-imidazo[4,5-b]pyridin-6-yl)methoxy)-1-((2-oxopyrrolidin-1-yl)methyl)-1,2,3,4-tetrahydroisoquinoline-2-carbonyl)cyclohexane-1-carboxylic acid;

(1S,2R)-2-((S)-5-chloro-8-((1-methyl-1H-benzo[d][1,2,3]triazol-5-yl)methoxy)-1-((2-oxopyrrolidin-1-yl)methyl)-1,2,3,4-tetrahydroisoquinoline-2-carbonyl)cyclohexane-1-carboxylic acid;

(1S,2R)-2-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-(imidazo[1,2-a]pyrimidin-2-ylmethoxy)-1-((2-oxopyrrolidin-1-yl)methyl)-1,2,3,4-tetrahydroisoquinoline-2-carbonyl)cyclohexane-1-carboxylic acid;

(1S,2R)-2-((S)-5-chloro-8-(isoxazolo[5,4-b]pyridin-3-ylmethoxy)-1-((2-oxopyrrolidin-1-yl)methyl)-1,2,3,4-tetrahydroisoquinoline-2-carbonyl)cyclohexane-1-carboxylic acid;

(1S,2R)-2-((S)-8-([1,2,4]triazolo[4,3-a]pyridin-3-ylmethoxy)-5-chloro-1-((2-oxopyrrolidin-1-yl)methyl)-1,2,3,4-tetrahydroisoquinoline-2-carbonyl)cyclohexane-1-carboxylic acid;

(1S,2R)-2-((S)-5-chloro-8-((3-methylisoxazolo[5,4-b]pyridin-6-yl)methoxy)-1-((2-oxopyrrolidin-1-yl)methyl)-1,2,3,4-tetrahydroisoquinoline-2-carbonyl)cyclohexane-1-carboxylic acid;

3-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)bicyclo[2.2.1]heptane-2-carboxylic acid;

3-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)tetrahydrofuran-2-carboxylic acid;

(1S,2R)-2-((S)-5-chloro-8-((1-methyl-1H-indazol-3-yl)methoxy)-1-((2-oxopyrrolidin-1-yl)methyl)-1,2,3,4-tetrahydroisoquinoline-2-carbonyl)cyclohexane-1-carboxylic acid;

(1S,2R)-2-((S)-5-chloro-8-((3-methyl-3H-imidazo[4,5-b]pyridin-5-yl)methoxy)-1-((2-oxopyrrolidin-1-yl)methyl)-1,2,3,4-tetrahydroisoquinoline-2-carbonyl)cyclohexane-1-carboxylic acid;

(1S,2R)-2-((S)-8-(benzo[d]isoxazol-3-ylmethoxy)-5-chloro-1-((2-oxopyrrolidin-1-yl)methyl)-1,2,3,4-tetrahydroisoquinoline-2-carbonyl)-1-methylcyclohexane-1-carboxylic acid;

2-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)-4,4-difluorocyclopentane-1-carboxylic acid;

(1S,2R)-2-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)-1-methylcyclopentane-1-carboxylic acid;

(1S,2R)-2-((S)-5-chloro-8-((4,5-dimethyl-4H-1,2,4-triazol-3-yl)methoxy)-1-((2-oxopyrrolidin-1-yl)methyl)-1,2,3,4-tetrahydroisoquinoline-2-carbonyl)cyclohexane-1-carboxylic acid;

(1S,2R)-2-((S)-5-chloro-8-((1-methyl-1H-1,2,3-triazol-4-yl)methoxy)-1-((2-oxopyrrolidin-1-yl)methyl)-1,2,3,4-tetrahydroisoquinoline-2-carbonyl)cyclohexane-1-carboxylic acid;

(1R,2S)-2-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)-1-fluorocyclohexane-1-carboxylic acid;

(1S,2R)-2-((S)-5-chloro-8-((1-methyl-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((1,5-dimethyl-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((1-methyl-5-(trifluoromethyl)-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-methyl-1H-1,2,3-triazol-4-yl)methoxy)-1-(((R)-4-methyl-2-oxopyrrolidin-1-yl)methyl)-1,2,3,4-tetrahydroisoquinoline-2-carbonyl)-1-methylcyclopentane-1-carboxylic acid;

(1S,2R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclopentane-1-carboxylic acid;

(1S,2R)-2-((S)-5-chloro-8-((5-(difluoromethyl)-1-methyl-1H-1,2,3-triazol-4-yl)methoxy)-1-(((R)-4-methyl-2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-methyl-1H-1,2,3-triazol-4-yl)methoxy)-1-(((R)-3-methyl-2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-methyl-1H-1,2,3-triazol-4-yl)methoxy)-1-(((R)-3-methyl-2-oxopyrrolidin-1-yl)methyl)-1,2,3,4-tetrahydroisoquinoline-2-carbonyl)-1-methylcyclopentane-1-carboxylic acid;

(1S,2R)-2-((S)-5-chloro-8-((5-(difluoromethyl)-1-methyl-1H-1,2,3-triazol-4-yl)methoxy)-1-(((S)-3-methyl-2-oxopyrrolidin-1-yl)methyl)-1,2,3,4-tetrahydroisoquinoline-2-carbonyl)-1-methylcyclopentane-1-carboxylic acid;

(1S,2R)-2-((S)-5-chloro-8-((5-(difluoromethyl)-1-methyl-1H-1,2,3-triazol-4-yl)methoxy)-1-(((S)-3-methyl-2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-methyl-1H-1,2,3-triazol-4-yl)methoxy)-1-(((S)-4-methyl-2-oxopyrrolidin-1-yl)methyl)-1,2,3,4-tetrahydroisoquinoline-2-carbonyl)-1-methylcyclopentane-1-carboxylic acid;

(1S,2R)-2-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)-1-ethylcyclohexane-1-carboxylic acid;

(1S,2R)-2-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)-1-ethylcyclopentane-1-carboxylic acid;

(1S,2R)-2-((S)-5-chloro-8-((5-(difluoromethyl)-1-ethyl-1H-1,2,3-triazol-4-yl)methoxy)-1-((2-oxopyrrolidin-1-yl)methyl)-1,2,3,4-tetrahydroisoquinoline-2-carbonyl)-1-methylcyclopentane-1-carboxylic acid;

(1S,2R)-2-((S)-5-chloro-8-((5-(difluoromethyl)-1-ethyl-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-isopropyl-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-isopropyl-1H-1,2,3-triazol-4-yl)methoxy)-1-((2-oxopyrrolidin-1-yl)methyl)-1,2,3,4-tetrahydroisoquinoline-2-carbonyl)-1-methylcyclopentane-1-carboxylic acid;

(1S,2R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((4,5-dimethylisoxazol-3-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((4-chloro-5-methylisoxazol-3-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((4-methylisoxazol-5-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-(methoxymethyl)-1-methyl-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-(2-methoxyethyl)-1-methyl-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-cyclopropyl-1-methyl-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-1-(((S)-3-methyl-2-oxopyrrolidin-1-yl)methyl)-8-((1-methyl-5-(trifluoromethyl)-1H-1,2,3-triazol-4-yl)methoxy)-1,2,3,4-tetrahydroisoquinoline-2-carbonyl)-1-methylcyclohexane-1-carboxylic acid;

(1S,2R)-2-((S)-5-chloro-1-(((R)-3-methyl-2-oxopyrrolidin-1-yl)methyl)-8-((1-methyl-5-(trifluoromethyl)-1H-1,2,3-triazol-4-yl)methoxy)-1,2,3,4-tetrahydroisoquinoline-2-carbonyl)-1-methylcyclohexane-1-carboxylic acid;

(1S,2R)-2-((S)-5-chloro-1-(((R)-4-methyl-2-oxopyrrolidin-1-yl)methyl)-8-((1-methyl-5-(trifluoromethyl)-1H-1,2,3-triazol-4-yl)methoxy)-1,2,3,4-tetrahydroisoquinoline-2-carbonyl)-1-methylcyclohexane-1-carboxylic acid;

(1S,2S)-2-((S)-5-chloro-1-(((R)-4-methyl-2-oxopyrrolidin-1-yl)methyl)-8-((1-methyl-5-(trifluoromethyl)-1H-1,2,3-triazol-4-yl)methoxy)-1,2,3,4-tetrahydroisoquinoline-2-carbonyl)-1-methylcyclohexane-1-carboxylic acid;

(1S,2R)-2-((S)-5-chloro-8-((1-cyclopropyl-5-(difluoromethyl)-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((4-(difluoromethyl)pyrimidin-5-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5,5-dimethyl-4,5-dihydroisoxazol-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((4-methylisoxazol-3-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-1-((2-oxopyrrolidin-1-yl)methyl)-8-((4,5,6,7-tetrahydrobenzo[d]isoxazol-3-yl)methoxy)-1,2,3,4-tetrahydroisoquinoline-2-carbonyl)-1-methylcyclohexane-1-carboxylic acid;

(1S,2R)-2-((S)-8-((2,5-bis(difluoromethyl)-2H-1,2,3-triazol-4-yl)methoxy)-5-chloro-1-((6-oxo-5-azaspiro[2.4]heptan-5-yl)methyl)-1,2,3,4-tetrahydroisoquinoline-2-carbonyl)-1-methylcyclohexane-1-carboxylic acid;

2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)tetrahydro-2H-pyran-3-carboxylic acid;

(R)-2-((S)-5-chloro-8-((5-(difluoromethyl)-1-methyl-1H-1,2,3-triazol-4-yl)methoxy)-1-((2-oxopyrrolidin-1-yl)methyl)-1,2,3,4-tetrahydroisoquinoline-2-carbonyl)bicyclo[2.2.2]octane-1-carboxylic acid;

(1S,2R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic-4,4-d2 acid;

(1S,2R)-2-((S)-5-chloro-8-((1,5-dimethyl-1H-1,2,3-triazol-4-yl)methoxy)-7-fluoro-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-7-fluoro-1-((6-oxo-5-azaspiro[2.4]heptan-5-yl)methyl)-8-((4,5,6,7-tetrahydro-[1,2,3]triazolo[1,5-a]pyridin-3-yl)methoxy)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-(2-methoxyethyl)-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5,6-dihydro-4H-pyrrolo[1,2-c][1,2,3]triazol-3-yl)methoxy)-7-fluoro-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-methyl-1H-1,2,3-triazol-4-yl)methoxy)-7-fluoro-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((1-methyl-2-oxo-1,2-dihydropyridin-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2S)-2-((S)-5-chloro-8-((5-(difluoromethyl)-1-methyl-1H-1,2,3-triazol-4-yl)methoxy)-1-(((R)-4-methyl-2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((1-methyl-5-(trifluoromethyl)-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

1-(((S)-5-chloro-8-((5-(difluoromethyl)-1-methyl-1H-1,2,3-triazol-4-yl)methoxy)-2-((1R,2S)-2-methyl-2-(2H-tetrazol-5-yl)cyclohexane-1-carbonyl)-1,2,3,4-tetrahydroisoquinolin-1-yl)methyl)pyrrolidin-2-one;

(1S,2R)-2-((S)-5-chloro-8-((5-(difluoromethyl)-1-methyl-1H-1,2,3-triazol-4-yl)methoxy)-1-((4,4-dimethyl-2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((1-methyl-5-(trifluoromethyl)-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclopentane-1-carboxylic acid;

(1S,2R)-2-((S)-5-chloro-8-((5-methyl-4-(trifluoromethyl)isoxazol-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-(2,2,2-trifluoroethyl)-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((1,5-dimethyl-1H-1,2,3-triazol-4-yl)methoxy)-1-((6-oxo-5-azaspiro[2.4]heptan- 5-yl)methyl)-1,2,3,4-tetrahydroisoquinoline-2-carbonyl)-1-methylcyclohexane-1-carboxylic acid;

(1S,2R)-2-((S)-5-chloro-8-((4-(difluoromethyl)-5-methylisoxazol-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5-cyclopropyl-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5-(methoxymethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((1-methyl-1H-1,2,3-triazol-4-yl)methoxy)-1-(((R)-4-methyl-2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-(methoxymethyl)-1-methyl-1H-1,2,3-triazol-4-yl)methoxy)-1-(((R)-4-methyl-2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-cyclopropyl-1-methyl-1H-1,2,3-triazol-4-yl)methoxy)-1-(((R)-4-methyl-2-oxopyrrolidin-1-yl)methyl)-1,2,3,4-tetrahydroisoquinoline-2-carbonyl)-1-methylcyclohexane-1-carboxylic acid;

(1S,2R)-2-((1S)-5-chloro-8-((7-fluoro-2,7a-dihydrobenzo[d]isoxazol-3-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((6,7-difluorobenzo[d]isoxazol-3-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-methylisoxazol-3-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((3-methyl-1,2,4-oxadiazol-5-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-methyl-1,2,4-oxadiazol-3-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2S)-2-((S)-5-chloro-8-((1-methyl-5-(trifluoromethyl)-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-1-((6-oxo-5-azaspiro[2.4]heptan-5-yl)methyl)-8-((4,5,6,7-tetrahydro-[1,2,3]triazolo[1,5-a]pyridin-3-yl)methoxy)-1,2,3,4-tetrahydroisoquinoline-2-carbonyl)-1-methylcyclohexane-1-carboxylic acid;

(1S,2R)-2-((S)-5-chloro-1-((6-oxo-5-azaspiro[2.4]heptan-5-yl)methyl)-8-((4-(trifluoromethyl)pyrimidin-5-yl)methoxy)-1,2,3,4-tetrahydroisoquinoline-2-carbonyl)-1-methylcyclohexane-1-carboxylic acid;

(1S,2R)-2-((S)-5-chloro-8-((1-cyclopropyl-5-(difluoromethyl)-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((1-(2-(dimethylamino)ethyl)-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-1-methyl-2-((S)-5-methyl-8-((1-methyl-5-(trifluoromethyl)-1H-1,2,3-triazol-4-yl)methoxy)-1-((2-oxopyrrolidin-1-yl)methyl)-1,2,3,4-tetrahydroisoquinoline-2-carbonyl)cyclohexane-1-carboxylic acid;

(1S,2R)-2-((S)-5-chloro-8-((4-methyl-4H-1,2,4-triazol-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5,6-dihydro-8H-[1,2,4]triazolo[3,4-c][1,4]oxazin-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((4-cyclopropyl-5-methyl-4H-1,2,4-triazol-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-fluoro-8-((1-methyl-5-(trifluoromethyl)-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((4,5-dimethyl-4H-1,2,4-triazol-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-1-((6-oxo-5-azaspiro[2.4]heptan-5-yl)methyl)-8-((4,5,6,7-tetrahydro-[1,2,3]triazolo[1,5-a]pyridin-3-yl)methoxy)-1,2,3,4-tetrahydroisoquinoline-2-carbonyl)-1-methylcyclopentane-1-carboxylic acid;

(1S,2R)-2-((S)-5-chloro-8-((5,6-dihydro-4H-pyrrolo[1,2-c][1,2,3]triazol-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-fluoro-1-((6-oxo-5-azaspiro[2.4]heptan-5-yl)methyl)-8-((4,5,6,7-tetrahydro-[1,2,3]triazolo[1,5-a]pyridin-3-yl)methoxy)-1,2,3,4-tetrahydroisoquinoline-2-carbonyl)-1-methylcyclohexane-1-carboxylic acid;

(1S,2R)-2-((S)-5-chloro-8-((6,7-dihydro-5H-pyrrolo[2,1-c][1,2,4]triazol-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5-cyclopropyl-4-methyl-4H-1,2,4-triazol-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((1-methyl-1H-imidazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-1-((6-oxo-5-azaspiro[2.4]heptan-5-yl)methyl)-8-((5,6,7,8-tetrahydro-[1,2,4]triazolo

[4,3-a]pyridin-3-yl)methoxy)-1,2,3,4-tetrahydroisoquinoline-2-carbonyl)-1-methylcyclohexane-1-carboxylic acid;

(1S,2R)-2-((S)-5-chloro-8-(((S)-1-(methylsulfonyl)pyrrolidin-3-yl)oxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-8-(((S)-1-acetylpyrrolidin-3-yl)oxy)-5-chloro-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((6,7-dihydro-4H-[1,2,3]triazolo[5,1-c][1,4]oxazin-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-1-methyl-2-((S)-8-((1-methyl-5-(trifluoromethyl)-1H-1,2,3-triazol-4-yl)methoxy)-1-((2-oxopyrrolidin-1-yl)methyl)-1,2,3,4-tetrahydroisoquinoline-2-carbonyl)cyclohexane-1-carboxylic acid;

(1S,2R)-2-((S)-5-bromo-8-((1-methyl-5-(trifluoromethyl)-1H-1,2,3-triazol-4-yl)methoxy)-1-((2-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-(oxetan-3-yl)-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-8-((1,5-bis(difluoromethyl)-1H-1,2,3-triazol-4-yl)methoxy)-5-chloro-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-methyl-1H-1,2,3-triazol-4-yl)methoxy)-1-(((R)-2-methyl-5-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-methyl-1H-1,2,3-triazol-4-yl)methoxy)-1-(((S)-2-methyl-5-oxopyrrolidin-1-yl)methyl)-1,2,3,4-tetrahydroisoquinoline-2-carbonyl)-1-methylcyclohexane-1-carboxylic acid;

(1S,2R)-2-((S)-5-chloro-1-((3-oxomorpholino)methyl)-8-((4,5,6,7-tetrahydro-[1,2,3]triazolo[1,5-a]pyridin-3-yl)methoxy)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)cyclohexane-1-carboxylic acid;

(1S,2R)-2-((S)-5-bromo-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((1-methyl-5-(oxetan-3-yl)-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-methyl-1H-1,2,3-triazol-4-yl)methoxy)-1-((3-oxomorpholino)methyl)-1,2,3,4-tetrahydroisoquinoline-2-carbonyl)-1-methylcyclohexane-1-carboxylic acid;

(1S,6R)-6-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohex-3-ene-1-carboxylic acid;

5-(((S)-2-((1R,2S)-2-(1H-tetrazol-5-yl)cyclohexane-1-carbonyl)-5-chloro-8-((5-(difluoromethyl)-1-methyl-1H-1,2,3-triazol-4-yl)methoxy)-1,2,3,4-tetrahydroisoquinolin-1-yl)methyl)-5-azaspiro[2.4]heptan-6-one;

(1S,2R)-2-((S)-5-chloro-8-((5-(difluoromethyl)-1-methyl-1H-1,2,3-triazol-4-yl)methoxy)-7-fluoro-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)thiazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5-methylthiazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((2-methyl-2H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1R,3S,4R,6S)-4-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-3-methylbicyclo[4.1.0]heptane-3-carboxylic acid;

(1S,3S,4R,6R)-4-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-3-methylbicyclo[4.1.0]heptane-3-carboxylic acid;

(1S,2R)-2-((1S)-5-chloro-8-((6,7-dihydro-5H-pyrrolo[2,1-c][1,2,4]triazol-7-yl)oxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R,4S,5R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic-4,5-d2 acid;

(1S,2R)-2-((S)-5-chloro-8-((1-methyl-2-oxo-1,2-dihydropyridin-3-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((1S)-5-chloro-8-((5-(difluoromethyl)-1-methyl-1H-1,2,3-triazol-4-yl)methoxy)-1-((2-oxo-4-(trifluoromethyl)pyrrolidin-1-yl)methyl)-1,2,3,4-tetrahydroisoquinoline-2-carbonyl)-1-methylcyclohexane-1-carboxylic acid;

(1S,2R)-2-((S)-5-chloro-8-((1-methyl-6-oxo-1,6-dihydropyridin-2-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((1S)-5-chloro-8-((1-methyl-1,4,5,6-tetrahydrocyclopenta[d][1,2,3]triazol-5-yl)oxy)-1-((6-oxo-5-azaspiro[2.4]heptan-5-yl)methyl)-1,2,3,4-tetrahydroisoquinoline-2-carbonyl)-1-methylcyclohexane-1-carboxylic acid;

(1S,2R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-4,4-difluoro-1-methylcyclohexane-1-carboxylic acid;

(1S,2R,4S)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-4-fluoro-1-methylcyclohexane-1-carboxylic acid;

(1S,2R,4R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-1-methylcyclohexane-1-carboxylic-4-d acid;

(1S,2R,4S)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-4-hydroxy-1-methylcyclohexane-1-carboxylic acid;

(1S,2R,5S)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-5-hydroxy-1-methylcyclohexane-1-carboxylic acid;

(1S,2R,5R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-5-hydroxy-1-methylcyclohexane-1-carboxylic acid;

(1S,2R,4R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-4-hydroxy-1-methylcyclohexane-1-carboxylic acid;

(2S,3R)-3-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)tetrahydro-2H-pyran-2-carboxylic acid;

(1R,2R,6S)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-6-hydroxy-1-methylcyclohexane-1-carboxylic acid;

(1R,2R,6R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-6-hydroxy-1-methylcyclohexane-1-carboxylic acid;

(1S,2S,3R)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-3-hydroxy-1-methylcyclohexane-1-carboxylic acid; and (1S,2S,3S)-2-((S)-5-chloro-8-((5-(difluoromethyl)-1-methyl-1H-1,2,3-triazol-4-yl)methoxy)-1-((6-oxo-5-azaspiro[2.4]heptan-5-yl)methyl)-1,2,3,4-tetrahydroisoquinoline-2-carbonyl)-3-hydroxy-1-methylcyclohexane-1-carboxylic acid;

or a pharmaceutically acceptable salt thereof.

18. A pharmaceutical composition comprising a compound according to claim 1, or a pharmaceutically acceptable salt thereof, and one or more pharmaceutically acceptable excipients.

19. A method of treating a disease or disorder selected from chronic obstructive pulmonary disease, acute, chronic and severe asthma, acute lung injury/acute respiratory distress syndrome with or without accompanying multi organ dysfunction syndrome, pulmonary fibrosis including idiopathic pulmonary fibrosis, cystic fibrosis, diabetes, atherosclerosis, hypertension, heart failure, myocardial infarction and repair, cardiac remodelling, cardiac arrhythmias, cardiac hypertrophy, heart failure with preserved ejection fraction, diabetic cardiomyopathy, obesity, metabolic syndrome, diabetes mellitus, insulin resistance, pulmonary arterial hypertension, subarachnoid haemorrhage, intracerebral haemorrhage, ischemic stroke, beta-thalassemia, sickle cell disease, rheumatoid arthritis, irritable bowel disorder, ulcerative colitis, Crohn's disease, psoriasis, radiation-induced dermatitis, atopic dermatitis, non-alcoholic fatty liver disease, non-alcoholic steatohepatitis, toxin-induced liver disease, viral hepatitis and cirrhosis, chronic kidney disease, diabetic nephropathy, autosomal dominant polycystic kidney disease, CKD associated with type 1 diabetes (T1D), IgA nephropathy (IgAN), Alport Syndrome, focal segmental glomerulosclerosis, Huntington's disease, Parkinson's disease, Alzheimer's disease, amyotrophic lateral sclerosis, frontotemporal dementia, multiple sclerosis, Friedreich's ataxia, lung cancer, breast cancer, colon cancer, age related macular degeneration (AMD), Fuchs Endothelial Corneal Dystrophy and uveitis, said method comprising administering to a subject in need of such a treatment a therapeutically effective amount of a compound according to claim 1, or a pharmaceutically acceptable salt thereof.

20. A compound according to claim 6, wherein $R^9$ is methyl.

21. A compound according to claim 7, wherein $R^1$ is $CH_2$—$R^{11}$.

22. A compound according to claim 15, wherein $R^4$ and $R^5$, taken together with the nitrogen atom to which they are attached, form a pyrazolyl ring optionally substituted with one or more substituents independently selected from $C_{1-4}$alkyl, halo and OH.

23. A compound according to claim 1, which is:

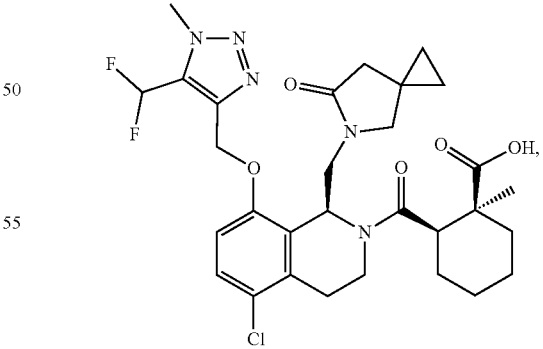

or a pharmaceutically acceptable salt thereof.

24. A compound according to claim 23, which is:

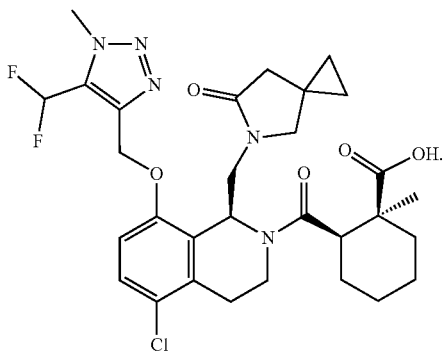 [SMILES: Cn1nnc(COc2ccc(Cl)c3c2[C@@H](CN2CC4(CC4)CC2=O)N(C(=O)[C@@H]2CCCC[C@]2(C)C(=O)O)CC3)c1C(F)F]

25. A compound according to claim 1, which is:

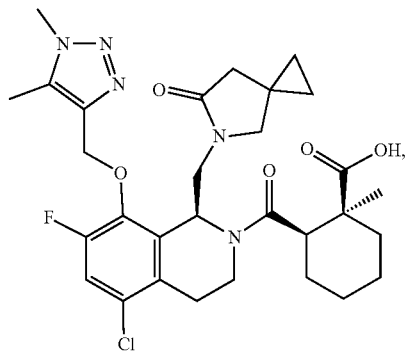 [SMILES: Cc1c(COc2c(F)cc(Cl)c3c2[C@@H](CN2CC4(CC4)CC2=O)N(C(=O)[C@@H]2CCCC[C@]2(C)C(=O)O)CC3)nnn1C]

or a pharmaceutically acceptable salt thereof.

26. A compound according to claim 25, which is:

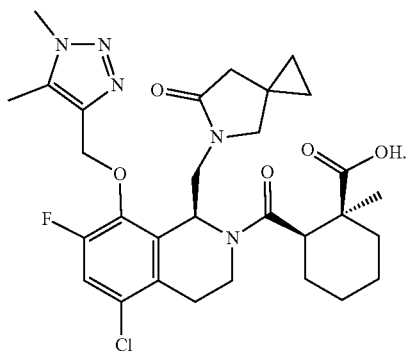 [SMILES: Cc1c(COc2c(F)cc(Cl)c3c2[C@@H](CN2CC4(CC4)CC2=O)N(C(=O)[C@@H]2CCCC[C@]2(C)C(=O)O)CC3)nnn1C]

27. A compound according to claim 1, which is:

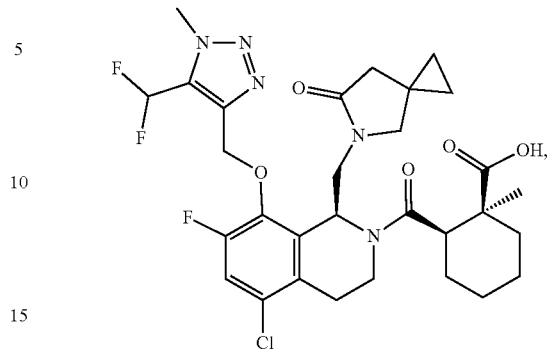

or a pharmaceutically acceptable salt thereof.

28. A compound according to claim 27, which is:

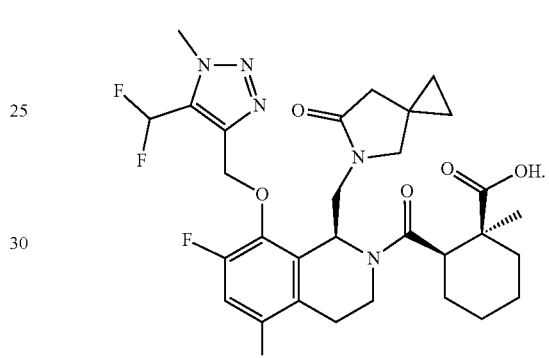

29. The method of claim 19, further comprising administering to the subject one or more additional therapeutic agents.

30. The method of claim 29, wherein the one or more additional therapeutic agents are selected from anti-inflammatory agents and anti-diabetic medications.

31. The method of claim 30, wherein the anti-inflammatory agents are selected from non-steroidal anti-inflammatory drugs (NSAIDs) selected from phosphodiesterase (PDE) inhibitors, leukotriene antagonists, JAK inhibitors, Pi3K inhibitors, inhibitors of leukotriene synthesis, tryptase and elastase inhibitors, beta-2 integrin antagonists, cytokine antagonists, and inhibitors of cytokine synthesis; and the anti-diabetic medications are selected from incretin mimetics/GLP-1 analogues, and sodium glucose co-transporter-2 (SGLT2) inhibitors.

32. The method of claim 31, wherein:
i. the PDE inhibitors are PDE4 inhibitors;
ii. the inhibitors of leukotriene synthesis are montelukast;
iii. the cytokine antagonists are CCR3 antagonists;
iv. the incretin mimetics/GLP-1 analogues are selected from liraglutide, exenatide, and dulaglutide; or
v. the SGLT2 inhibitors are selected from canagliflozin, dapagliflozin and empagliflozin.

* * * * *